United States Patent
Bae et al.

(10) Patent No.: US 11,912,672 B2
(45) Date of Patent: Feb. 27, 2024

(54) ORGANIC COMPOUND AND ORGANIC ELECTROLUMINESCENT DEVICE USING SAME

(71) Applicant: SOLUS ADVANCED MATERIALS CO., LTD., Iksan-si (KR)

(72) Inventors: Hyungchan Bae, Yongin-si (KR); Young Bae Kim, Yongin-si (KR); Hoe Moon Kim, Yongin-si (KR); Ho Jun Son, Yongin-si (KR); Jin Woong Kim, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 564 days.

(21) Appl. No.: 17/052,933

(22) PCT Filed: Jul. 12, 2019

(86) PCT No.: PCT/KR2019/008657
§ 371 (c)(1),
(2) Date: Nov. 4, 2020

(87) PCT Pub. No.: WO2020/027463
PCT Pub. Date: Feb. 6, 2020

(65) Prior Publication Data
US 2021/0253542 A1    Aug. 19, 2021

(30) Foreign Application Priority Data

Jul. 31, 2018 (KR) .......... 10-2018-0089408

(51) Int. Cl.
| | | |
|---|---|---|
| C07D 251/24 | (2006.01) | |
| C07D 495/14 | (2006.01) | |
| C07D 497/14 | (2006.01) | |
| H10K 85/60 | (2023.01) | |
| H10K 50/12 | (2023.01) | |

(52) U.S. Cl.
CPC ......... *C07D 251/24* (2013.01); *C07D 495/14* (2013.01); *C07D 497/14* (2013.01); *H10K 85/622* (2023.02); *H10K 85/654* (2023.02); *H10K 85/6574* (2023.02); *H10K 85/6576* (2023.02); *H10K 50/12* (2023.02)

(58) Field of Classification Search
None
See application file for complete search history.

(56) References Cited

U.S. PATENT DOCUMENTS

| | | | |
|---|---|---|---|
| 10,297,762 B2 | 5/2019 | Zeng et al. | |
| 10,622,565 B2 | 4/2020 | Parham et al. | |
| 2007/0042220 A1* | 2/2007 | Inoue ............... | H05B 33/14 585/27 |
| 2008/0303433 A1* | 12/2008 | Ito .................. | C07C 13/615 313/504 |
| 2014/0197393 A1 | 7/2014 | Lee et al. | |
| 2015/0249221 A1* | 9/2015 | Zeng ................ | C07D 333/76 548/440 |
| 2016/0028021 A1* | 1/2016 | Zeng ................ | C07D 405/10 252/301.16 |
| 2016/0093808 A1 | 3/2016 | Adamovich et al. | |
| 2017/0025618 A1 | 1/2017 | Zheng et al. | |
| 2017/0222157 A1* | 8/2017 | Jatsch ............. | C07D 405/14 |

FOREIGN PATENT DOCUMENTS

| | | | | |
|---|---|---|---|---|
| CN | 105315265 A | 2/2016 | | |
| CN | 107108504 A | 8/2017 | | |
| EP | 3127901 A1 * | 2/2017 | .......... | C07C 255/51 |
| EP | 3127988 A1 * | 2/2017 | .......... | C07D 209/82 |
| KR | 10-2014-0092742 A | 7/2014 | | |
| KR | 10-2016-0006633 A | 1/2016 | | |
| KR | 10-2016-0028524 A | 3/2016 | | |

OTHER PUBLICATIONS

International Search Report for PCT/KR2019/008657 dated Oct. 29, 2019 (PCT/ISA/210).

* cited by examiner

*Primary Examiner* — Robert S Loewe
(74) *Attorney, Agent, or Firm* — Sughrue Mion, PLLC

(57) ABSTRACT

A novel compound having excellent light emission and heat stability is disclosed. Also disclosed is an organic electroluminescent device having properties such as light emitting efficiency, an operation voltage, and a service life improved by including the compound in at least one organic layer of the device.

14 Claims, No Drawings

ORGANIC COMPOUND AND ORGANIC ELECTROLUMINESCENT DEVICE USING SAME

CROSS REFERENCE TO RELATED APPLICATIONS

This application is a National Stage of International Application No. PCT/KR2019/008657 filed Jul. 12, 2019, claiming priority based on Korean Patent Application No. 10-2018-0089408 filed Jul. 31, 2018.

TECHNICAL FIELD

The present invention relates to a novel organic electroluminescent compound and to an organic electroluminescent device using the organic electroluminescent compound, and more particularly, to a compound having excellent electron transporting ability and to an organic electroluminescent device having properties such as light emitting efficiency, a driving voltage, and a service life improved by including the compound in at least one organic layer.

DISCUSSION OF RELATED ART

In a study on an organic electroluminescent (EL) device (hereinafter, simply referred to as 'organic EL device'), which has continued from the start point of observing an organic thin film light emission by Bernanose in the 1950s to blue electric light emission using an anthracene single crystal in 1965, an organic EL device having a lamination structure, which is divided into functional layers of a hole layer and a light-emitting layer, was proposed by Tang in 1987. Until now, the organic EL device has been developed in the form of introducing each characteristic organic layer into a device in order to manufacture the organic EL device having high efficiency and a long service life (service life), thereby leading to the development of specialized materials used therein.

When voltage is applied between two electrodes of the organic EL device, holes are injected into the organic layer at the anode and electrons are injected into the organic layer at the cathode. When the injected holes and electrons meet each other, an exciton is formed, and when the exciton falls down to a bottom state, light is emitted. Materials used as the organic layer may be classified into a light-emitting material, a hole injection material, a hole transporting material, an electron transporting material, an electron injection material, and the like according to the function.

Materials for forming the light-emitting layer of the organic EL device may be divided into blue, green, and red light-emitting materials according to the light-emitting color. In addition, yellow and orange light-emitting materials are also used as a light-emitting material for implementing a much better natural color. Further, a host/dopant system may be used as a light-emitting material in order to enhance color purity and light-emitting efficiency through an energy transfer. Dopant materials may be divided into a fluorescent dopant using an organic material and a phosphorescent dopant in which a metal complex compound including heavy atoms such as Ir and Pt is used. Since the development of the phosphorescent material may theoretically enhance light-emitting efficiency by up to 4 times compared to the development of the fluorescent material, interests in not only phosphorescent dopant, but also phosphorescent host materials have come into focus.

As the hole transporting layer, the hole blocking layer and the electron transporting layer, NPB, BCP, $Alq_3$ and the like represented by the following Chemical Formulae have been widely known until now, and for the light-emitting material, anthracene derivatives have been reported as a fluorescent dopant/host material. In particular, for the phosphorescent material having a great advantage in terms of enhancing the efficiency, metal complex compounds including Ir, such as Firpic, $Ir(ppy)_3$ and $(acac)Ir(btp)_2$, have been used as blue, green and red dopant materials. Until now, CBP have exhibited excellent characteristics as a phosphorescent host material.

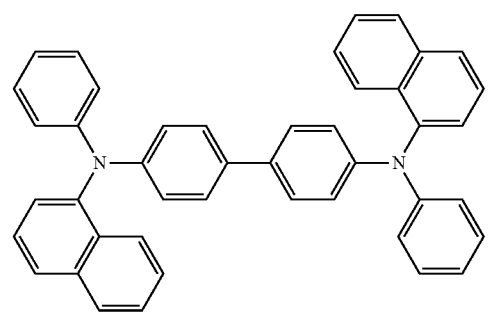

NPB

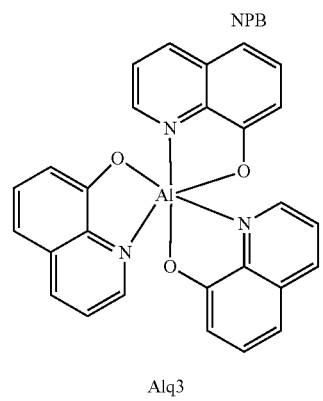

Alq3

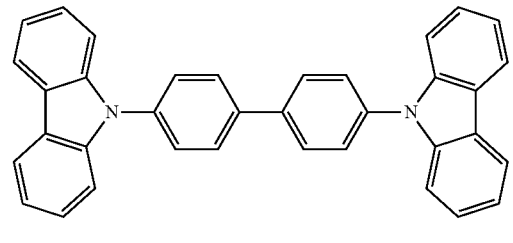

CBP

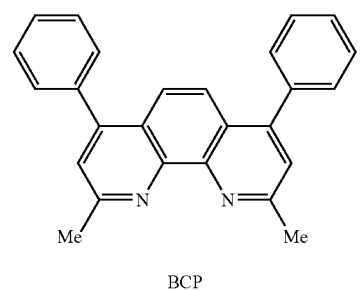

BCP

-continued

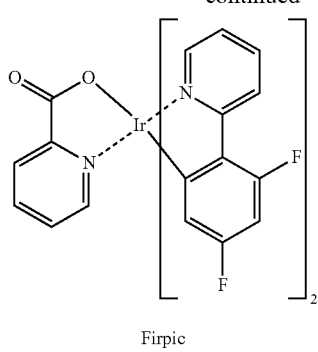

Firpic

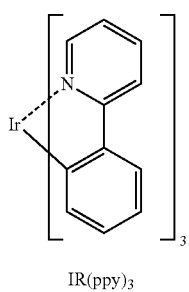

IR(ppy)₃

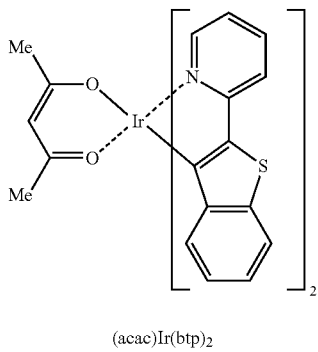

(acac)Ir(btp)₂

However, the existing materials are advantageous in terms of light-emitting characteristics, but have a low glass transition temperature and very poor thermal stability, and thus fall short of a level that sufficiently satisfies the service life in the organic EL device.

DETAILED DESCRIPTION OF THE INVENTION

Technical Objectives

The present invention is directed to a novel organic compound, applicable to an organic electroluminescent device, having excellent hole and electron injection and transporting abilities and high luminous efficiency.

In addition, the present invention is directed to an organic electroluminescent device including the novel organic compound, thereby having a low driving voltage, high luminous efficiency and improved service life.

Technical Solution to the Problem

Embodiments of the present invention provides a compound represented by the following Chemical Formula 1:

[Chemical Formula 1]

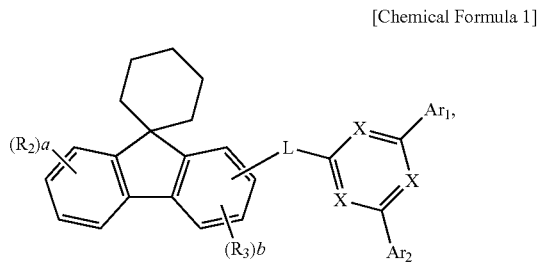

where the plurality of X are the same as or different from each other, each independently being $C(R_1)$ or N, provided that at least one of the plurality of X is N, $R_1$, $R_2$, and $R_3$ are the same as or different from each other, each independently being selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphonyl group, a $C_6$ to $C_{60}$ arylphosphine group, a $C_6$ to $C_{60}$ arylphosphine oxide group and a $C_6$ to $C_{60}$ arylamine group, a is an integer ranging from 0 to 4, b is an integer ranging from 0 to 3, L is represented by any one of the following Chemical Formulas 2 and 3:

[Formula 2]

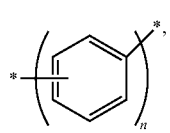

[Formula 3]

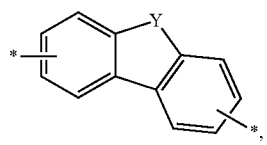

in Chemical Formula 2 or Chemical Formula 3,

\* is a site in which a bond with the compound represented by Chemical Formula 1 is made, Y is selected from the group consisting of O, S and Se, n is an integer ranging from 1 to 5, $Ar_1$ and $Ar_2$ are the same as or different from each other, each independently being selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphonyl group, a $C_6$ to $C_{60}$ arylphosphine group, a $C_6$ to $C_{60}$ arylphosphine oxide group and a $C_6$ to $C_{60}$ arylamine group, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphonyl group, the arylphosphine group, the arylphosphine oxide group and the arylamine group of $Ar_1$ and $Ar_2$ and $R_1$, $R_1$ and $R_3$ are each independently substitutable or unsubstitutable with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

In addition, embodiments of the present invention provide an organic electroluminescent device including an anode, a cathode and one or more organic layers disposed between the anode and the cathode, where at least one of the one or more organic layers includes the compound represented by Chemical Formula 1.

Effects of the Invention

A compound according to one or more embodiments of the present invention has excellent thermal stability, carrier transporting ability, and luminous efficiency, thus applicable to a material of an organic layer of an organic electroluminescent device.

In addition, an organic electroluminescent device including the compound according to one or more embodiments of the present invention is greatly improved in terms of the light emitting performance, driving voltage, serving life, and efficiency thereof, thus applicable to a full-color display panel or the like.

MODES FOR CARRYING OUT THE INVENTION

Hereinafter, embodiments of the present invention will be described in detail.
<Novel Organic Compound>
Embodiments of the present invention provide novel fluorene-based compounds having excellent thermal stability, carrier transporting ability, and luminous efficiency.

In specific, the novel organic compound according to embodiments of the present invention adopts, as a core, a fluorene substituted in 9-position with an aliphatic cyclic group, such as a cyclohexyl group, in a spiro form, and an electron withdrawing group (EWG) having excellent electron transporting ability is bonded to a phenyl group of the core structure to form a basic skeleton.

By forming an aliphatic cyclic group in the 9-position of the fluorene, such a compound represented by Chemical Formula 1 is electrochemically stable and has a high glass transition temperature (Tg) and excellent thermal stability, as compared to a conventional dimethyl fluorene structure. In addition, by introducing an azine group, which is a functional group having a strong electron withdrawing ability (EWG), in order to improve the electron transfer speed, the compound represented by Chemical Formula 1 may have physicochemical properties more suitable for electron injection and electron transporting.

In addition, since the compound represented by Chemical Formula 1 according to an embodiment has a high triplet energy, excitons generated in a light-emitting layer may be prevented from diffusing (migrating) to an adjacent electron transporting layer or hole transporting layer. Accordingly, the number of excitons contributing to light emission in the light-emitting layer is increased, and accordingly, the luminous efficiency of the device may be improved and durability and stability of the device may be improved, thereby improving the serving life of the device. Most of the developed materials enable low voltage driving and thus provide physical properties of improved serving life.

In addition, according to an embodiment of the present invention, the fluorene core in which an aliphatic cyclic group is introduced in the 9-position may include at least one or more dibenzo-based moiety [e.g., dibenzofuran (DBF) or dibenzothiophene (DBT)] having amphoteric physicochemical properties for holes and electrons. A combination of such a dibenzo-based moiety and a nitrogen-containing aromatic ring (e.g., pyridine, pyrazine, and triazine), which is a strong electron-withdrawing group (EWG), may serve as a green phosphorescent material having excellent luminous efficiency. In addition, such a combination may enable a low voltage driving to increase the serving life and may provide excellent device characteristics in terms of, for example, thermal stability, high glass transition temperature, and uniform morphology.

As described above, when the compound represented by Chemical Formula 1 according to an embodiment is used as an organic layer material of an organic electroluminescent device, preferably a light-emitting layer material (a blue, green and/or red phosphorescent host material), an electron transporting layer/injection layer material, and a hole transporting layer/injection layer material, a light-emitting auxiliary layer material, and a life improvement layer material, the performance and life characteristics of the organic electroluminescent device may be greatly improved. Accordingly, the organic electroluminescent device may substantially maximize the performance of a full-color organic electroluminescent panel.

According to an embodiment of the present invention, the compound represented by Chemical Formula 1 uses, as a core, a fluorene substituted in 9-position with a cyclohexyl group in a spiro form, and a linker L and an electron withdrawing group (EWG) with excellent electron transporting ability are sequentially bonded to the core structure to form a basic skeleton.

In Chemical Formula 1, $R_2$ and $R_3$ may be introduced into the fluorene core in which an aliphatic cyclic group is formed. These $R_2$ and $R_3$ may be the same as or different from each other, and may each independently be selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphonyl group, a $C_6$ to $C_{60}$ arylphosphine group, a $C_6$ to $C_{60}$ arylphosphine oxide group and a $C_6$ to $C_{60}$ arylamine group. Specifically, it is preferable that $R_2$ and $R_3$ are the same as or different from each other and each independently selected from the group consisting of: hydrogen, a $C_1$ to $C_{40}$ alkyl group, a $C_6$ to $C_{60}$ aryl group, and a heteroaryl group having 5 to 60 nuclear atoms.

Herein, a is an integer ranging from 0 to 4, and b is an integer ranging from 0 to 3. When a is 0, $R_2$ may be hydrogen, and when a is 1 to 4, $R_2$ may have the aforementioned substituents excluding hydrogen. Similarly, when b is 0, $R_3$ may be hydrogen, and when b is 1 to 3, $R_3$ may have the aforementioned substituents excluding hydrogen.

In Chemical Formula 1 according to an embodiment, L may be a linker of a conventional divalent group known in the art. For example, L may be selected from the group consisting of a $C_6$ to $C_{60}$ arylene group and a heteroarylene group having 5 to 60 nuclear atoms, and specifically, L has an arylene group moiety of the following Chemical Formula 2 or a dibenzo-based moiety of the following Chemical Formula 3.

The moiety of Chemical Formula 2 may be an arylene group linker known in the art, and specific examples thereof may include a phenylene group, a biphenylene group, a naphthylene group, an anthracenylene group, an indenylene group, a pyrantrenylene group, a carbazolylene group, a thiophenylene group, an indolylene group, a furinylene group, a quinolinylene group, a pyrrolylene group, an imidazolylene group, an oxazolylene group, a thiazolylene group, a pyridinylene group, a pyrimidinylene group, and the like. More specifically, it is preferable that the linker L represented by Chemical Formula 2 is a phenylene group or a biphenylene group.

As an embodiment of the present invention, the linker L of Chemical Formula 2 may be a linker selected from the following Structural Formulas:

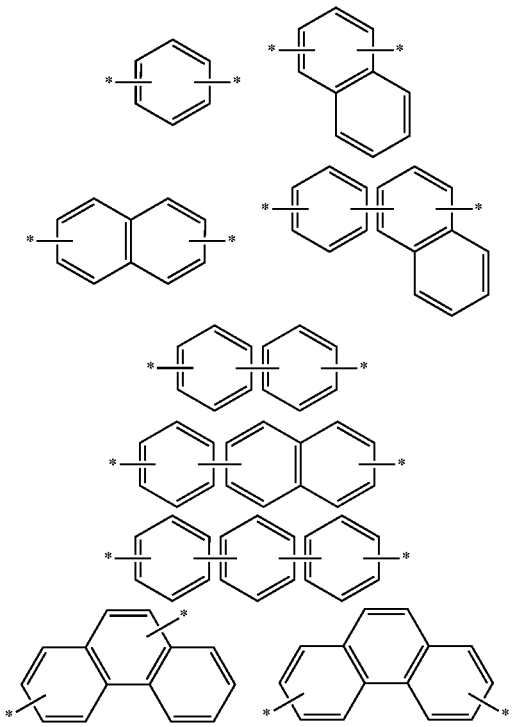

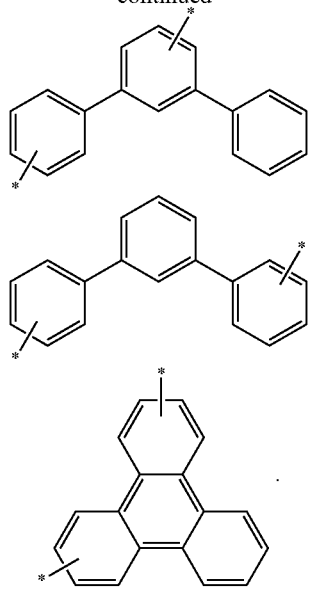

In addition, the linker of Chemical Formula 3 may be a dibenzo-based moiety known in the art. For example, it has a dibenzofuran-based (Y=O) moiety, a dibenzothiophene-based (Y=S) moiety, and/or a dibenzoselenophenone-based (Y=Se) moiety.

The dibenzo-based moiety represented by Chemical Formula 3 may be further embodied by the following Structural Formulas:

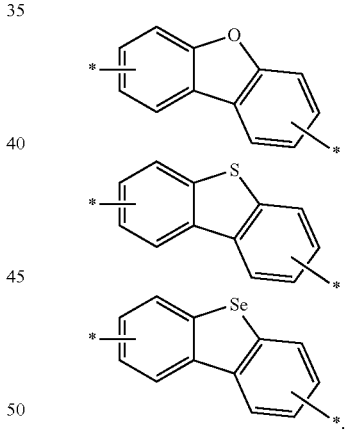

The linkers L of Chemical Formulas 2 and 3 described above may be substituted with at least one or more substituents (e.g., R) known in the art, although not illustrated in the Chemical Formulas.

In the compound represented by Chemical Formula 1 according to an embodiment, a nitrogen-containing aromatic ring, which is a kind of electron withdrawing group (EWG) having excellent electron transporting ability, is bonded to the core structure substituted in 9-position with a cyclohexyl group in a spiro form.

In Chemical Formula 1, the plurality of X are the same as or different from each other and each independently are $C(R_1)$ or N, provided that at least one of the plurality of X is N. For example, the number of nitrogen (N) may be 1 to 3.

$Ar_1$ and $Ar_2$ are the same as or different from each other, and each independently are selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphonyl group, a $C_6$ to $C_{60}$ arylphosphine group, a $C_6$ to $C_{60}$ arylphosphine oxide group and a $C_6$ to $C_{60}$ arylamine group. In specific, it is preferable that $Ar_1$ and $Ar_2$ are the same as or different from each other, and each independently are selected from the group consisting of: a $C_6$ to $C_{60}$ aryl group and a heteroaryl group having 5 to 60 nuclear atoms.

The nitrogen-containing aromatic rings may be embodied in any one of the following Chemical Formulas A-1 to A-5.

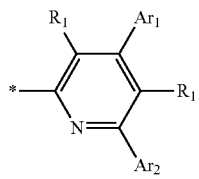

A-1

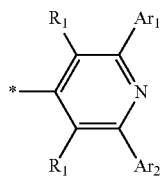

A-2

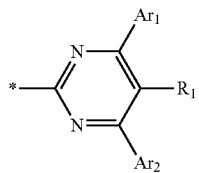

A-3

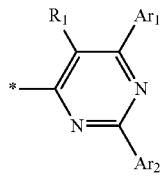

A-4

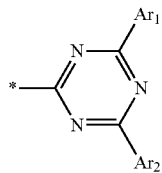

A-5

In A-1 to A-5, $R_1$, $Ar_1$ and $Ar_2$ are as defined in Chemical Formula 1, respectively. In addition to the above-described A-1 to A-5, a polycyclic structure in which two or more of A-1 to A-5 are fused are also within the scope of the present invention.

According to an embodiment, the compound represented by Chemical Formula 1 may be further embodied in any one of the following Chemical Formulas 4 to 7. However, embodiments are not limited thereto.

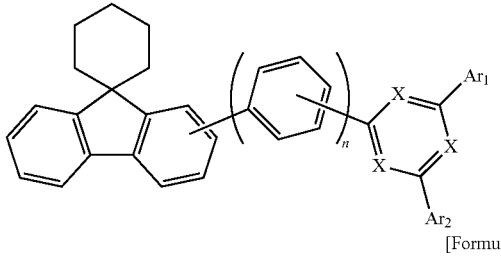

[Formula 4]

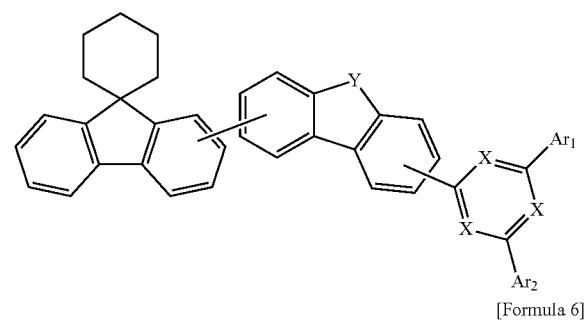

[Formula 5]

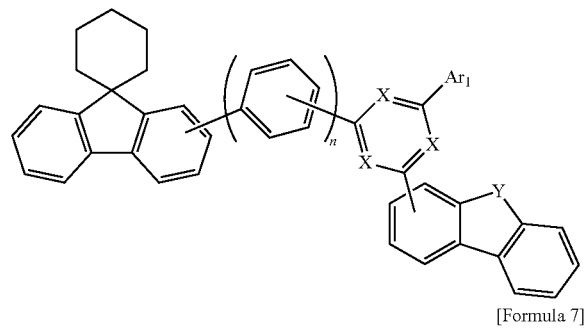

[Formula 6]

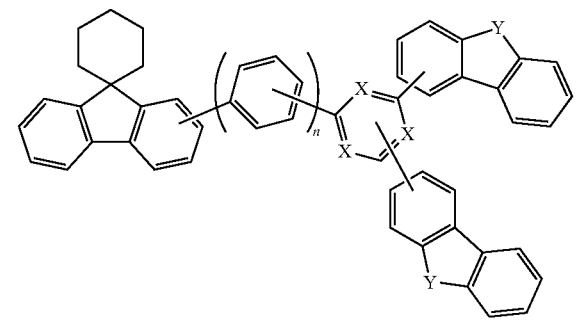

[Formula 7]

In Chemical Formulas 4 to 7,

X, Y, $R_2$, $R_3$, $Ar_1$, $Ar_2$, a, b, and n are as defined in Chemical Formula 1, respectively.

For a preferred example of the compound represented by any one of Chemical Formulas 4 to 7, the plurality of X are the same or different from each other, include 1 to 3 N, and Y may be O or S.

$Ar_1$ and $Ar_2$ may be the same as or different from each other, and may each independently be selected from the group consisting of a $C_6$-$C_{60}$ aryl group and a heteroaryl group having 5 to 60 nuclear atoms. Specifically, $Ar_1$ and $Ar_2$ are different from each other, and may each independently be a $C_6$ to $C_{60}$ aryl group or a heteroaryl group having 5 to 60 nuclear atoms.

Here, n may be 1 to 5.

The compounds represented by the above-described Chemical Formulas 4 to 7 may be further embodied in any one of Chemical Formulas 8 to 11 described below. However, embodiments are not limited thereto.

[Formula 8]

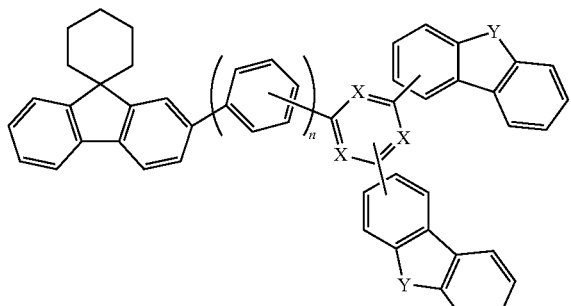

[Formula 9]

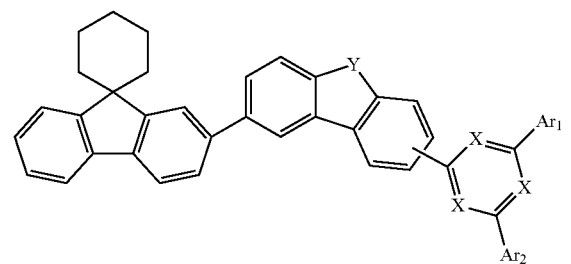

[Formula 10]

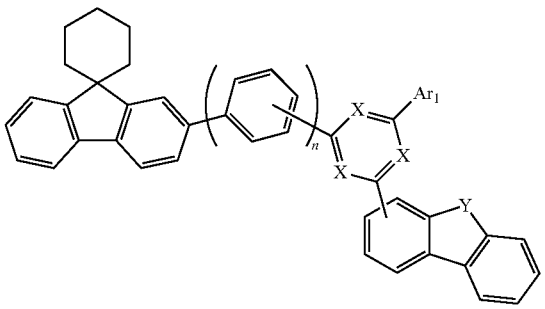

[Formula 11]

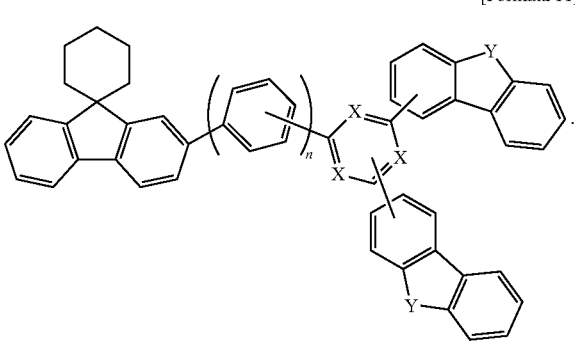

In Chemical Formulas 8 to 11,

X, Y, $Ar_1$, $Ar_2$, and n are as defined in Chemical Formula 1, respectively.

The compound represented by Chemical Formula 1 according to an embodiment described above may be further embodied as the following compounds, for example, compounds represented by Inv 1 to Inv 864. However, the compound represented by Chemical Formula 1 of the present invention is not limited by those illustrated below.

Inv 1

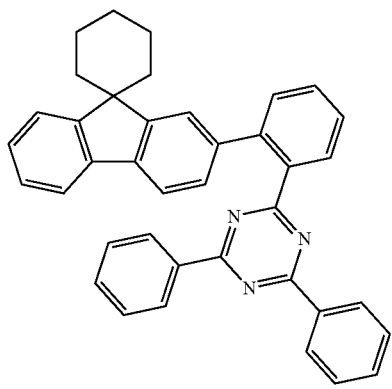

Inv 2

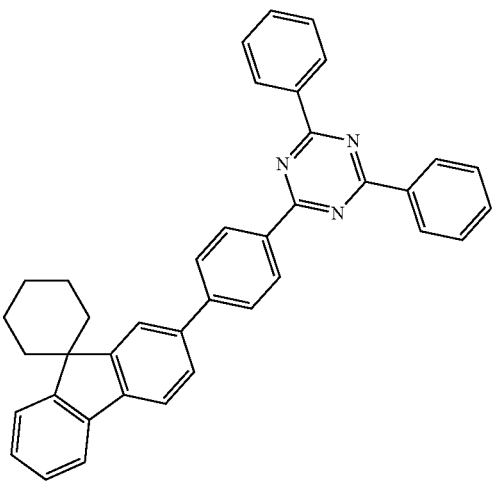

-continued
Inv 3
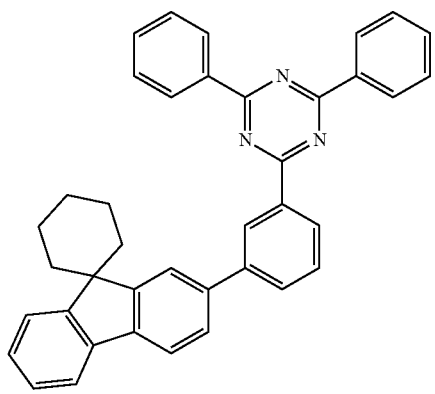
Inv 4
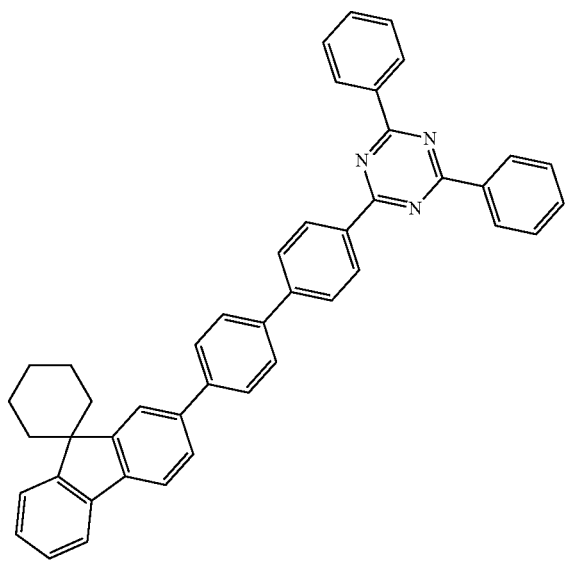
Inv 5
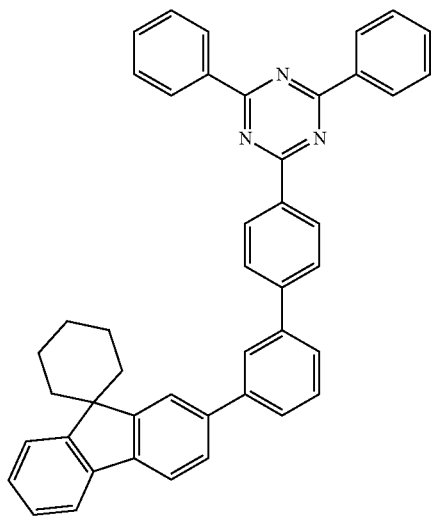
Inv 6
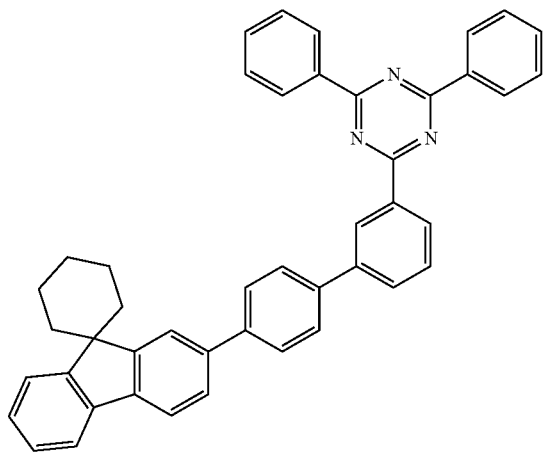

-continued
Inv 7
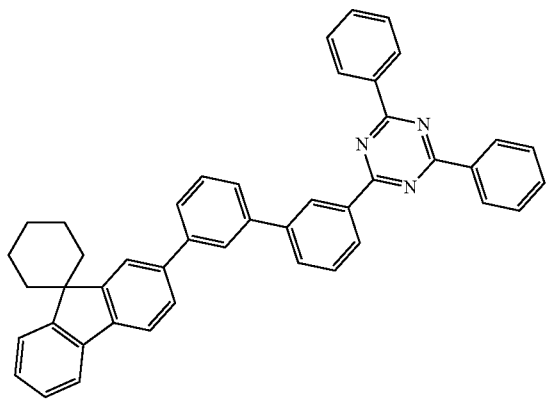
Inv 8
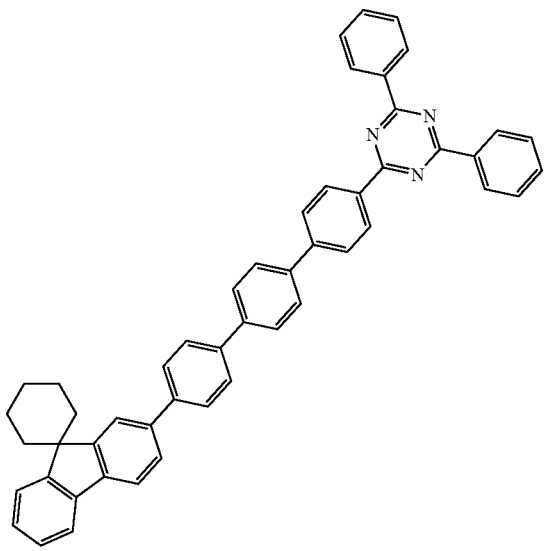
Inv 9
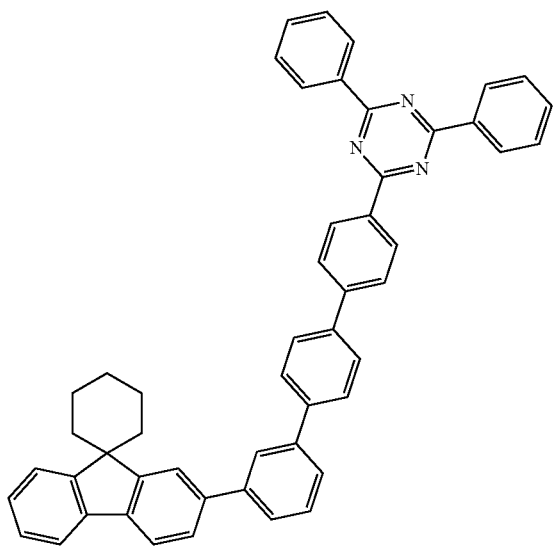
Inv 10
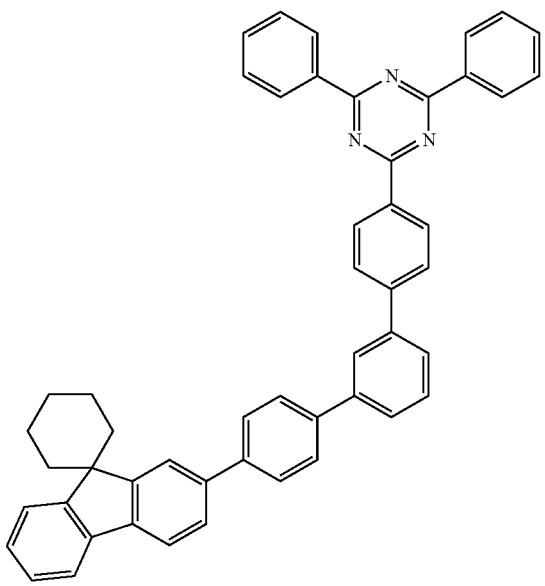

-continued
Inv 11
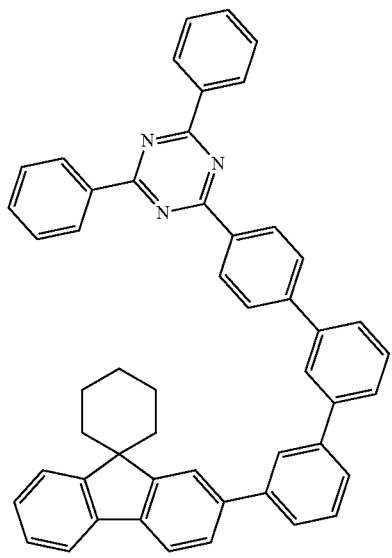
Inv 12
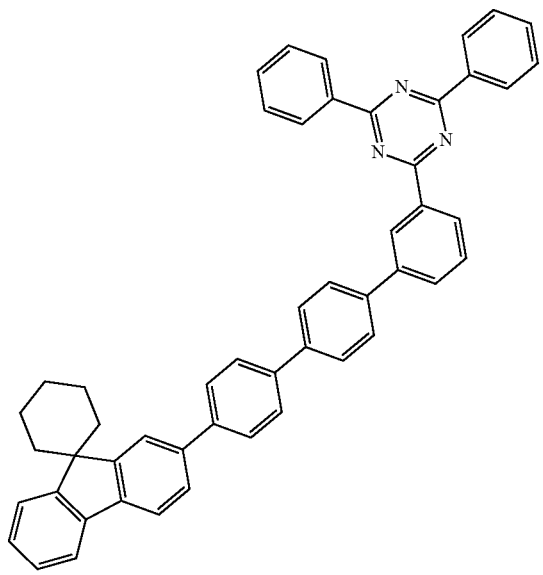
Inv 13
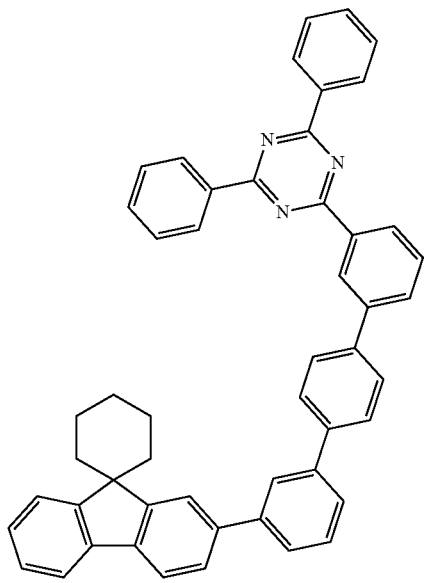
Inv 14
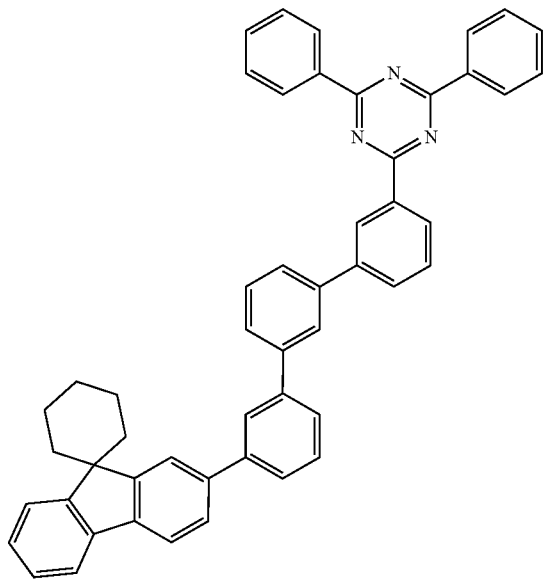

-continued
Inv 15
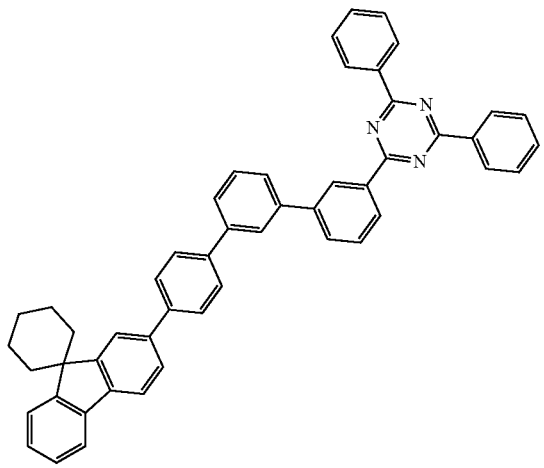
Inv 16
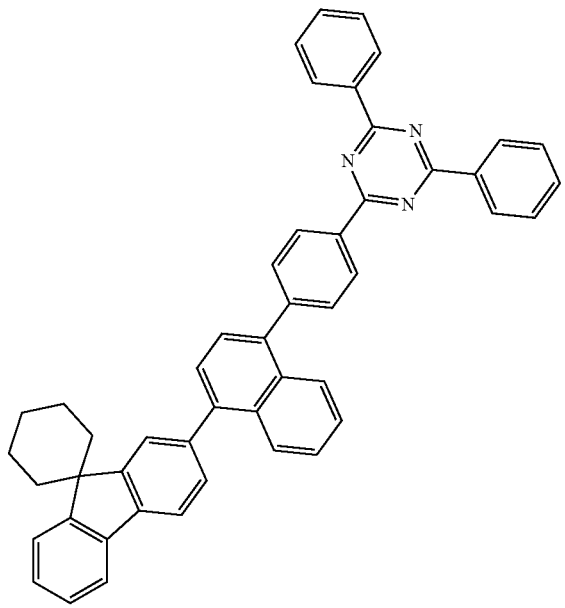
Inv 17
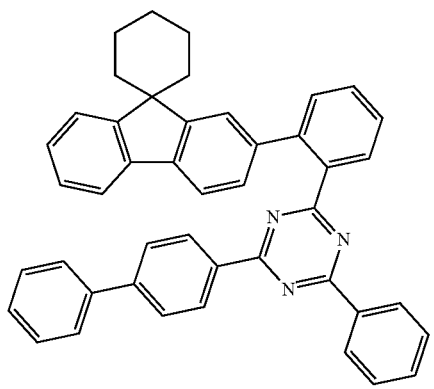
Inv 18
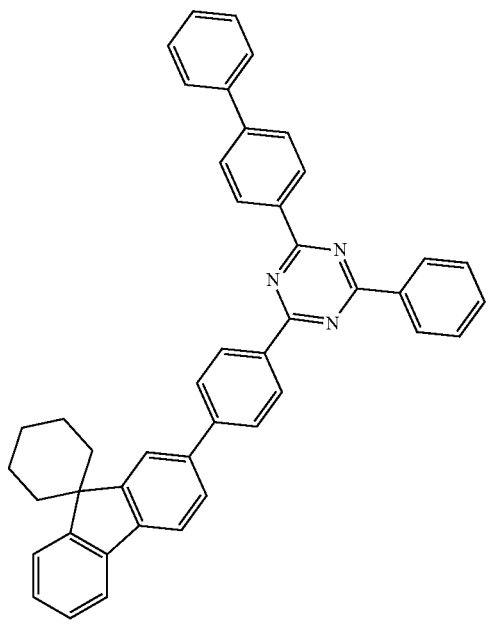

-continued
Inv 19
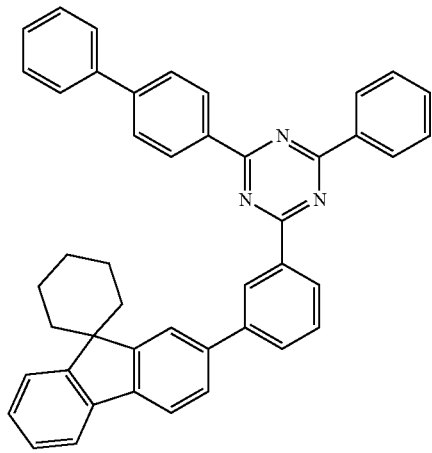
Inv 20
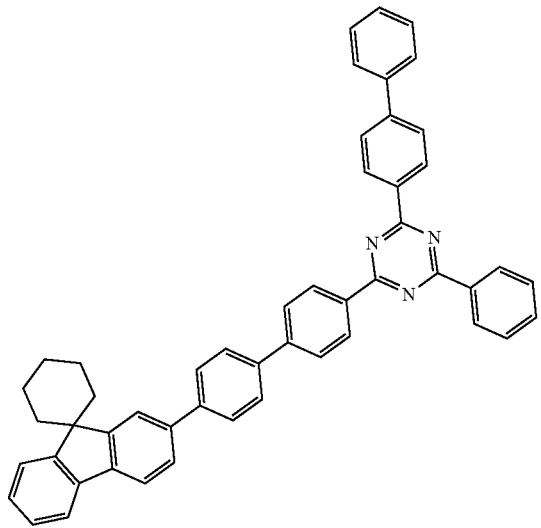
Inv 21
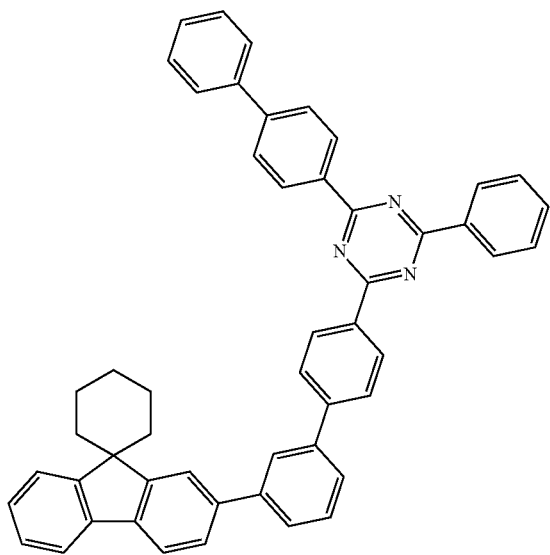
Inv 22
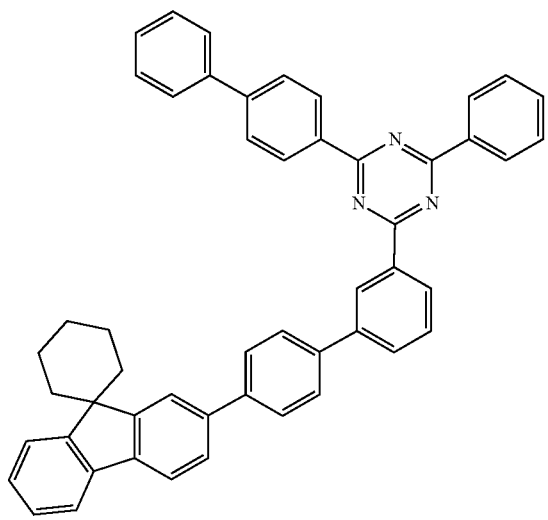

-continued
Inv 23
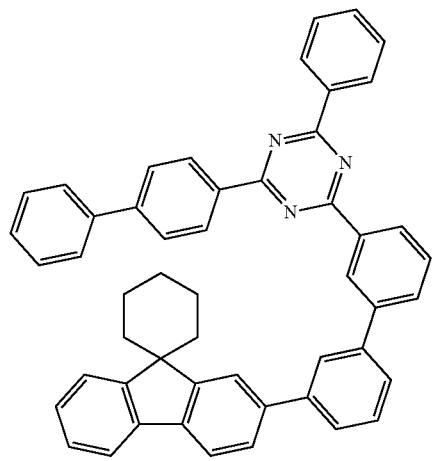
Inv 24
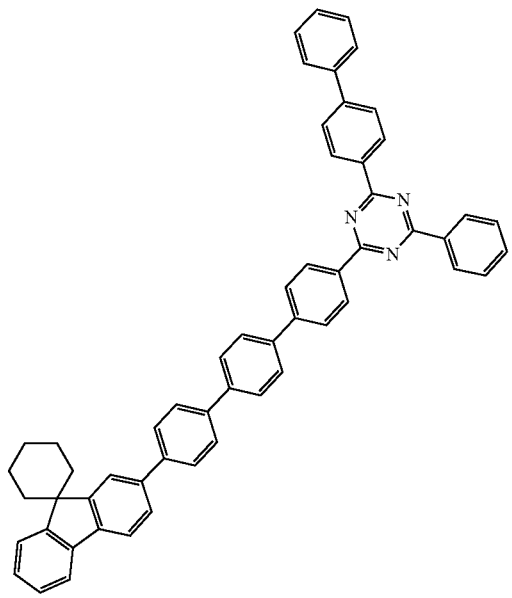
Inv 25
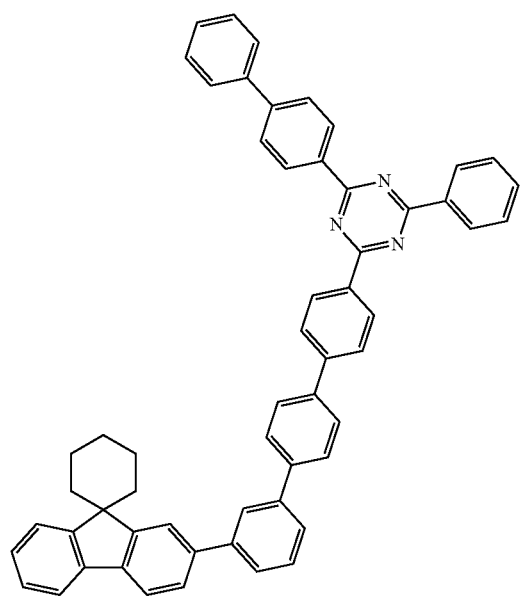
Inv 26
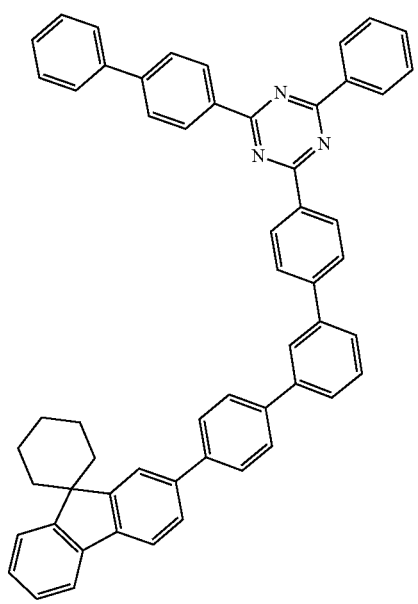

-continued
Inv 27
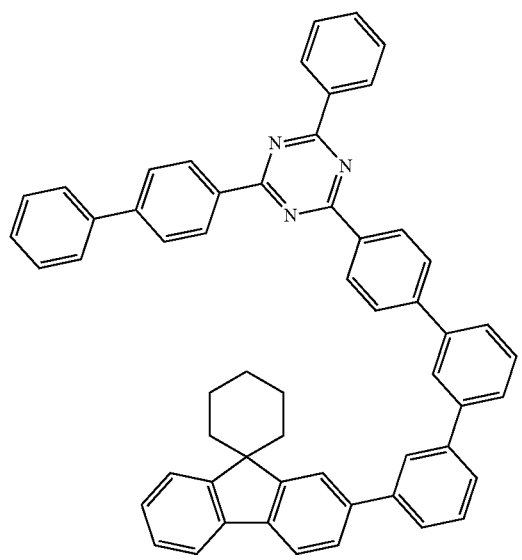
Inv 28
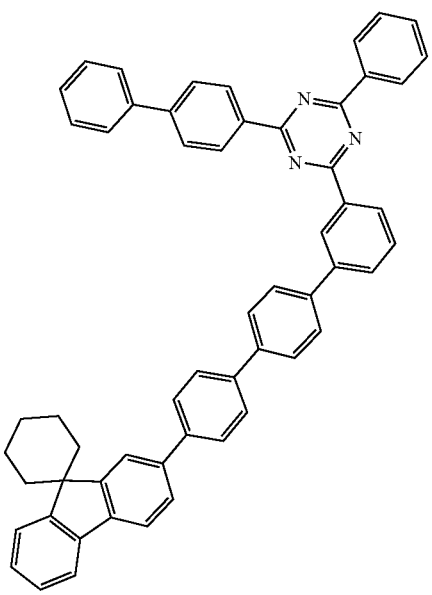
Inv 29
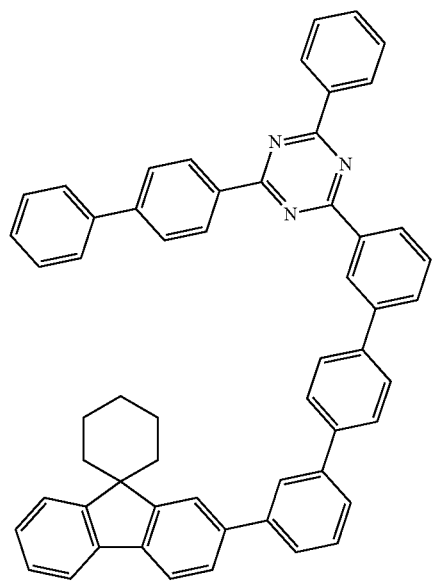
Inv 30
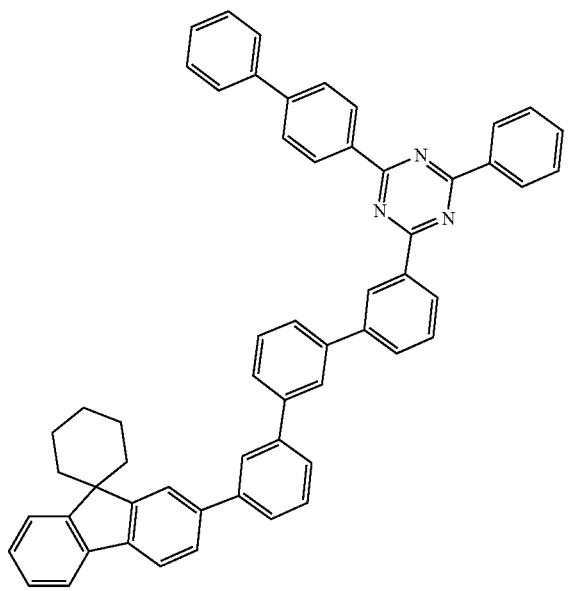

-continued
Inv 31
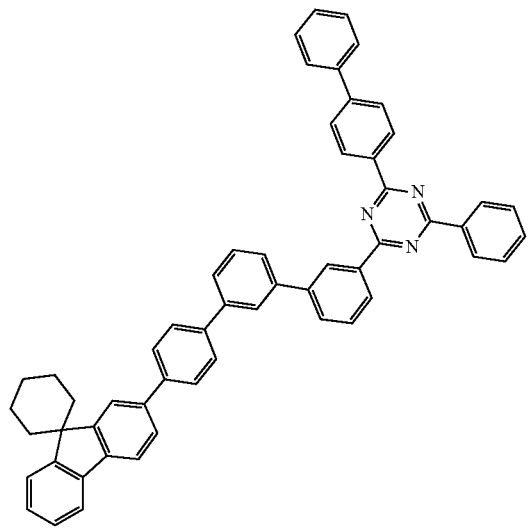
Inv 32
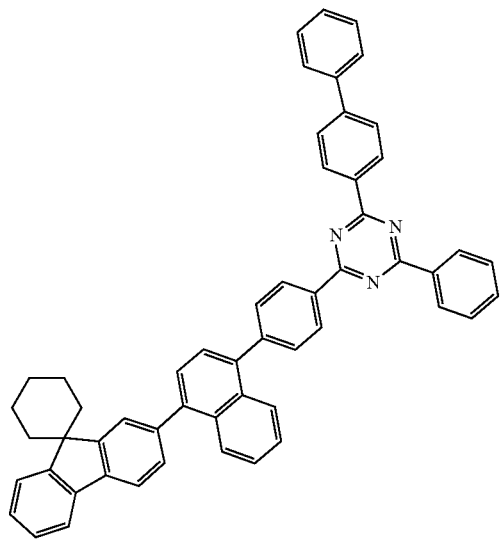
Inv 33
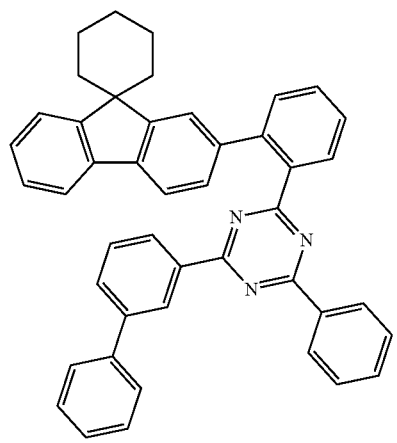
Inv 34
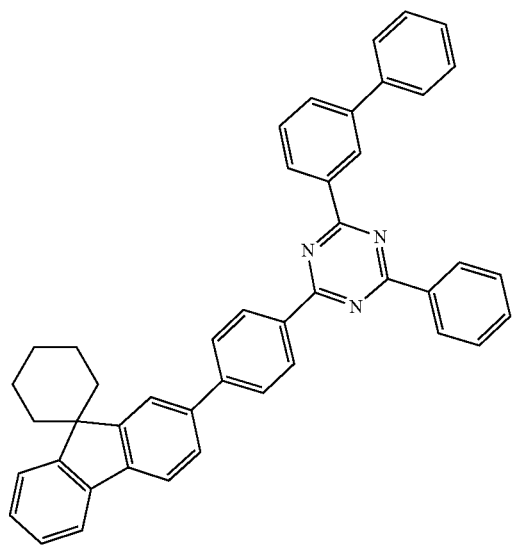
Inv 35
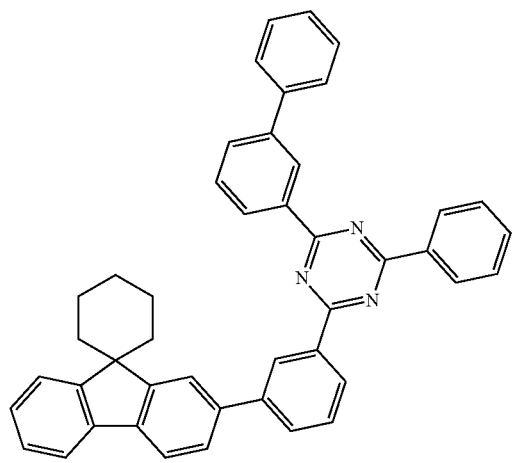
Inv 36
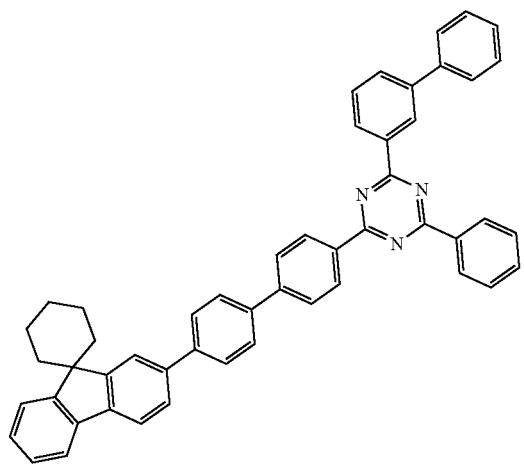

-continued
Inv 37
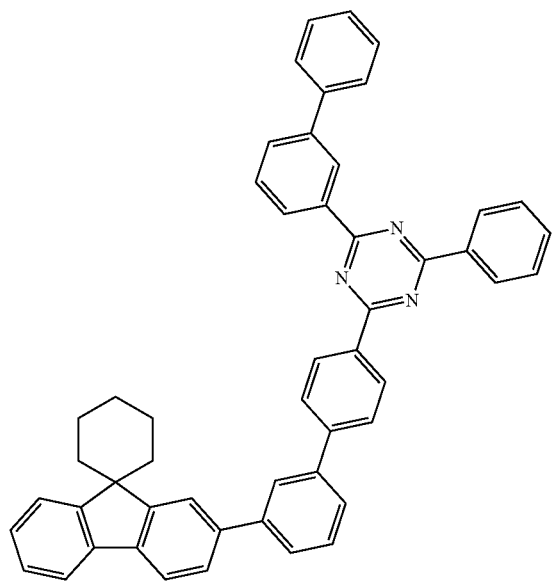
Inv 38
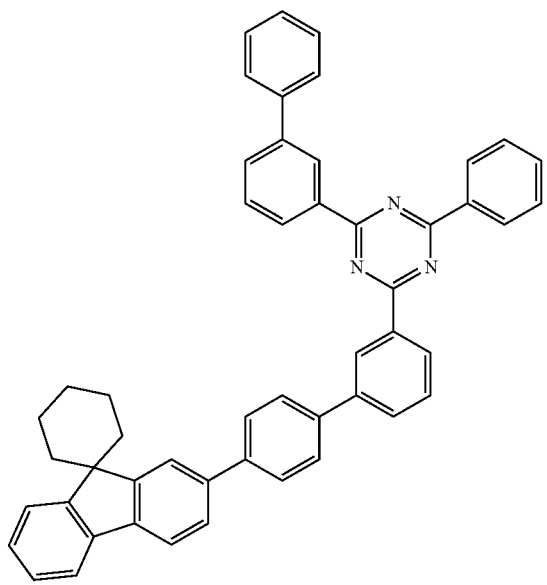
Inv 39
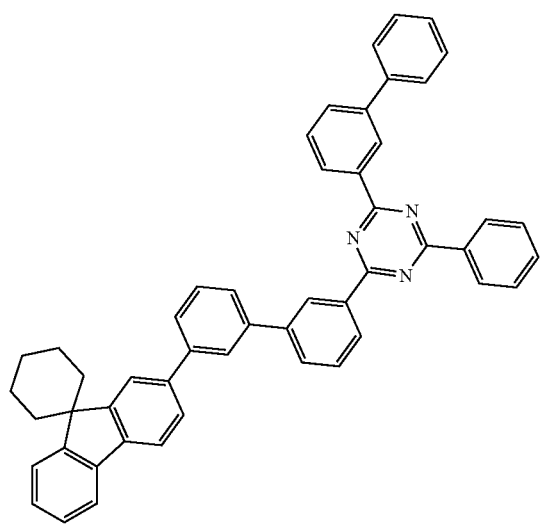
Inv 40
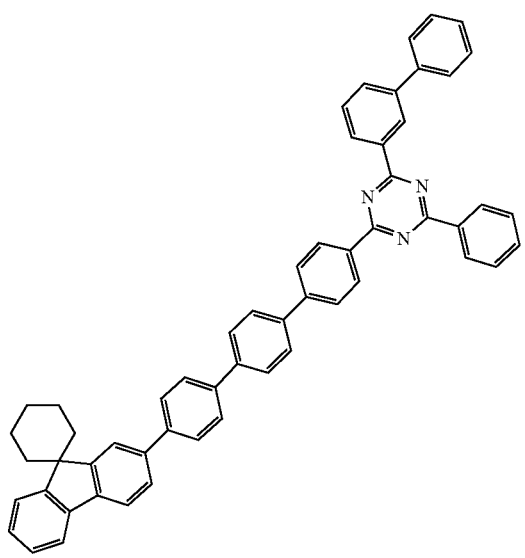

-continued
Inv 41
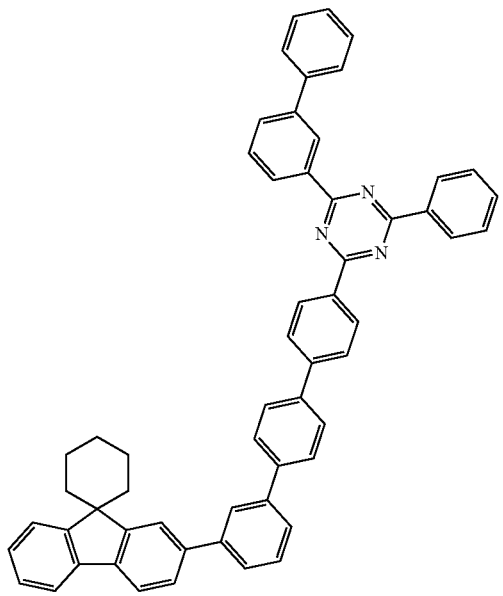
Inv 42
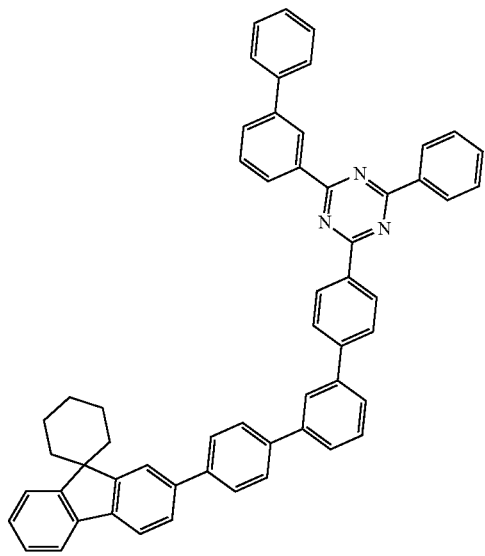
Inv 43
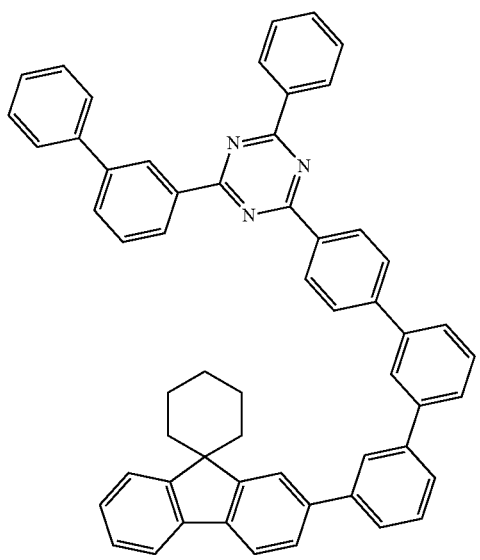
Inv 44
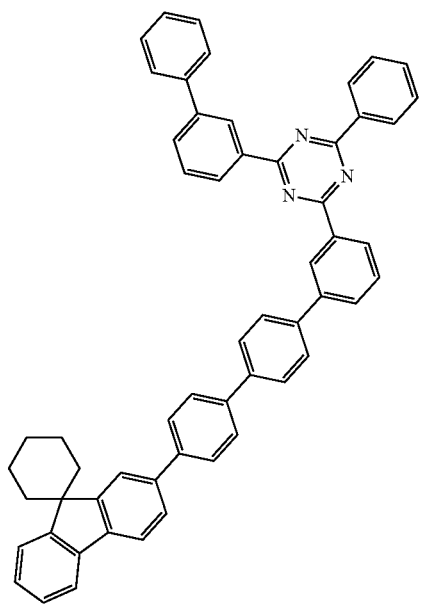

Inv 45
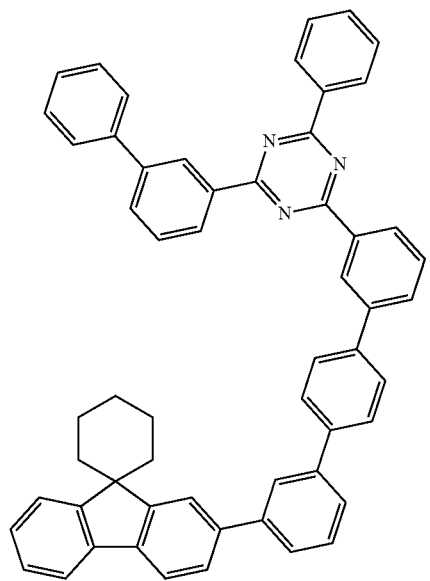
Inv 46
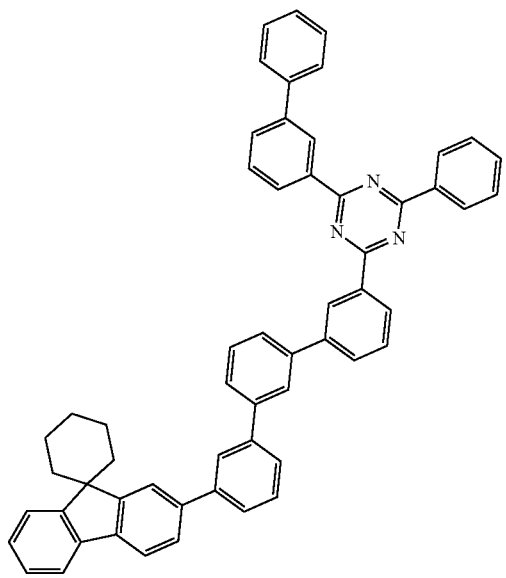
Inv 47
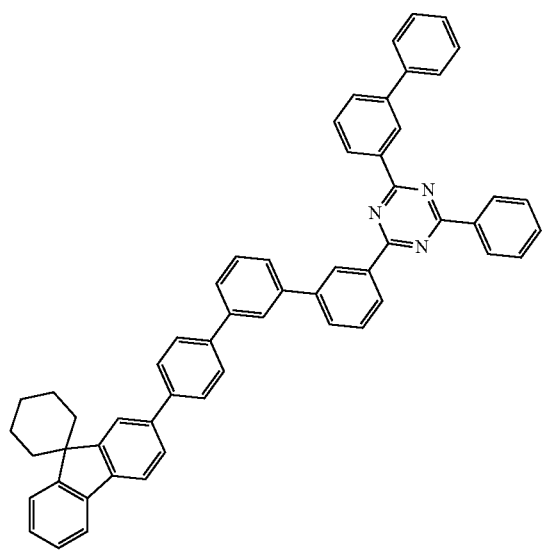
Inv 48
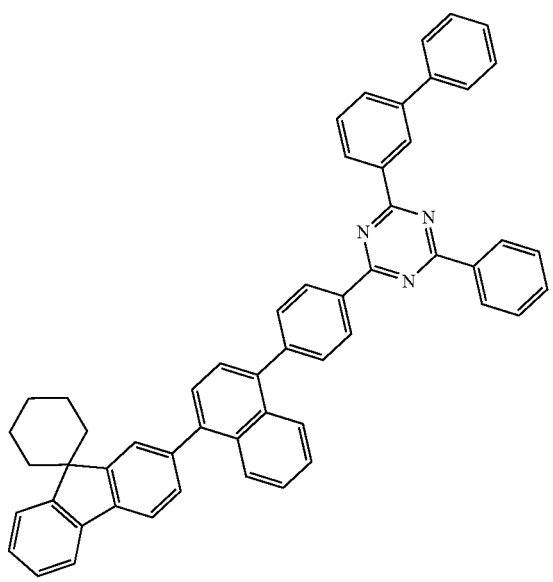

-continued
Inv 49
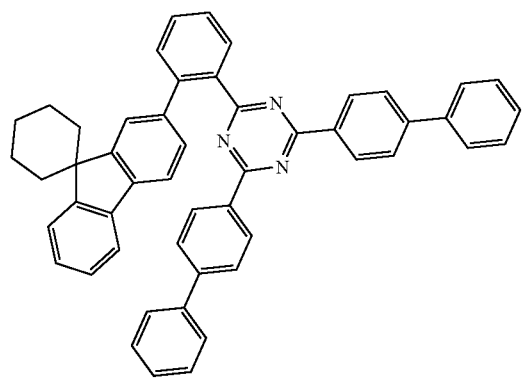
Inv 50
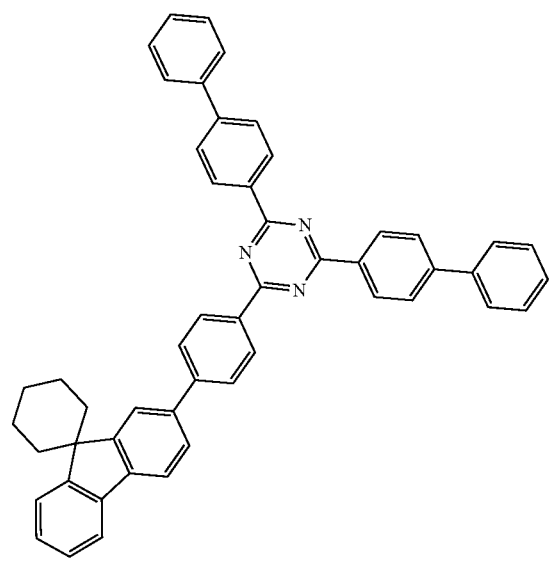
Inv 51
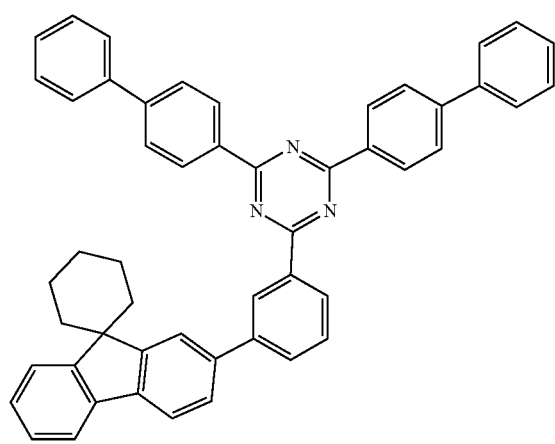
Inv 52
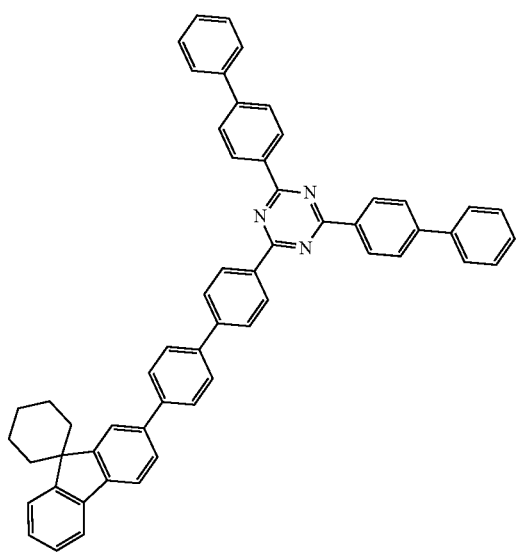

Inv 53
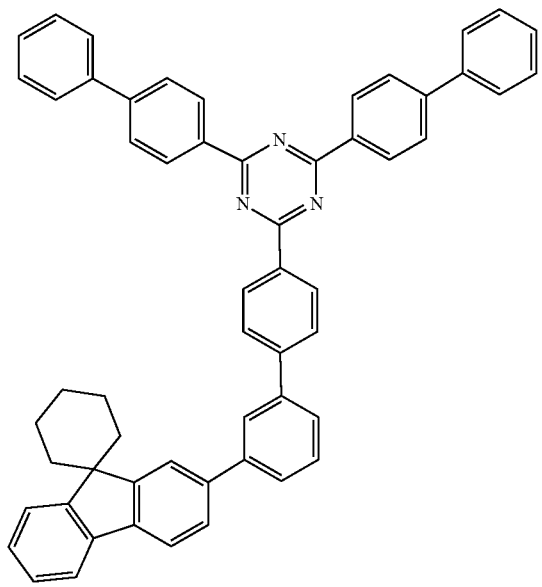
Inv 54
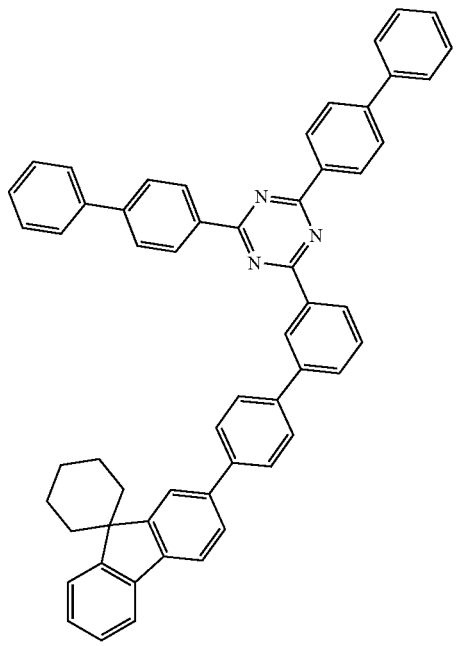
Inv 55
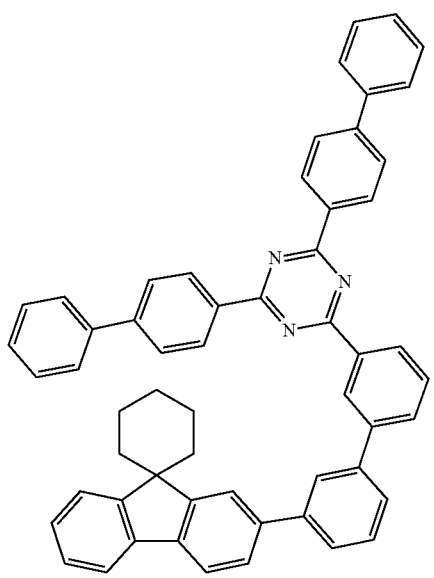
Inv 56
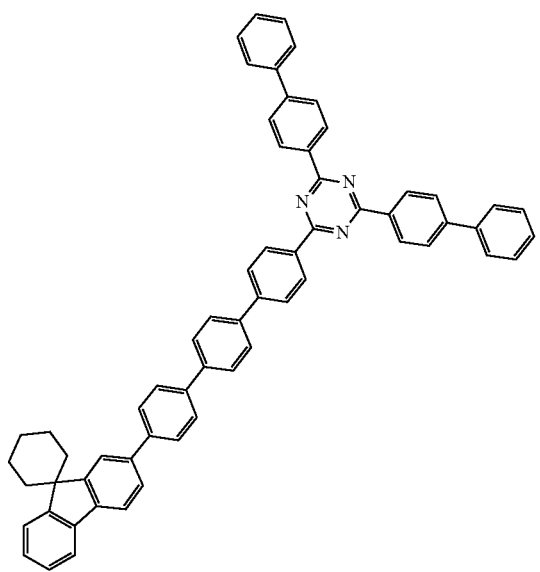

-continued
Inv 57
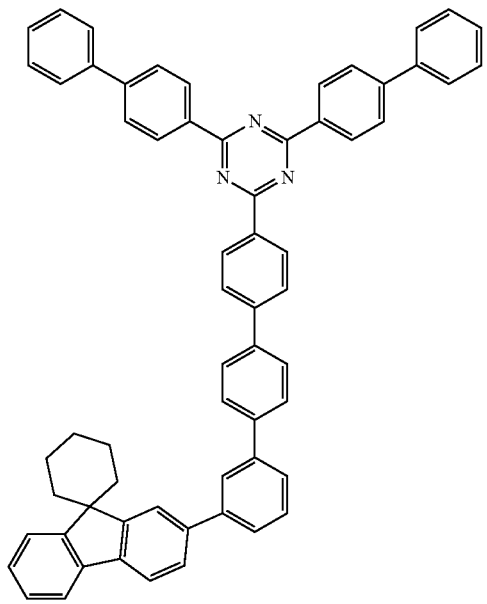
Inv 58
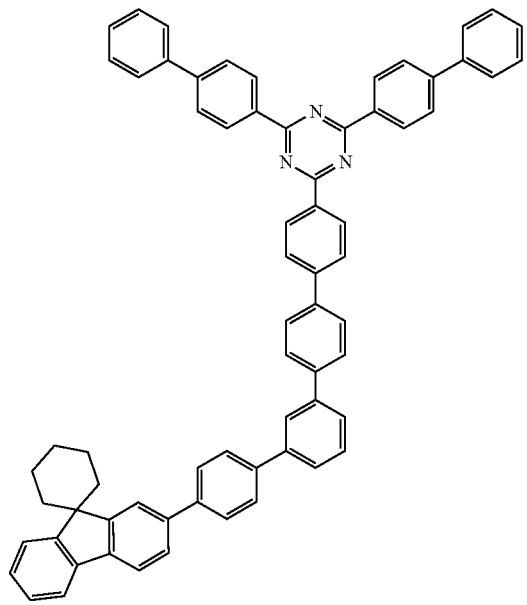
Inv 59
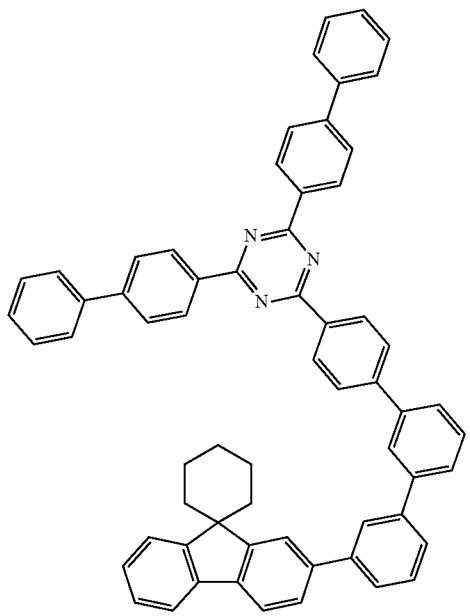
Inv 60
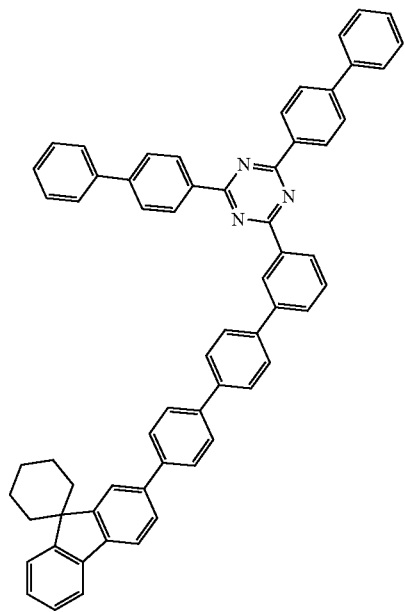

-continued
Inv 61
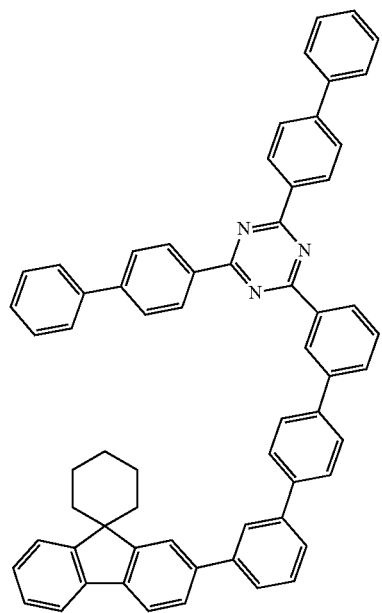
Inv 62
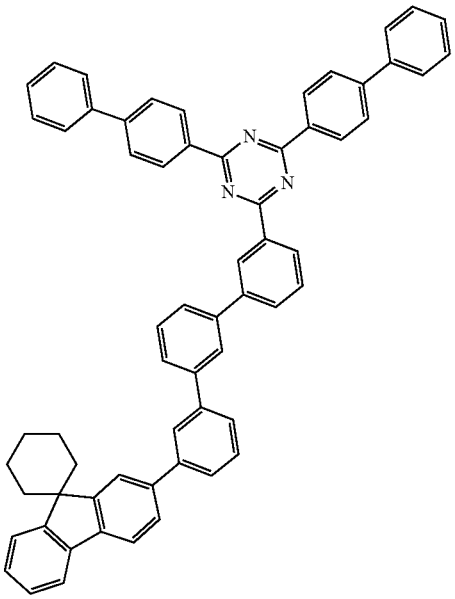
Inv 63
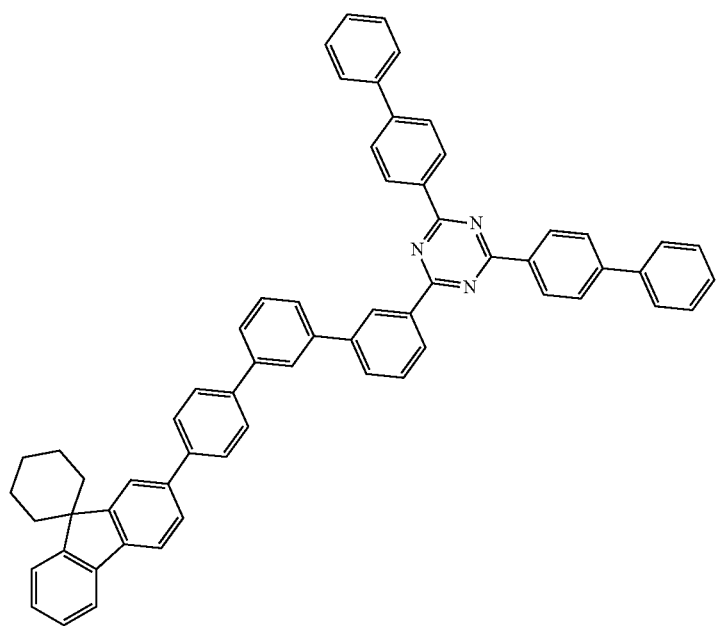

-continued
Inv 64
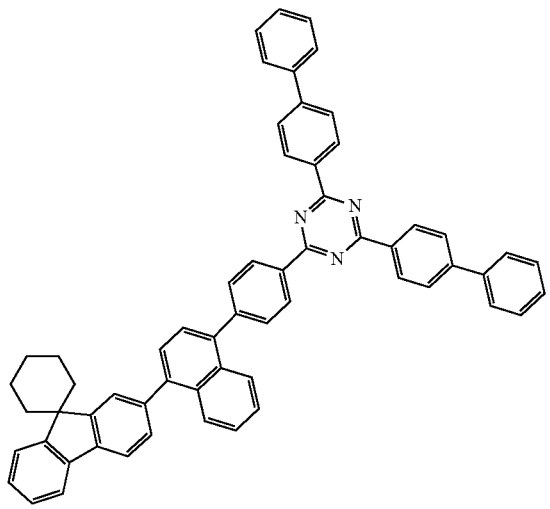
Inv 65
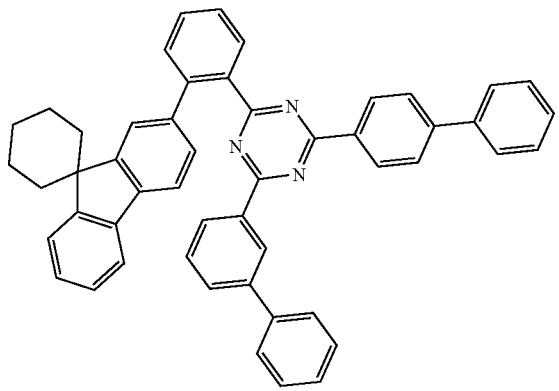
Inv 66
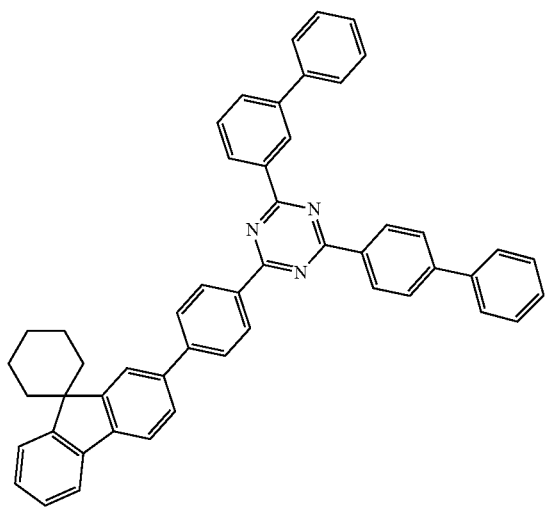
Inv 67
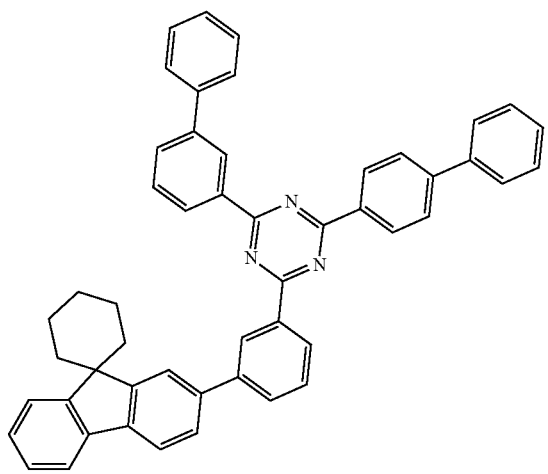
Inv 68
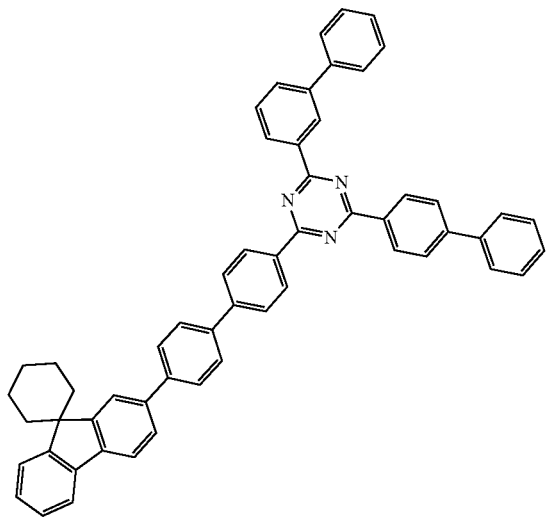
Inv 69
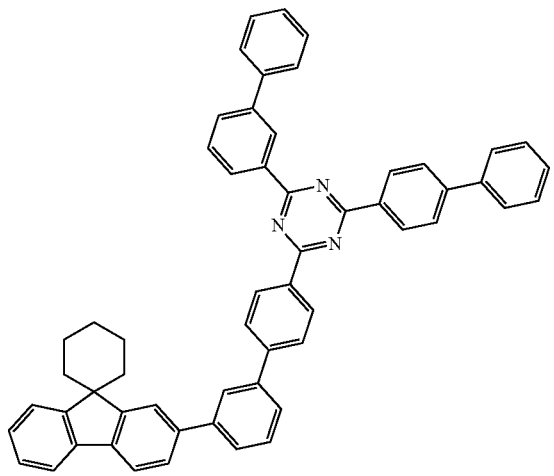

-continued
Inv 70
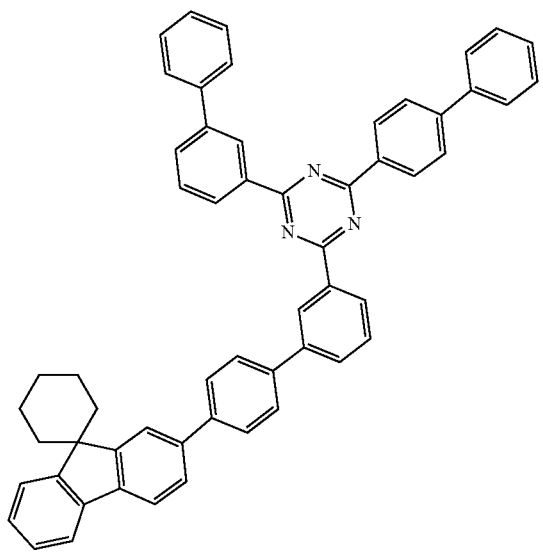
Inv 71
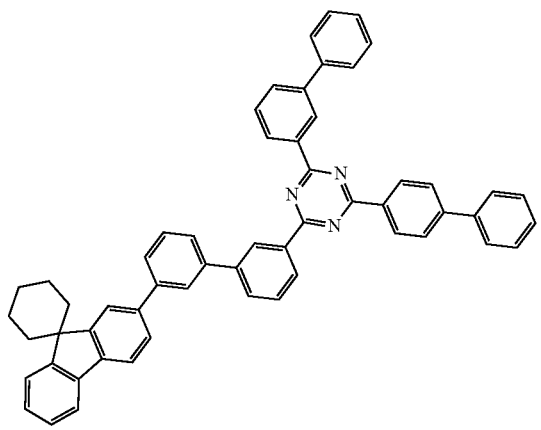
Inv 72
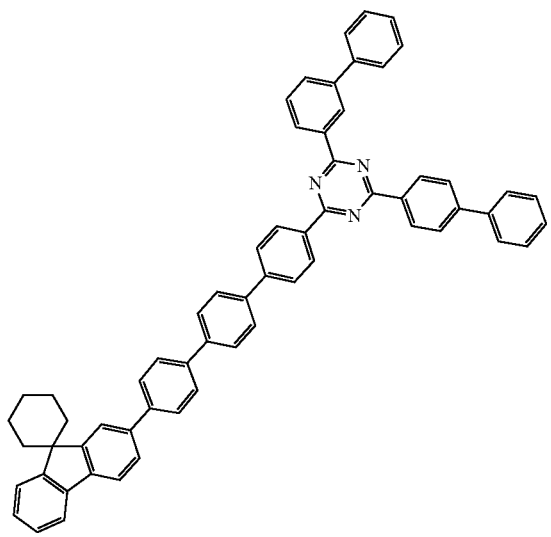
Inv 73
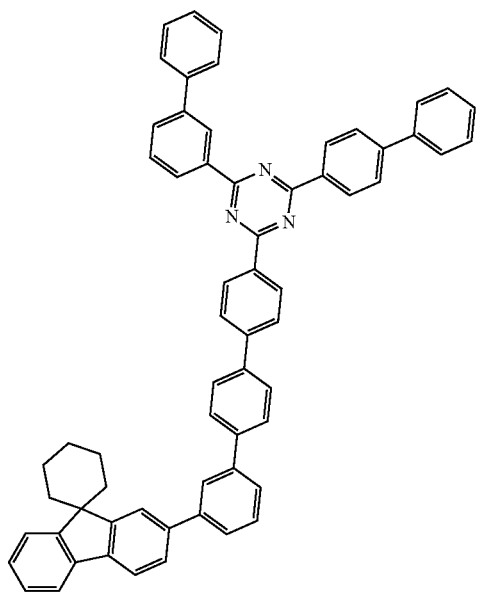

-continued
Inv 74
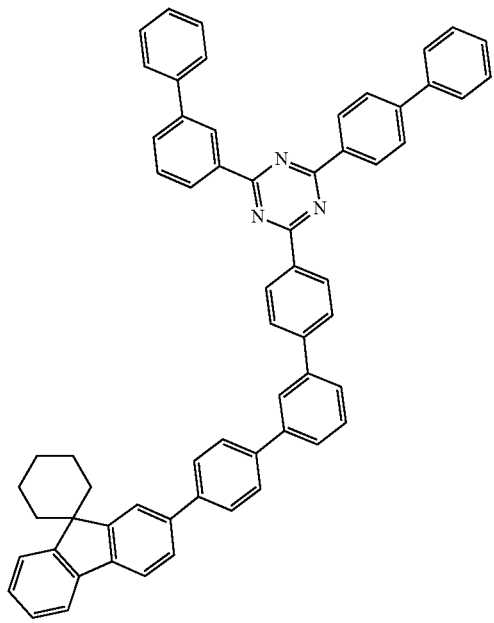
Inv 75
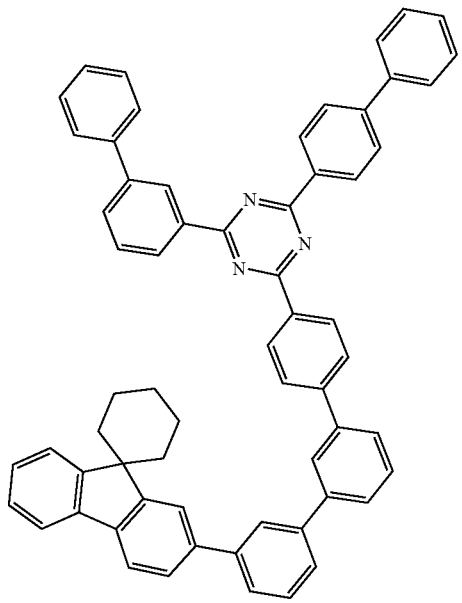
Inv 76
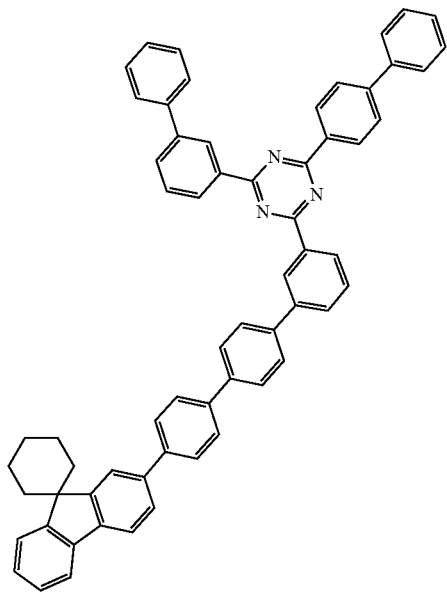
Inv 77
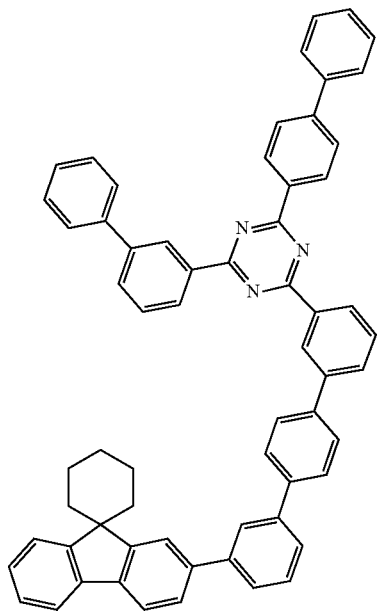

Inv 78
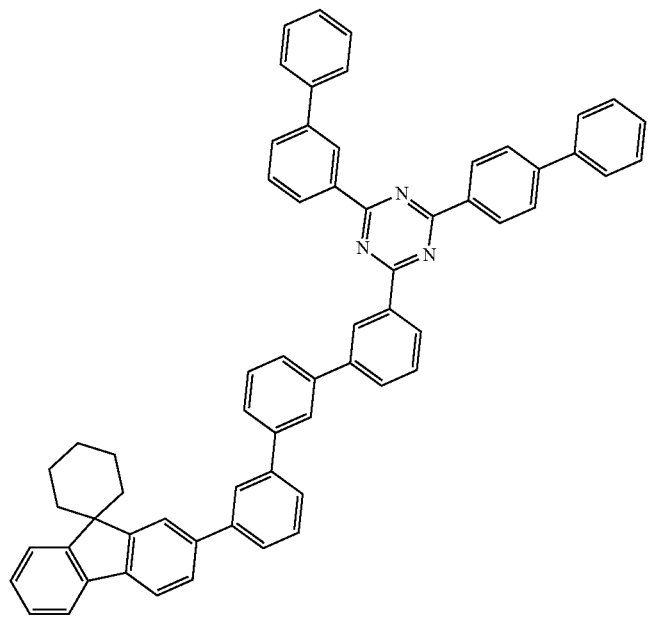
Inv 79
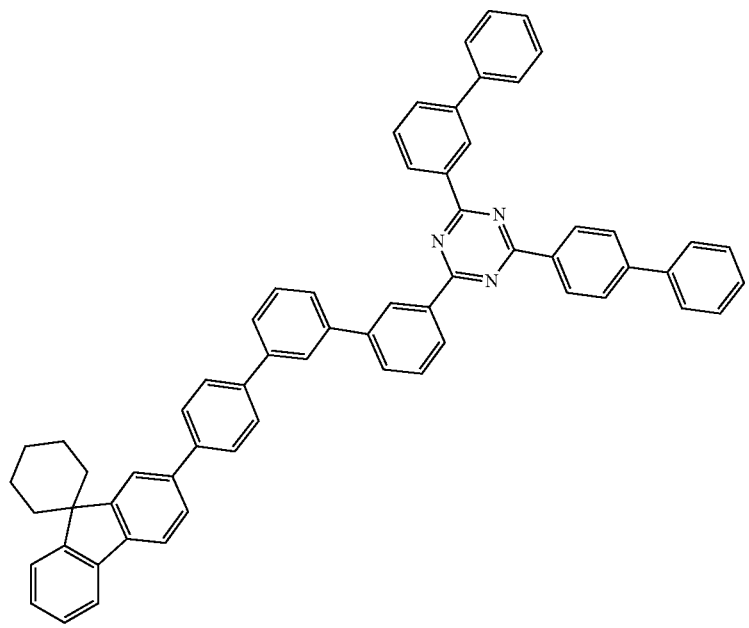

-continued
Inv 80
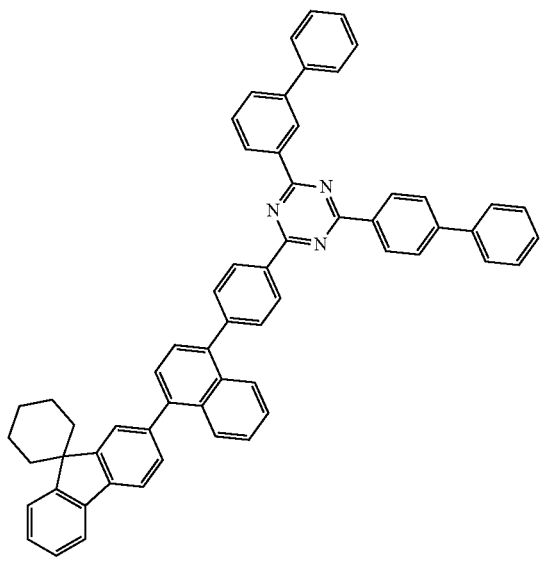
Inv 81
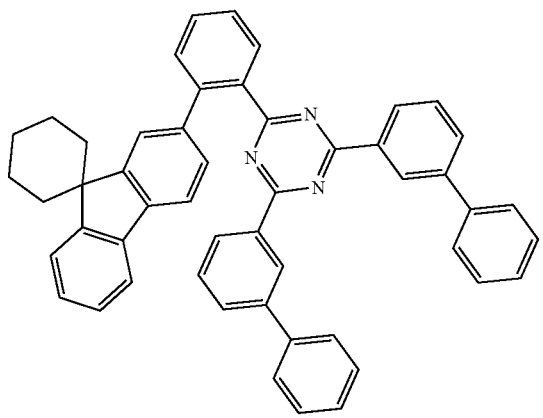
Inv 82
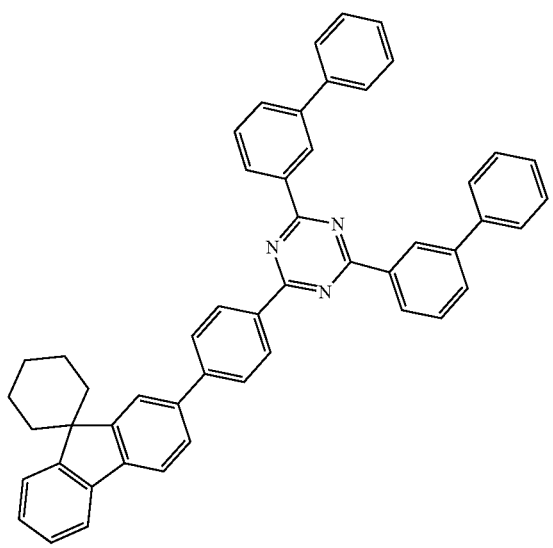
Inv 83
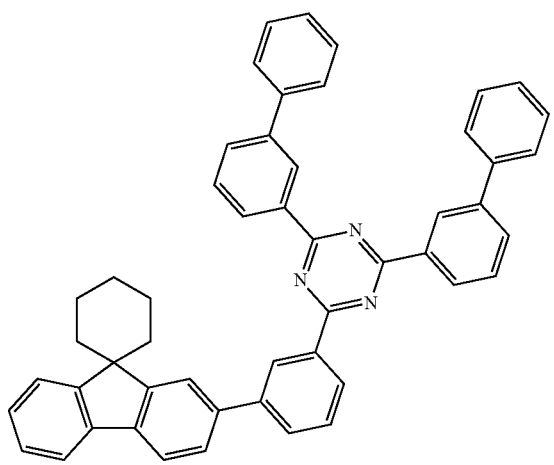

Inv 84
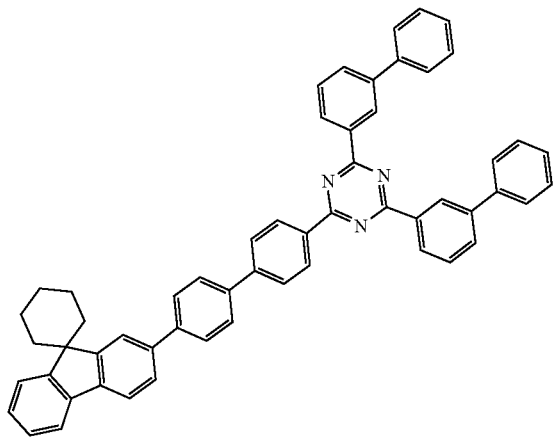
Inv 85
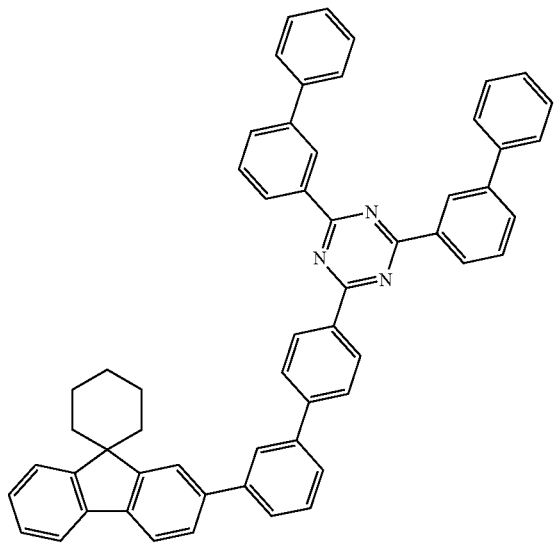
Inv 86
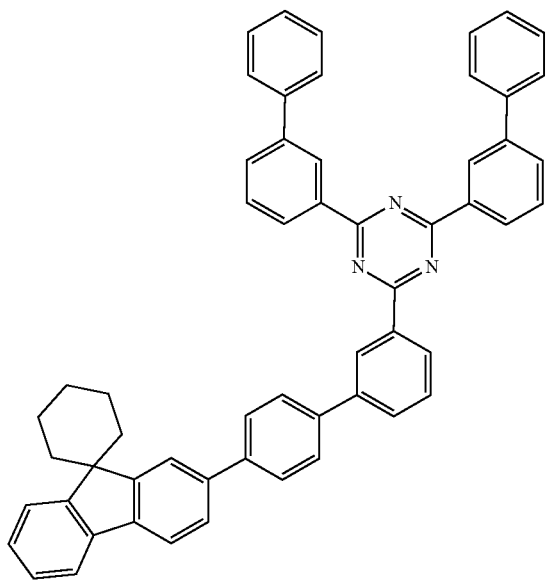
Inv 87
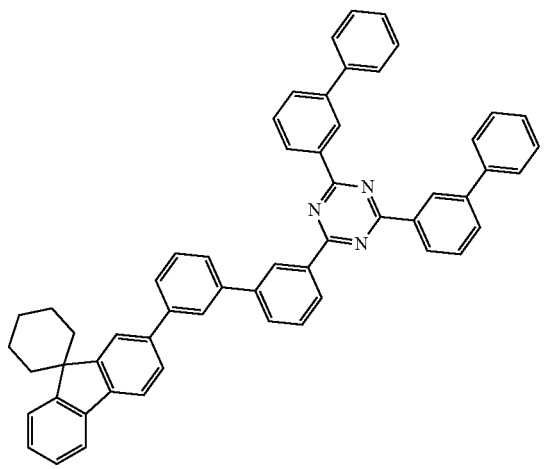

Inv 88
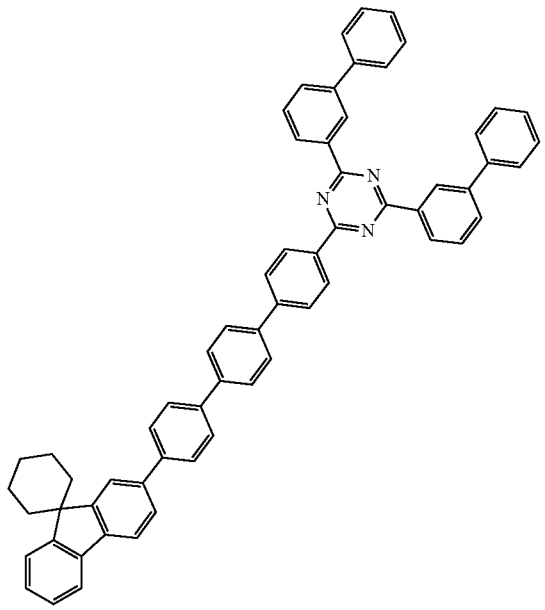
Inv 89
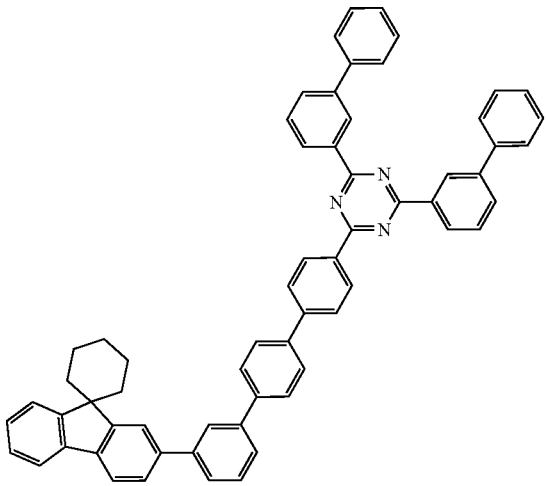
Inv 90
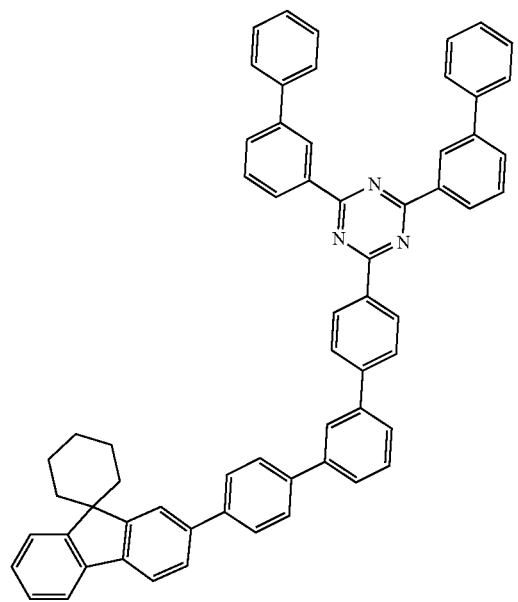
Inv 91

-continued
Inv 92
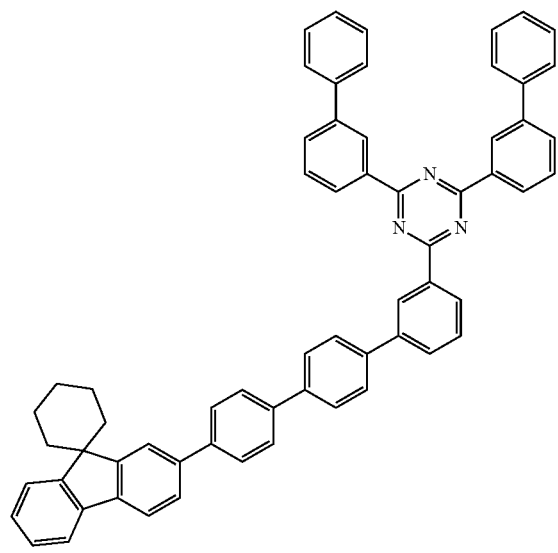
Inv 93
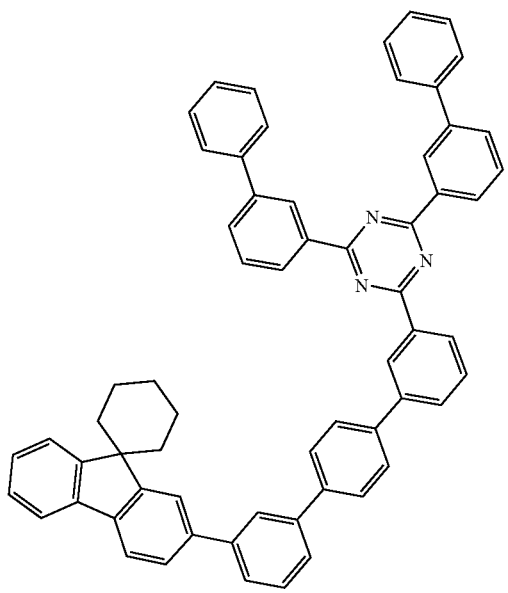
Inv 94
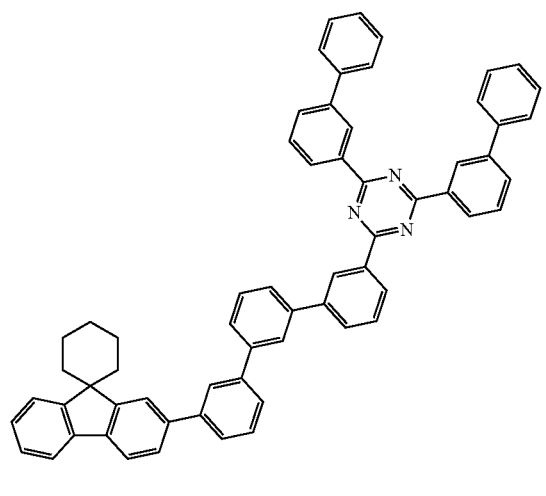
Inv 95
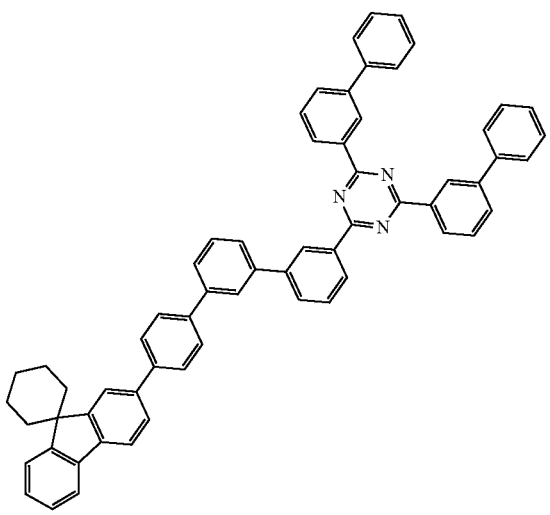
Inv 96
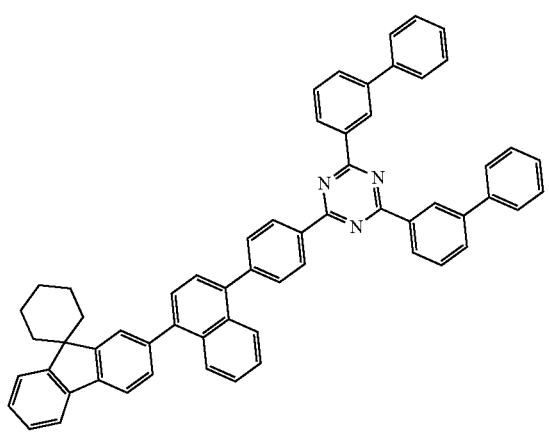
Inv 97
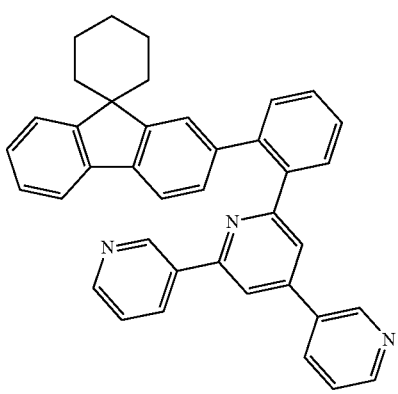

-continued
Inv 98
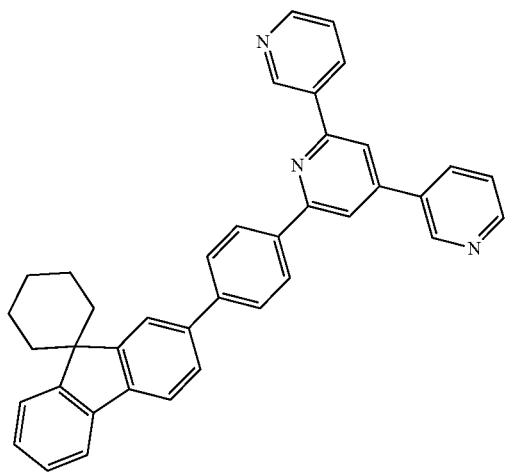
Inv 99
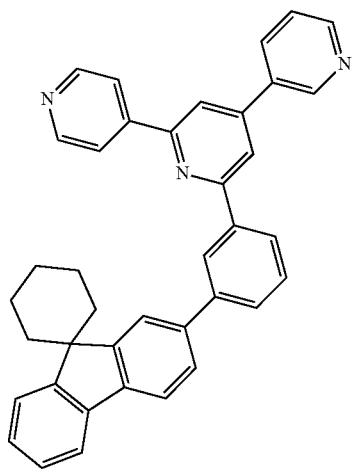
Inv 100
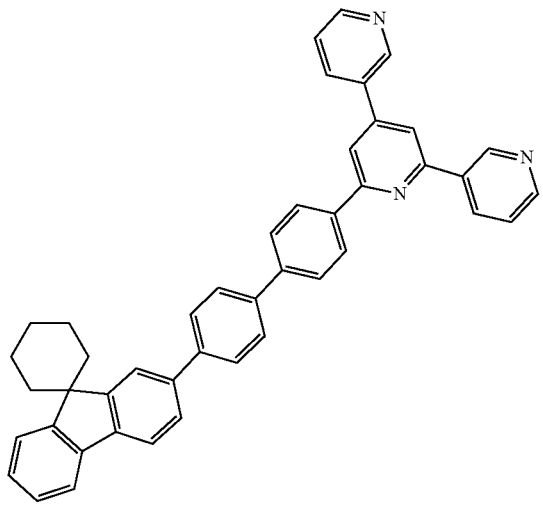
Inv 101
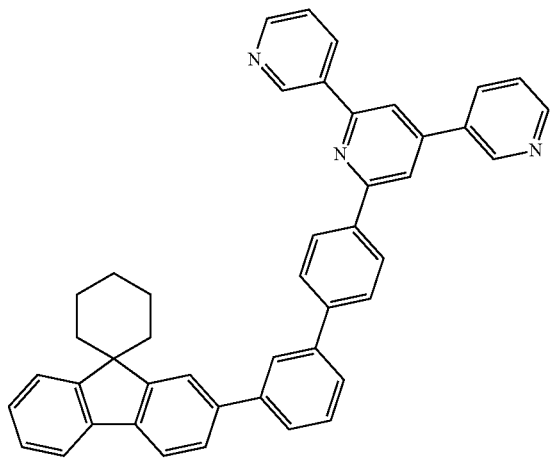
Inv 102
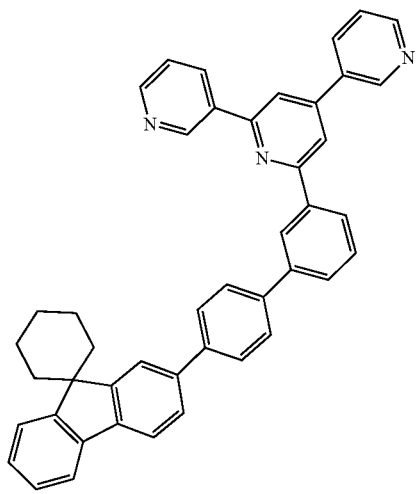
Inv 103
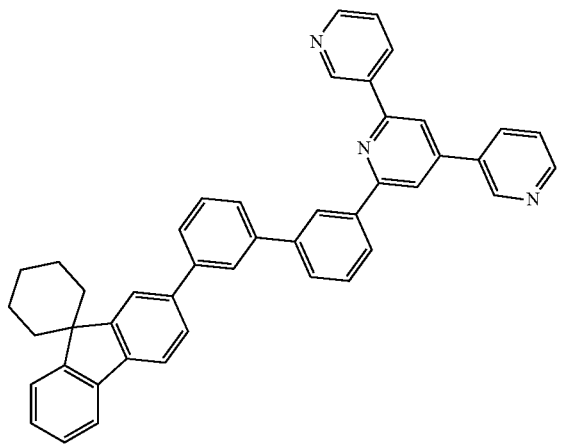

-continued
Inv 104
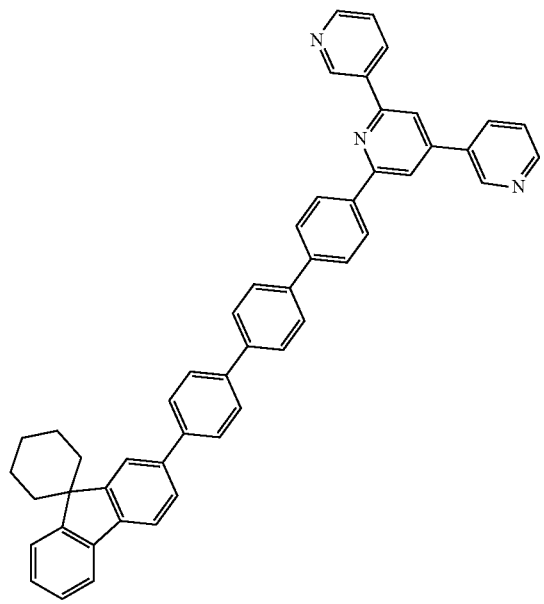
Inv 105
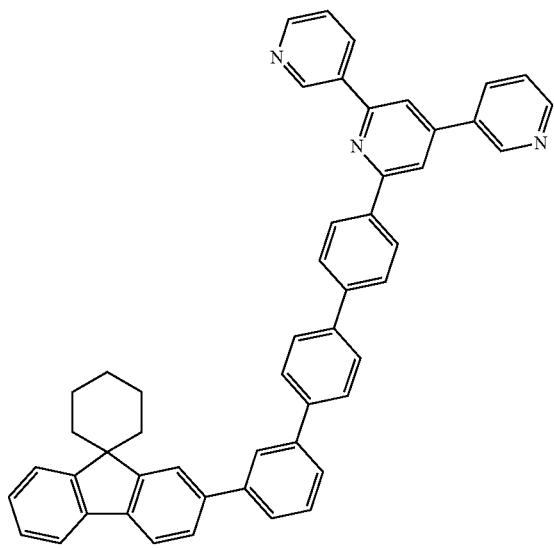
Inv 106
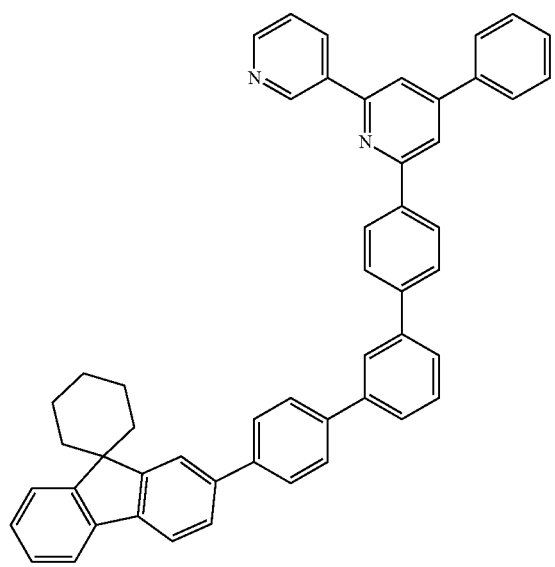
Inv 107
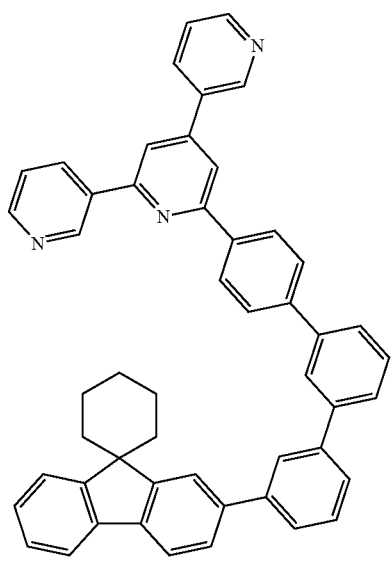

-continued
Inv 108
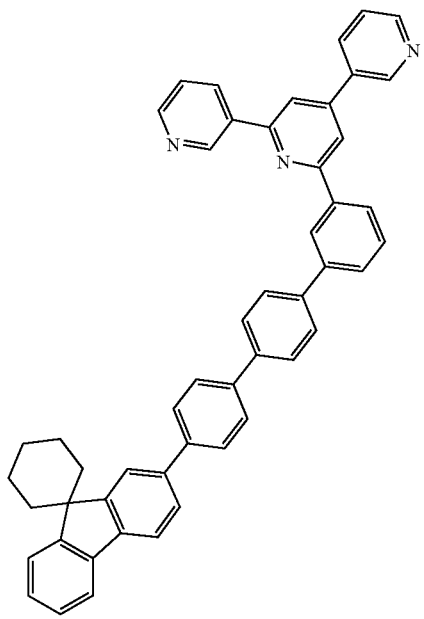
Inv 109
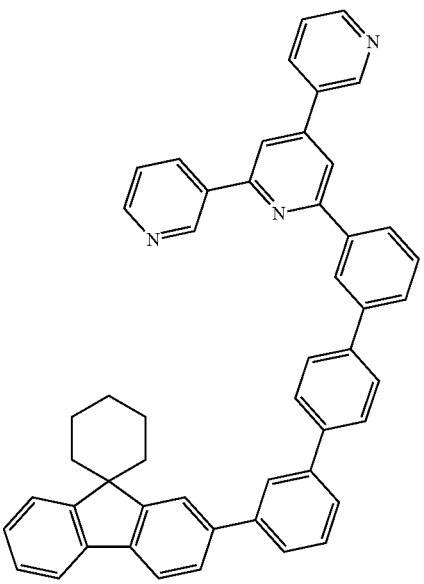
Inv 110
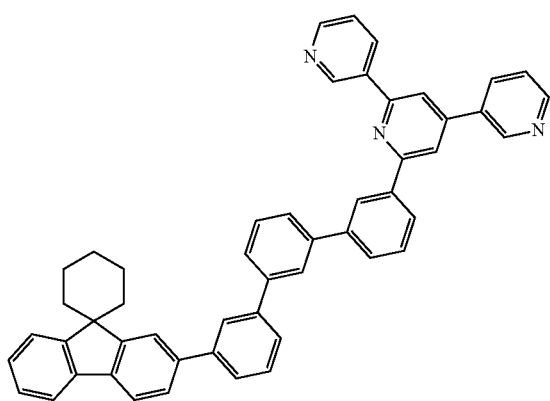
Inv 111
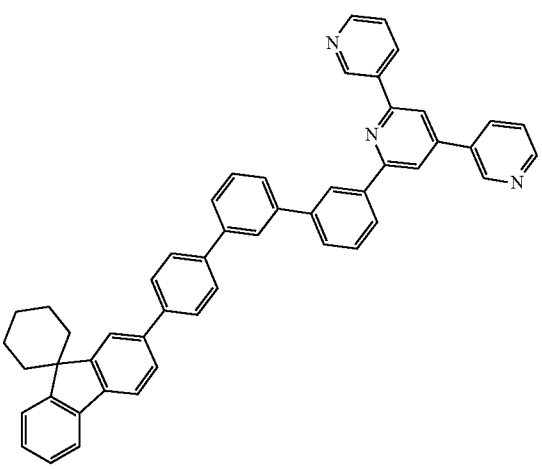
Inv 112
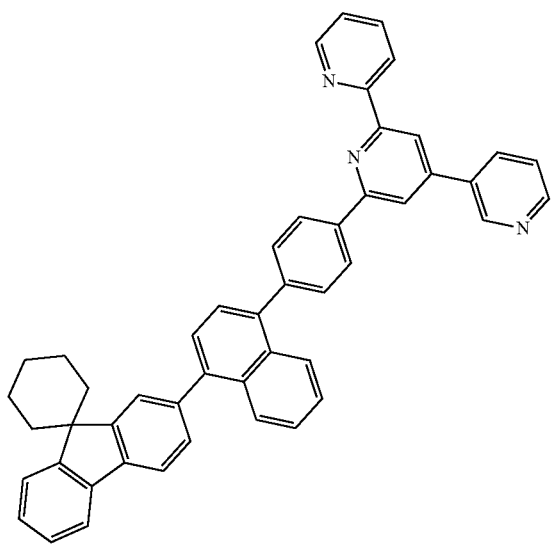
Inv 113
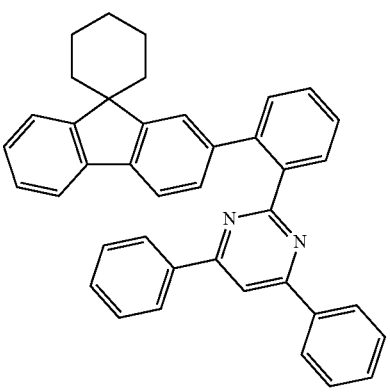

-continued
Inv 114
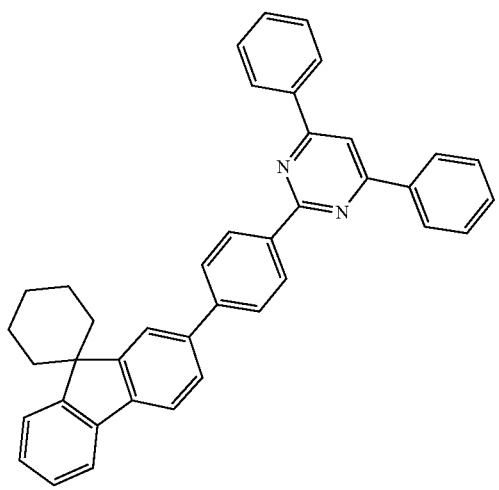
Inv 115
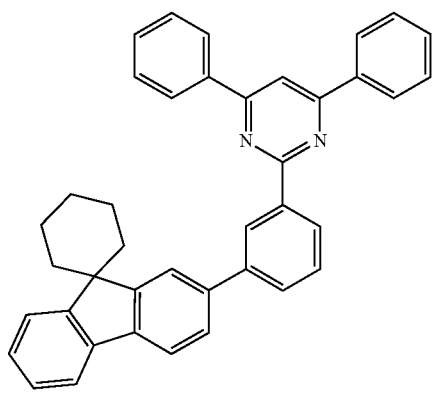
Inv 116
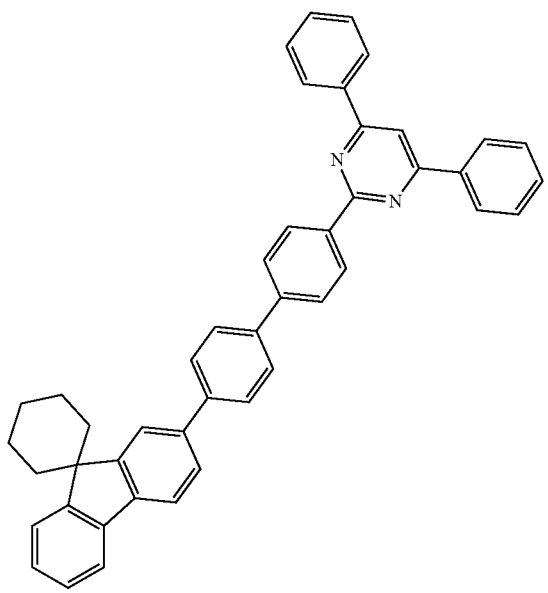
Inv 117
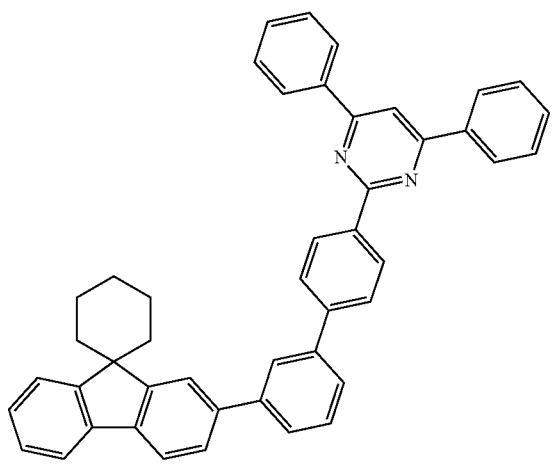
Inv 118
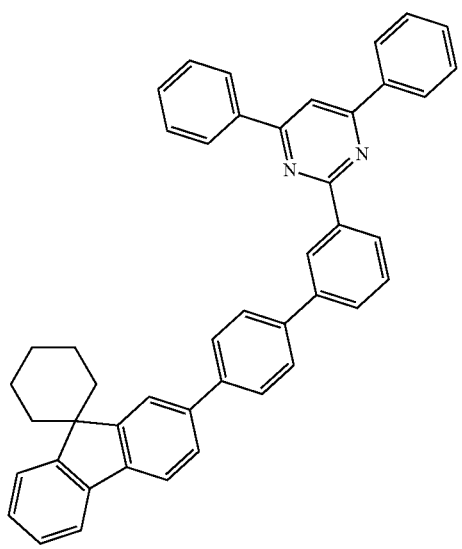
Inv 119
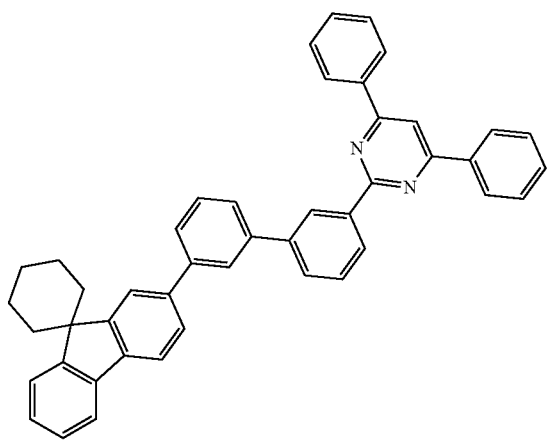

-continued
Inv 120
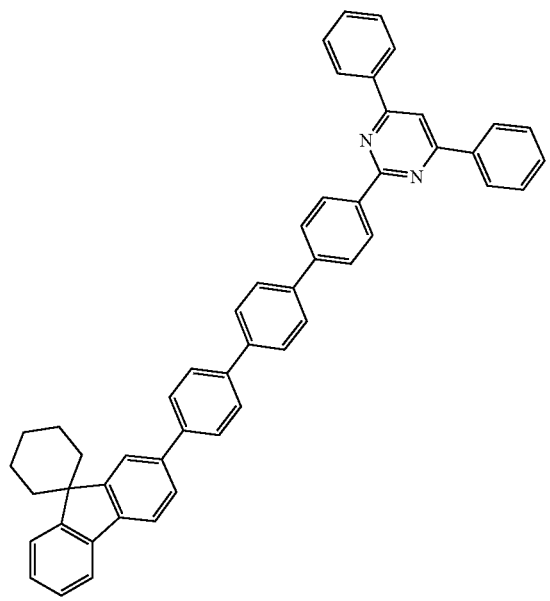
Inv 121
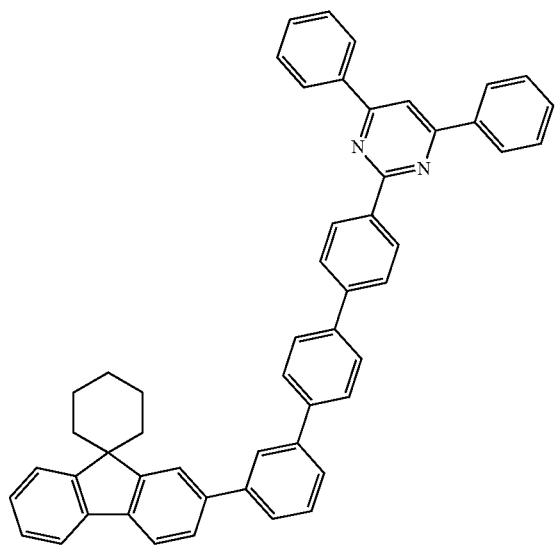
Inv 122
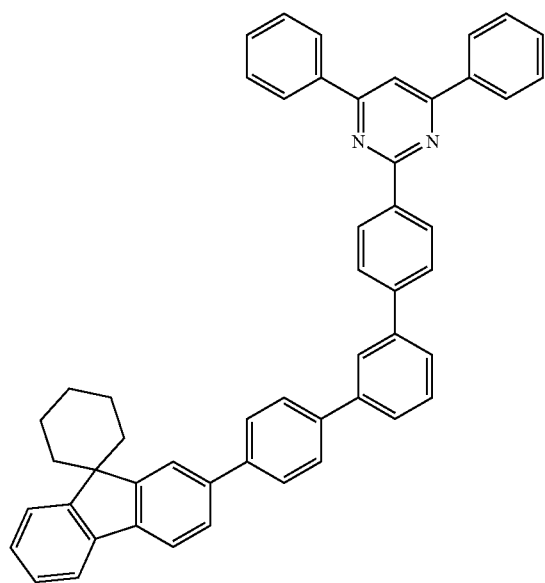
Inv 123
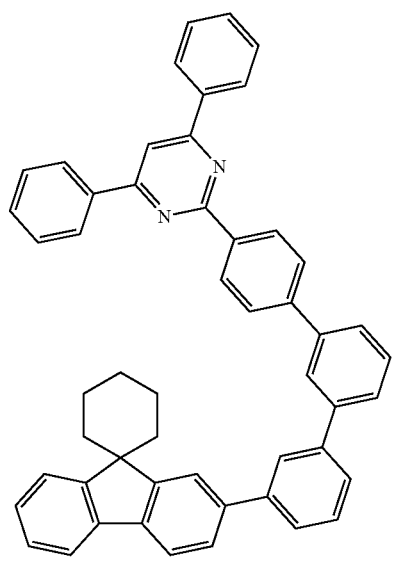

-continued
Inv 124
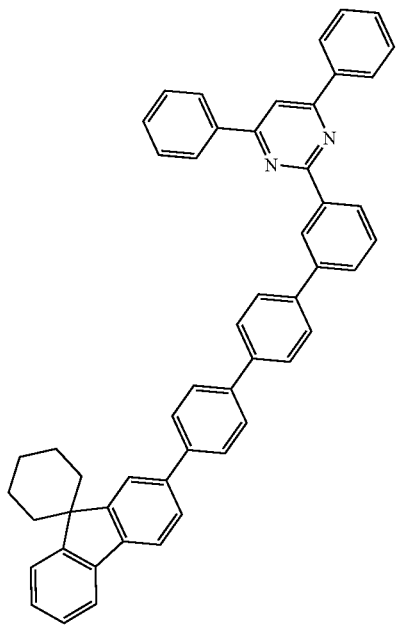
Inv 125
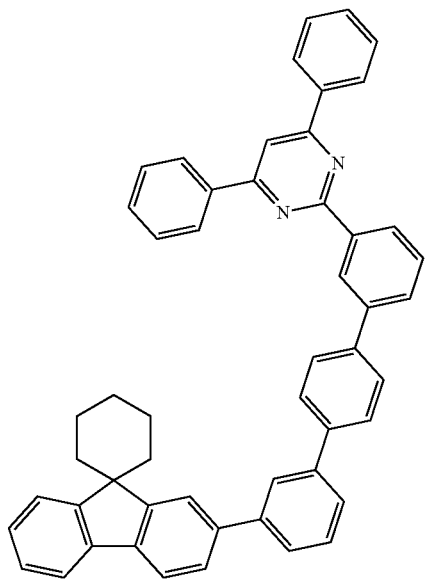
Inv 126
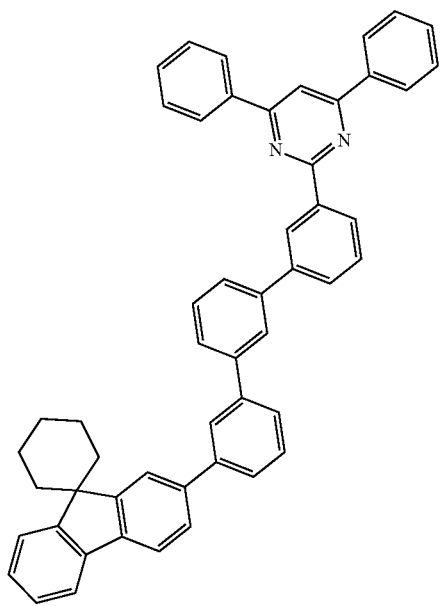
Inv 127
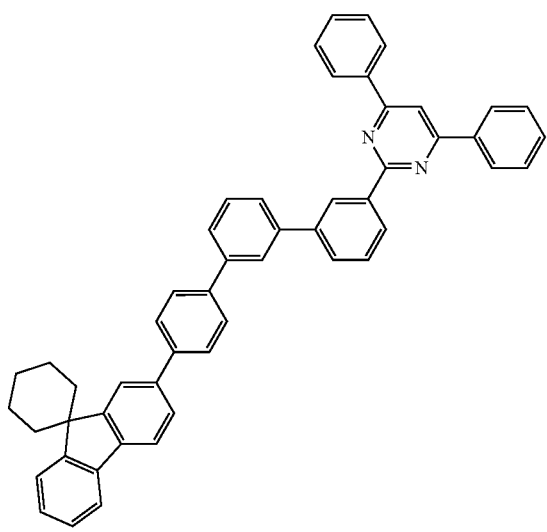

-continued
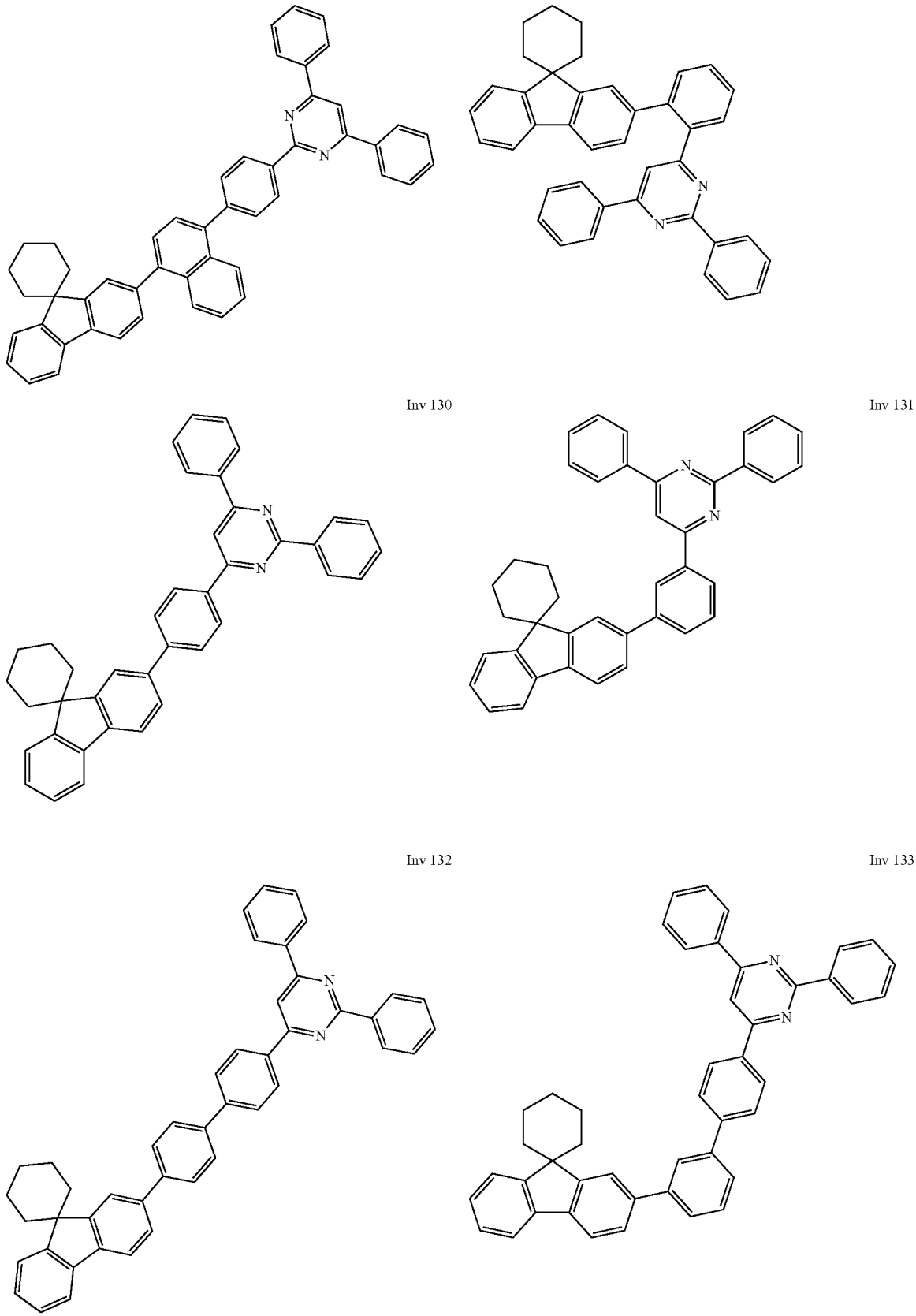

Inv 134
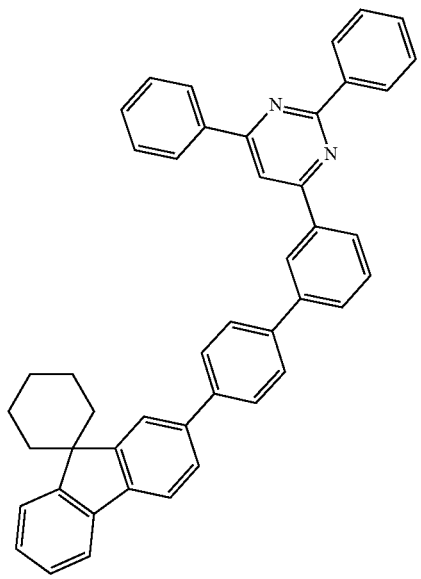
Inv 135
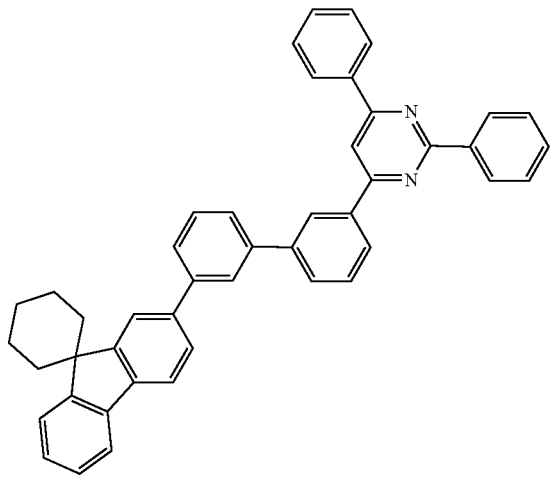
Inv 136
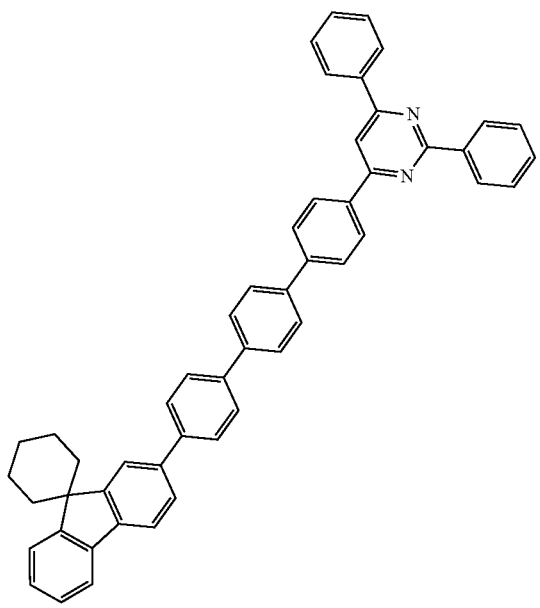
Inv 137
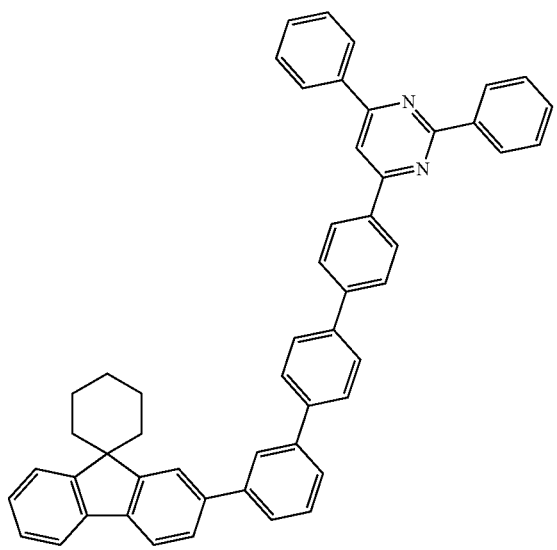

-continued
Inv 138
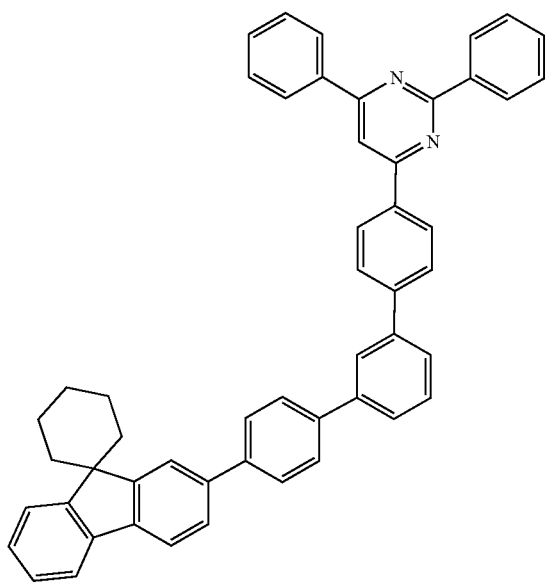
Inv 139
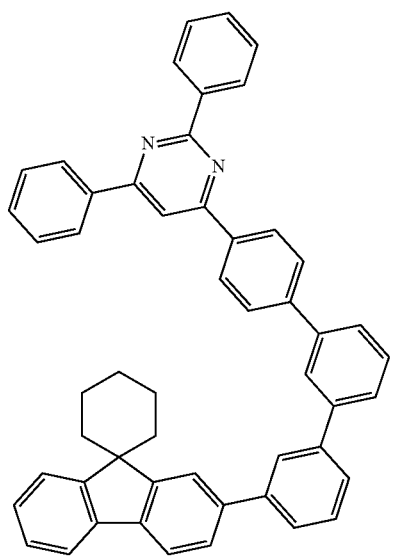
Inv 140
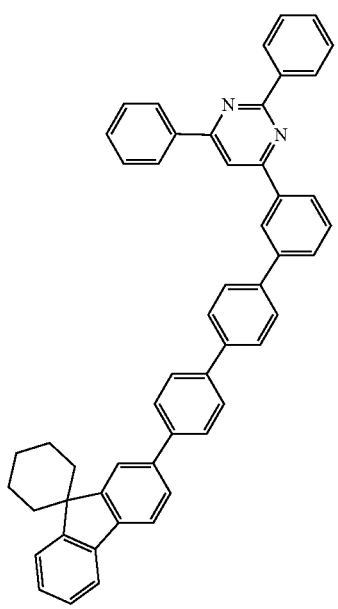
Inv 141
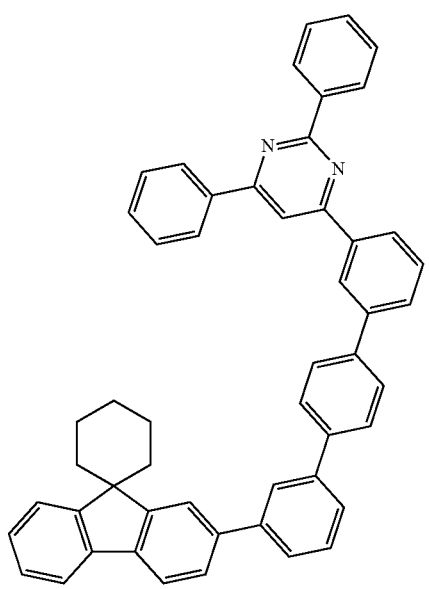

-continued
Inv 142
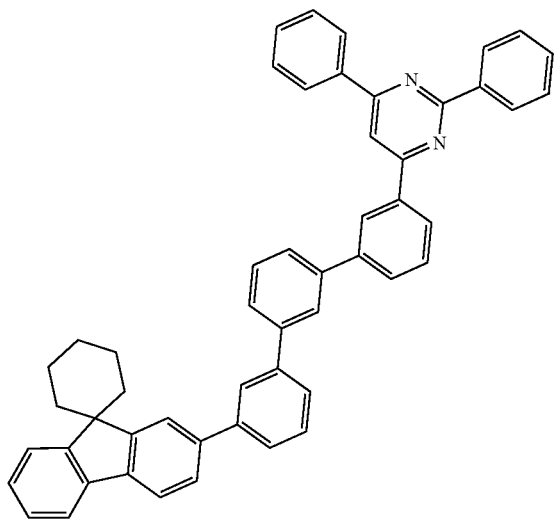
Inv 143
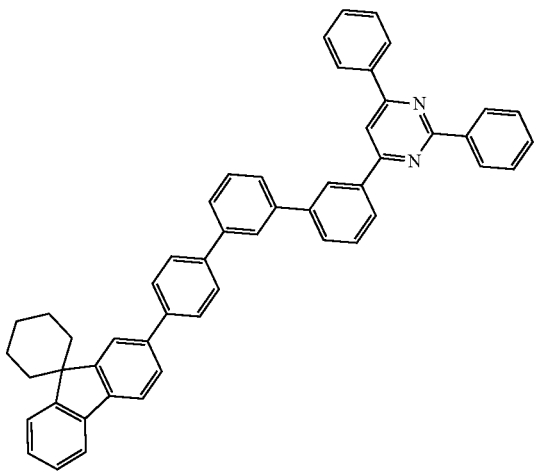
Inv 144
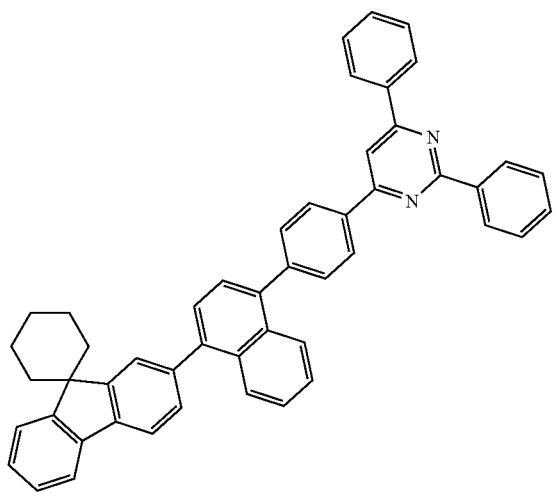
Inv 145
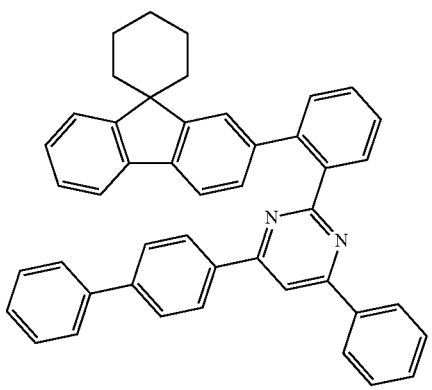
Inv 146
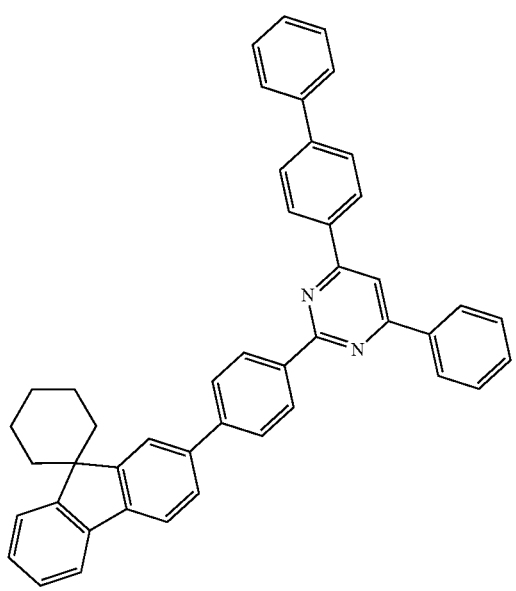
Inv 147
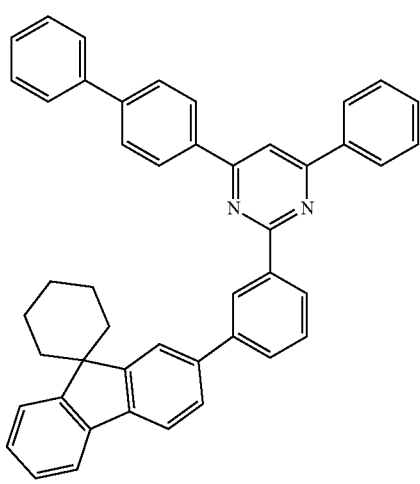

-continued
Inv 148
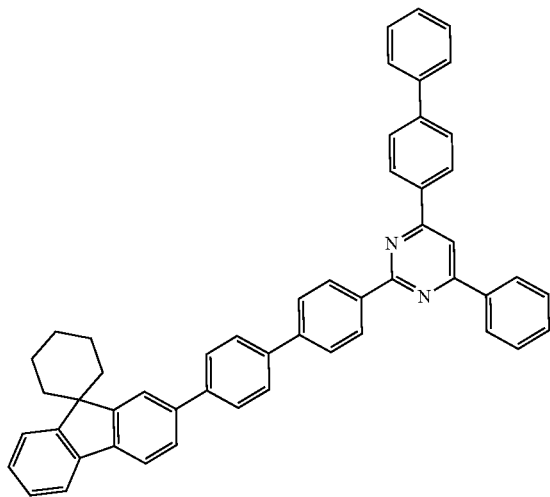
Inv 149
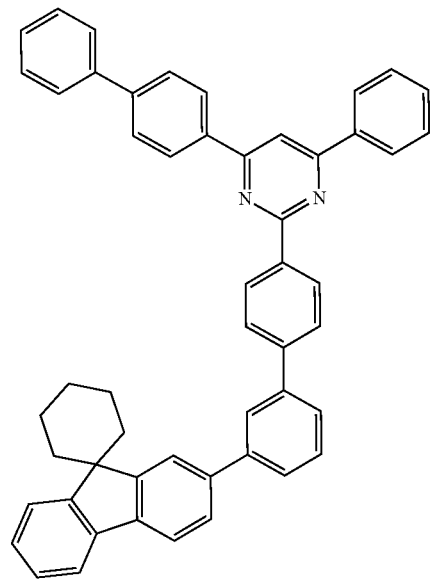
Inv 150
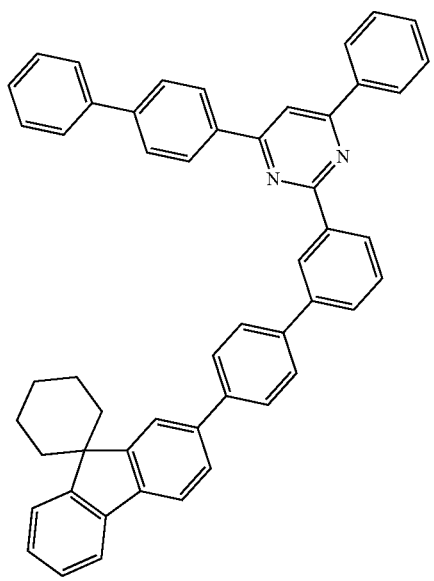
Inv 151
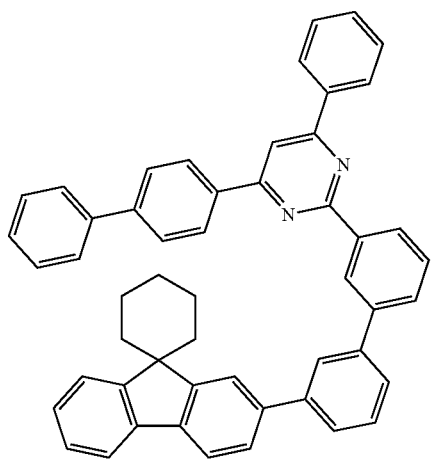

-continued
Inv 152
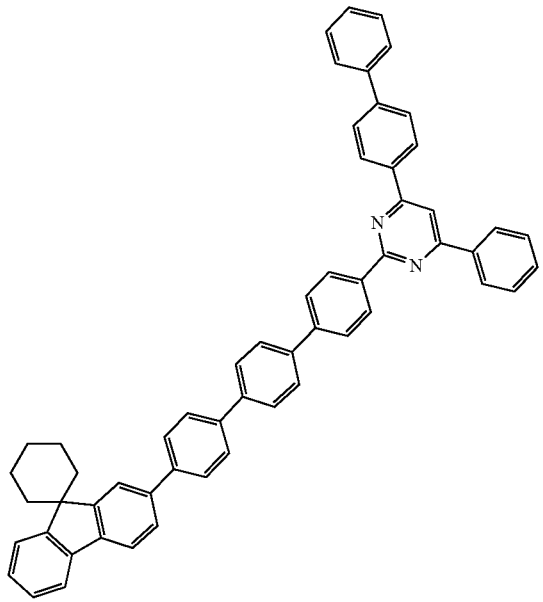
Inv 153
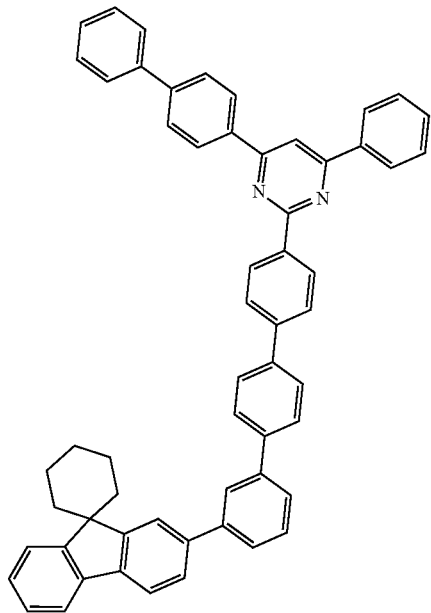
Inv 154
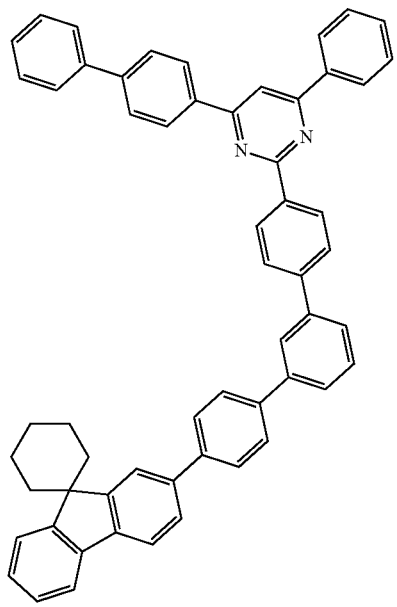
Inv 155
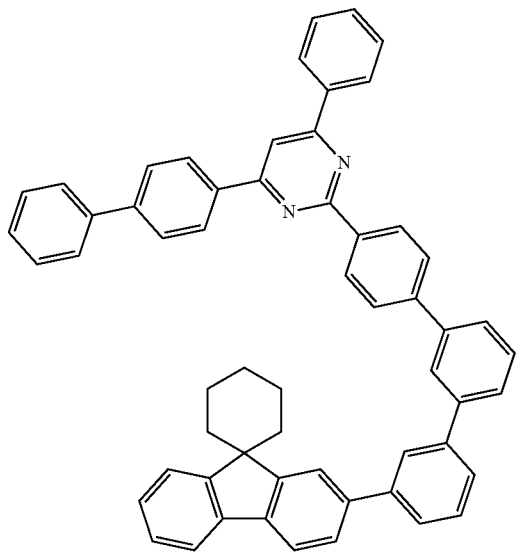

Inv 156
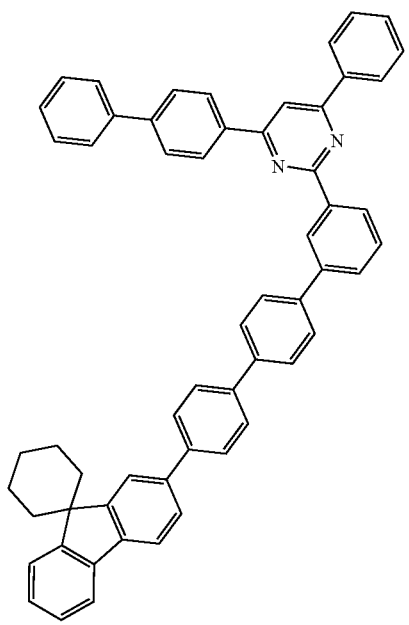
Inv 157
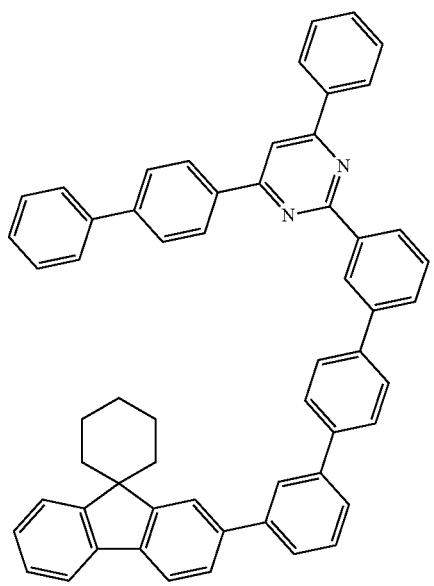
Inv 158
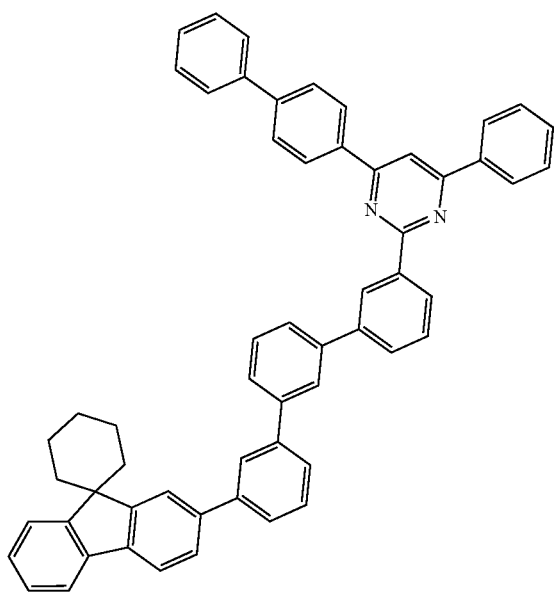
Inv 159
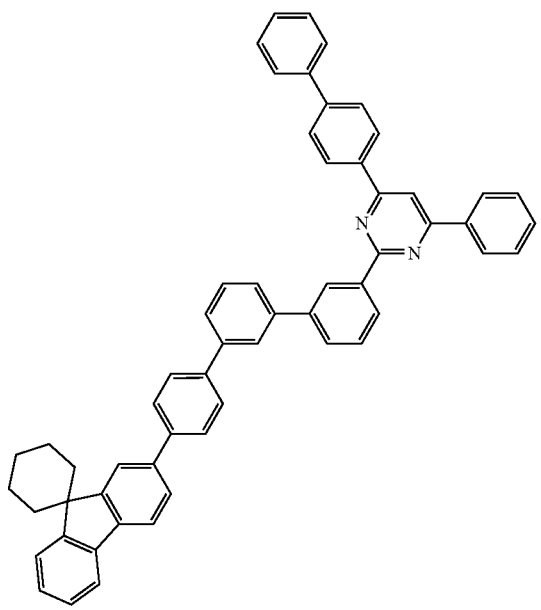

-continued
Inv 160
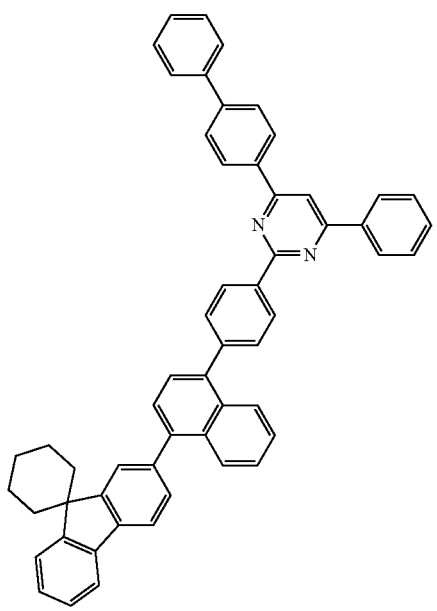
Inv 161
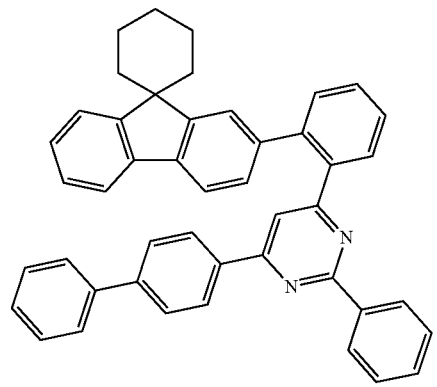
Inv 162
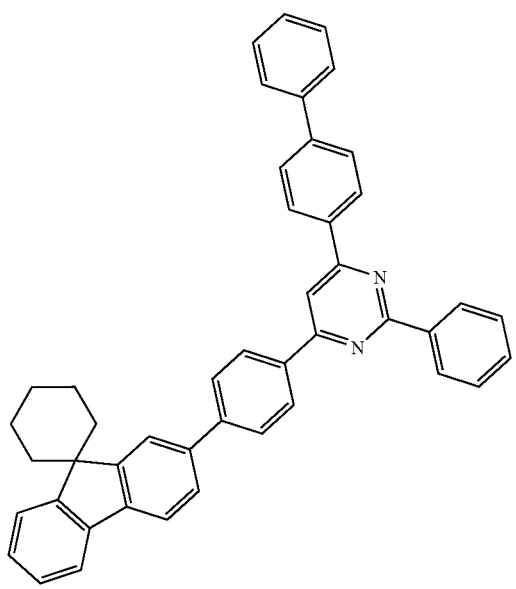
Inv 163
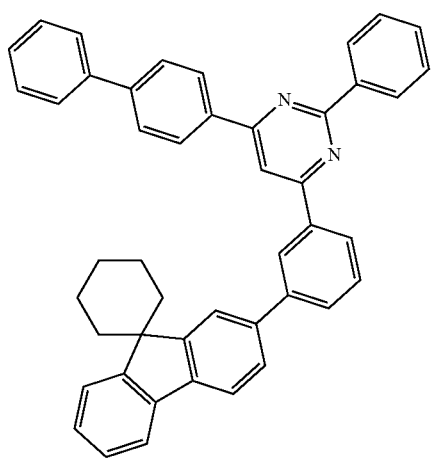

-continued
Inv 164
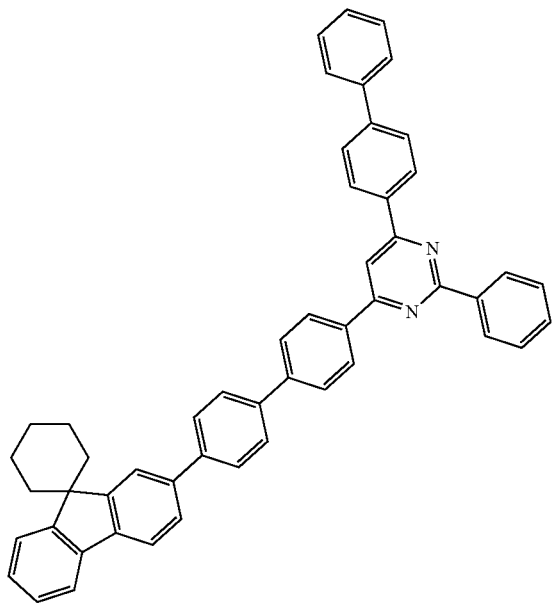
Inv 165
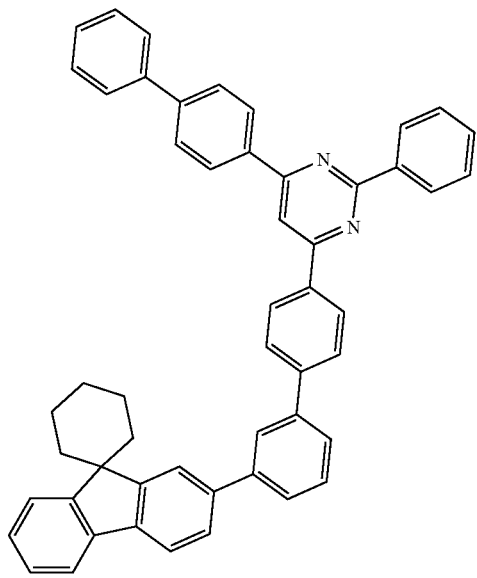
Inv 166
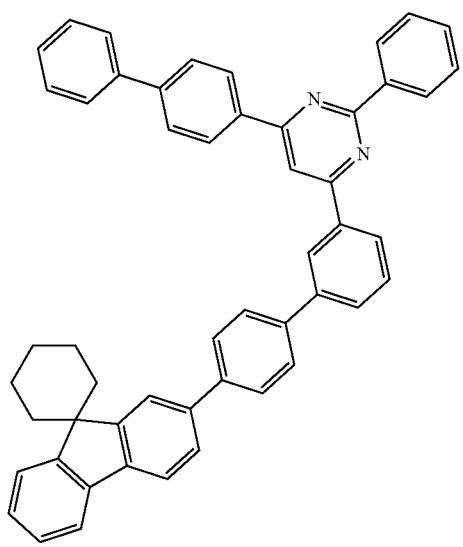
Inv 167
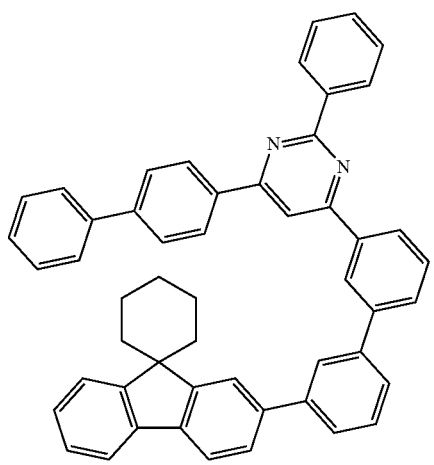

-continued
Inv 168
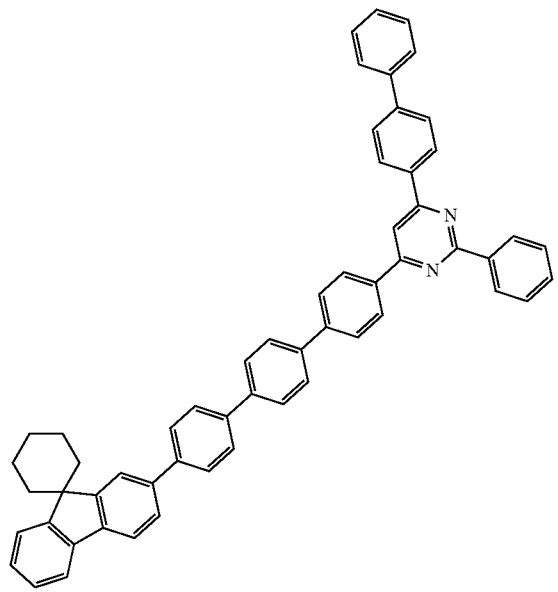
Inv 169
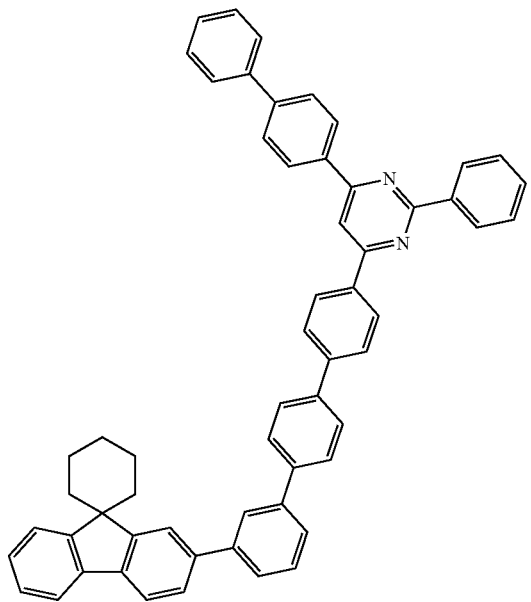
Inv 170
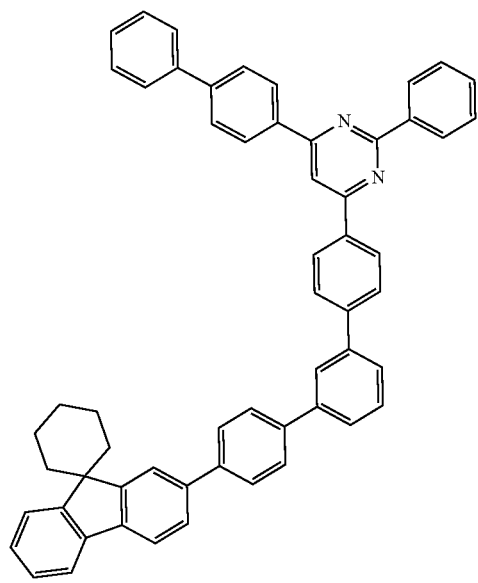
Inv 171
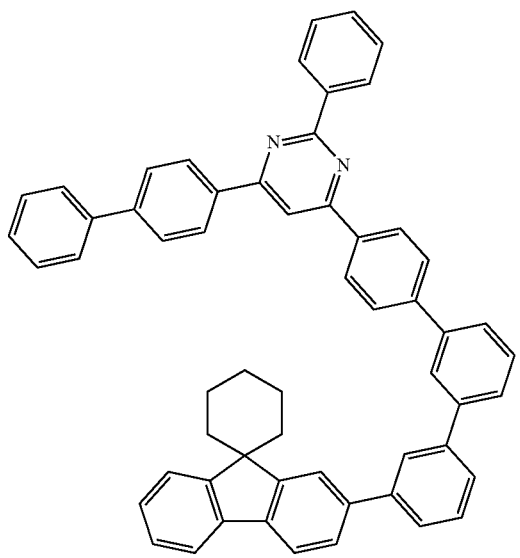

-continued
Inv 172
Inv 173
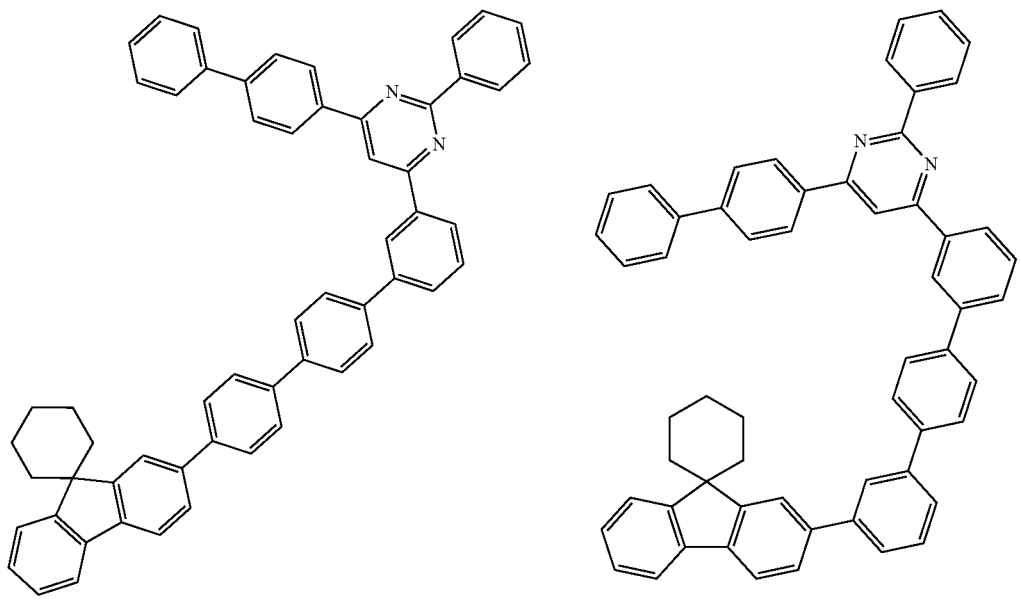
Inv 174
Inv 175
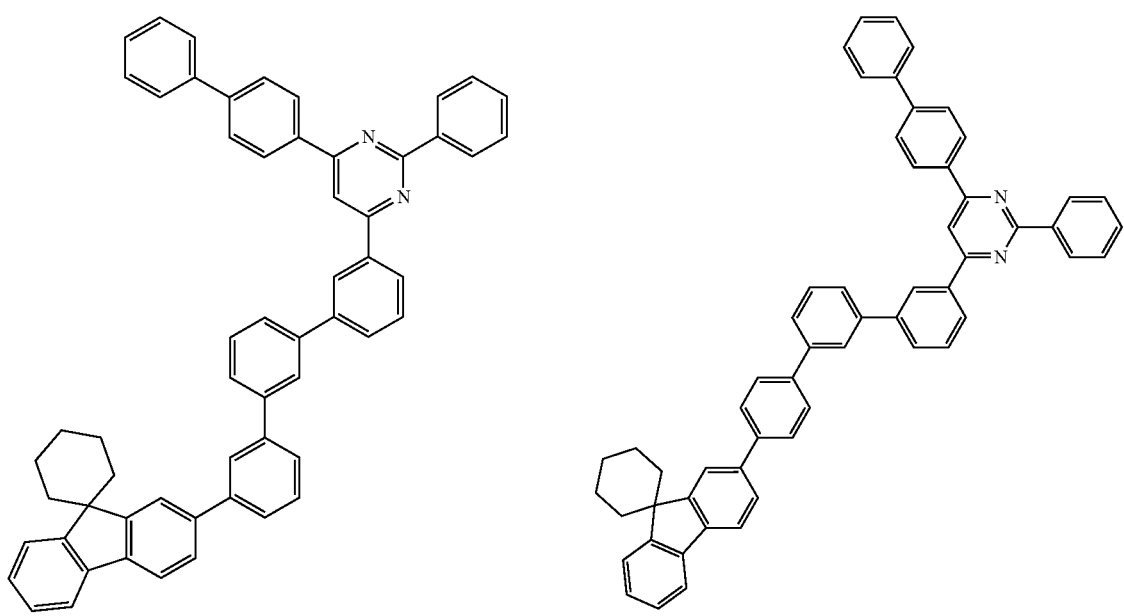

Inv 176
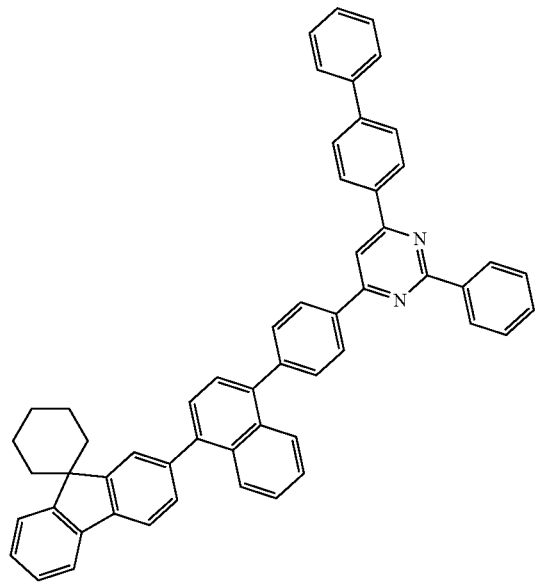
Inv 177
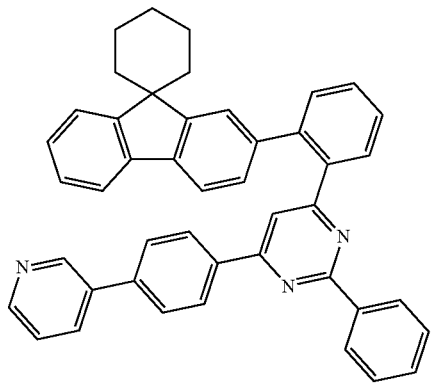
Inv 178
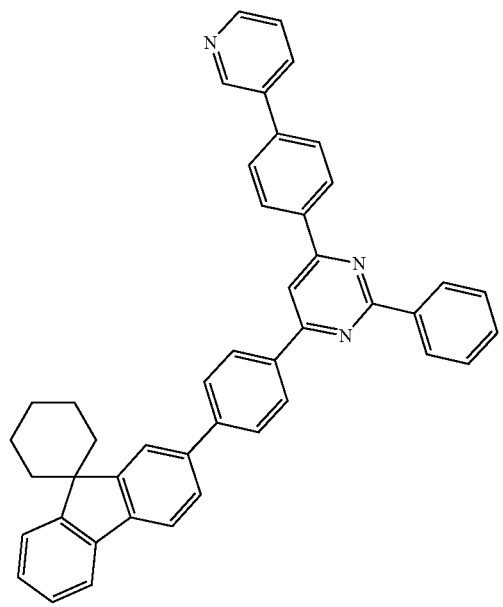
Inv 179
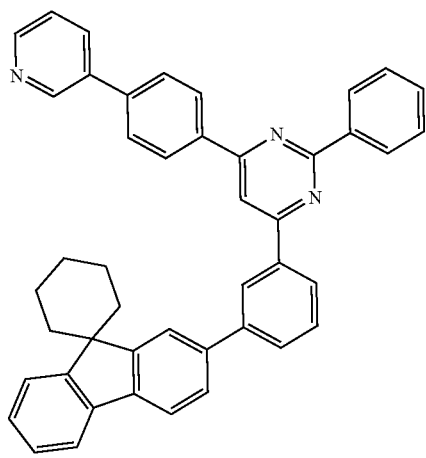

-continued
Inv 180
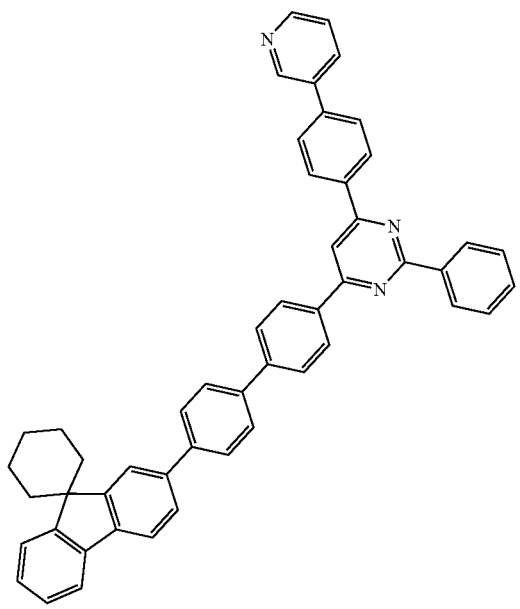
Inv 181
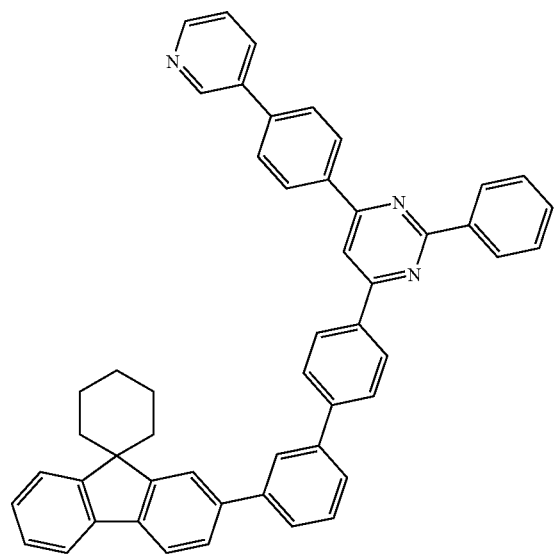
Inv 182
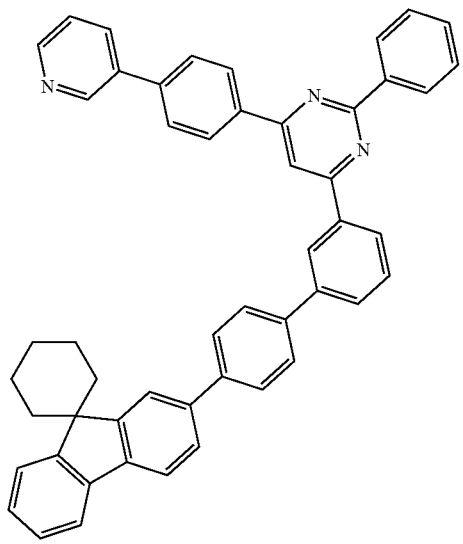
Inv 183
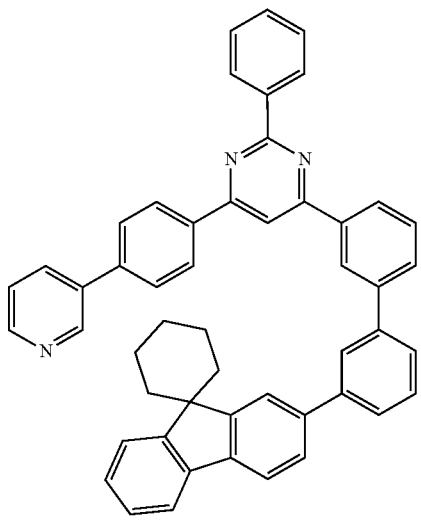

-continued
Inv 184
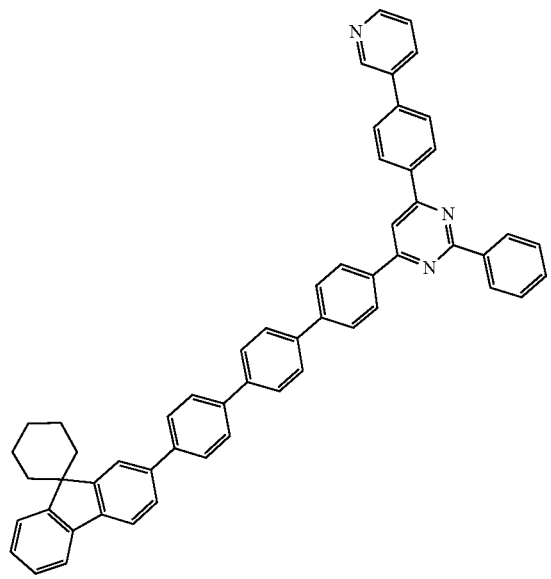
Inv 185
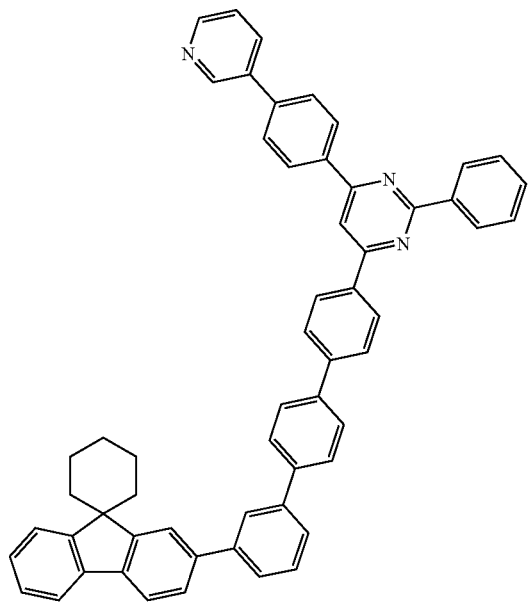
Inv 186
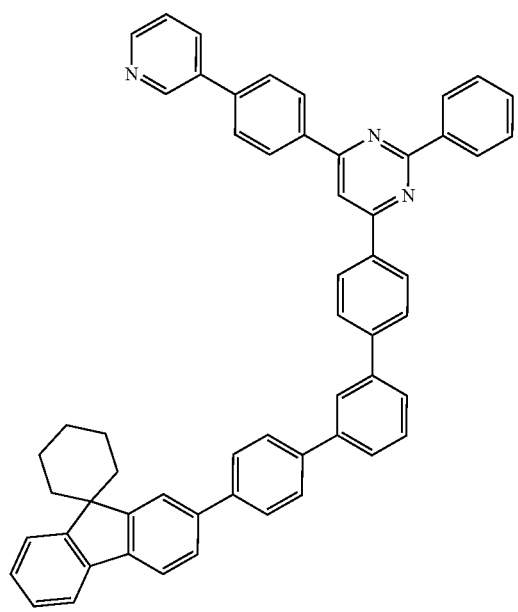
Inv 187
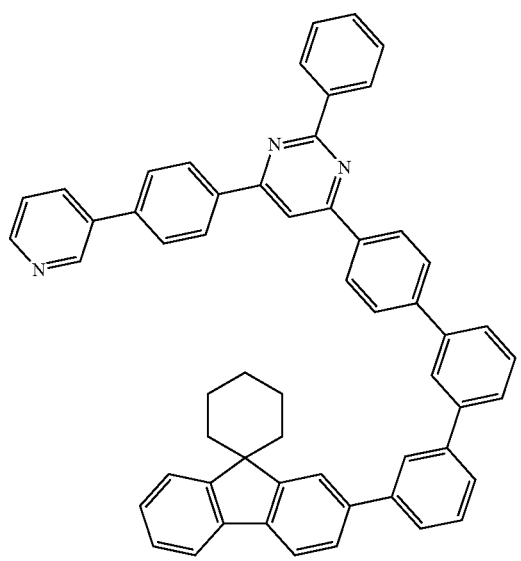

Inv 188
Inv 189
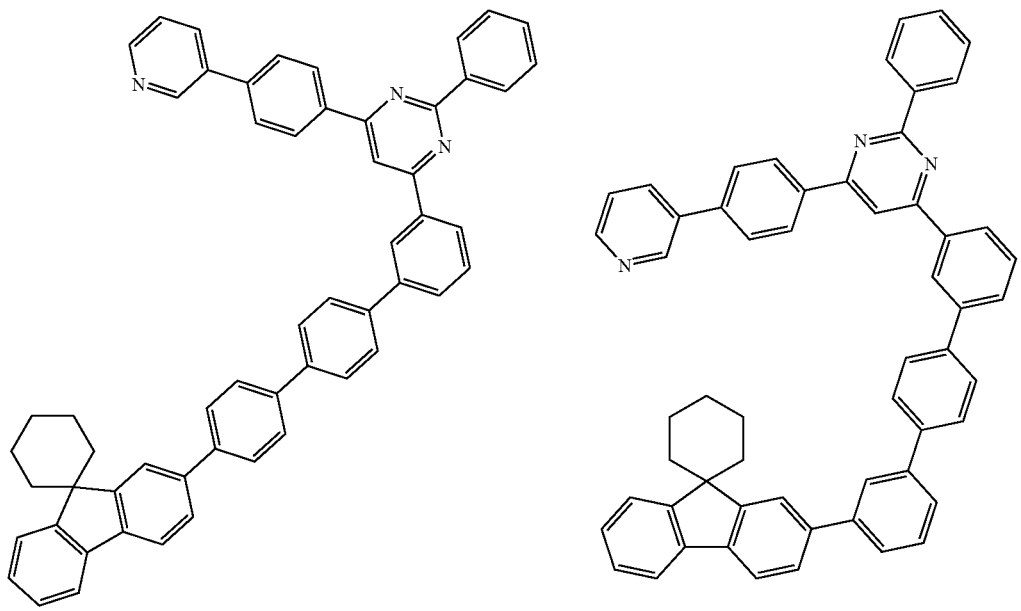
Inv 190
Inv 191
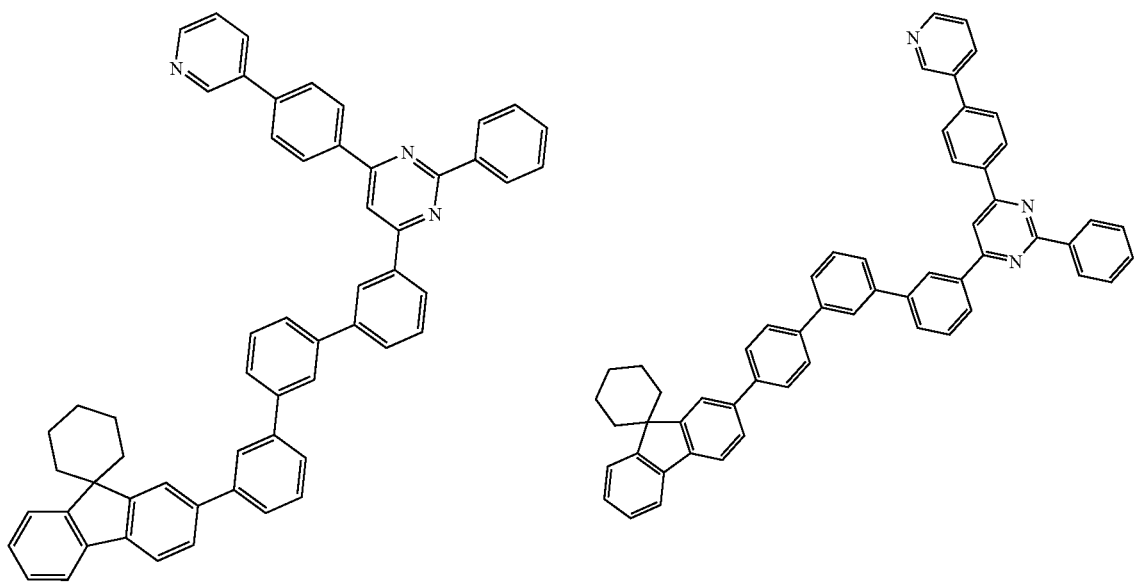

Inv 192
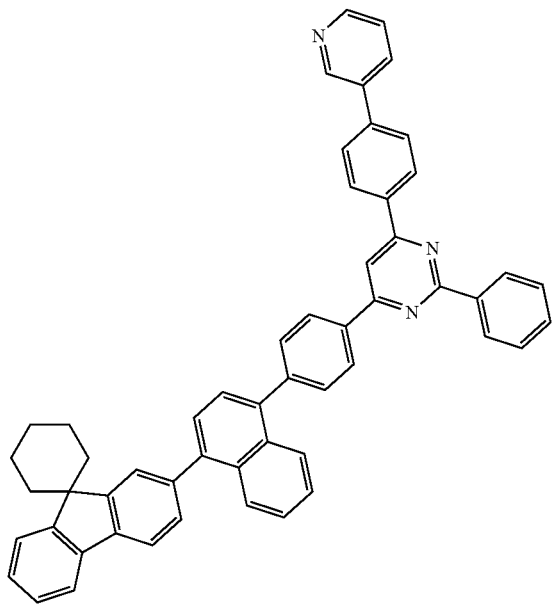
Inv 193
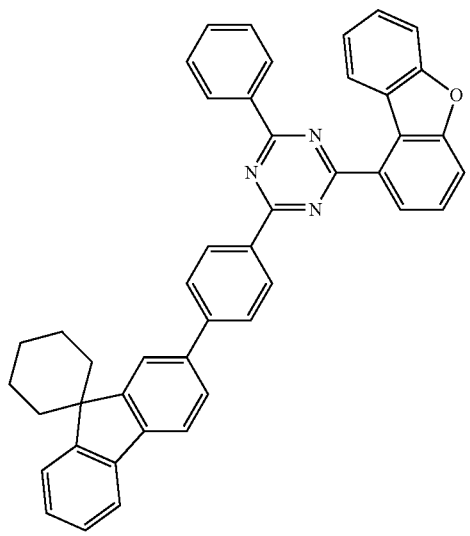
Inv 194
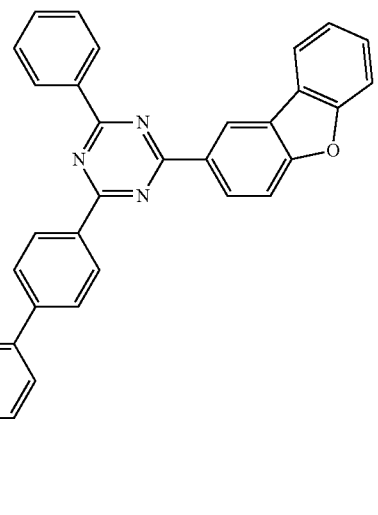

Inv 195
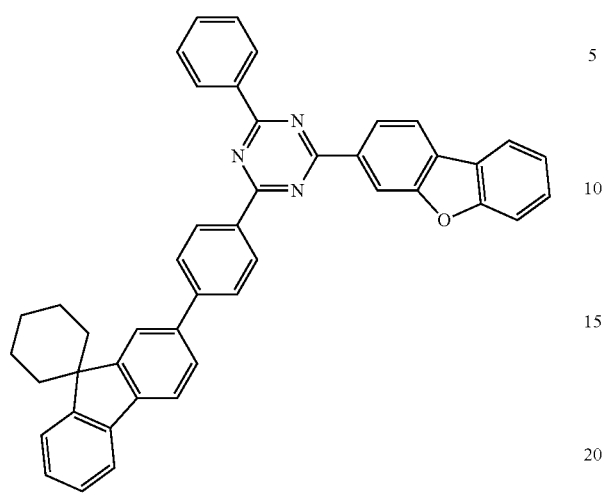
Inv 196
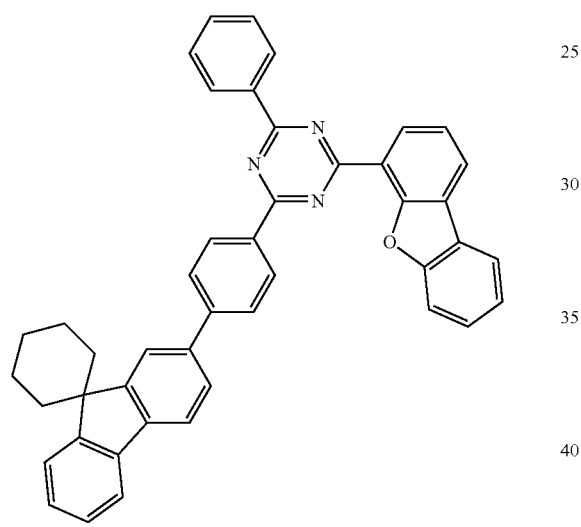
Inv 197
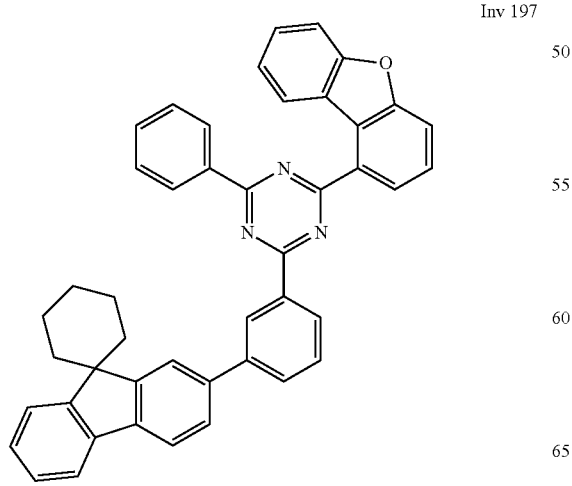
Inv 198
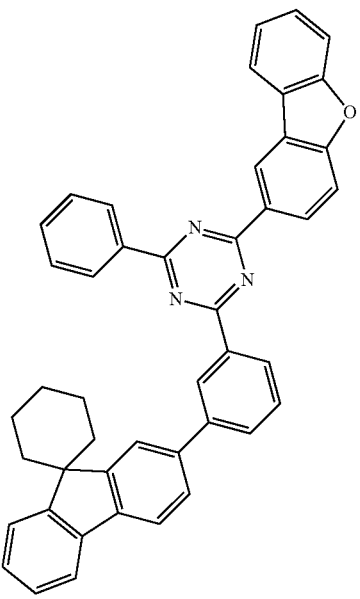
Inv 199
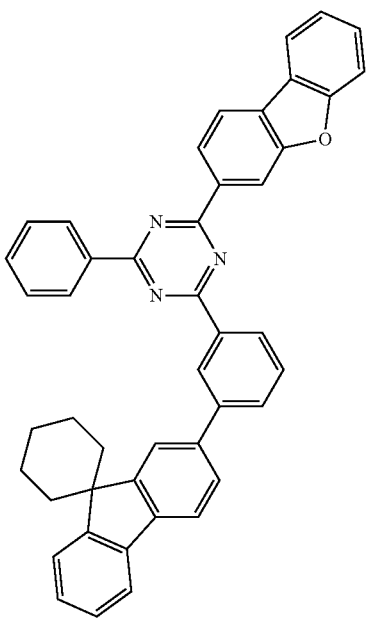

-continued
Inv 200
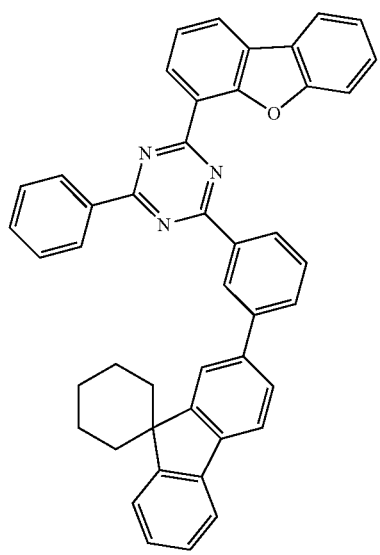
Inv 201
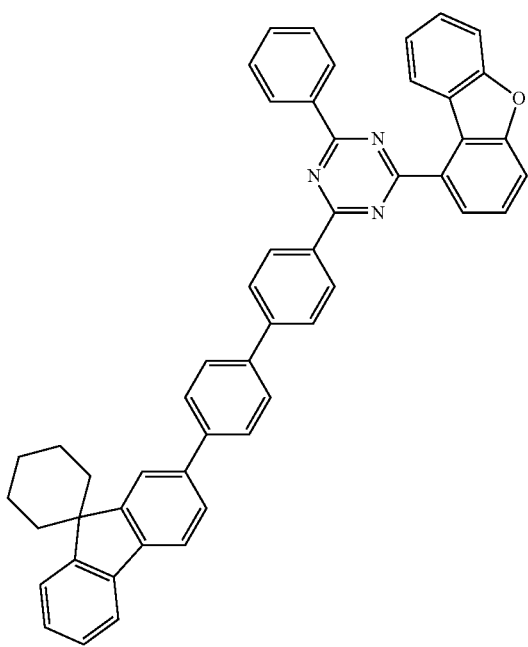
Inv 202
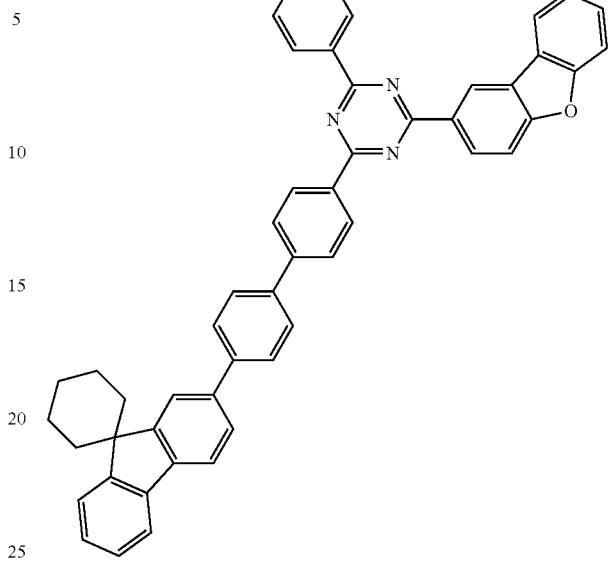
Inv 203
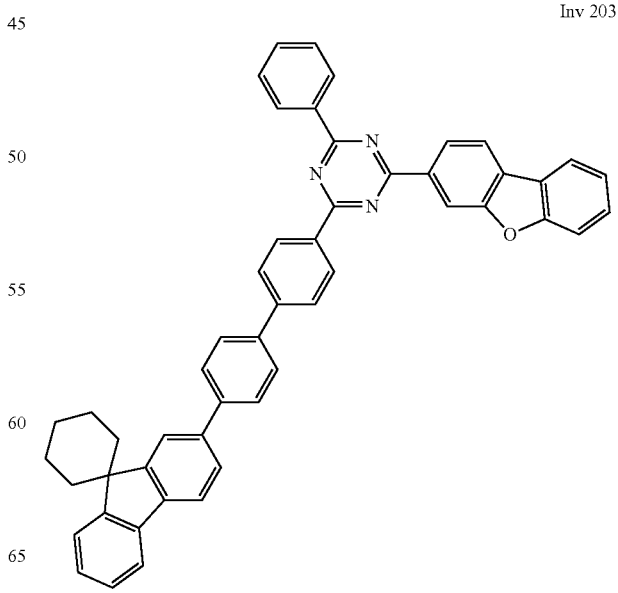

Inv 204
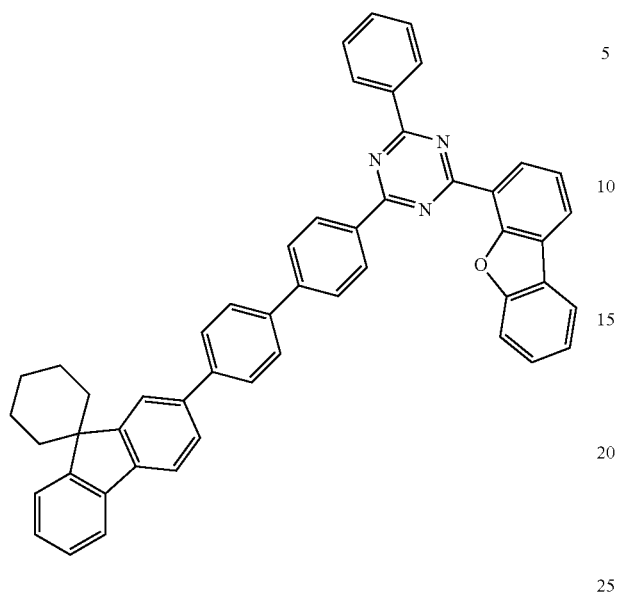
Inv 205
Inv 206
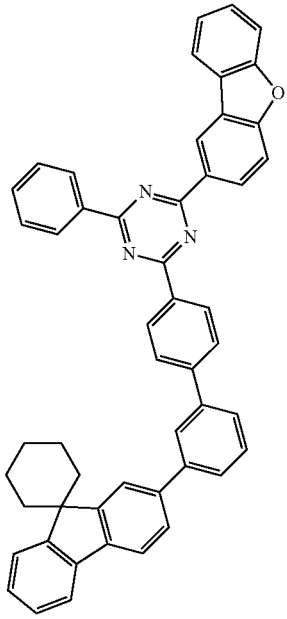
Inv 207
Inv 208
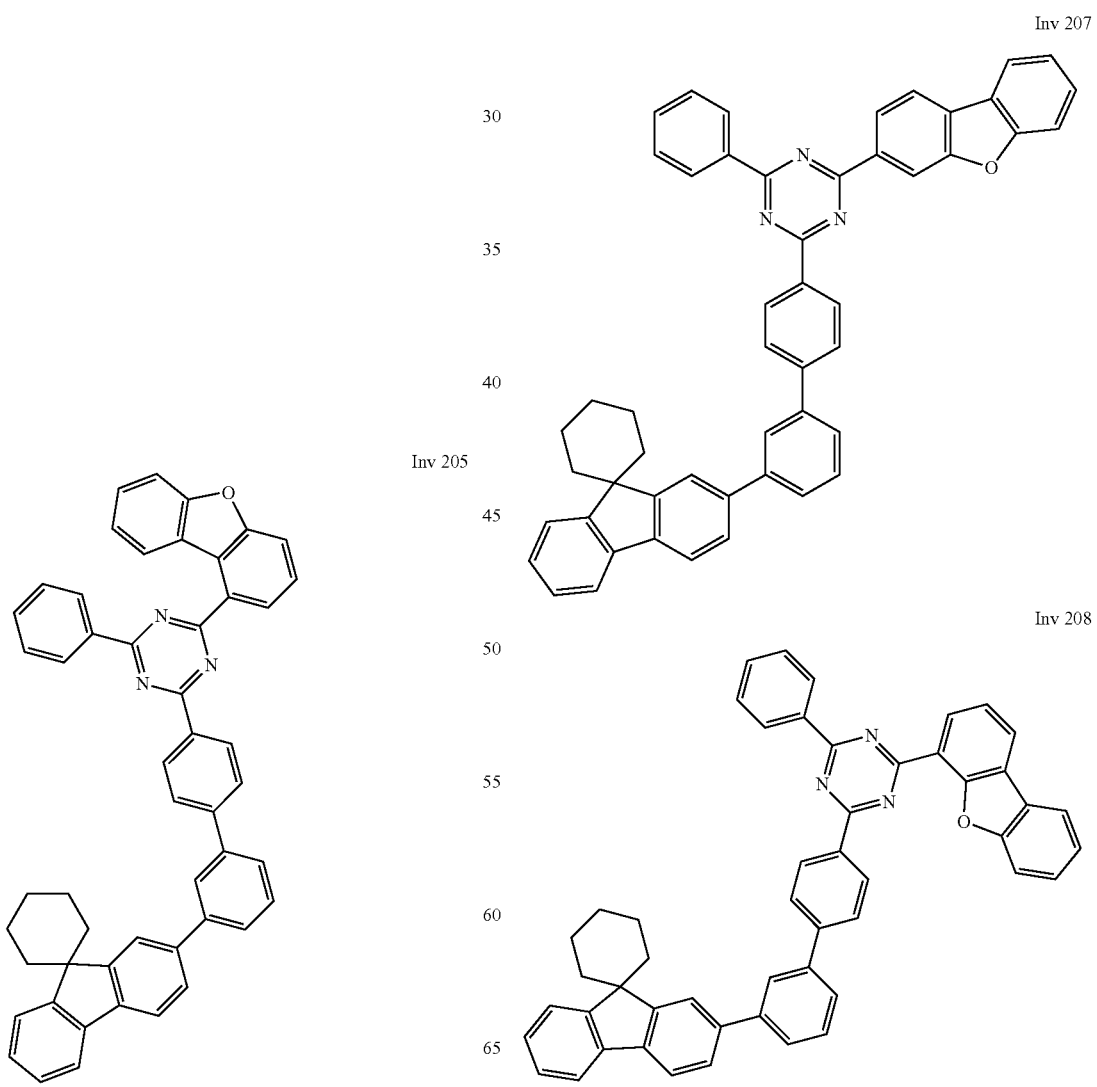

Inv 209
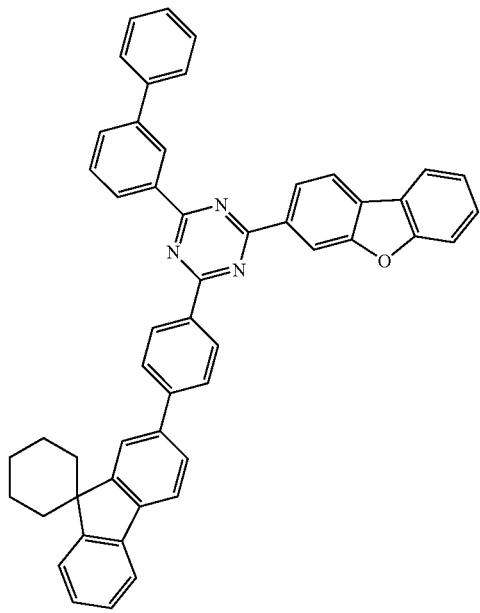
Inv 210
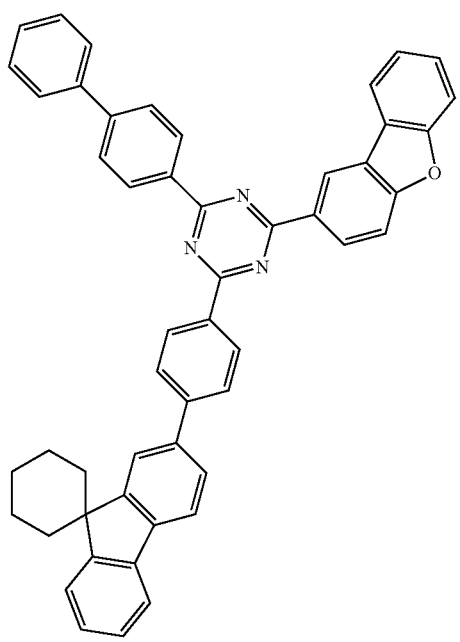
Inv 211
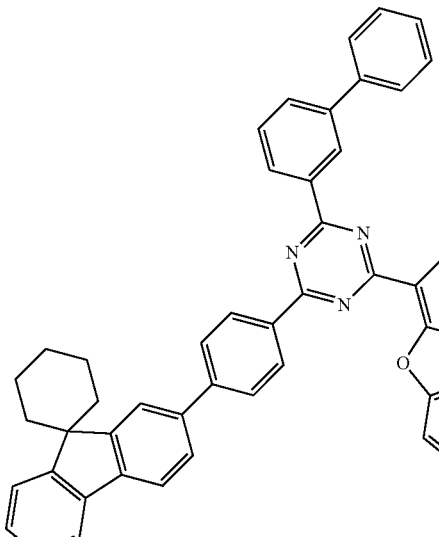
Inv 212
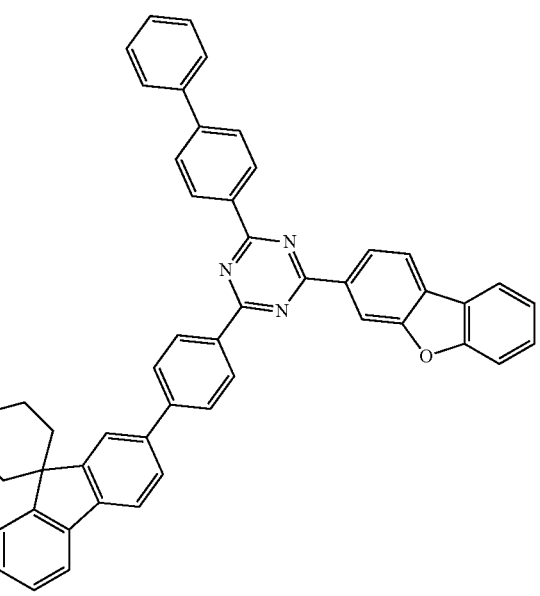

Inv 213
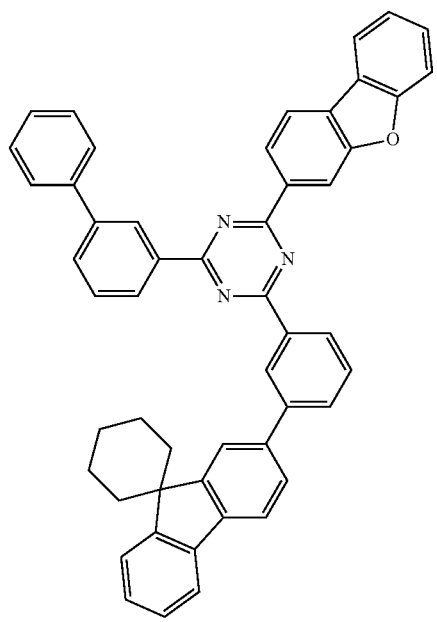
Inv 214
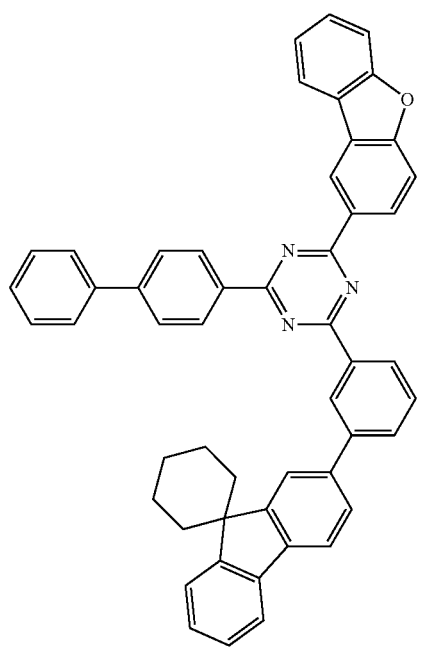
Inv 215
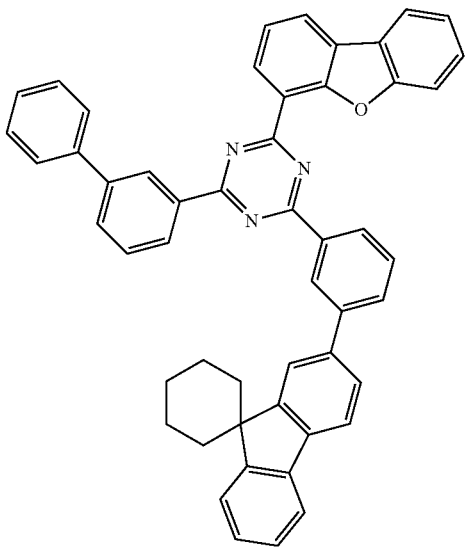
Inv 216
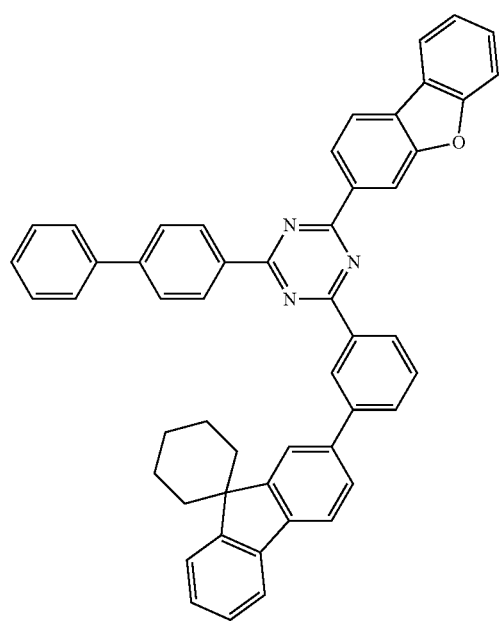

Inv 217
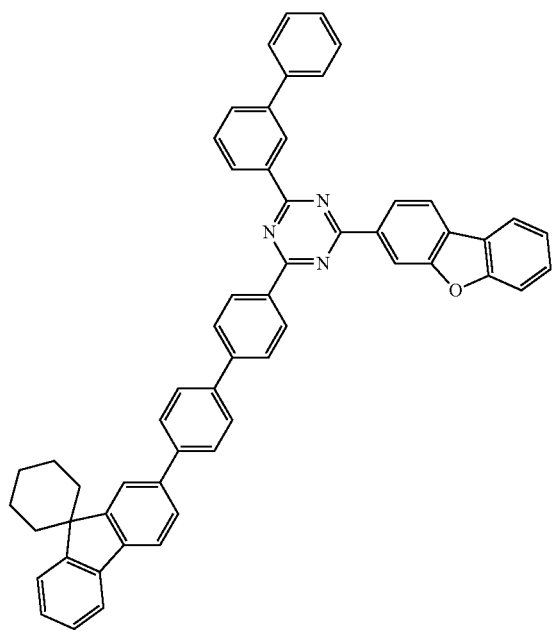
Inv 219
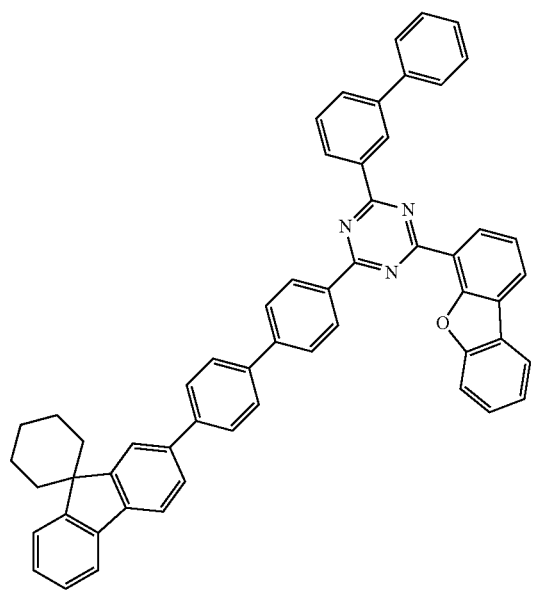
Inv 218
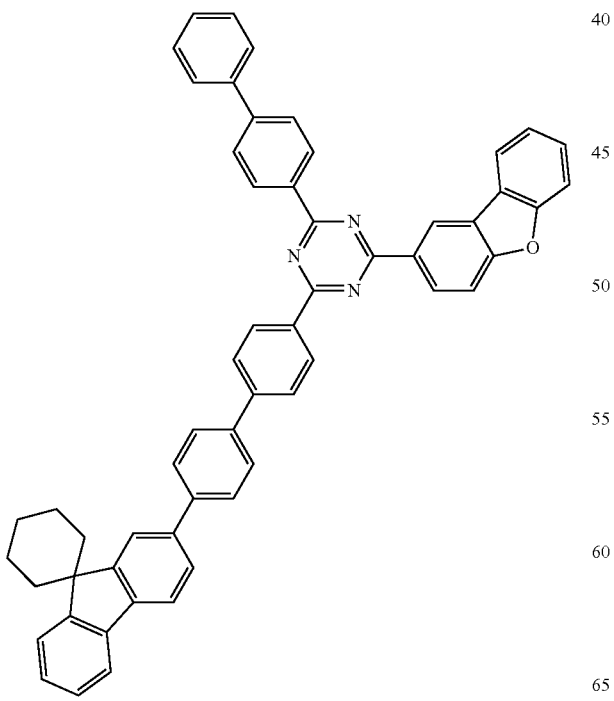
Inv 220
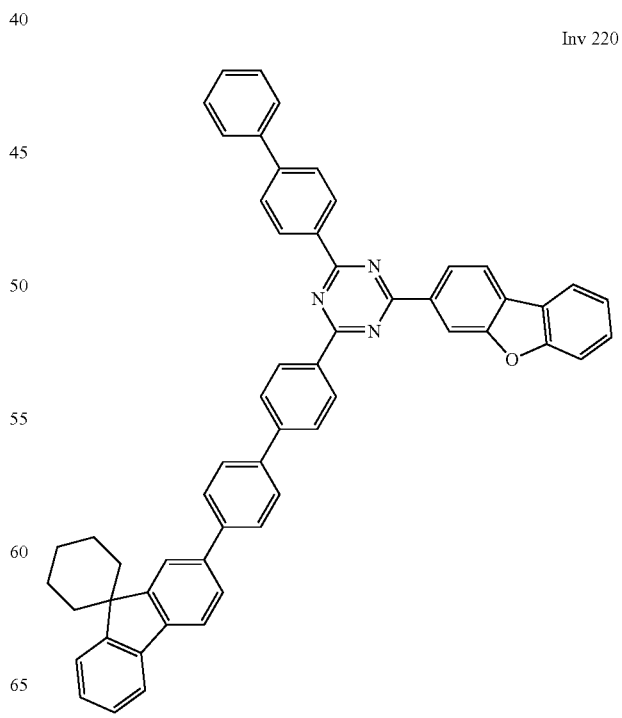

Inv 221
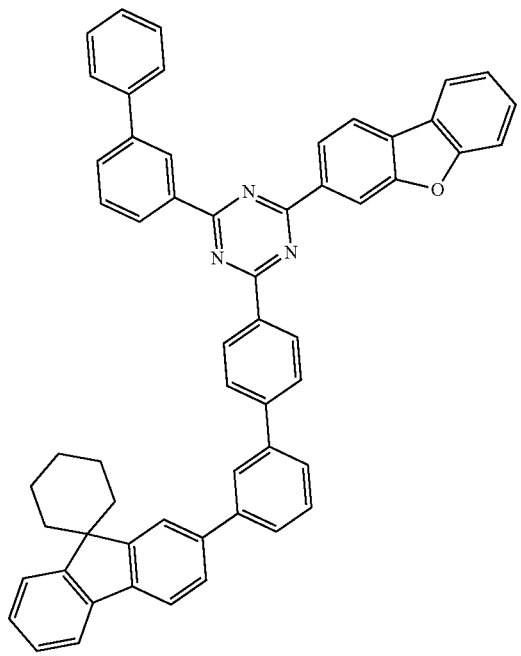
Inv 222
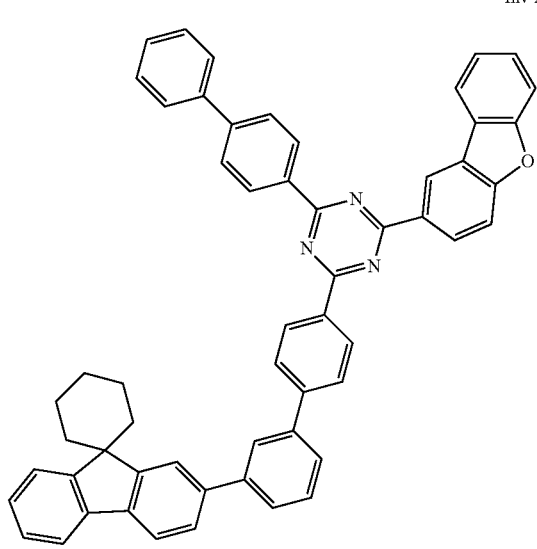
Inv 223
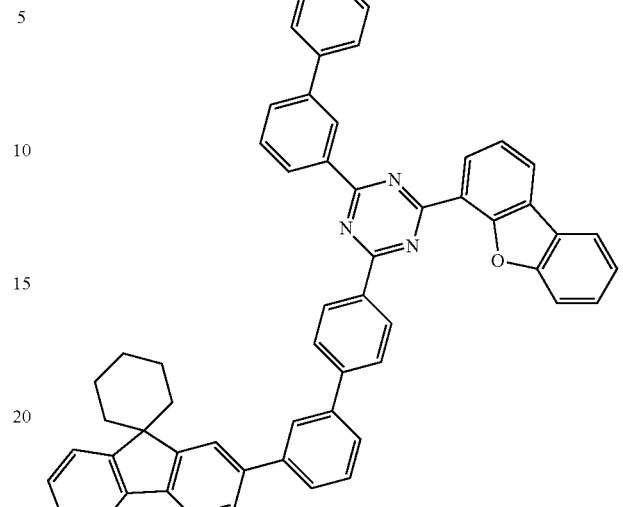
Inv 224
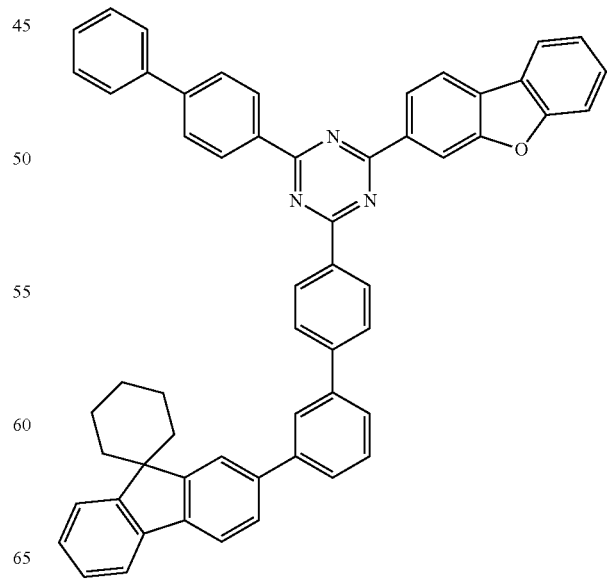

Inv 225
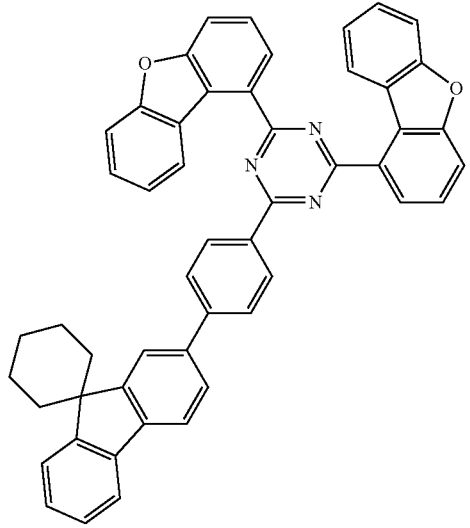
Inv 227
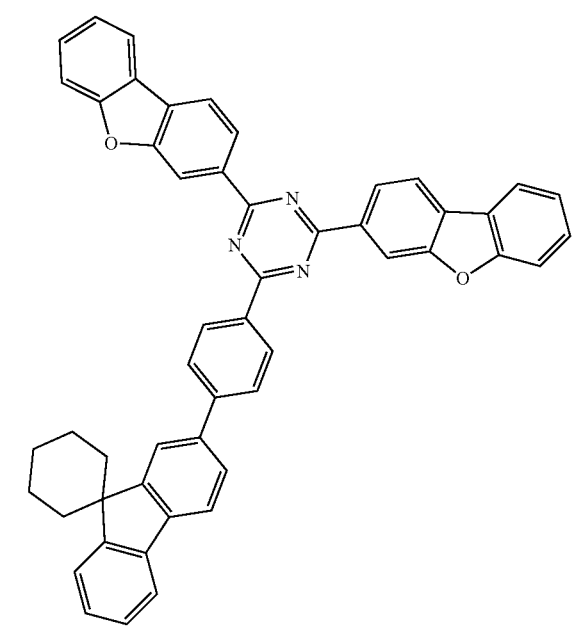
Inv 226
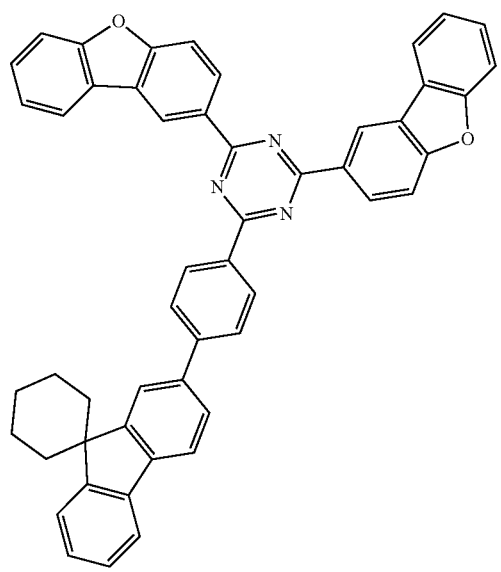
Inv 228
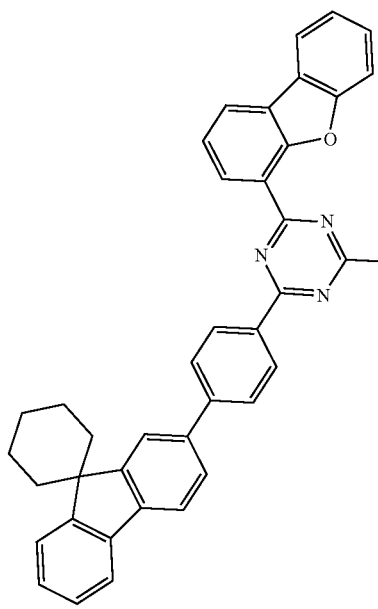

Inv 229
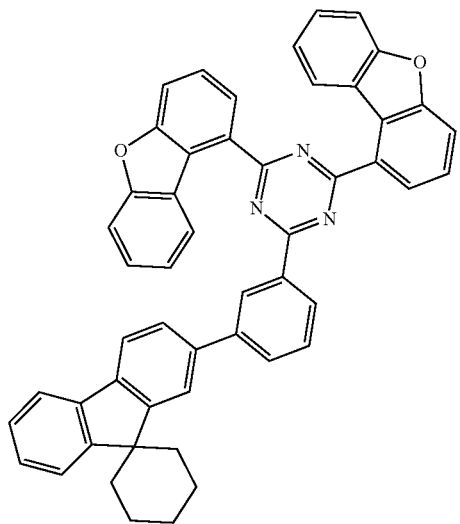
Inv 230
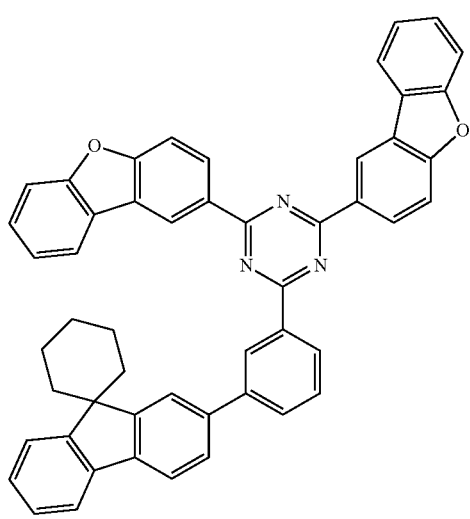
Inv 231
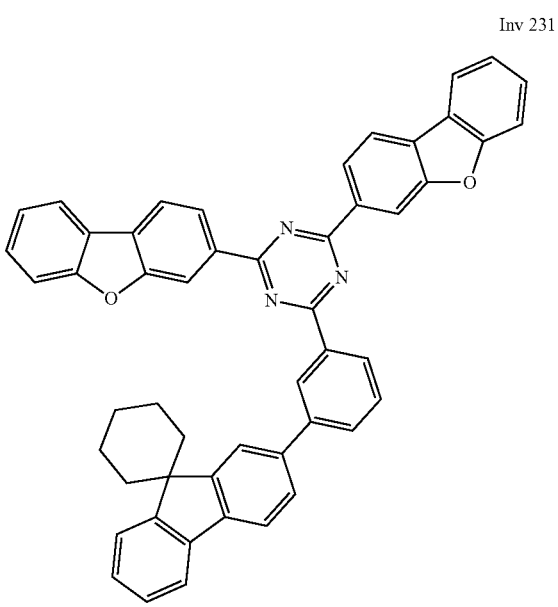
Inv 232
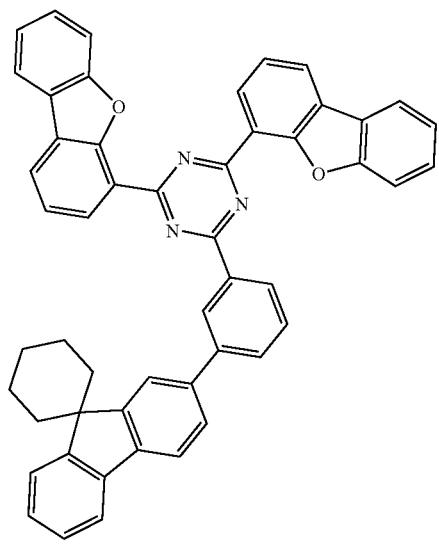
Inv 233
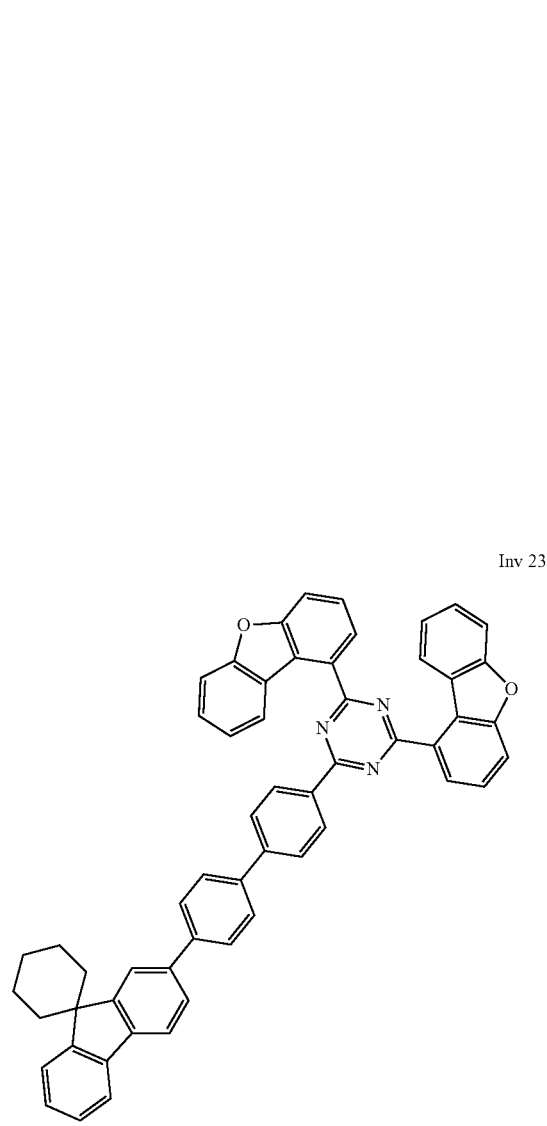

121
-continued
Inv 234
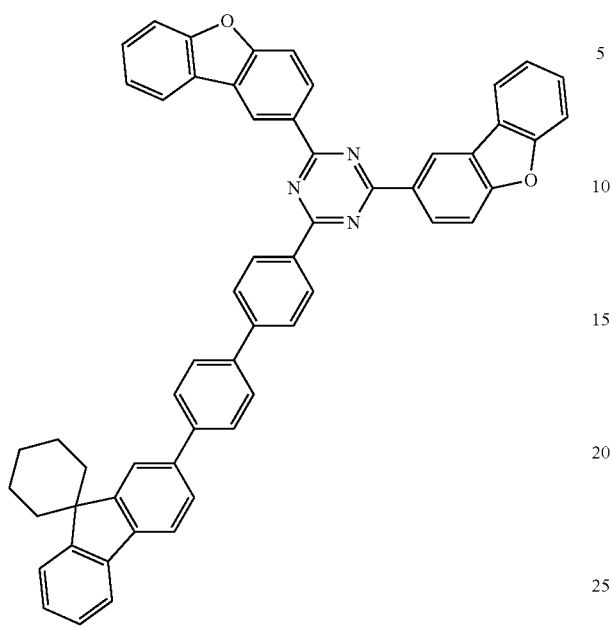
122
-continued
Inv 236
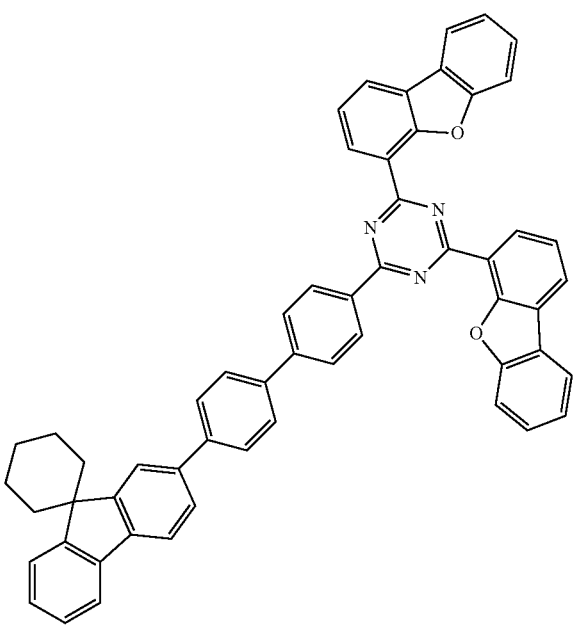
Inv 235
Inv 237
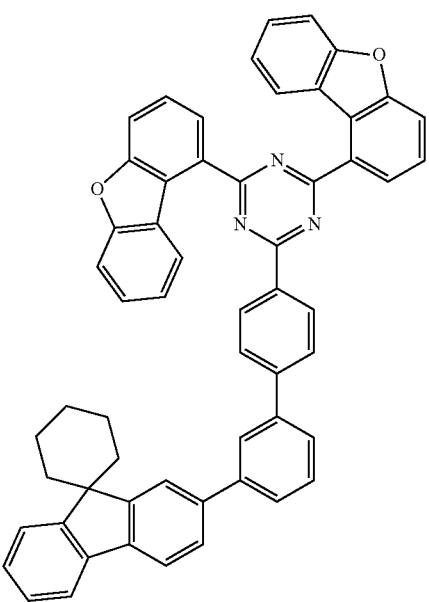

Inv 238
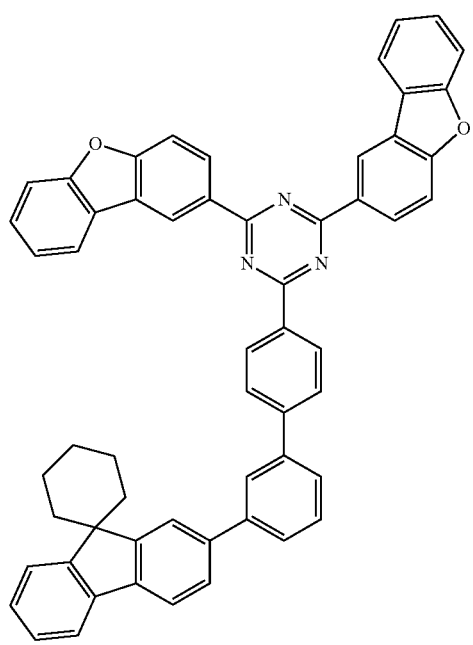
Inv 239
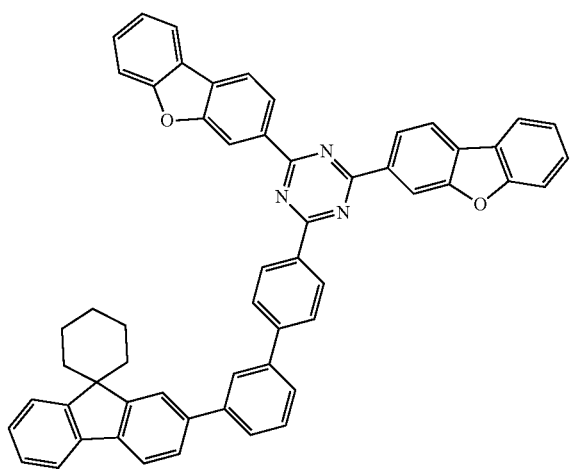
Inv 240
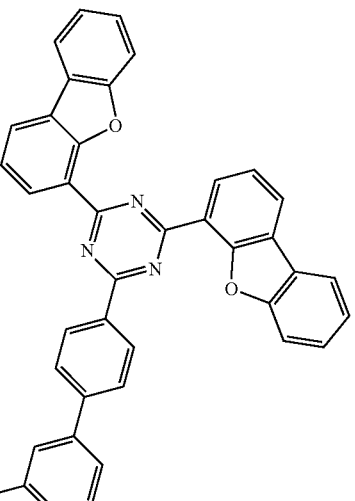
Inv 241
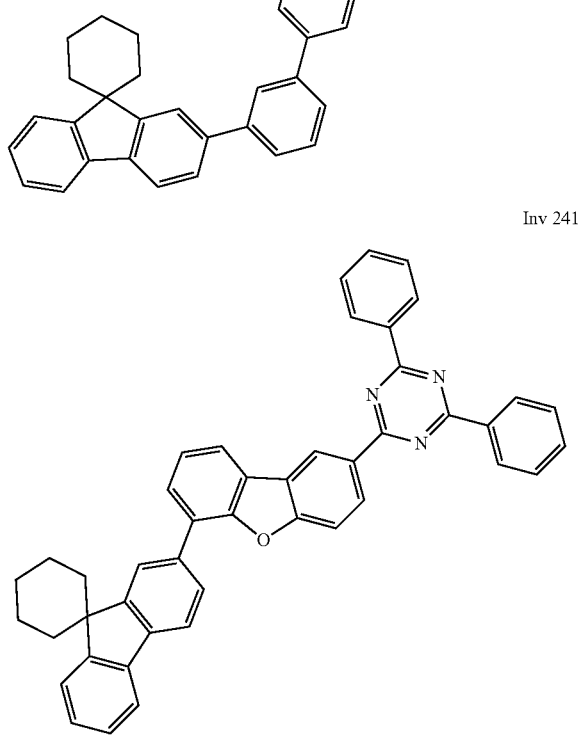
Inv 242
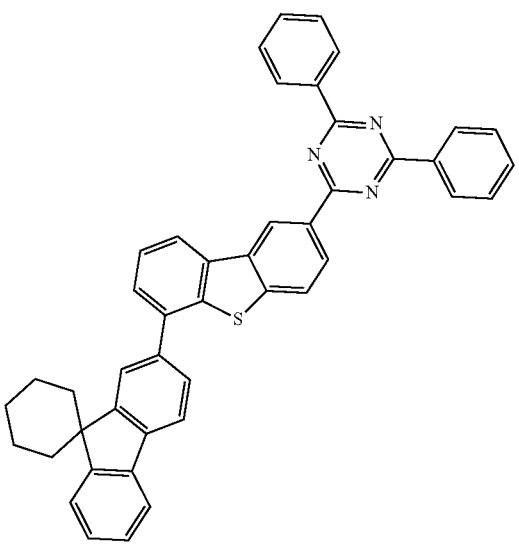

Inv 243
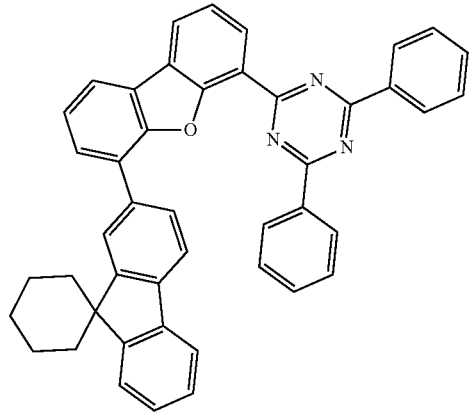
Inv 244
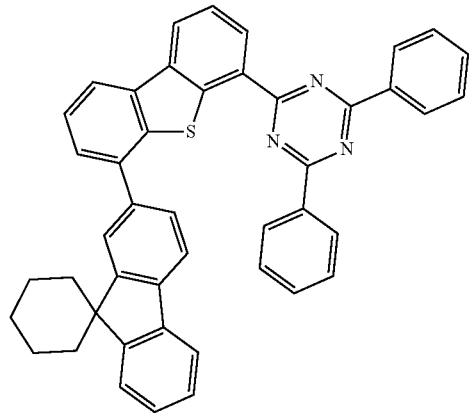
Inv 245
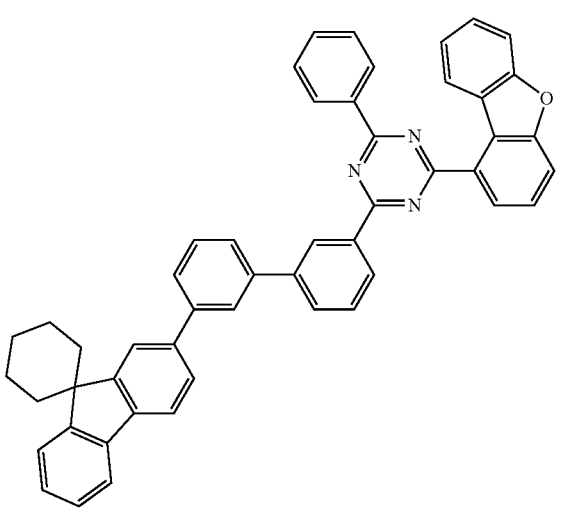
Inv 246
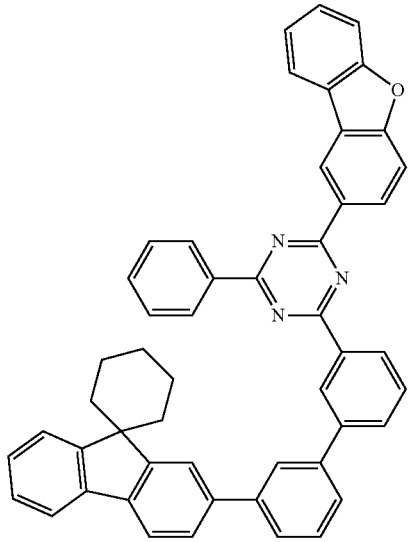
Inv 247
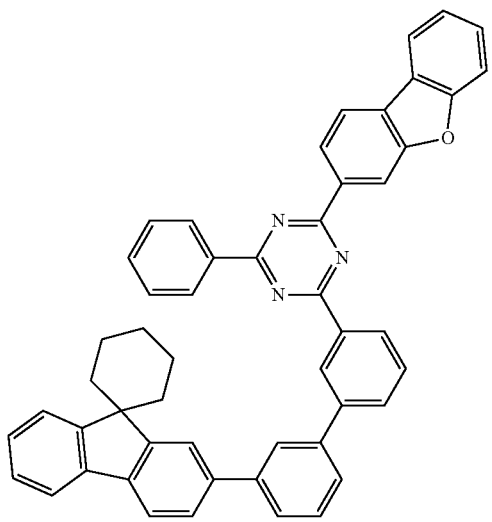
Inv 248
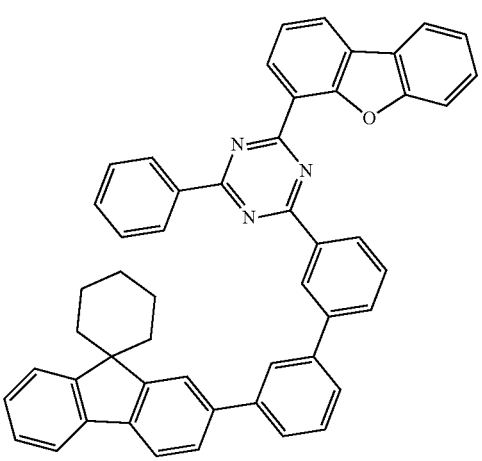

Inv 249
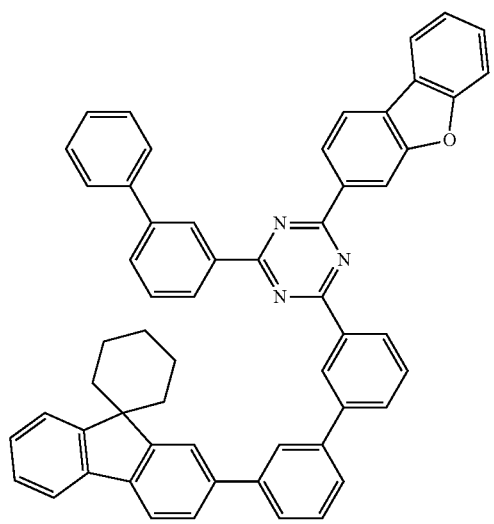
Inv 250
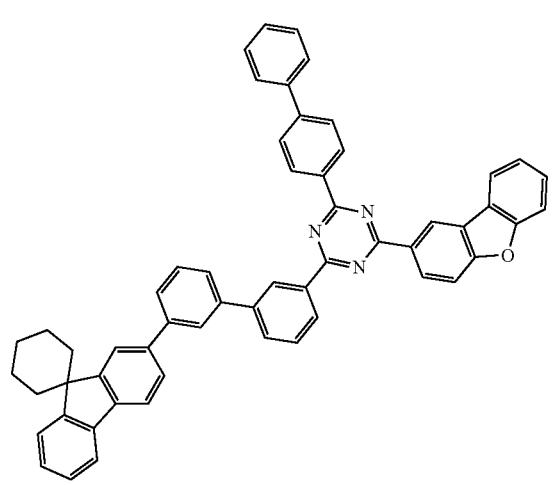
Inv 251
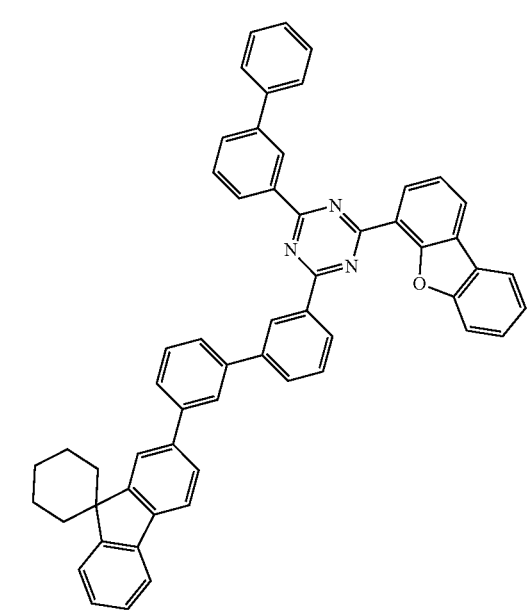
Inv 252
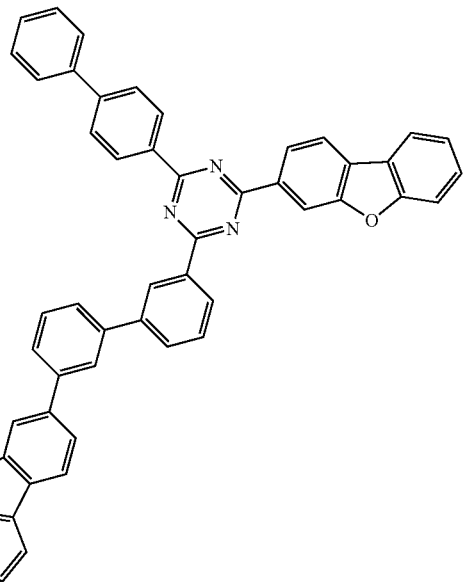
Inv 253
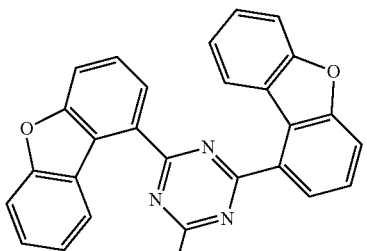
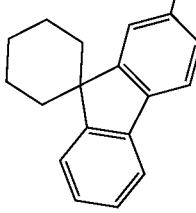
Inv 254
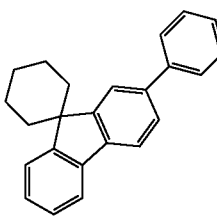

-continued
Inv 255
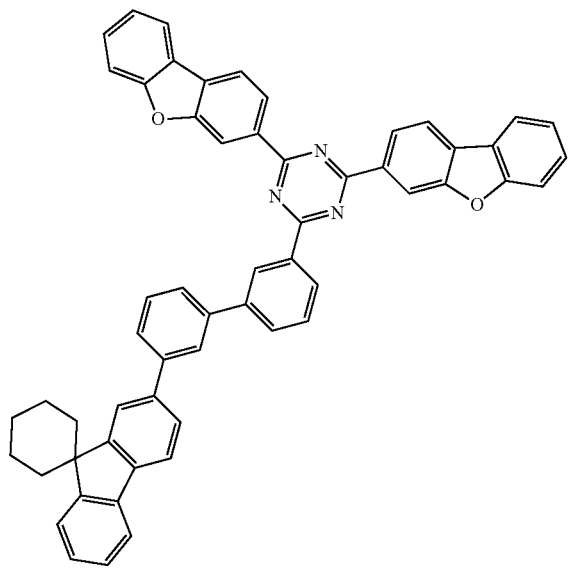
Inv 256
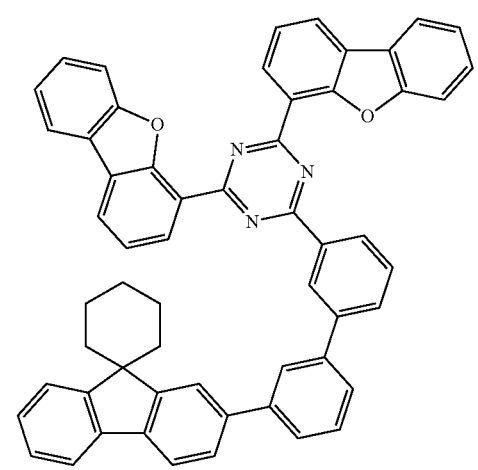
Inv 257
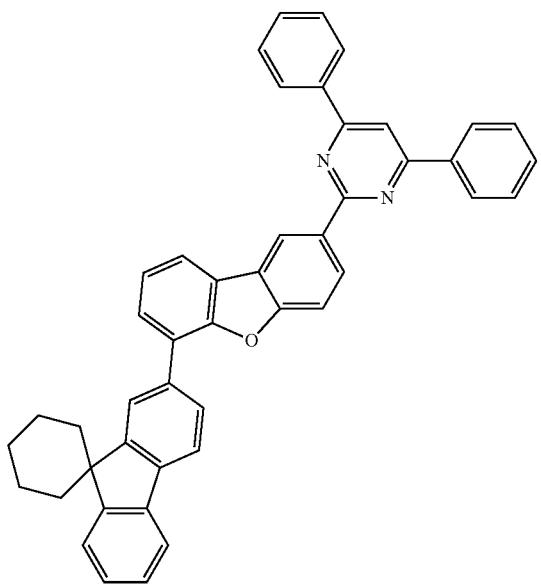
-continued
Inv 258
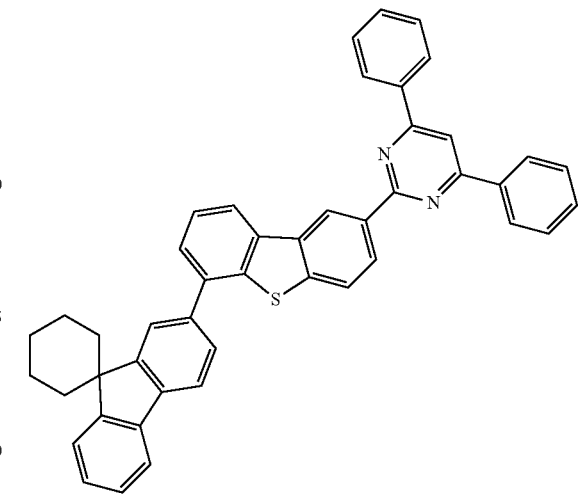
Inv 259
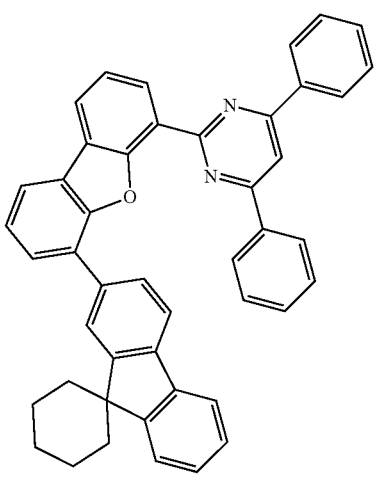
Inv 260
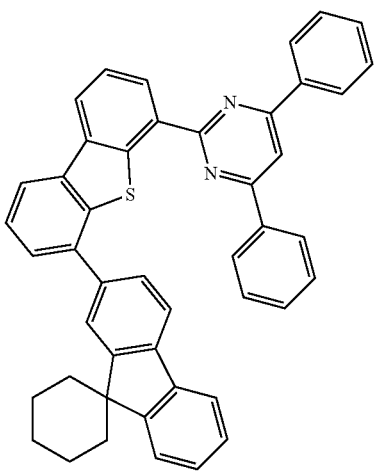

Inv 261
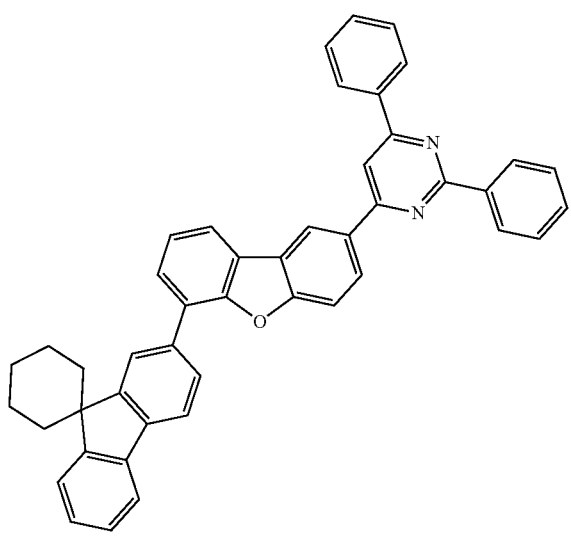
Inv 262
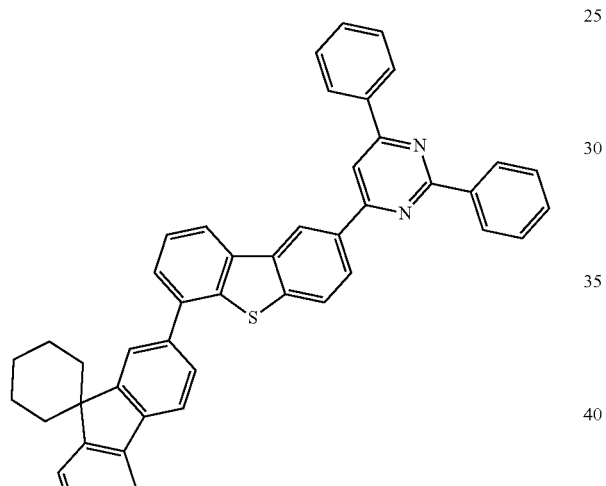
Inv 263
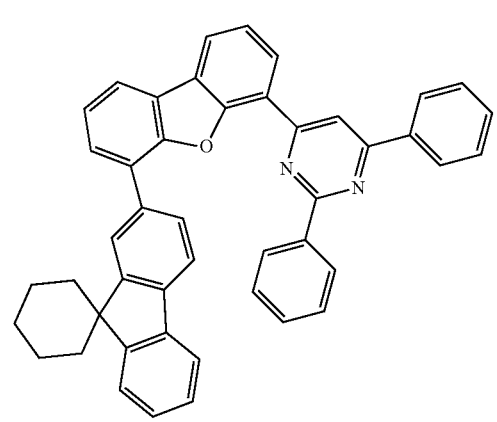
Inv 264
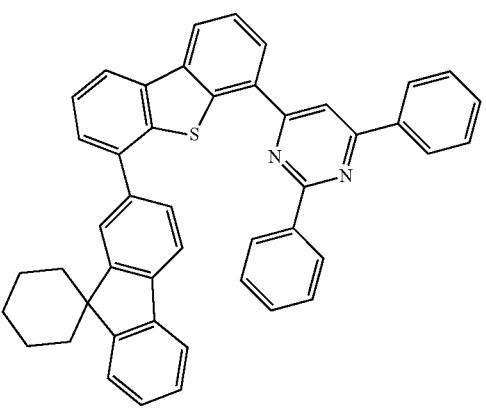
Inv 265
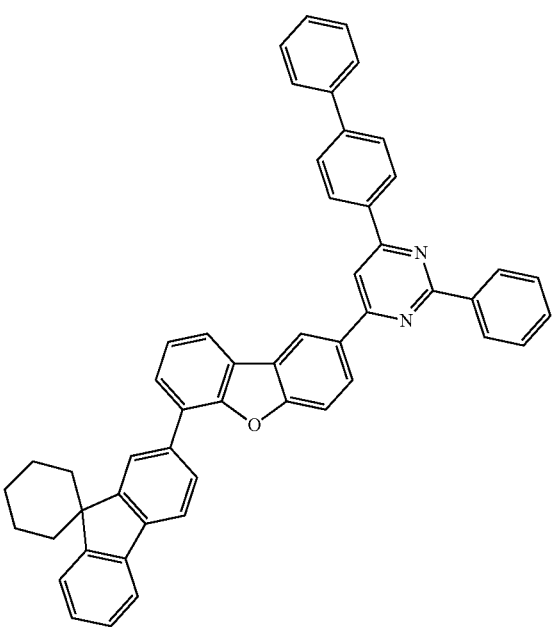

Inv 266
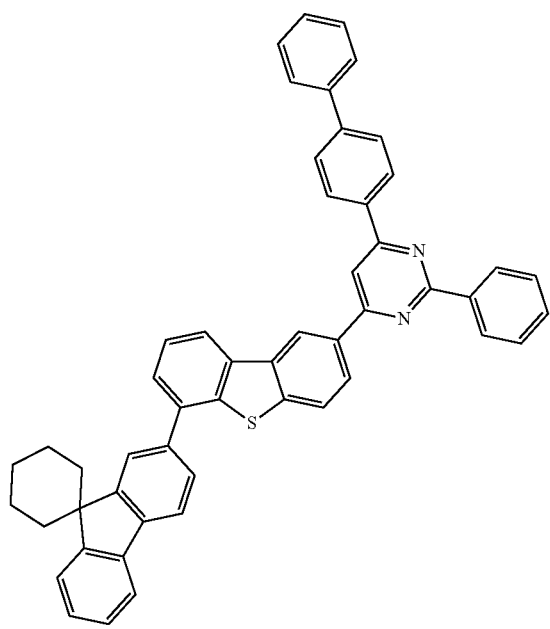
Inv 268
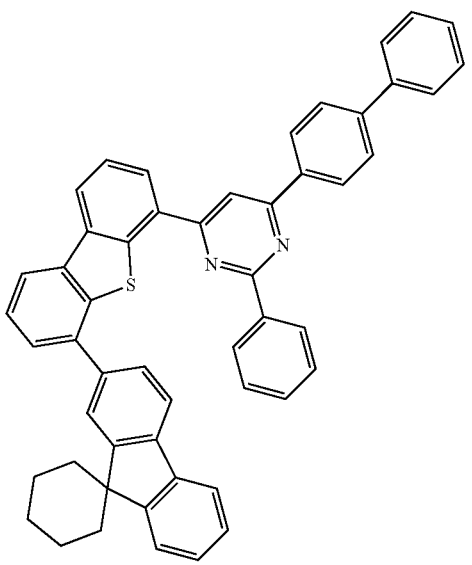
Inv 267
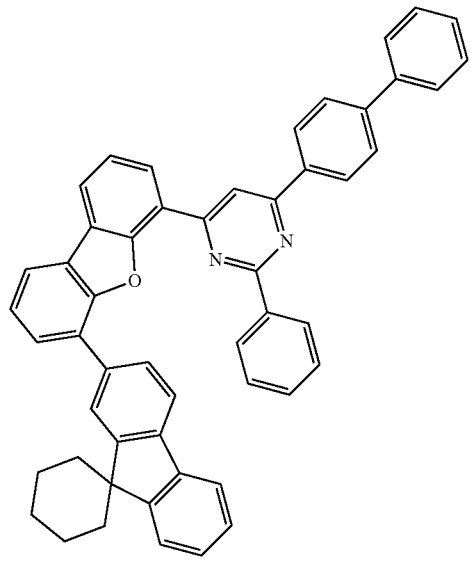
Inv 269
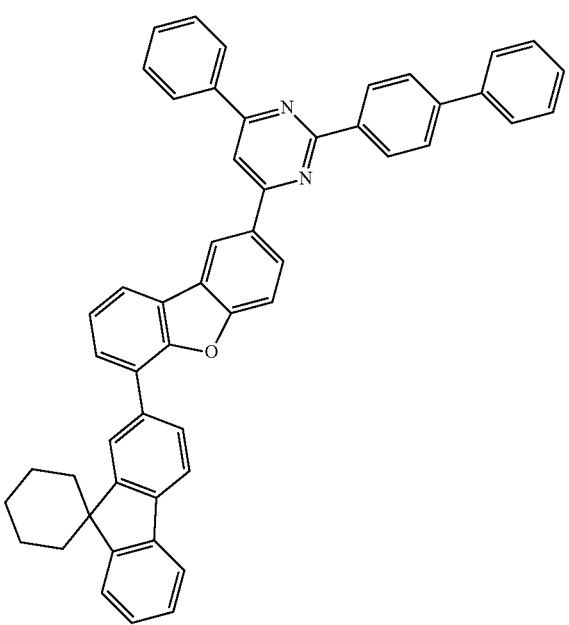

Inv 270
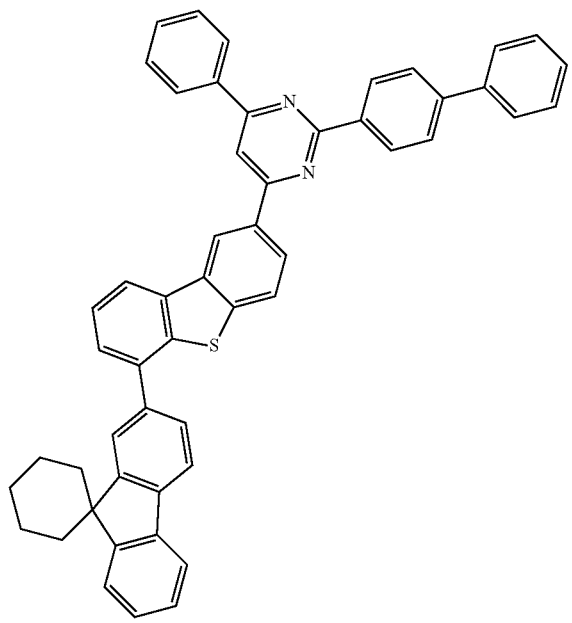
Inv 271
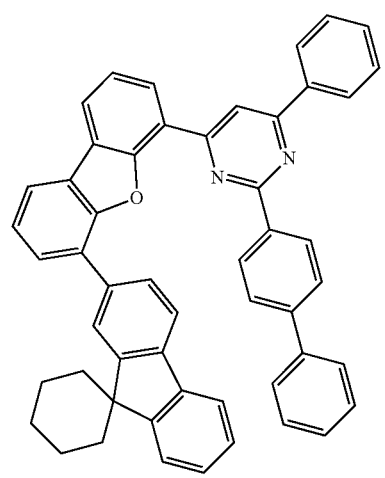
Inv 272
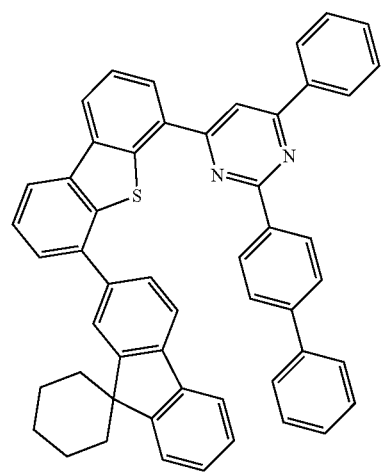
Inv 273
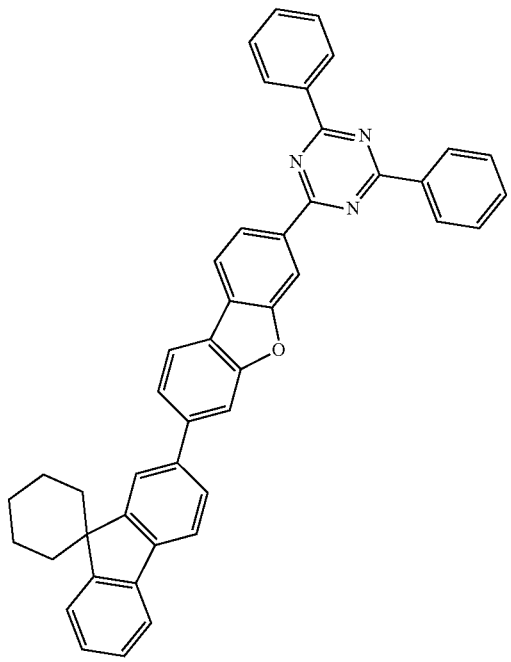
Inv 274
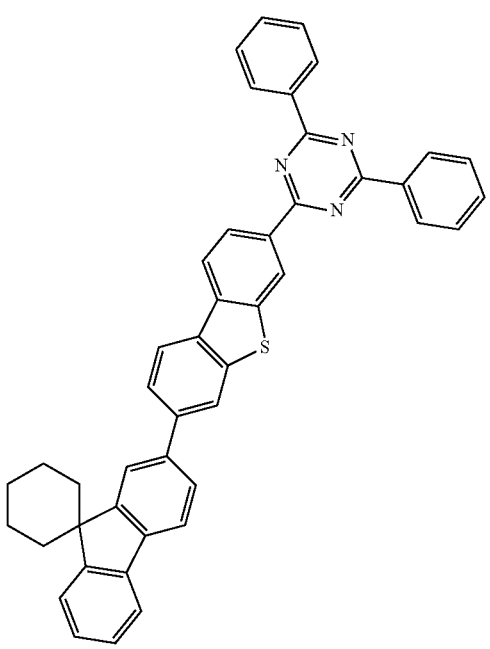

Inv 275
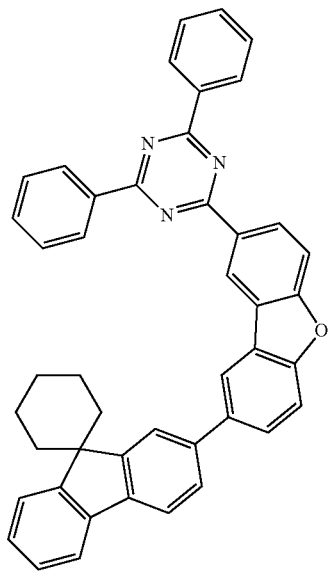
Inv 277
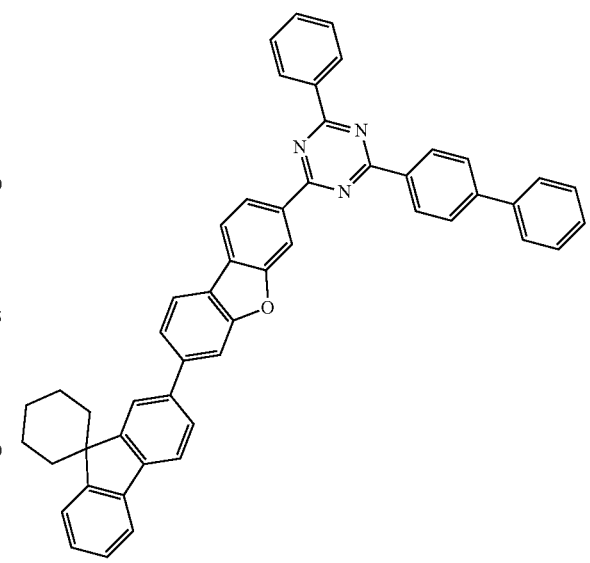
Inv 276
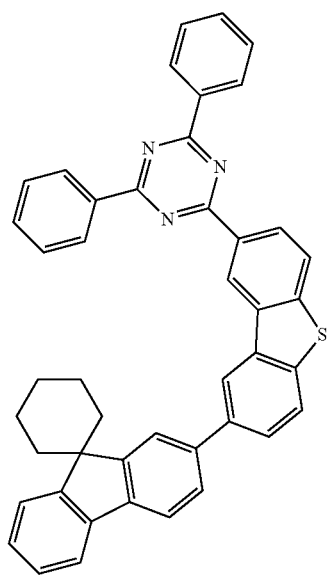
Inv 278
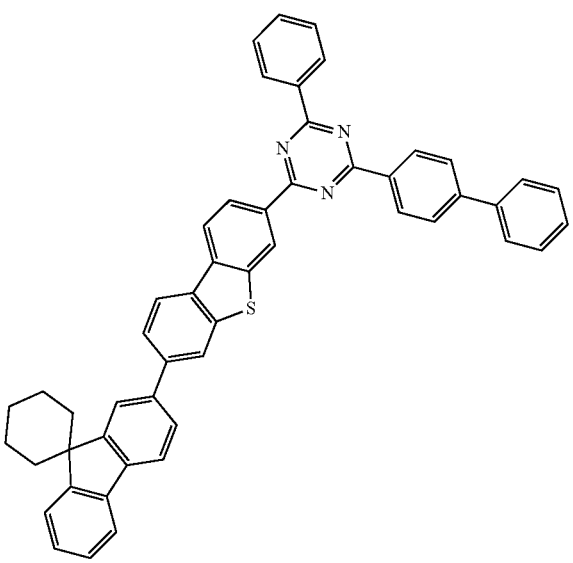

139
-continued
Inv 279
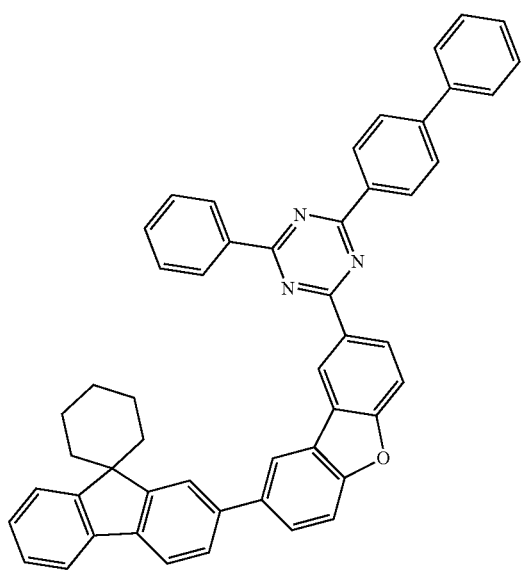
Inv 280
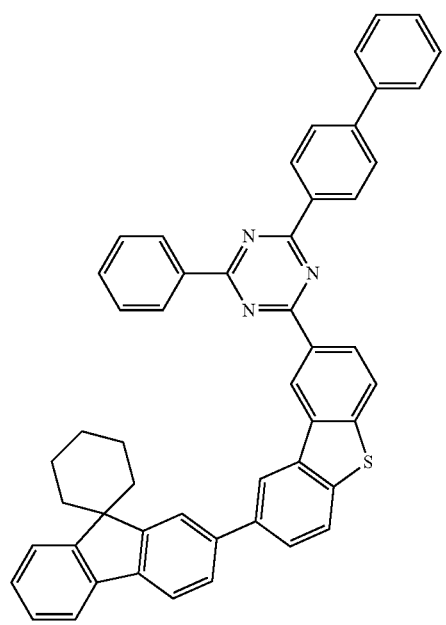
140
-continued
Inv 281
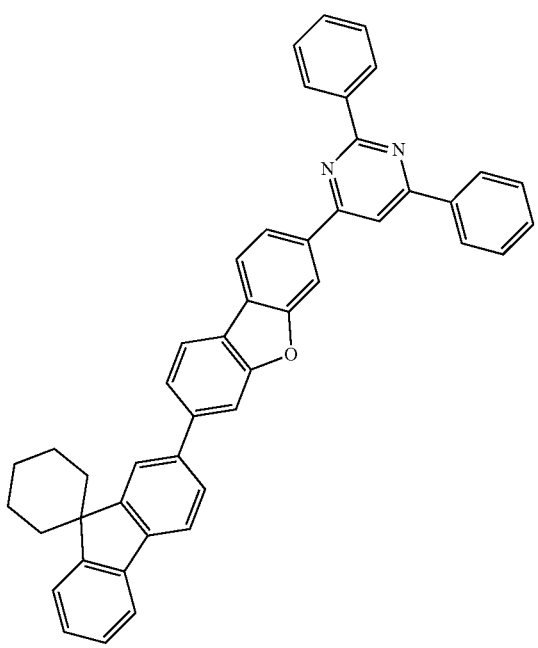
Inv 282
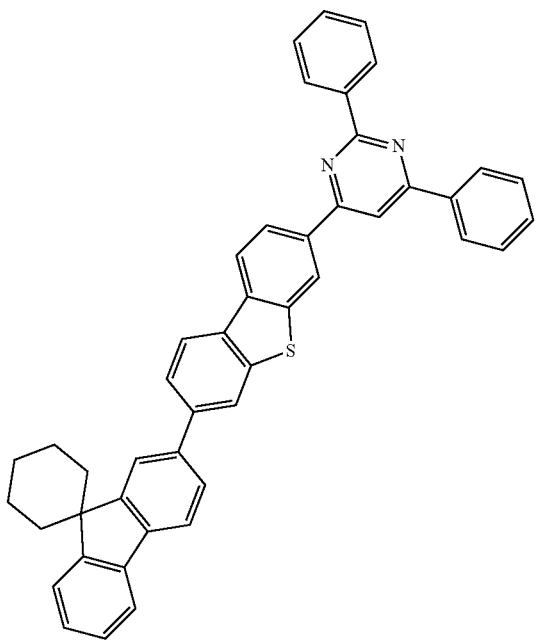

Inv 283
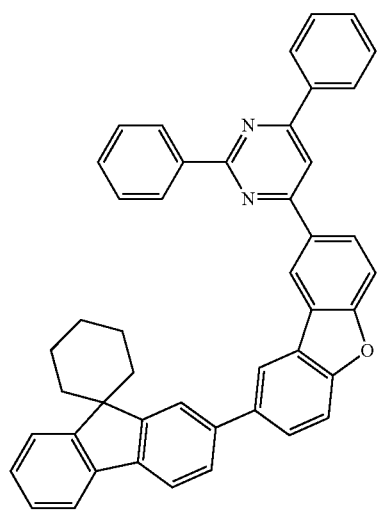
Inv 284
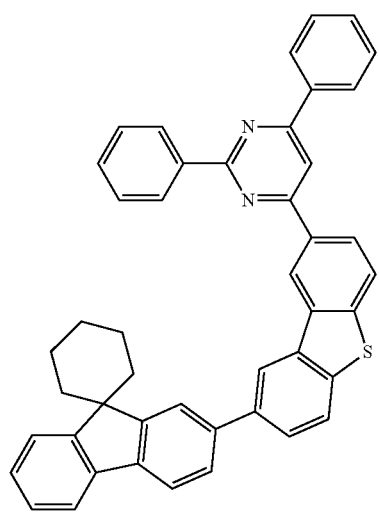
Inv 285
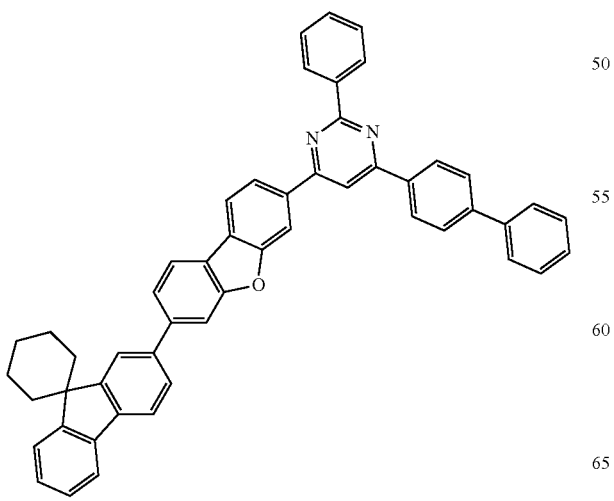
Inv 286
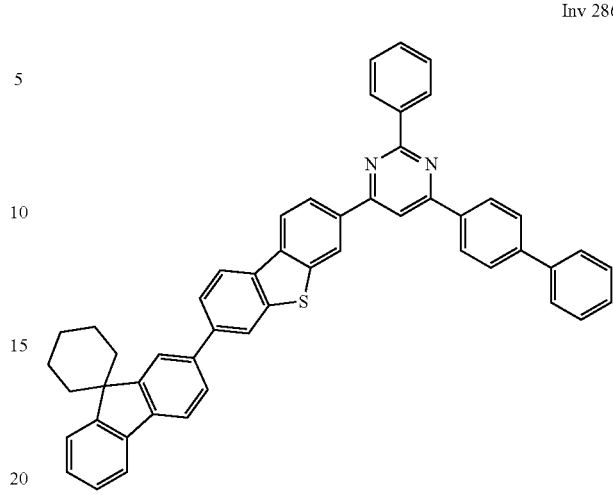
Inv 287
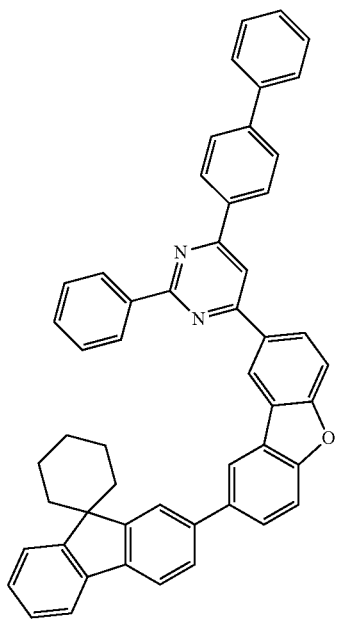

Inv 288
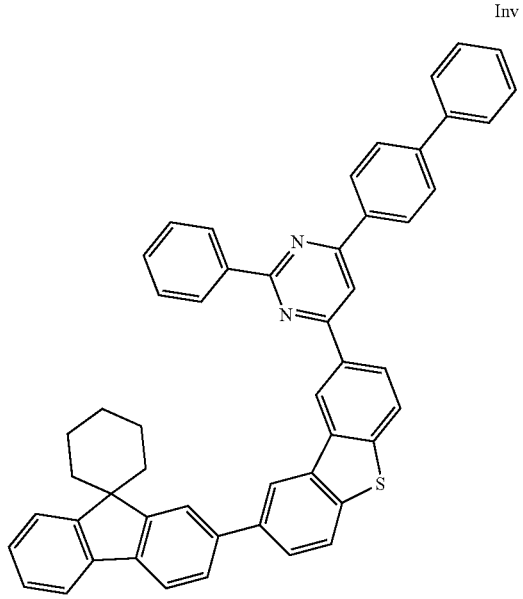
Inv 291
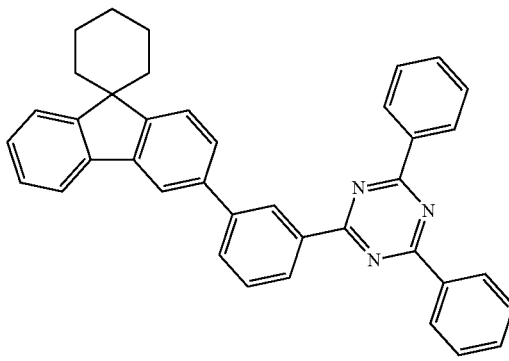
Inv 292
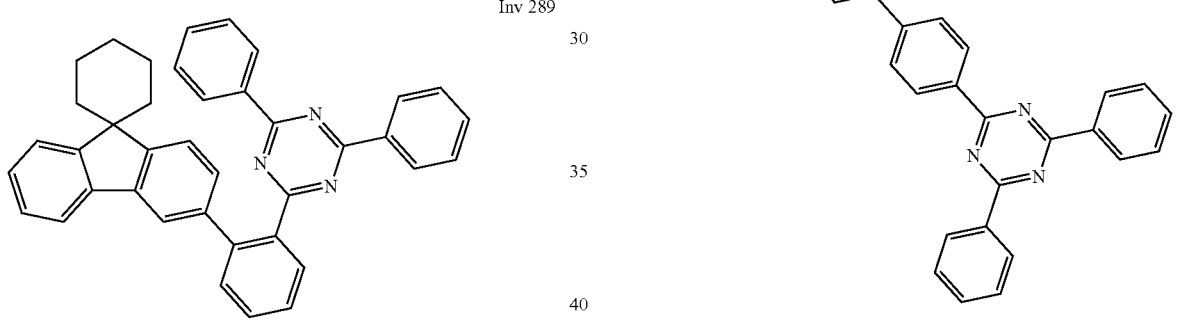
Inv 289
Inv 290
Inv 293
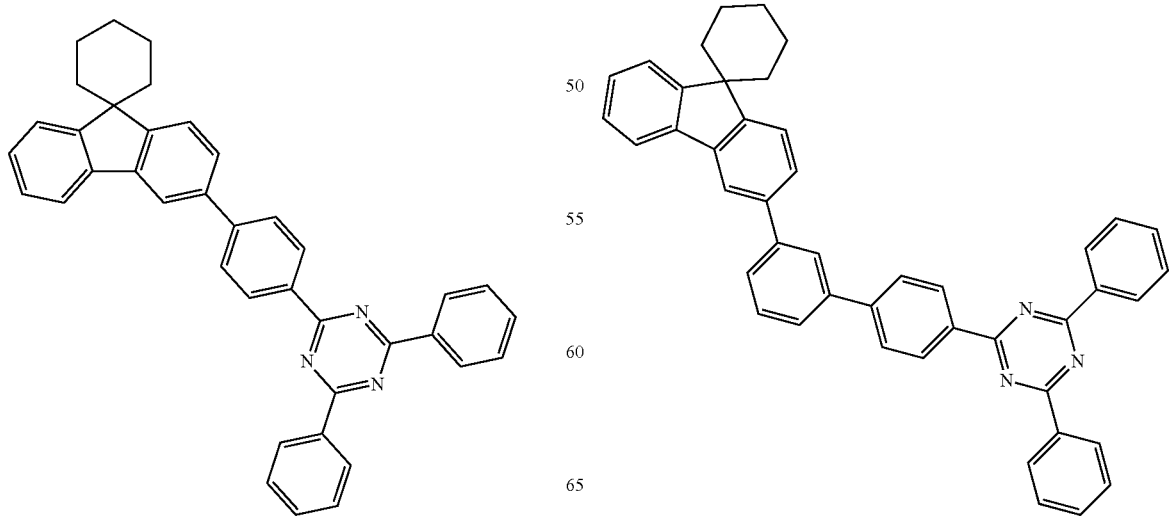

Inv 294
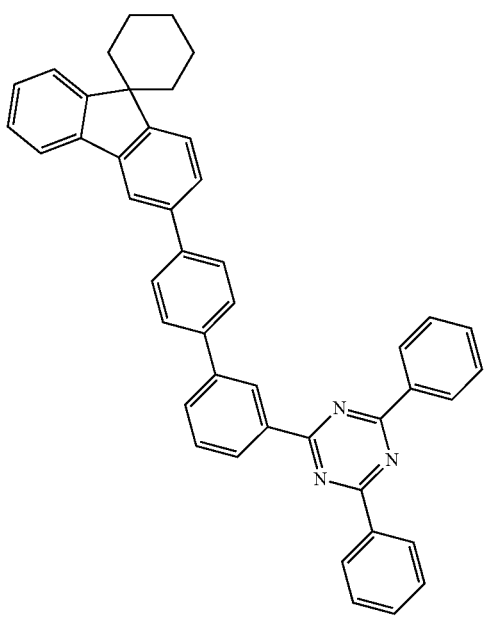
Inv 296
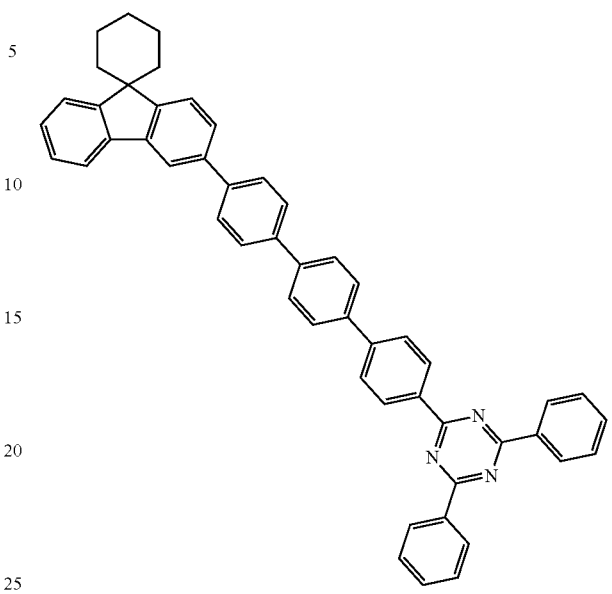
Inv 295
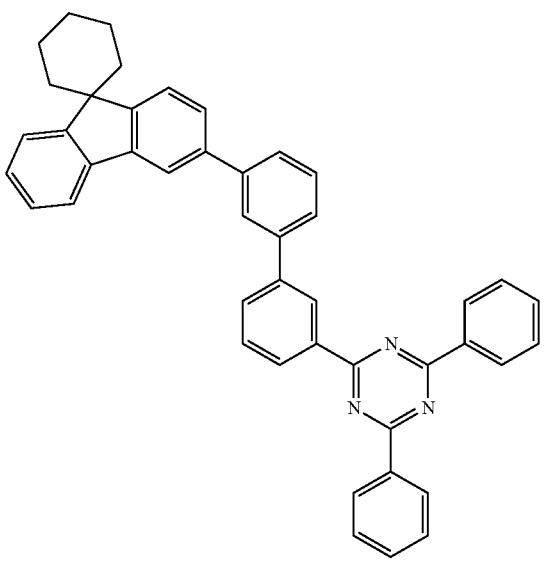
Inv 297
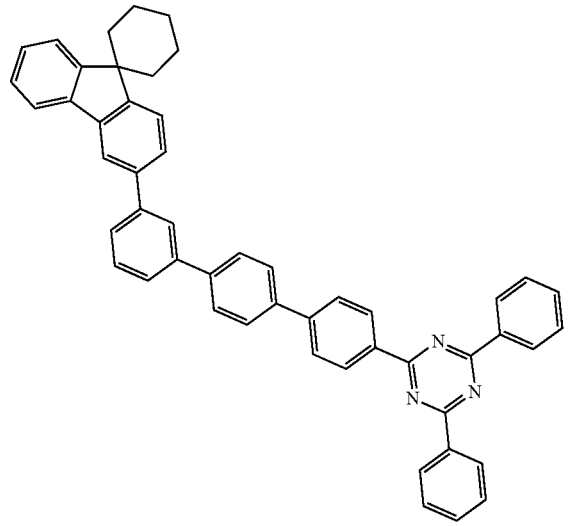

Inv 298
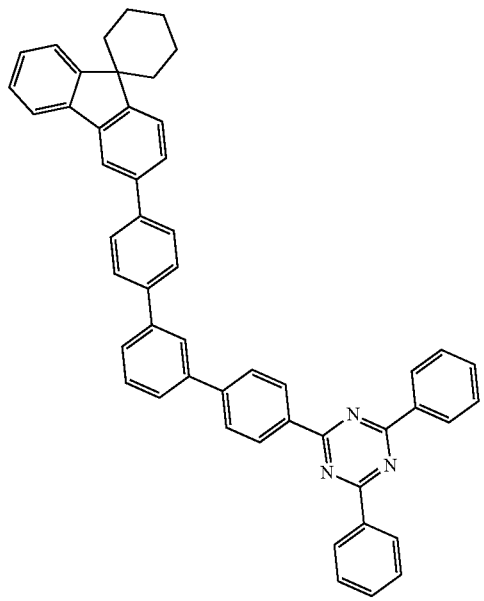
Inv 299
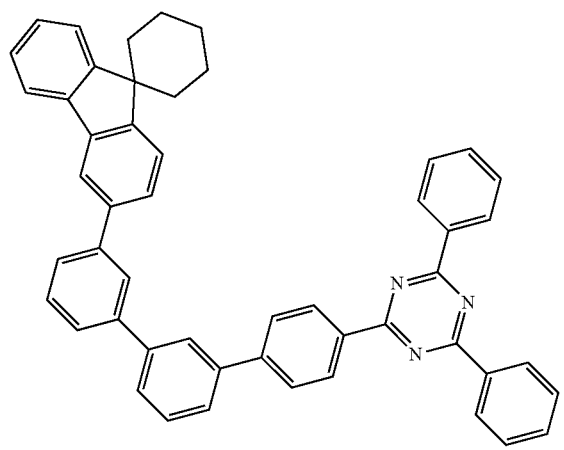
Inv 300
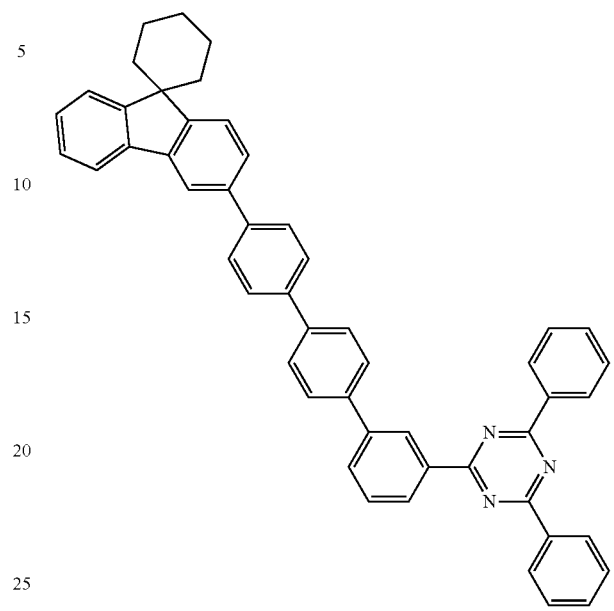
Inv 301
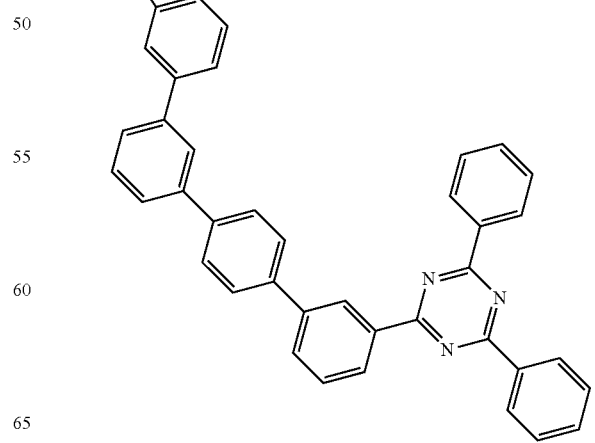

Inv 302
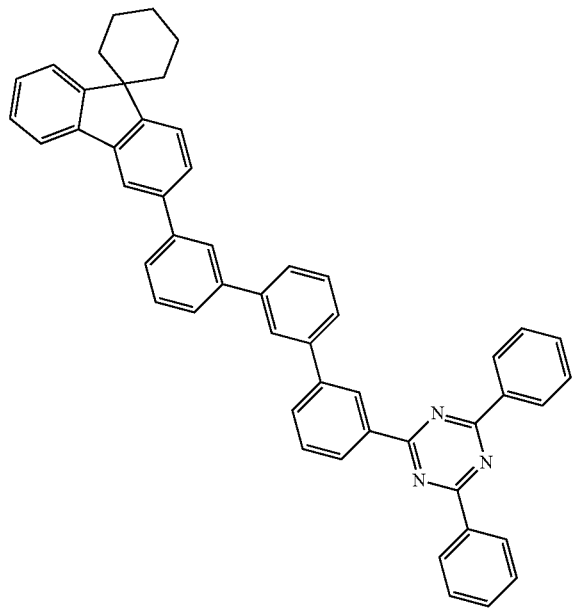
Inv 303
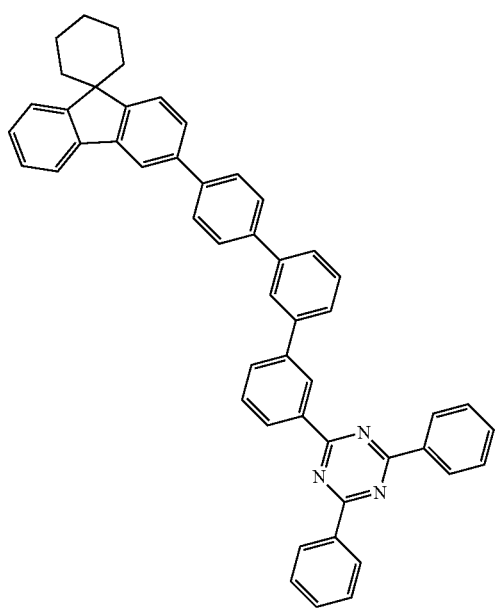
Inv 304
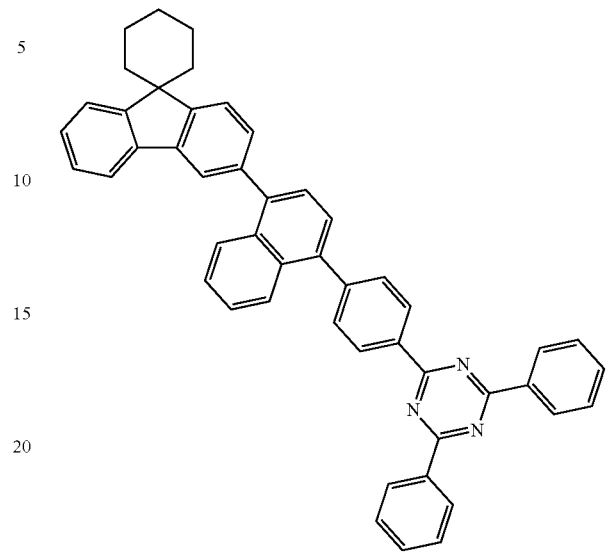
Inv 305
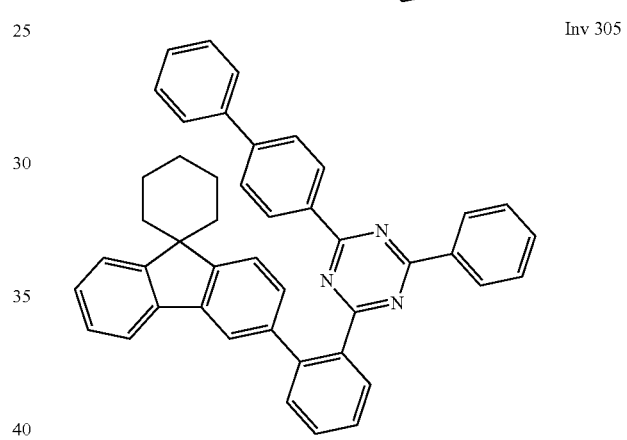
Inv 306
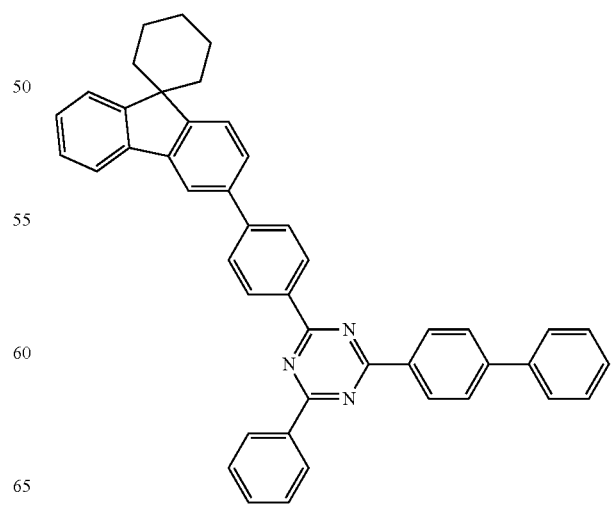

Inv 307
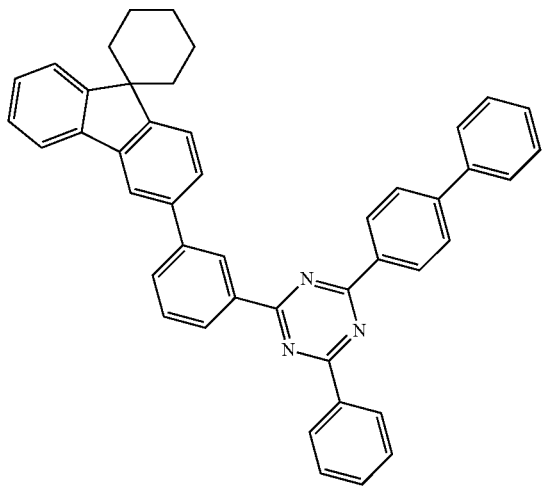
Inv 308
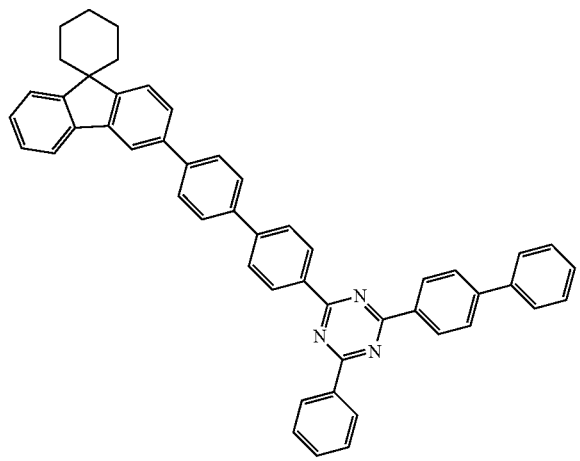
Inv 309
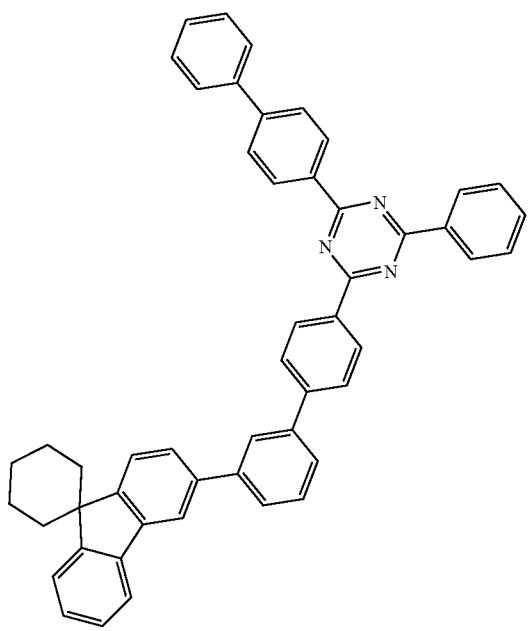
Inv 310
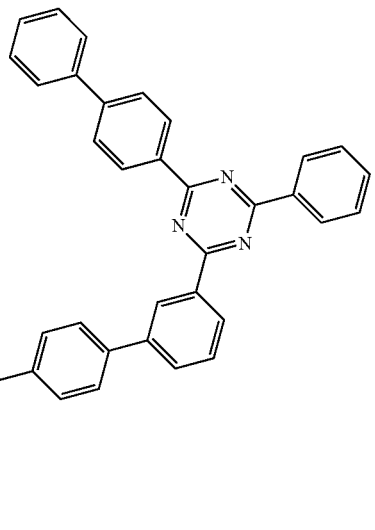
Inv 311
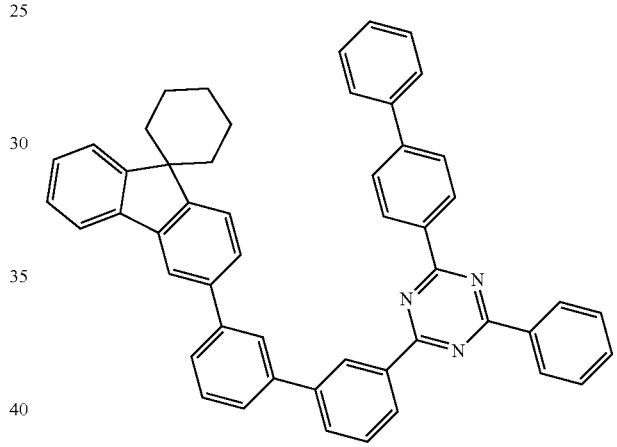
Inv 312
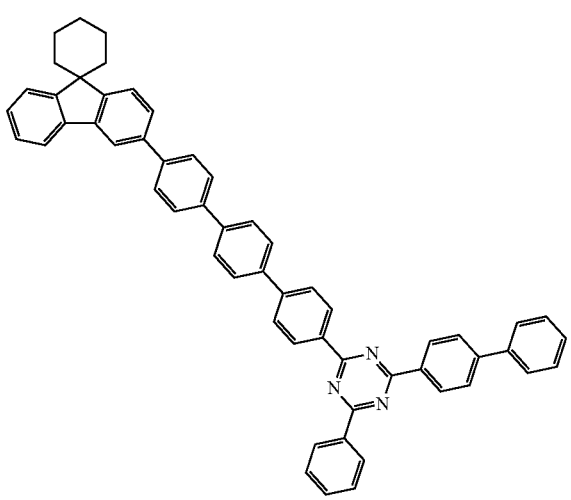

Inv 313
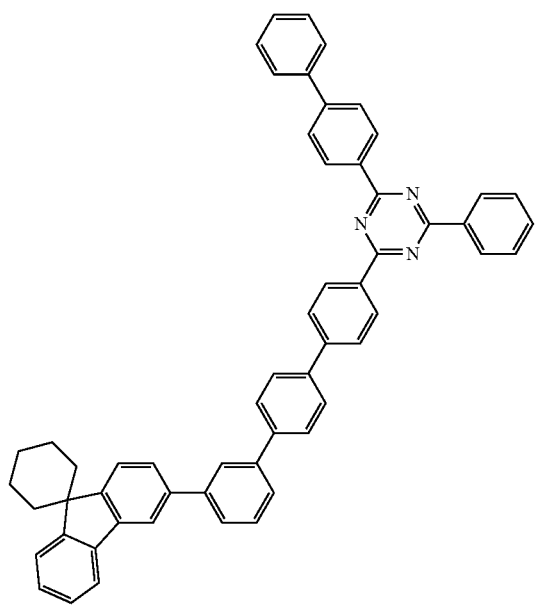
Inv 314
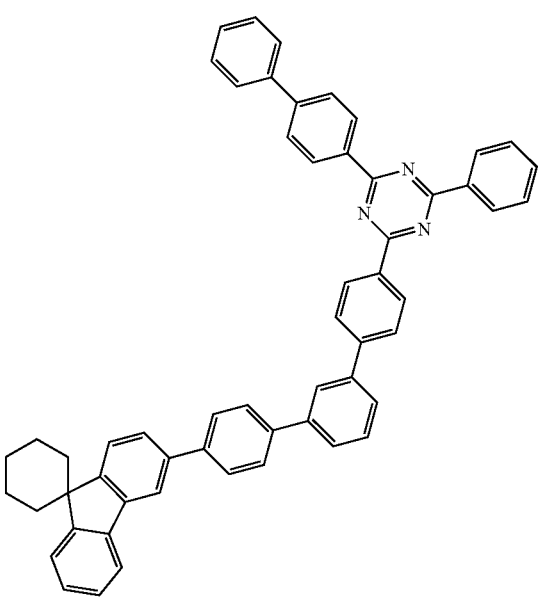
Inv 315
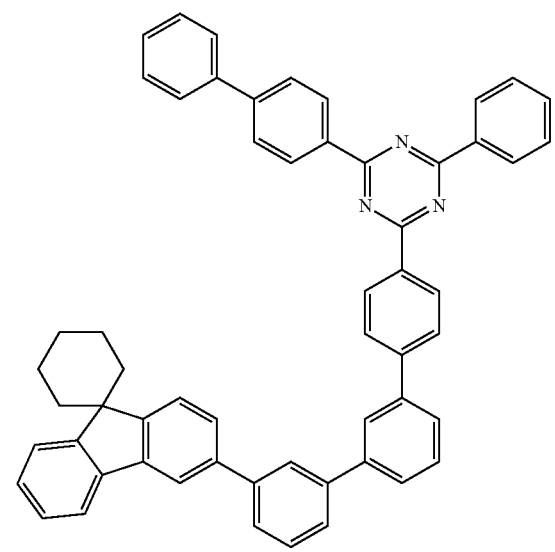
Inv 316
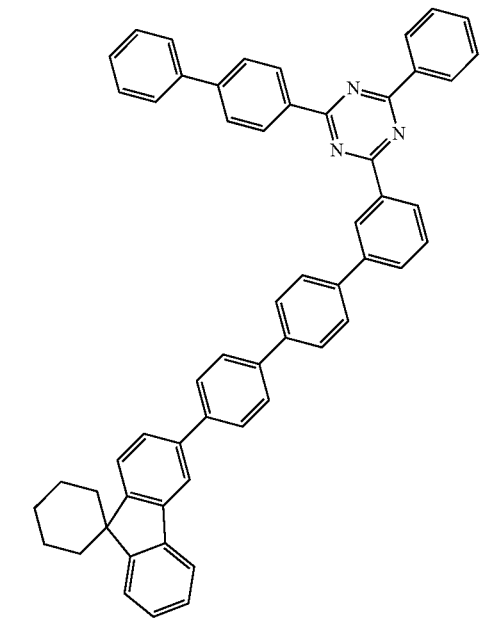

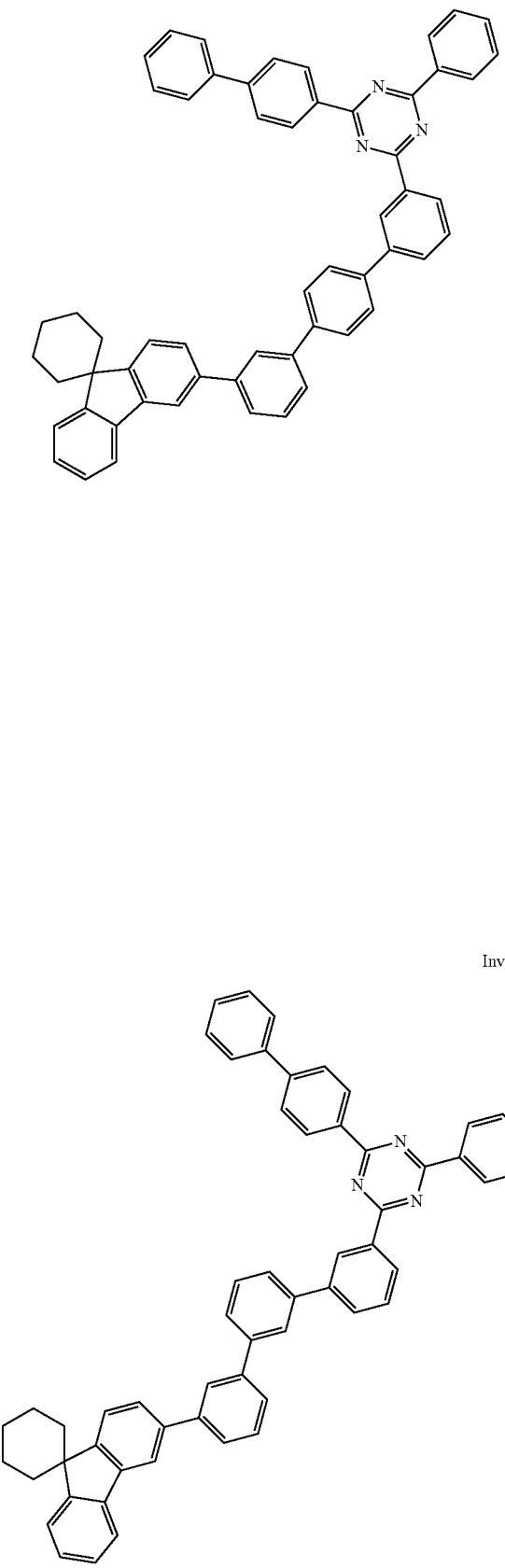
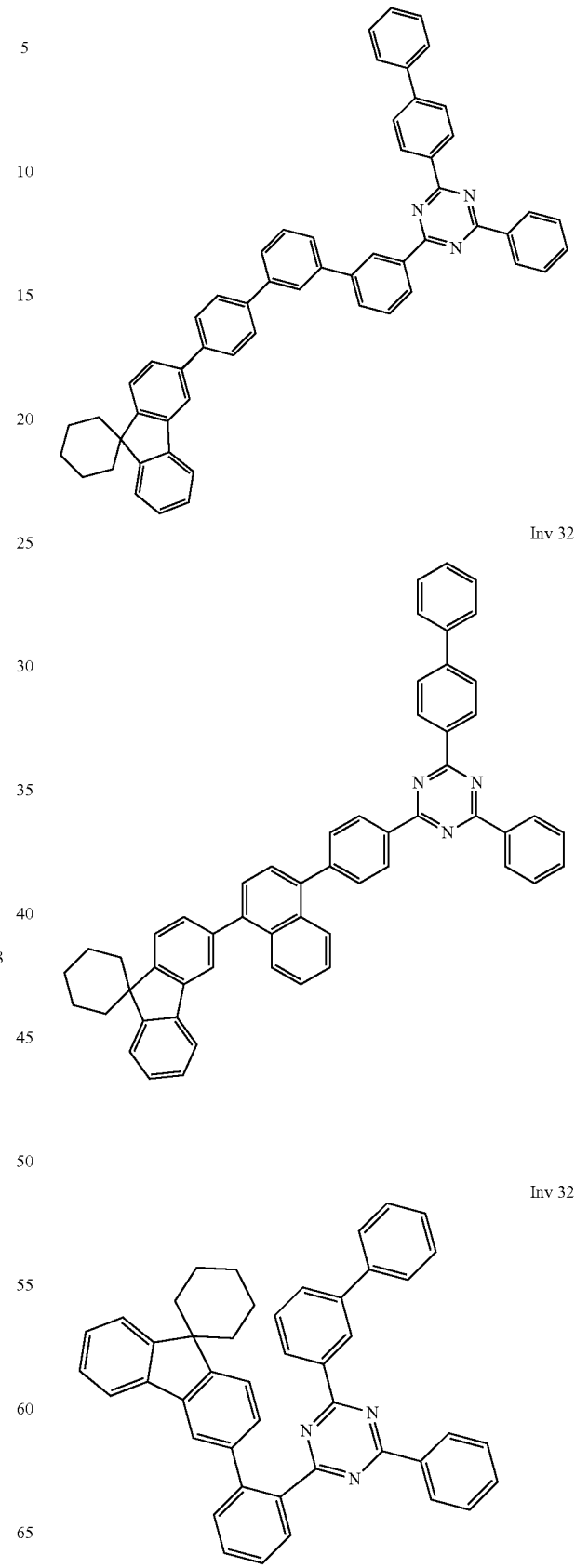

Inv 322
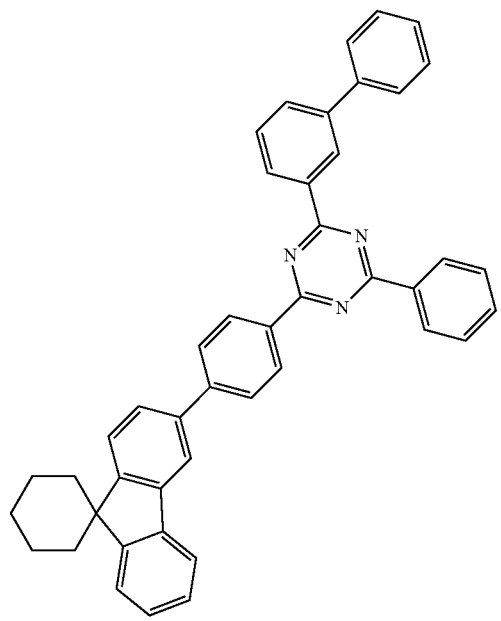
Inv 323
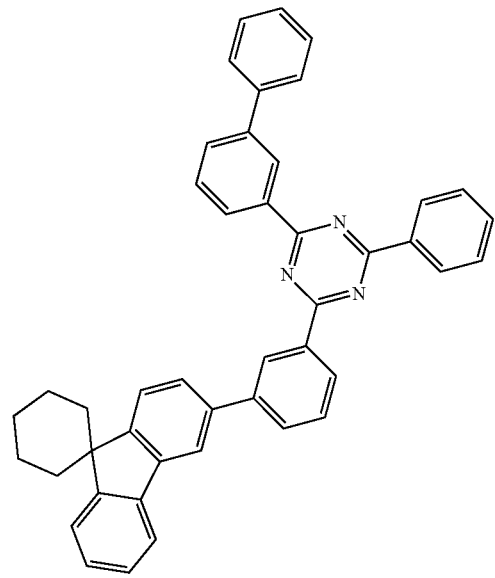
Inv 324
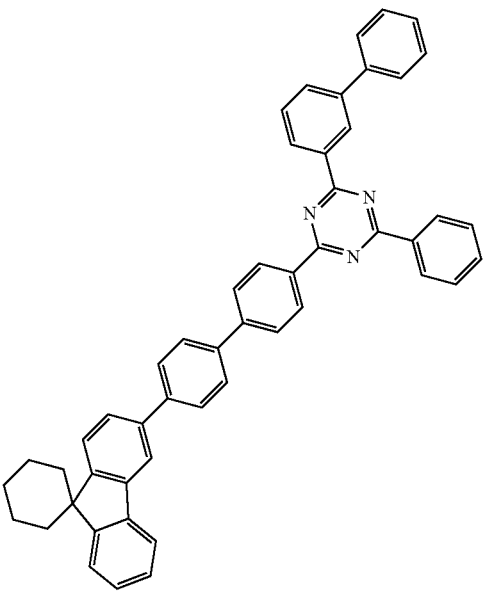
Inv 325
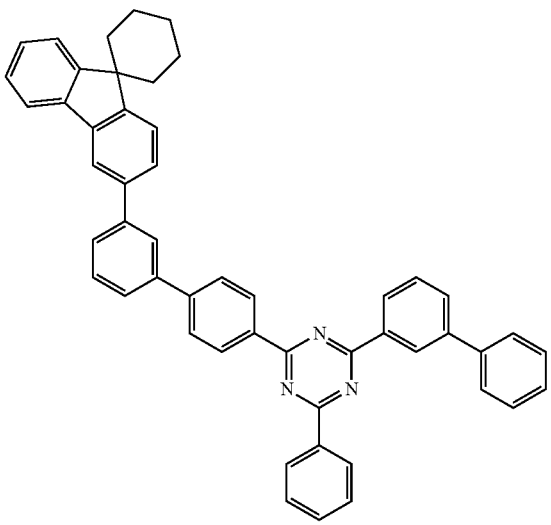

Inv 326
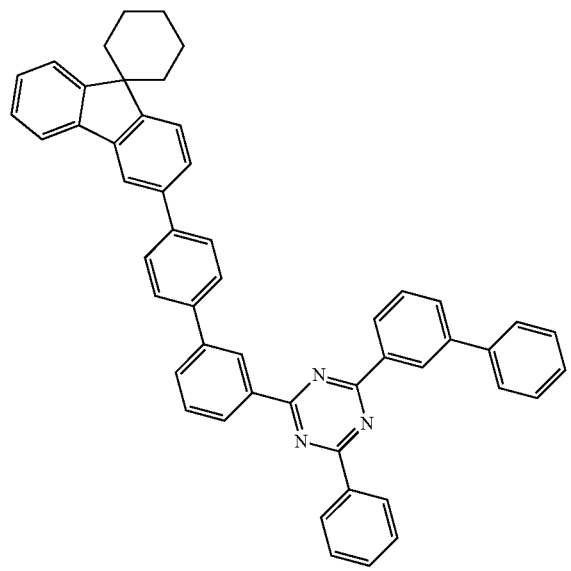
Inv 328
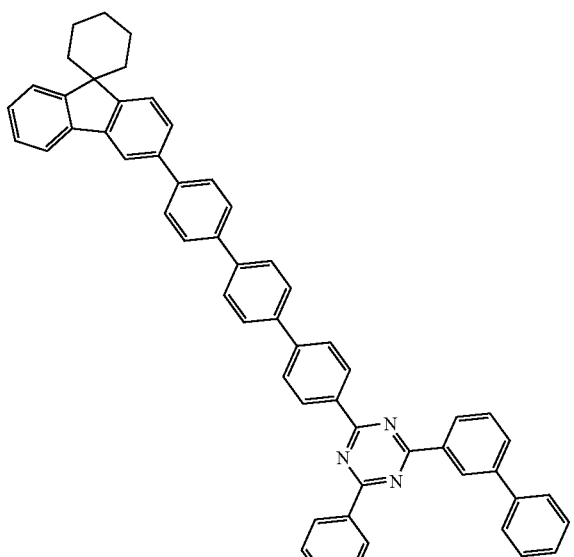
Inv 327
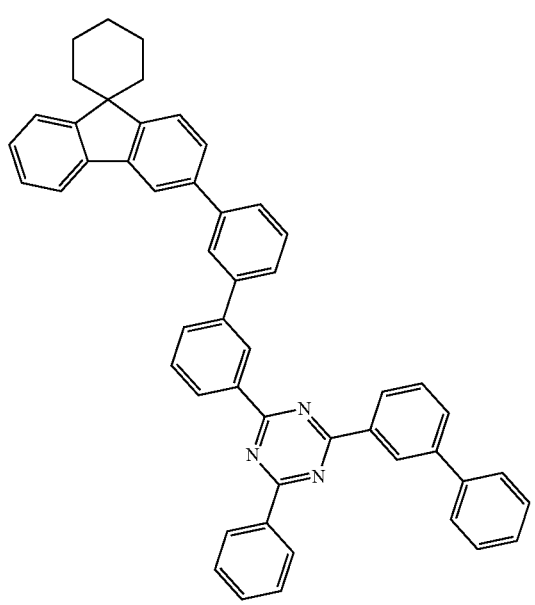
Inv 329
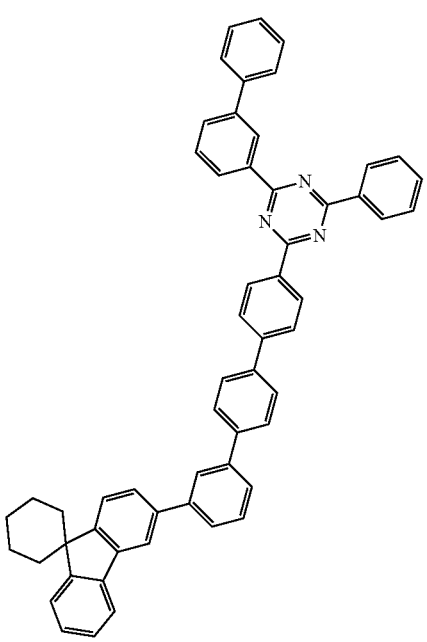

-continued
Inv 330
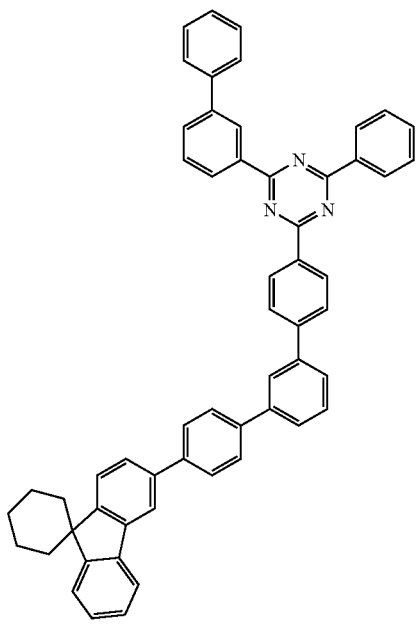
Inv 331
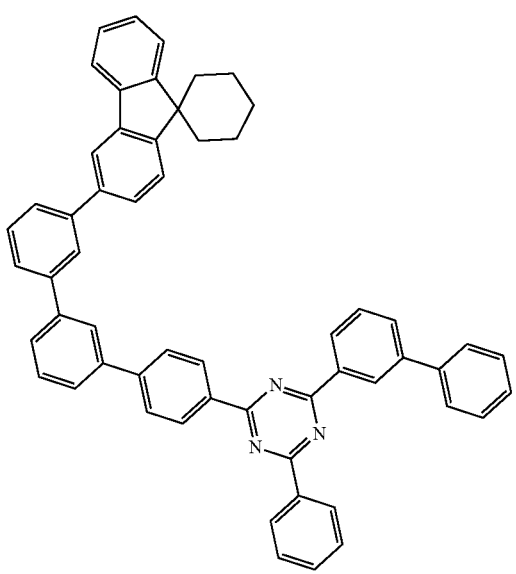
Inv 332
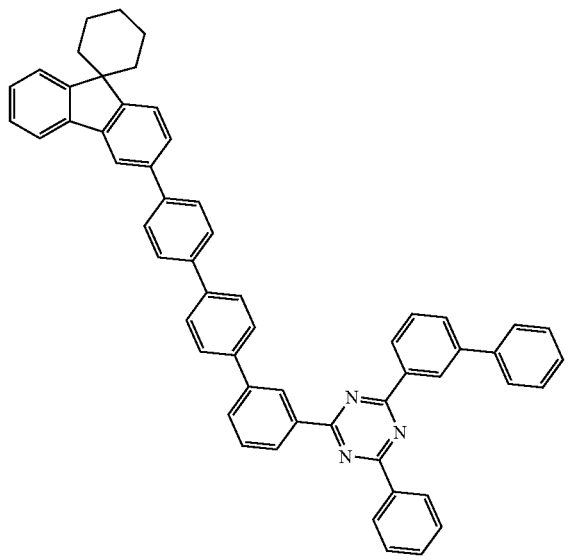
Inv 333
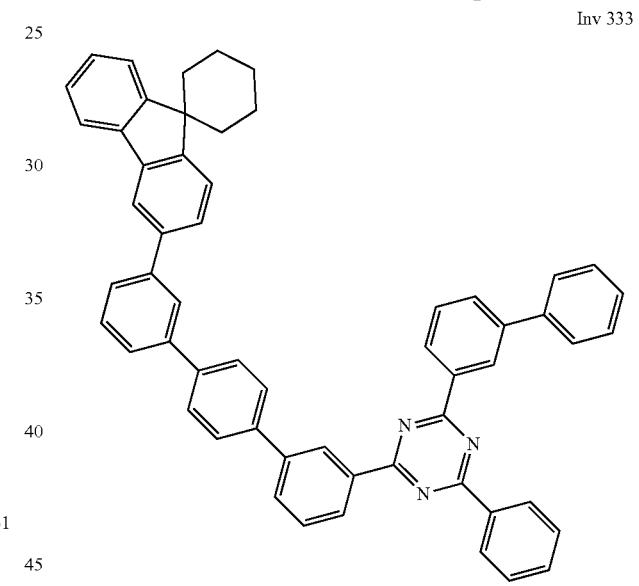
Inv 334
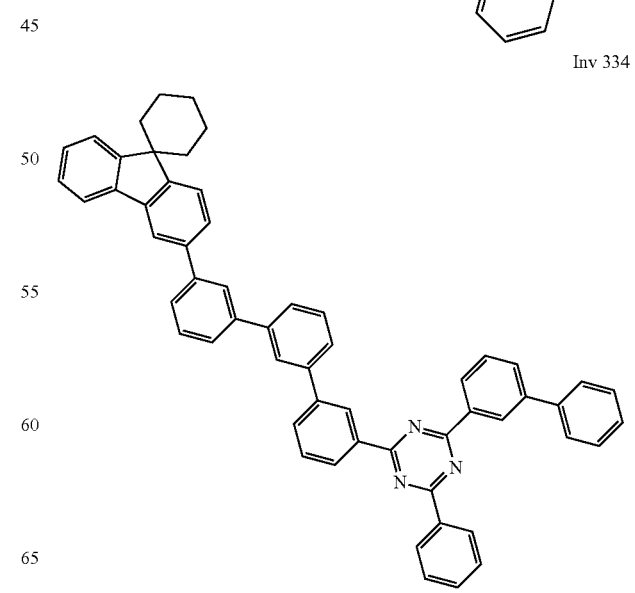

-continued
Inv 335
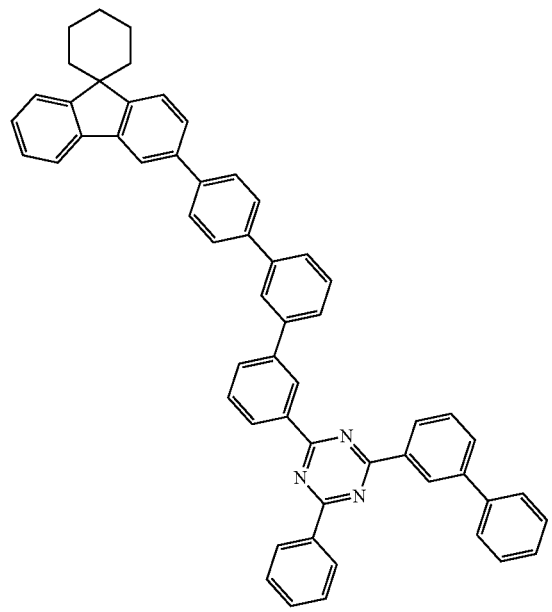
Inv 338
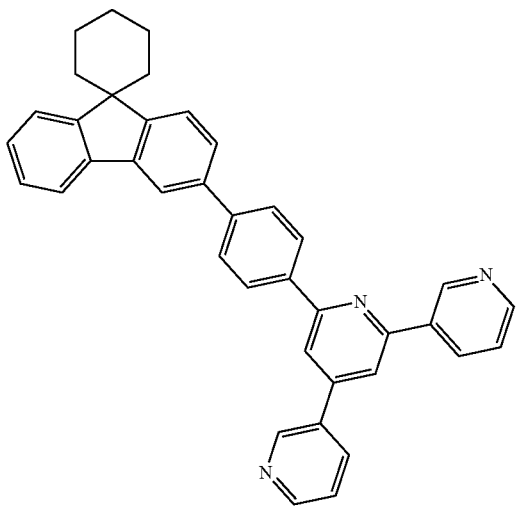
Inv 336
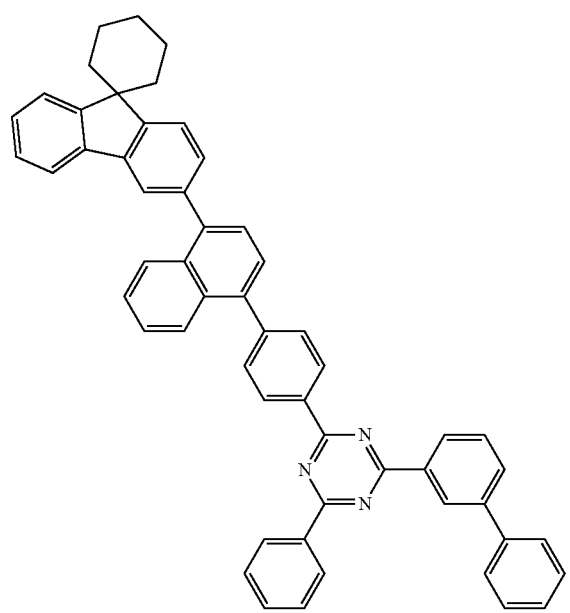
Inv 339
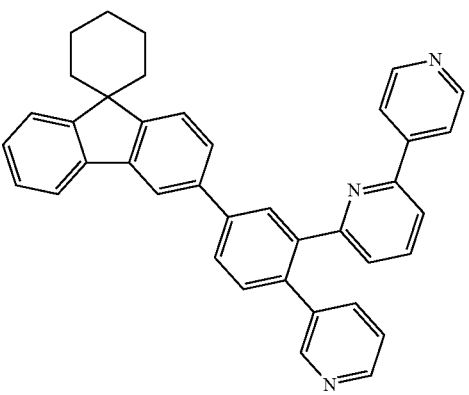
Inv 337
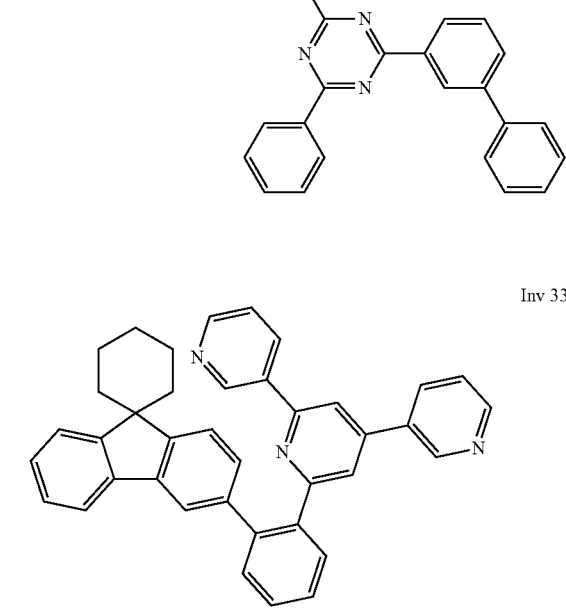
Inv 340
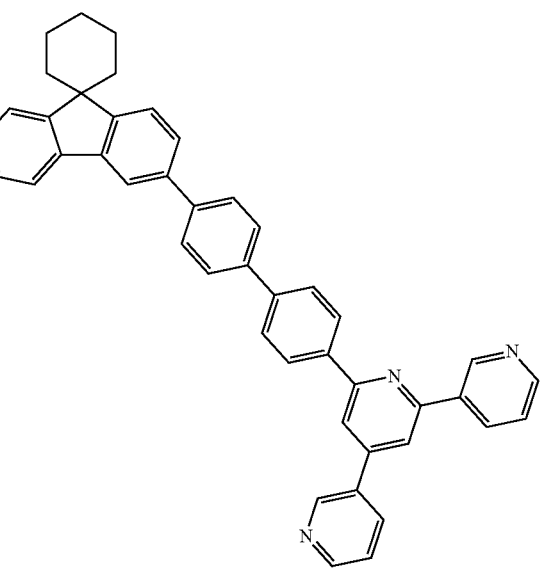

Inv 341
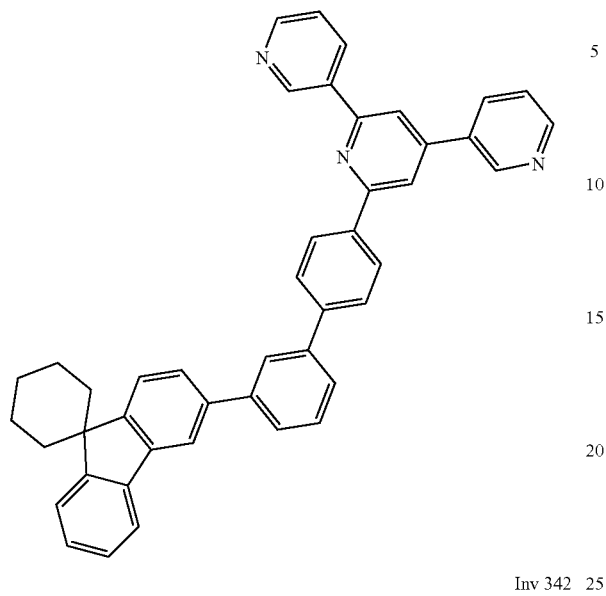
Inv 344
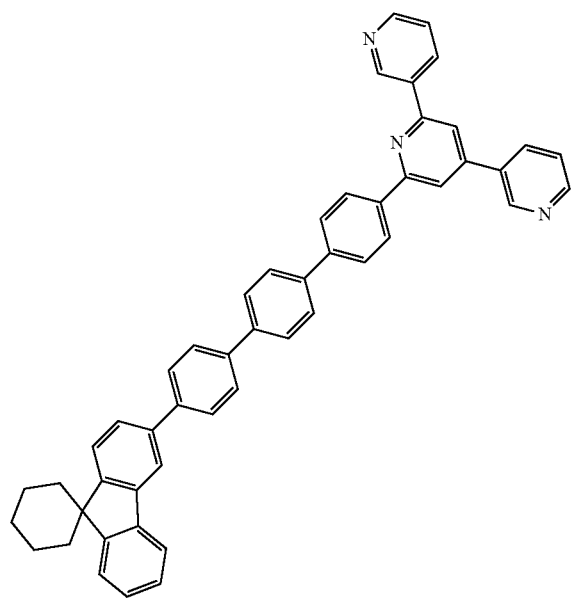
Inv 342
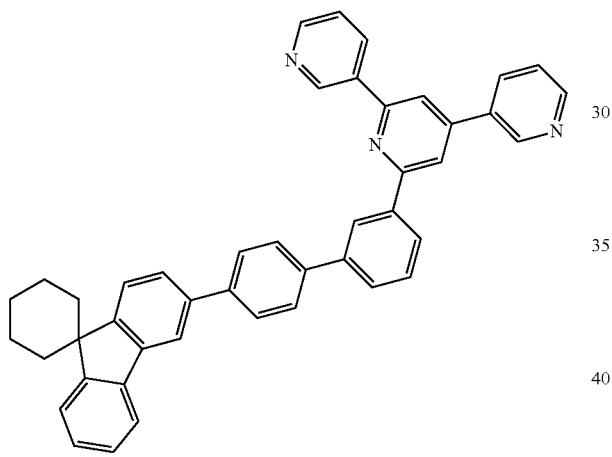
Inv 345
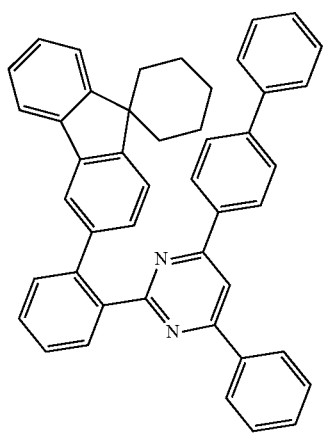
Inv 343
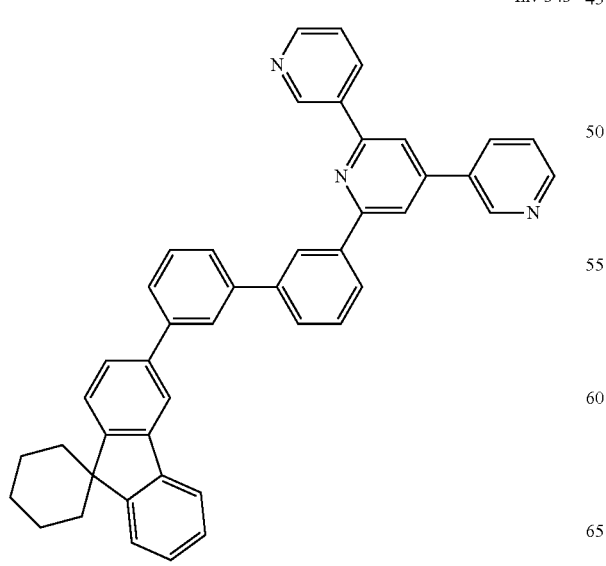
Inv 346
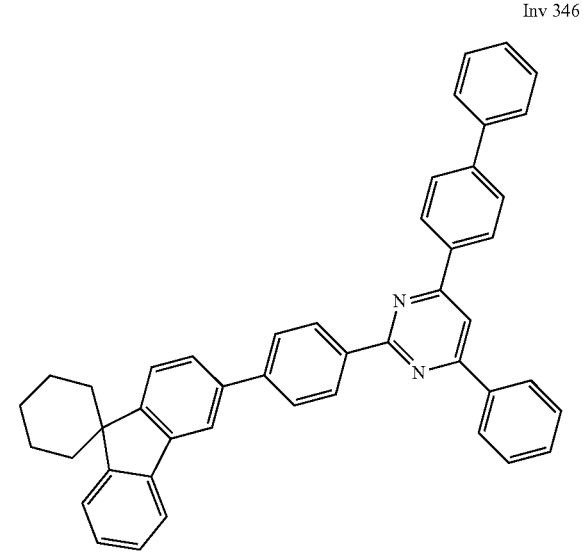

-continued
Inv 347
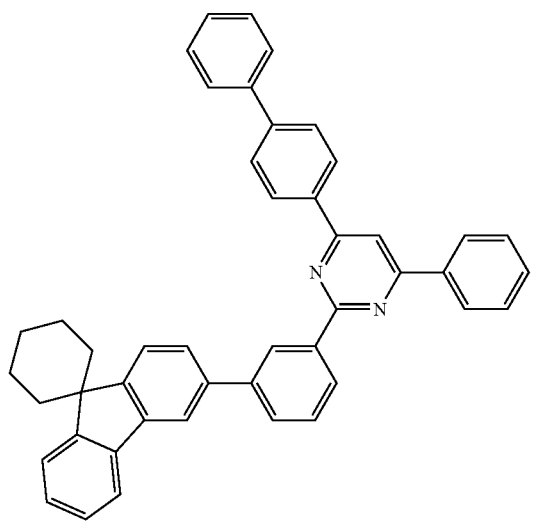
Inv 348
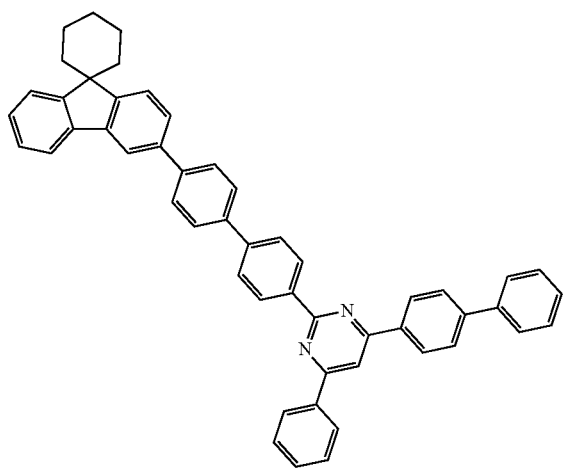
Inv 349
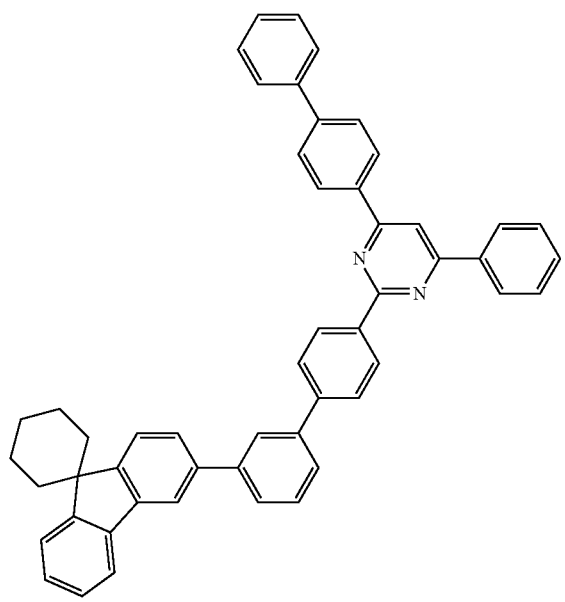
-continued
Inv 350
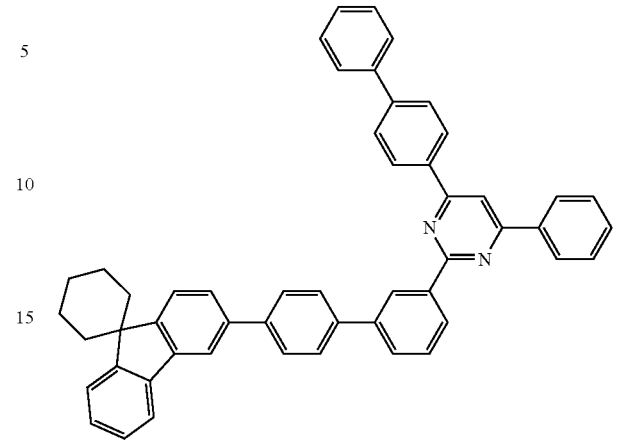
Inv 351
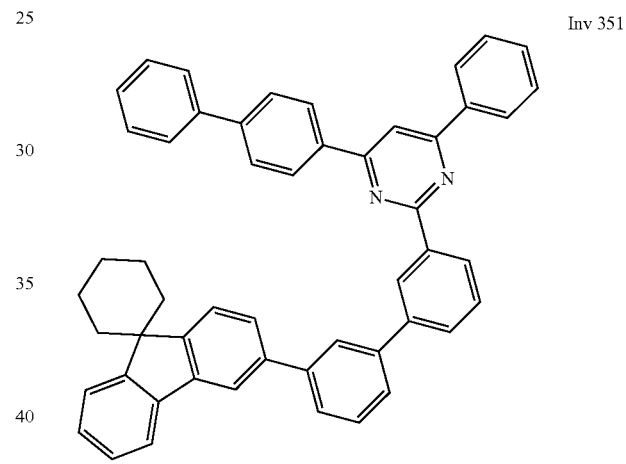
Inv 352
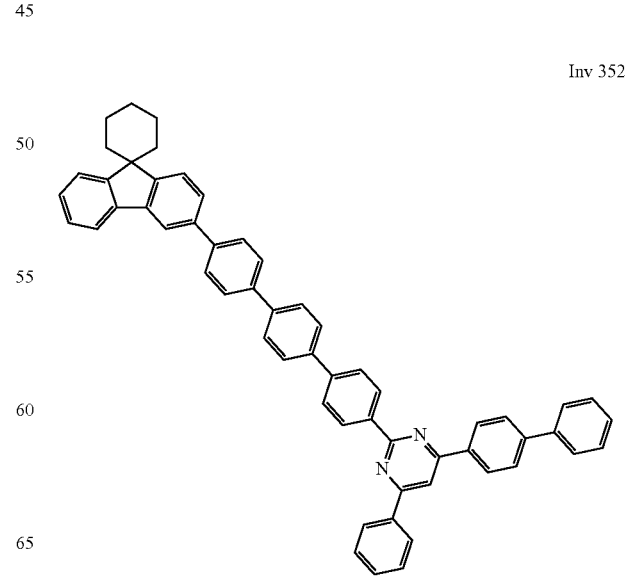

-continued
Inv 353
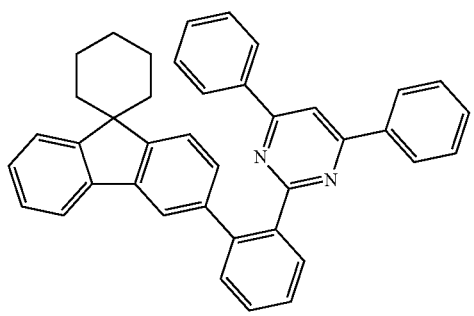
Inv 354
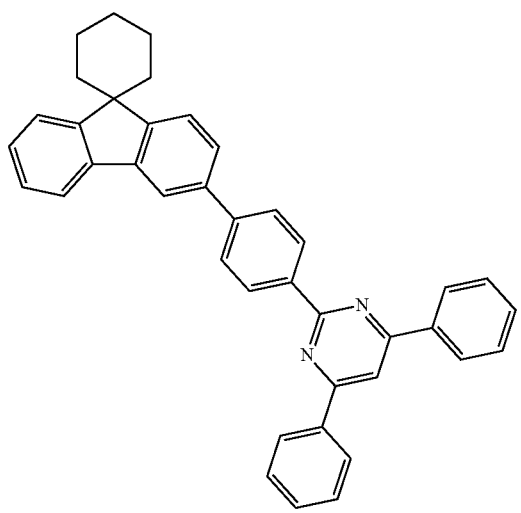
Inv 355
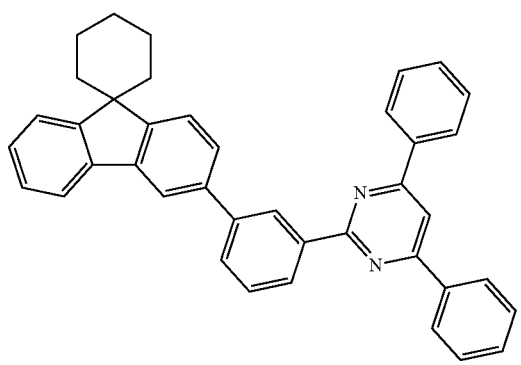
-continued
Inv 356
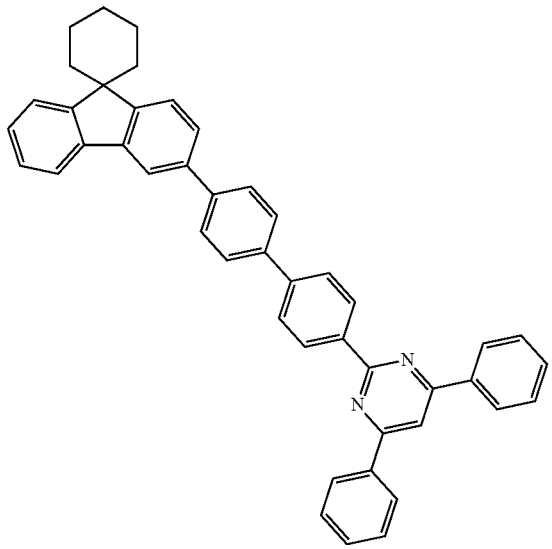
Inv 357
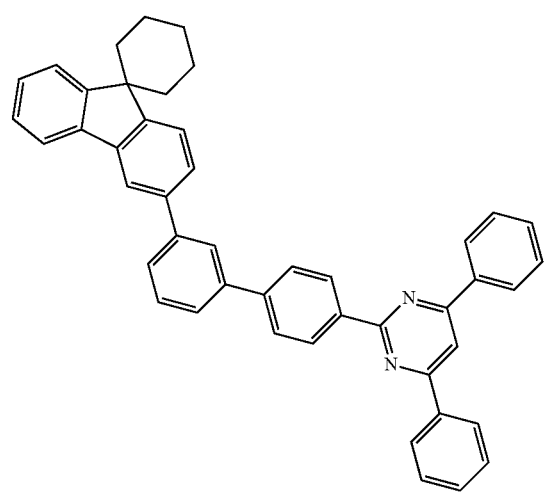
Inv 358

Inv 359
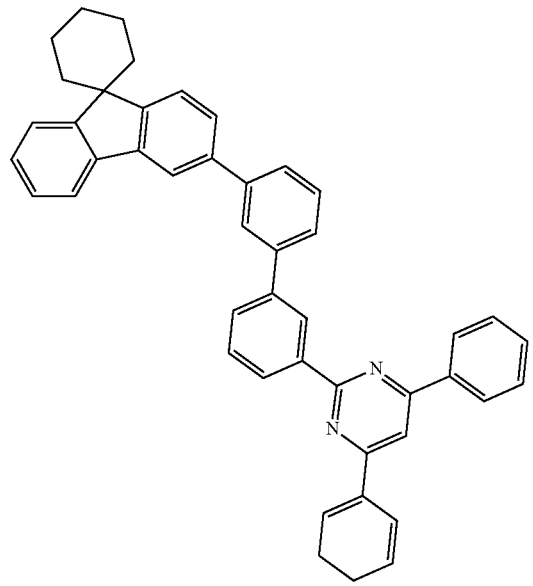
Inv 360
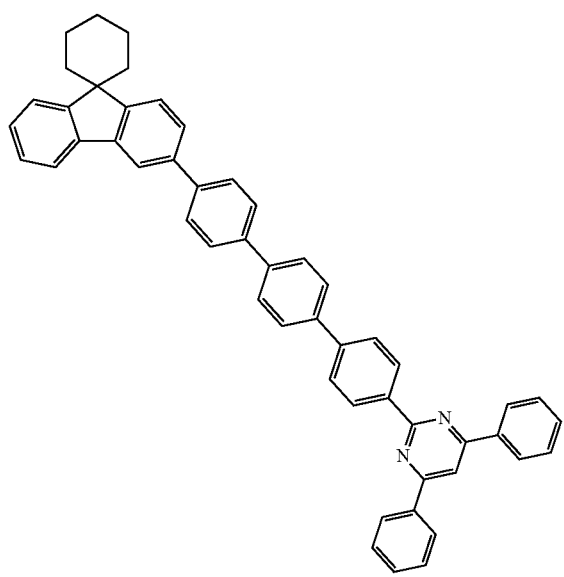
Inv 361
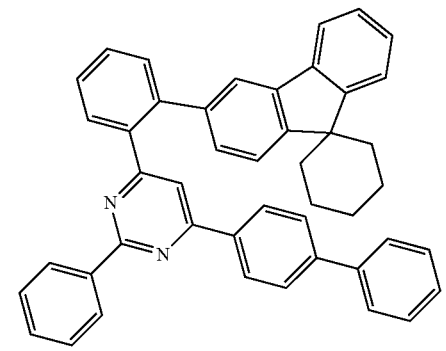
Inv 362
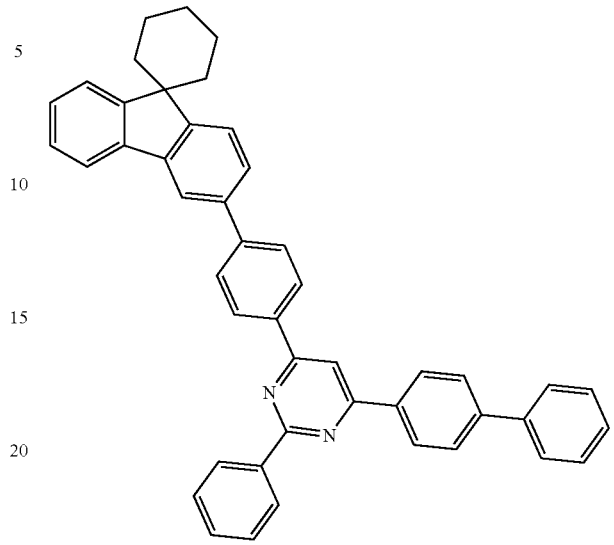
Inv 363
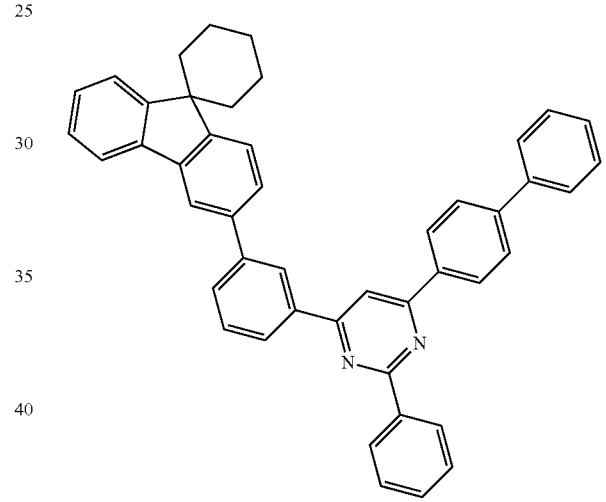
Inv 364
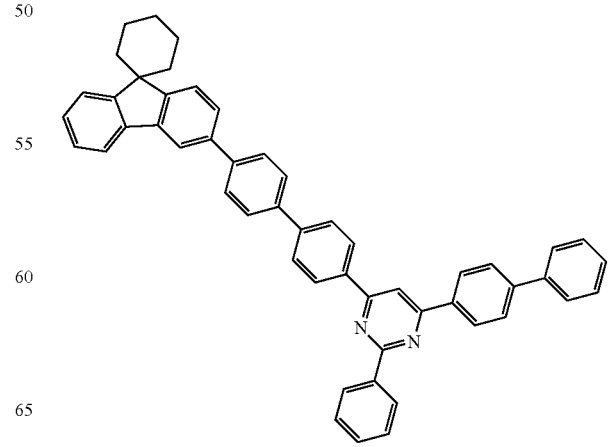

-continued
Inv 365
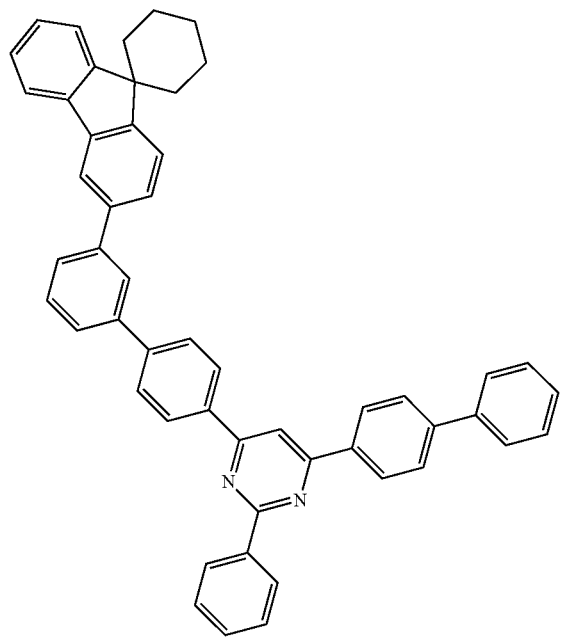
Inv 368
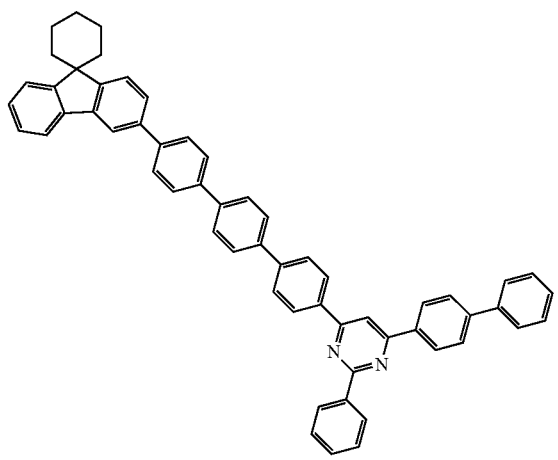
Inv 366
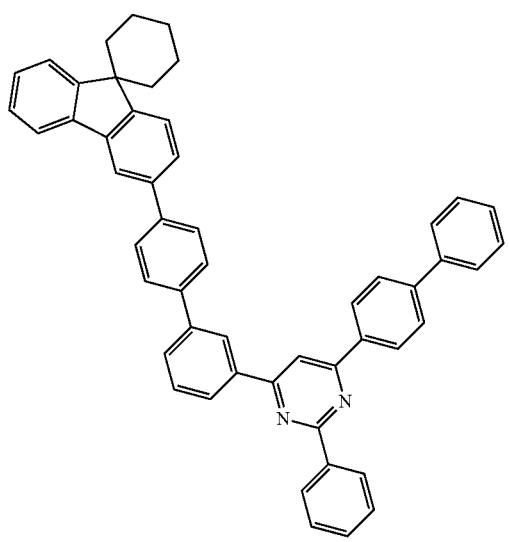
Inv 369
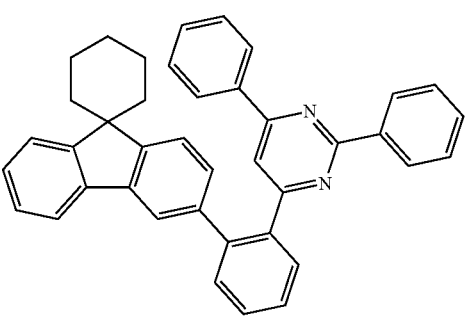
Inv 367
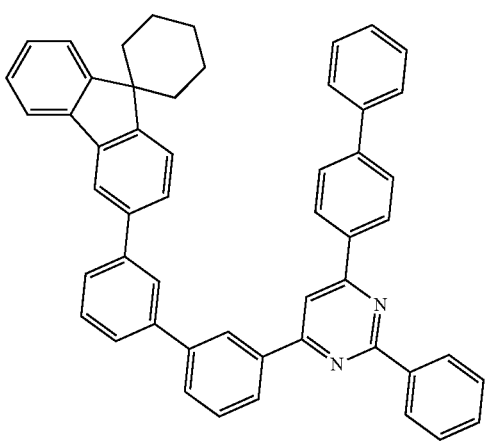
Inv 370
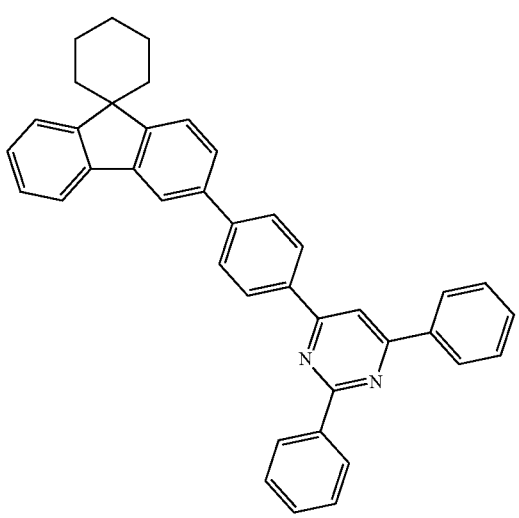

Inv 371
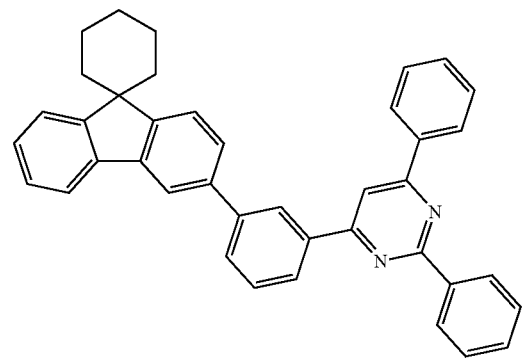
Inv 372
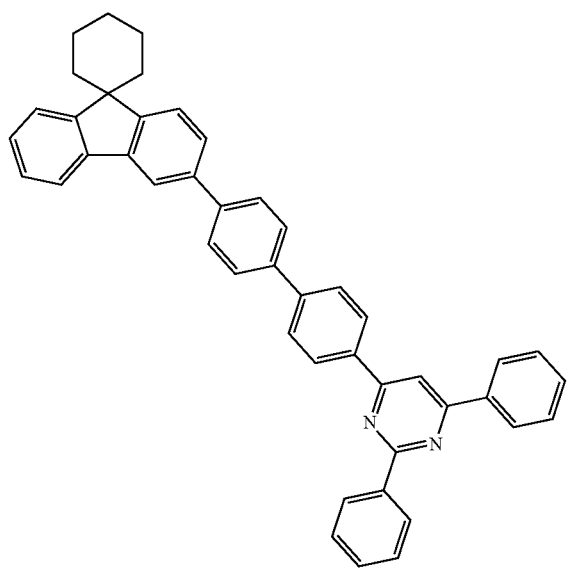
Inv 373
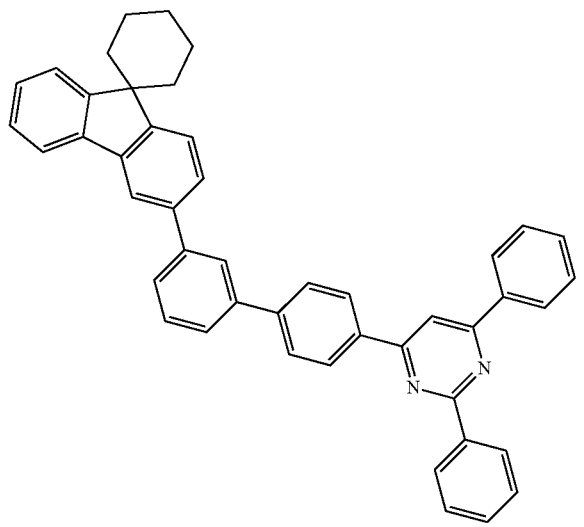
Inv 374
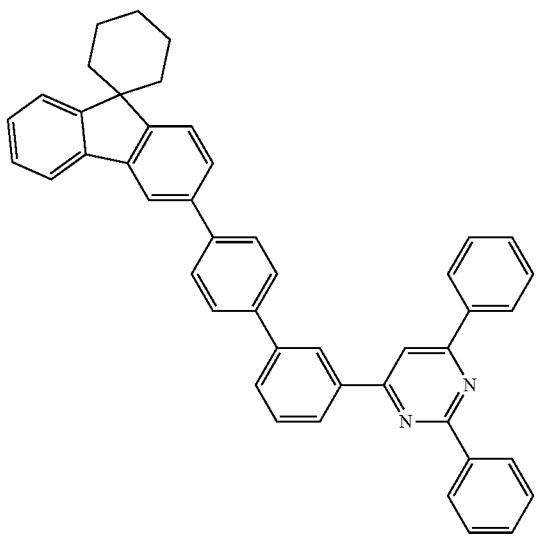
Inv 375
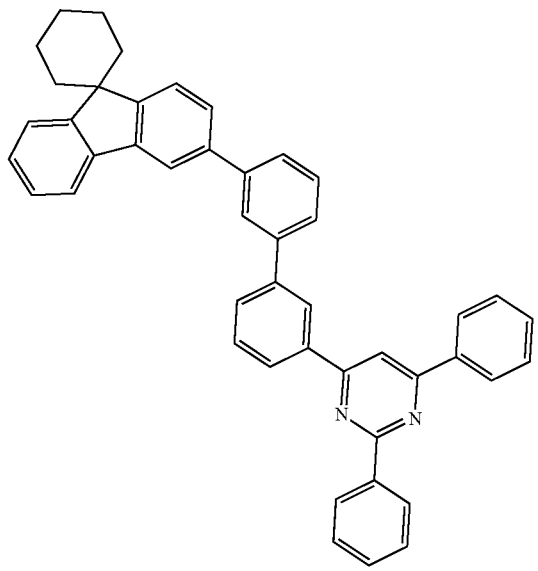

Inv 376
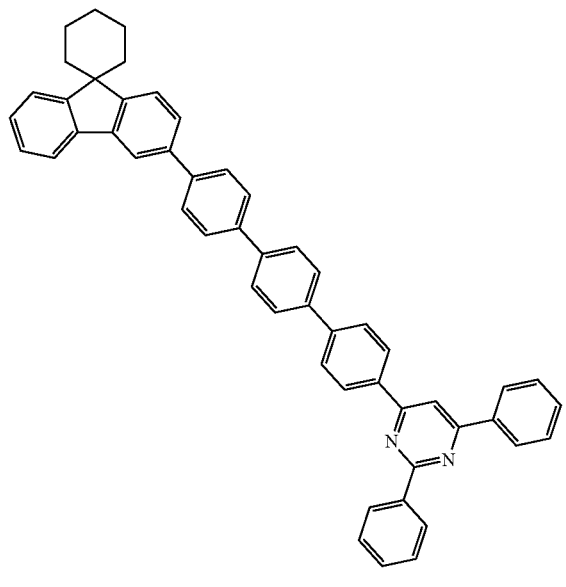
Inv 377
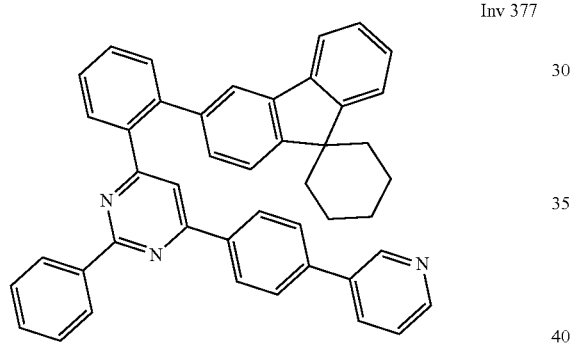
Inv 378
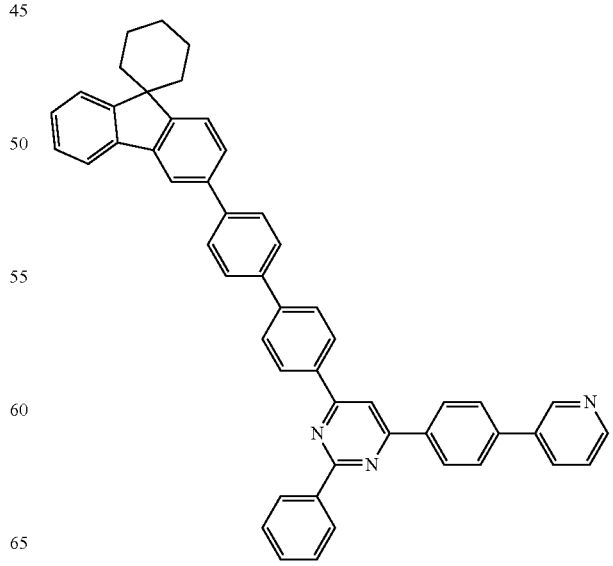
Inv 379
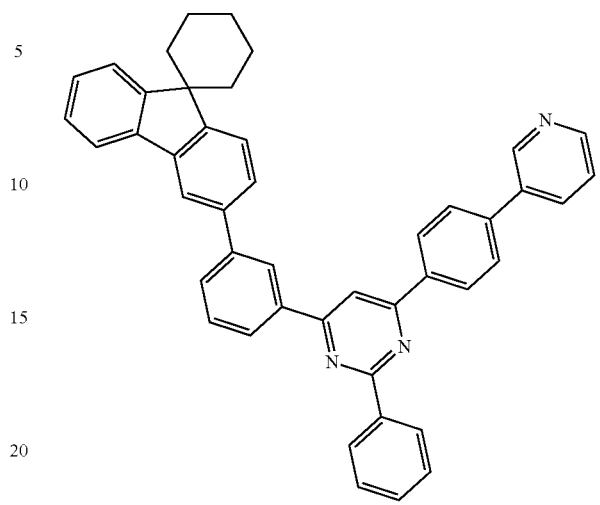
Inv 380

Inv 381
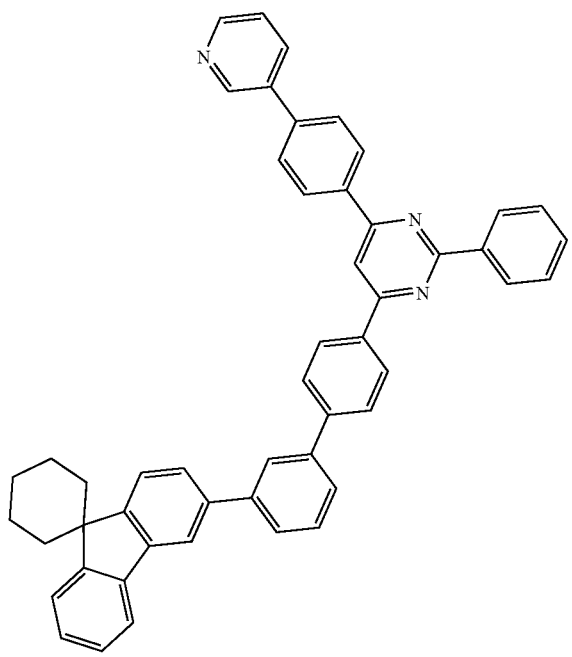
Inv 382
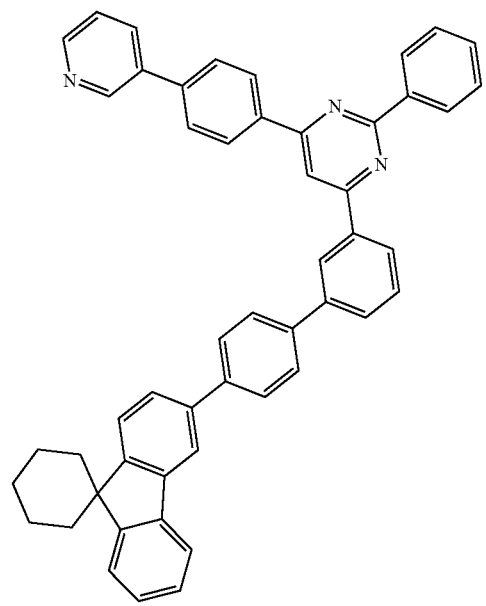
Inv 383
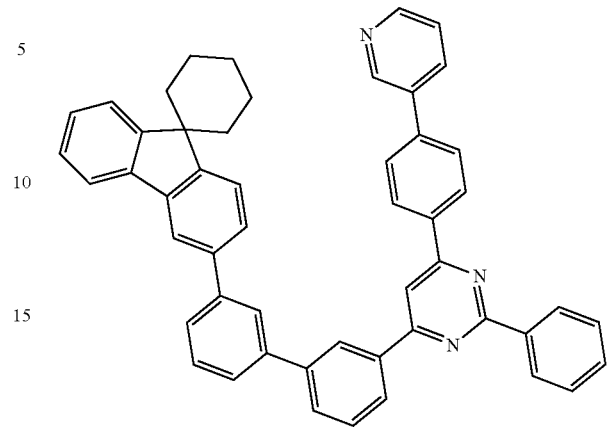
Inv 384
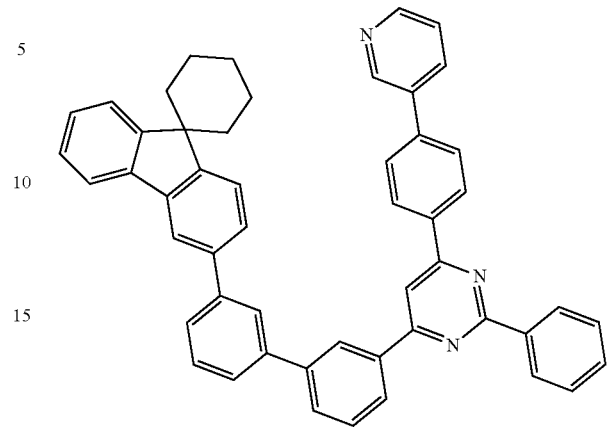
Inv 385
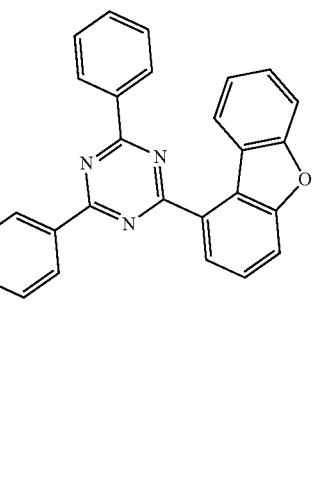

Inv 386
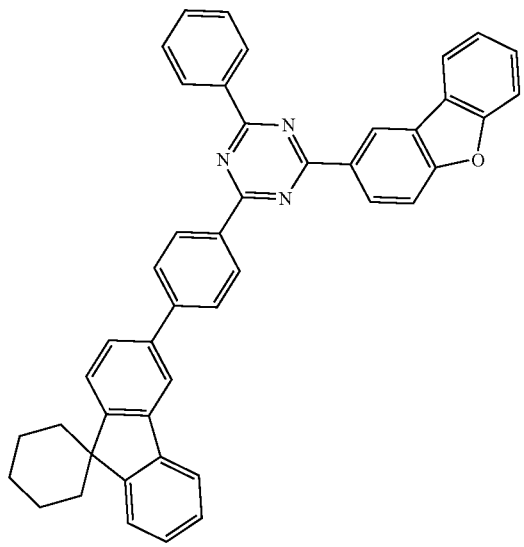
Inv 387
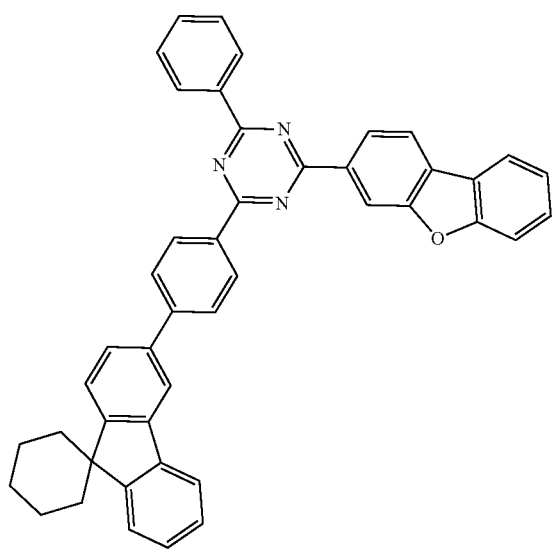
Inv 388
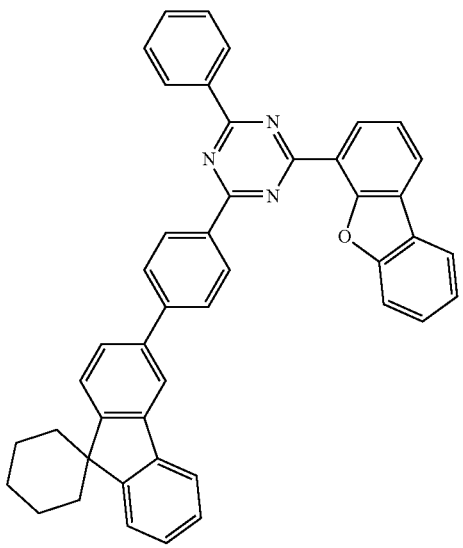
Inv 389
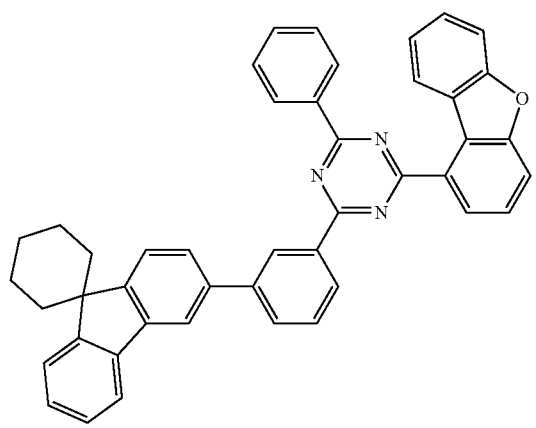
Inv 390
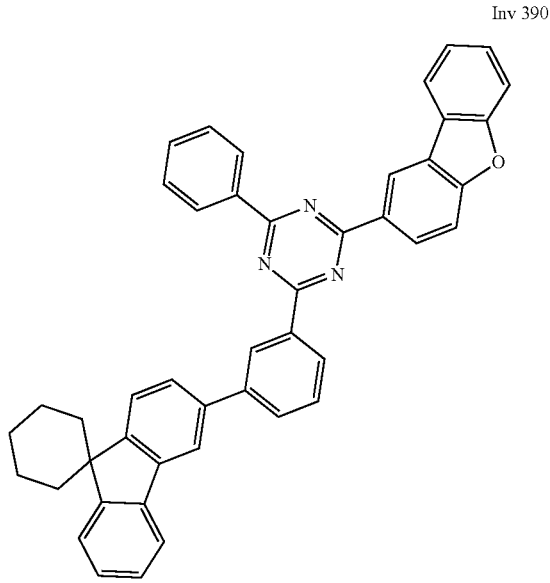

Inv 391
Inv 392
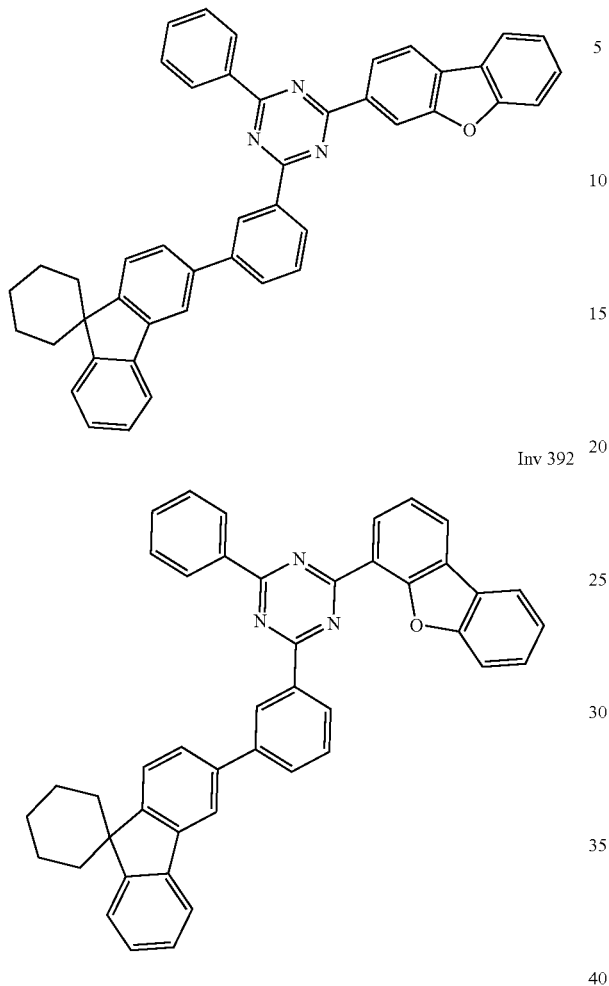
Inv 394
Inv 395
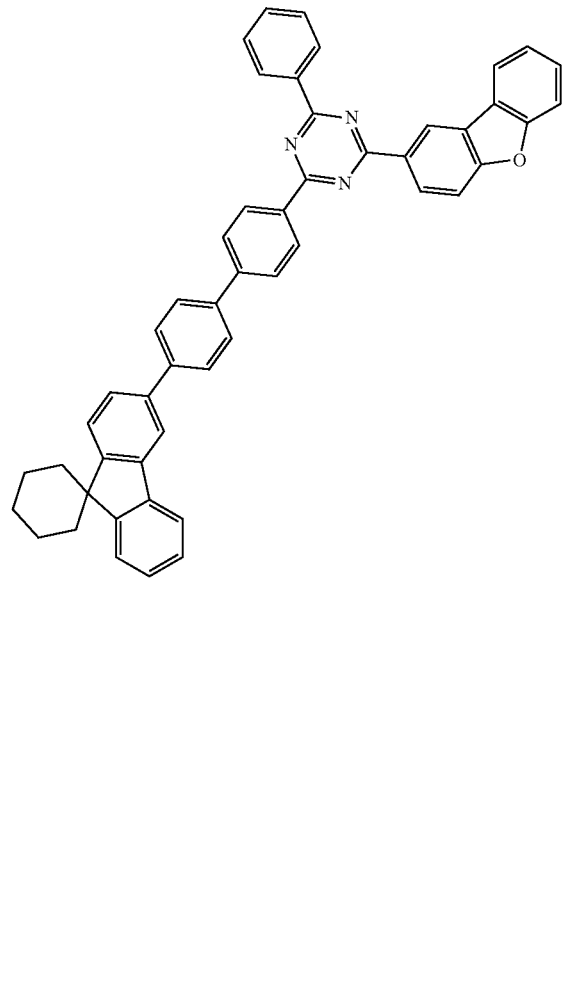
Inv 393
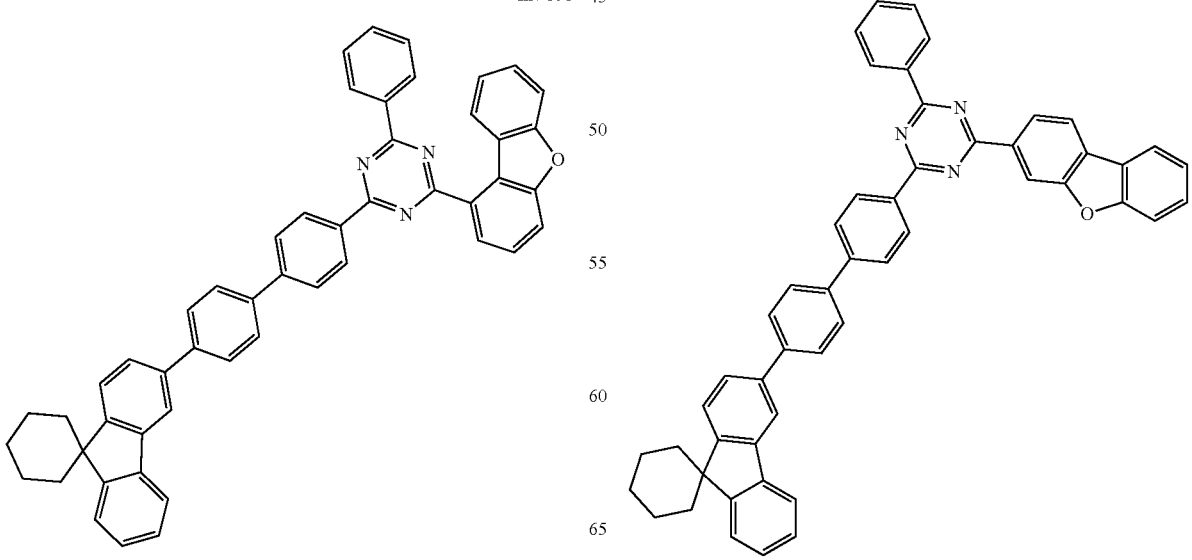

Inv 396
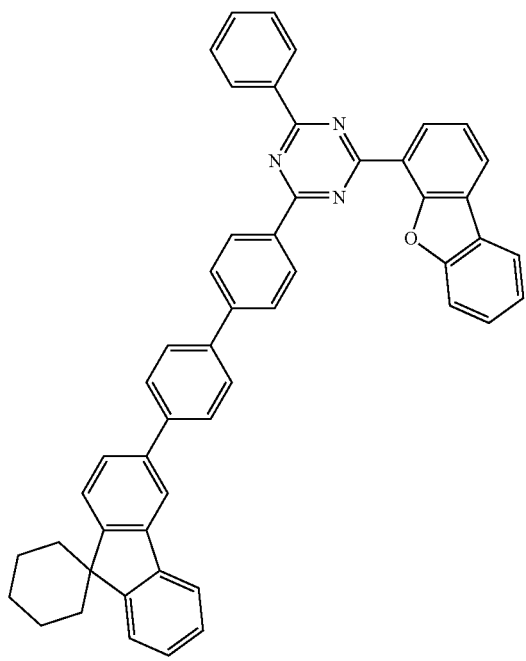
Inv 398
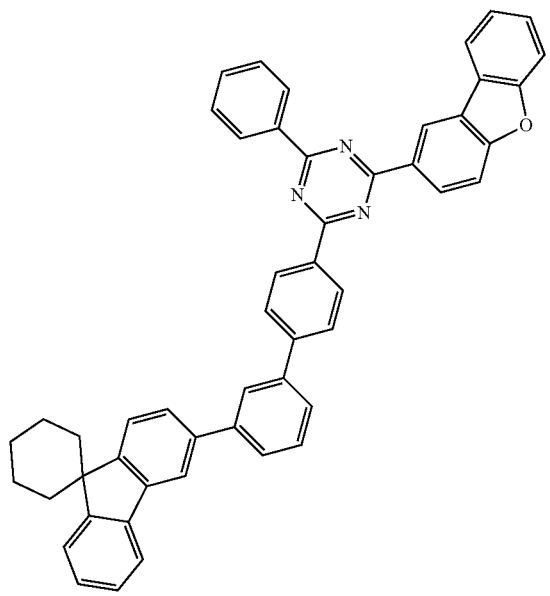
Inv 397
Inv 399
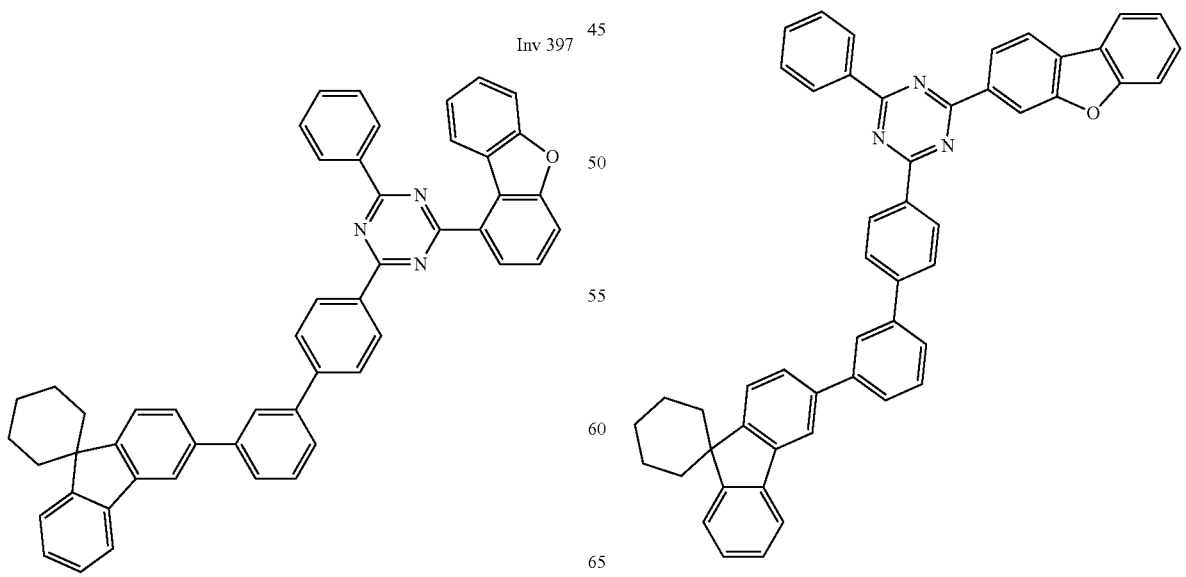

Inv 400
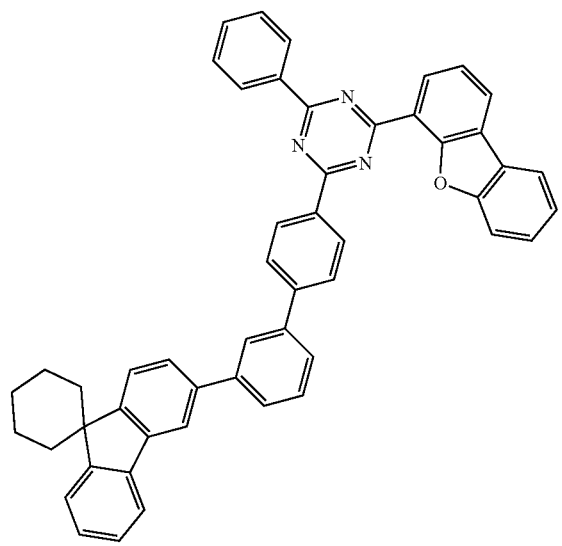
Inv 401
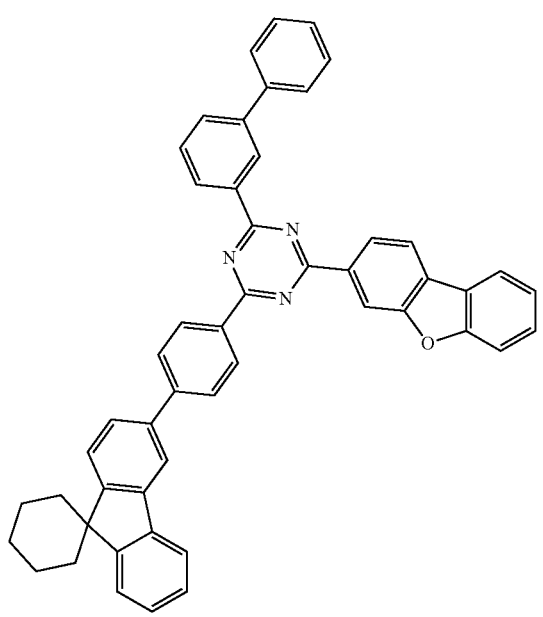
Inv 402
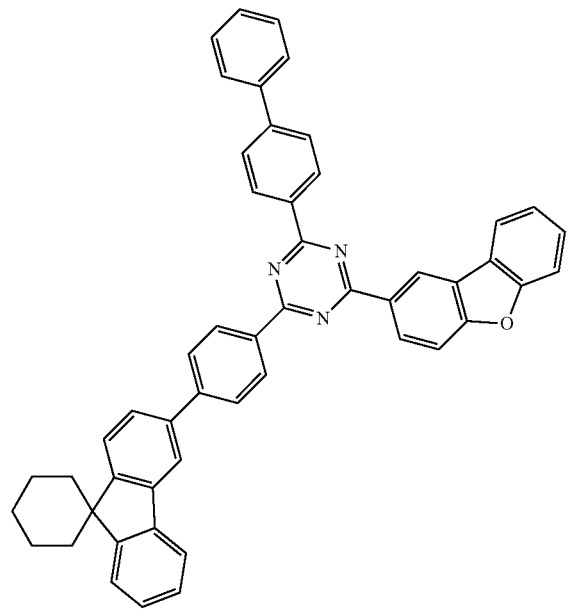
Inv 403
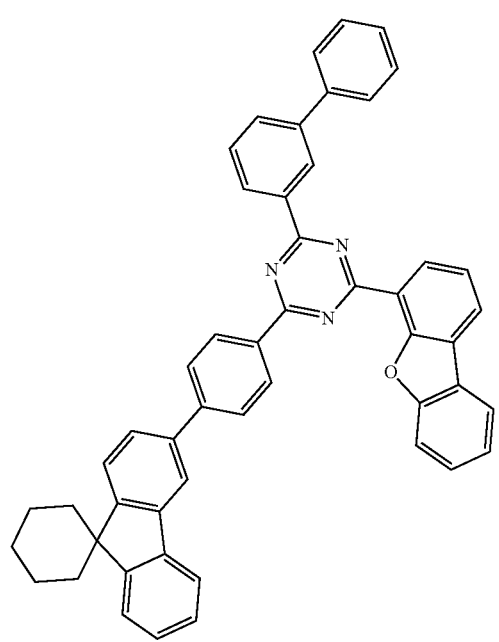

Inv 404
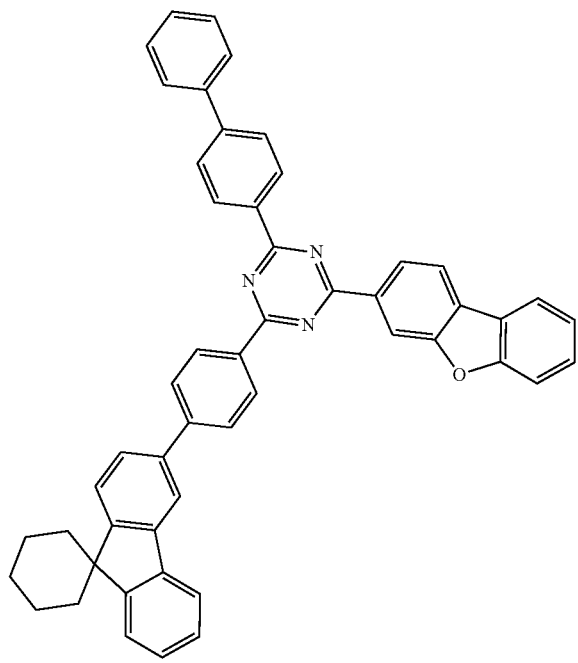
Inv 405
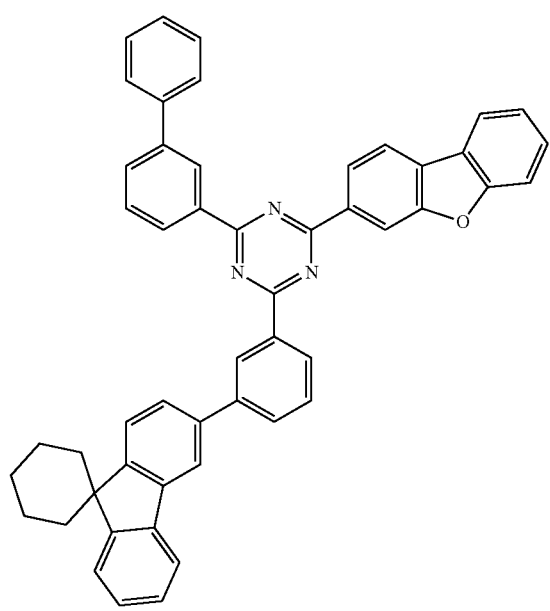
Inv 406
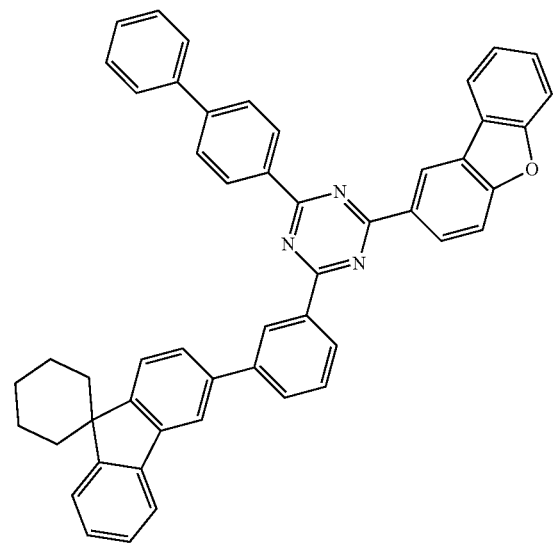
Inv 407
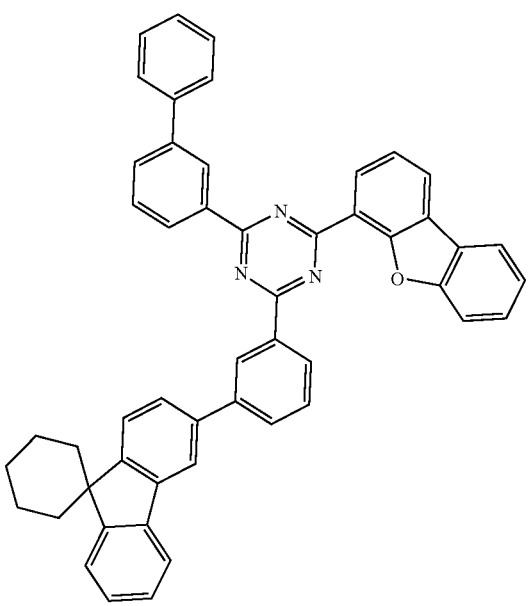

Inv 408
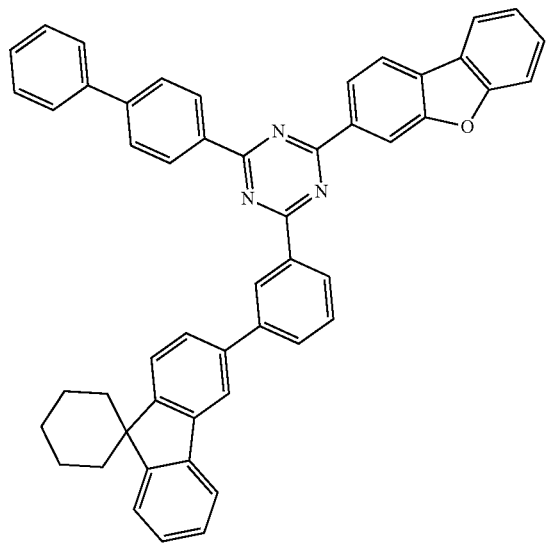
Inv 410
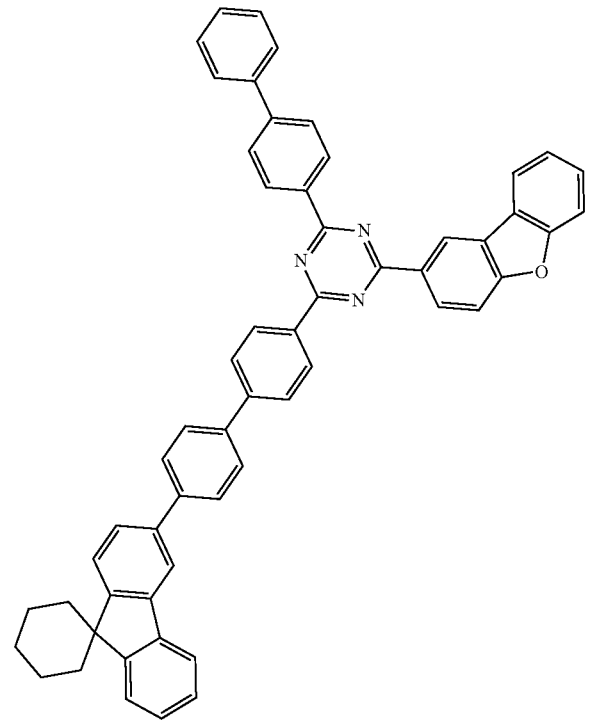
Inv 409
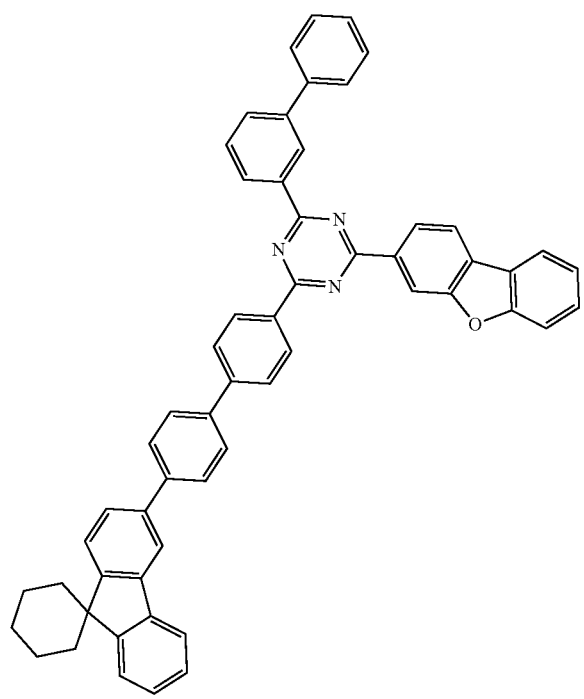
Inv 411
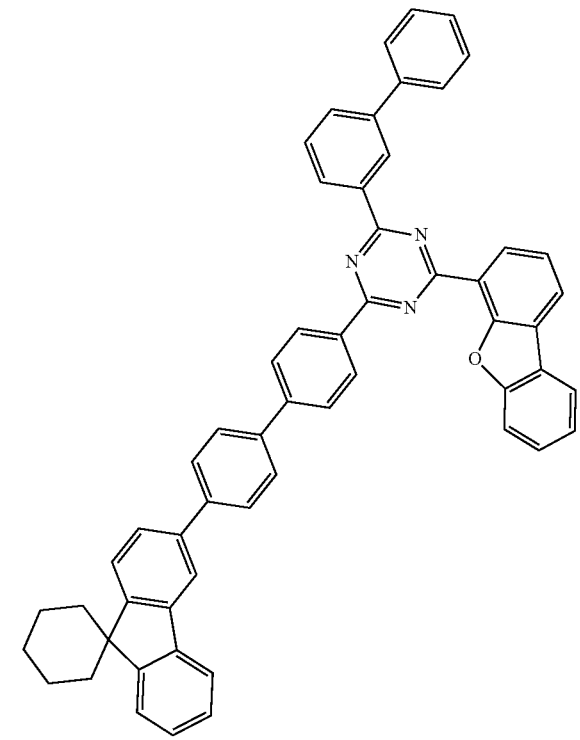

Inv 412
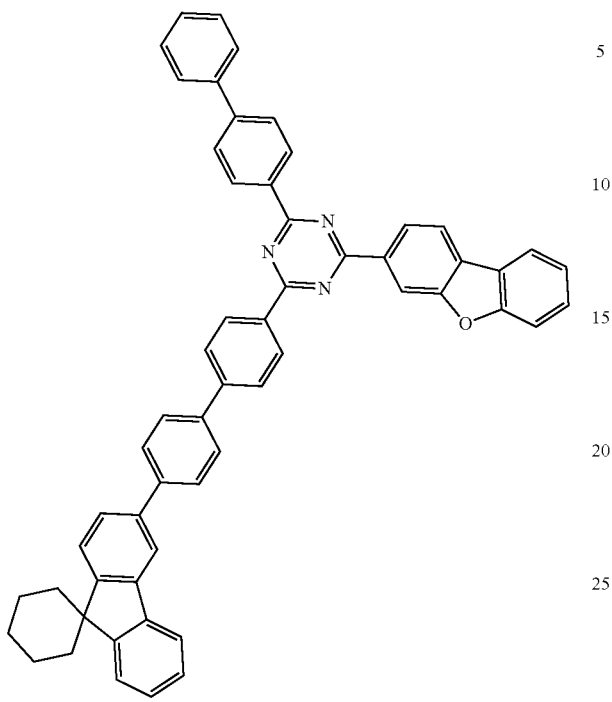
Inv 414
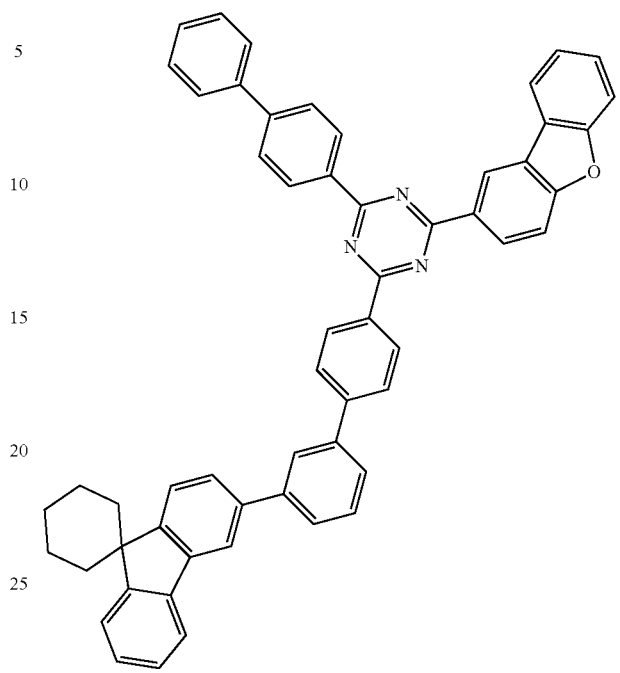
Inv 413
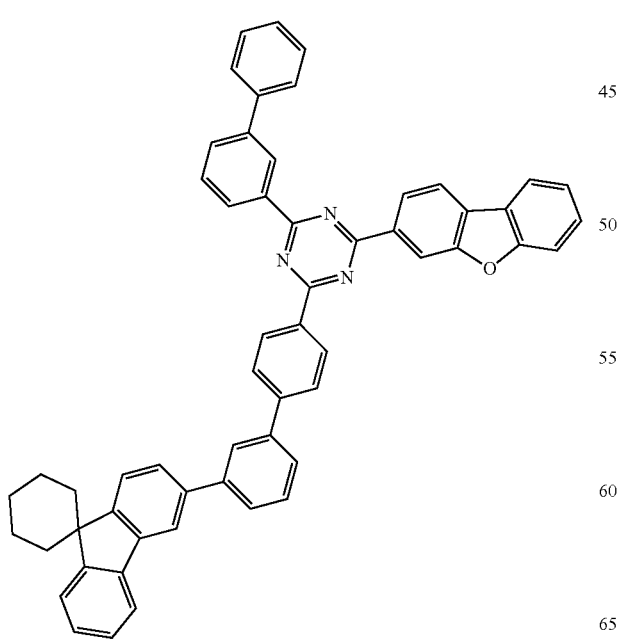
Inv 415
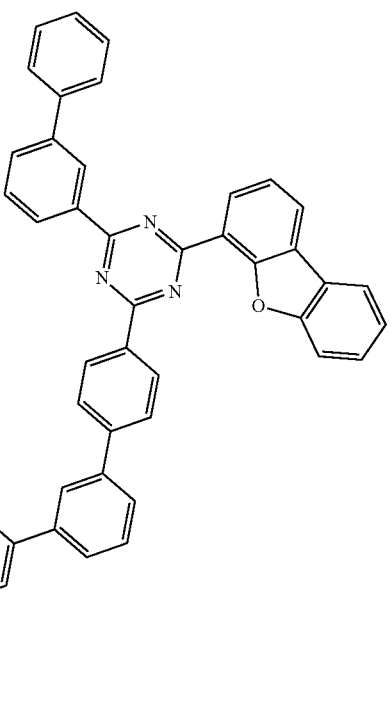

Inv 416
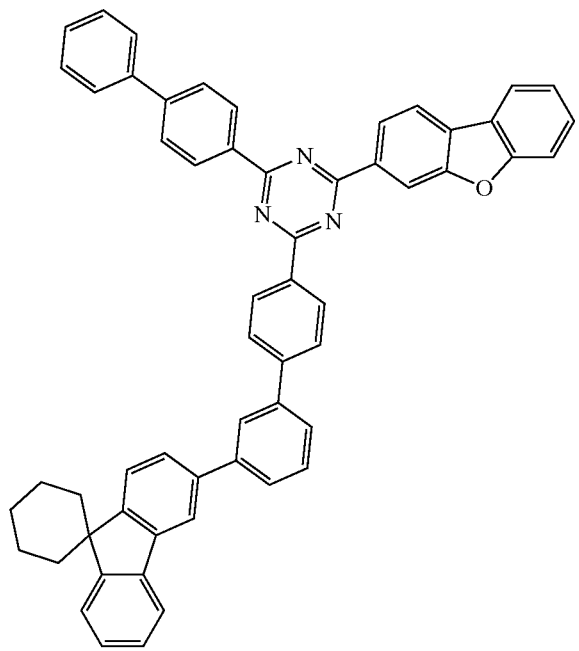
Inv 418
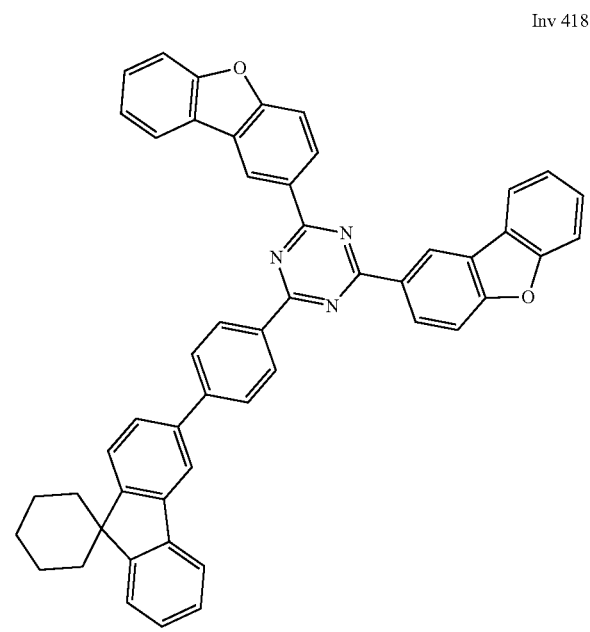
Inv 417
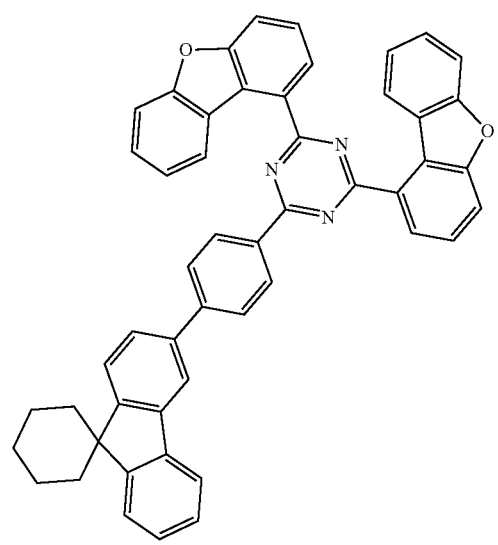
Inv 419
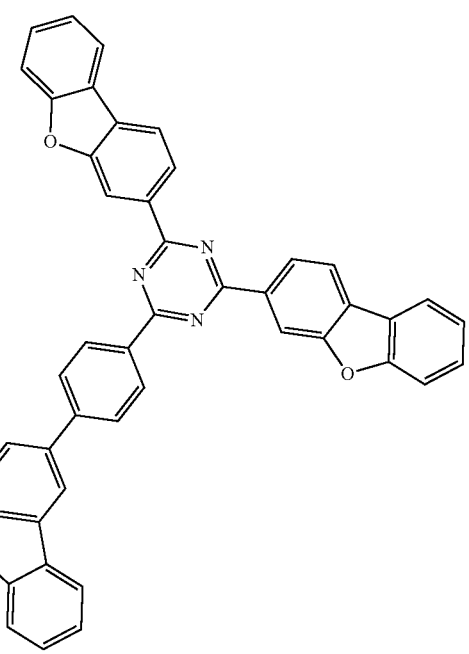

-continued
Inv 420
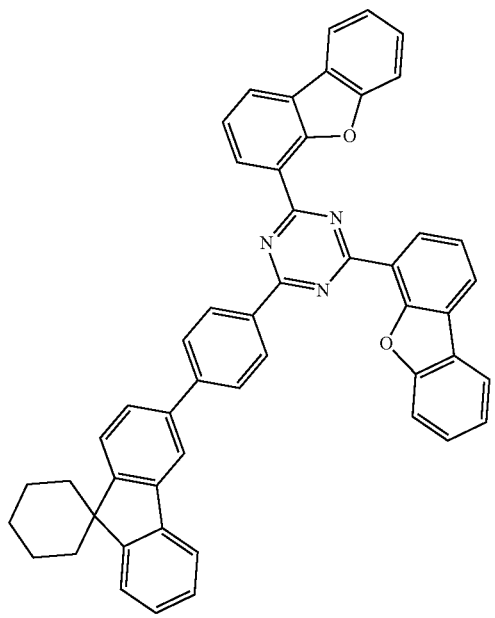
Inv 421
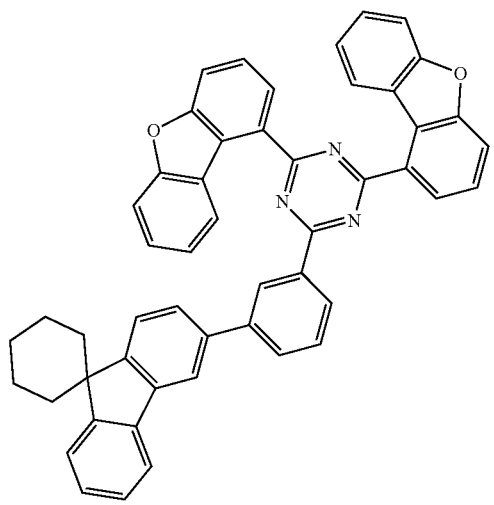
-continued
Inv 422
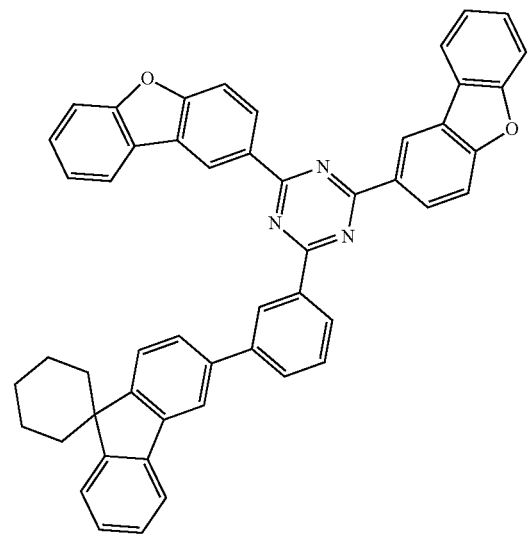
Inv 423
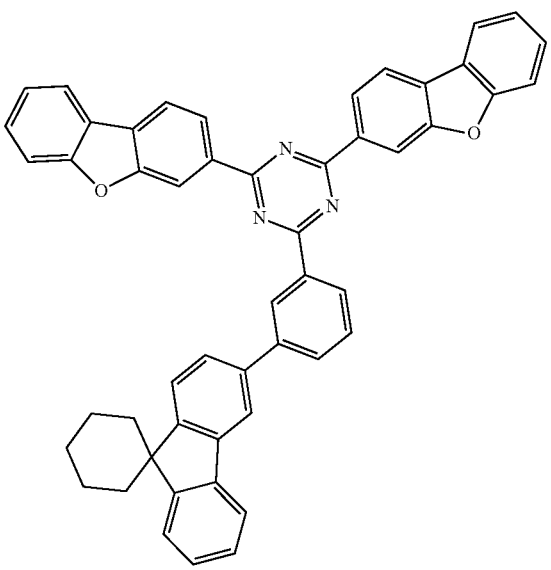

Inv 424
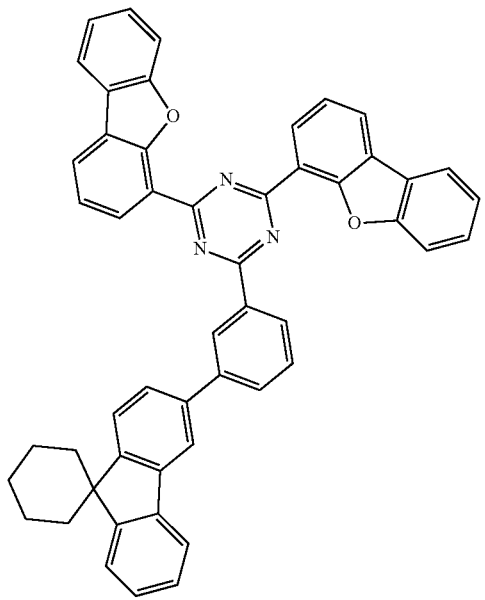
Inv 426
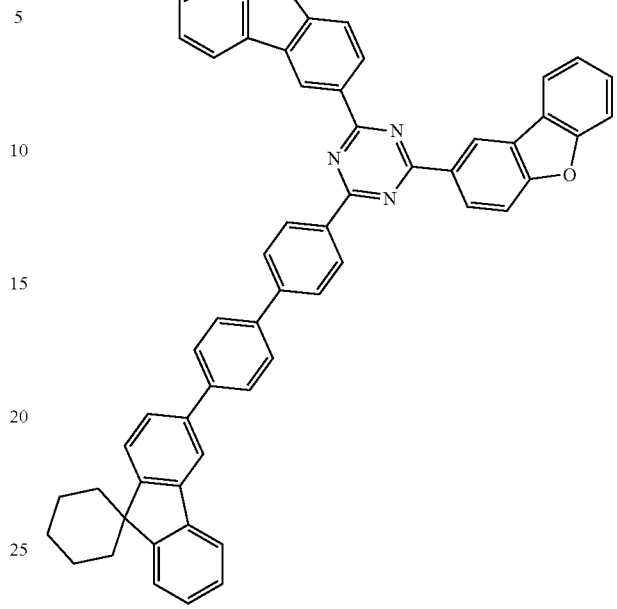
Inv 425
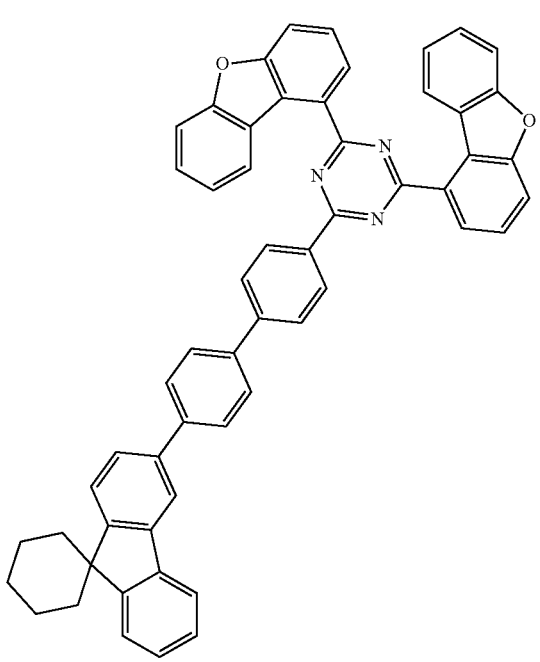
Inv 427
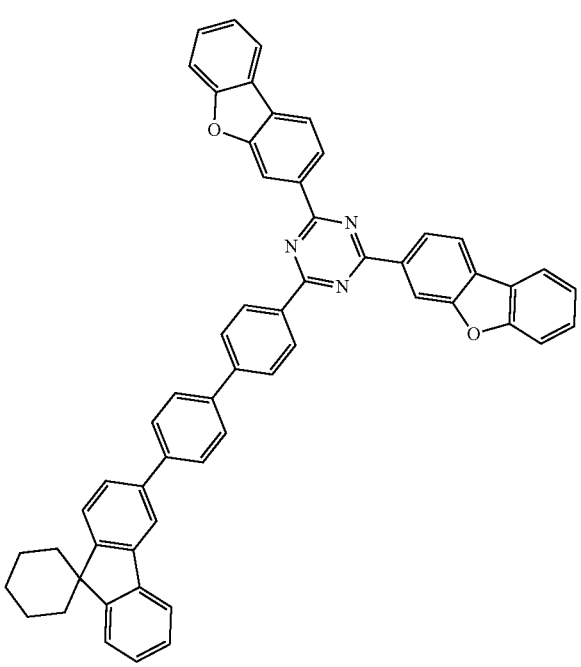

201
-continued
Inv 428
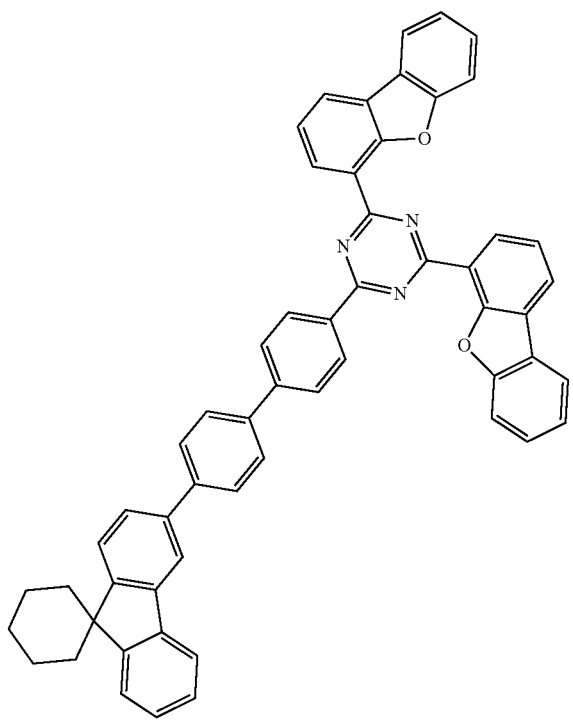
Inv 429
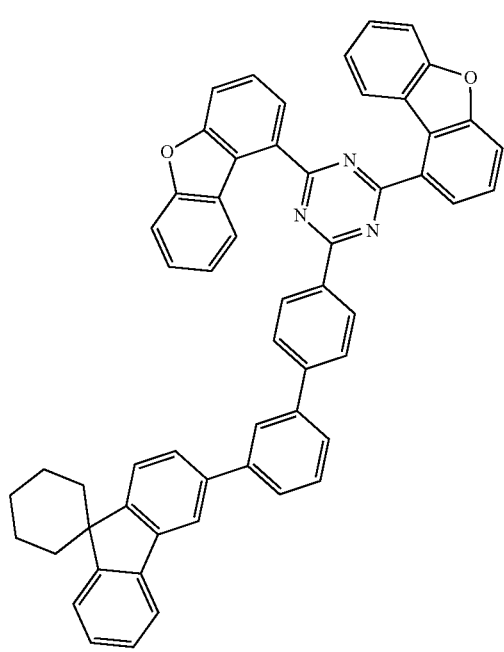
202
-continued
Inv 430
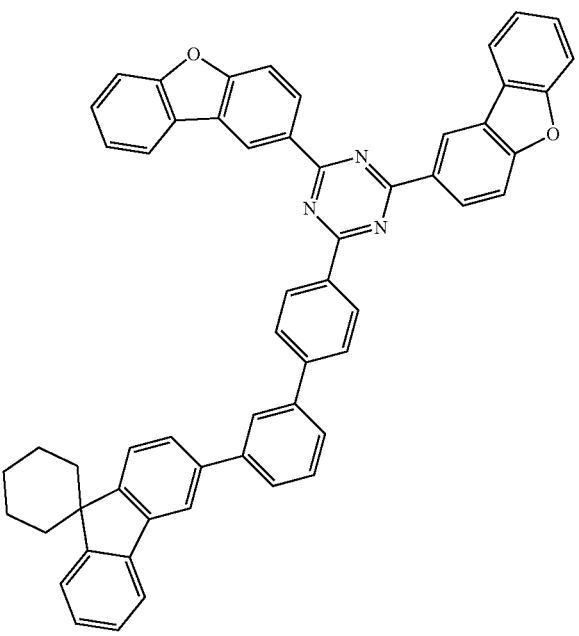
Inv 431

Inv 432
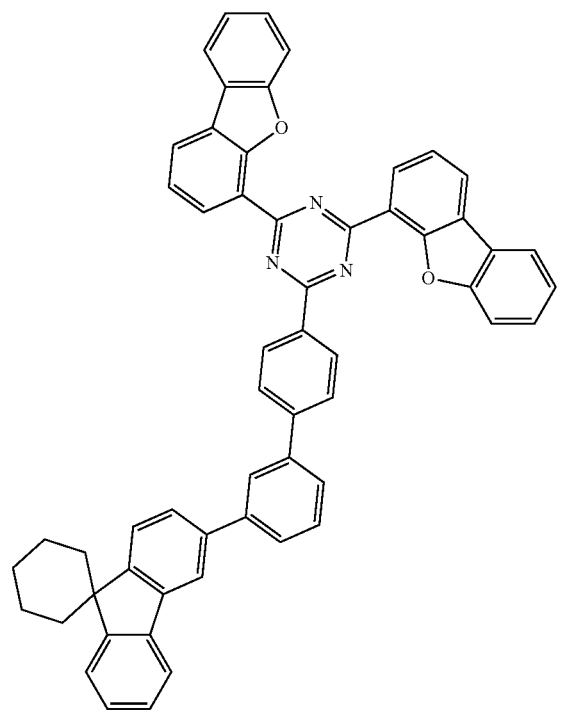
Inv 433
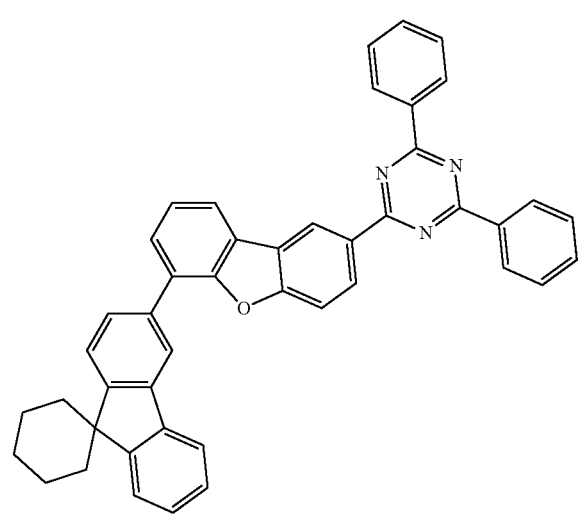
Inv 434
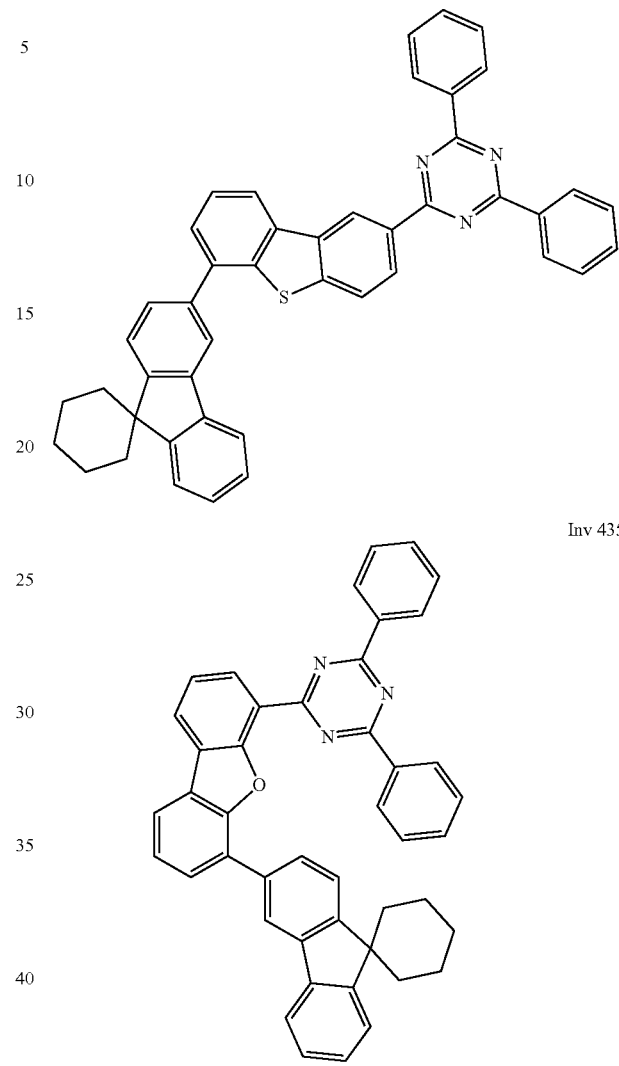
Inv 435
Inv 436
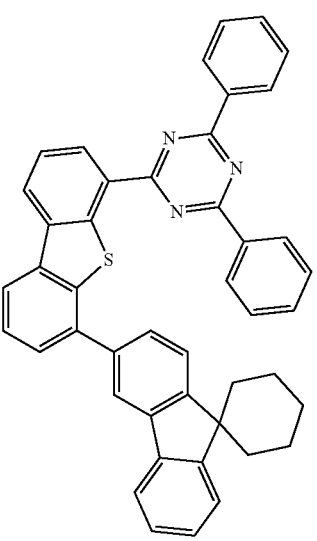

Inv 437
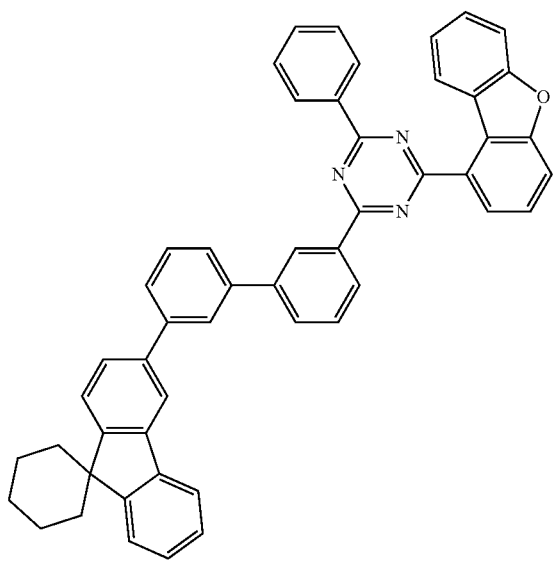
Inv 438
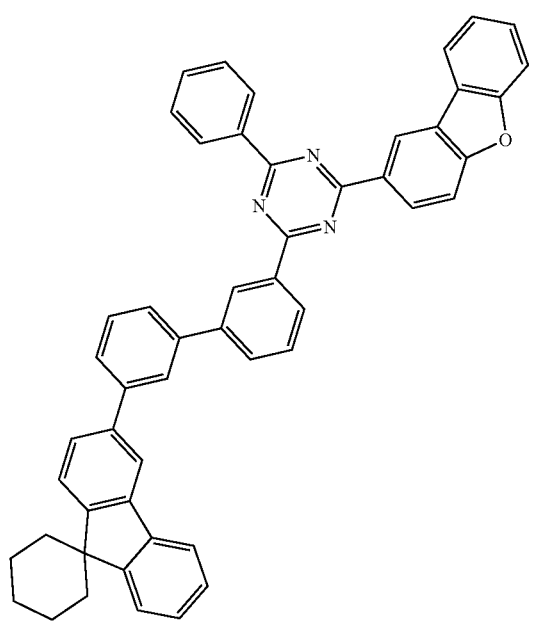
Inv 439
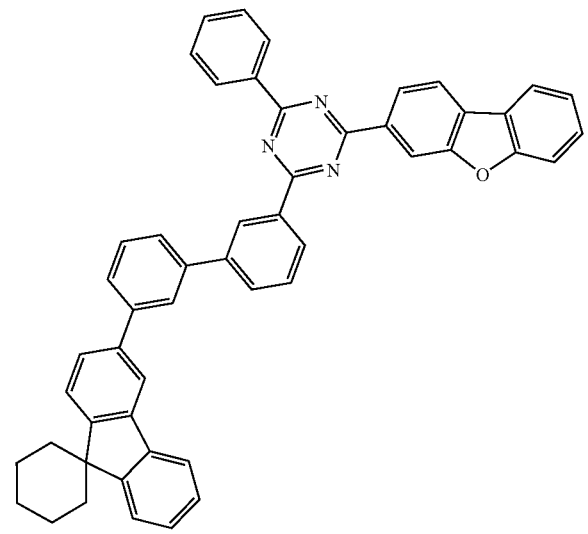
Inv 440
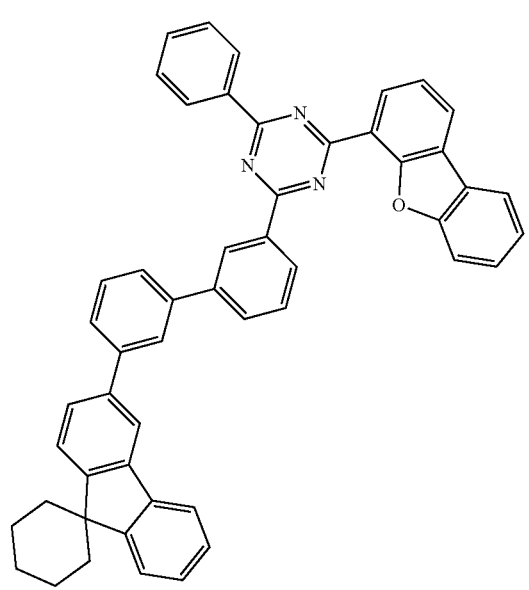

Inv 441
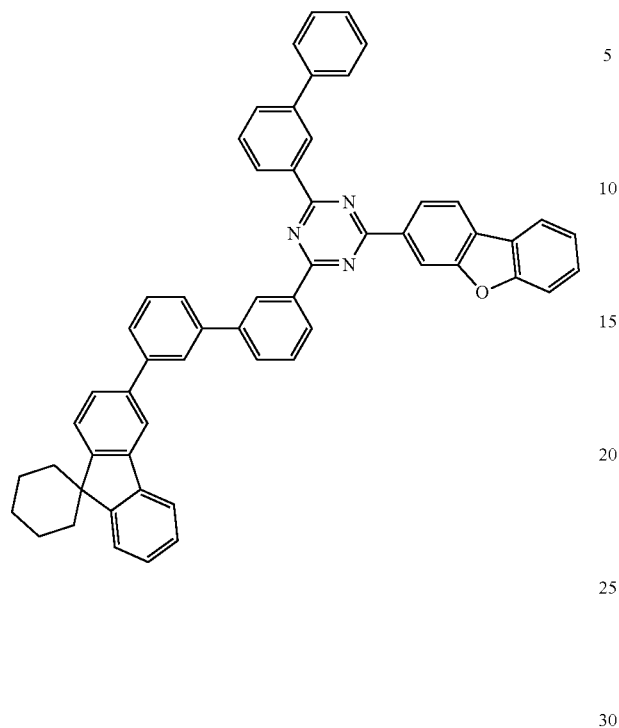
Inv 443
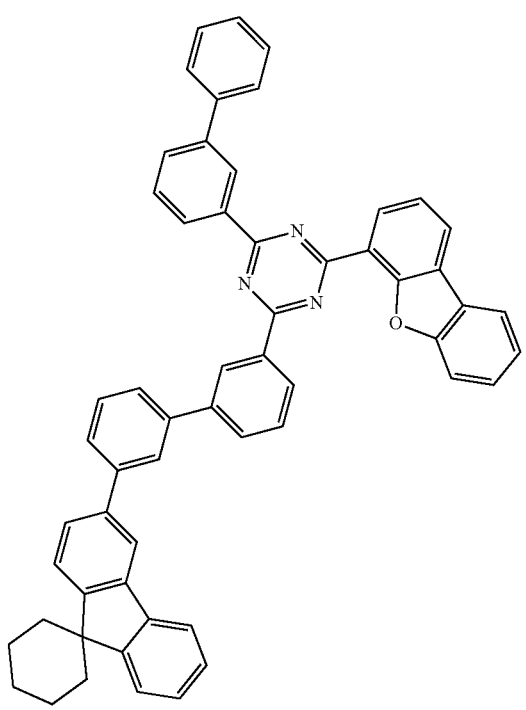
Inv 442
Inv 444
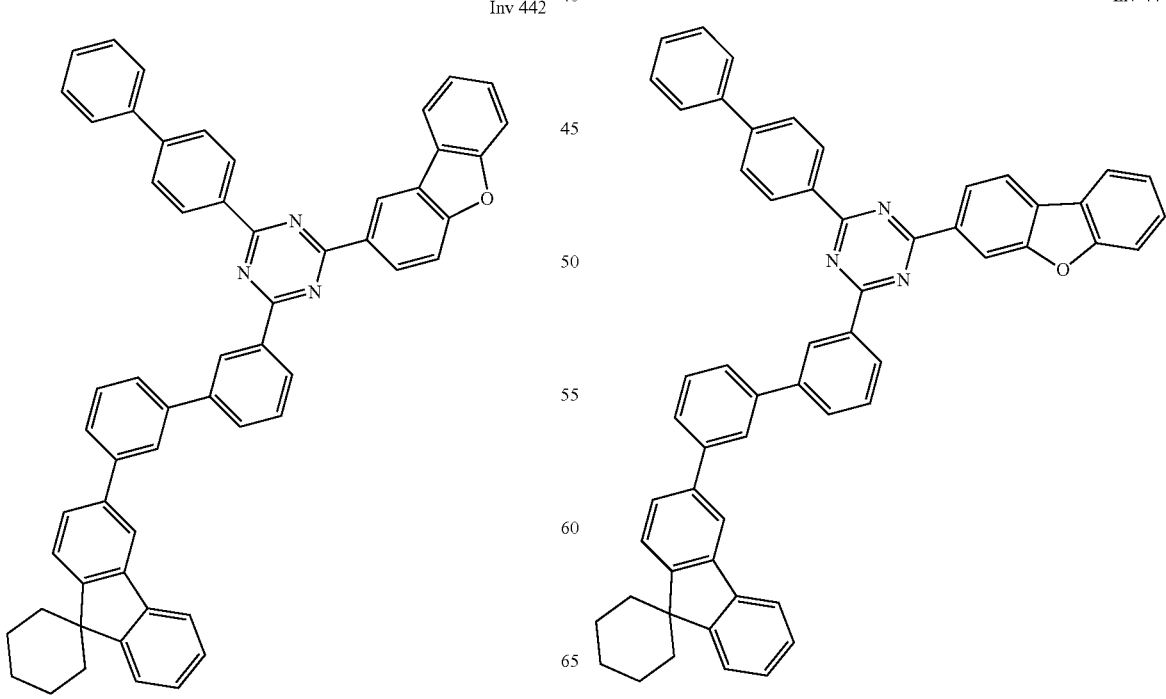

Inv 445
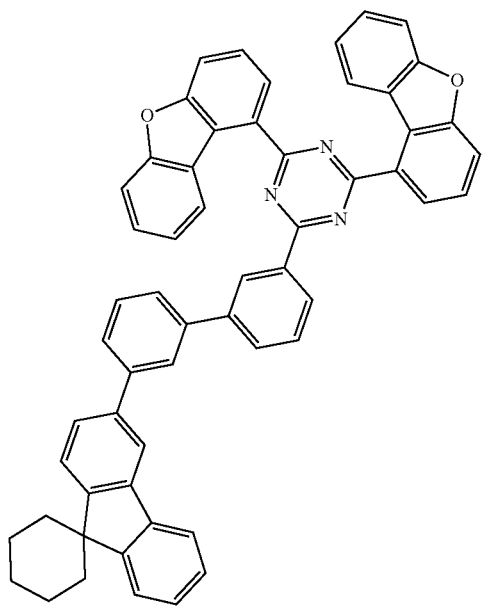
Inv 447
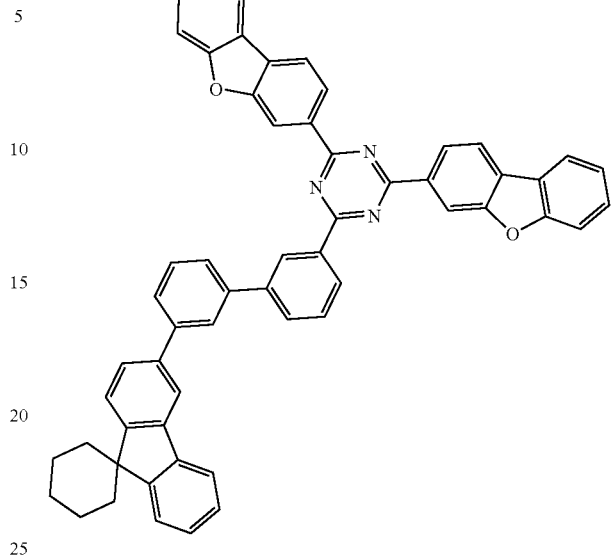
Inv 446
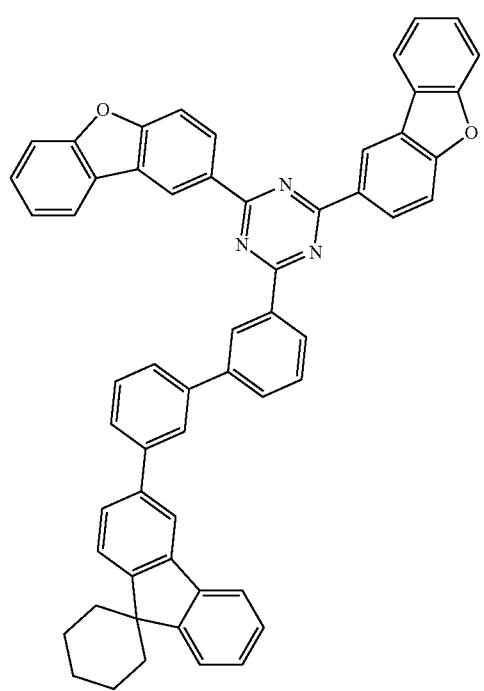
Inv 448
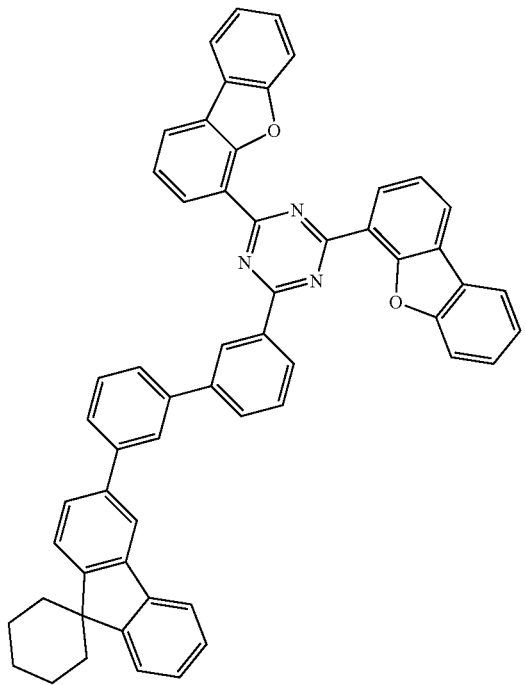

Inv 449
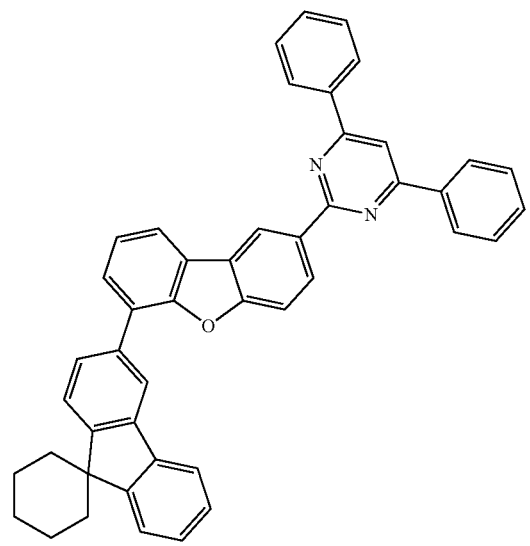
Inv 450
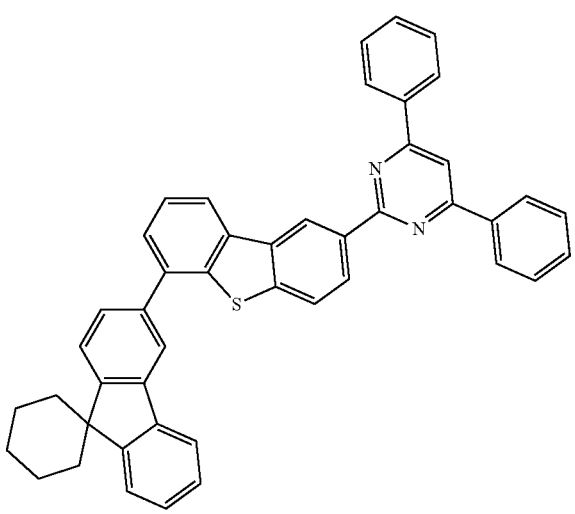
Inv 451
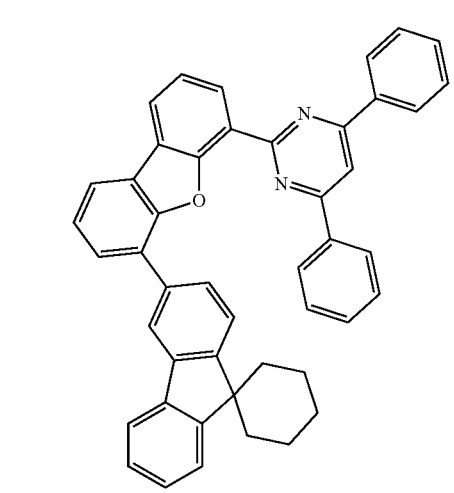
Inv 452
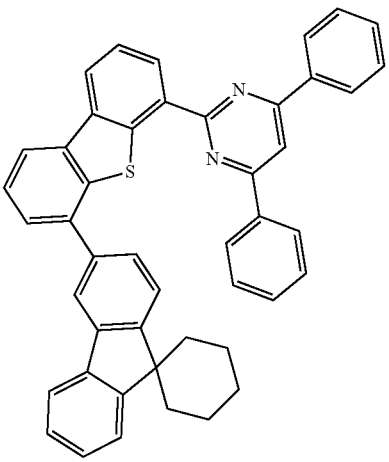
Inv 453
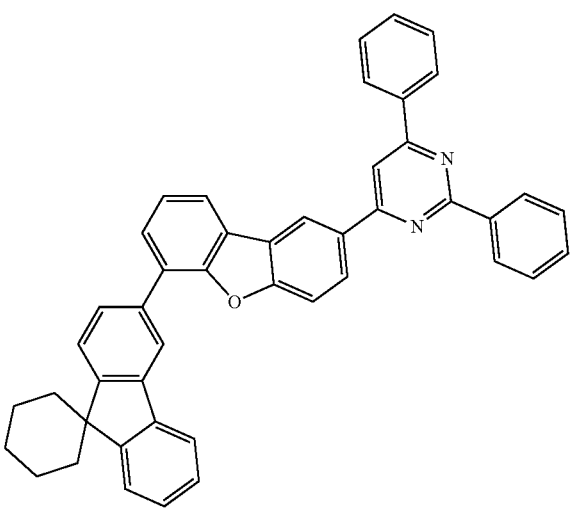
Inv 454
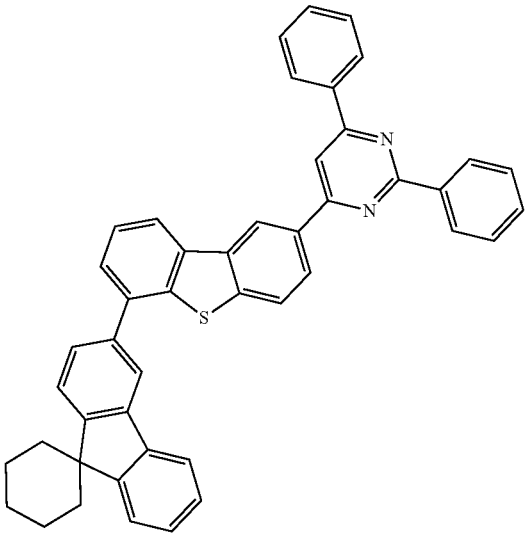

Inv 455
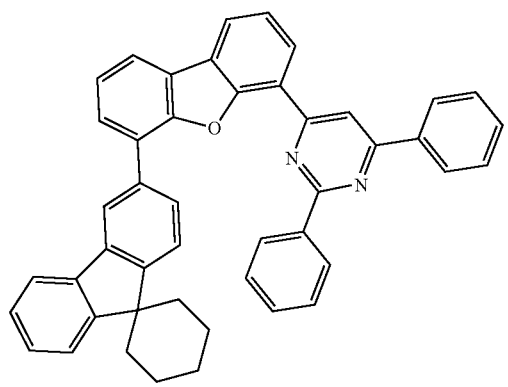
Inv 456
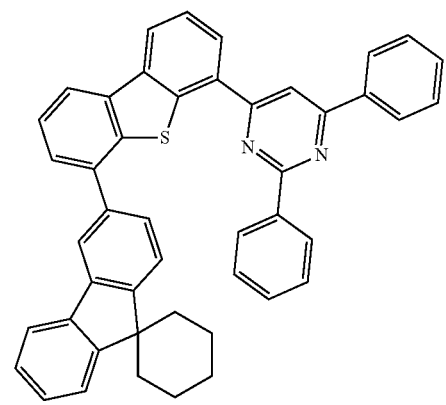
Inv 458
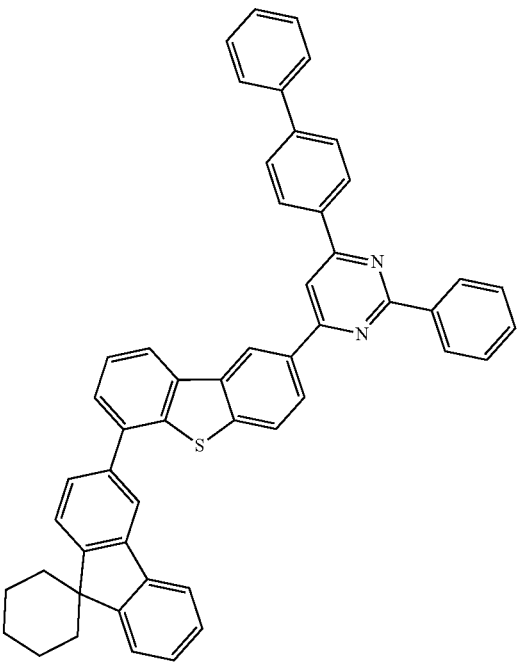
Inv 457
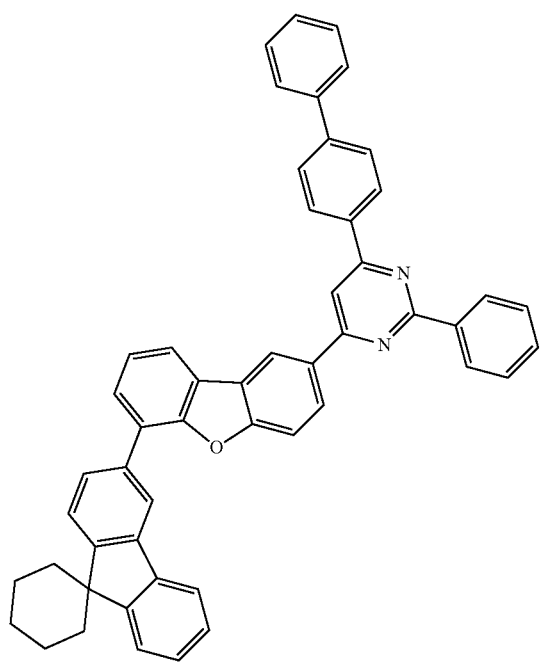
Inv 459
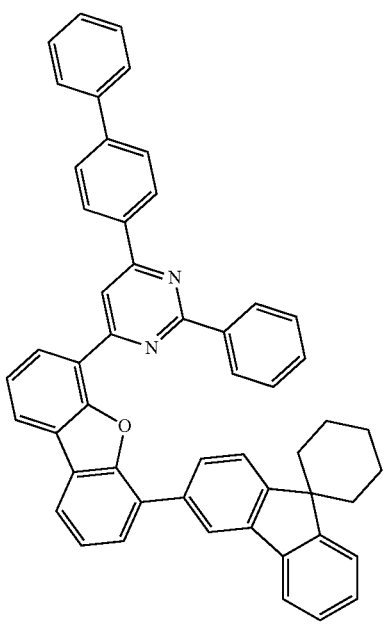

Inv 460
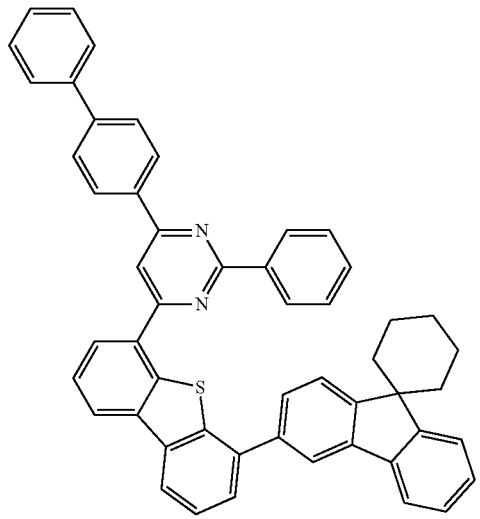
Inv 461
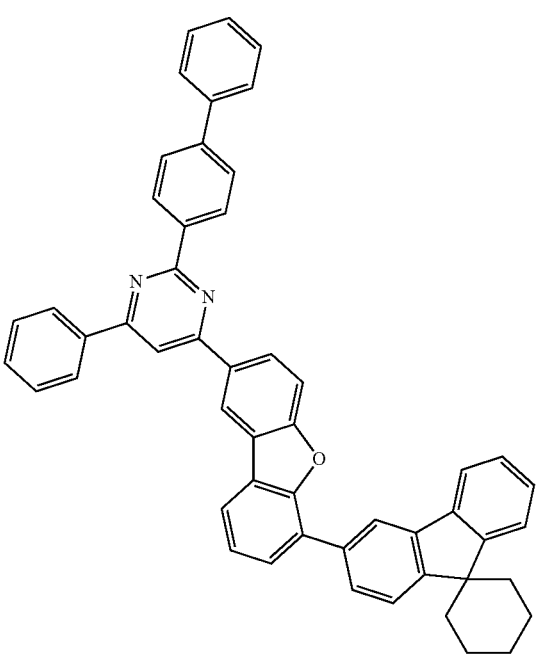
Inv 462
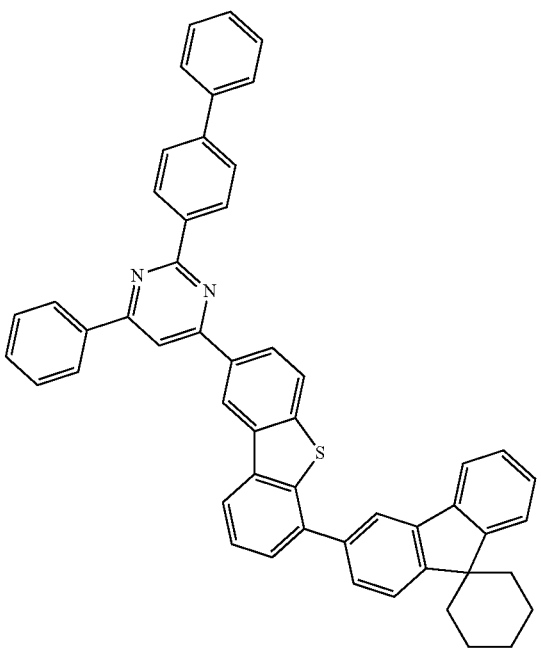
Inv 463
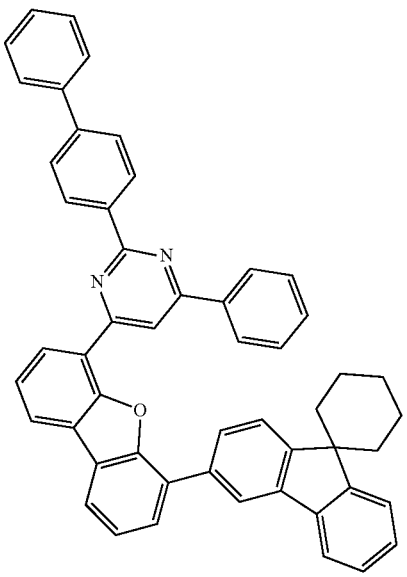

Inv 464
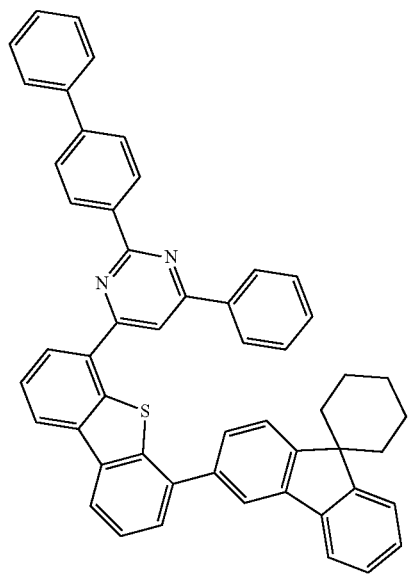
Inv 466
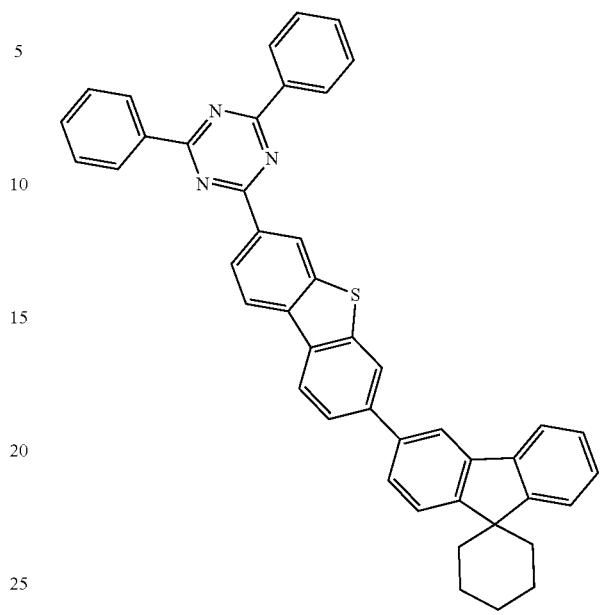
Inv 465
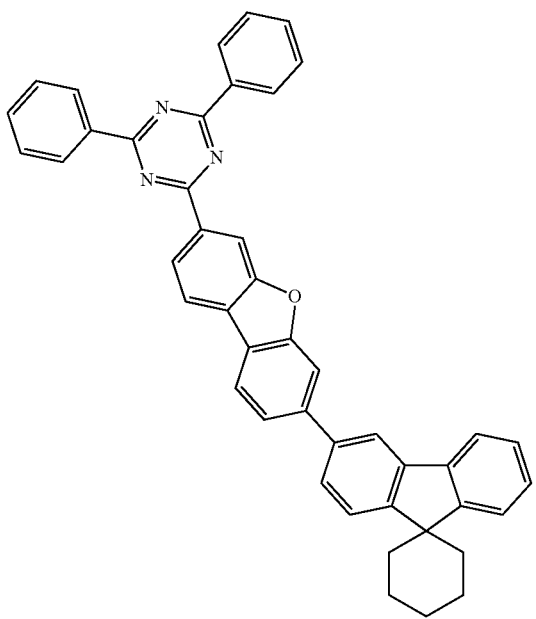
Inv 467
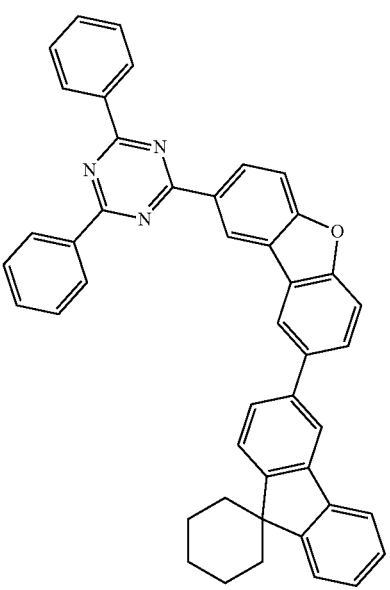

Inv 468
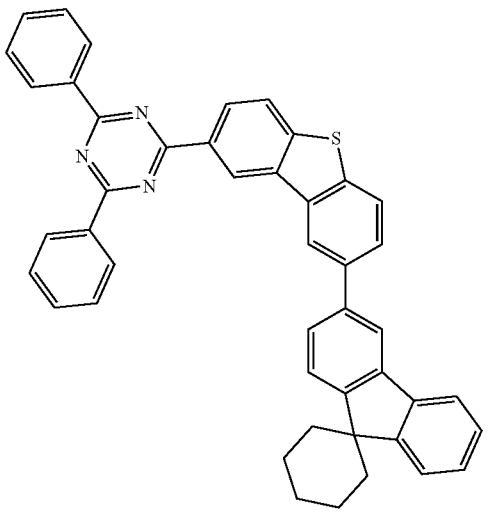
Inv 469
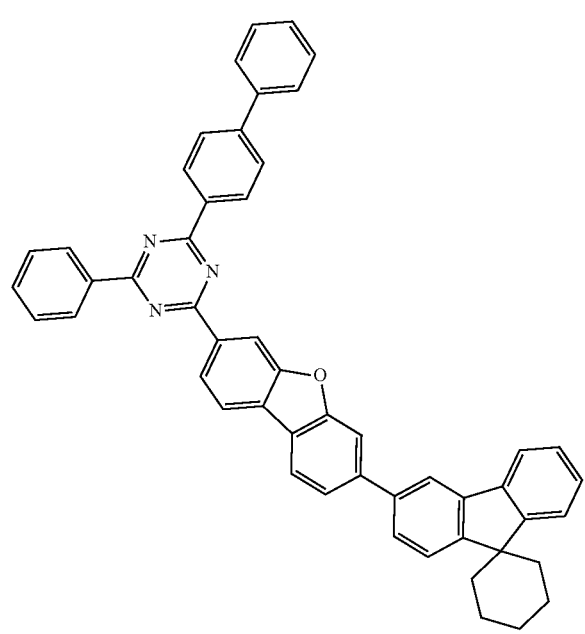
Inv 470
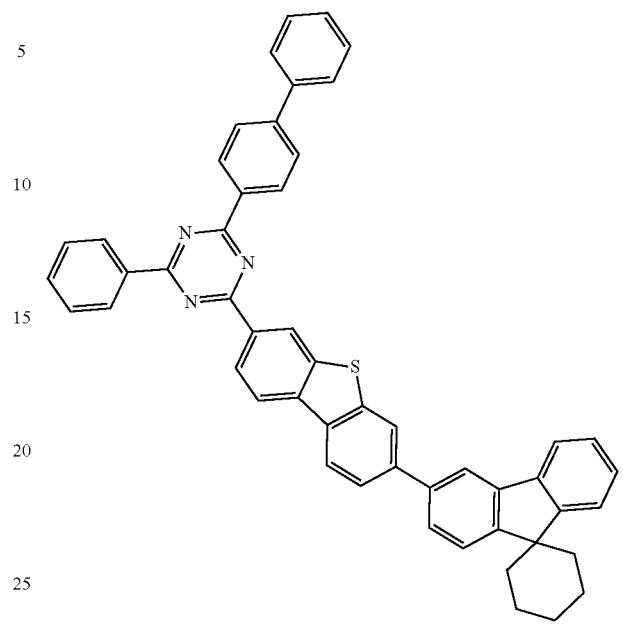
Inv 471
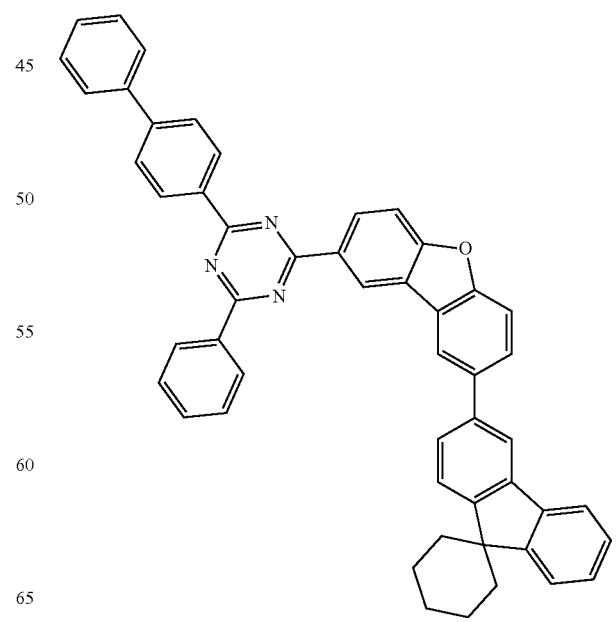

Inv 472
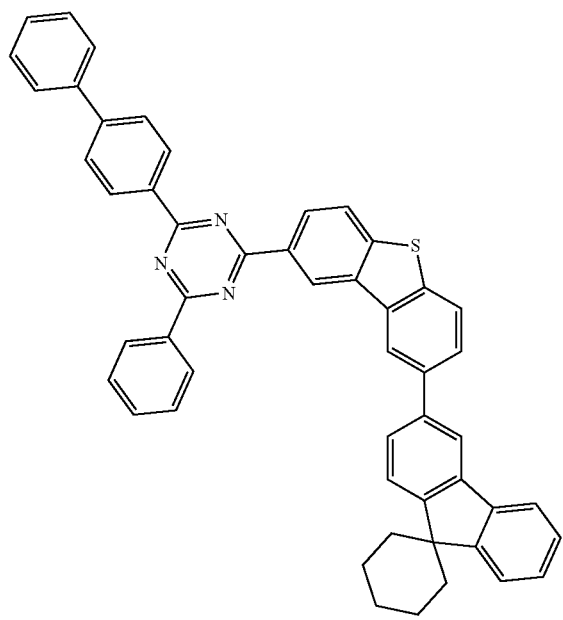
Inv 473
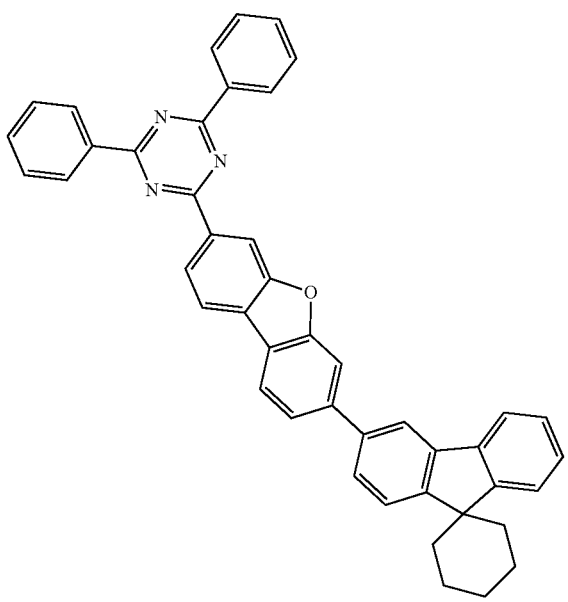
Inv 474
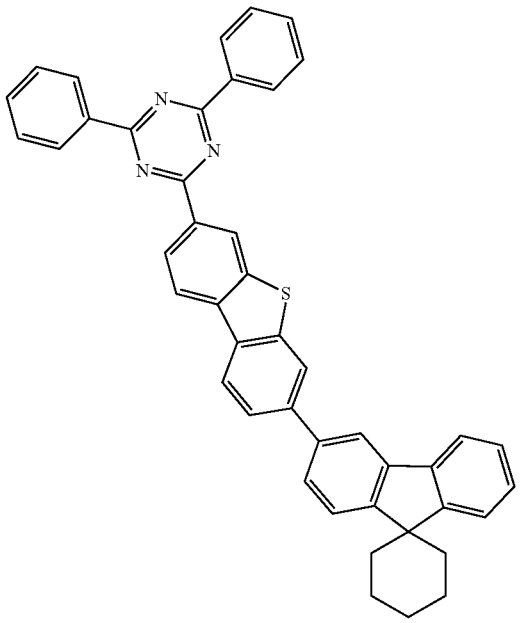
Inv 475
Inv 476
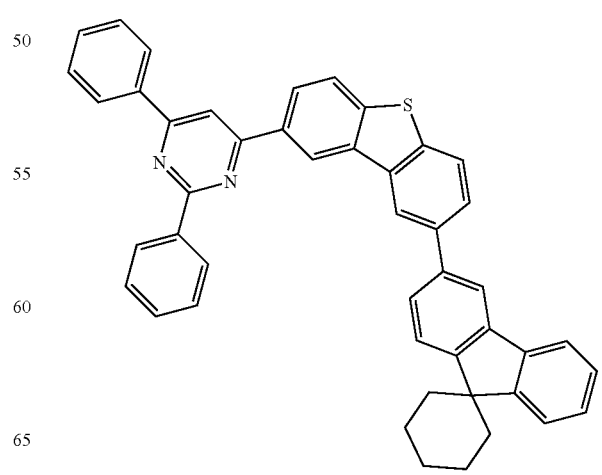

Inv 477
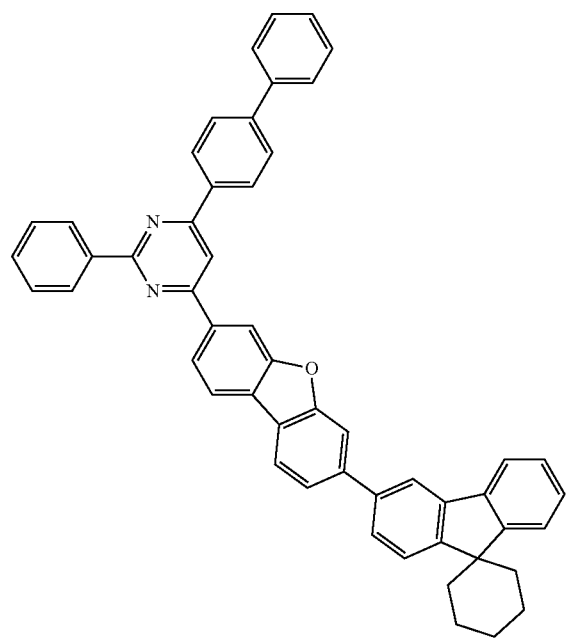
Inv 479
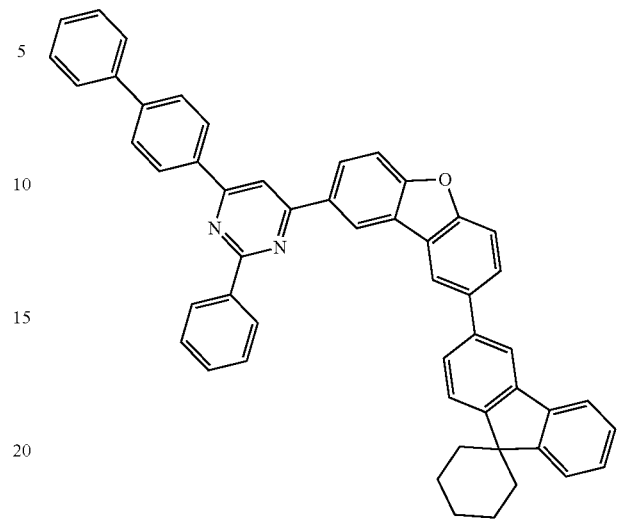
Inv 480
Inv 478
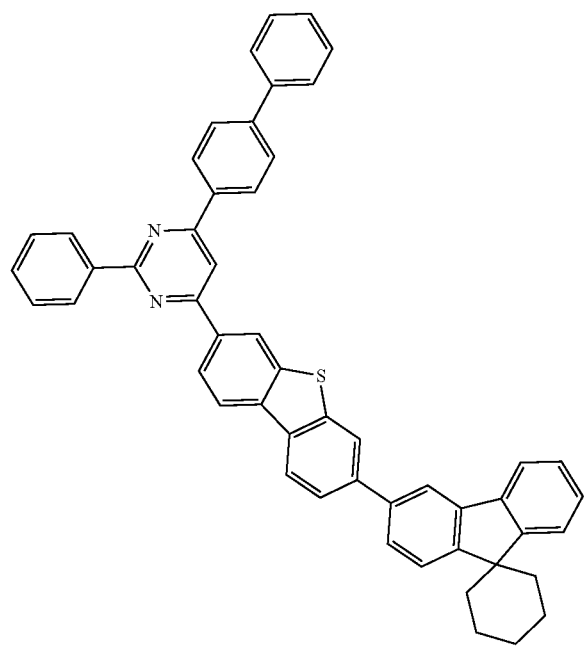
Inv 481
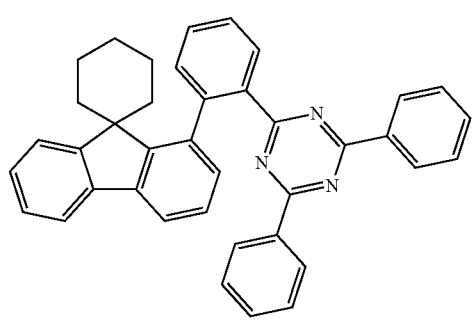

Inv 482
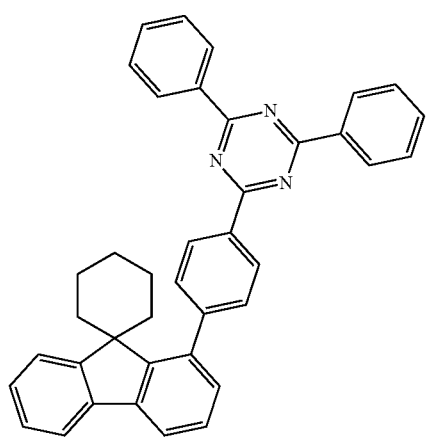
Inv 483
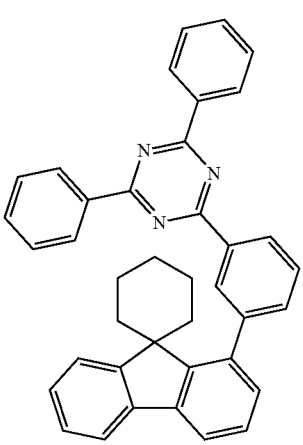
Inv 484
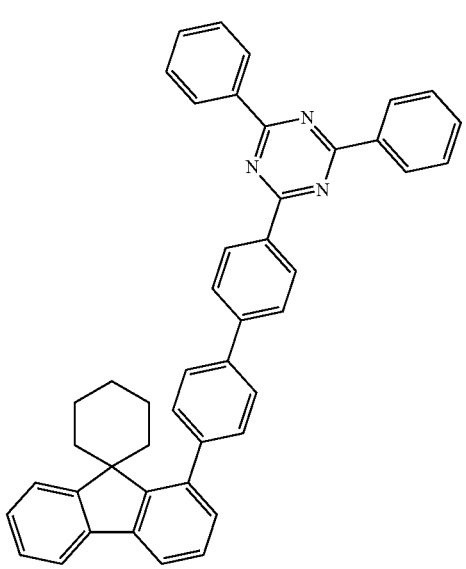
Inv 485
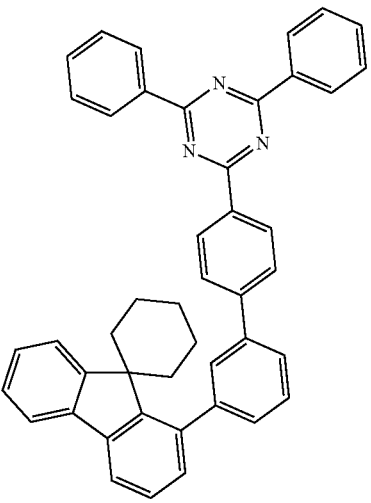
Inv 486
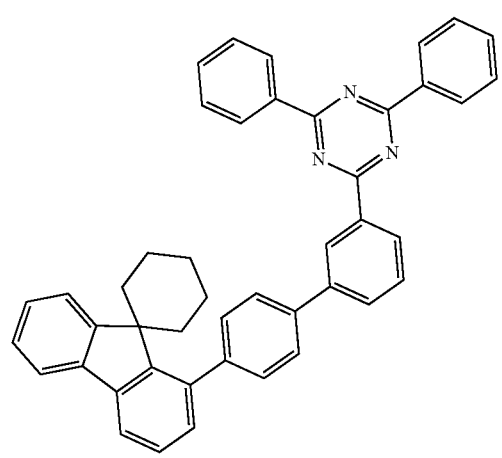
Inv 487
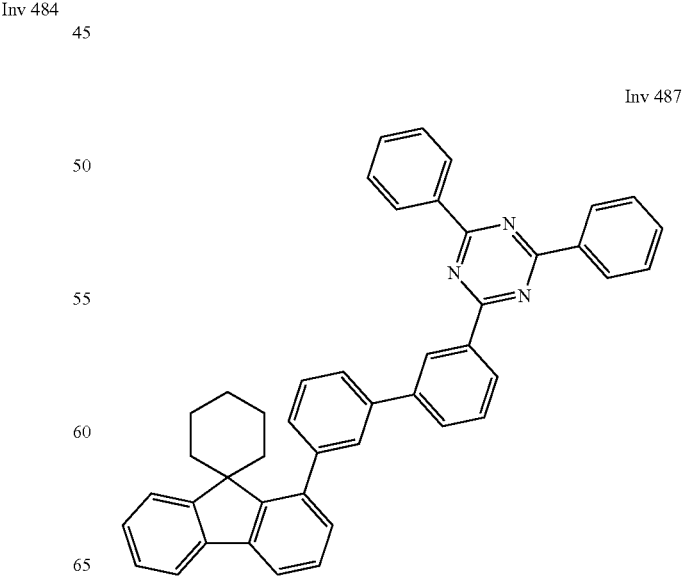

Inv 488
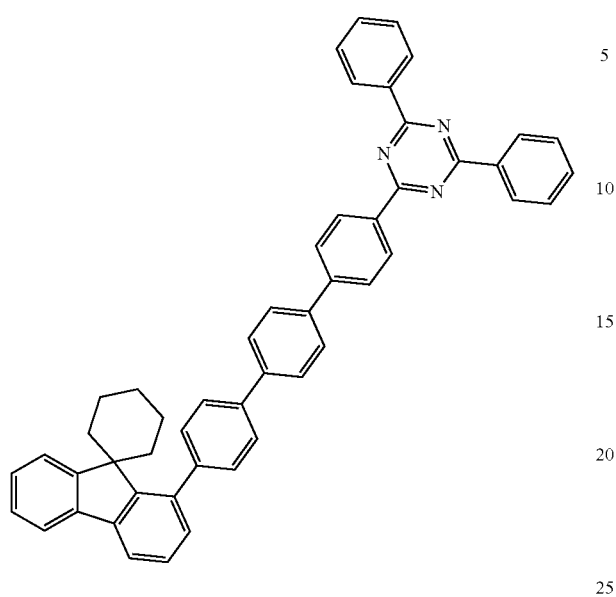
Inv 490
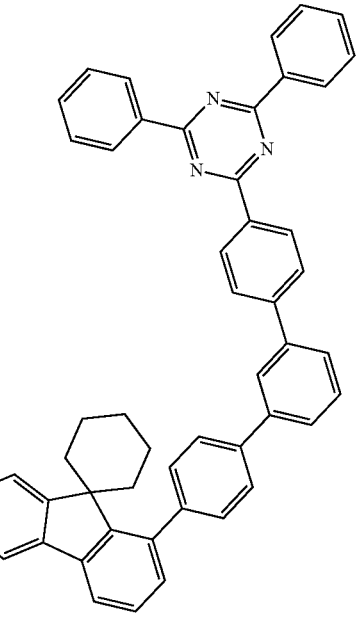
Inv 489
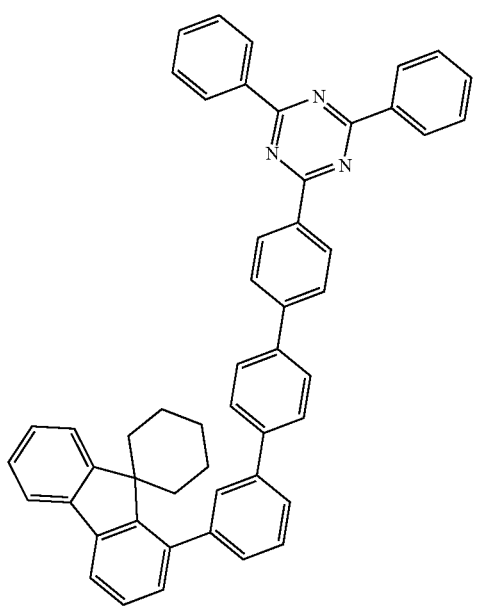
Inv 491
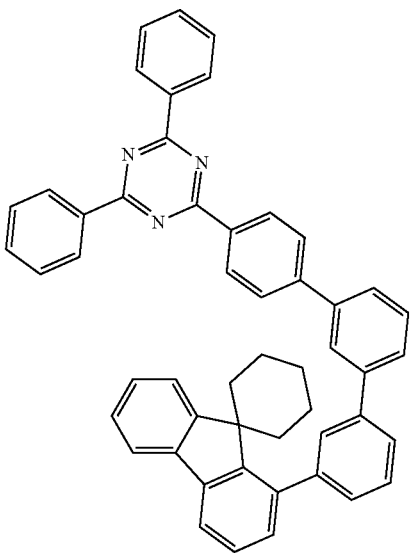

Inv 492
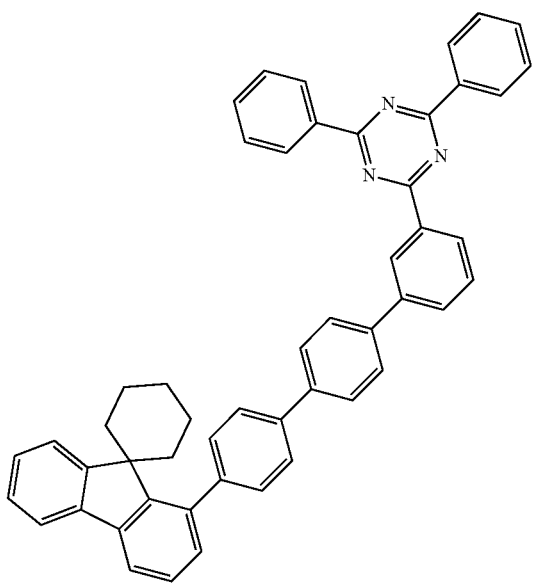
Inv 494
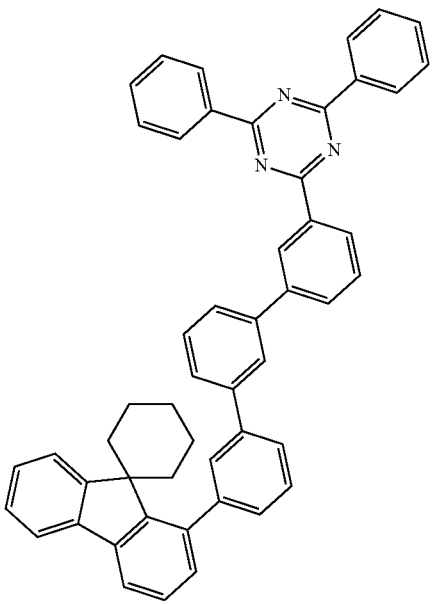
Inv 493
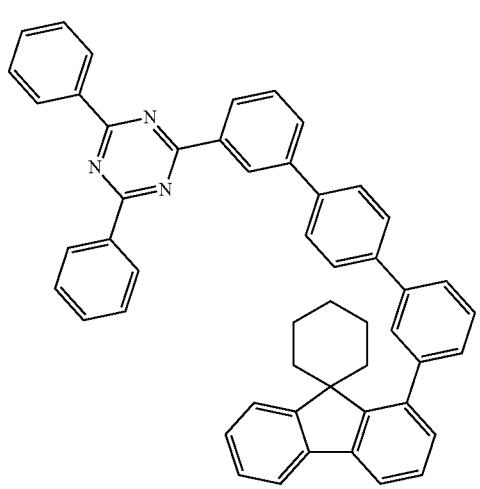
Inv 495
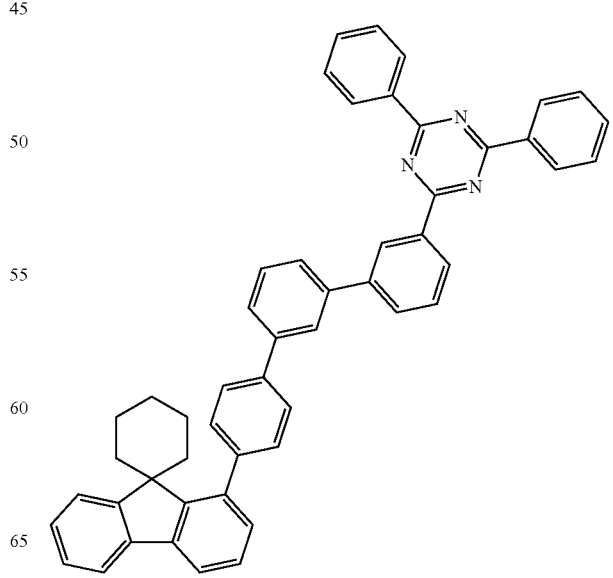

-continued
Inv 496
Inv 497
Inv 498
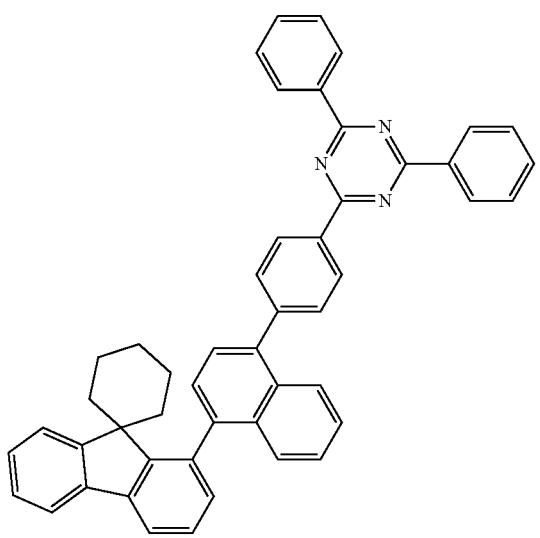
Inv 499
Inv 500
Inv 501
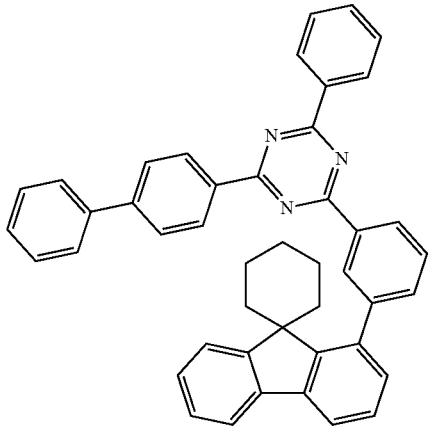
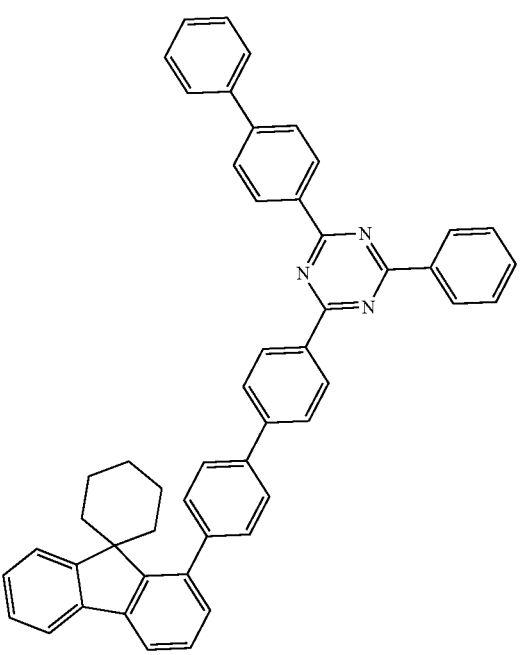
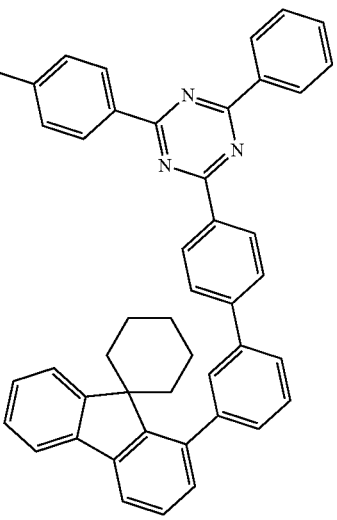

Inv 502
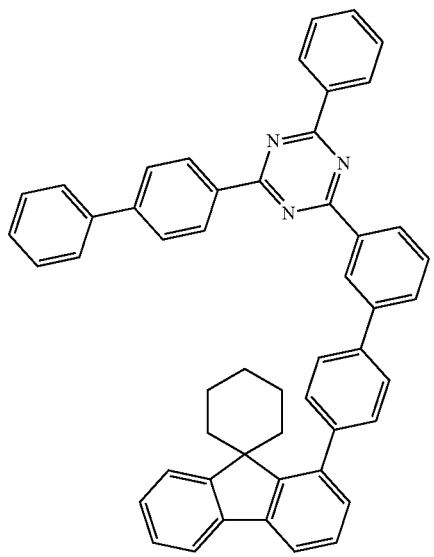
Inv 503
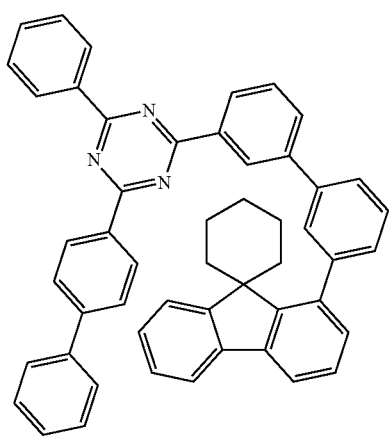
Inv 504
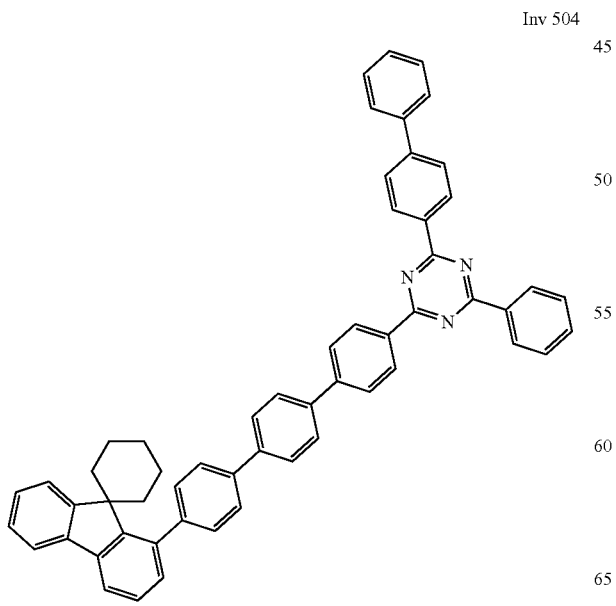
Inv 505
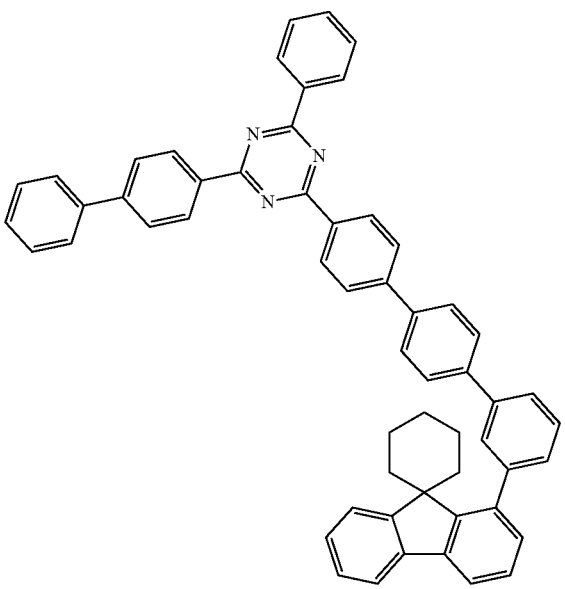
Inv 506
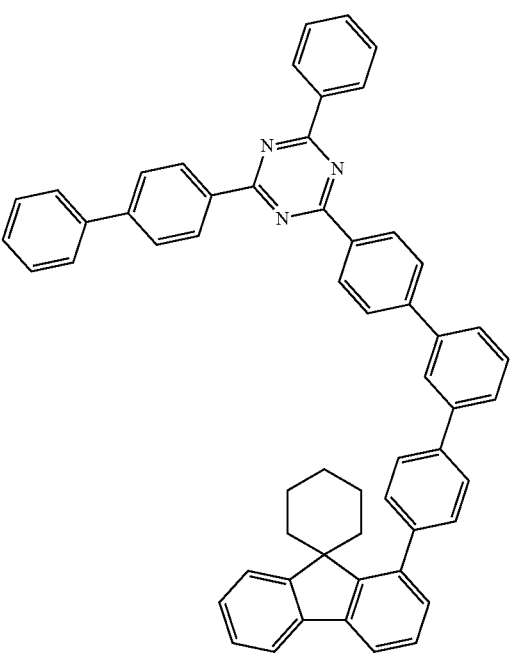

Inv 507
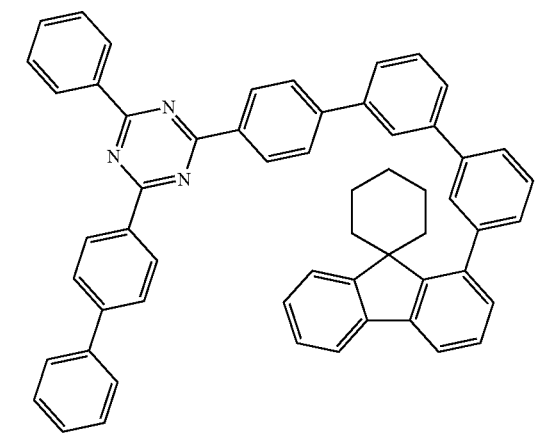
Inv 508
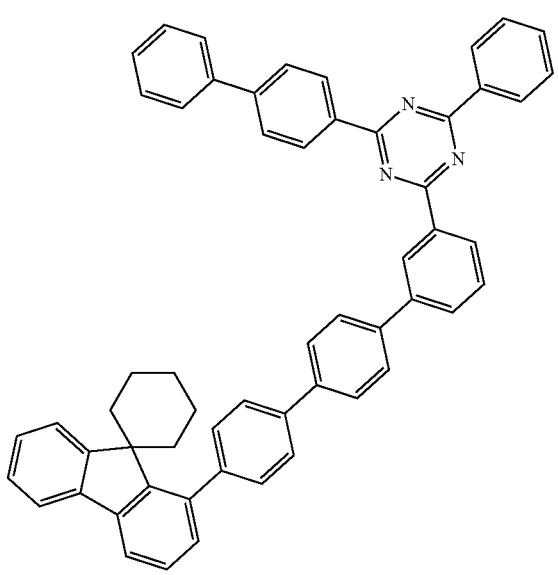
Inv 509
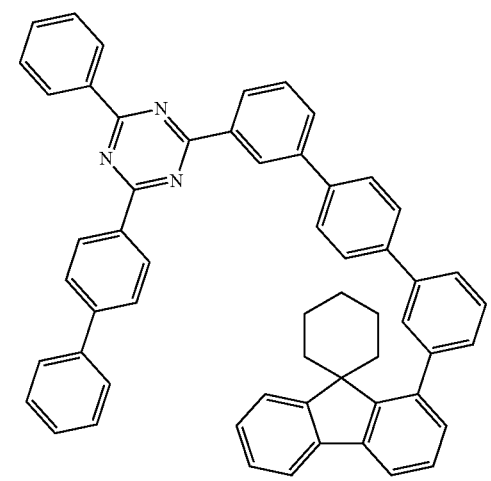
Inv 510
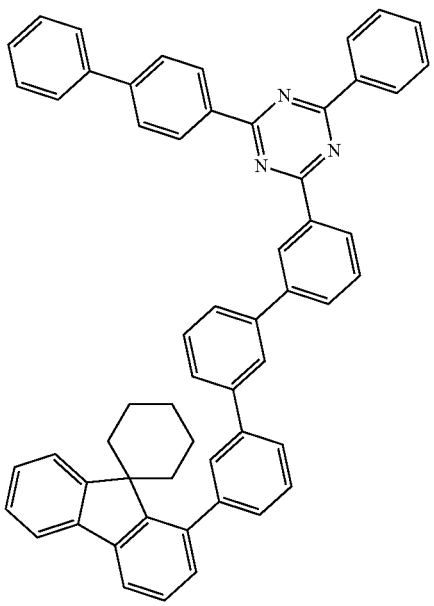
Inv 511
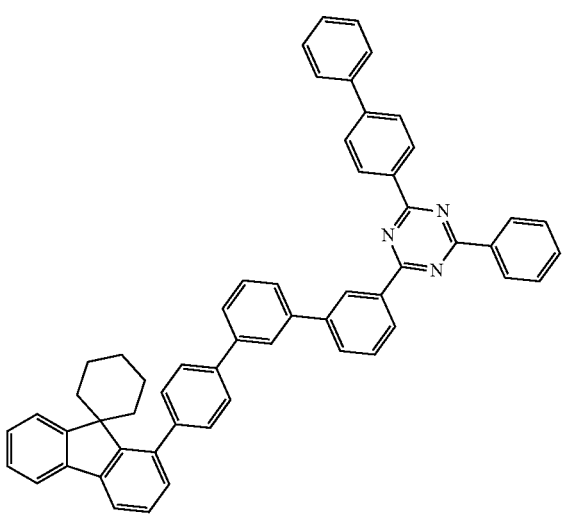

-continued
Inv 512
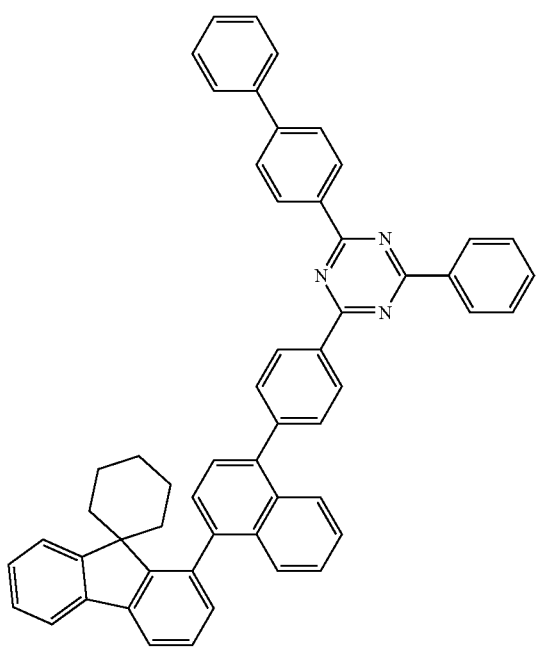
Inv 513
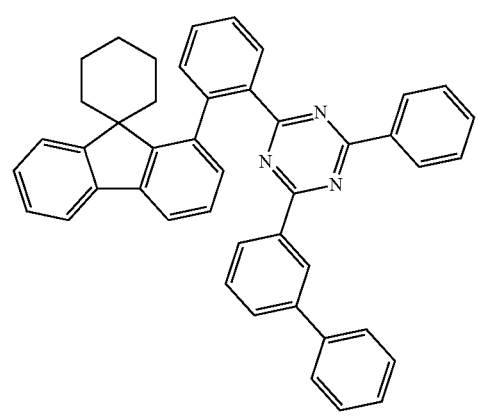
Inv 514
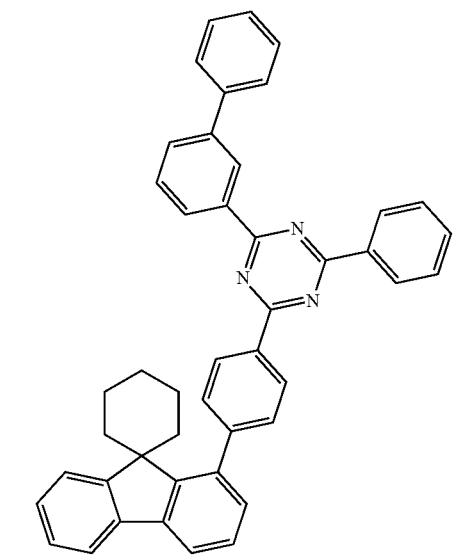
-continued
Inv 515
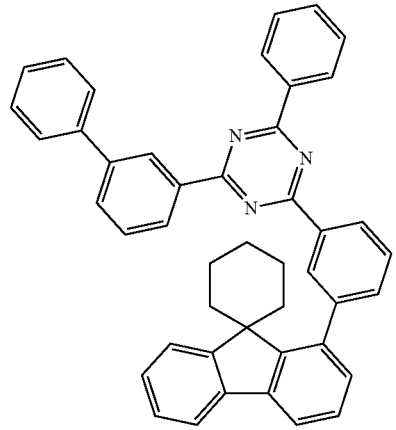
Inv 516
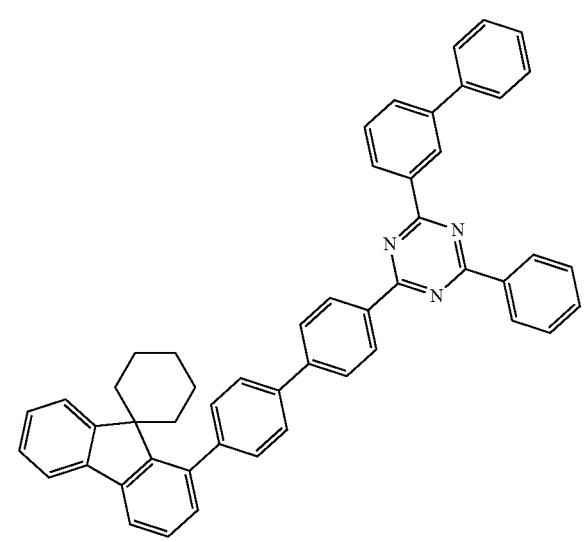
Inv 517
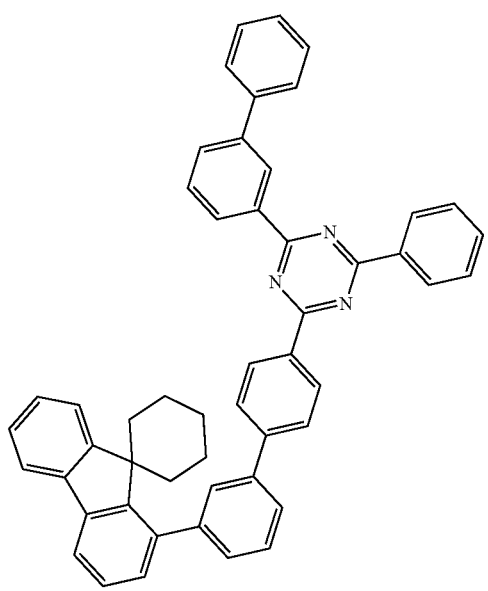

Inv 518
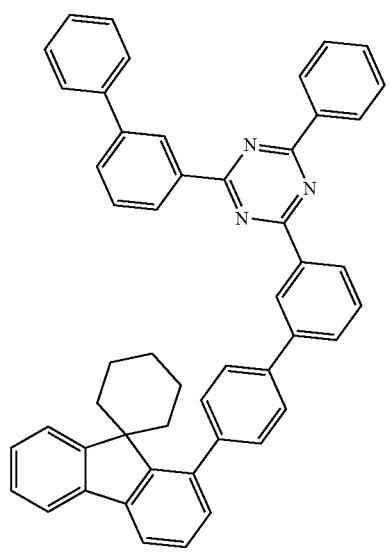
Inv 520
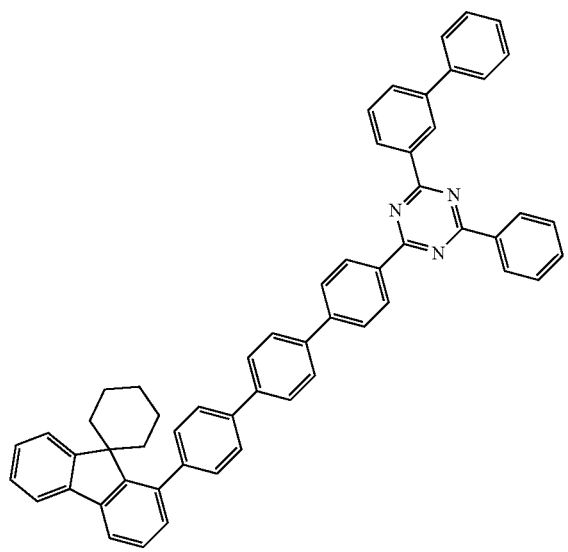
Inv 519
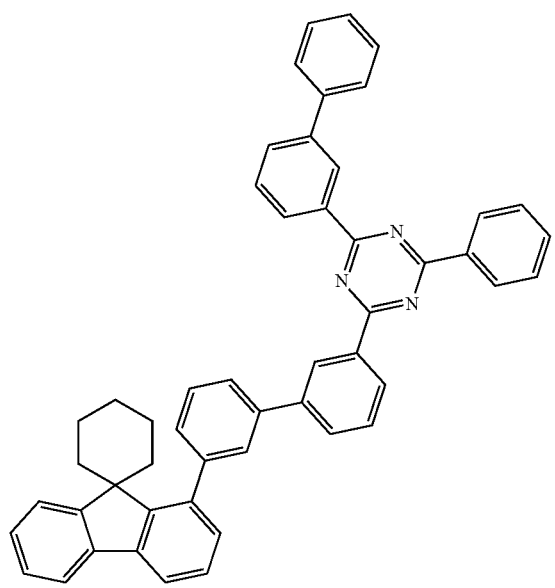
Inv 521
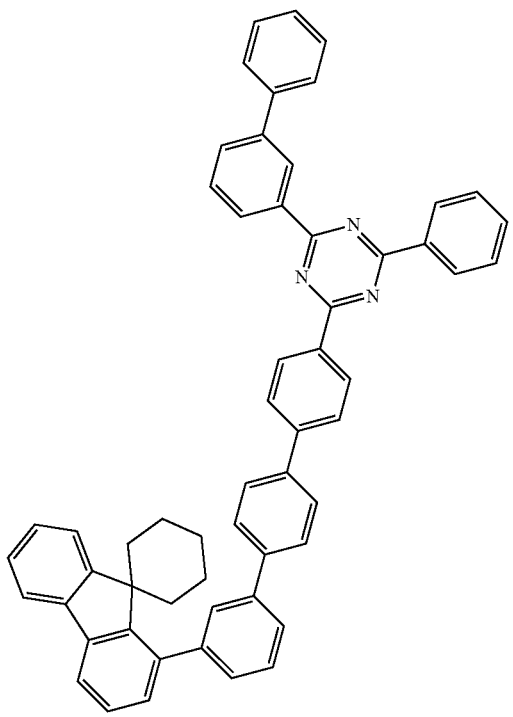

Inv 522
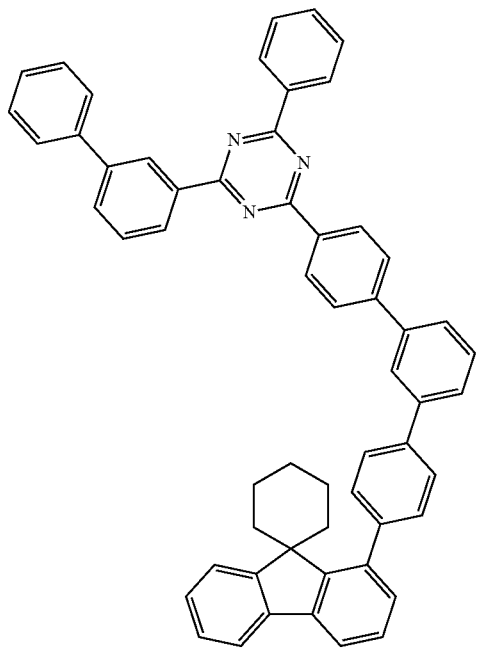
Inv 523
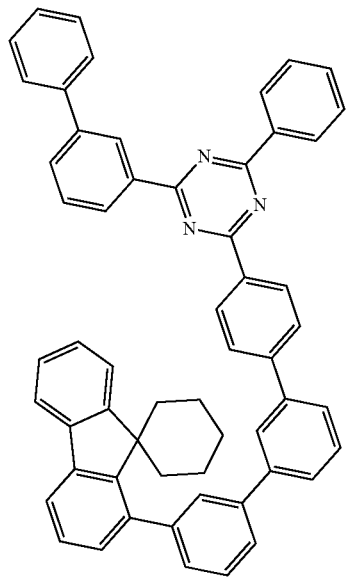
Inv 524
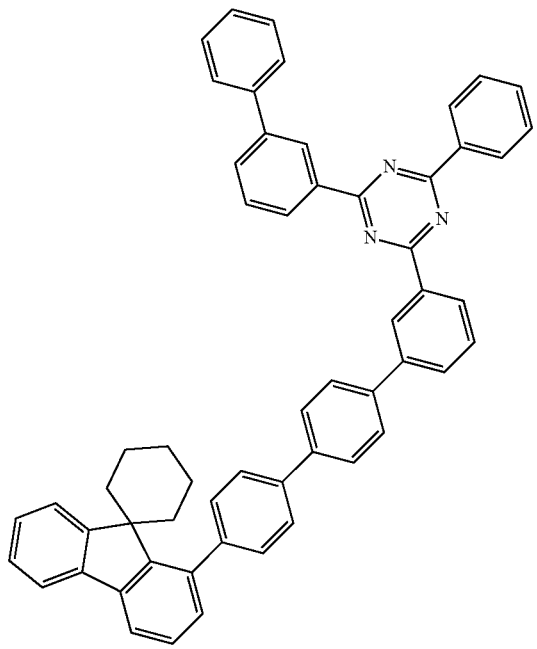
Inv 525
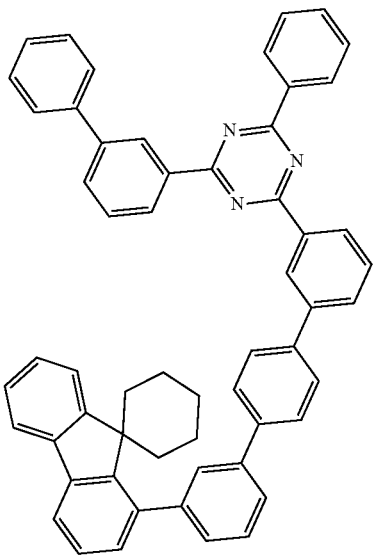

Inv 526
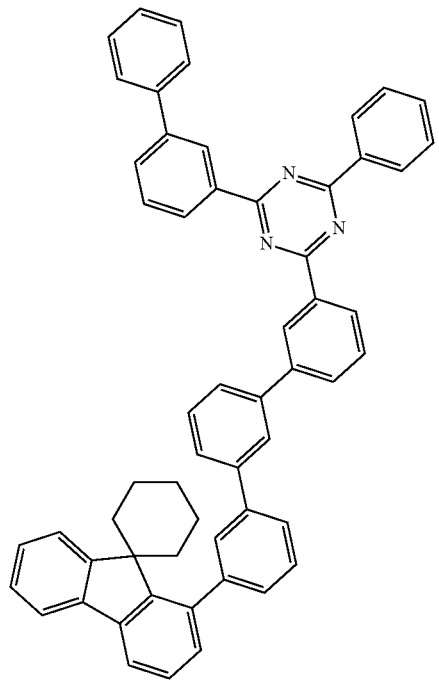
Inv 528
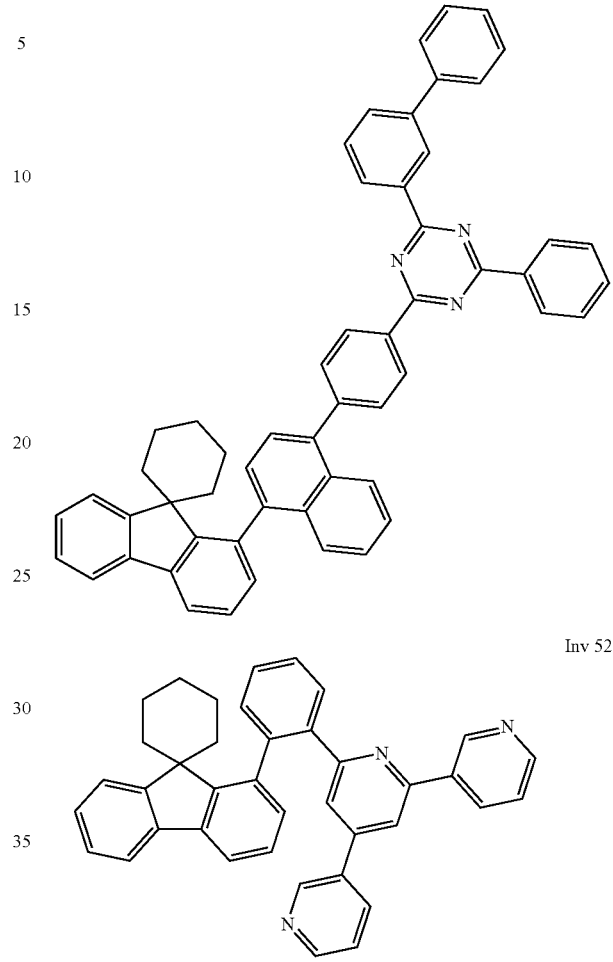
Inv 529
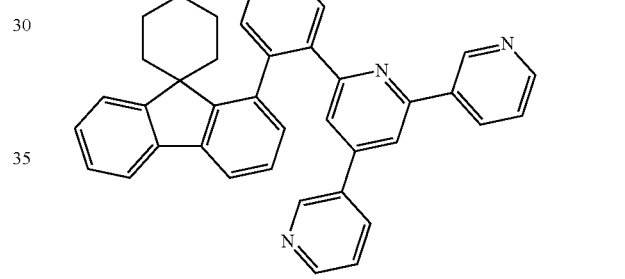
Inv 527
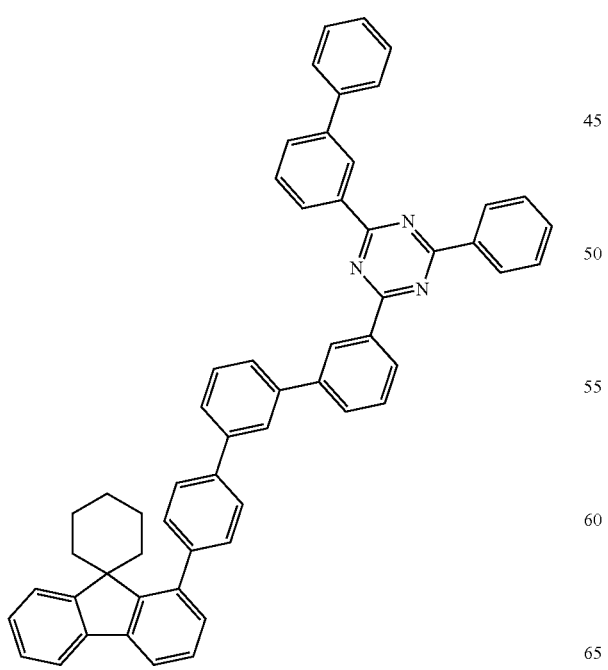
Inv 530
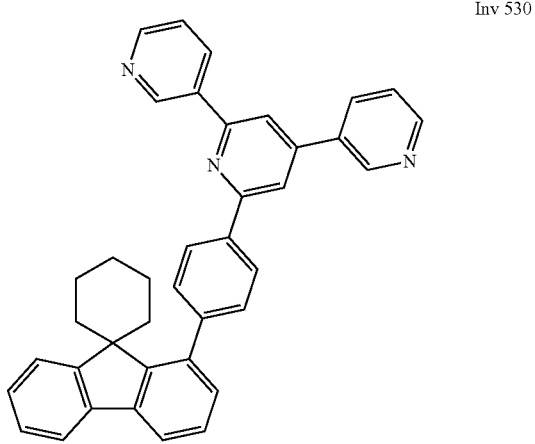

-continued
Inv 531
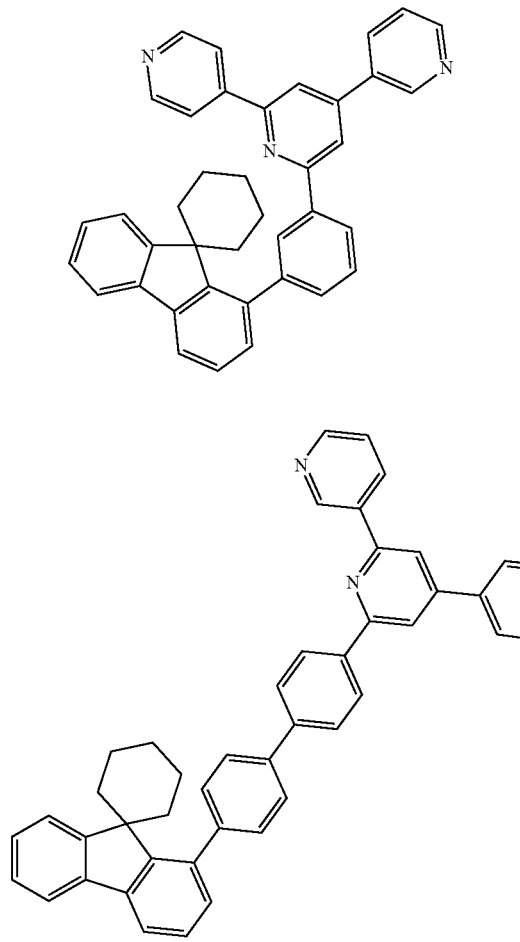
Inv 532
Inv 533
Inv 534
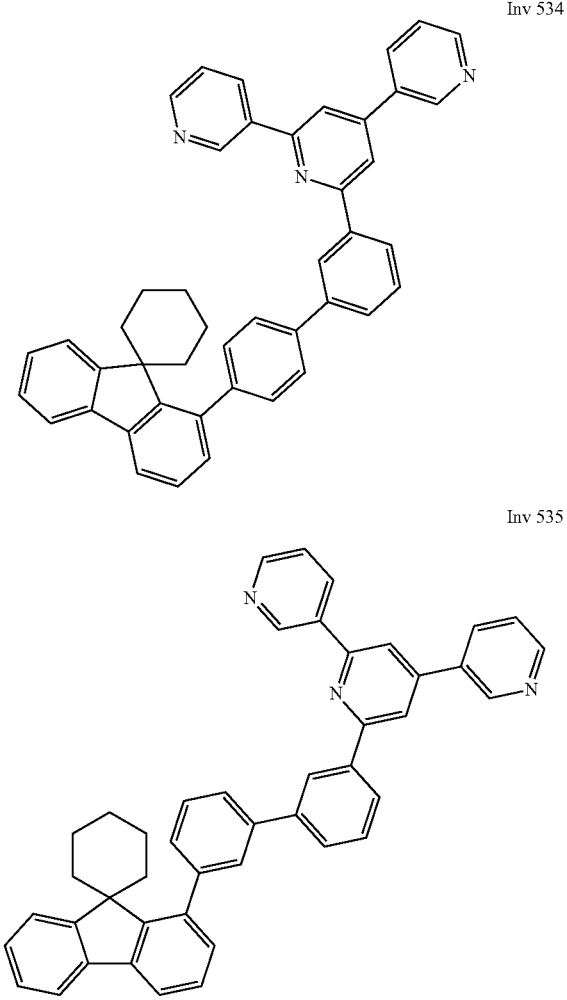
Inv 535
Inv 536
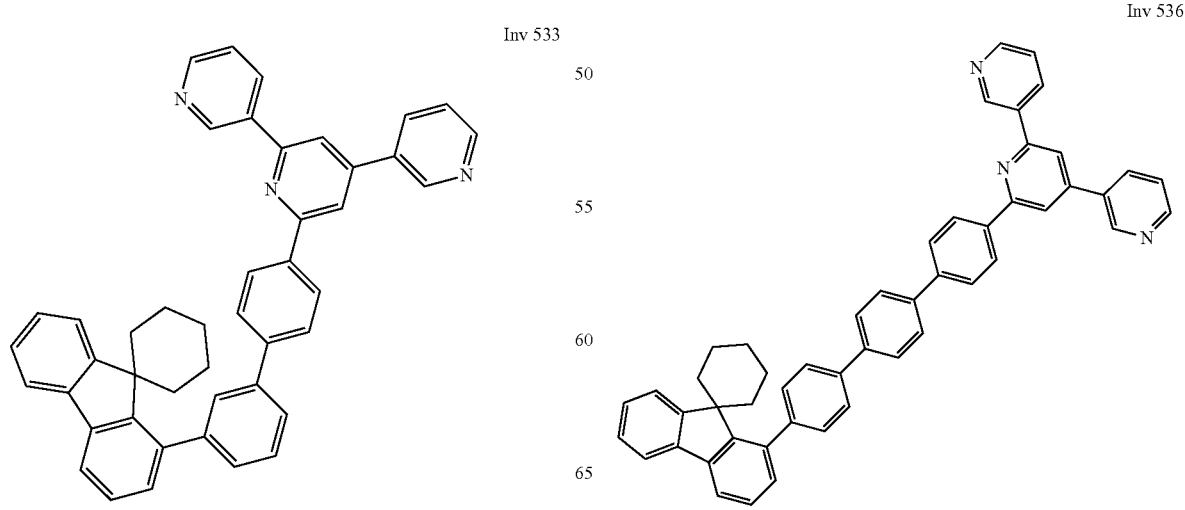

Inv 537
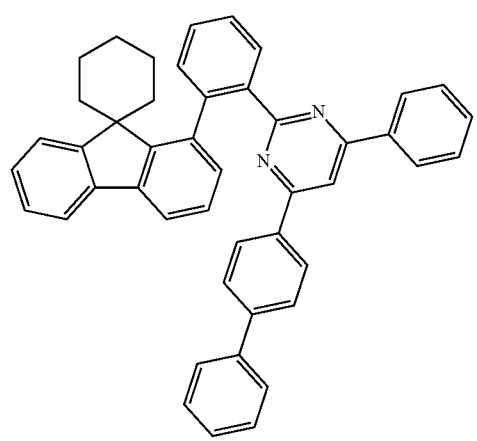
Inv 539
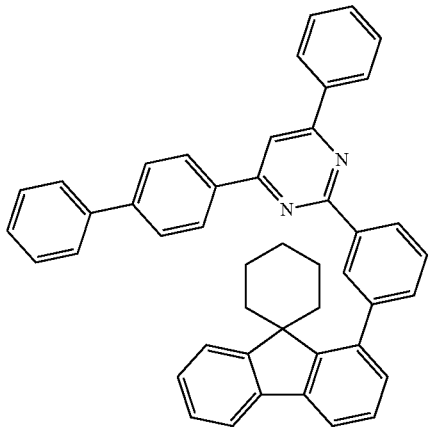
Inv 538
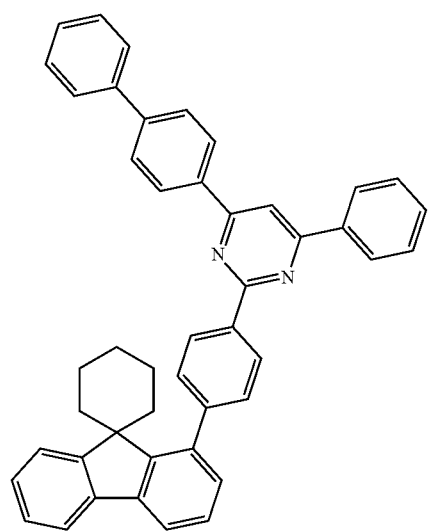
Inv 540
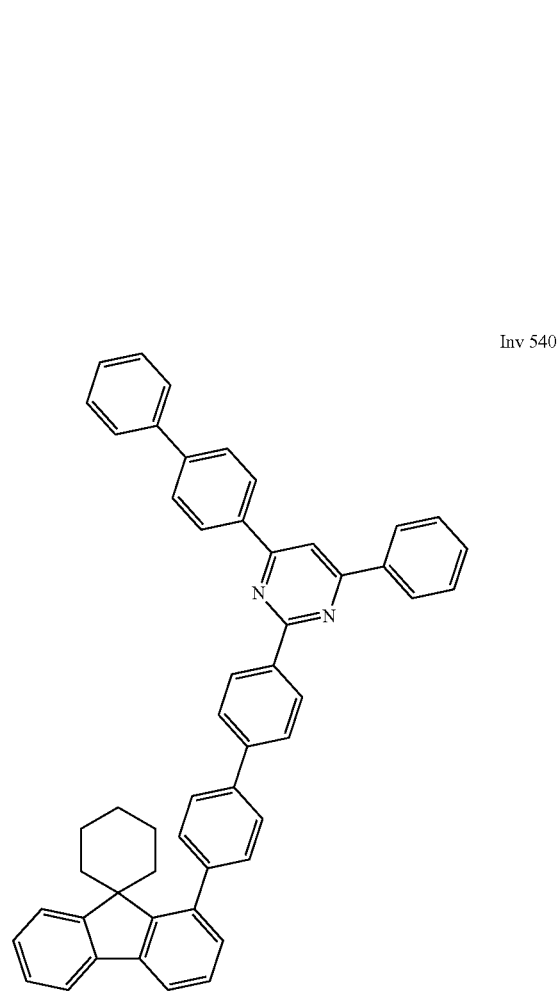

Inv 541
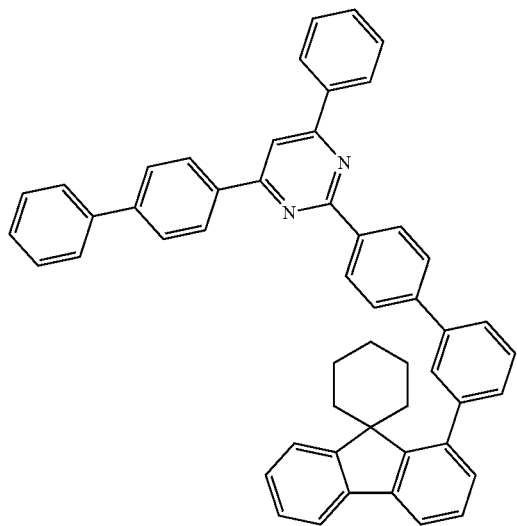
Inv 543
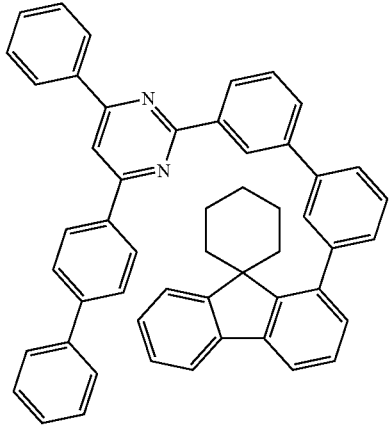
Inv 542
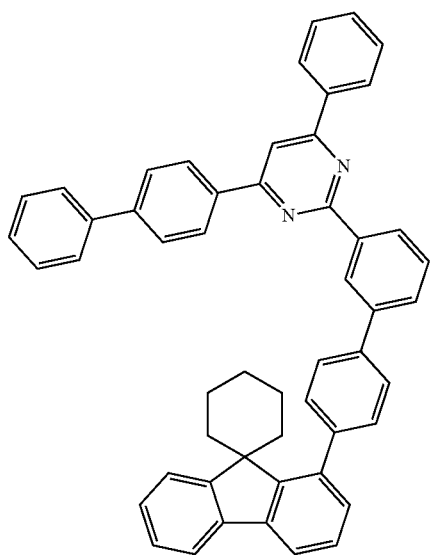
Inv 544
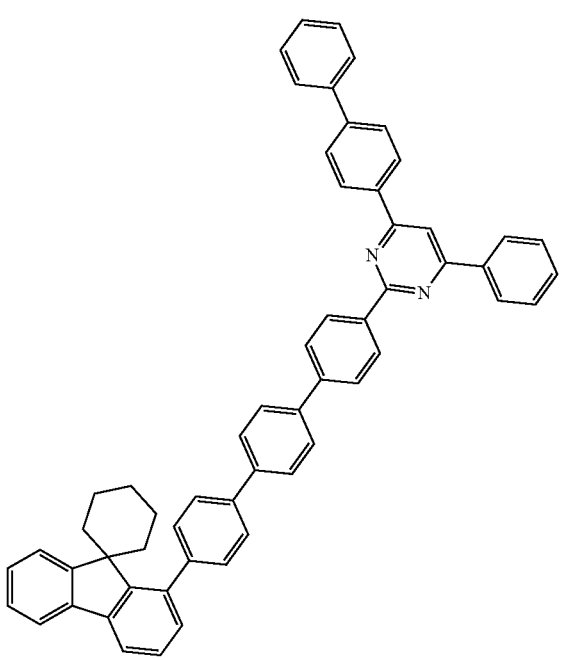

251 252
Inv 545
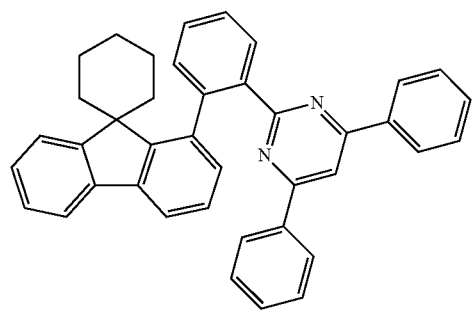
Inv 546
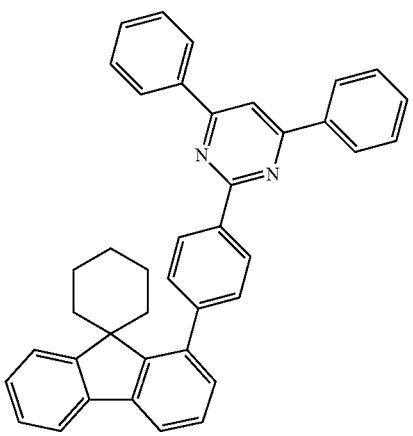
Inv 547
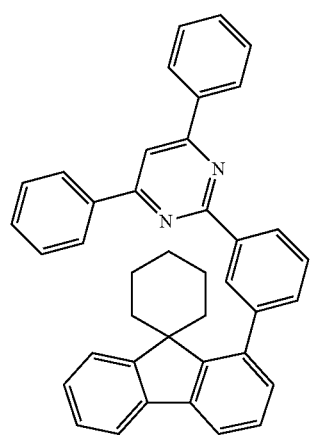
Inv 548
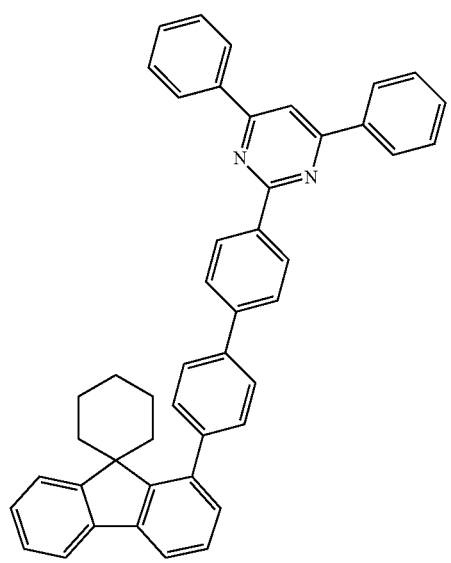
Inv 549
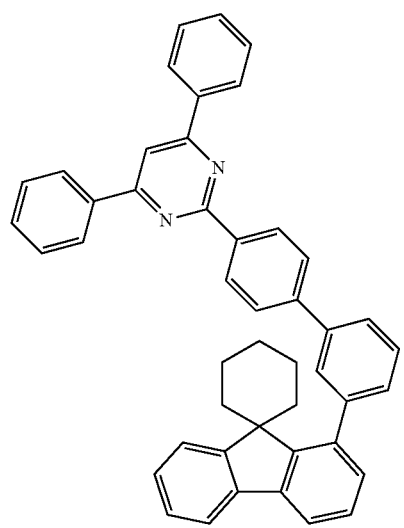
Inv 550
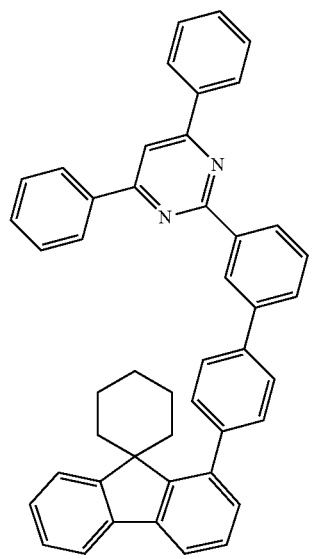

-continued
Inv 551
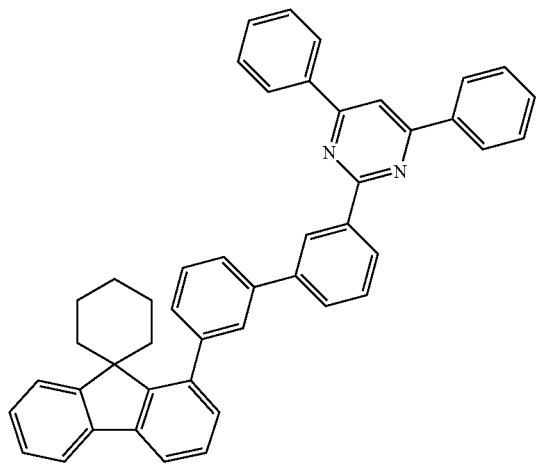
Inv 552
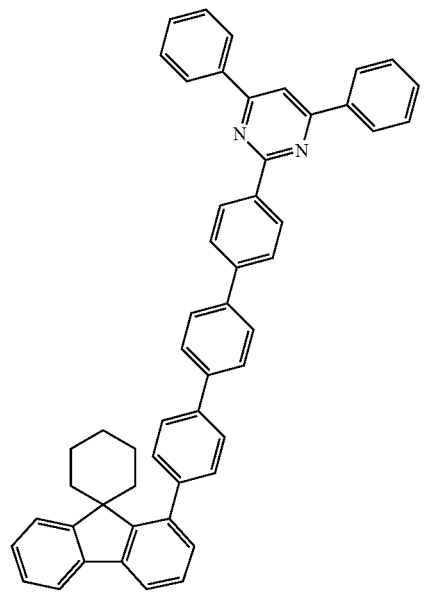
Inv 553
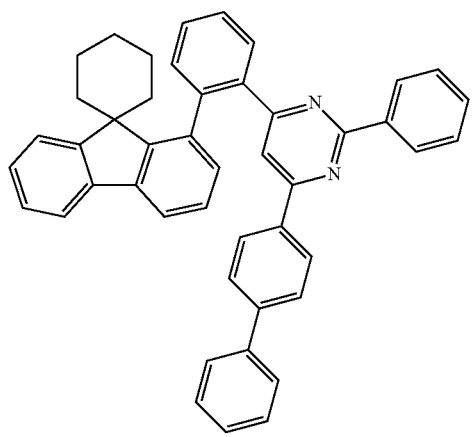
Inv 554
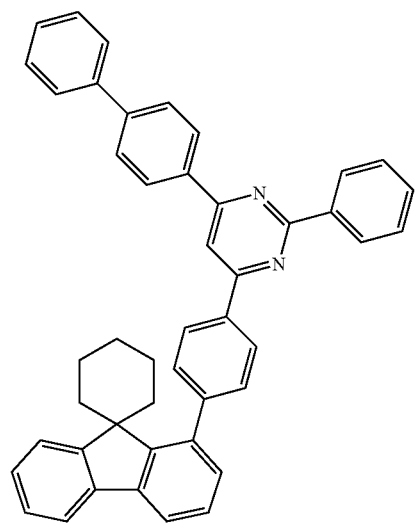

-continued
Inv 555
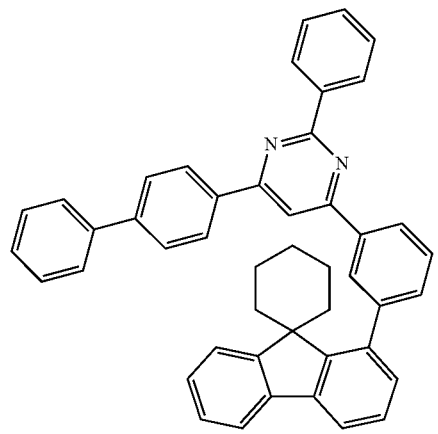
Inv 556
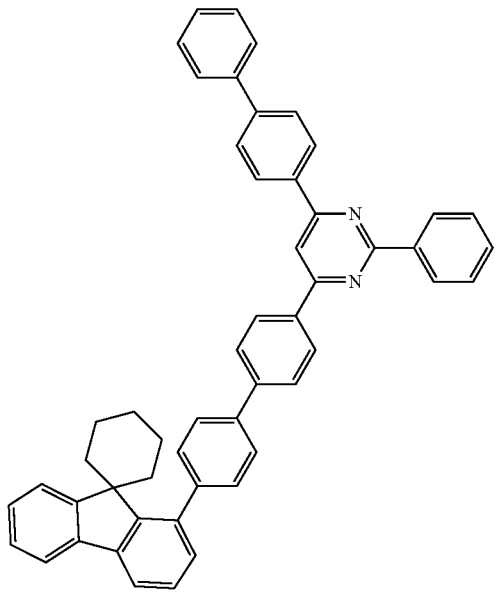
Inv 557
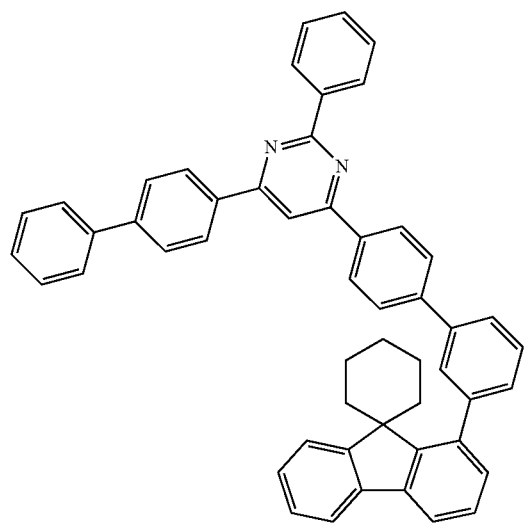
Inv 558
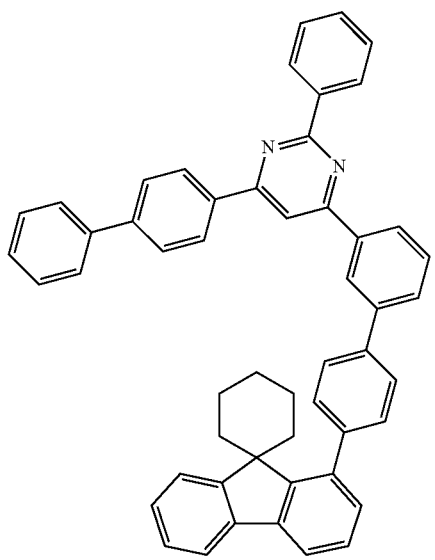

-continued
Inv 559
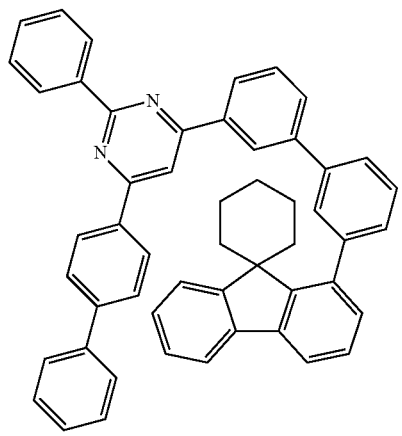
Inv 560
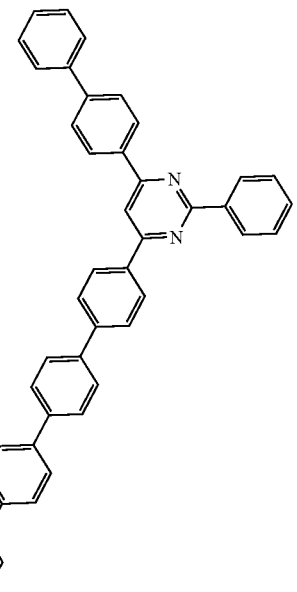
Inv 561
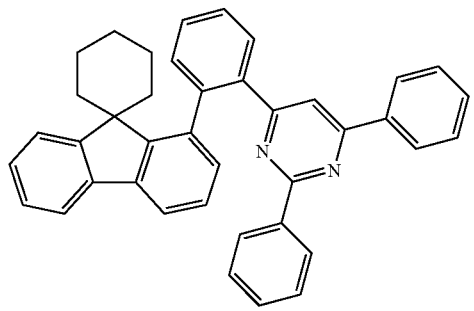
Inv 562
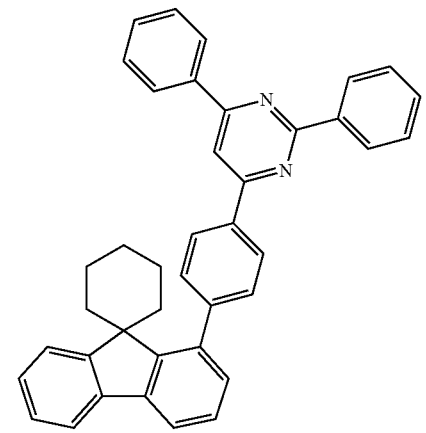
Inv 563
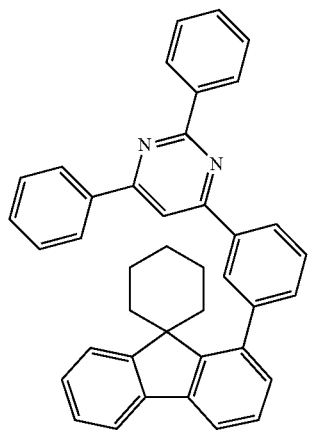
Inv 564
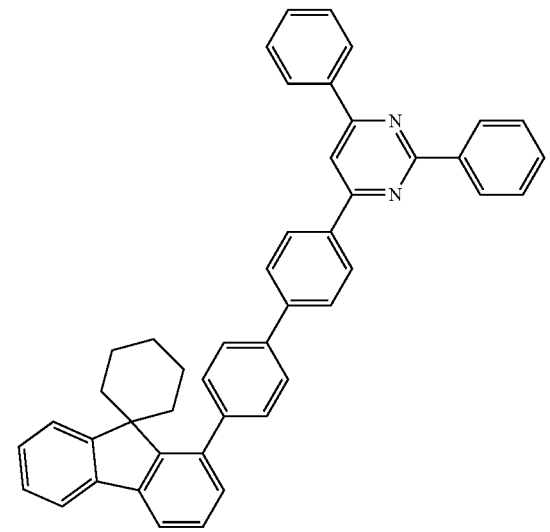

-continued
Inv 565
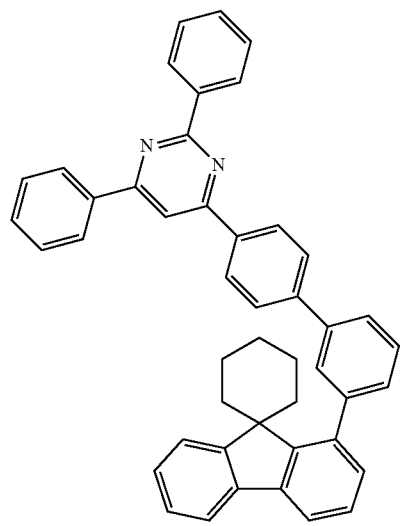
Inv 566
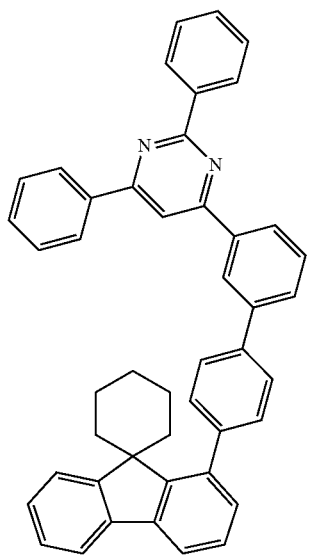
Inv 567
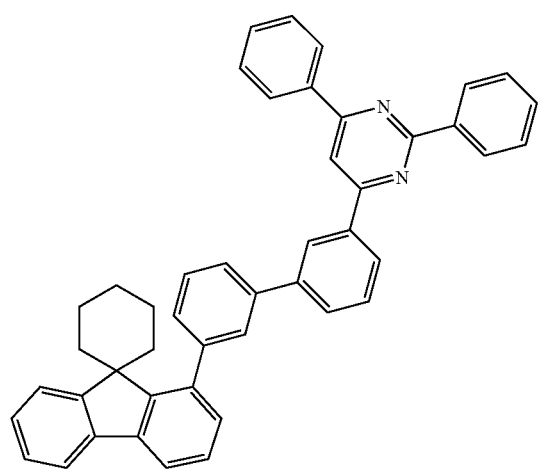
Inv 568
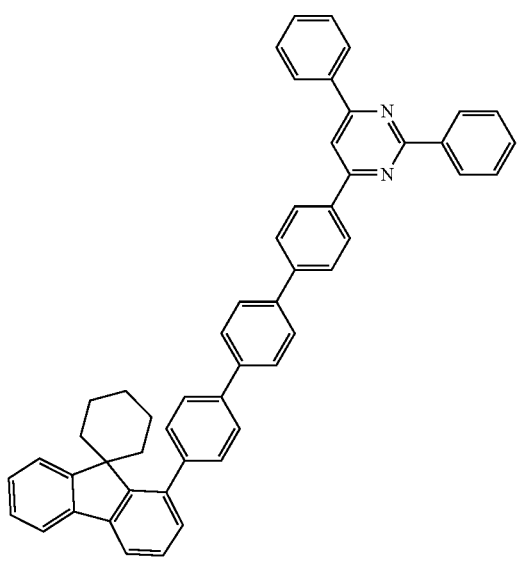
Inv 569
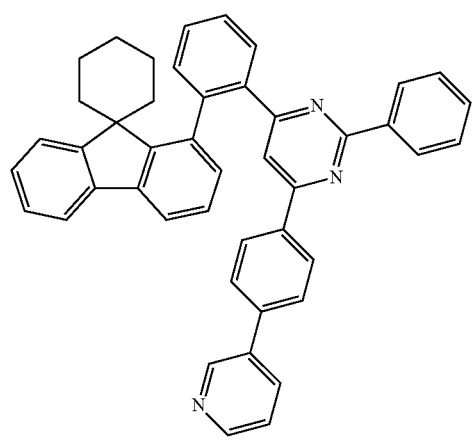
Inv 570
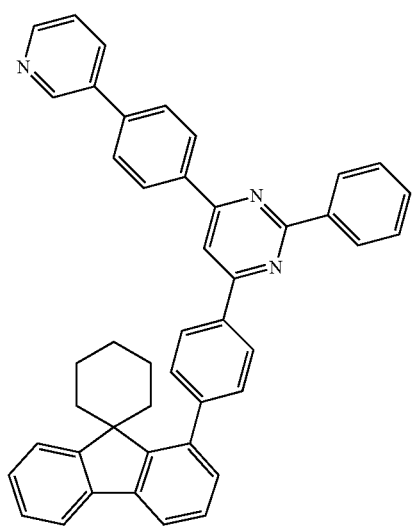

-continued
Inv 571
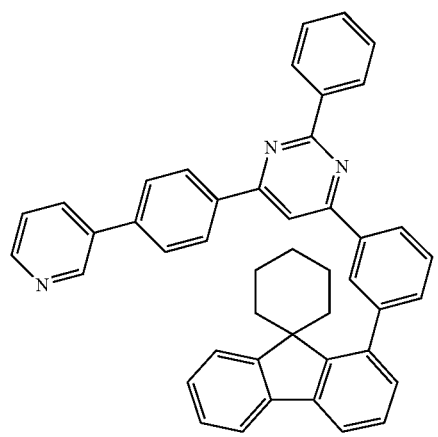
Inv 572
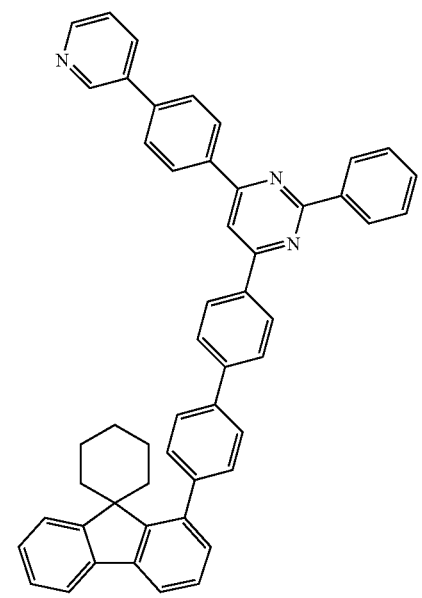
Inv 573
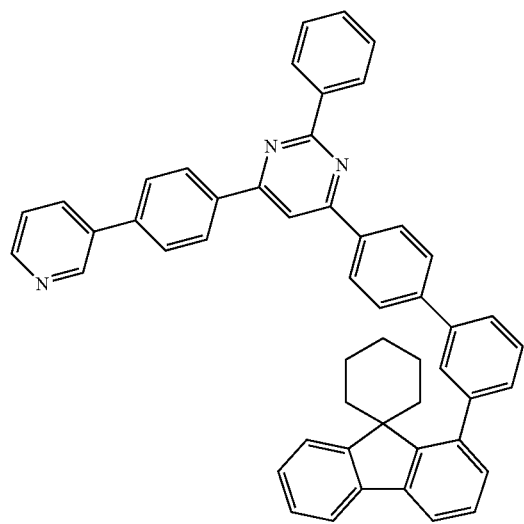
Inv 574
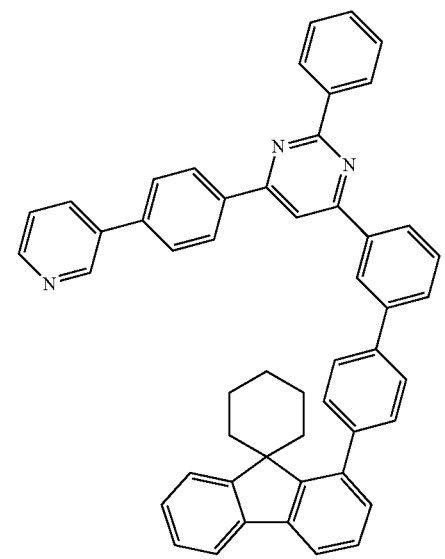

-continued
Inv 575
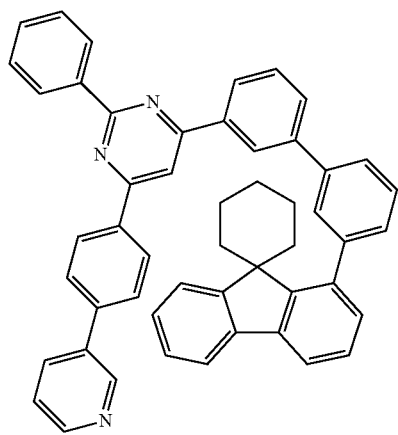
Inv 576
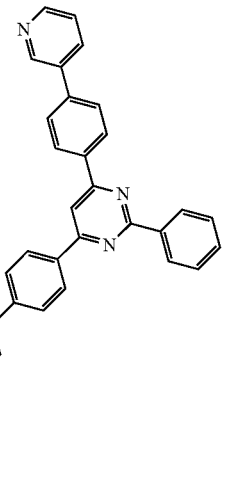
Inv 577
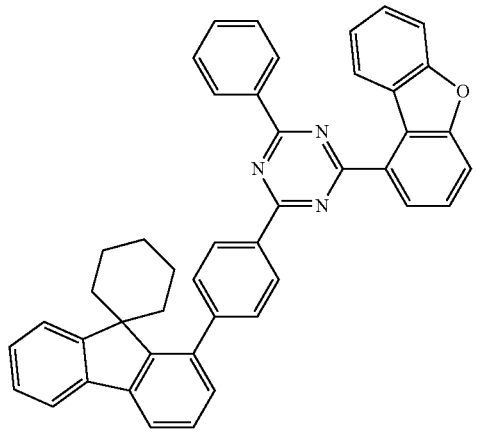
Inv 578
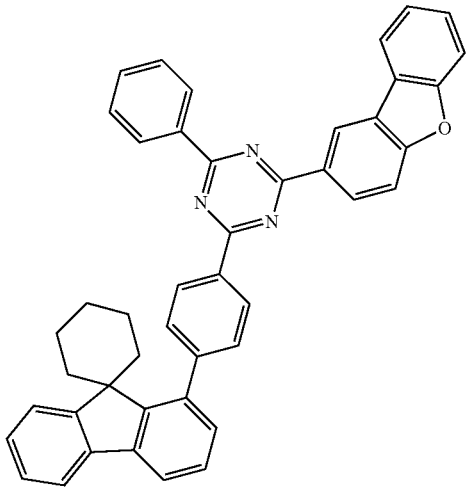
Inv 579
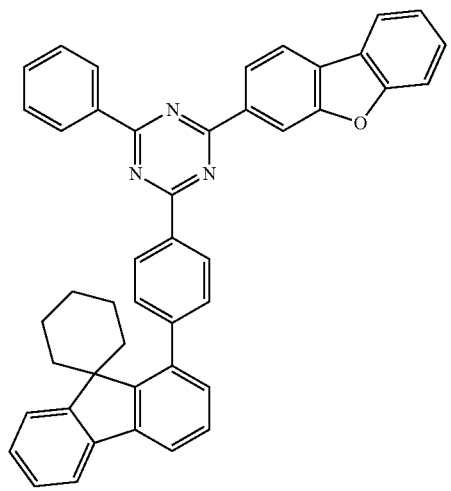
Inv 580
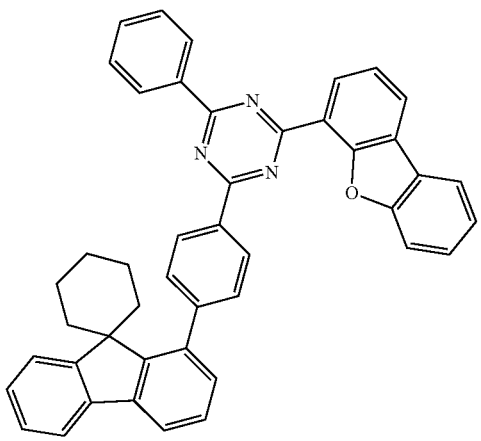

-continued
Inv 581
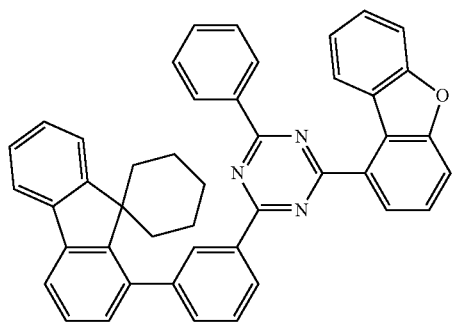
Inv 582
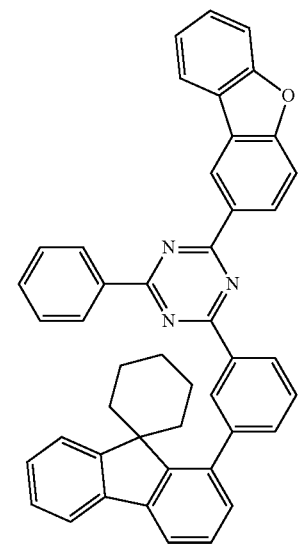
Inv 583
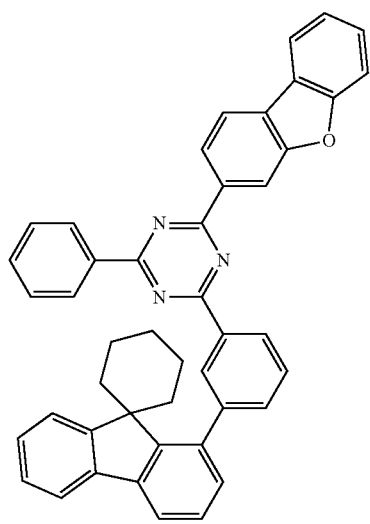
Inv 584
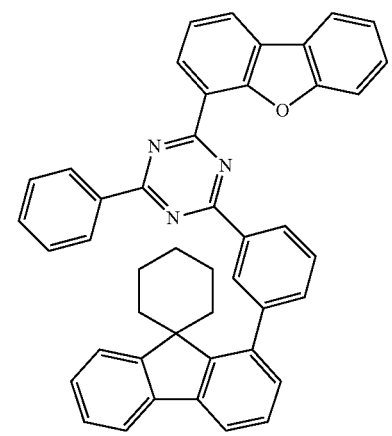
Inv 585
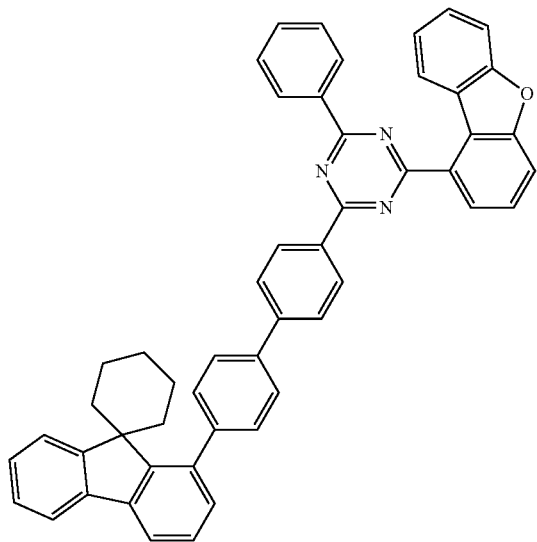
Inv 586
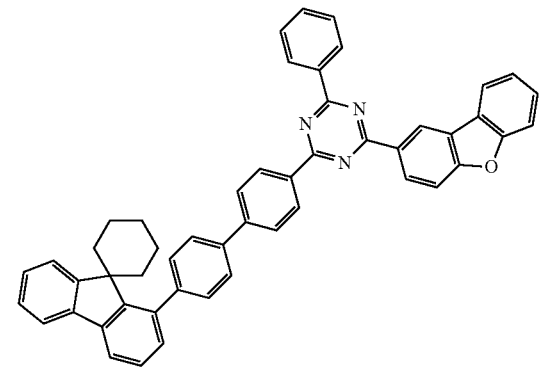

Inv 587
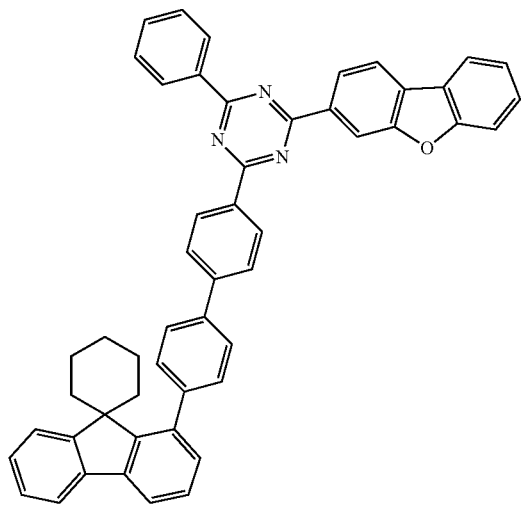
Inv 588
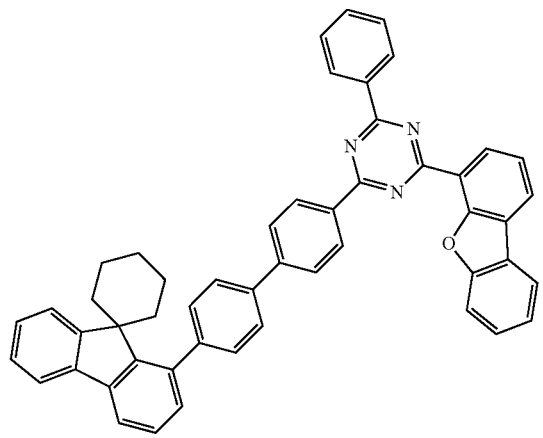
Inv 589
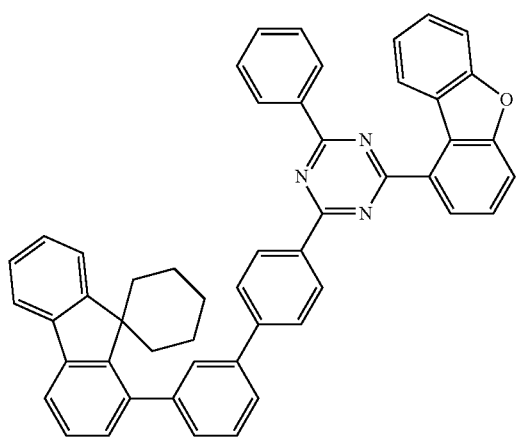
Inv 590
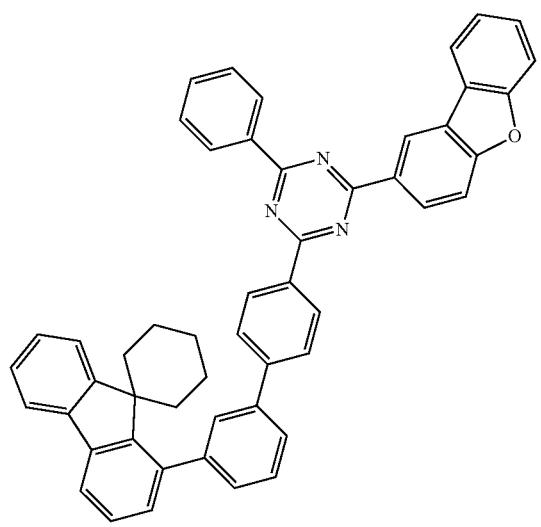
Inv 591
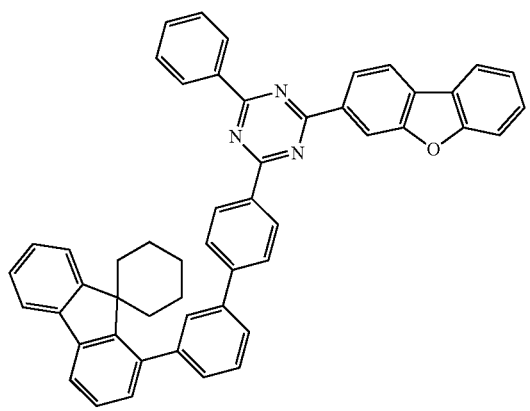
Inv 592
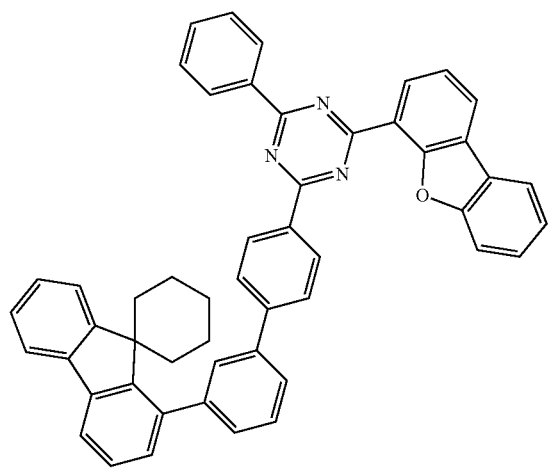

Inv 593
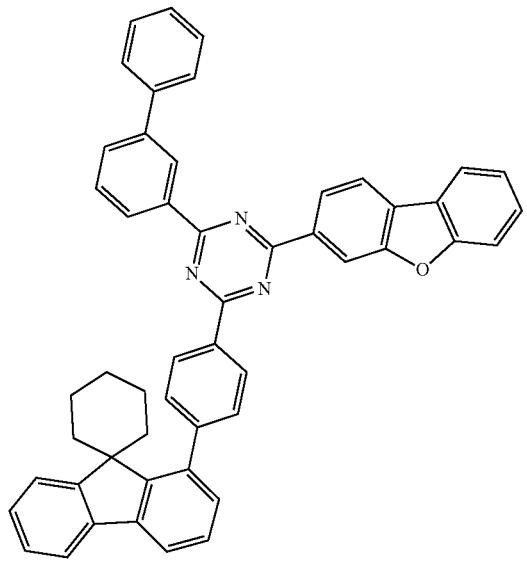
Inv 594
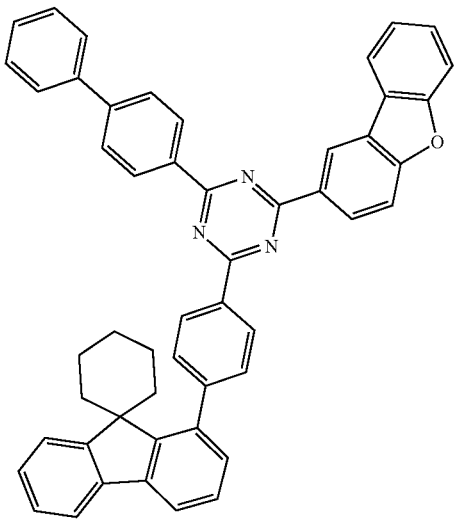
Inv 595
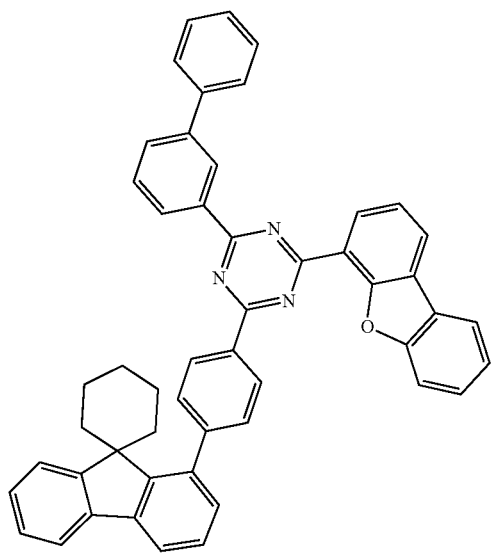
Inv 596
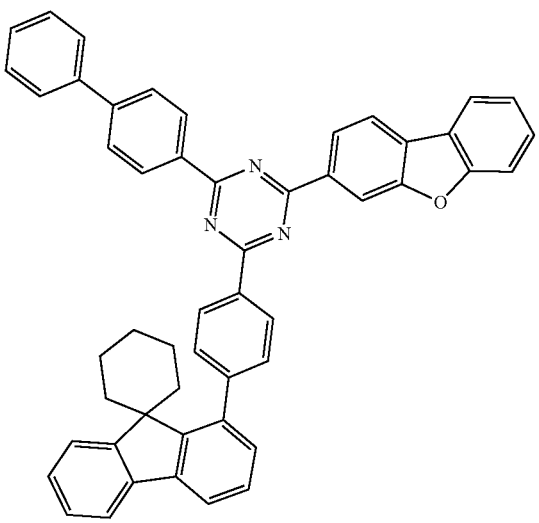

-continued
Inv 597
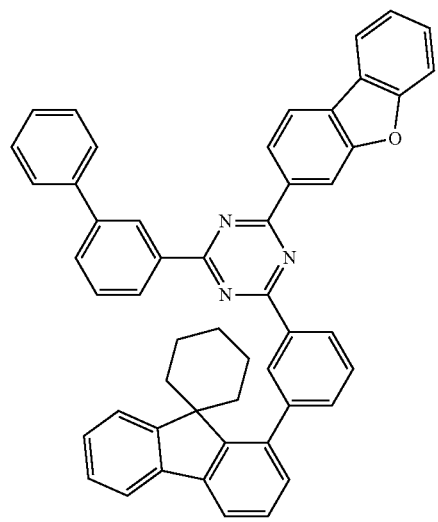
Inv 598
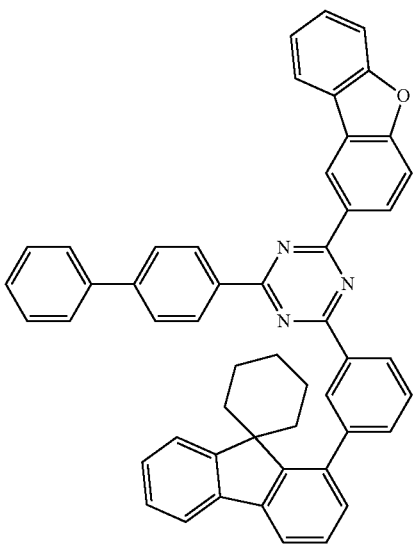
Inv 599
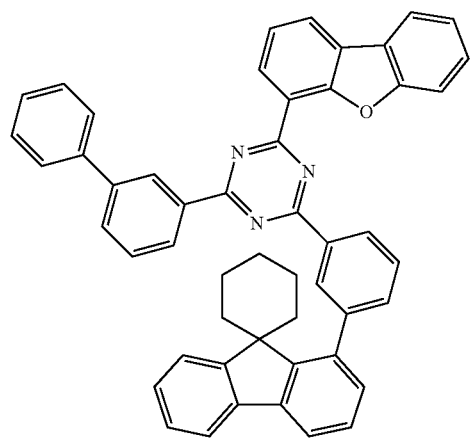
Inv 600
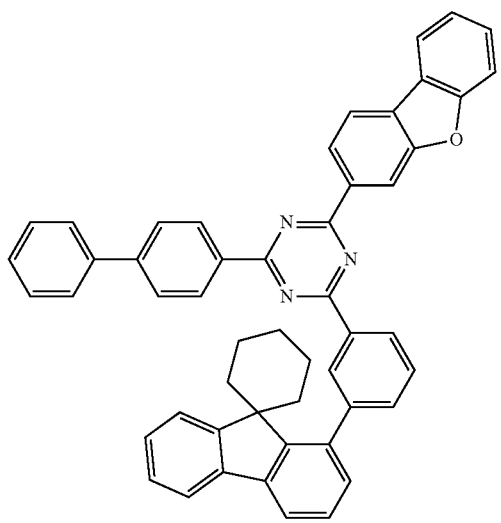
Inv 601
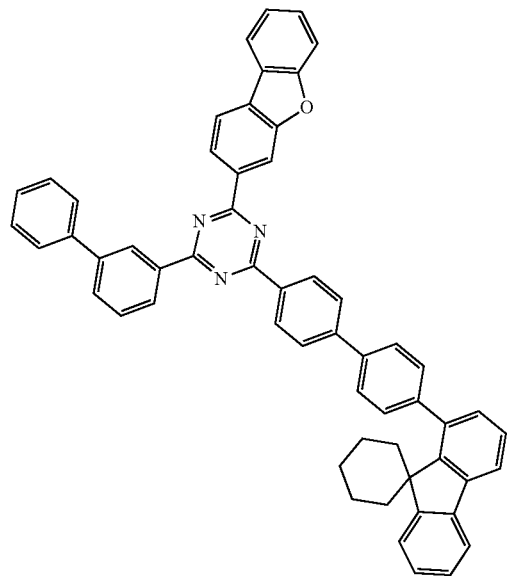
Inv 602
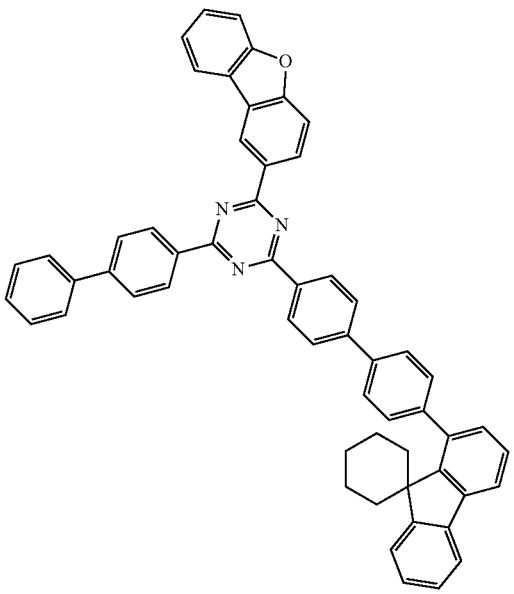

-continued
Inv 603
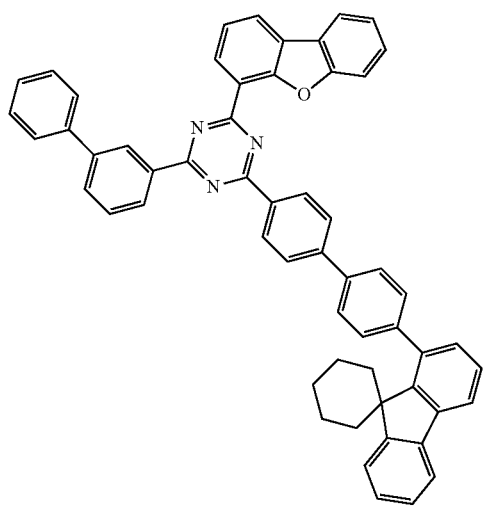
Inv 604
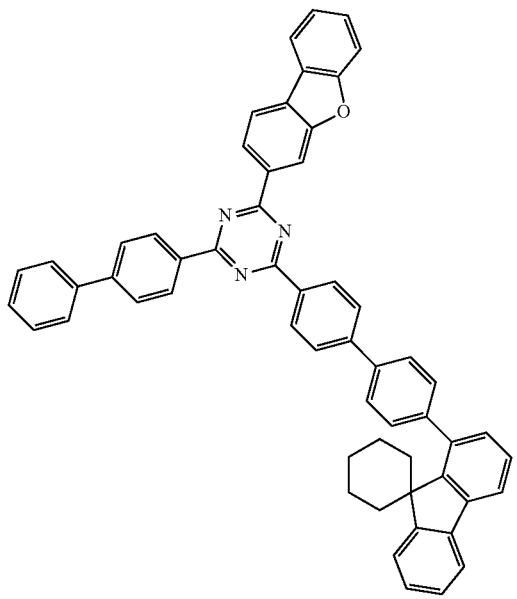
Inv 605
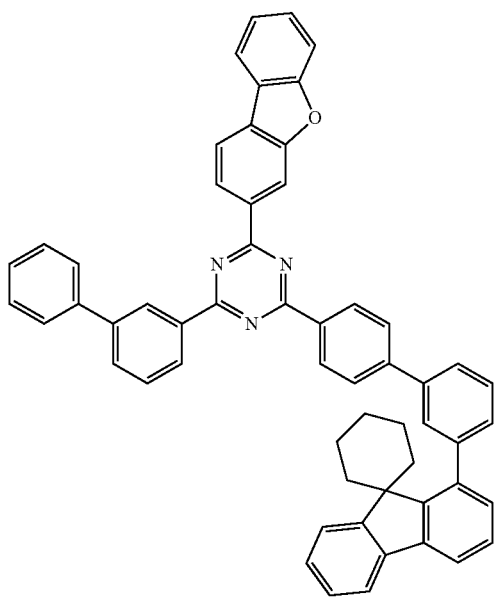
Inv 606
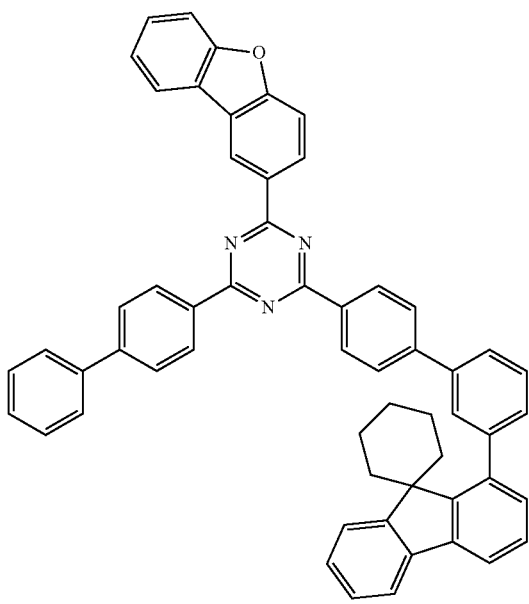

-continued
Inv 607
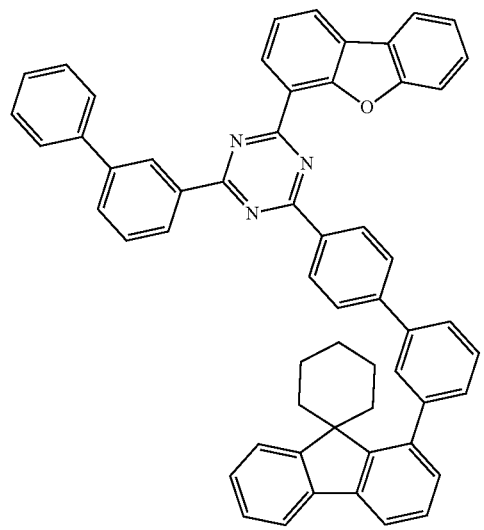
Inv 608
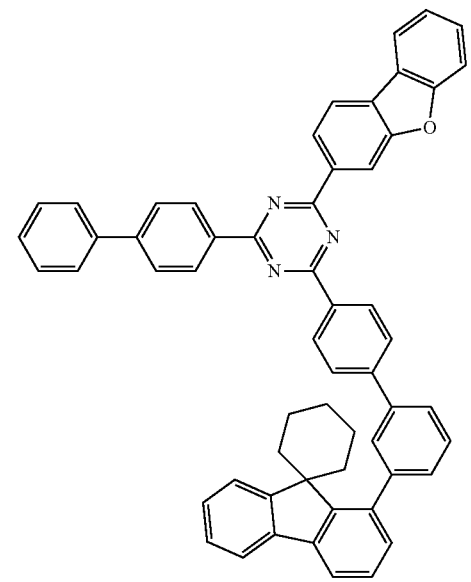
Inv 609
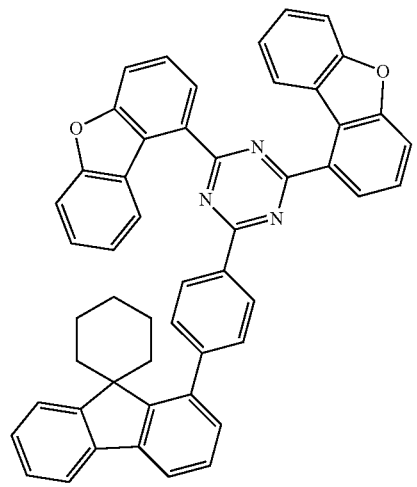
Inv 610
Inv 611
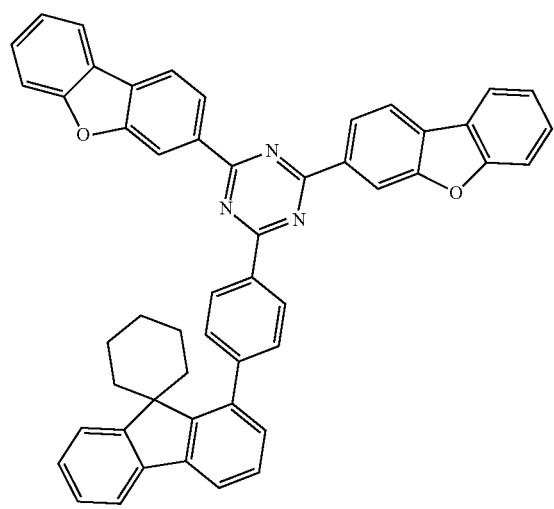
Inv 612
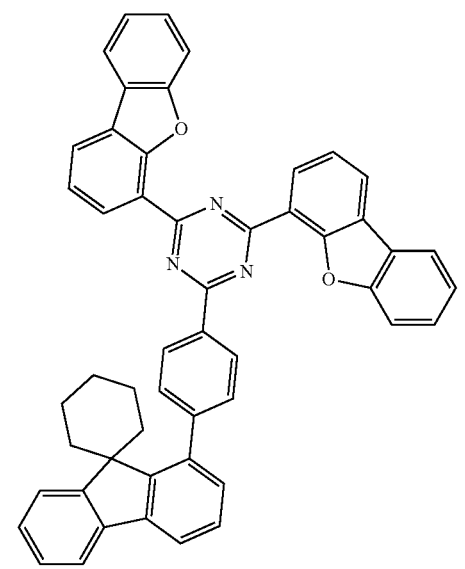

-continued
Inv 613
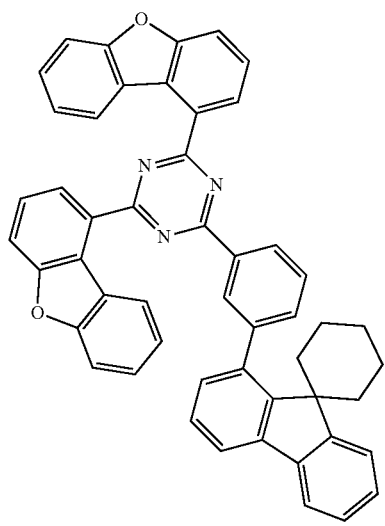
Inv 614
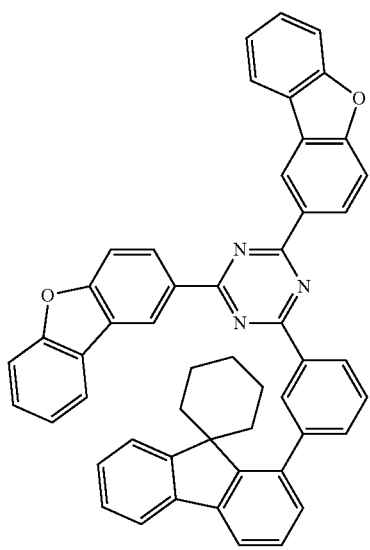
Inv 615
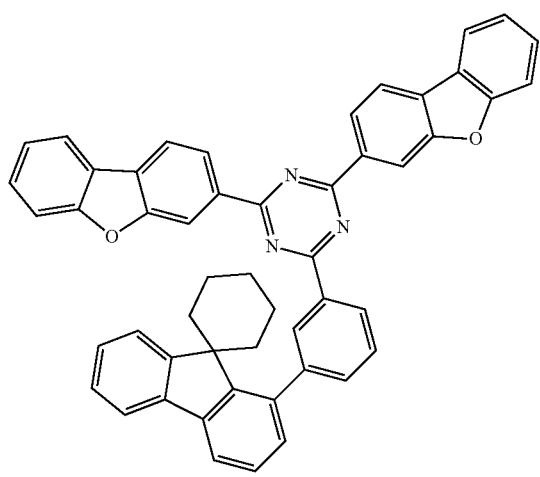
Inv 616
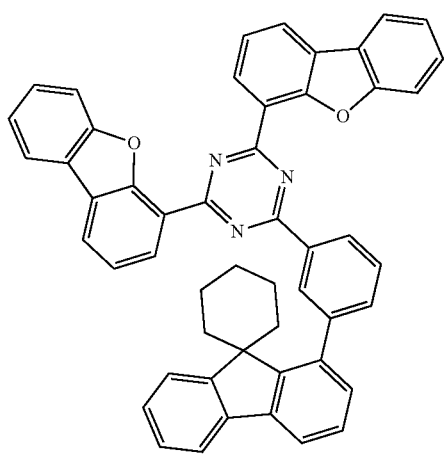
Inv 617
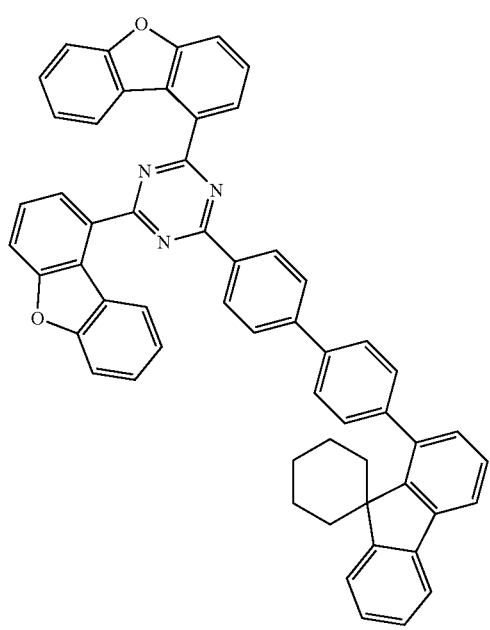
Inv 618
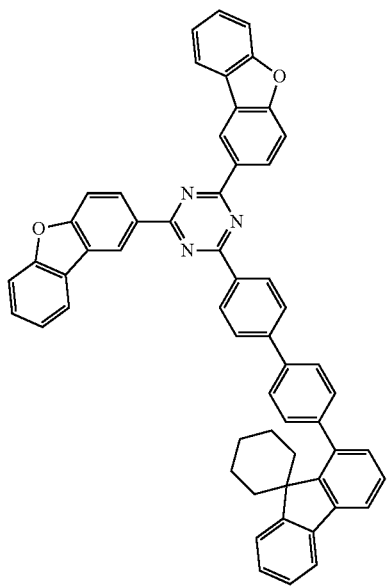

-continued
Inv 619
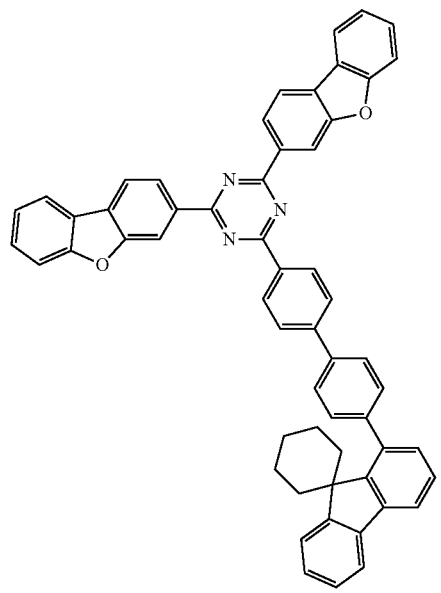
Inv 620
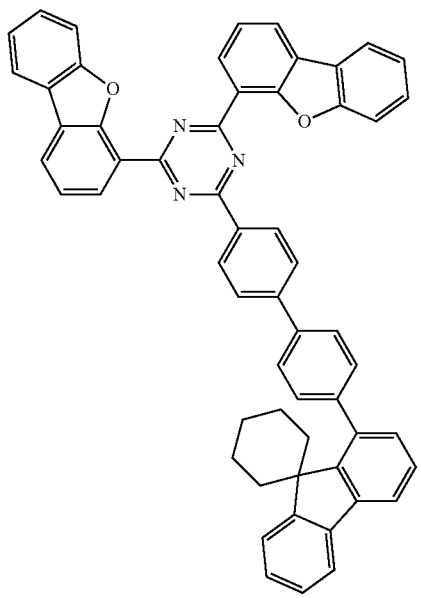
Inv 621
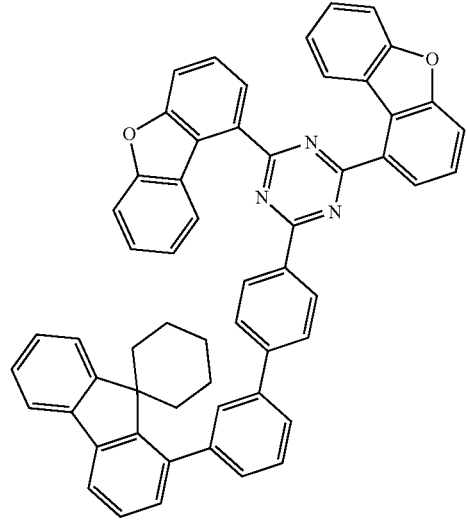
Inv 622
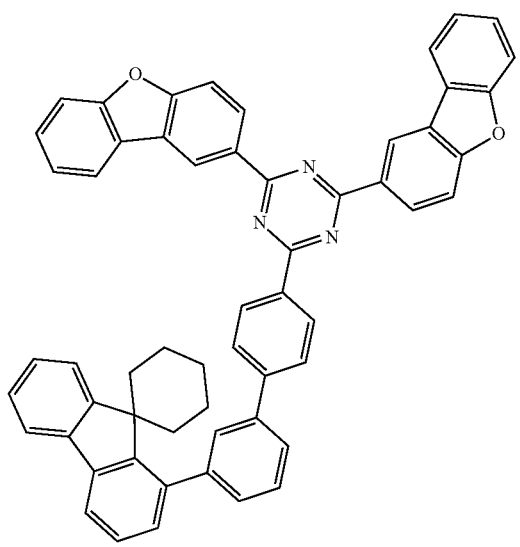
Inv 623
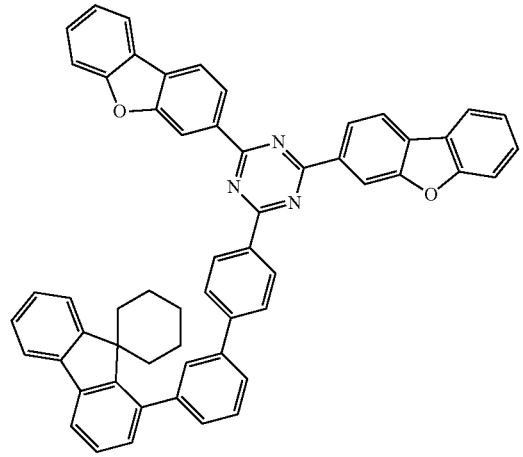
Inv 624
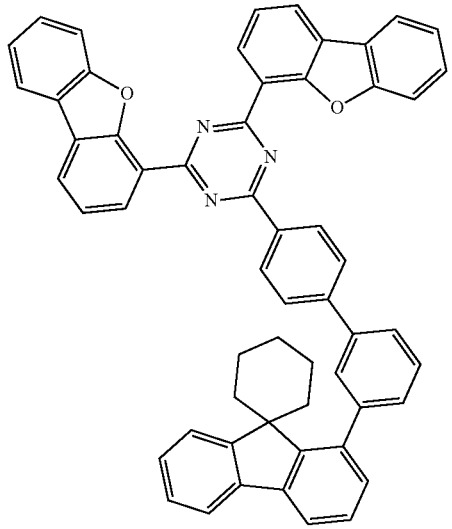

-continued
Inv 625
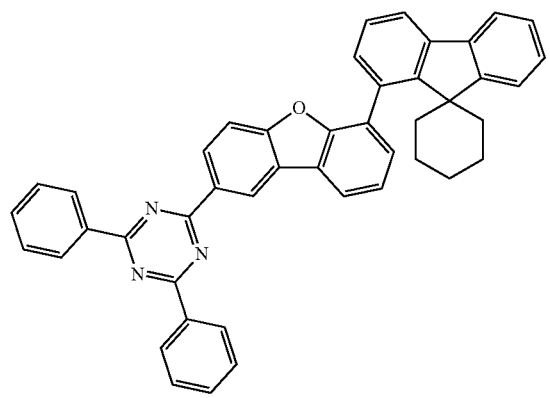
Inv 626
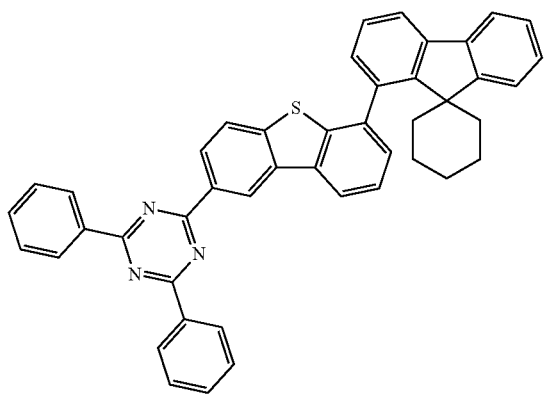
Inv 627
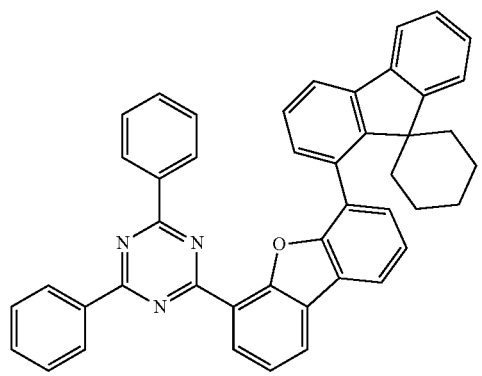
Inv 628
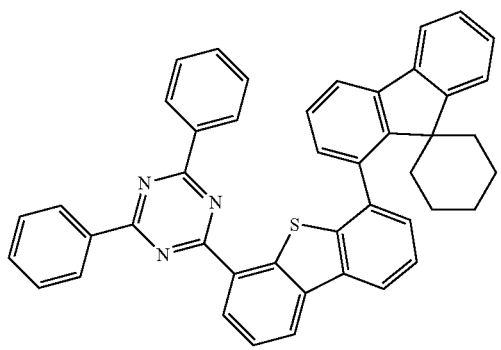
Inv 629
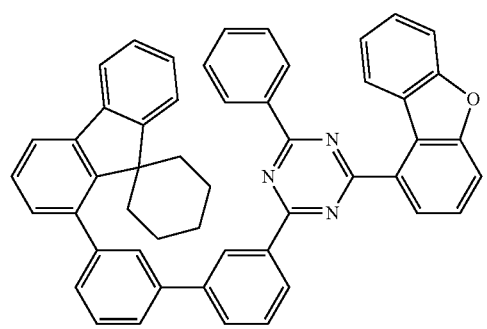
Inv 630
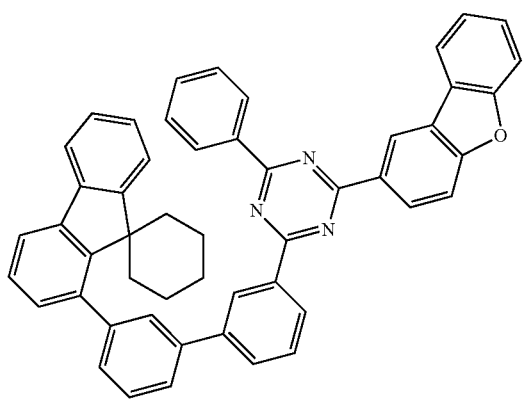

-continued
Inv 631
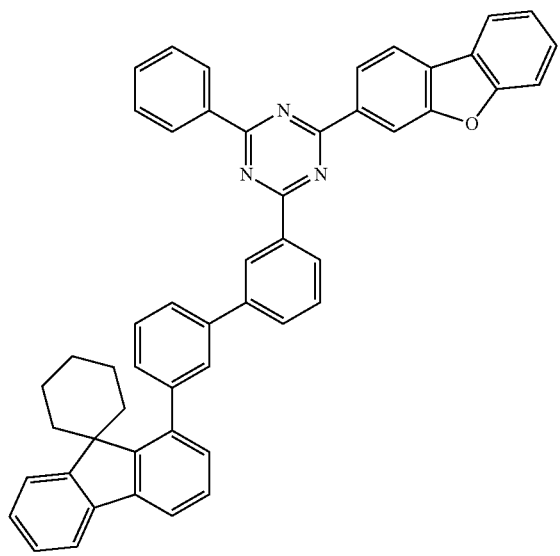
Inv 632
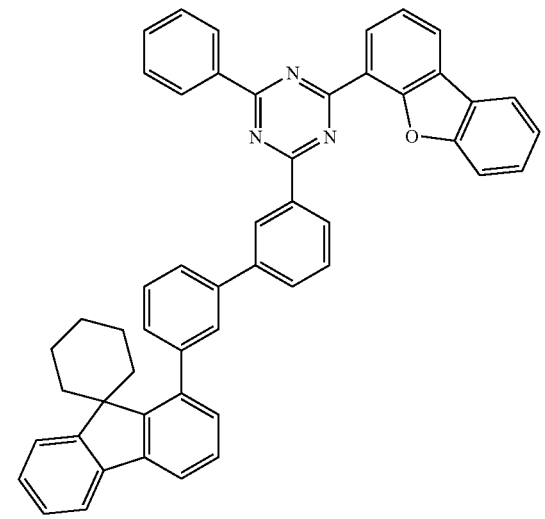
Inv 633
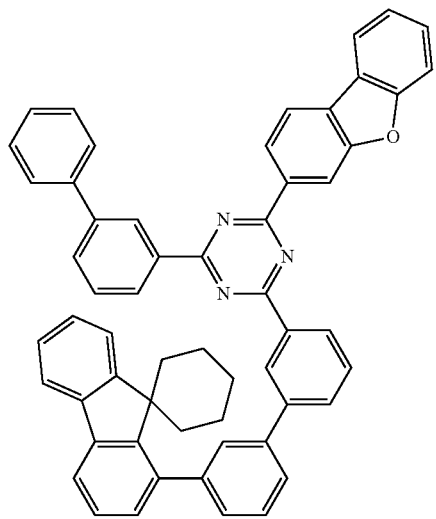
Inv 634
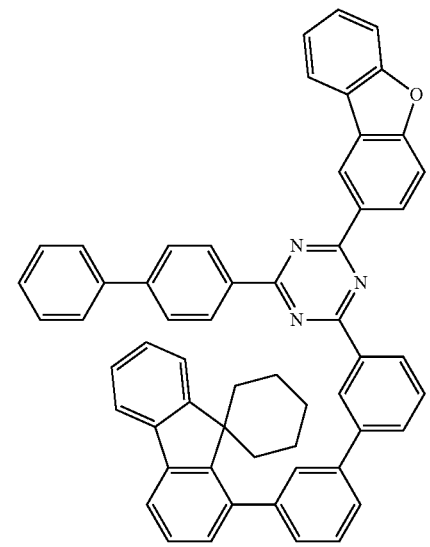
Inv 635
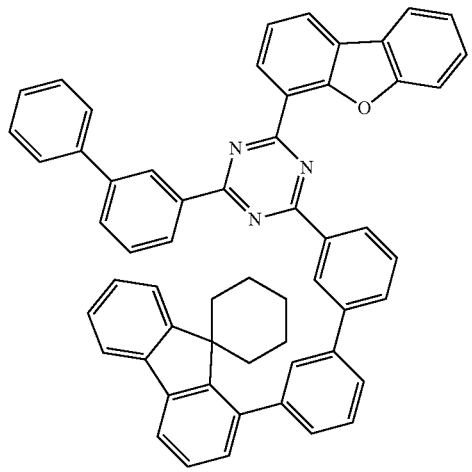
Inv 636
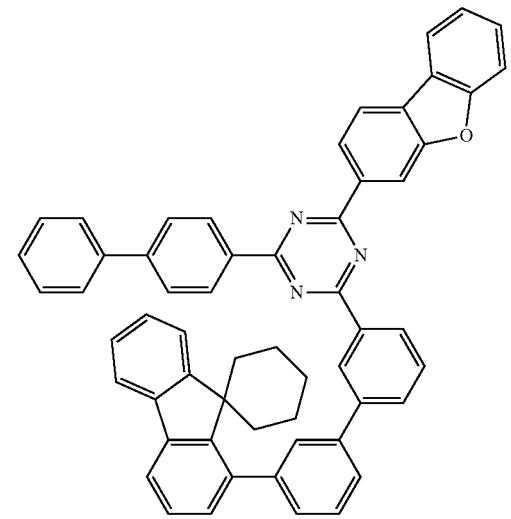

-continued
Inv 637
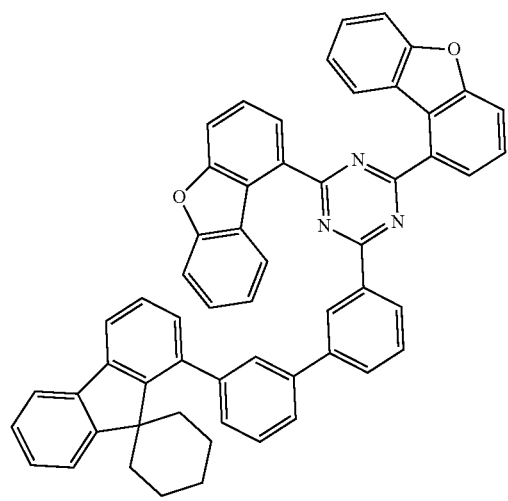
Inv 638
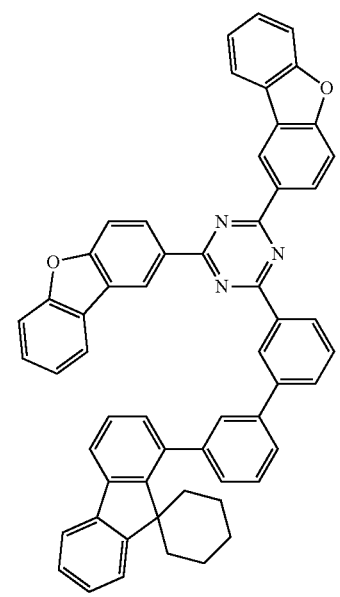
Inv 639
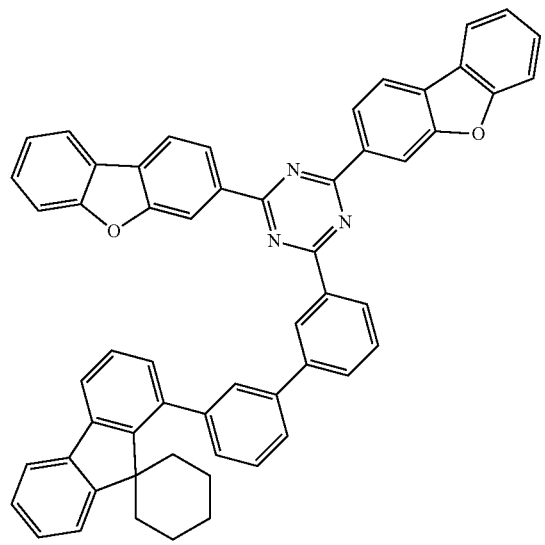
Inv 640
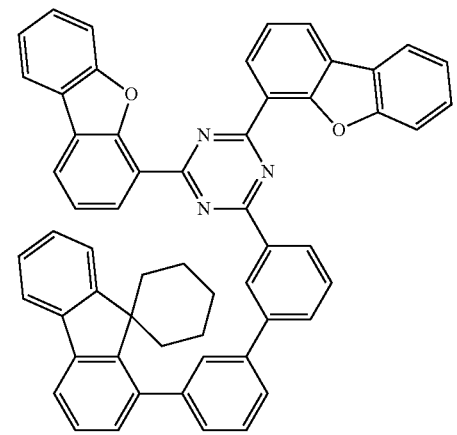
Inv 641
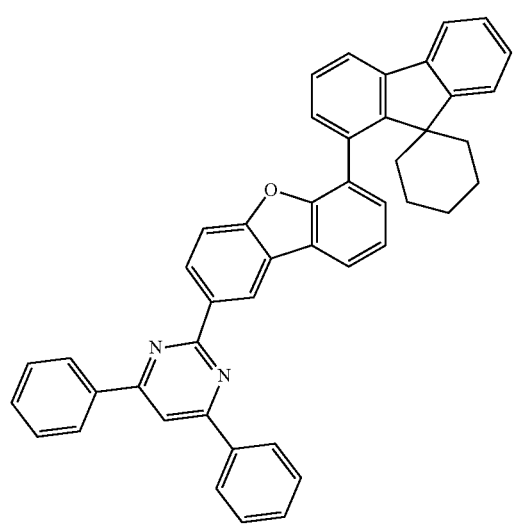
Inv 642
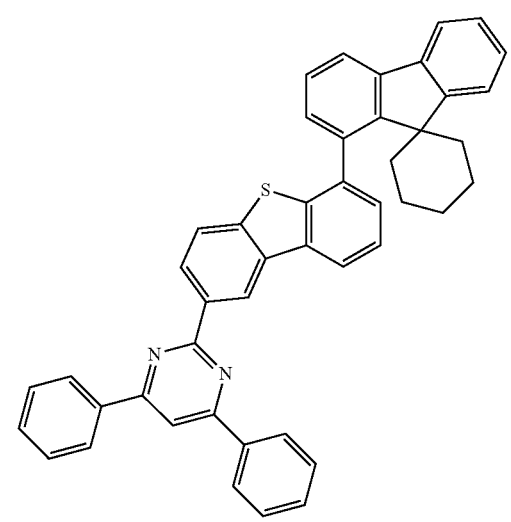

Inv 643
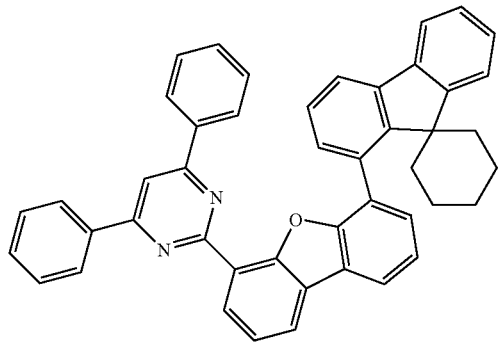
Inv 644
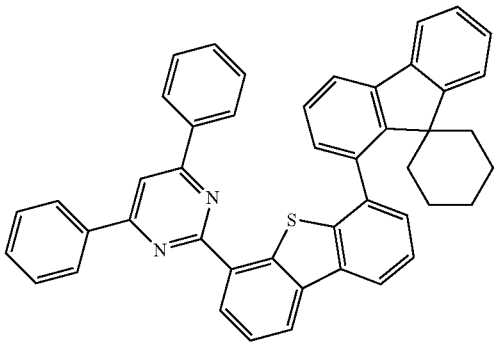
Inv 645
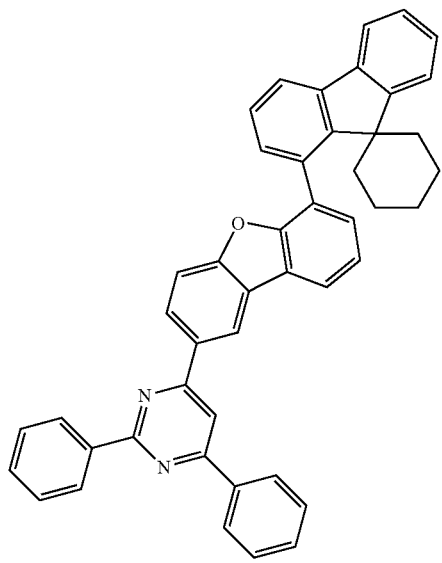
Inv 646
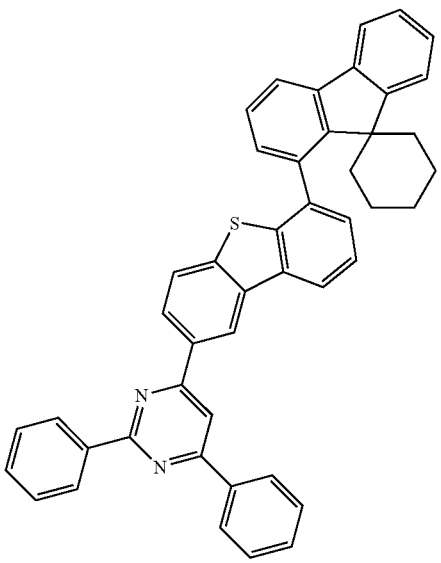
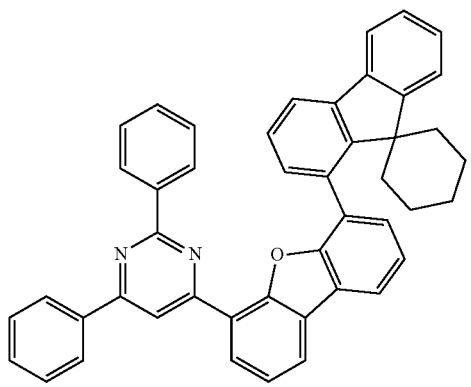
Inv 648
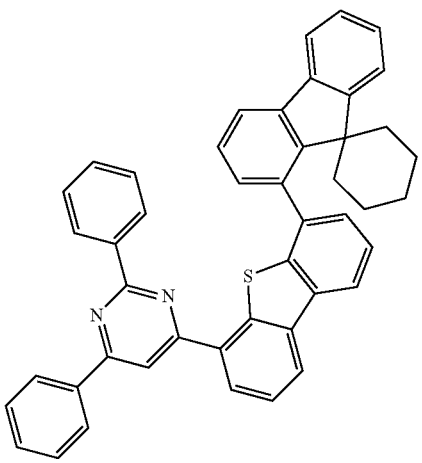

-continued
Inv 649
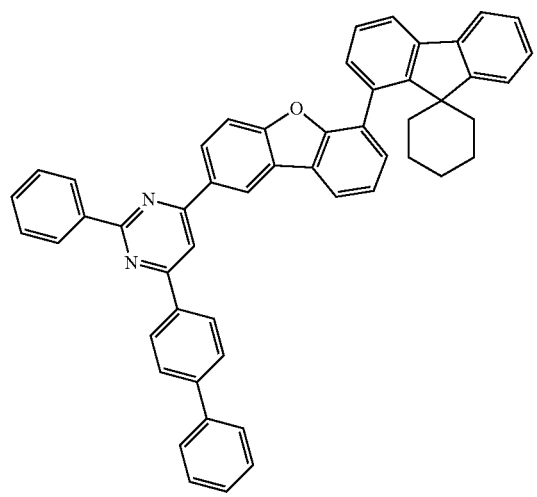
Inv 650
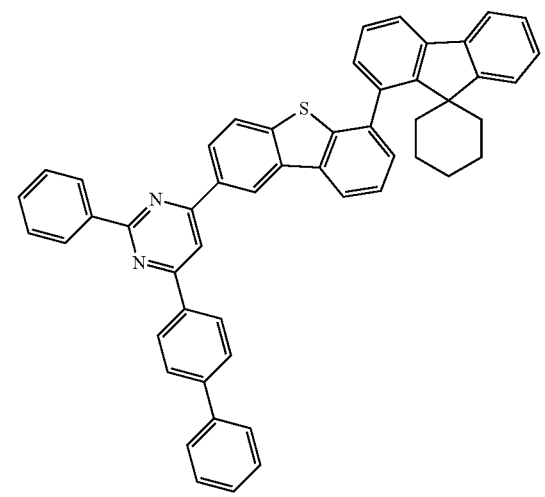
Inv 651
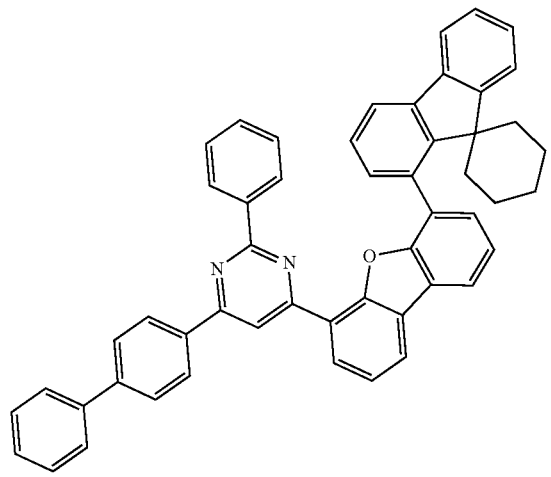
Inv 652
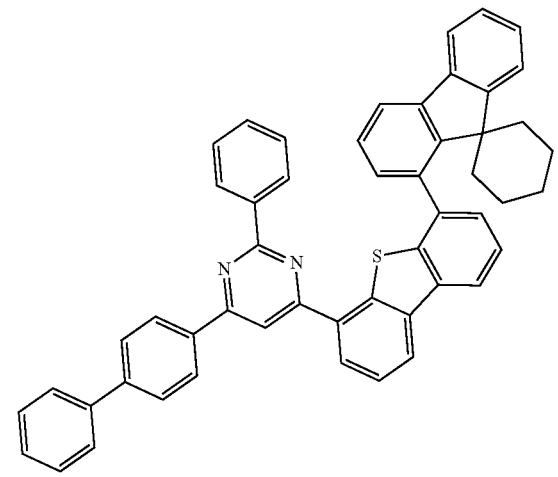
Inv 653
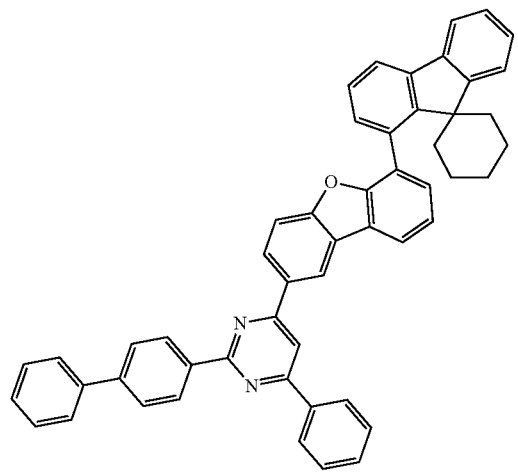
Inv 654
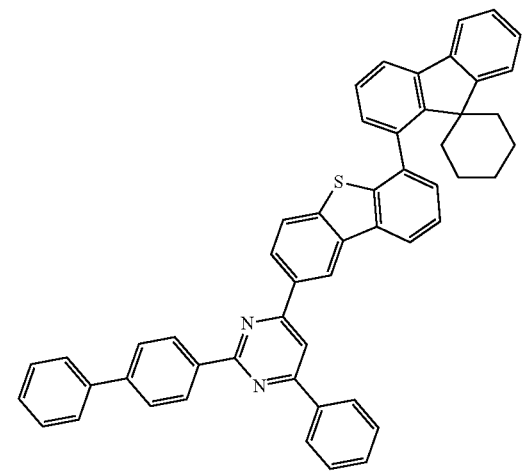

-continued
Inv 655
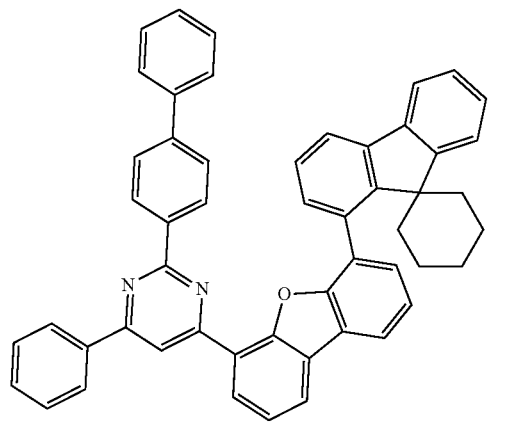
Inv 656
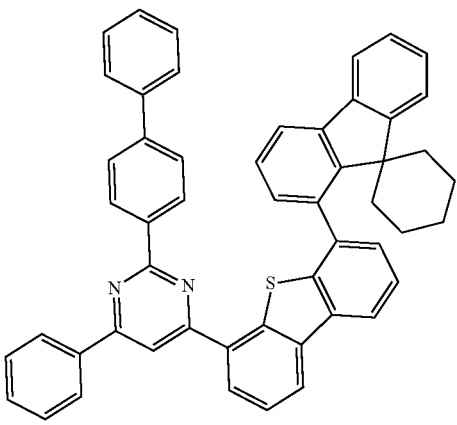
Inv 657
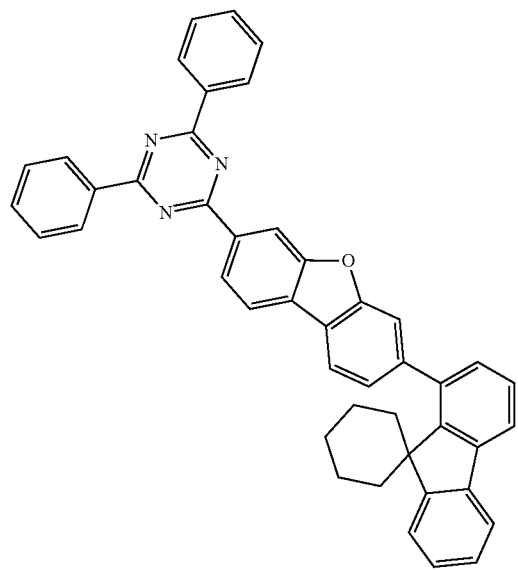
Inv 658
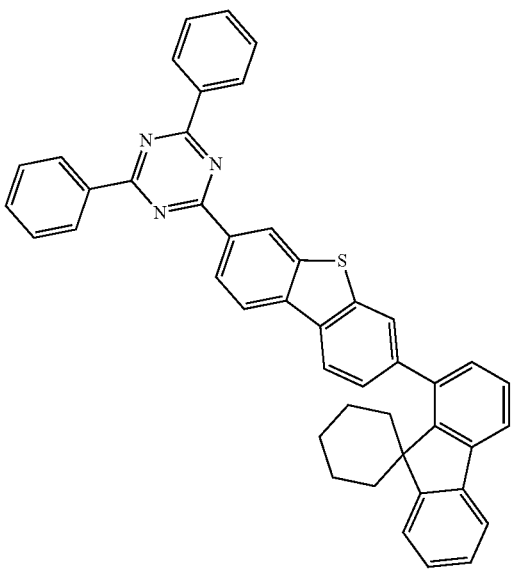
Inv 659
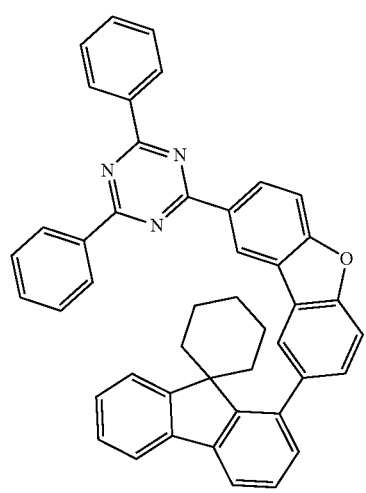
Inv 660
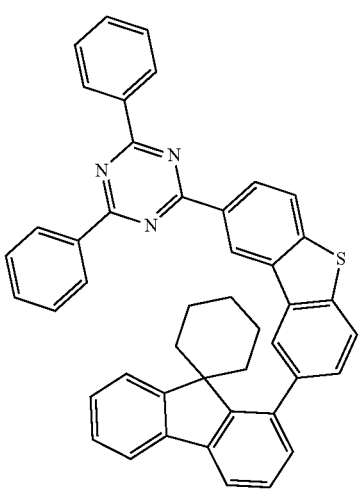

-continued
Inv 661
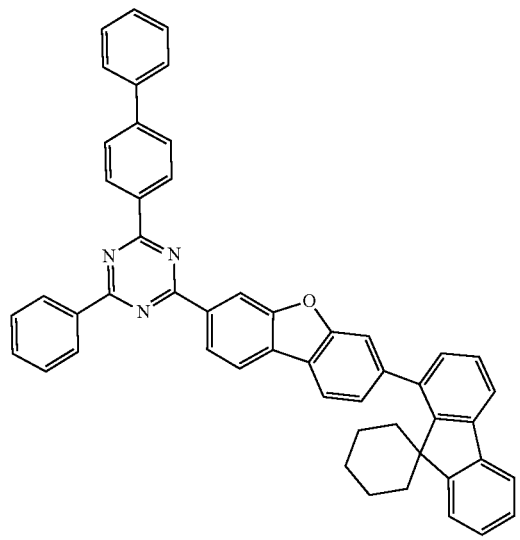
Inv 662
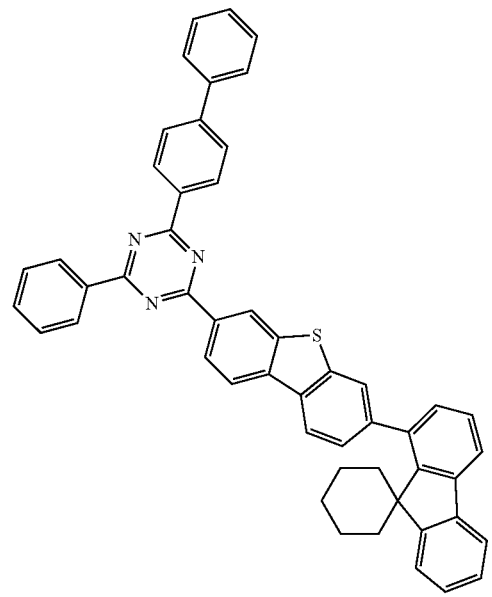
Inv 663
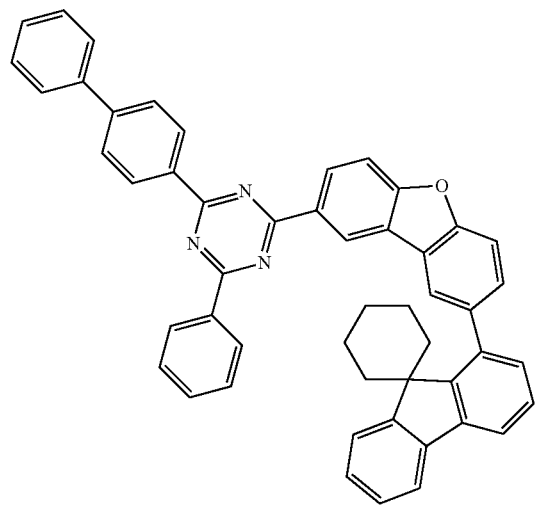
Inv 664
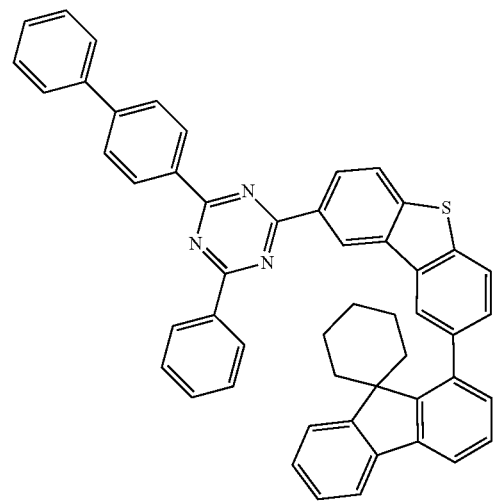

-continued
Inv 665
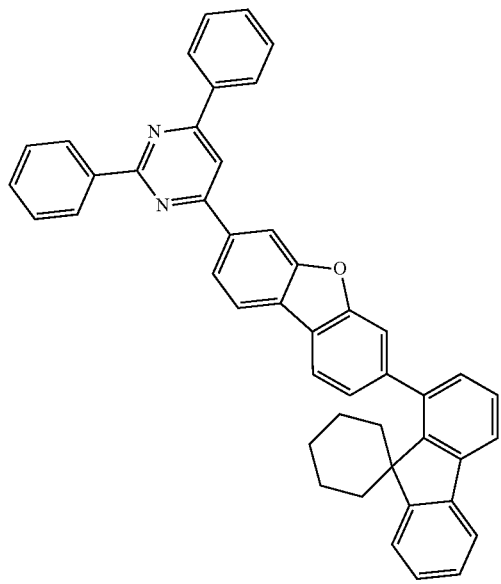
Inv 666
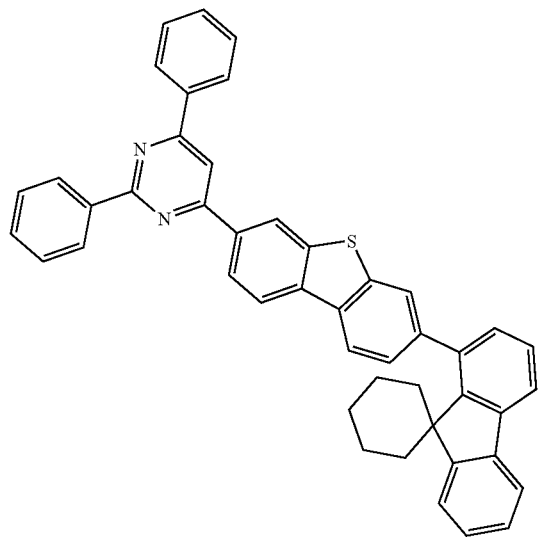
Inv 667
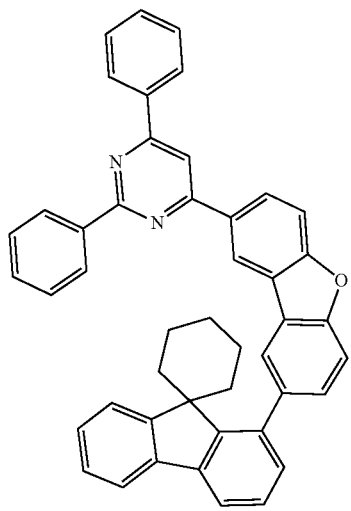
Inv 668
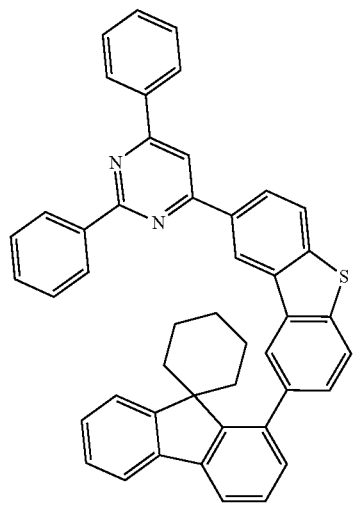

Inv 669
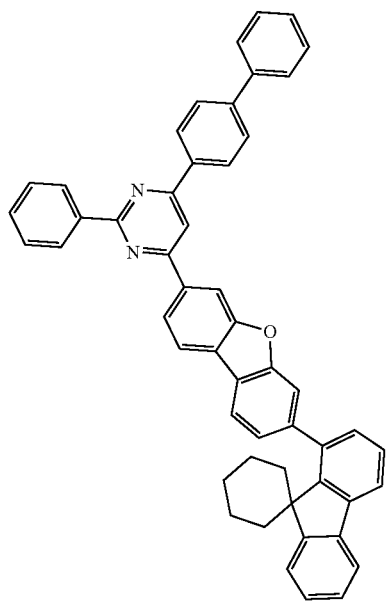
Inv 670
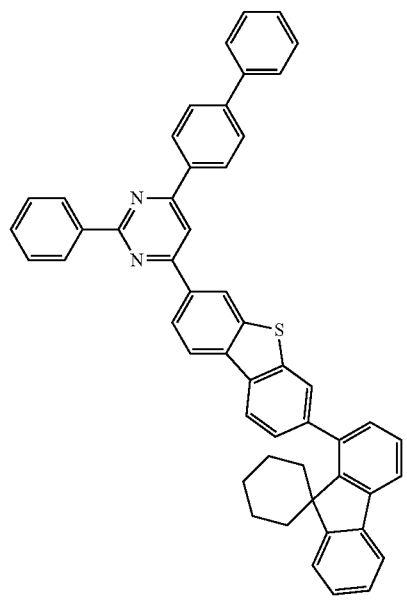
Inv 671
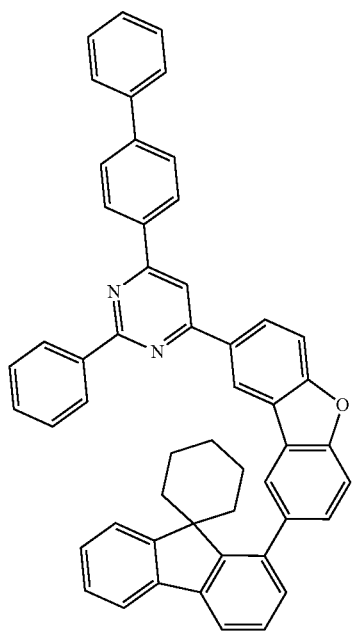
Inv 672
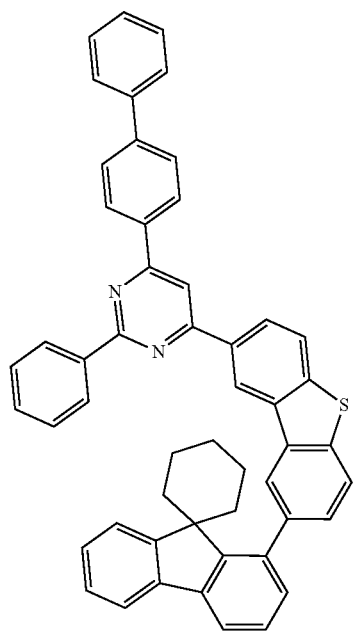

Inv 673
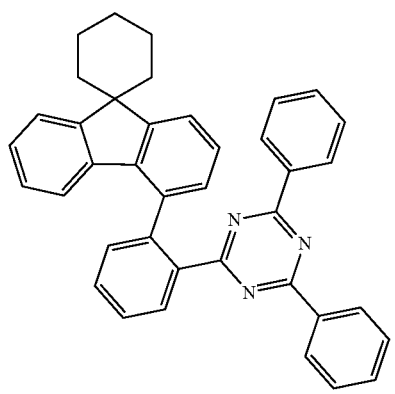
Inv 674
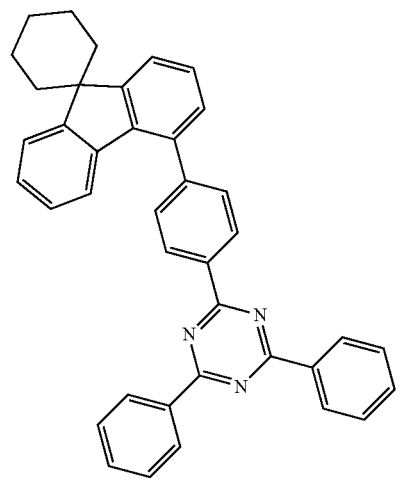
Inv 675
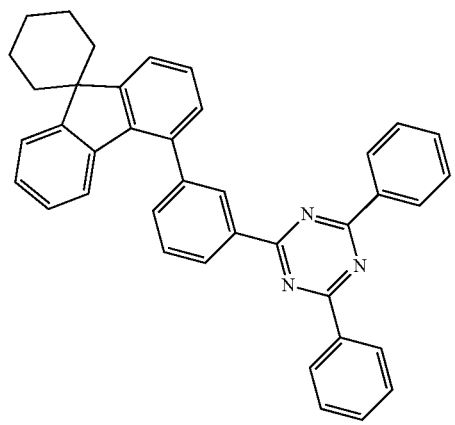
Inv 676
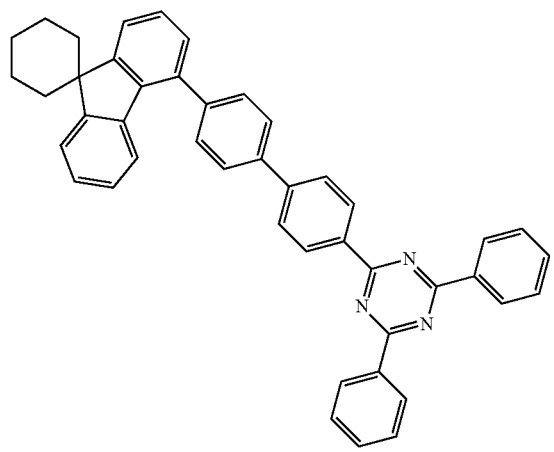
Inv 677
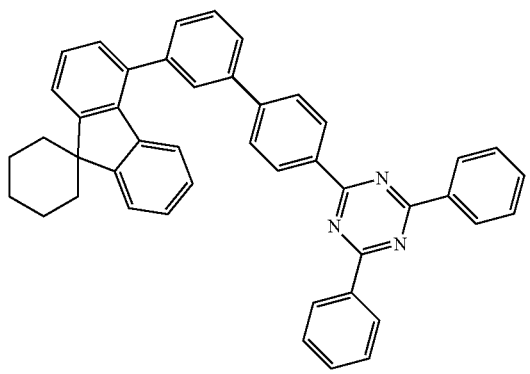
Inv 678
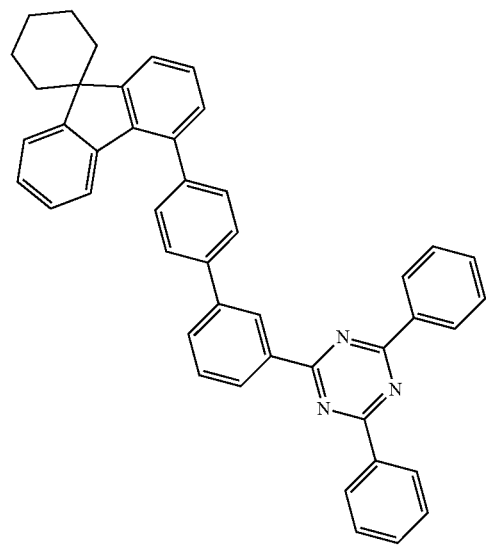

-continued
Inv 679
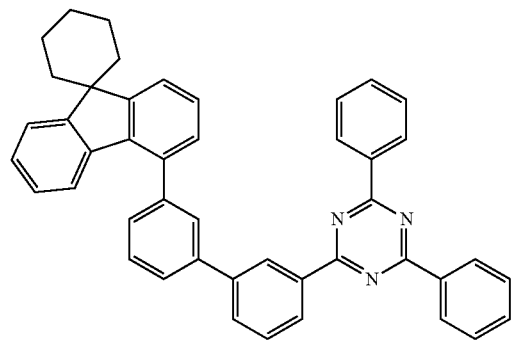
Inv 680
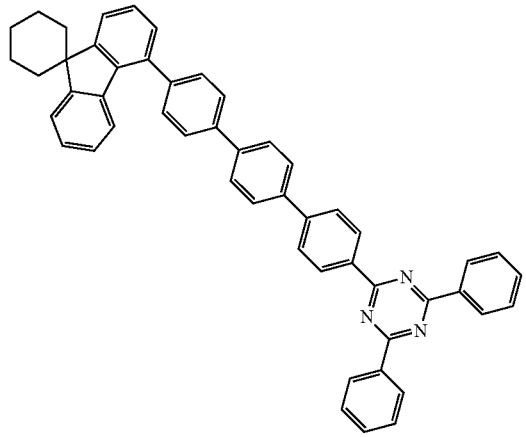
Inv 681
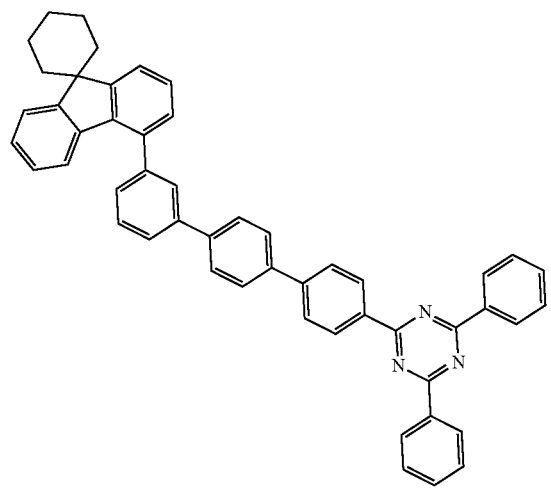
Inv 682
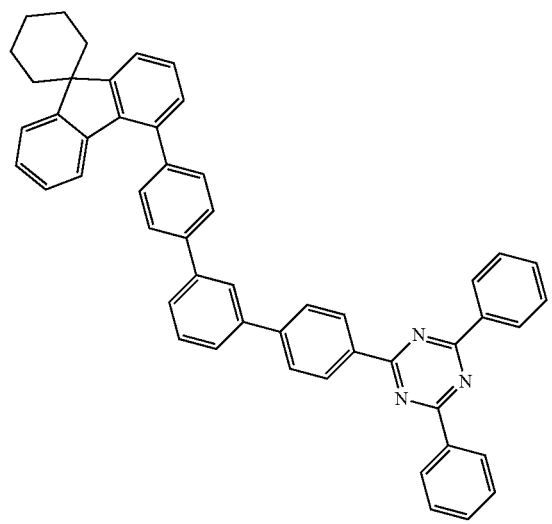
Inv 683
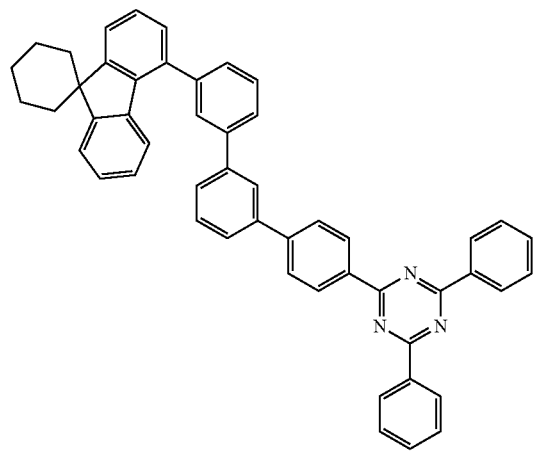
Inv 684
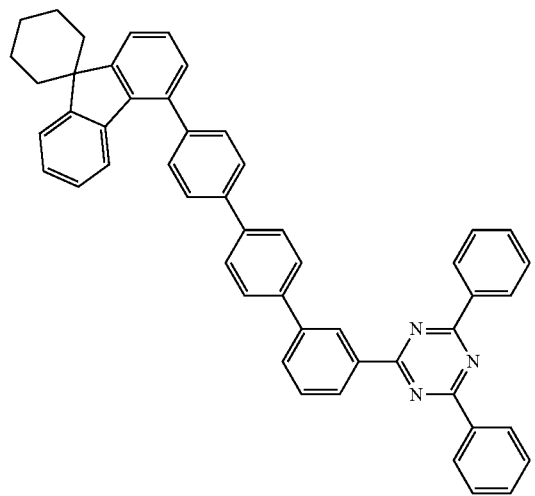

-continued
Inv 685
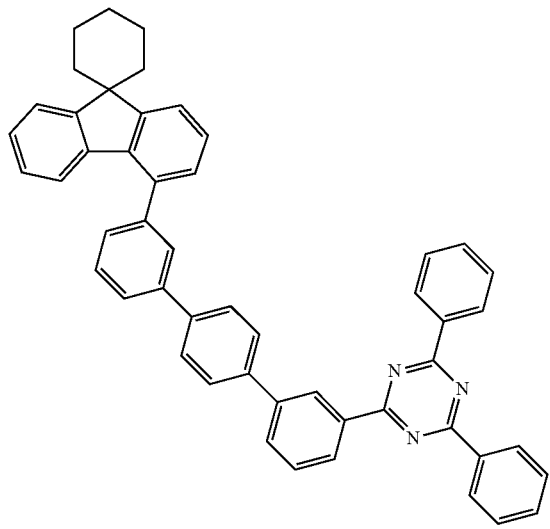
Inv 686
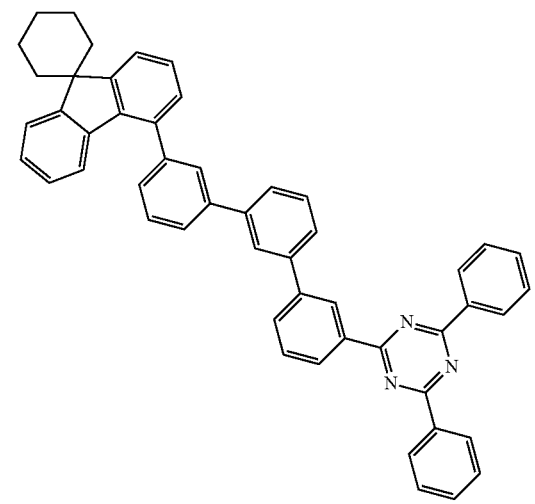
Inv 687
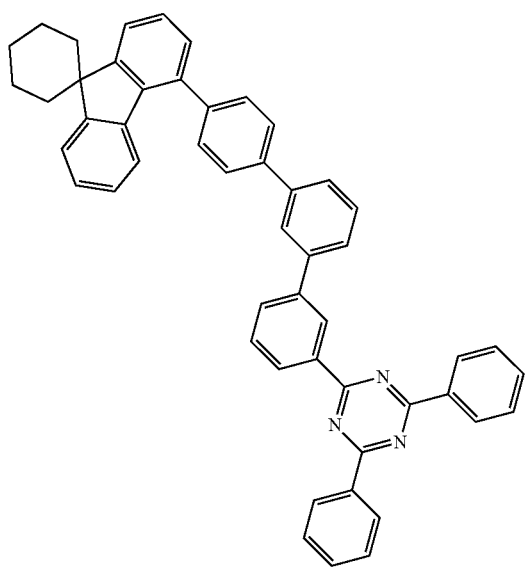
Inv 688
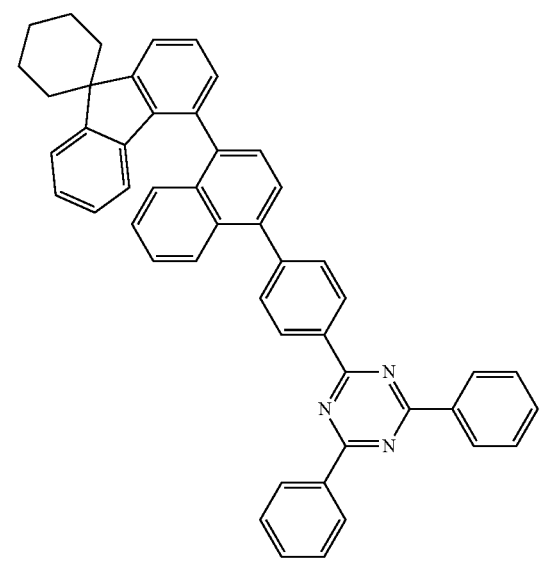
Inv 689
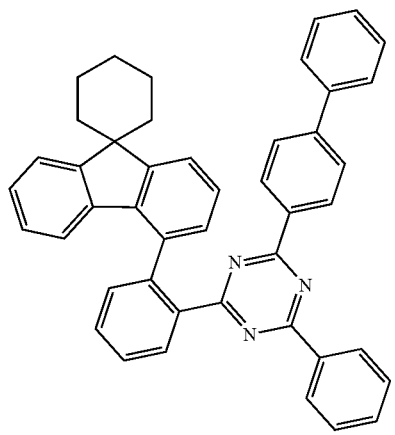
Inv 690
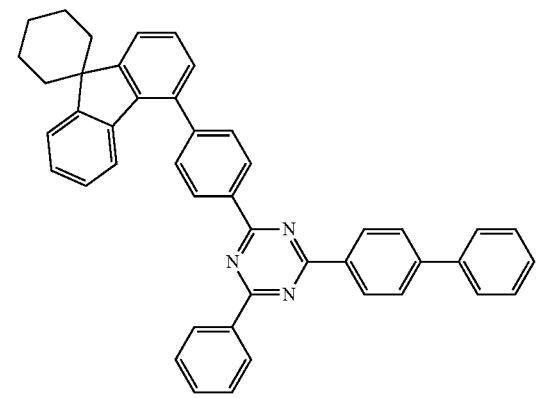

-continued
Inv 691
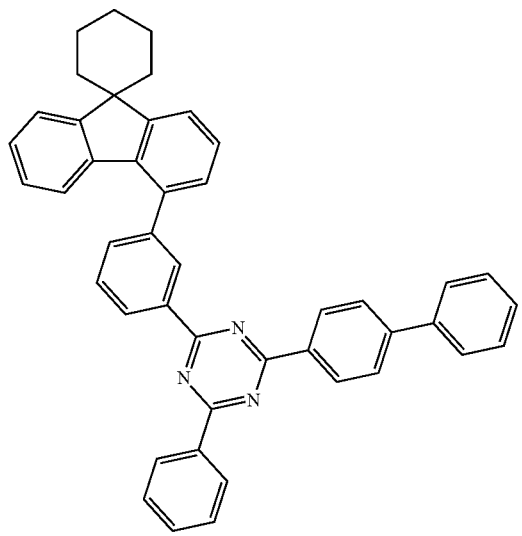
Inv 692
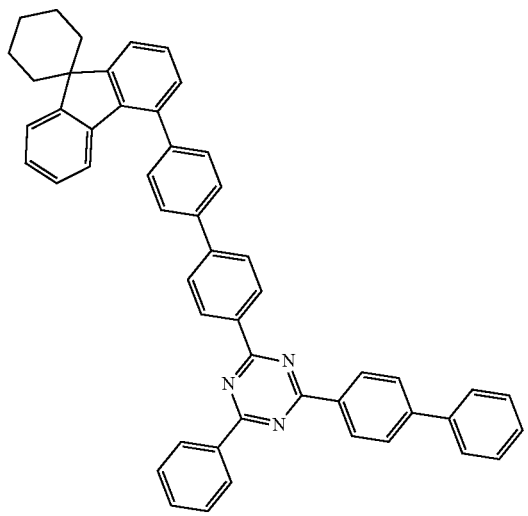
Inv 693
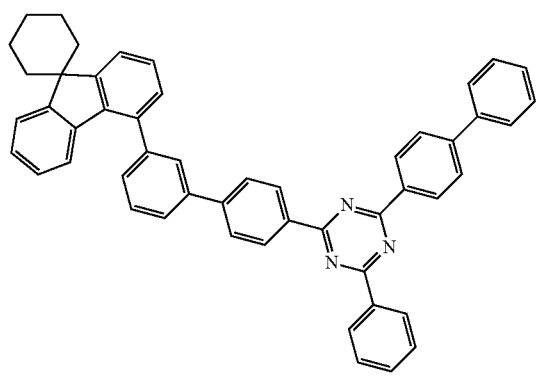
Inv 694
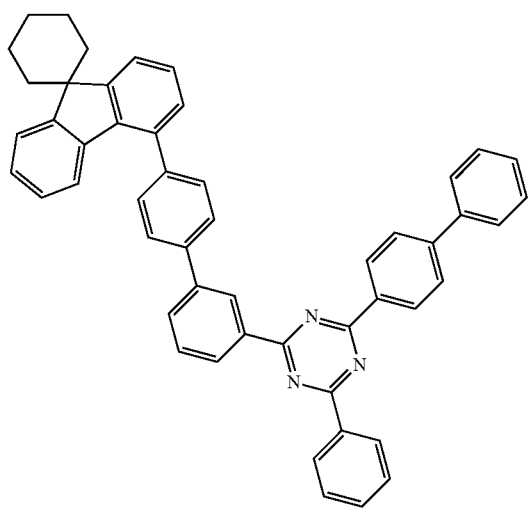
Inv 695
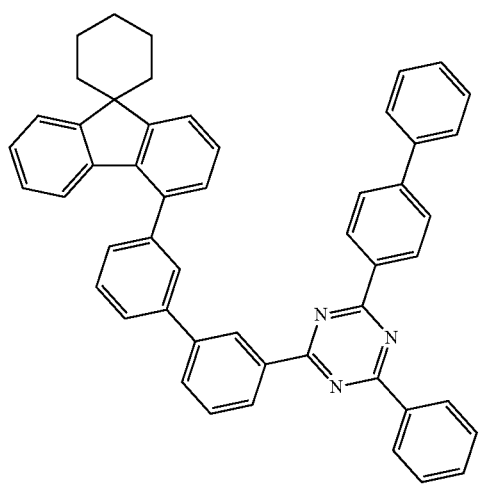
Inv 696
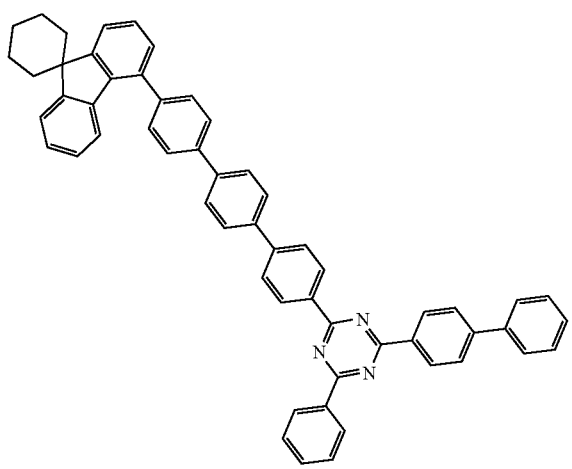

-continued
Inv 697
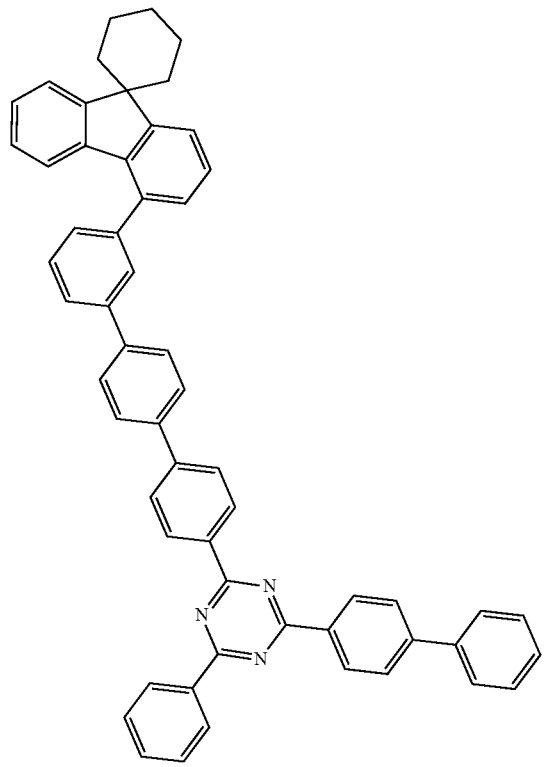
Inv 698
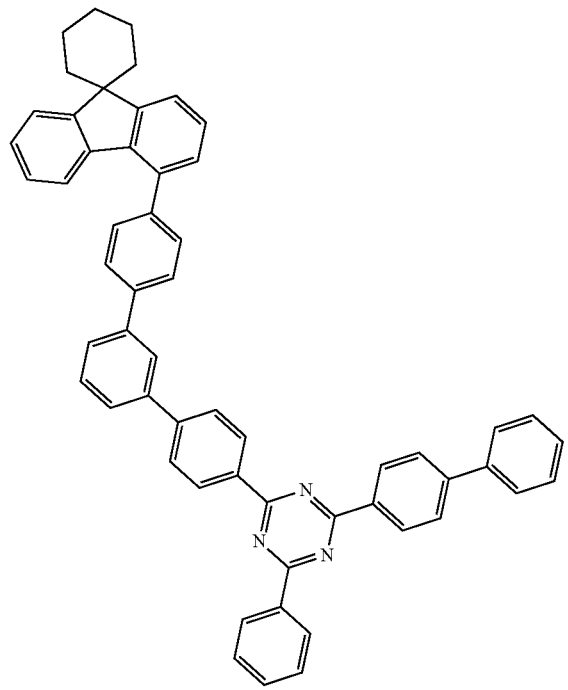
Inv 699
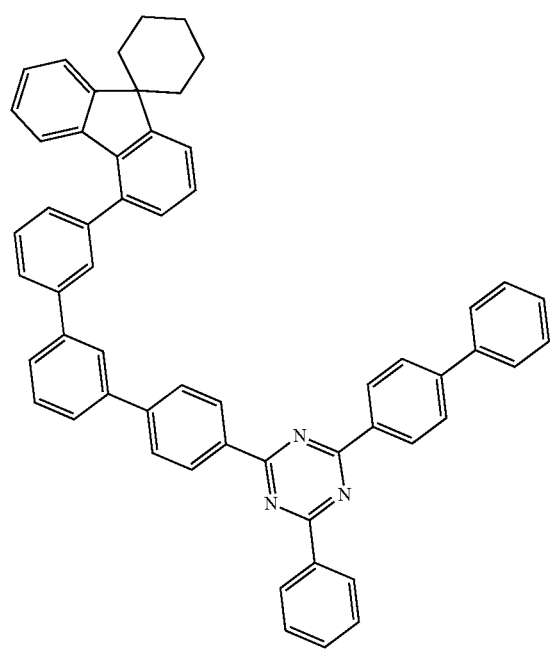
Inv 670
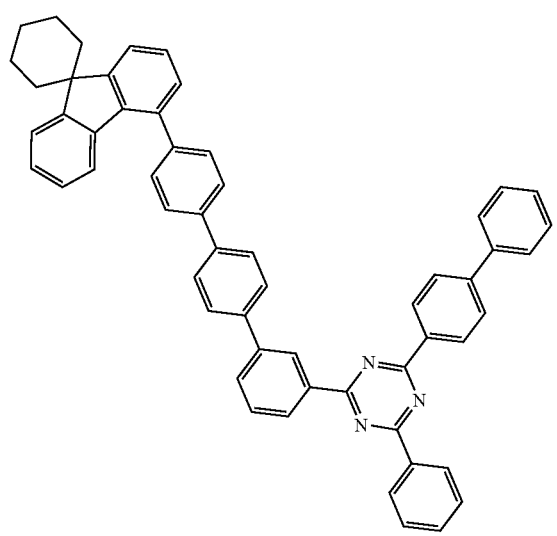

-continued
Inv 701
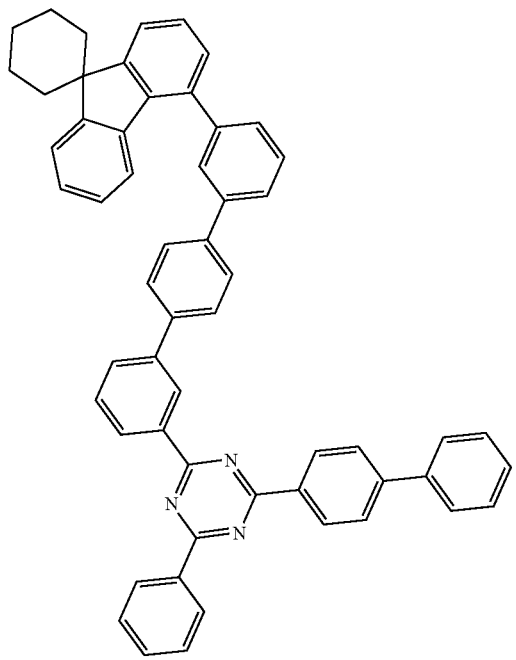
Inv 702
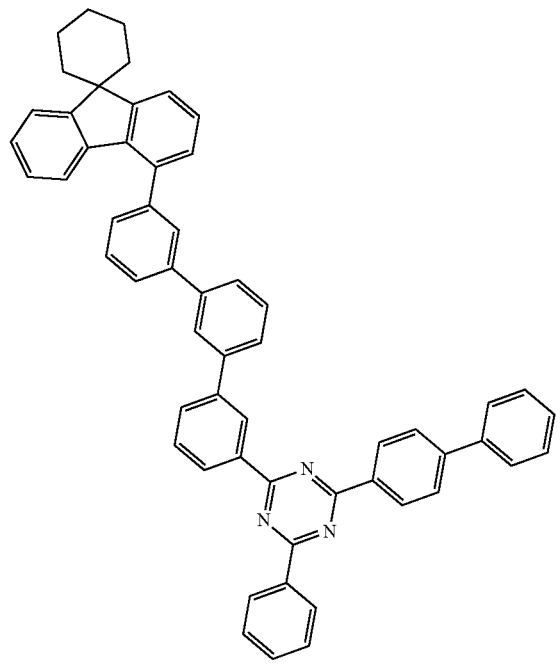
Inv 703
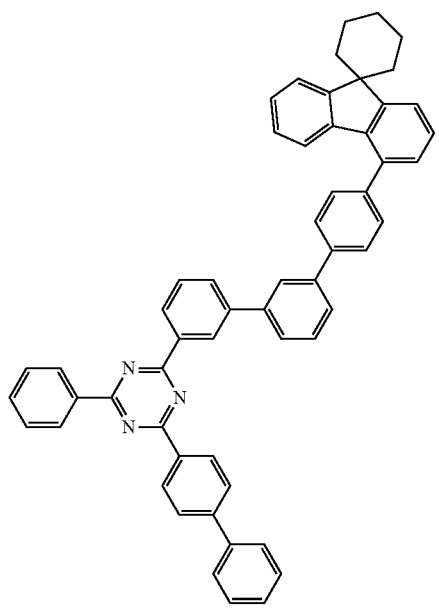
Inv 704
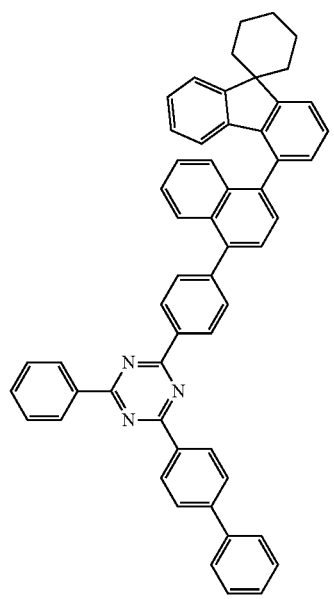

Inv 705
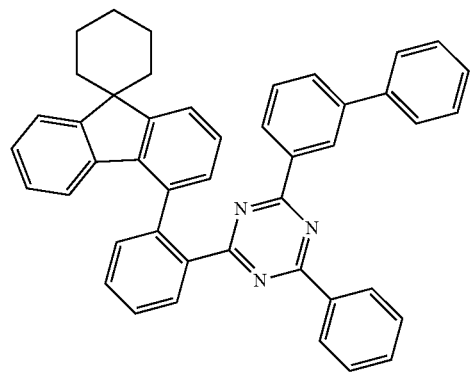
Inv 706
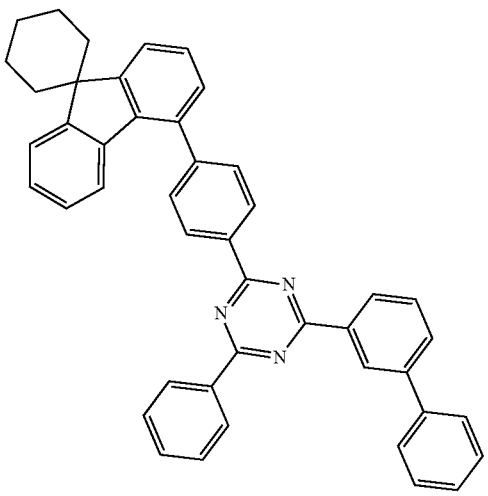
Inv 707
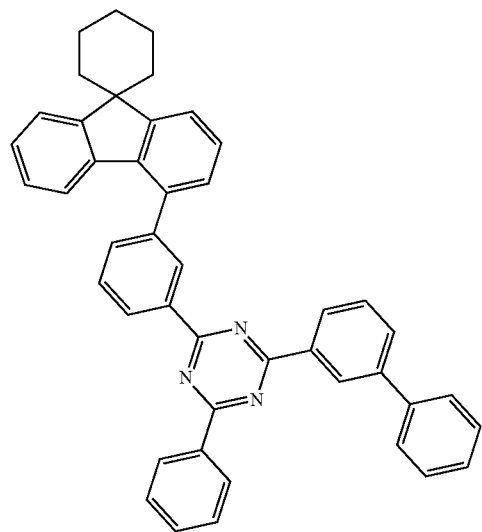
Inv 708
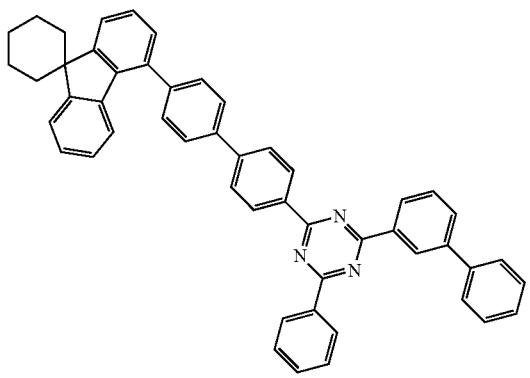

-continued
Inv 709
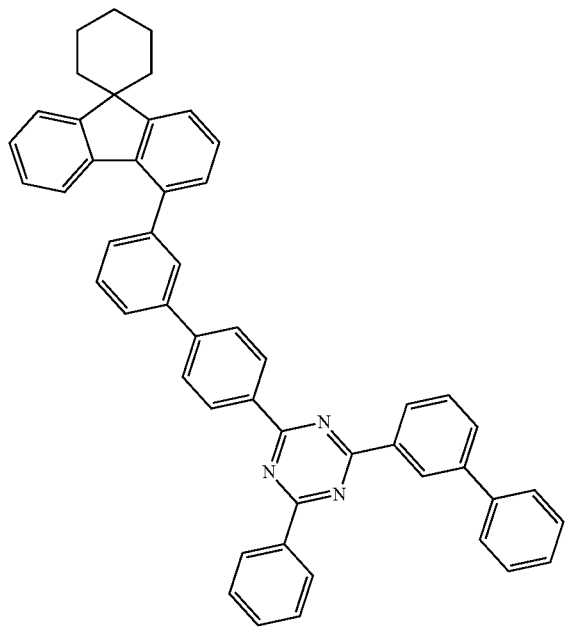
Inv 710
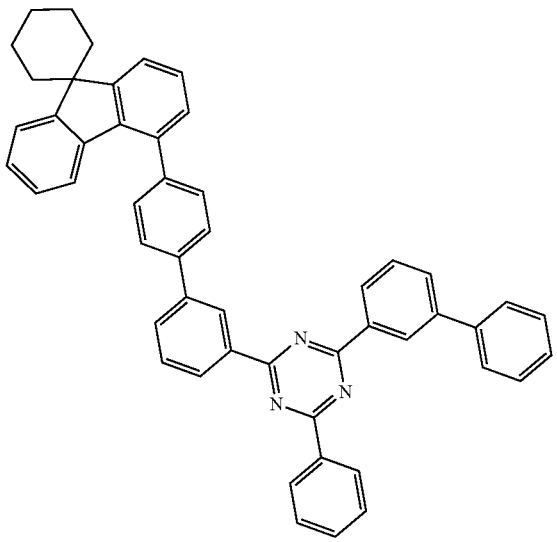
Inv 711
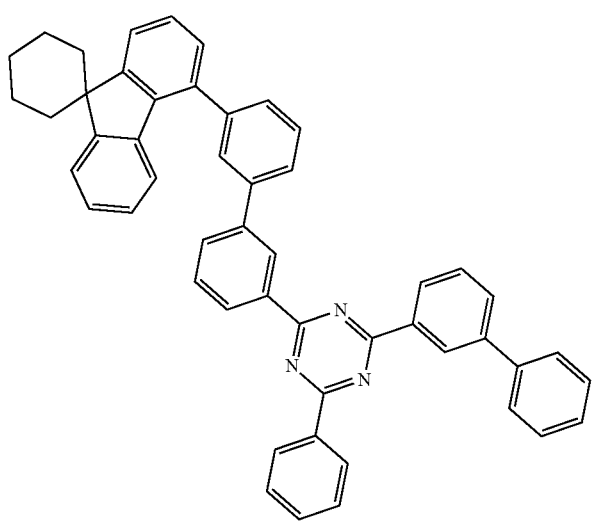

Inv 712
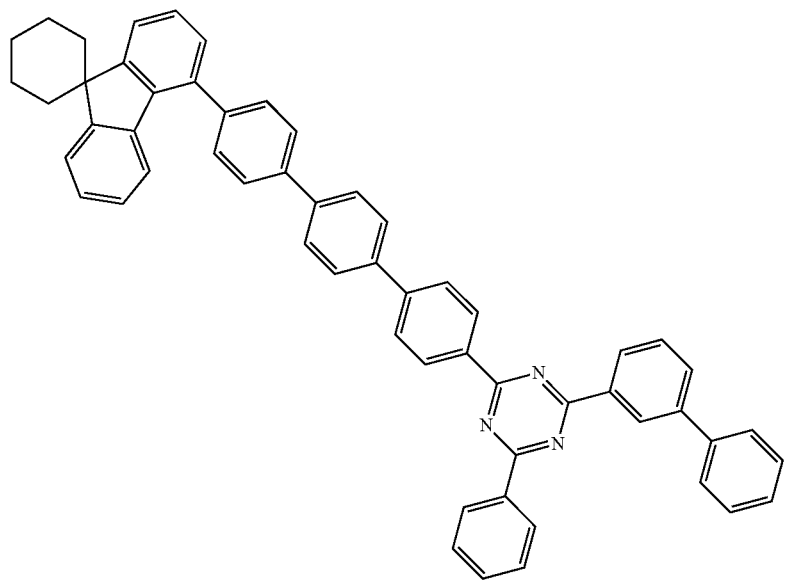
Inv 713
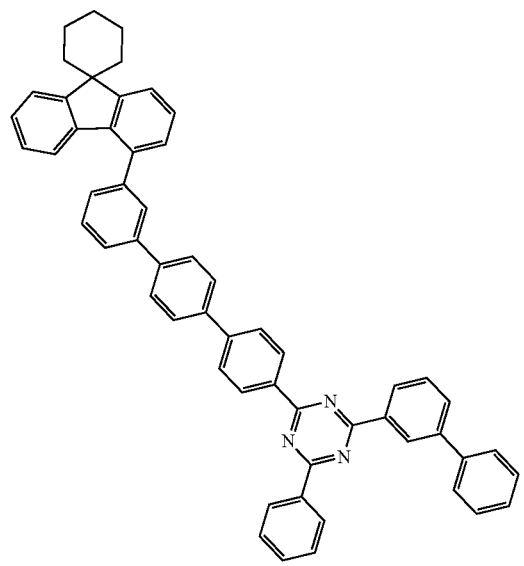
Inv 714
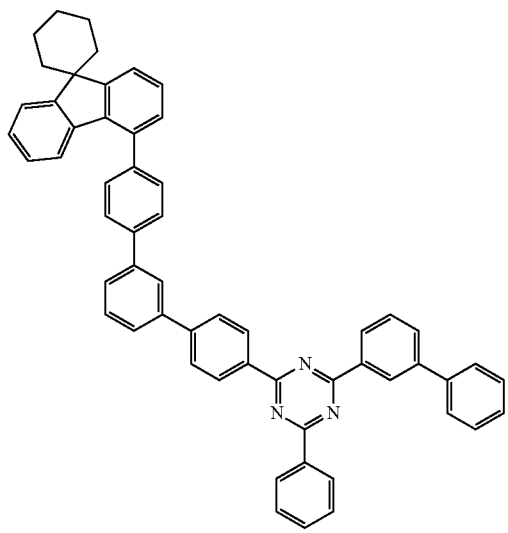

-continued
Inv 715
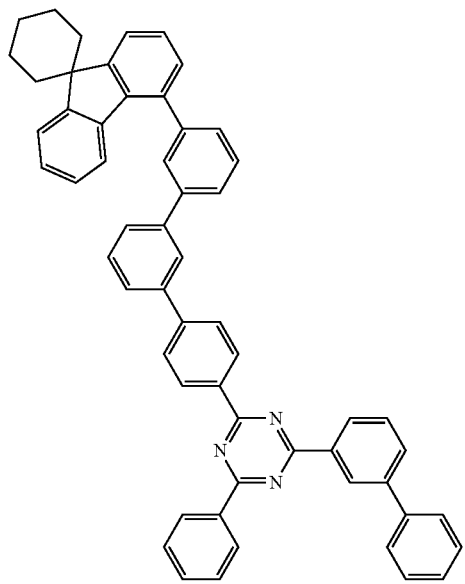
Inv 716
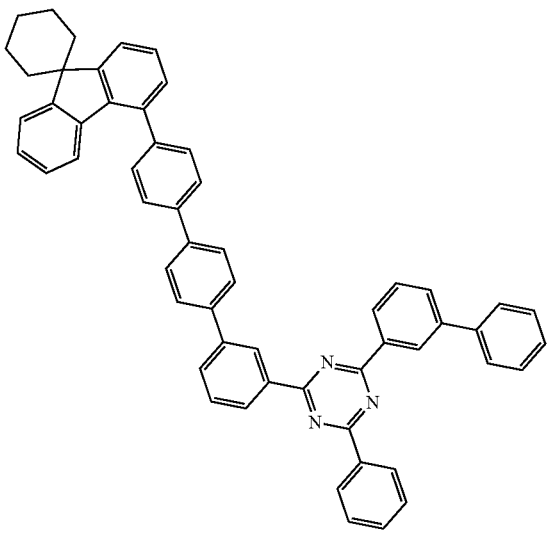
Inv 717
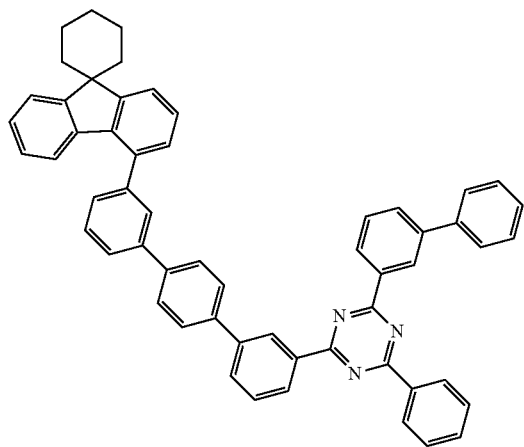
Inv 718
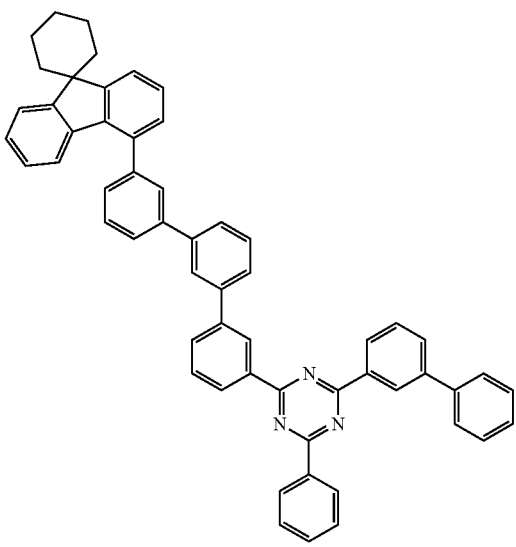
Inv 719
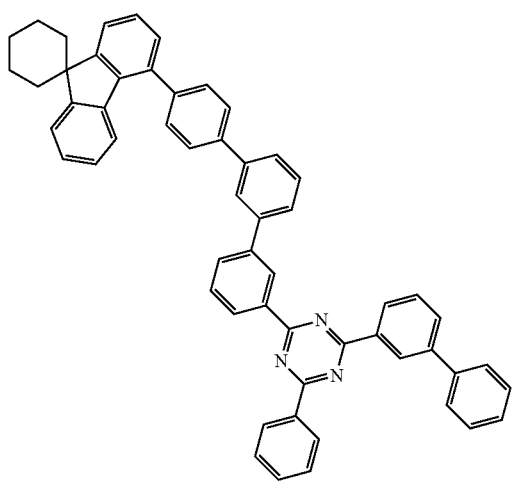
Inv 720

Inv 721
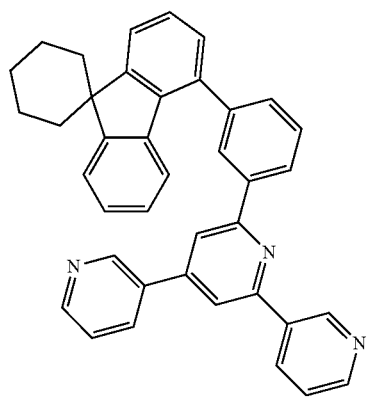
Inv 724
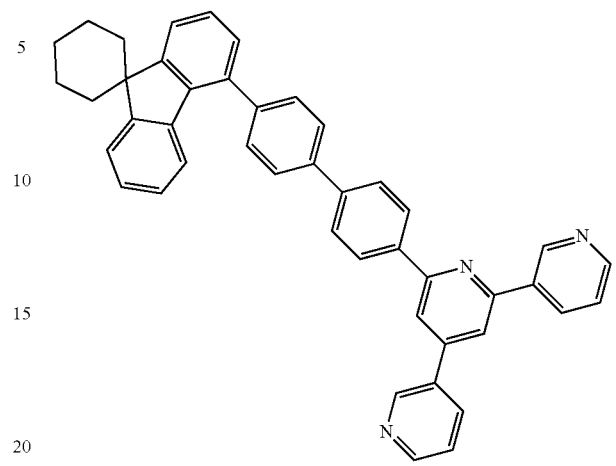
Inv 722
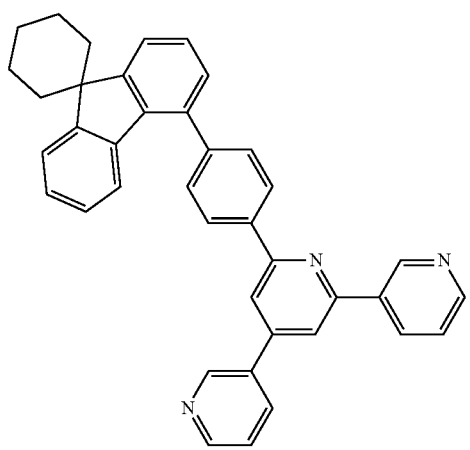
Inv 725
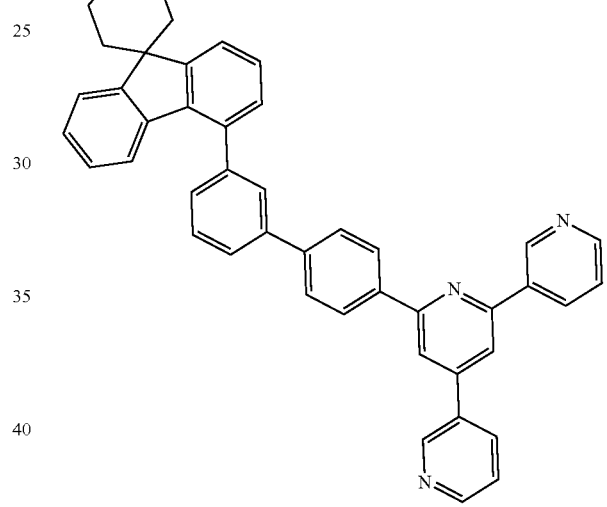
Inv 723
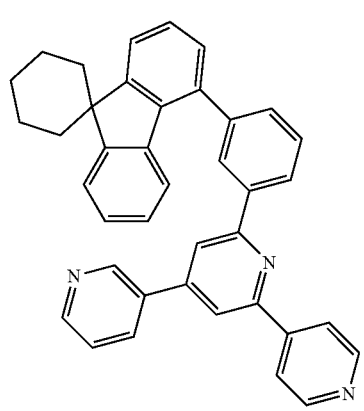
Inv 726
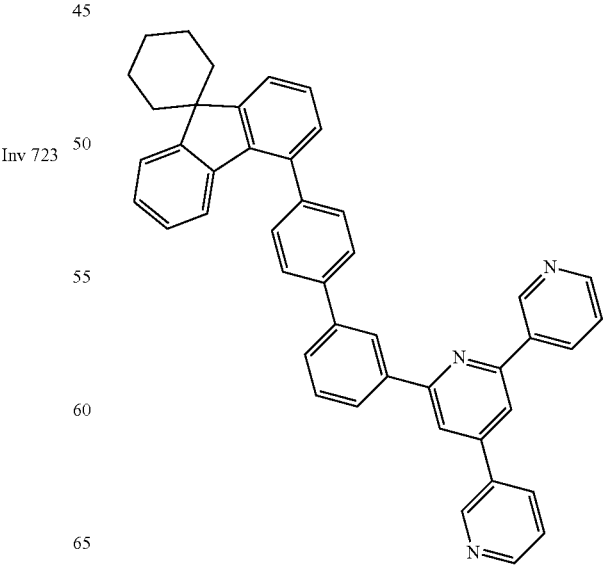

-continued
Inv 727
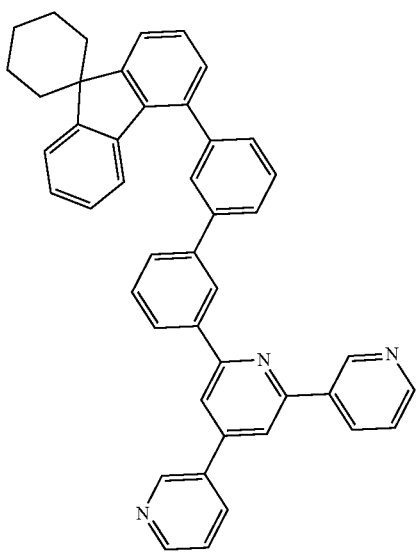
Inv 728
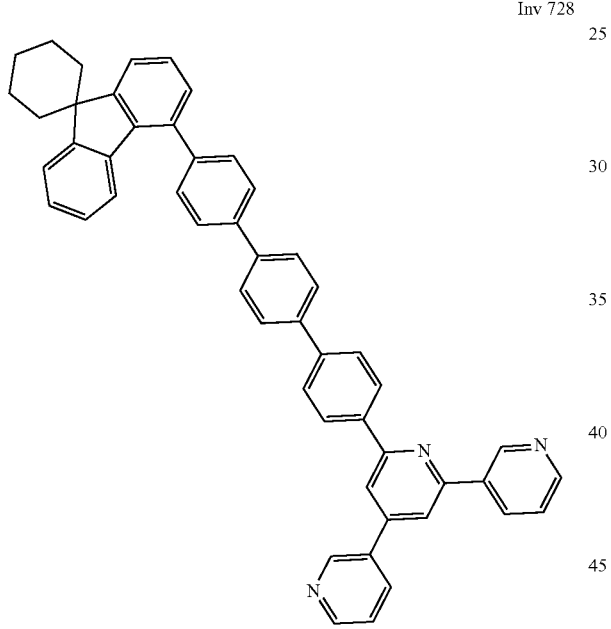
Inv 729
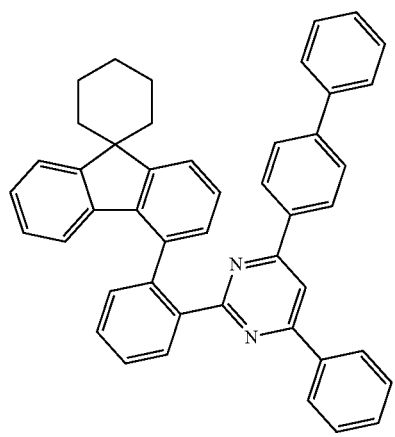
-continued
Inv 730
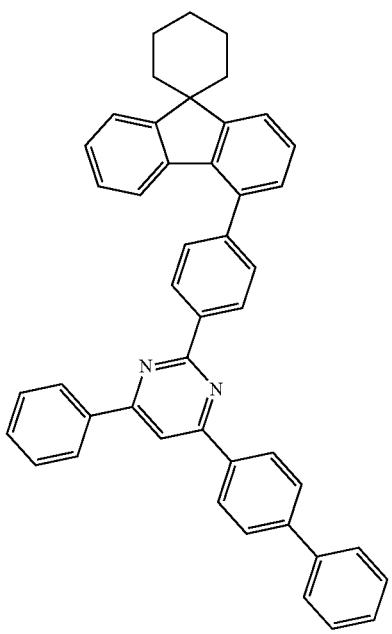
Inv 731
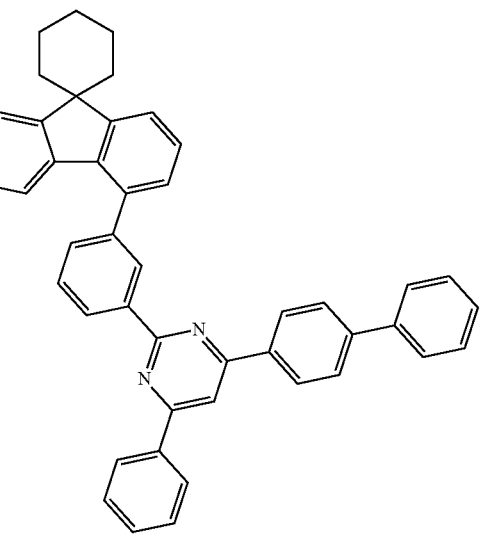

Inv 732
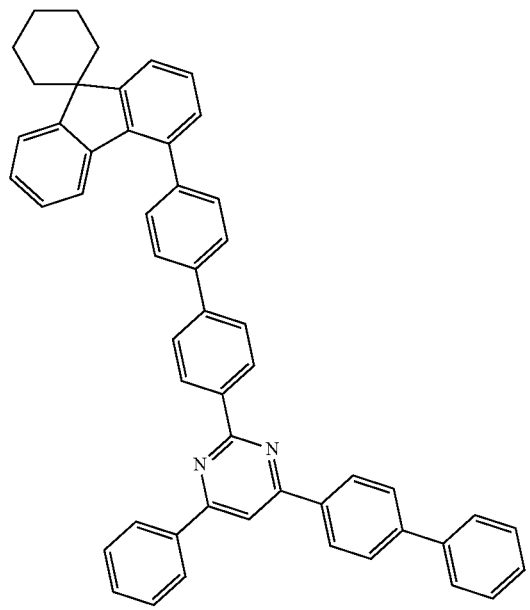
Inv 733
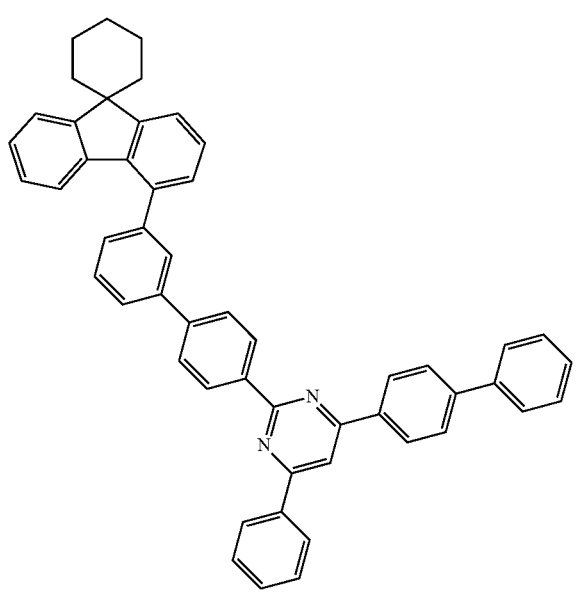
Inv 734
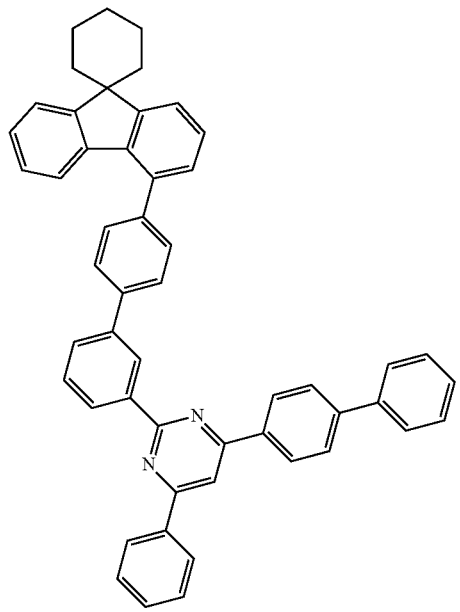
Inv 735
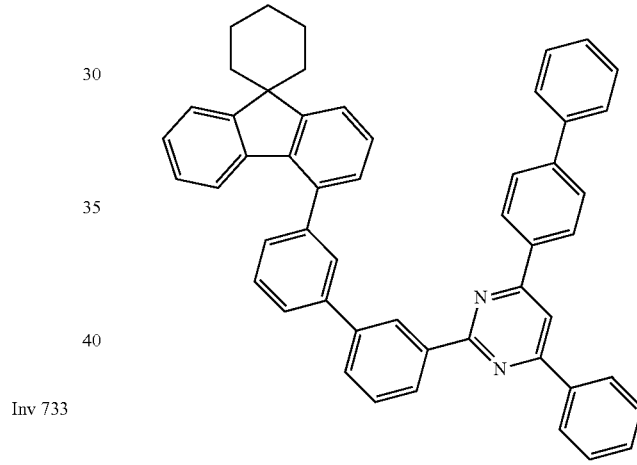
Inv 736
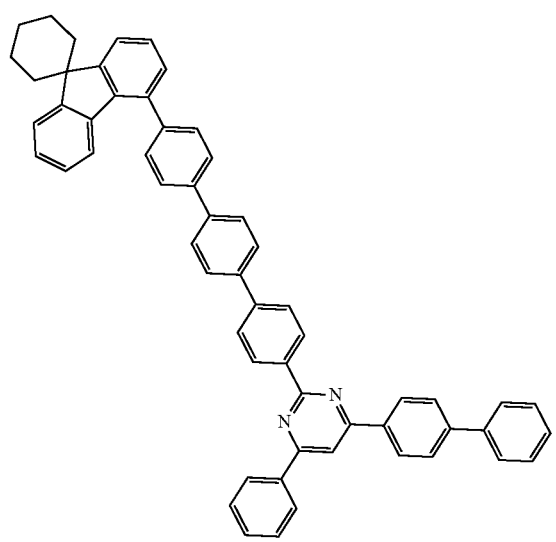

Inv 737
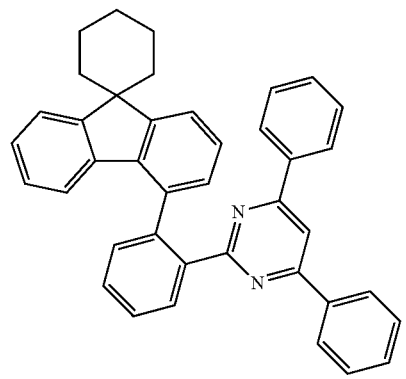
Inv 738
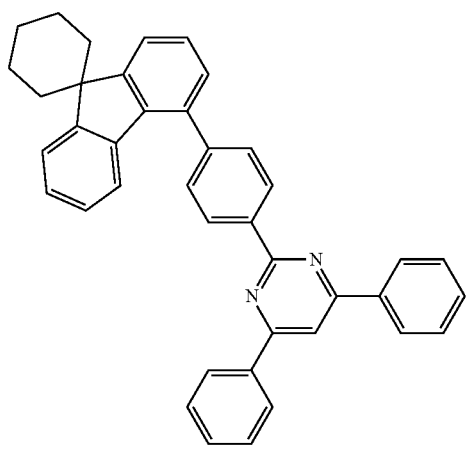
Inv 739
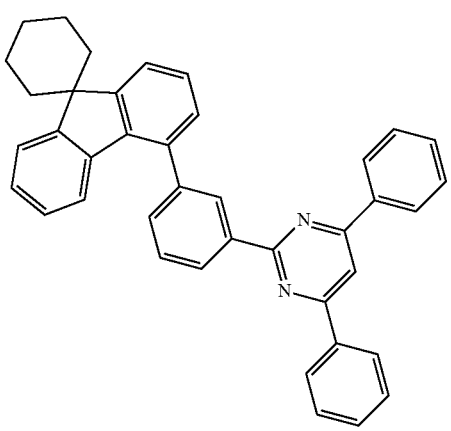
Inv 740
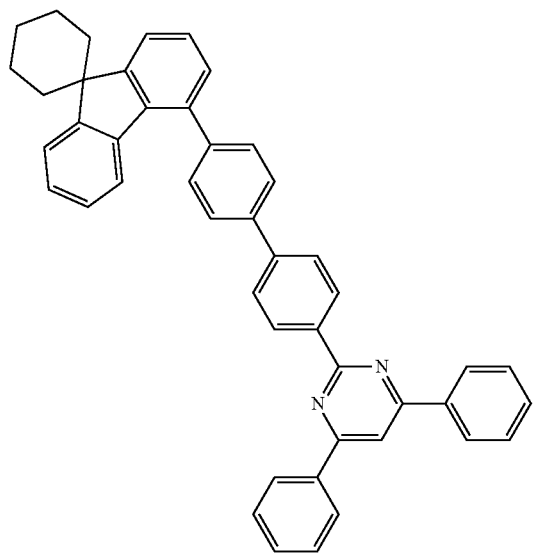
Inv 741
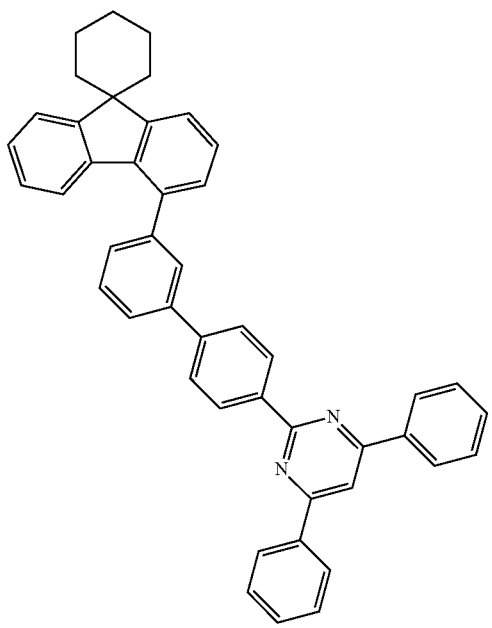

Inv 742
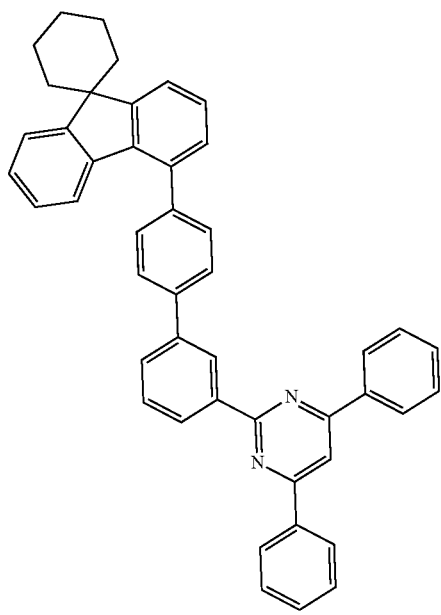
Inv 743
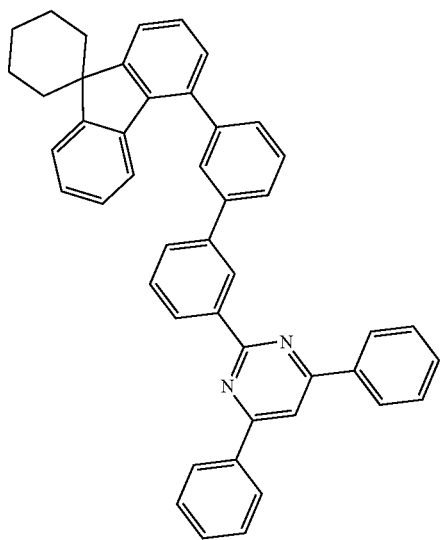
Inv 744
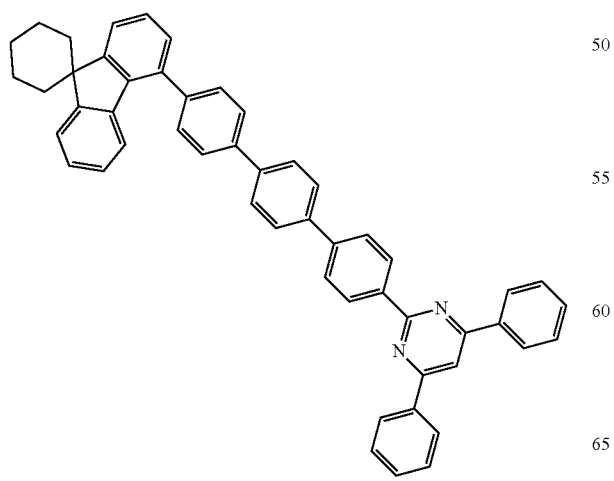
Inv 745
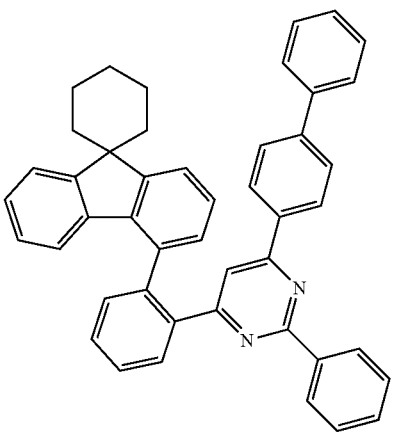
Inv 746
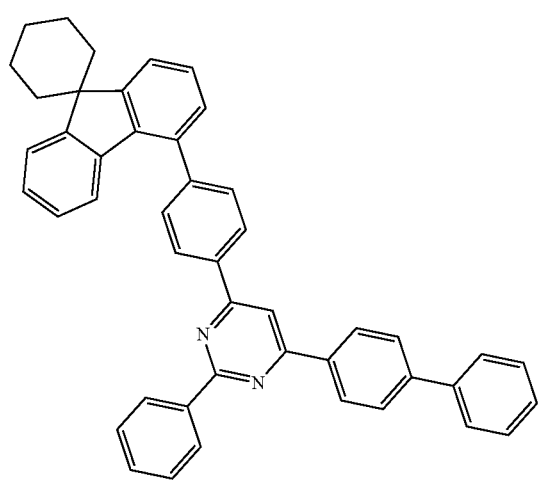
Inv 747
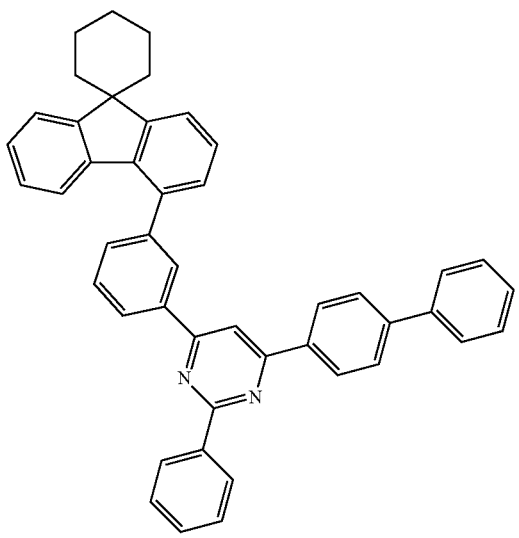

Inv 748
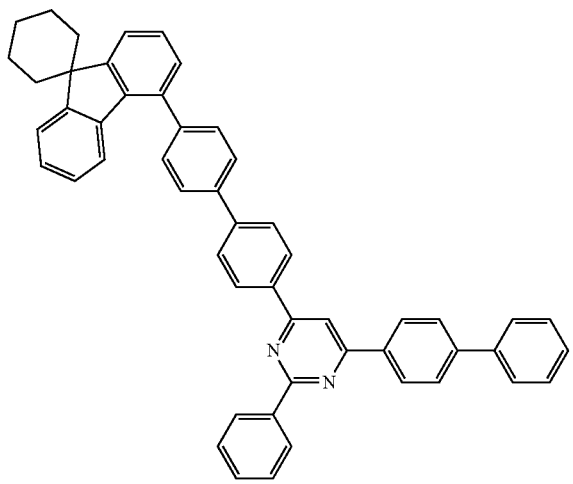
Inv 749
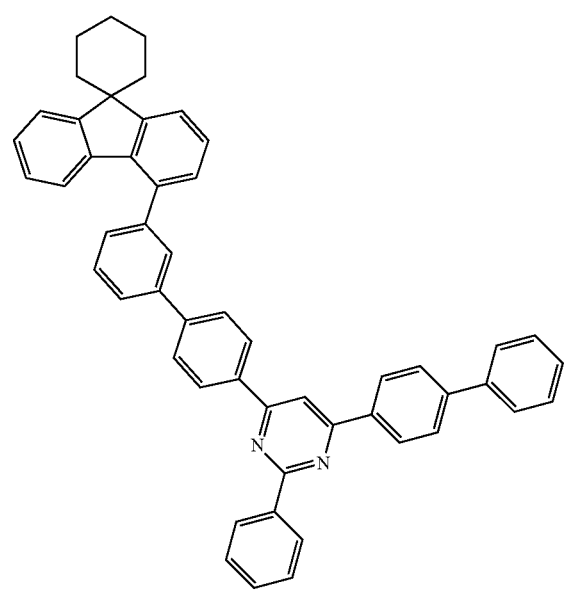
Inv 750
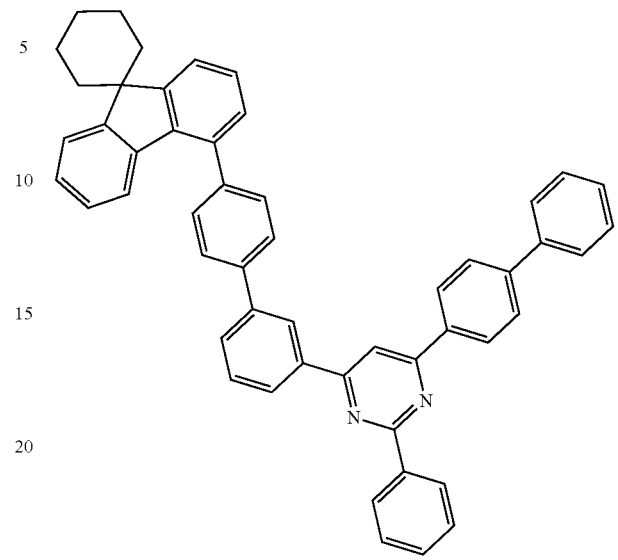
Inv 751
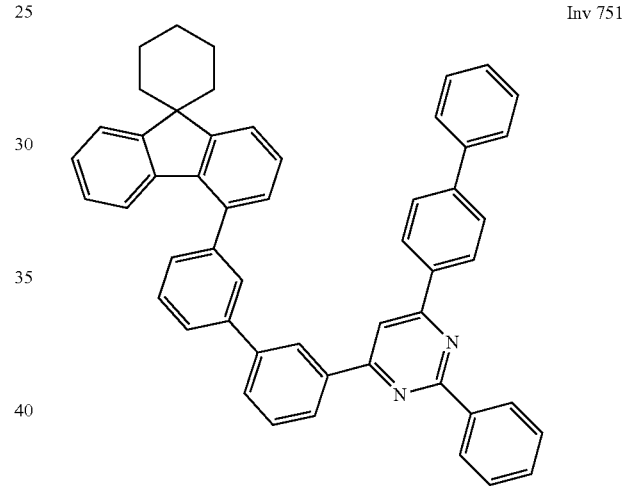
Inv 752
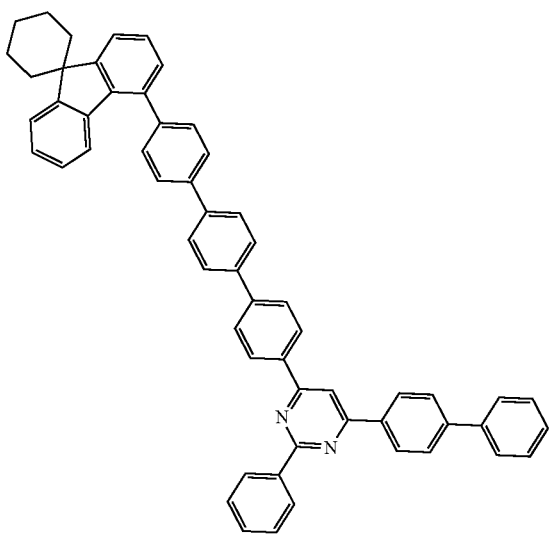

Inv 753
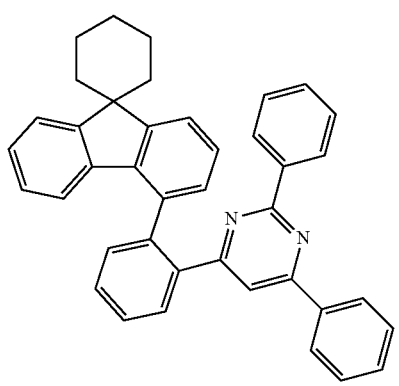
Inv 754
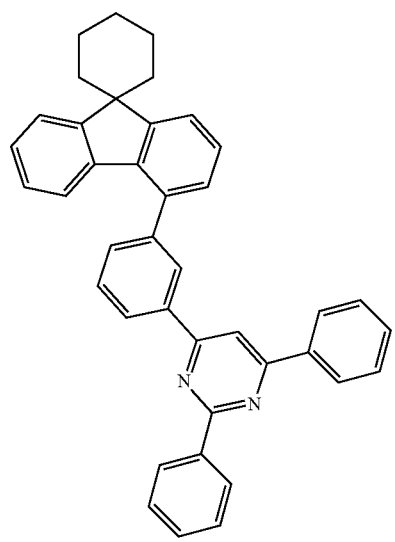
Inv 755
Inv 756
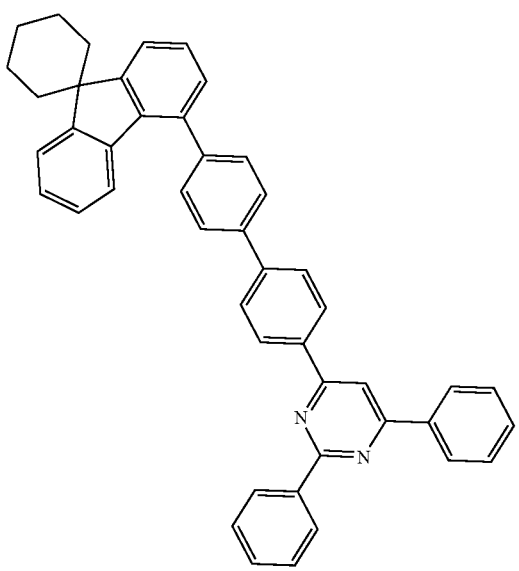
Inv 757
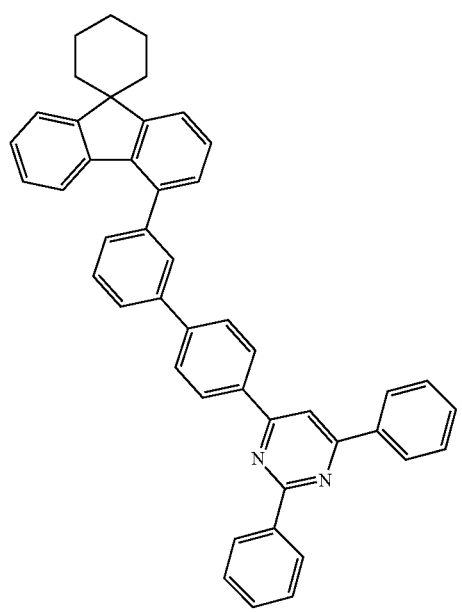

Inv 758
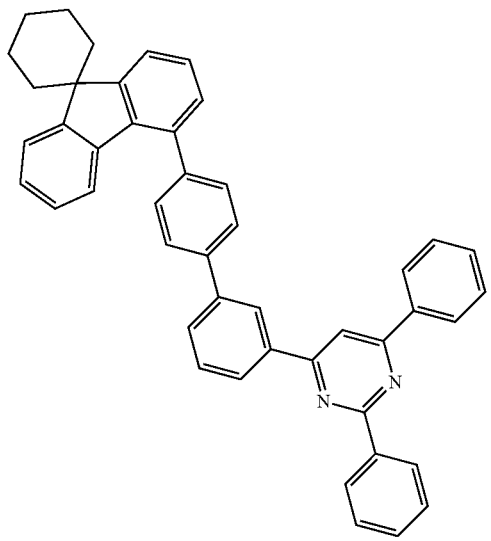
Inv 759
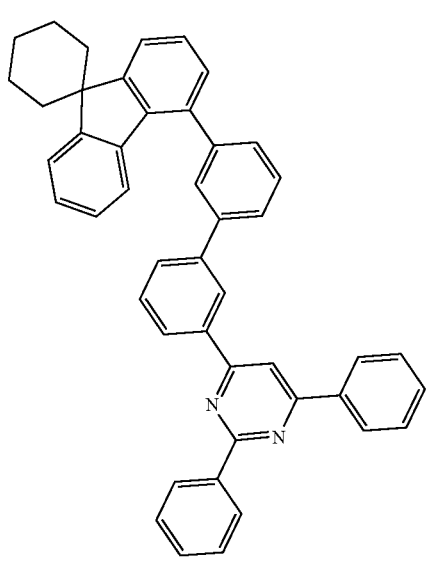
Inv 760
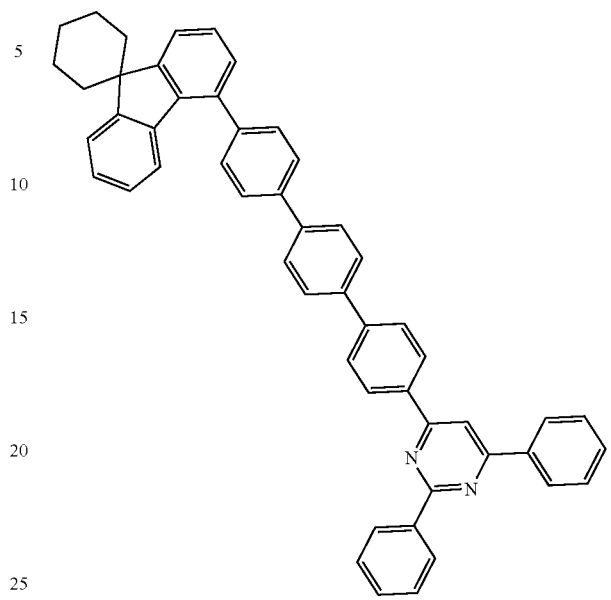
Inv 761
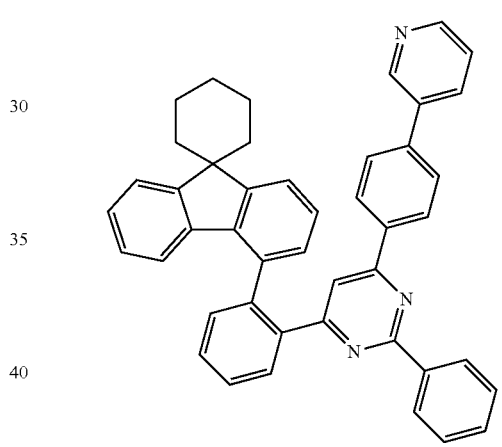
Inv 762
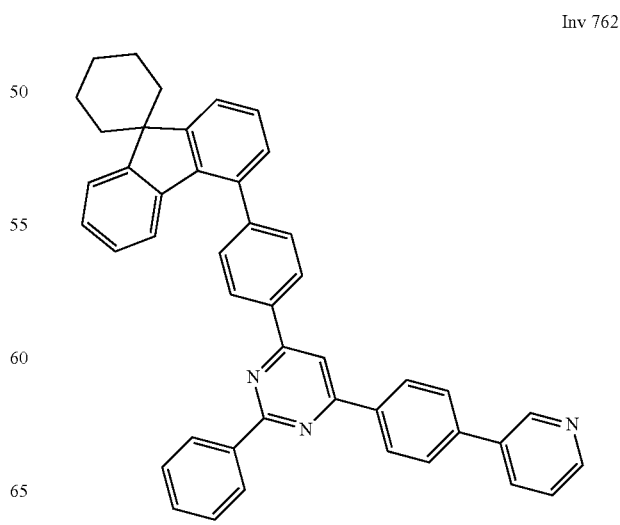

335
-continued
Inv 763
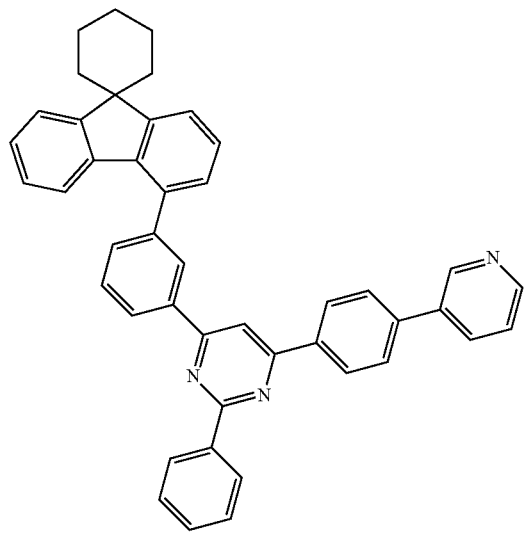
Inv 764
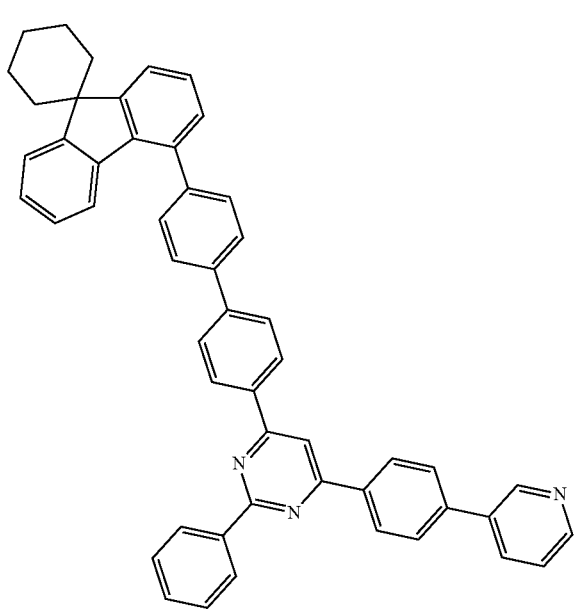
336
-continued
Inv 765
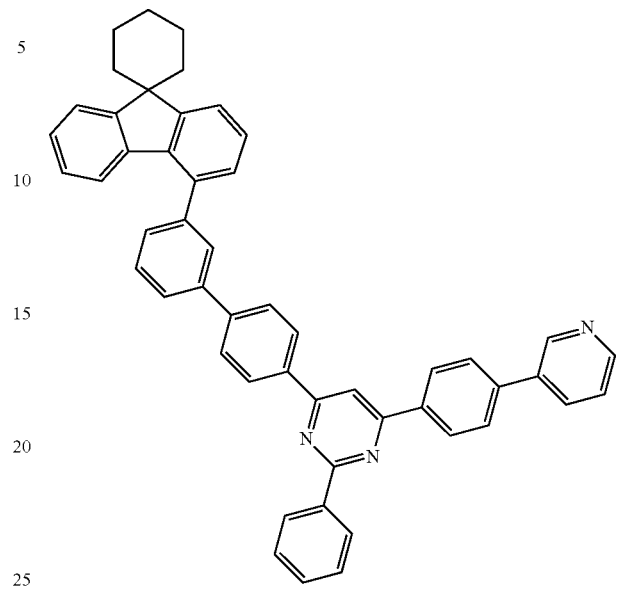
Inv 766
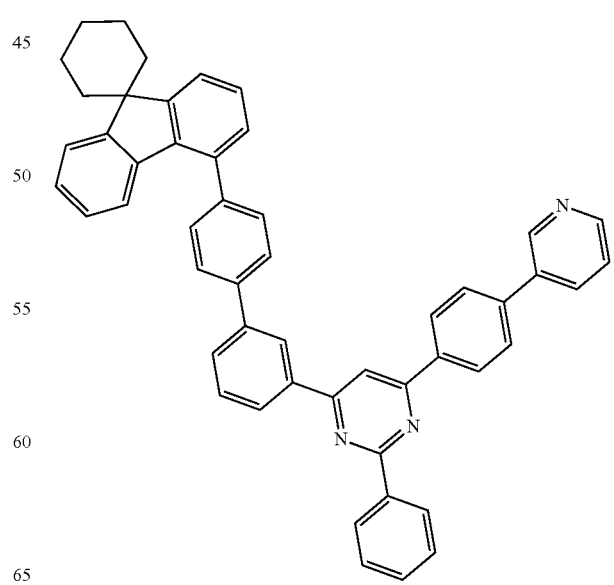

-continued
Inv 767
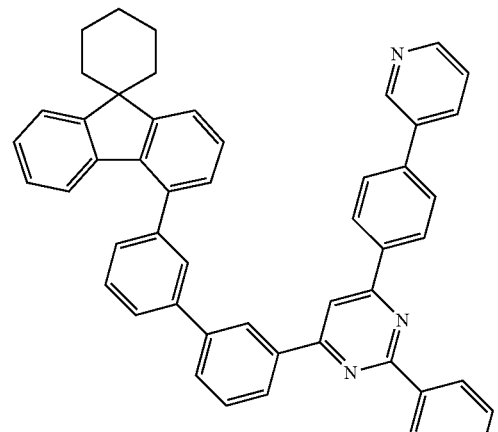
Inv 768
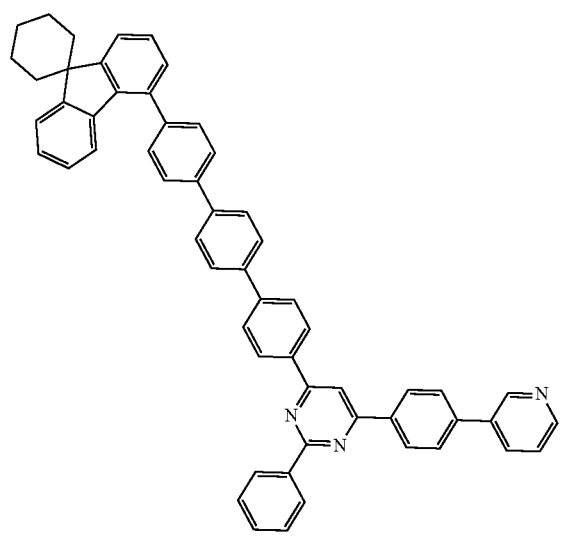
Inv 769
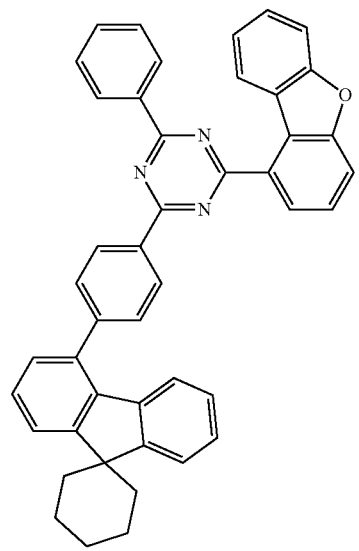
-continued
Inv 770
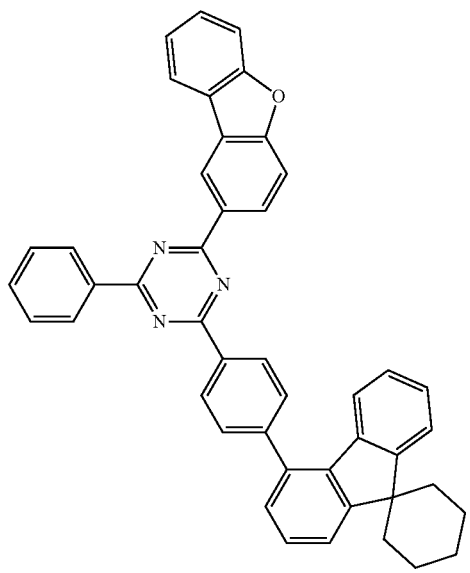
Inv 771
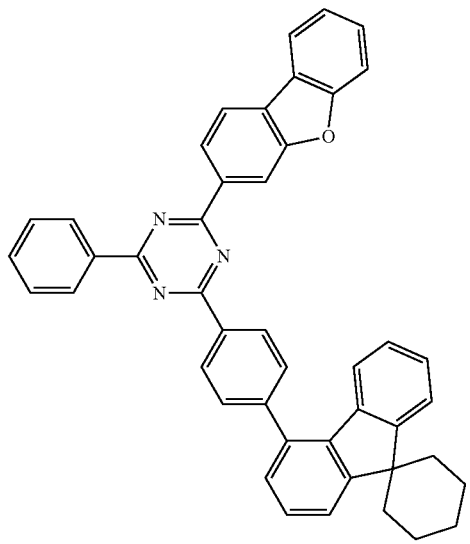
Inv 772
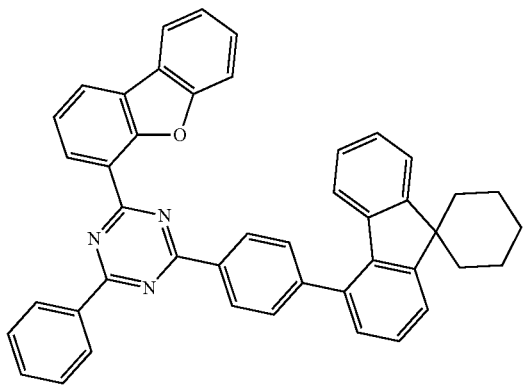

Inv 773
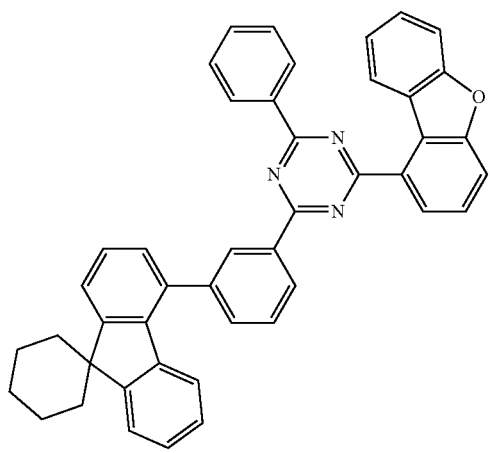
Inv 774
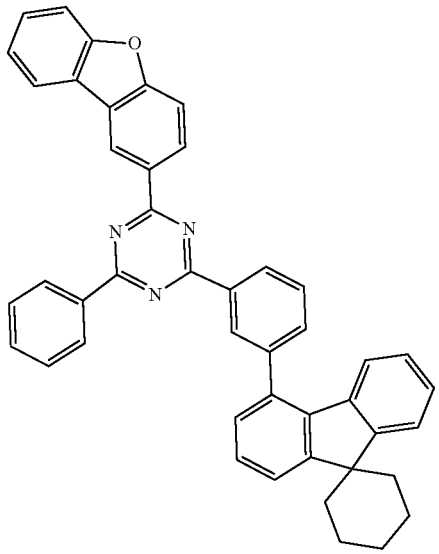
Inv 775
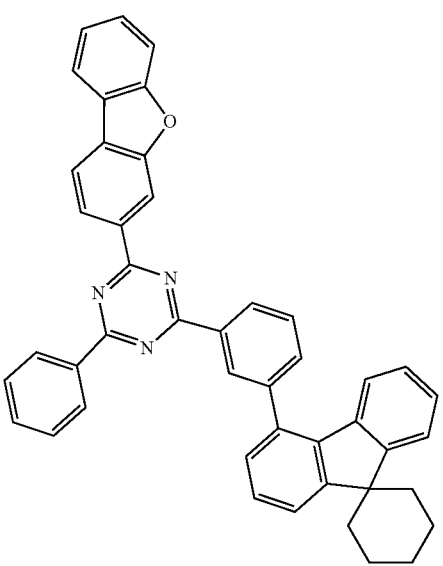
Inv 776
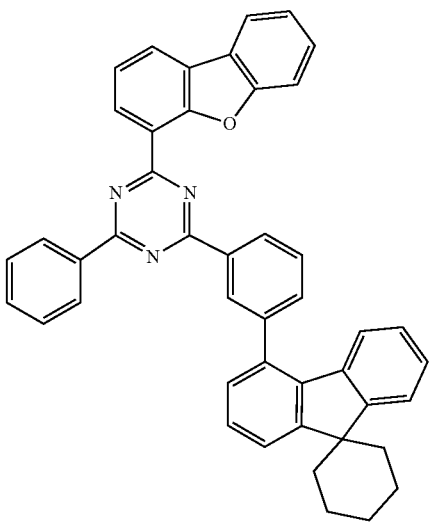
Inv 777
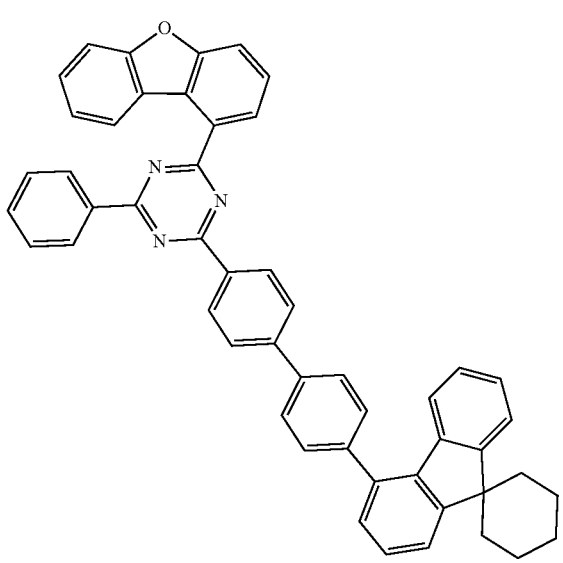

Inv 778
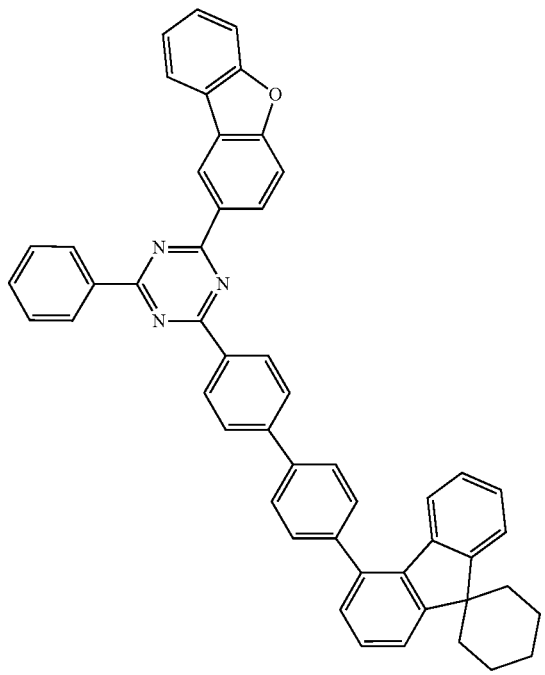
Inv 779
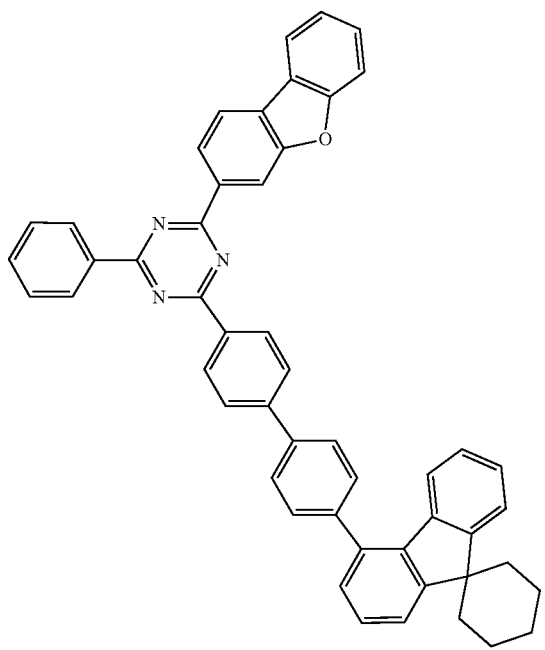
Inv 780
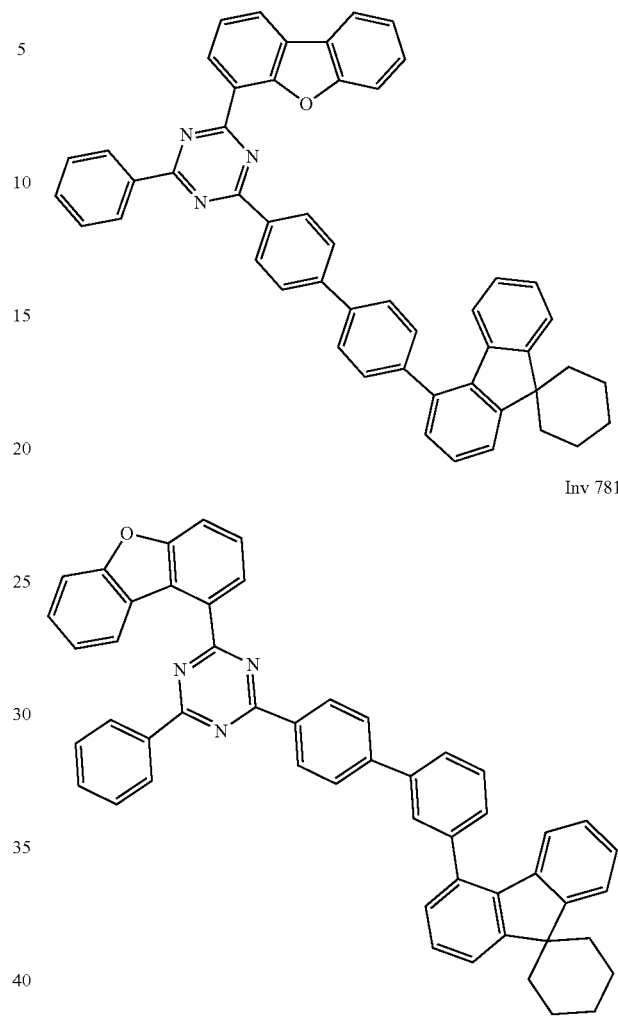
Inv 781
Inv 782
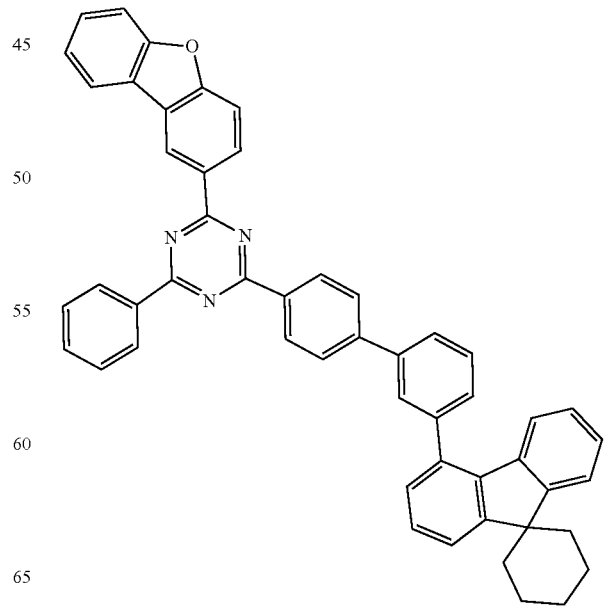

Inv 783
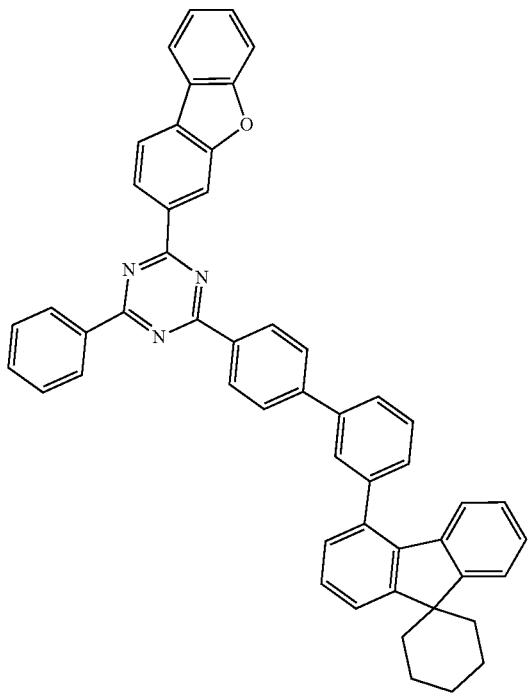
Inv 784
Inv 785
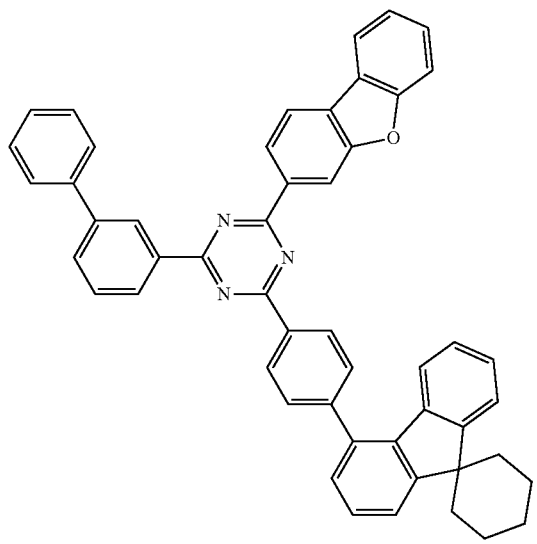
Inv 786
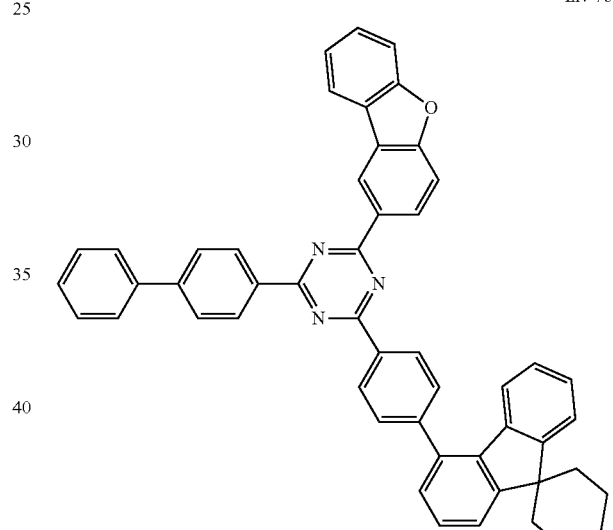
Inv 787
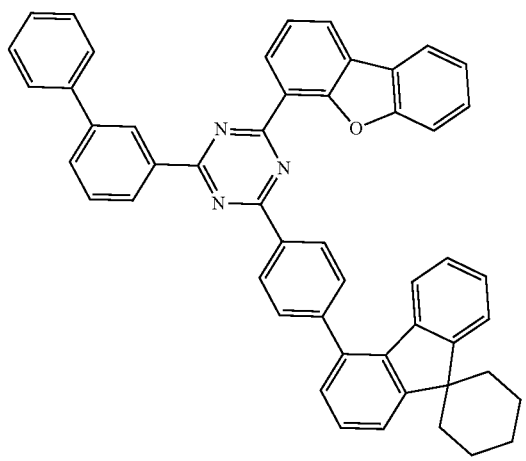

345
-continued
Inv 788
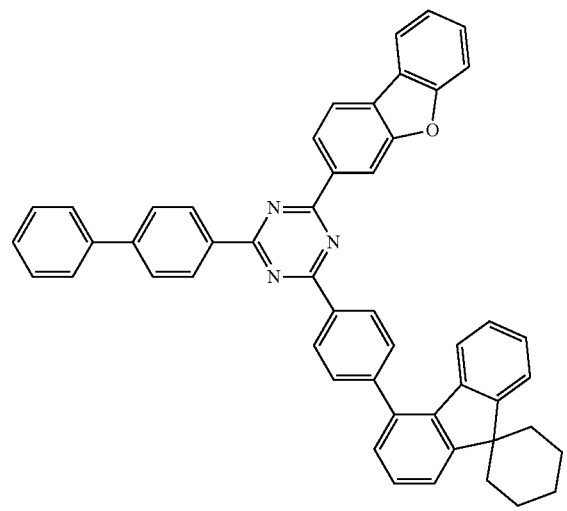
Inv 789
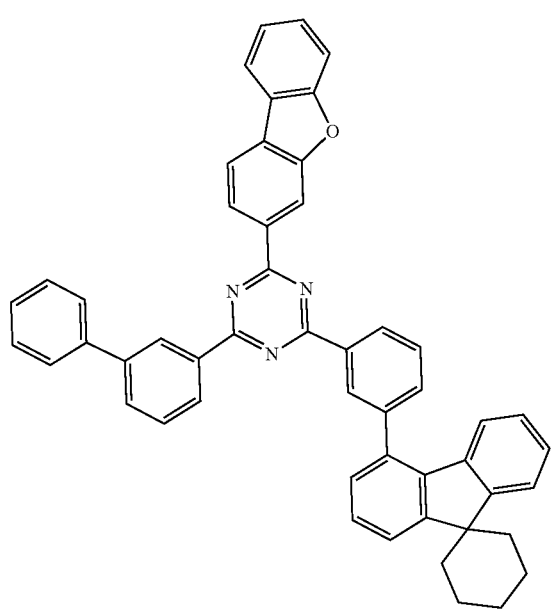
346
-continued
Inv 790
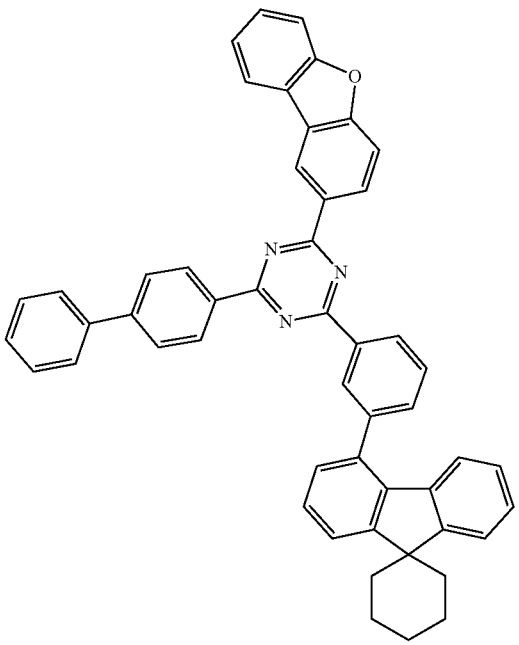
Inv 791
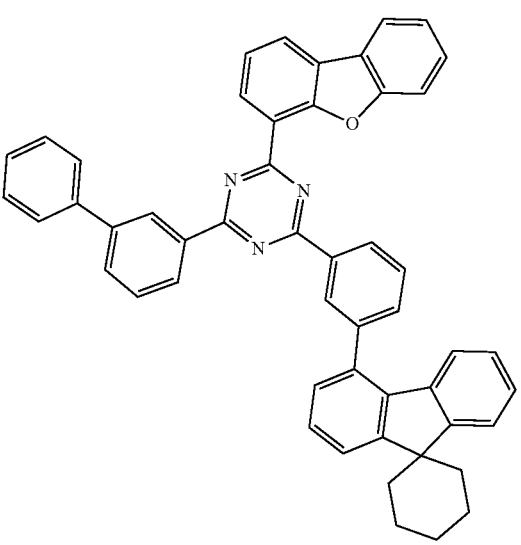

-continued
Inv 792
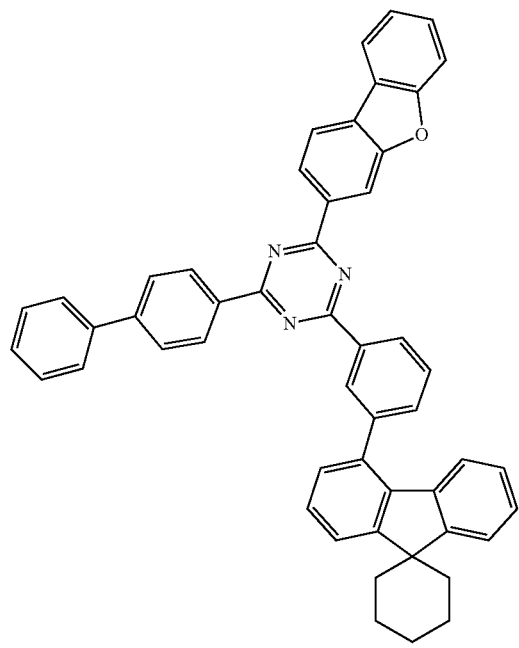
Inv 793
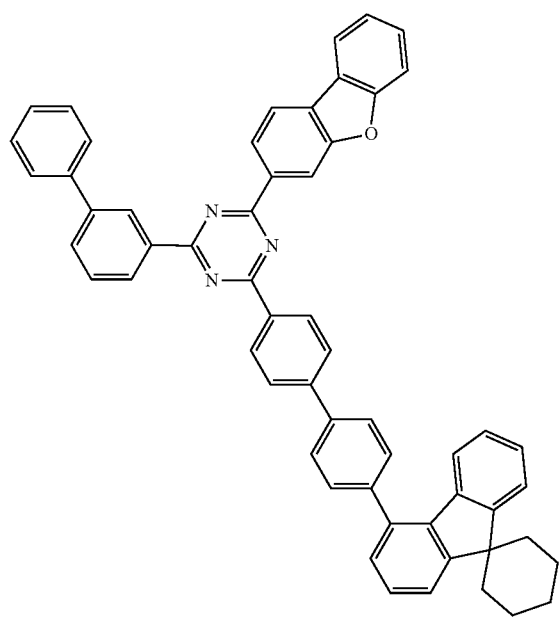
-continued
Inv 794
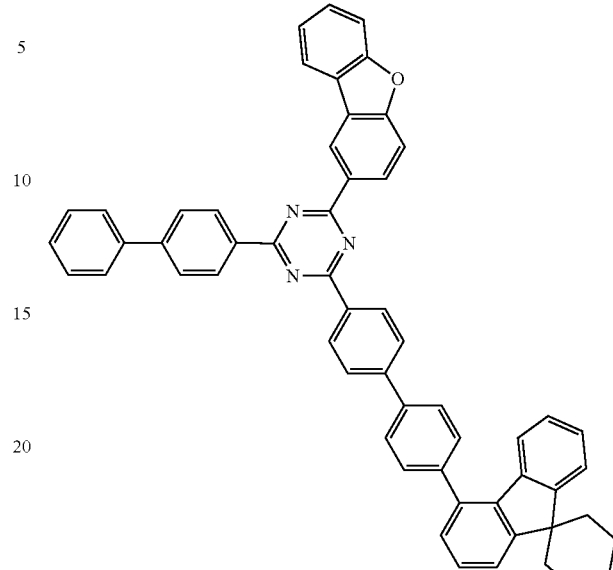
Inv 795
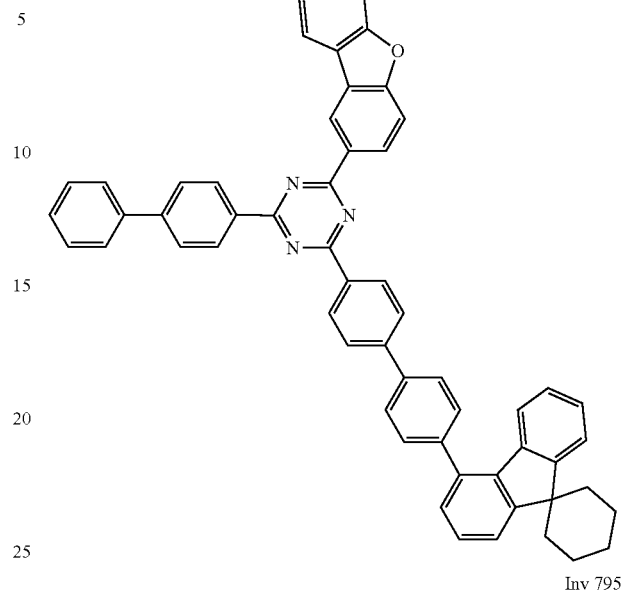
Inv 796
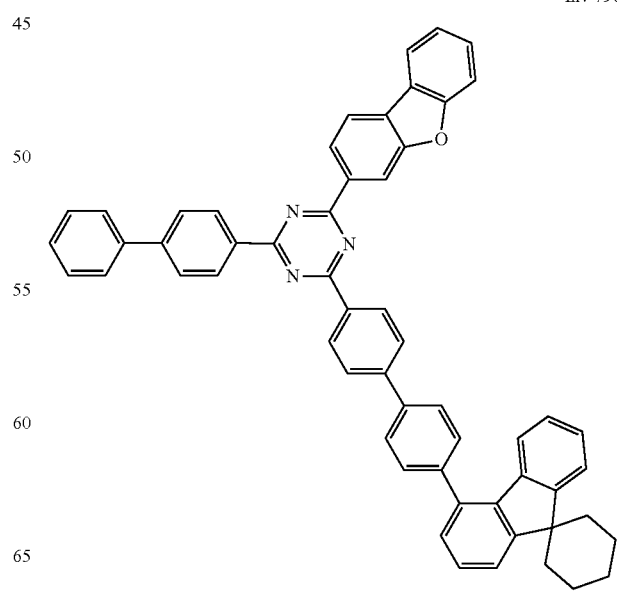

Inv 797
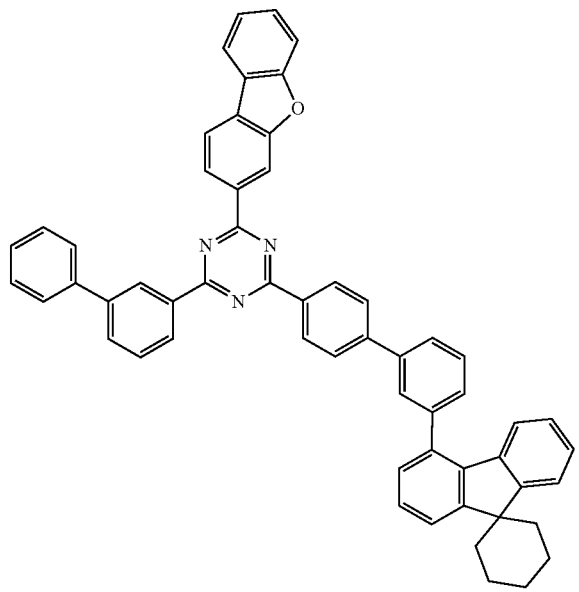
Inv 799
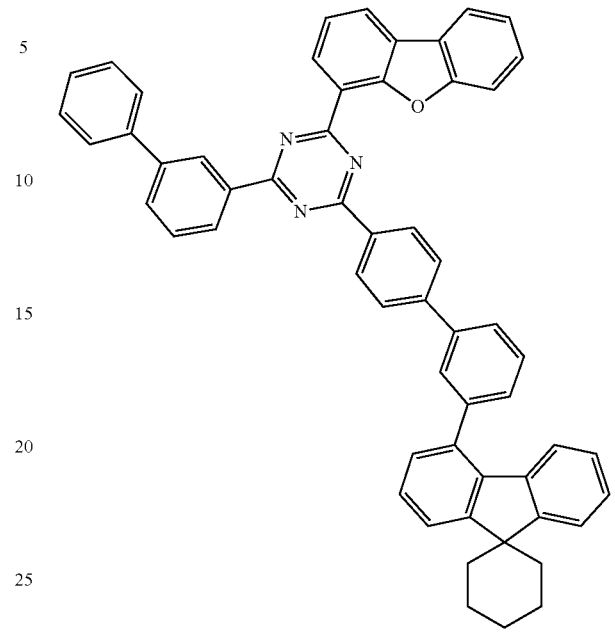
Inv 798
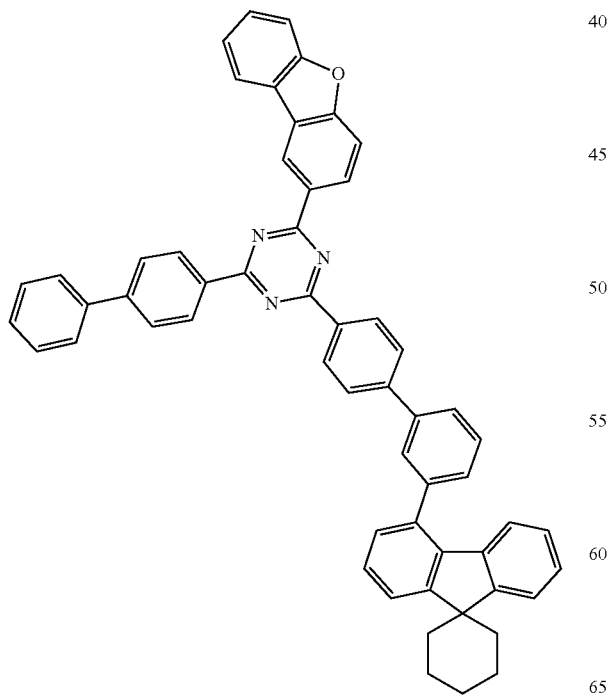
Inv 800

Inv 801
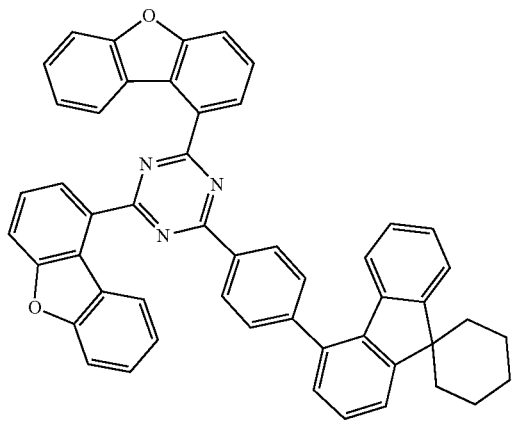
Inv 802
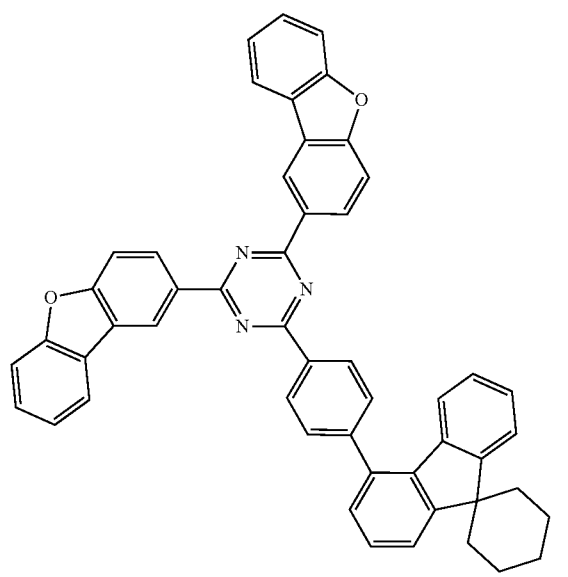
Inv 803
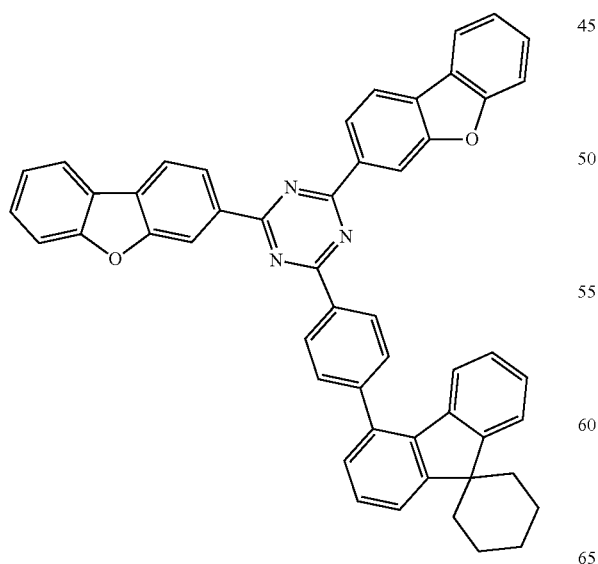
Inv 804
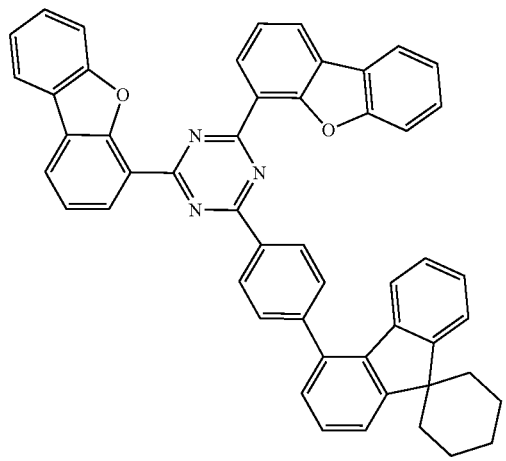
Inv 805
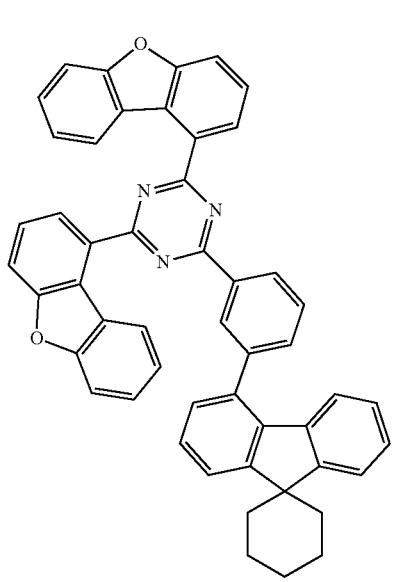

-continued
Inv 806
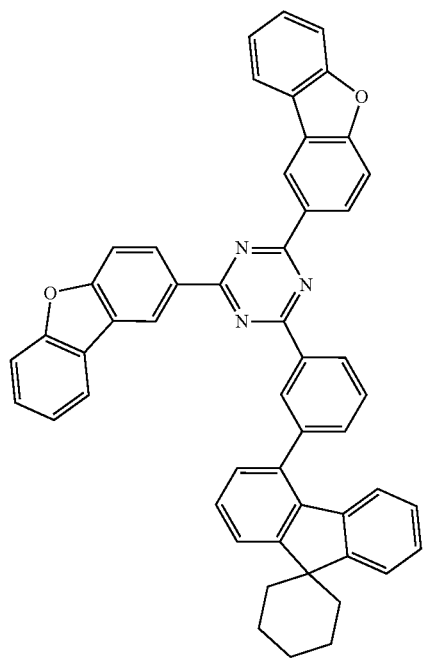
Inv 807
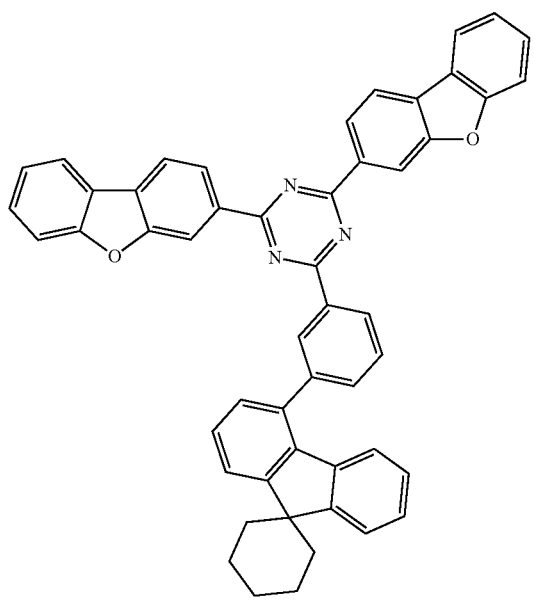
-continued
Inv 808
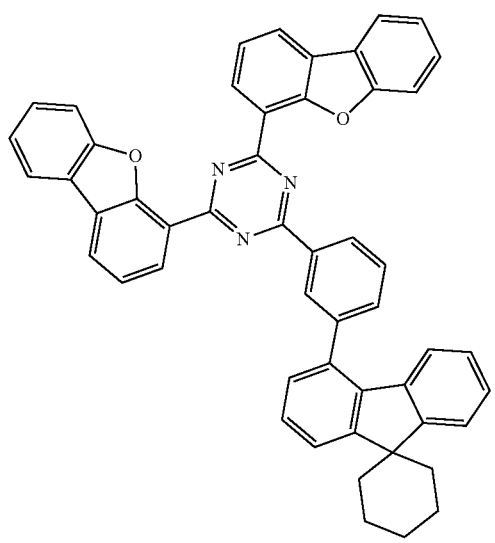
Inv 809
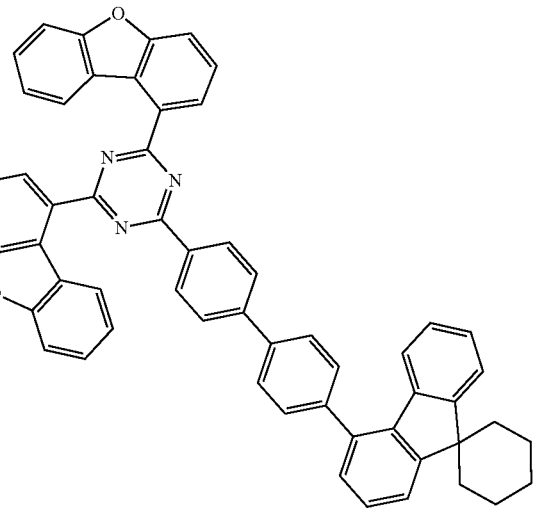

Inv 810
Inv 812
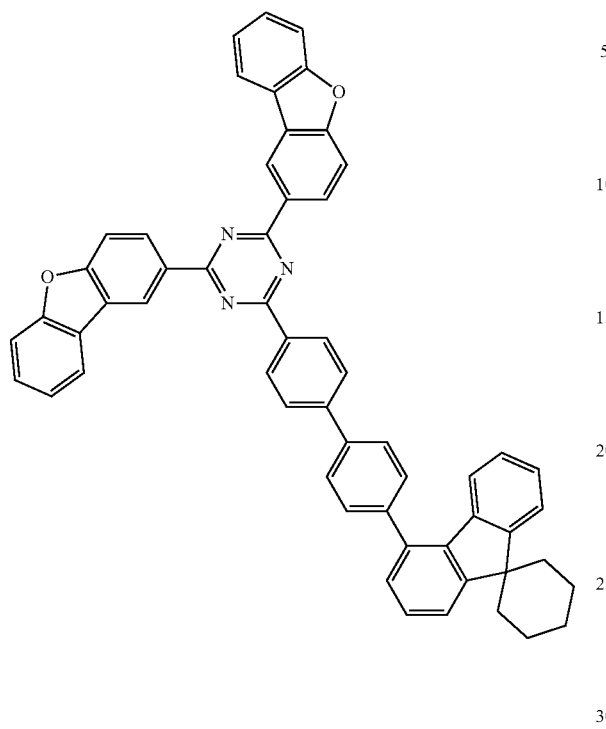
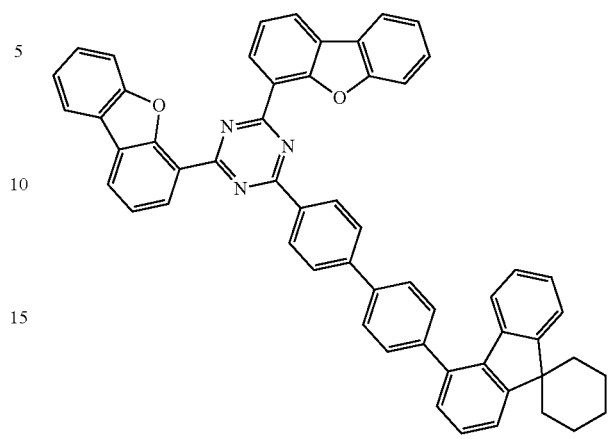
Inv 811
Inv 813
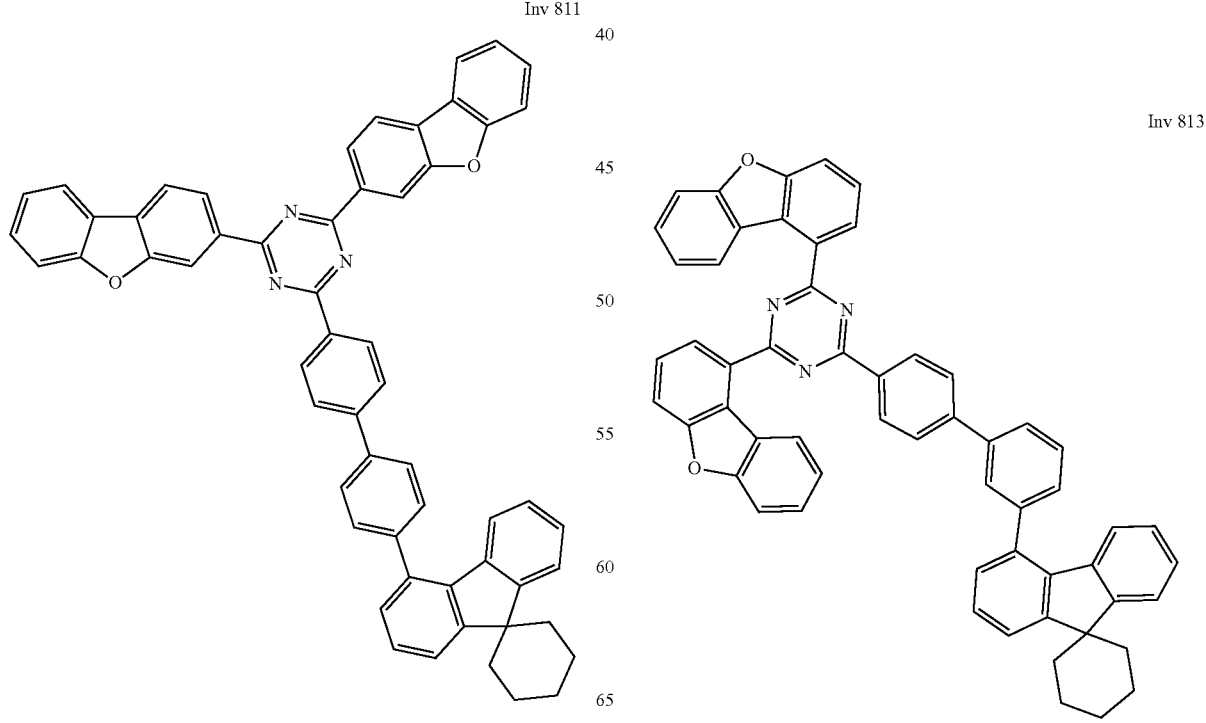

Inv 814
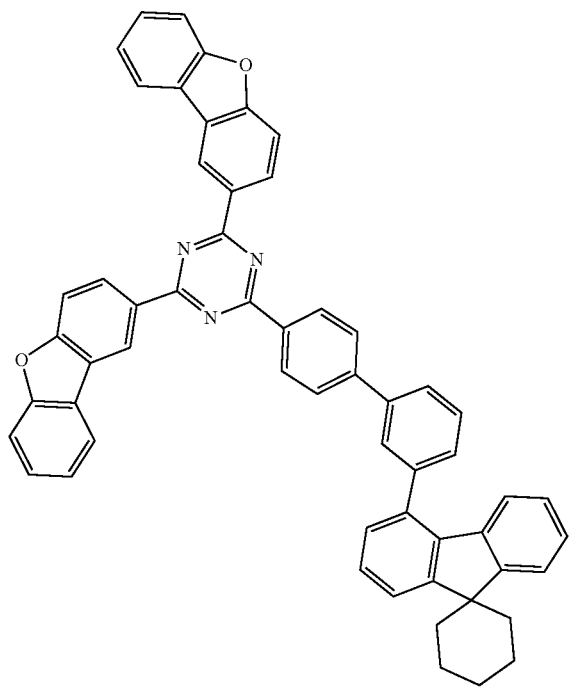
Inv 816
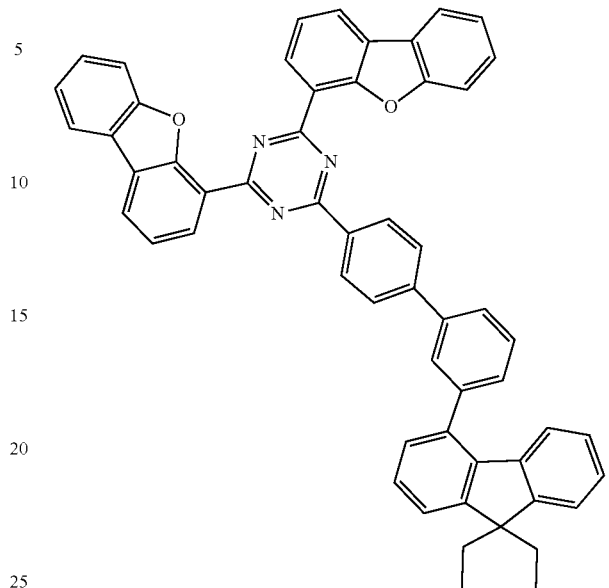
Inv 817
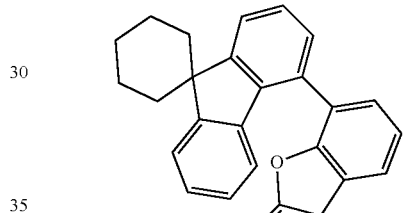
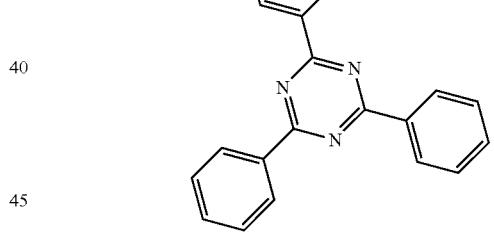
Inv 815
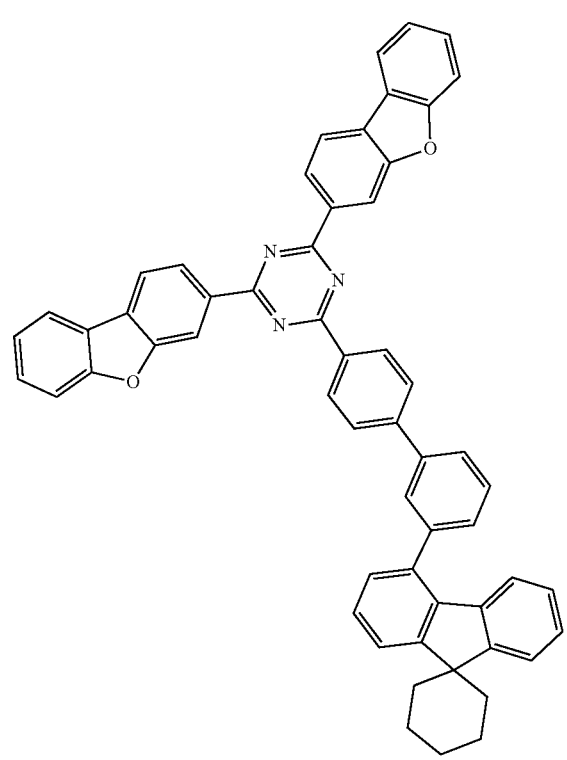
Inv 818
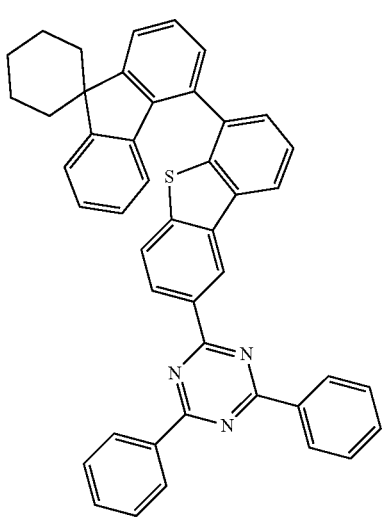

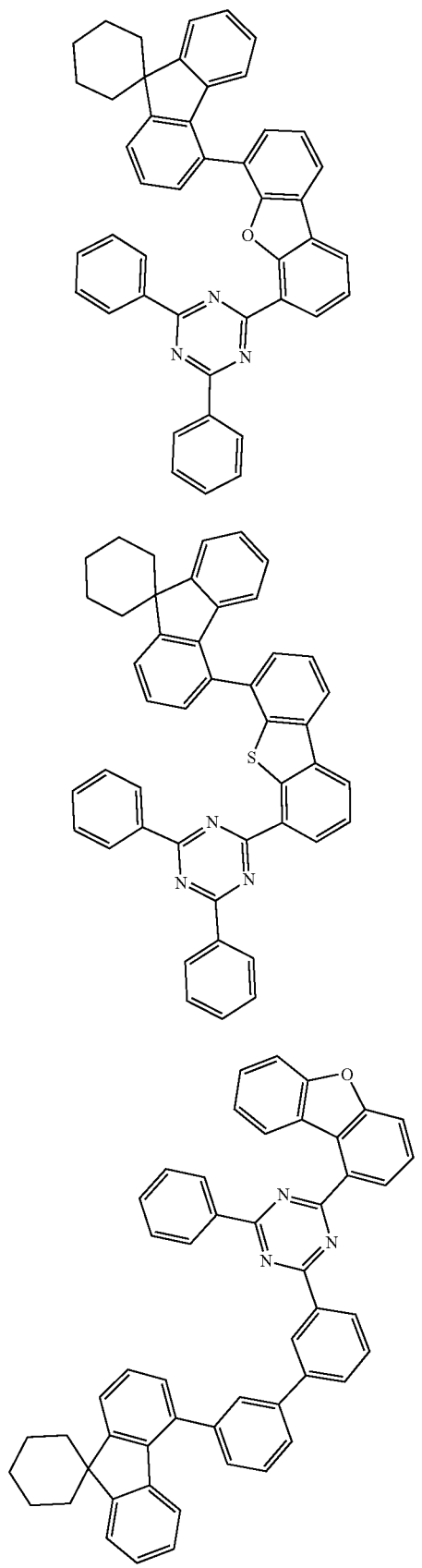

Inv 824
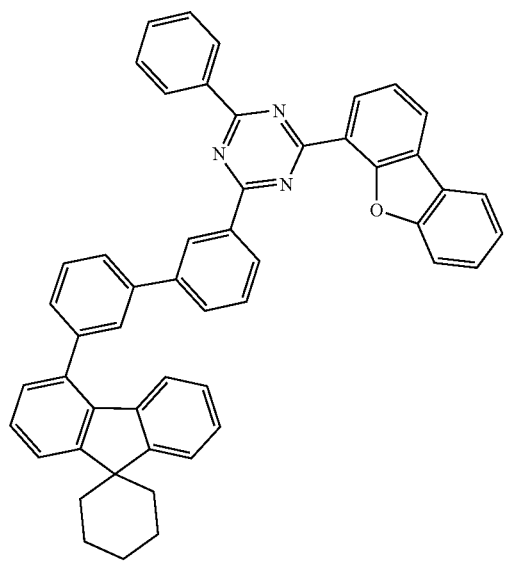
Inv 825
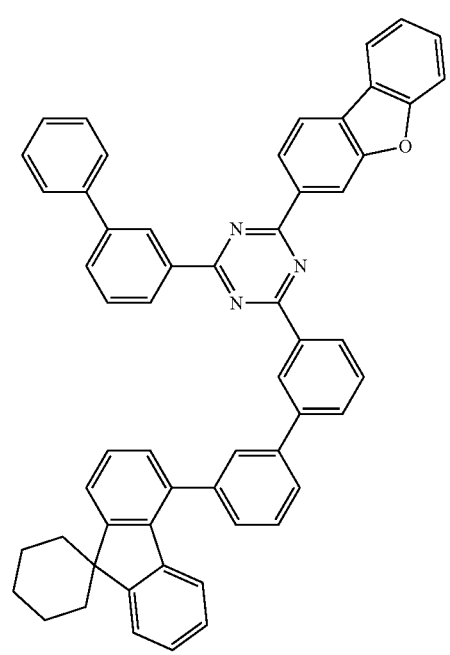
Inv 826
Inv 827
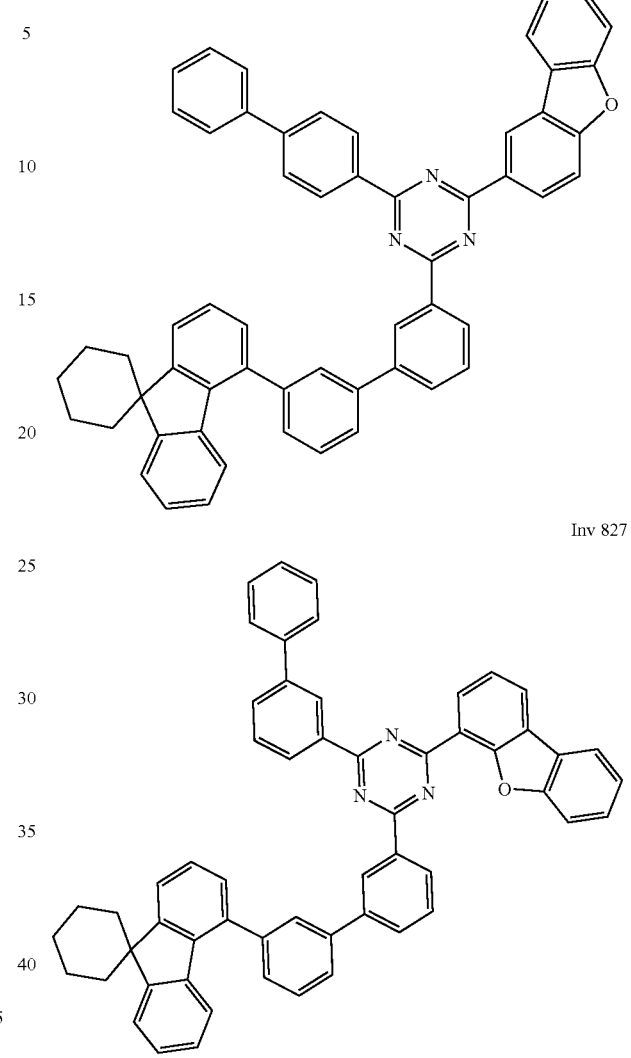
Inv 828
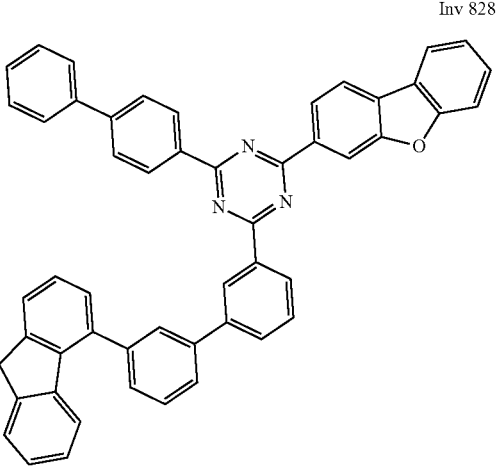

Inv 829
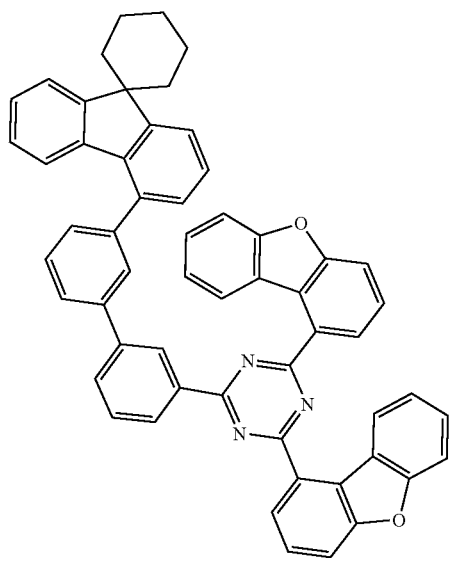
Inv 831
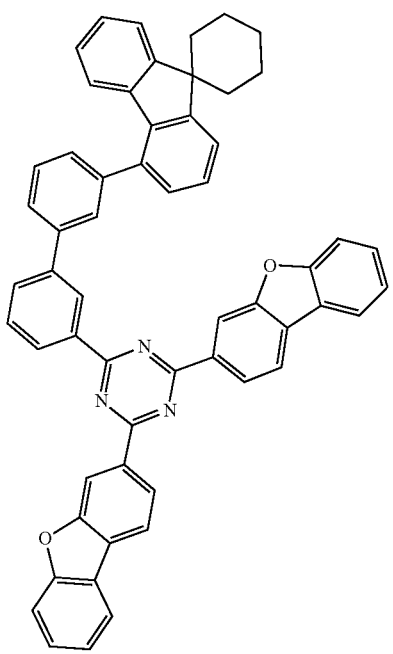
Inv 830
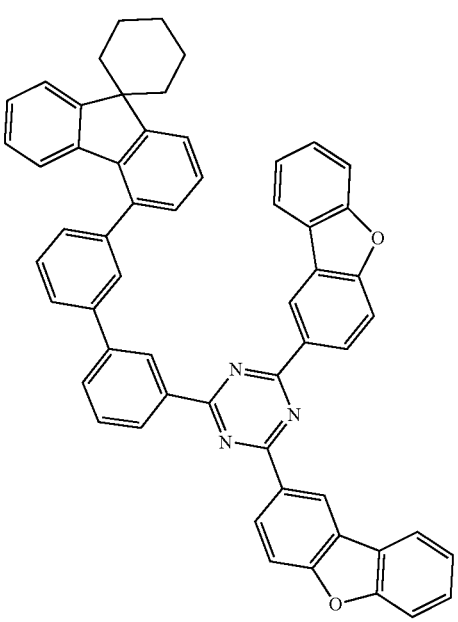
Inv 832
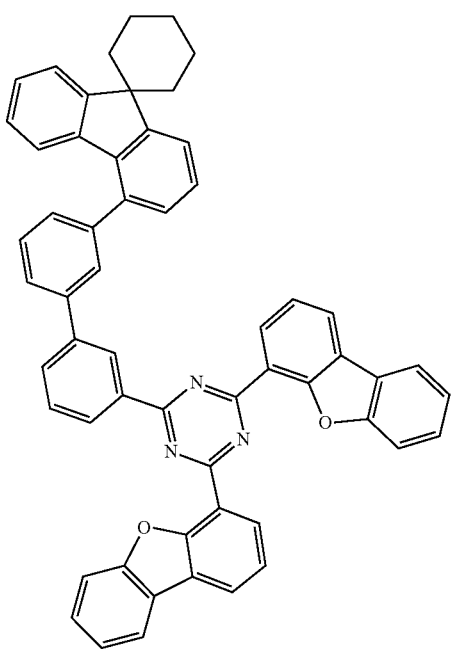

Inv 833
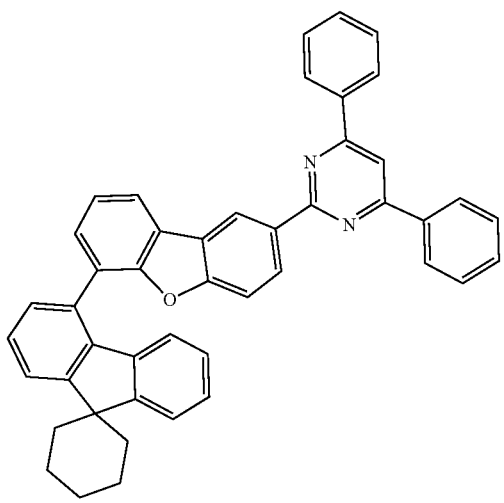
Inv 834
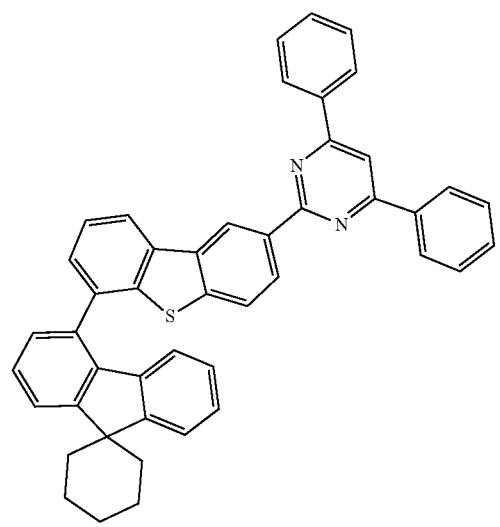
Inv 835
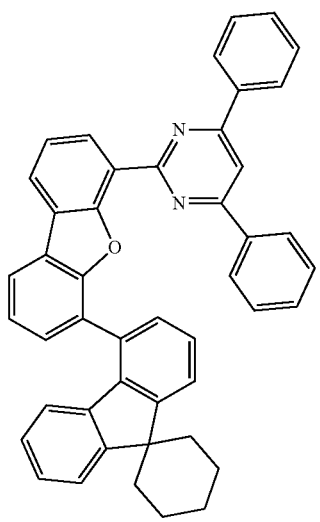
Inv 836
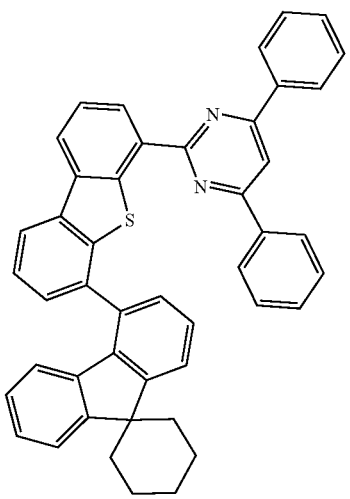
Inv 837
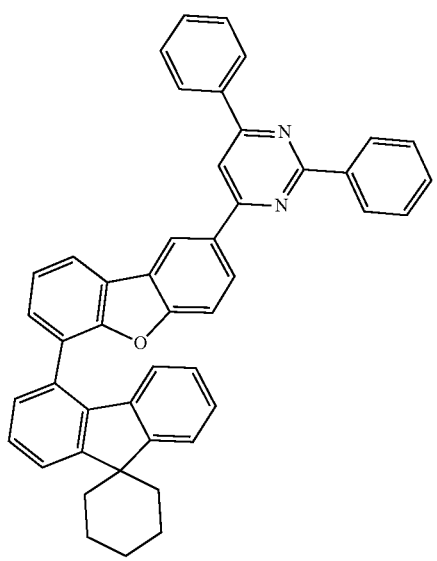
Inv 838
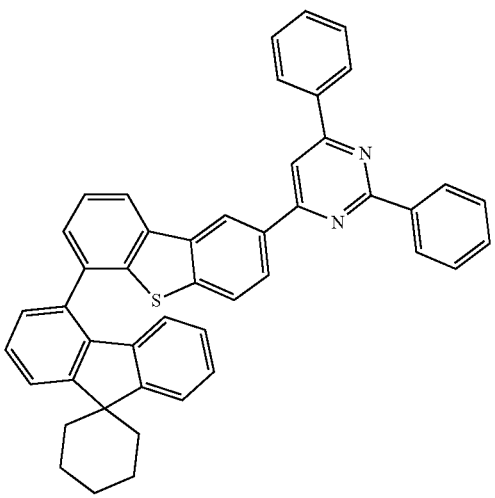

-continued
Inv 839
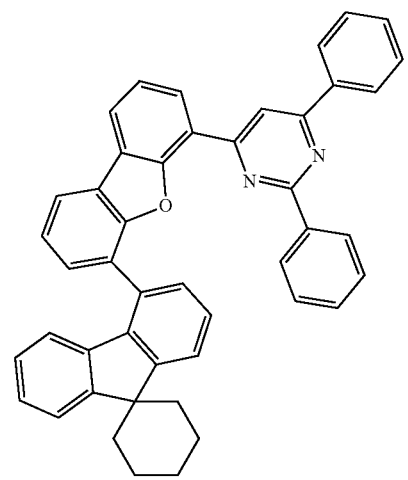
Inv 840
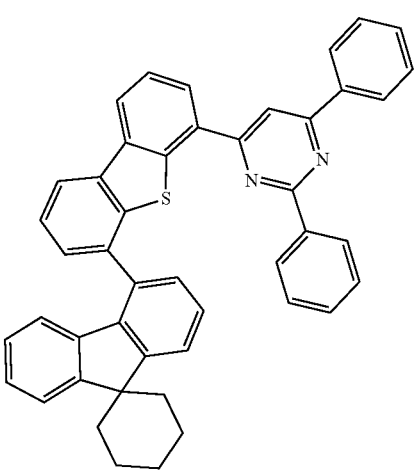
Inv 841
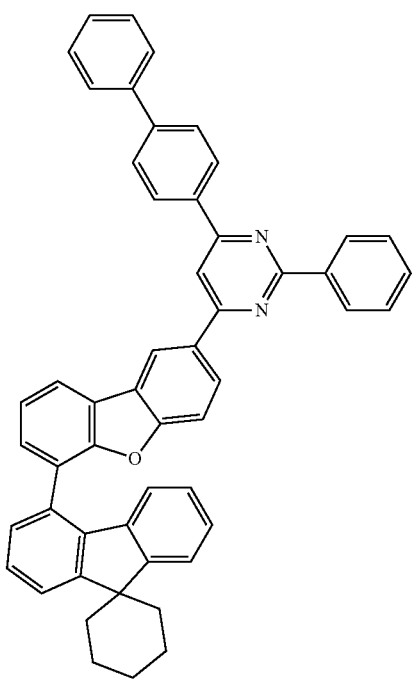
-continued
Inv 842
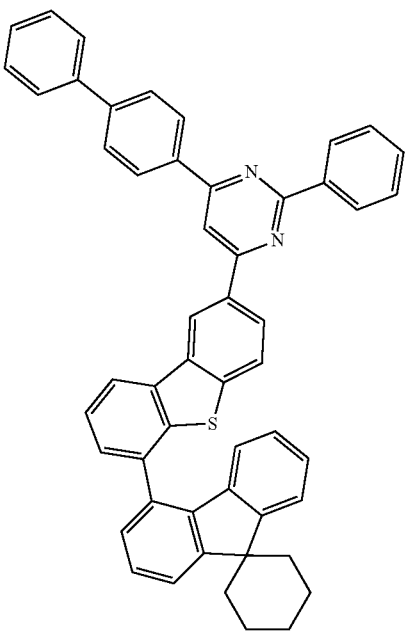
Inv 843
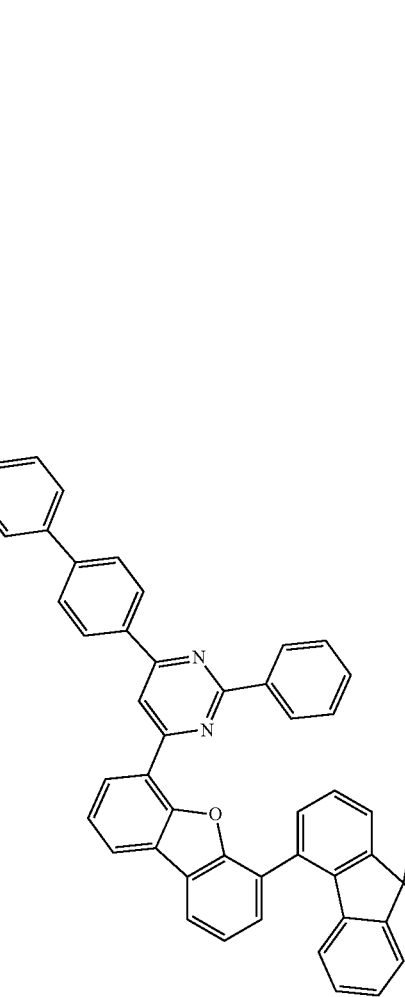

Inv 844
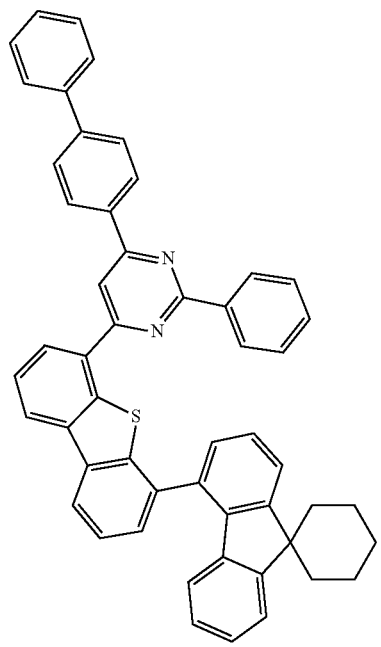
Inv 846
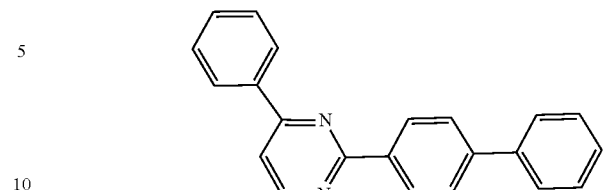
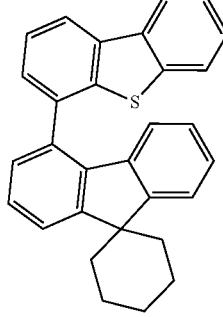
Inv 847
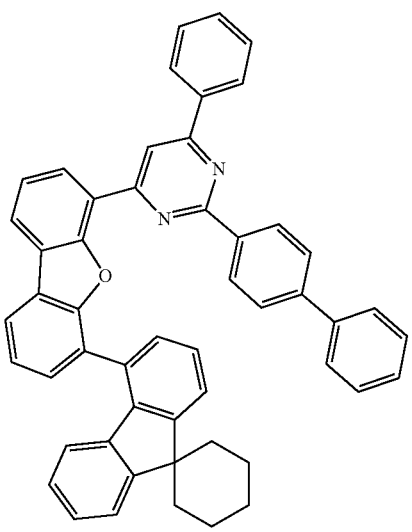
Inv 845
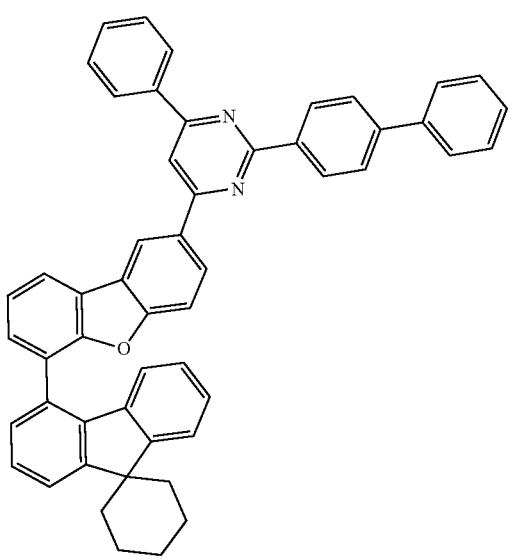
Inv 848
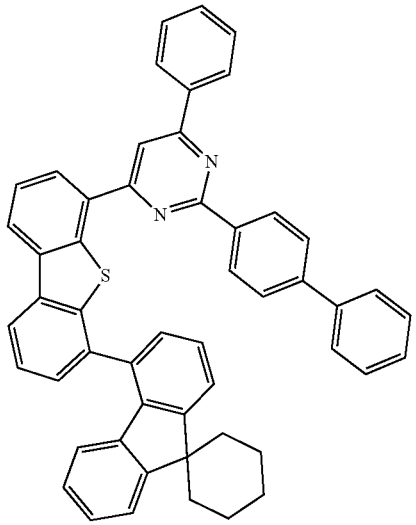

Inv 849
Inv 850
Inv 851
Inv 852
Inv 853
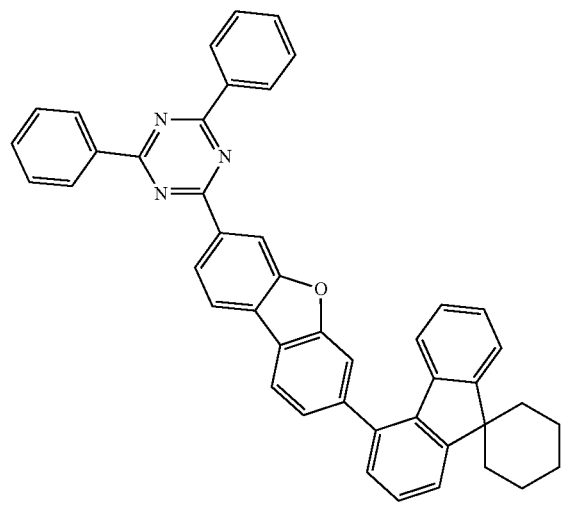
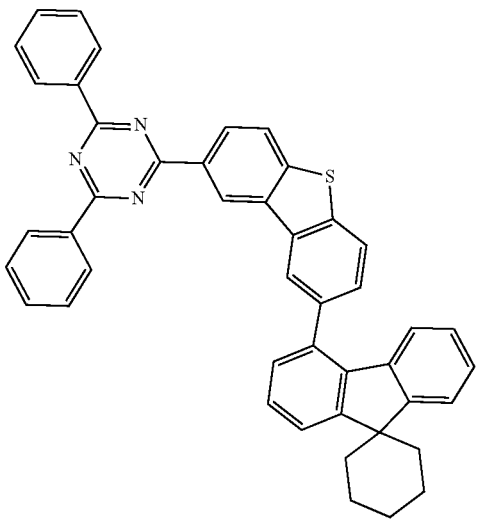
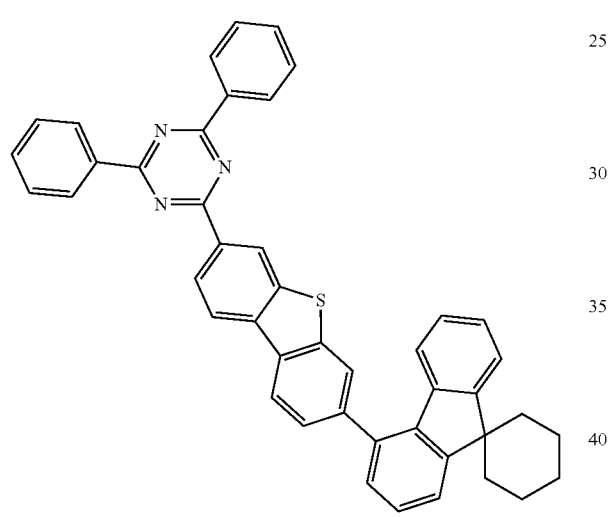
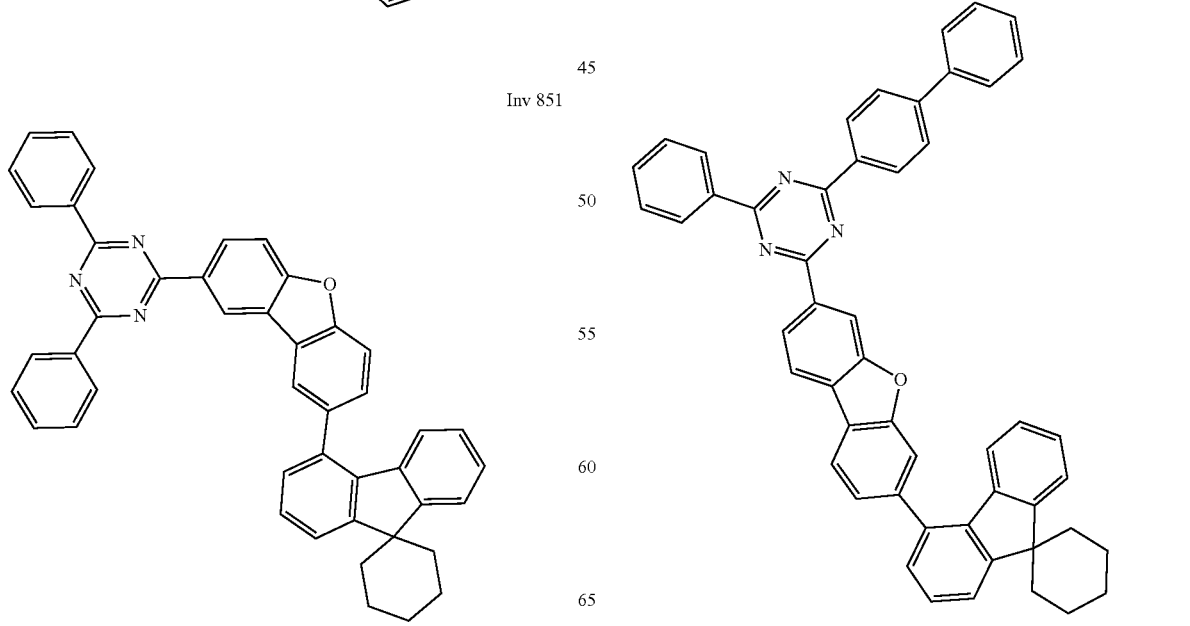

373
-continued
Inv 854
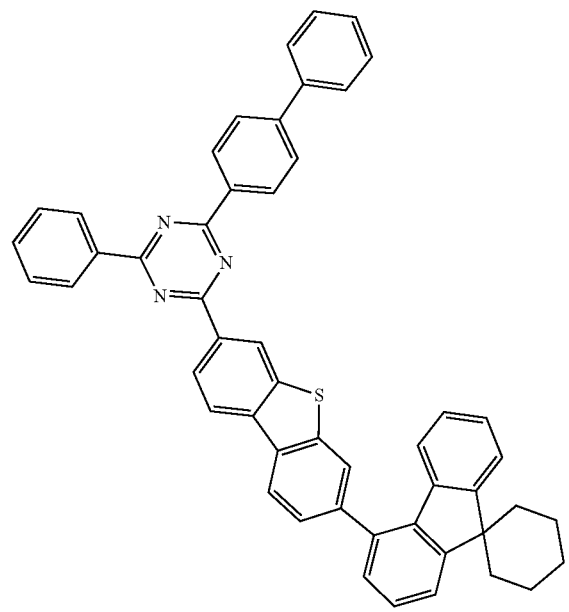
Inv 855
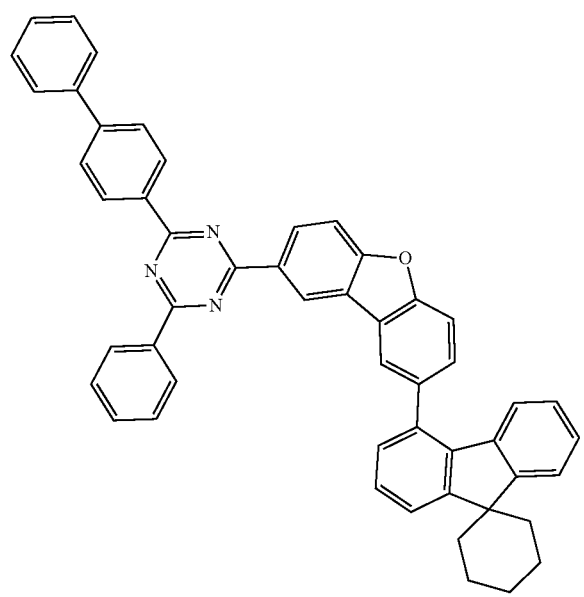
374
-continued
Inv 856
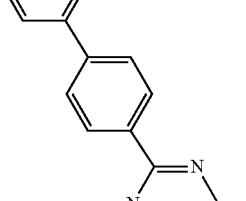
Inv 857

Inv 858
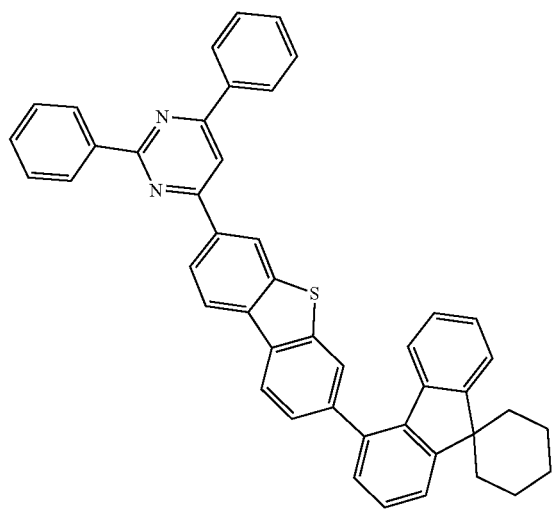
Inv 859
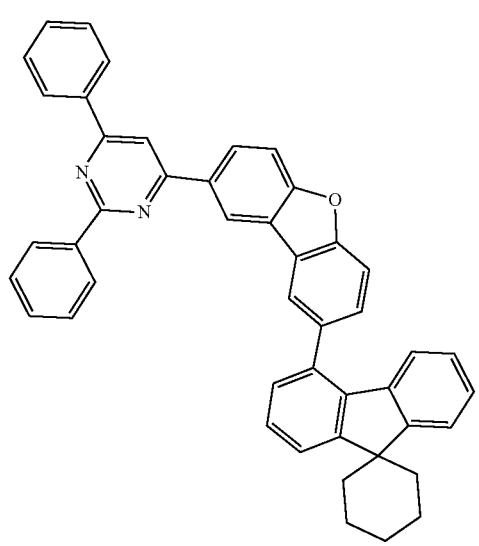
Inv 860
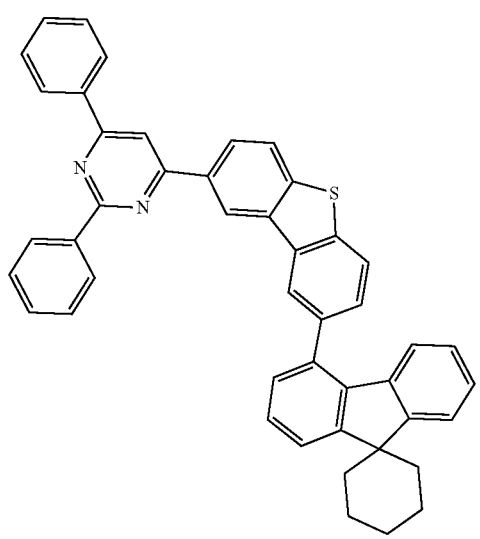
Inv 861
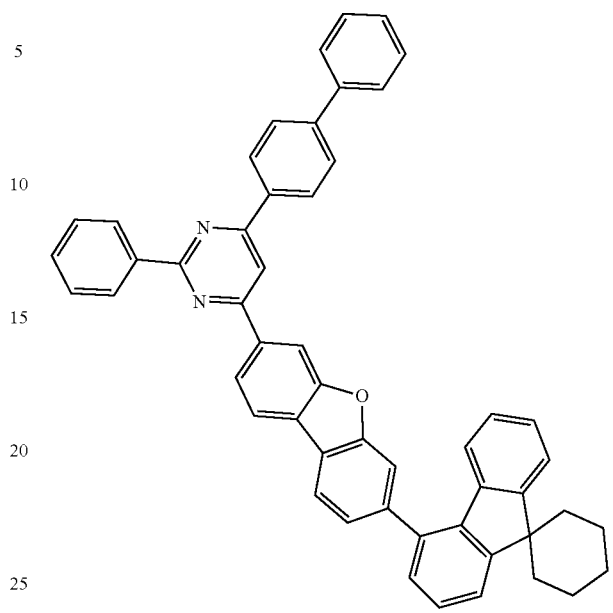
Inv 862

-continued

Inv 863

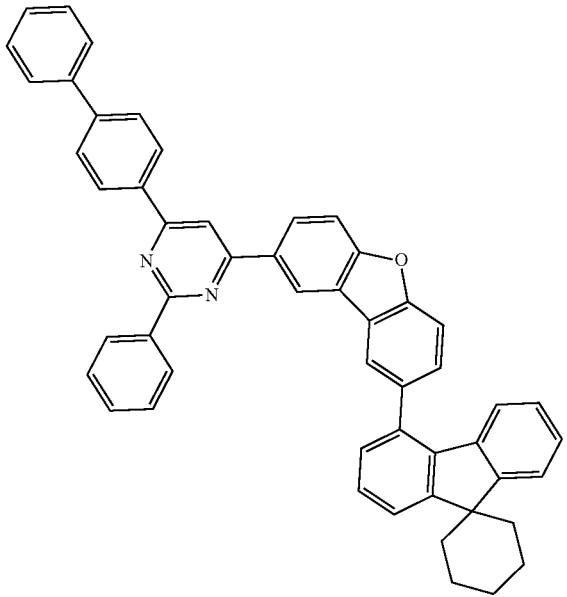

Inv 864

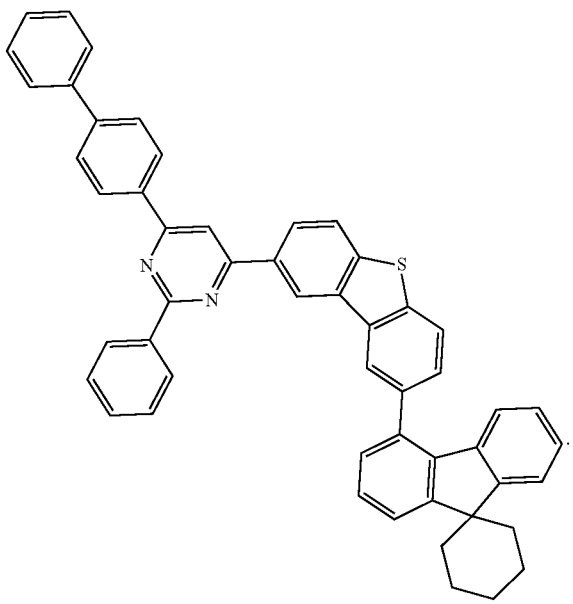

The "alkyl" used in the present invention means a monovalent functional group obtained by removing a hydrogen atom from a linear or branched, saturated hydrocarbon having 1 to 40 carbon atoms. Non-limiting examples thereof include methyl, ethyl, propyl, isobutyl, sec-butyl, pentyl, iso-amyl, hexyl, and the like.

The "alkenyl" used in the present invention means a monovalent functional group obtained by removing a hydrogen atom from a linear or branched, unsaturated hydrocarbon having 2 to 40 carbon atoms, which has one or more carbon-carbon double bonds. Non-limiting examples thereof include vinyl, allyl, isopropenyl, 2-butenyl, and the like.

The "alkynyl" used in the present invention means a monovalent functional group obtained by removing a hydrogen atom from a linear or branched, unsaturated hydrocarbon having 2 to 40 carbon atoms, which has one or more carbon-carbon triple bonds. Non-limiting examples thereof include ethynyl, 2-propynyl, and the like.

The "aryl" used in the present invention means a monovalent functional group obtained by removing a hydrogen atom from an aromatic hydrocarbon having 6 to 40 carbon atoms, in which a single ring or two or more rings are combined. In this case, the two or more rings may be simply pendant to each other or pendant to each other in a fused form. Non-limiting examples thereof include phenyl, biphenyl, terphenyl, naphthyl, phenanthryl, anthryl, and the like.

The "heteroaryl" used in the present invention is a monovalent functional group obtained by removing a hydrogen atom from a monoheterocyclic or polyheterocyclic aromatic hydrocarbon having 5 to 40 nuclear atoms, and one or more carbons in the ring, preferably 1 to 3 carbons are substituted with a heteroatom such as nitrogen (N), oxygen (O), sulfur (S), or selenium (Se). In this case, the two or more rings may be simply pendant to each other or pendant to each other in a fused form in the heteroaryl, and furthermore, the heteroaryl may also include a form fused with an aryl group. Non-limiting examples of the heteroaryl include: a 6-membered monocyclic ring, such as pyridyl, pyrazinyl, pyrimidinyl, pyridazinyl, and triazinyl; a polycyclic ring, such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like.

The "aryloxy" used in the present invention means a monovalent functional group represented by RO—, and the R is an aryl having 5 to 40 carbon atoms. Non-limiting examples of the aryloxy include phenyloxy, naphthyloxy, diphenyloxy, and the like.

The "alkyloxy" used in the present invention means a monovalent functional group represented by RO—, and the R is an alkyl having 1 to 40 carbon atoms, and may include a linear, branched, or cyclic structure. Non-limiting examples of the alkyloxy include methoxy, ethoxy, n-propoxy, 1-propoxy, t-butoxy, n-butoxy, pentoxy, and the like.

The "arylamine" means an amine which is substituted with an aryl having 6 to 60 carbon atoms.

The "cycloalkyl" used in the present invention means a monovalent functional group obtained by removing a hydrogen atom from a monocyclic or polycyclic non-aromatic hydrocarbon (saturated cyclic hydrocarbon) having 3 to 40 carbon atoms. Non-limiting examples thereof include cyclopropyl, cyclopentyl, cyclohexyl, norbornyl, adamantine, and the like.

The "heterocycloalkyl" used in the present invention means a monovalent functional group obtained by removing a hydrogen atom from a non-aromatic hydrocarbon (saturated cyclic hydrocarbon) having 3 to 40 nuclear atoms, and one or more carbons in the ring, preferably 1 to 3 carbons are substituted with a heteroatom such as N, O, Se, or S. Non-limiting examples thereof include morpholine, piperazine, and the like.

The "alkylsilyl" used in the present invention means a silyl which is substituted with an alkyl having 1 to 40 carbon atoms, the "arylsilyl" means a silyl which is substituted with an aryl having 5 to 40 carbon atoms, The "fused ring" used in the present invention means a fused aliphatic ring, a fused aromatic ring, a fused heteroaliphatic ring, a fused heteroaromatic ring, or a combined form thereof.

<Organic Electroluminescent Device>

Another aspect of the present invention relates to an organic electroluminescent device ("organic EL device")

including the compound represented by the above-described Chemical Formula 1 according to an embodiment of the present invention.

Specifically, according to an embodiment, an organic EL device includes an anode, a cathode, and one or more organic layers interposed between the anode and the cathode, and at least one of the one or more organic layers includes the compound represented by Chemical Formula 1. In this case, the compound may be used alone or in combination of two or kinds thereof.

The one or more organic layers may be any one or more of a hole injection layer, a hole transporting layer, a light-emitting layer, a light-emitting auxiliary layer, an electron transporting layer, an electron transporting auxiliary layer, and an electron injection layer, of which at least one organic layer includes the compound represented by Chemical Formula 1 described above. Specifically, it is preferable that the organic layer including the compound of Chemical Formula 1 is the light-emitting layer, the electron transporting layer, and/or the electron transporting auxiliary layer.

The light-emitting layer of the organic EL device according to an embodiment of the present invention includes a host material and a dopant material, and in this case, the compound of Chemical Formula 1 may be included as the host material. In addition, the light-emitting layer according to an embodiment may include a compound known in the art other than the compound of Chemical Formula 1 as hosts.

When the compound represented by Chemical Formula 1 is included as a material for the light-emitting layer of the organic EL device, preferably as a phosphorescent host material of blue, green, and red, a binding force between holes and electrons in the light-emitting layer increases, and thus the efficiency (luminous efficiency and power efficiency), life, luminance, and driving voltage of the organic EL device may be improved. Specifically, the compound represented by Chemical Formula 1 is preferably included in the organic EL device as a material for green and/or red phosphorescent hosts, fluorescent hosts, or dopants. In particular, it is preferable that the compound represented by Chemical Formula 1 according to an embodiment is a green phosphorescent exciplex N-type host material of the light-emitting layer having high efficiency.

A structure of the organic EL device according to an embodiment is not particularly limited, but may have a structure in which a substrate, the anode, the hole injection layer, the hole transporting layer, the light-emitting auxiliary layer, the light-emitting layer, the electron transporting layer, and the cathode are sequentially stacked. In such a case, at least one of the hole injection layer, the hole transporting layer, the light-emitting auxiliary layer, the light-emitting layer, the electron transporting layer, and the electron injection layer may include the compound represented by Chemical Formula 1, and preferably the light-emitting layer, more preferably the phosphorescent host may include the compound represented by Chemical Formula 1. In an embodiment, an electron injection layer may be further stacked on the electron transporting layer.

The organic EL device according to an embodiment may have a structure in which an insulating layer or an adhesive layer is inserted at an interface between the electrodes and the organic layers.

The organic EL device according to an embodiment may be manufactured by forming the organic layers and the electrodes using materials and methods known in the art, except that at least one of the aforementioned organic layers includes the compound represented by Chemical Formula 1.

The organic layer may be formed by a vacuum deposition method or a solution coating method. Examples of the solution coating method may include, but not limited to, spin coating, dip coating, doctor blading, inkjet printing, or thermal transfer scheme, but embodiments are not limited thereto.

The substrate used in the manufacturing of the organic EL device according to an embodiment is not particularly limited, and for example, a silicon wafer, quartz, a glass plate, a metal plate, a plastic film, a sheet, and the like may be used.

In addition, any anode material known in the art may be used as a material for the anode without limitation. For example, metals such as vanadium, chromium, copper, zinc, gold, or alloys thereof; metal oxides such as zinc oxide, indium oxide, indium tin oxide (ITO), and indium zinc oxide (IZO); combinations of metals and oxides such as ZnO:Al or $SnO_2$:Sb; conductive polymers such as polythiophene, poly (3-methylthiophene), poly[3,4-(ethylene-1,2-dioxy)thiophene] (PEDT), polypyrrole or polyaniline; and carbon black may be used, but embodiments are not limited thereto.

In addition, any cathode material known in the art may be used as a material for the cathode without limitation. For example, metals such as magnesium, calcium, sodium, potassium, titanium, indium, yttrium, lithium, gadolinium, aluminum, silver, tin, or lead, or alloys thereof; and a multi-layered material such as LiF/Al or $LiO_2$/Al and the like may be used, but embodiments are not limited thereto.

In addition, materials for the hole injection layer, the hole transporting layer, the electron injection layer, and the electron transporting layer are not particularly limited, and conventional materials known in the art may be used without limitation.

Hereinafter, the present invention will be described in detail through embodiments. However, the following embodiments are only illustrative of the present invention, and the present invention is not limited by the following embodiments.

[Preparation Example 1] Synthesis of Core 1

<Step 1> Synthesis of 2'-bromospiro[cyclohexane-1,9'-fluorene]

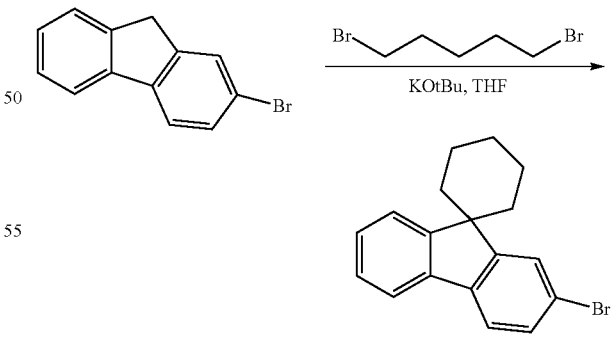

2-bromo-9H-fluorene (100 g, 407.96 mmol) was put into a 2 L reactor, 500 ml of THF was added thereto, the mixture was put into an ice bath while stirring, and an internal temperature was set to -0° C. Then, KOtBu (93.8 g, 1019 mmol) was added thereto in portions for 15 minutes, followed by stirring for 10 minutes. Next, 1,5-dibromopentane (42.7 g, 407.93 mmol) was added dropwise for 5 minutes.

The temperature was slowly raised to room temperature and the 1,5-dibromopentane-added mixture was stirred for 8 hours. After completion of the reaction, the mixture was extracted with methylene chloride, and MgSO₄ was added thereto, followed by filtering. After removing a solvent of a filtered organic layer, a target compound 2'-bromospiro [cyclohexane-1,9'-fluorene] (78.2 g, yield 61%) was obtained by column chromatography.

¹H-NMR: δ 1.58 (m, 2H) 1.77 (m, 8H), 7.33 (m, 2H), 7.55 (d, 1H), 7.74 (d, 1H), 7.85 (m, 3H).

[LCMS]: 314

<Step 2> Synthesis of Core 1

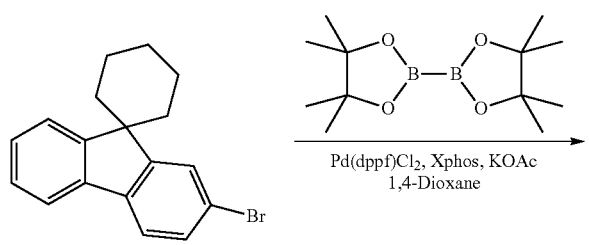

Pd(dppf)Cl₂, Xphos, KOAc
1,4-Dioxane

2'-bromospiro[cyclohexane-1,9'-fluorene] (78.2.2 g, 249.6 mmol) and 4,4,4',4',5,5,5',5'-octamethyl-2,2'-bi(1,3,2-dioxaborolane) (76 g, 299.5 mmol) and Pd(dppf)Cl₂ (5.48 g, 7.48 mmol), KOAc (73.5 g, 748.9 mmol), Xphos (11.9 g, 24.96 mmol) were put into 750 ml of 1,4-Dioxane, and heated to reflux for 12 hours. After completion of the reaction, the mixture was extracted with methylene chloride, and MgSO₄ was added thereto, followed by filtering. After removing a solvent of a filtered organic layer, a target compound Core 1 (70.2 g, yield 78%) was obtained by column chromatography.

¹H-NMR: δ 1.57 (s, 12H), 1.65 (m, 2H), 1.78 (m, 8H), 7.40 (m, 2H), 7.62 (d, 1H), 7.82 (d, 1H), 7.88 (m, 3H).

[LCMS]: 361.

[Preparation Example 2] Synthesis of Core 2

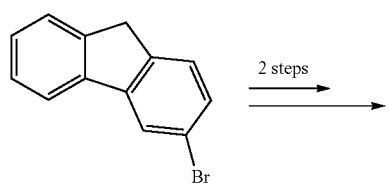

2 steps

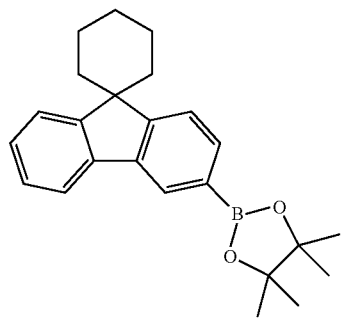

Except that 3-bromo-9H-fluorene was used as the reactant of <Step 2>, the same procedure as in [Preparation Example 1] was performed to obtain 68.8 g (yield 80%) of a compound Core 2.

¹H-NMR: δ 1.56 (s, 12H), 1.68 (m, 2H), 1.82 (m, 8H), 7.42 (m, 2H), 7.65 (t, 1H), 7.83 (m, 2H), 8.02 (s, 1H), 8.15 (d, 1H).

[LCMS]: 361.

[Preparation Example 3] Synthesis of Core 3

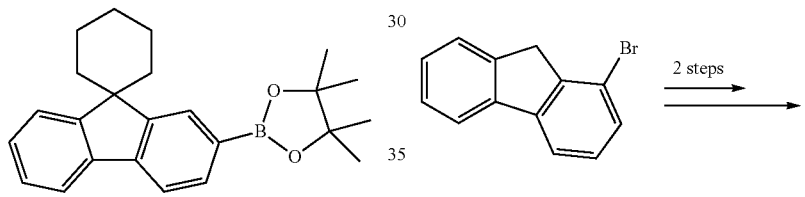

2 steps

Except that 1-bromo-9H-fluorene was used as the reactant of <Step 2>, the same procedure as in [Preparation Example 1] was performed to obtain 65.4 g (yield 79%) of a compound Core 3.

¹H-NMR: δ 1.55 (s, 12H), 1.68 (m, 2H), 1.82 (m, 8H), 7.38 (m, 2H), 7.62m, 2H), 7.85d, 1H), 8.05 (m, 2H).

[LCMS]: 361.

[Preparation Example 4] Synthesis of Core 4

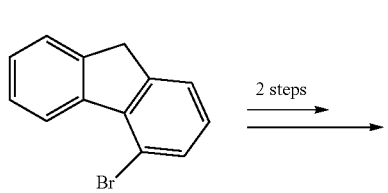

2 steps

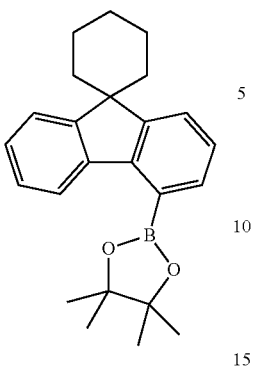

Except that 4-bromo-9H-fluorene was used as the reactant of <Step 2>, the same procedure as in [Preparation Example 1] was performed to obtain 70.6 g (yield 80%) of a compound Core 4.

$^1$H-NMR: δ 1.56 (s, 12H), 1.68 (m, 2H), 1.82 (m, 8H), 7.42 (m, 2H), 7.65 (m, 2H), 7.72 (m, 2H), 7.94 (d, 1H).
[LCMS]: 361.

[Synthesis Example 1] Synthesis of Compound Inv 3

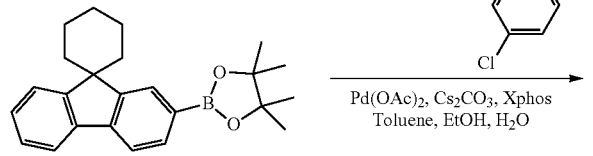

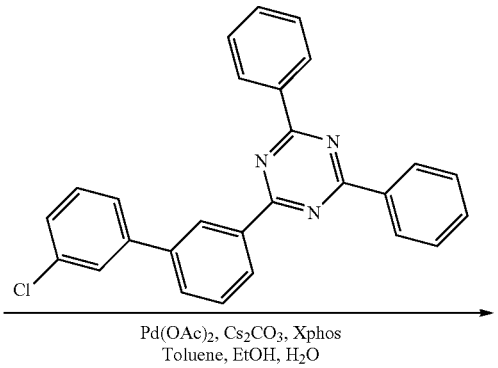

Core 1 (6.3 g, 17.4 mmol) of [Preparation Example 1] and 2-(3-chlorophenyl)-4,6-diphenyl-1,3,5-triazine (5.0 g, 14.5 mmol), Pd(OAc)$_2$ (0.09 g, 0.43 mmol), Cs$_2$CO$_3$ (9.4 g, 29.1 mmol), and Xphos (0.69 g, 1.45 mmol) were added to 100 ml of Toluene, 25 ml of EtOH, 25 ml of H$_2$O, and heated to reflux for 12 hours. After completion of the reaction, the mixture was extracted with methylene chloride, and MgSO$_4$ was added thereto, followed by filtering. After removing a solvent of a filtered organic layer, a target Compound Inv 3 (5.3 g, yield 67%) was obtained by column chromatography.
[LCMS]: 542.

[Synthesis Example 2] Synthesis of Compound Inv 7

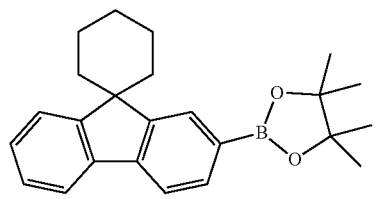

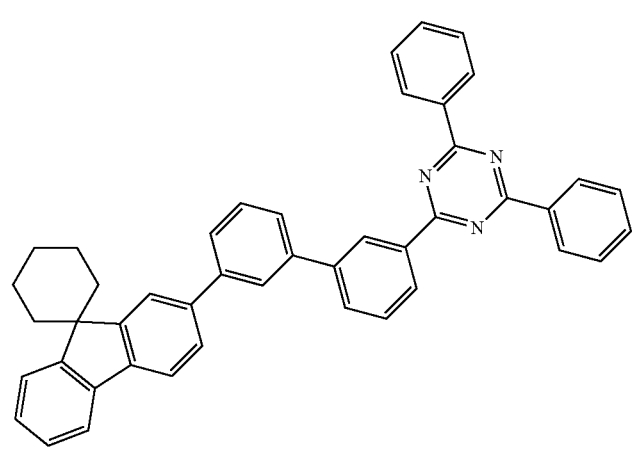

Except that 2-(3-chlorophenyl)-4,6-diphenyl-1,3,5-triazine (5.0 g, 11.9 mmol) was used instead of 2-(3-chlorophenyl)-4,6-diphenyl-1,3,5-triazine, the same procedure as in [Synthesis Example 1] was performed to obtain a target Compound Inv 7 (4.8 g, yield 65%).

[LCMS]: 618.

[Synthesis Example 3] Synthesis of Compound Inv 14

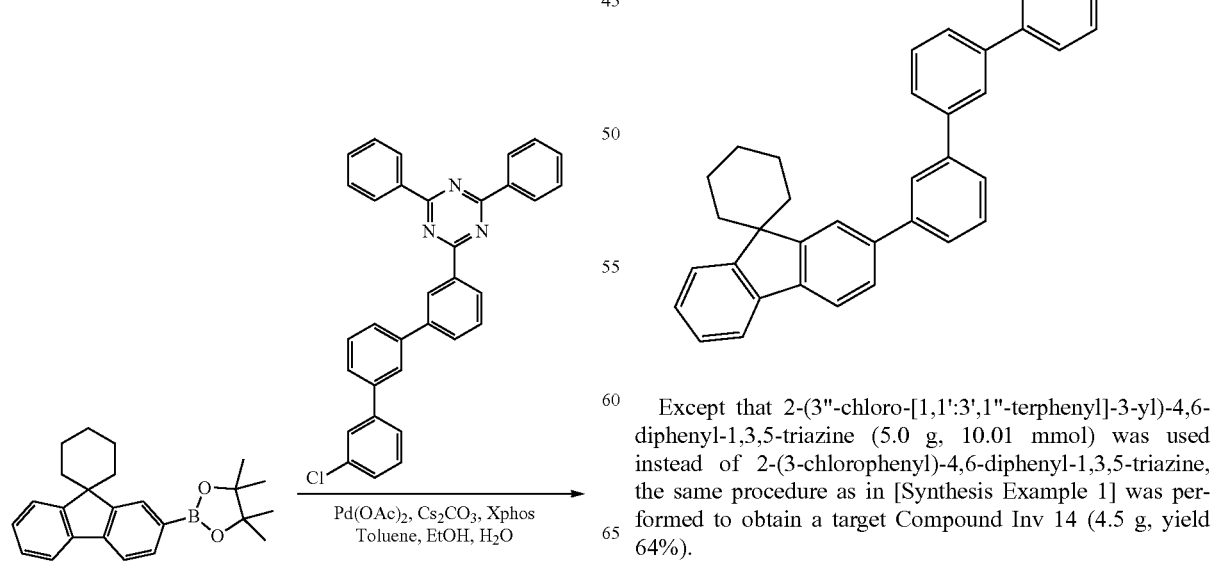

Except that 2-(3''-chloro-[1,1':3',1''-terphenyl]-3-yl)-4,6-diphenyl-1,3,5-triazine (5.0 g, 10.01 mmol) was used instead of 2-(3-chlorophenyl)-4,6-diphenyl-1,3,5-triazine, the same procedure as in [Synthesis Example 1] was performed to obtain a target Compound Inv 14 (4.5 g, yield 64%).

[LCMS]: 694.

[Synthesis Example 4] Synthesis of Compound Inv 18
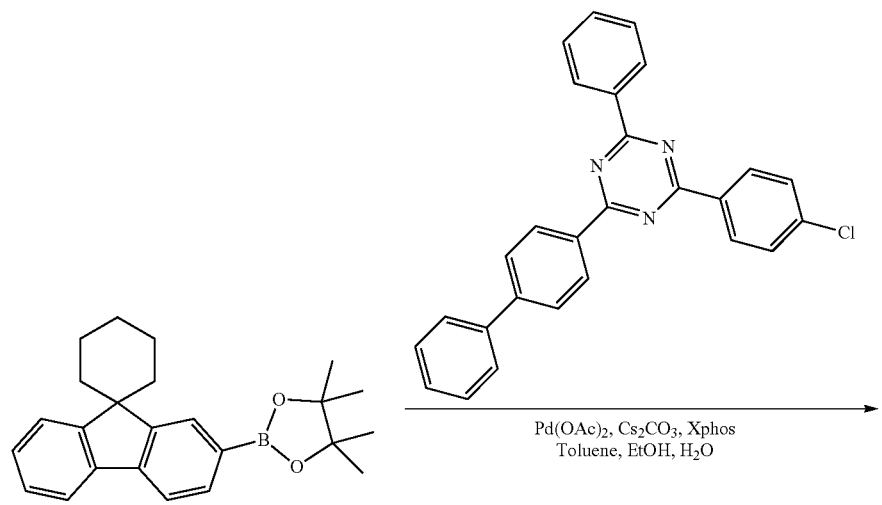
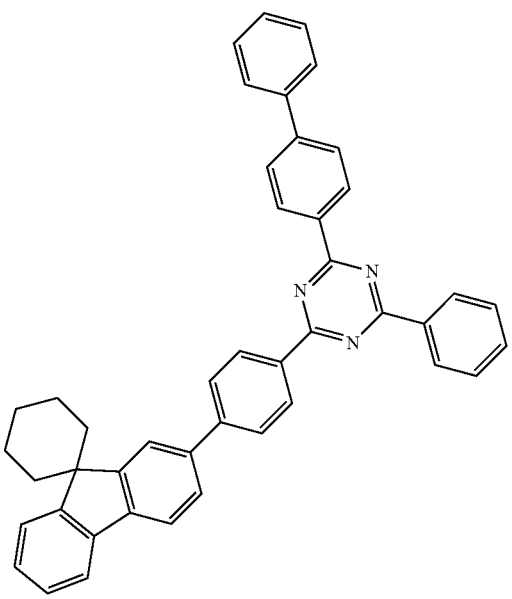
Except that 2-([1,1'-biphenyl]-4-yl)-4-(4-chlorophenyl)-6-phenyl-1,3,5-triazine (5.0 g, 11.9 mmol) was used instead of 2-(3-chlorophenyl)-4,6-diphenyl-1,3,5-triazine, the same procedure as in [Synthesis Example 1] was performed to obtain a target Compound Inv 18 (4.7 g, yield 64%).
[LCMS]: 618.

[Synthesis Example 5] Synthesis of Compound Inv 51

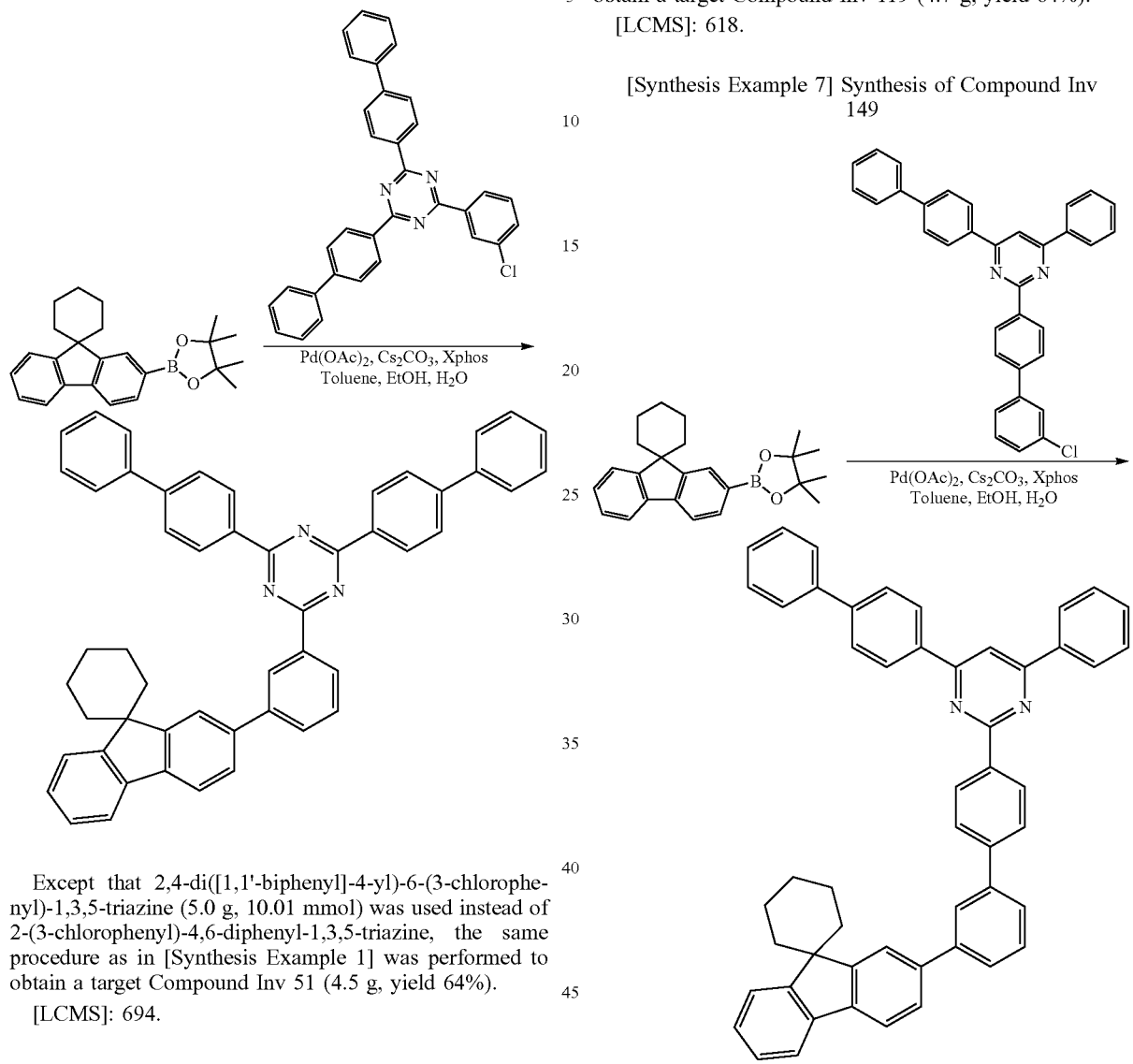

Except that 2,4-di([1,1'-biphenyl]-4-yl)-6-(3-chlorophenyl)-1,3,5-triazine (5.0 g, 10.01 mmol) was used instead of 2-(3-chlorophenyl)-4,6-diphenyl-1,3,5-triazine, the same procedure as in [Synthesis Example 1] was performed to obtain a target Compound Inv 51 (4.5 g, yield 64%).

[LCMS]: 694.

[Synthesis Example 6] Synthesis of Compound Inv 119

Except that 2-(3'-chloro-[1,1'-biphenyl]-3-yl)-4,6-diphenylpyrimidine (5.0 g, 11.9 mmol) was used instead of 2-(3-chlorophenyl)-4,6-diphenyl-1,3,5-triazine, the same procedure as in [Synthesis Example 1] was performed to obtain a target Compound Inv 119 (4.7 g, yield 64%).

[LCMS]: 618.

[Synthesis Example 7] Synthesis of Compound Inv 149

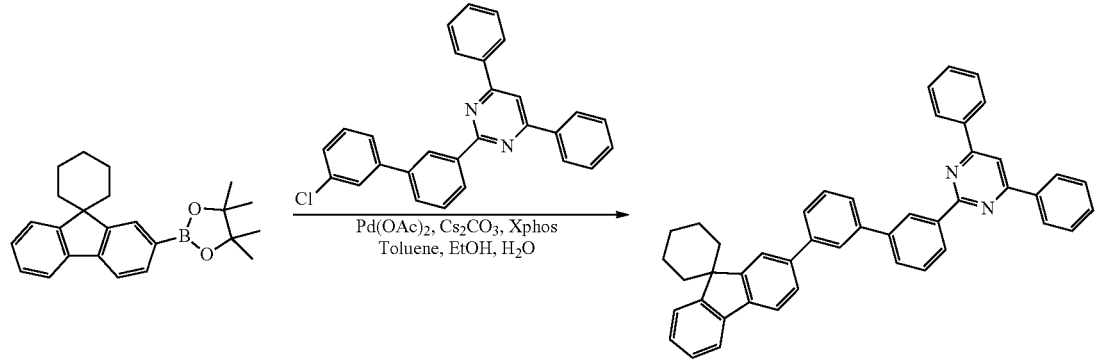 [SMILES: CC1(C)OB(c2ccc3c(c2)C2(CCCCC2)c2ccccc2-3)OC1(C)C ; Clc1cccc(-c2cccc(-c3nc(-c4ccccc4)cc(-c4ccccc4)n3)c2)c1 ; c1ccc(-c2cc(-c3ccccc3)nc(-c3cccc(-c4cccc(-c5ccc6c(c5)C5(CCCCC5)c5ccccc5-6)c4)c3)n2)cc1]

Except that 4-([1,1'-biphenyl]-4-yl)-2-(3'-chloro-[1,1'-biphenyl]-4-yl)-6-phenylpyrimidine (5.0 g, 10.1 mmol) was used instead of 2-(3-chlorophenyl)-4,6-diphenyl-1,3,5-triazine, the same procedure as in [Synthesis Example 1] was performed to obtain a target Compound Inv 149 (4.2 g, yield 60%).

[LCMS]: 694.

[Synthesis Example 8] Synthesis of Compound Inv 162

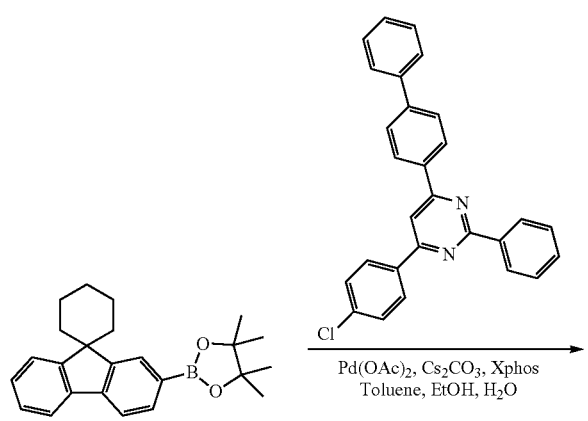

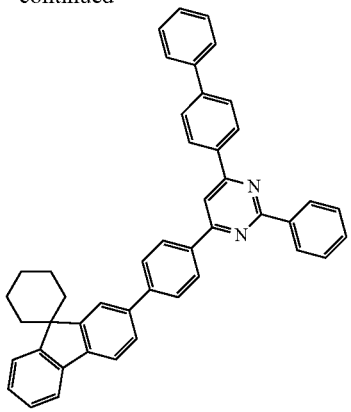

Except that 4-([1,1'-biphenyl]-4-yl)-6-(4-chlorophenyl)-2-phenylpyrimidine (5.0 g, 11.93 mmol) was used instead of 2-(3-chlorophenyl)-4,6-diphenyl-1,3,5-triazine, the same procedure as in [Synthesis Example 1] was performed to obtain a target Compound Inv 162 (4.6 g, yield 62%).

[LCMS]: 618.

[Synthesis Example 9] Synthesis of Compound Inv 167

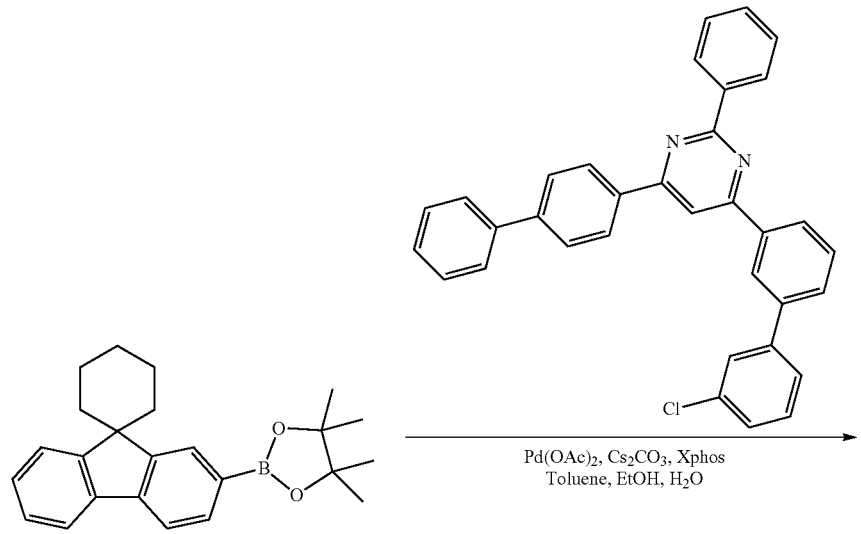

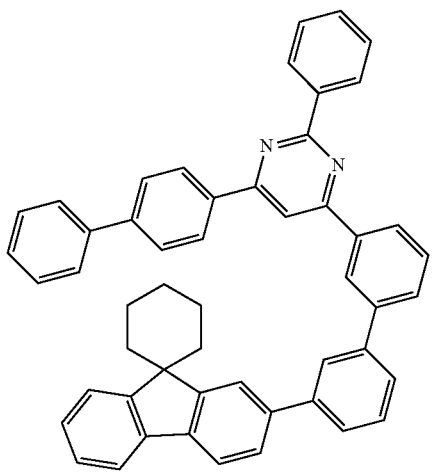
Except that 4-([1,1'-biphenyl]-4-yl)-6-(3'-chloro-[1,1'-biphenyl]-3-yl)-2-phenylpyrimidine (5.0 g, 10.1 mmol) was used instead of 2-(3-chlorophenyl)-4,6-diphenyl-1,3,5-triazine, the same procedure as in [Synthesis Example 1] was performed to obtain a target Compound Inv 167 (4.3 g, yield 61%).
[LCMS]: 694.
[Synthesis Example 10] Synthesis of Compound Inv 183
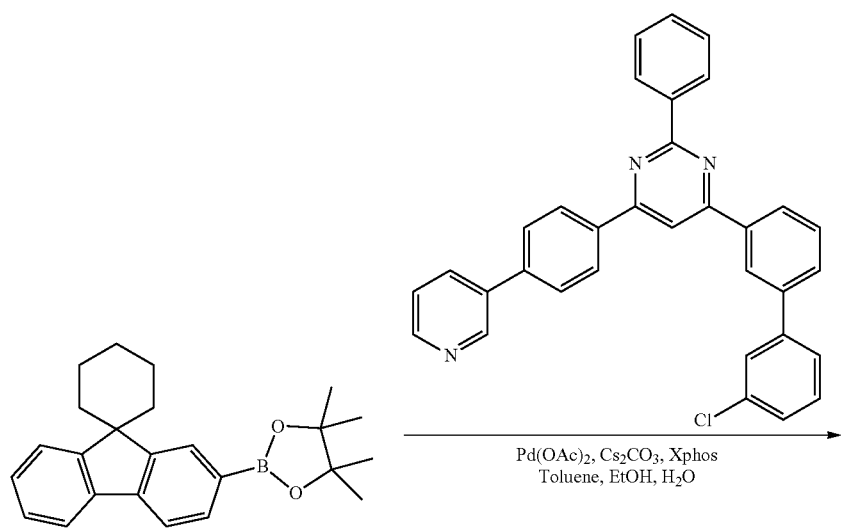

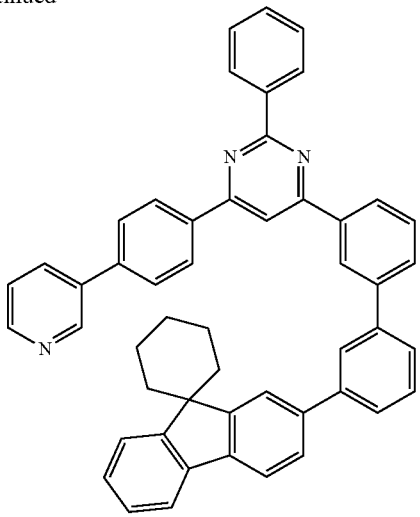

Except that 4-(3'-chloro-[1,1'-biphenyl]-3-yl)-2-phenyl-6-(4-(pyridin-3-yl)phenyl)pyrimidine (5.0 g, 10.1 mmol) was used instead of 2-(3-chlorophenyl)-4,6-diphenyl-1,3,5-triazine, the same procedure as in [Synthesis Example 1] was performed to obtain a target Compound Inv 183 (4.3 g, yield 61%).

[LCMS]: 695.

[Synthesis Example 11] Synthesis of Compound Inv 196

[Synthesis Example 12] Synthesis of Compound Inv 199

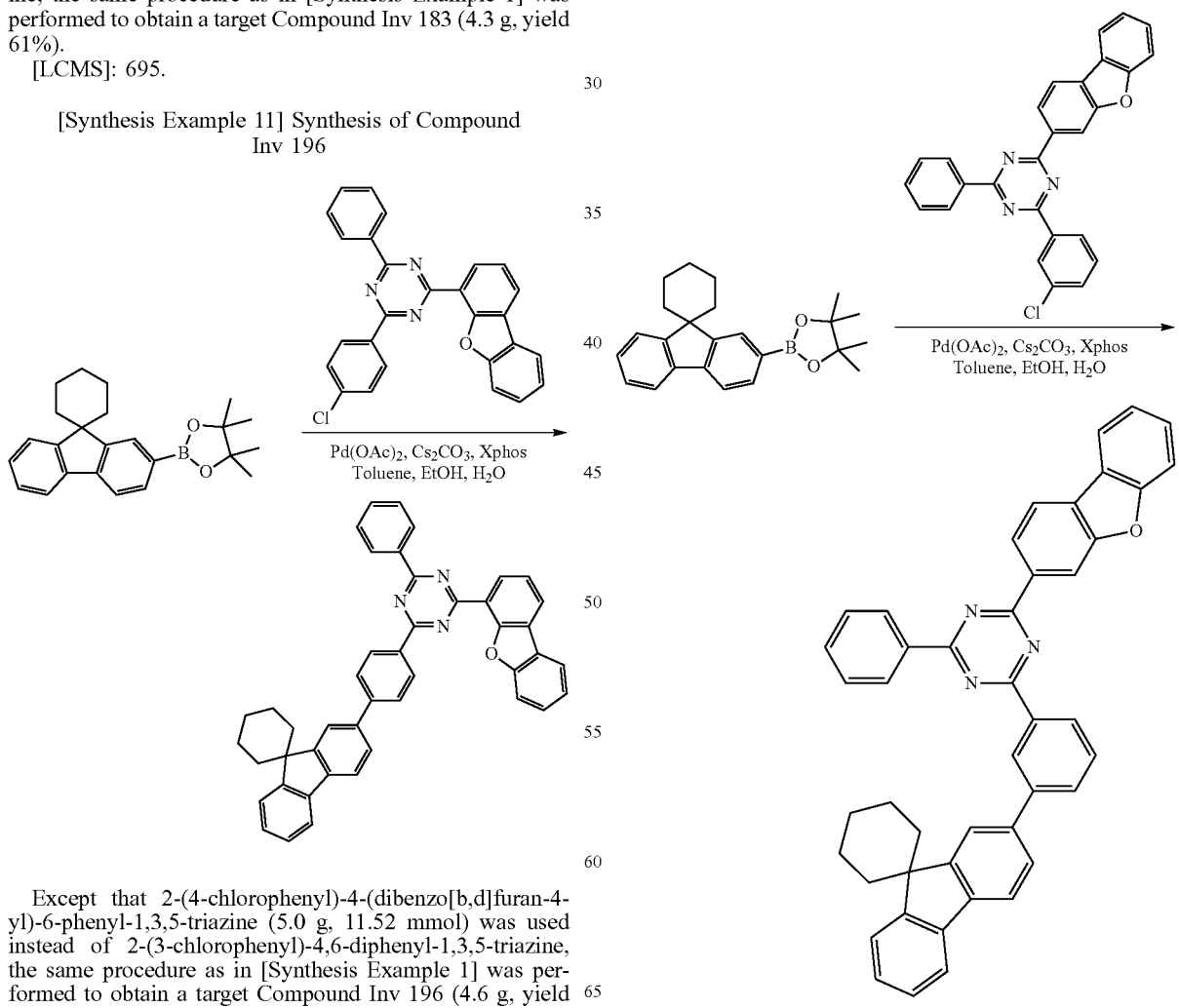

Except that 2-(4-chlorophenyl)-4-(dibenzo[b,d]furan-4-yl)-6-phenyl-1,3,5-triazine (5.0 g, 11.52 mmol) was used instead of 2-(3-chlorophenyl)-4,6-diphenyl-1,3,5-triazine, the same procedure as in [Synthesis Example 1] was performed to obtain a target Compound Inv 196 (4.6 g, yield 63%).

[LCMS]: 633.

Except that 2-(3-chlorophenyl)-4-(dibenzo[b,d]furan-3-yl)-6-phenyl-1,3,5-triazine (5.0 g, 11.52 mmol) was used instead of 2-(3-chlorophenyl)-4,6-diphenyl-1,3,5-triazine, the same procedure as in [Synthesis Example 1] was performed to obtain a target Compound Inv 199 (4.4 g, yield 60%).
[LCMS]: 633.
[Synthesis Example 13] Synthesis of Compound Inv 214
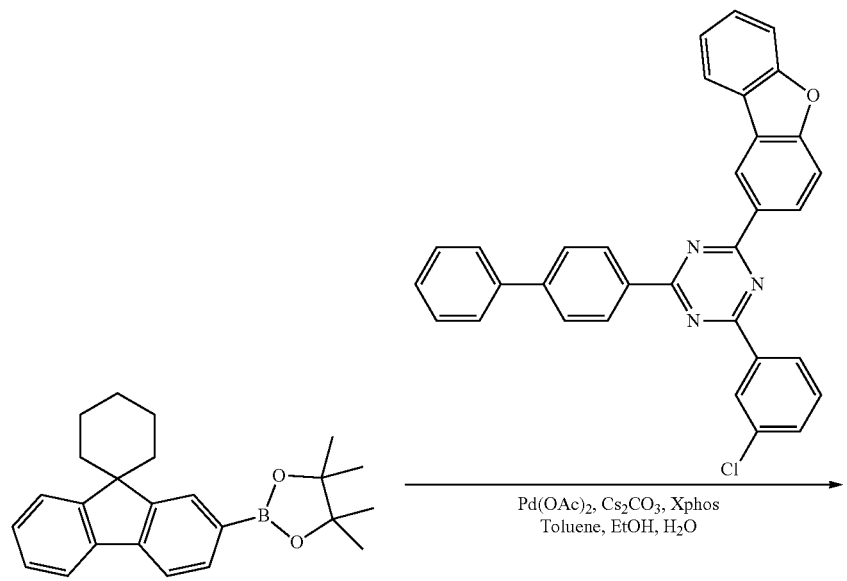
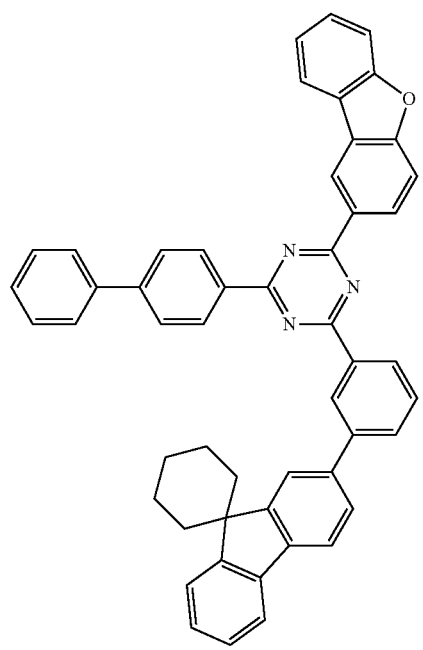

Except that 2-([1,1'-biphenyl]-4-yl)-4-(3-chlorophenyl)-6-(dibenzo[b,d]furan-2-yl)-1,3,5-triazine (5.0 g, 98.04 mmol) was used instead of 2-(3-chlorophenyl)-4,6-diphenyl-1,3,5-triazine, the same procedure as in [Synthesis Example 1] was performed to obtain a target Compound Inv 214 (4.5 g, yield 64%).

[LCMS]: 709.

[Synthesis Example 14] Synthesis of Compound Inv 228

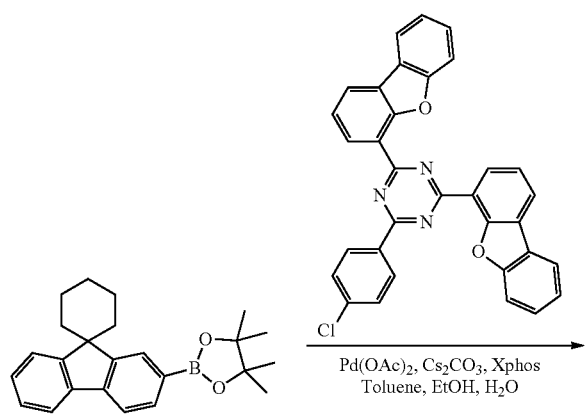

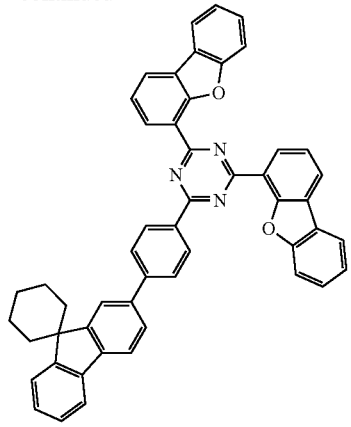

Except that 2-(4-chlorophenyl)-4,6-bis(dibenzo[b,d]furan-4-yl)-1,3,5-triazine (5.0 g, 9.54 mmol) was used instead of 2-(3-chlorophenyl)-4,6-diphenyl-1,3,5-triazine, the same procedure as in [Synthesis Example 1] was performed to obtain a target Compound Inv 228 (4.2 g, yield 60%).

[LCMS]: 723.

[Synthesis Example 15] Synthesis of Compound Inv 231

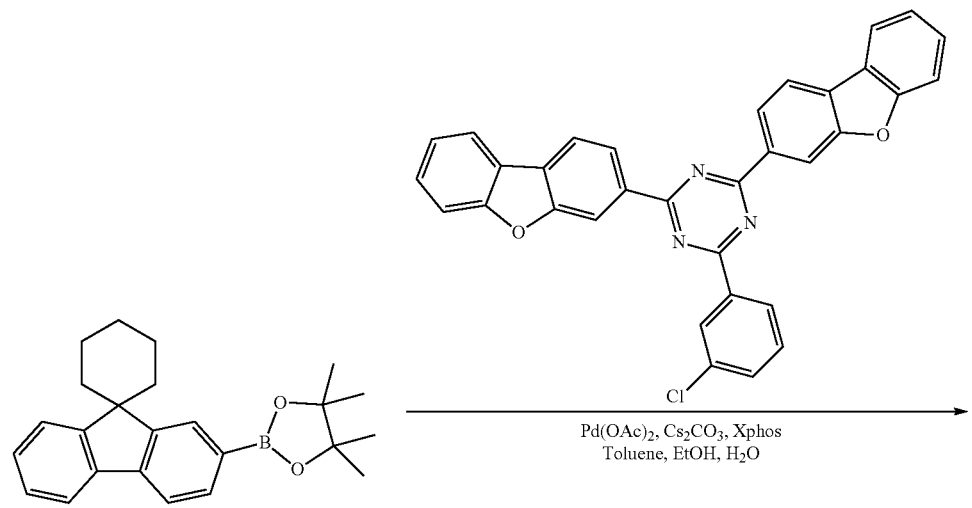

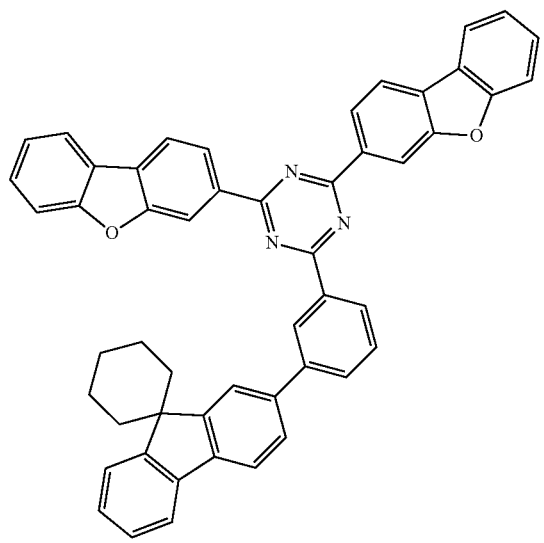
Except that 2-(3-chlorophenyl)-4,6-bis(dibenzo[b,d]furan-3-yl)-1,3,5-triazine (5.0 g, 10.01 mmol) was used instead of 2-(3-chlorophenyl)-4,6-diphenyl-1,3,5-triazine, the same procedure as in [Synthesis Example 1] was performed to obtain a Inv 231 (4.3 g, yield 62%).
[LCMS]: 723.
[Synthesis Example 16] Synthesis of Compound Inv 241
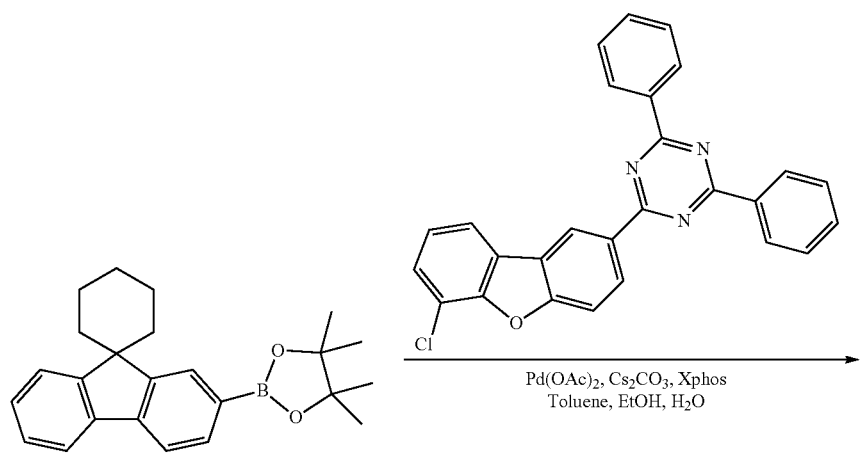

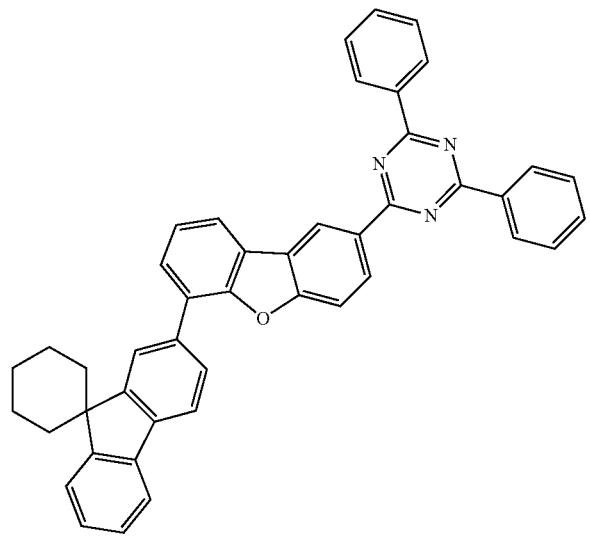

Except that 2-(6-chlorodibenzo[b,d]furan-2-yl)-4,6-diphenyl-1,3,5-triazine (5.0 g, 11.52 mmol) was used instead of 2-(3-chlorophenyl)-4,6-diphenyl-1,3,5-triazine, the same procedure as in [Synthesis Example 1] was performed to obtain a target Compound Inv 241 (4.5 g, yield 61%).

[LCMS]: 633.

[Synthesis Example 17] Synthesis of Compound Inv 247

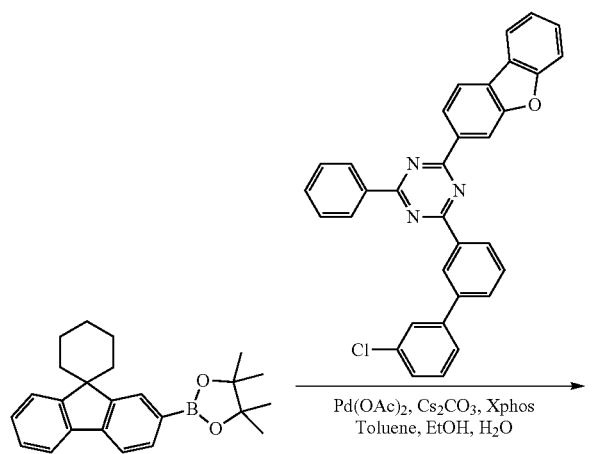

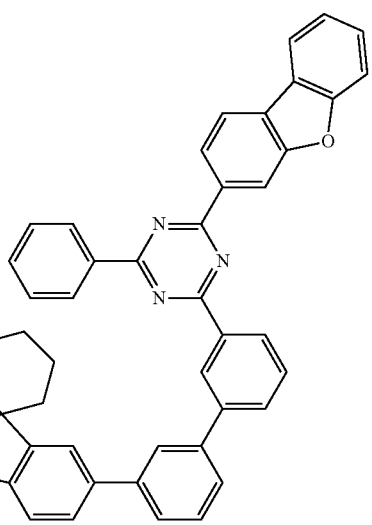

Except that 2-(3'-chloro-[1,1'-biphenyl]-3-yl)-4-(dibenzo[b,d]furan-3-yl)-6-phenyl-1,3,5-triazine (5.0 g, 9.80 mmol) was used instead of 2-(3-chlorophenyl)-4,6-diphenyl-1,3,5-triazine, the same procedure as in [Synthesis Example 1] was performed to obtain a target Compound Inv 247 (4.4 g, yield 63%).

[LCMS]: 709.

[Synthesis Example 18] Synthesis of Compound Inv 263
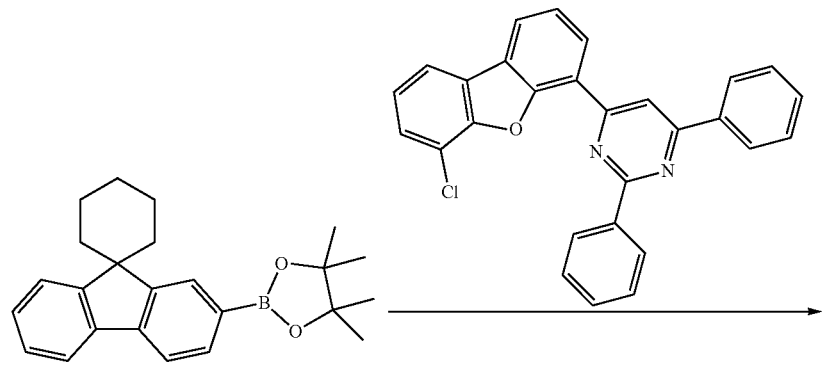
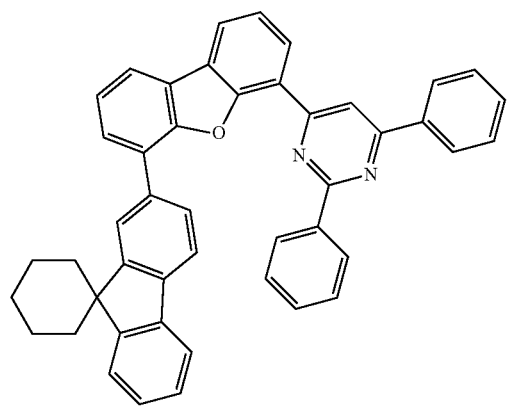
Except that 4-(6-chlorodibenzo[b,d]furan-4-yl)-2,6-diphenylpyrimidine (5.0 g, 11.54 mmol) was used instead of 2-(3-chlorophenyl)-4,6-diphenyl-1,3,5-triazine, the same procedure as in [Synthesis Example 1] was performed to obtain a target Compound Inv 263 (4.7 g, yield 64%).
[LCMS]: 632.
[Synthesis Example 19] Synthesis of Compound Inv 275
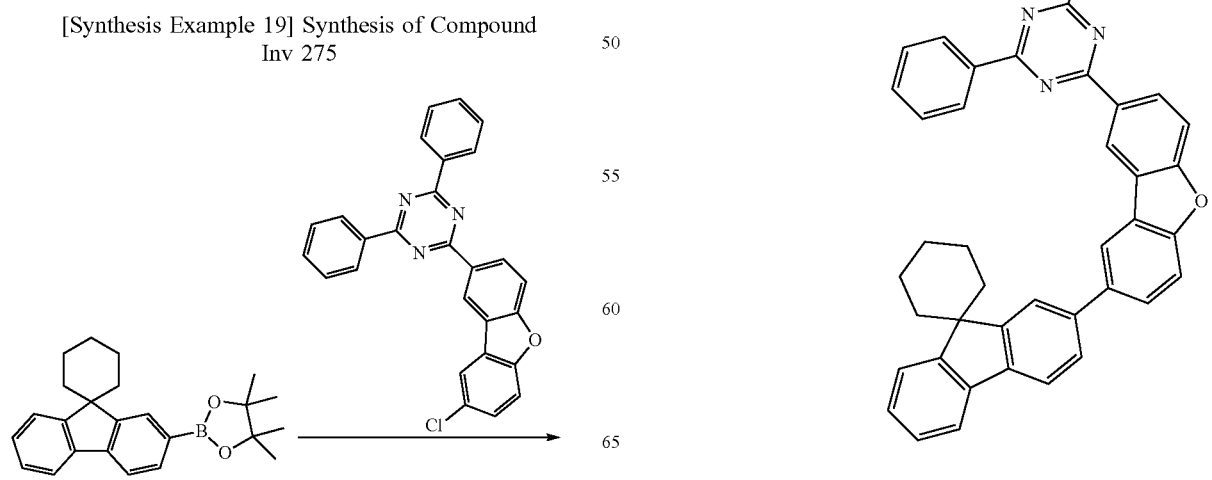
-continued Except that 2-(8-chlorodibenzo[b,d]furan-2-yl)-4,6-diphenyl-1,3,5-triazine (5.0 g, 11.54 mmol) was used instead of 2-(3-chlorophenyl)-4,6-diphenyl-1,3,5-triazine, the same procedure as in [Synthesis Example 1] was performed to obtain a target Compound Inv 275 (4.3 g, yield 59%).

[LCMS]: 632.

[Synthesis Example 20] Synthesis of Compound Inv 287

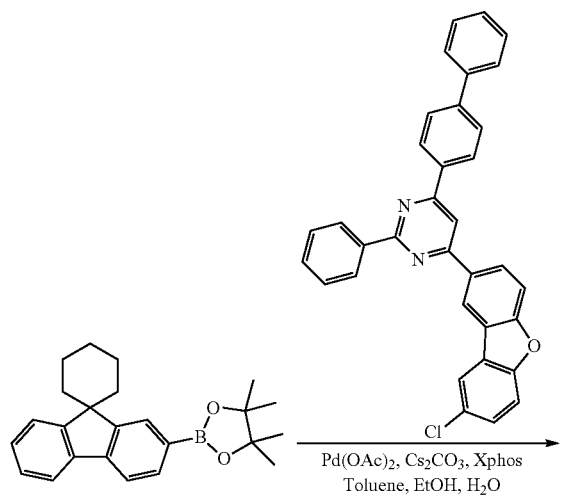

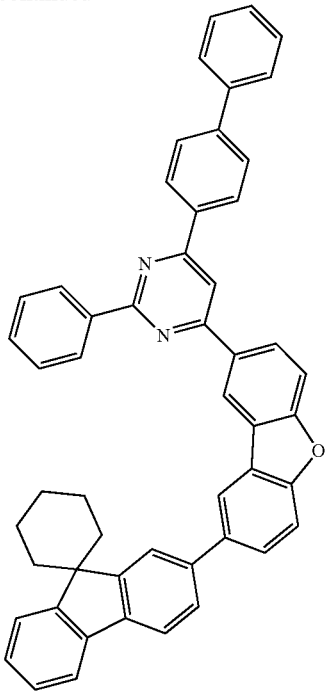

Except that 4-([1,1'-biphenyl]-4-yl)-6-(8-chlorodibenzo[b,d]furan-2-yl)-2-phenylpyrimidine (5.0 g, 9.82 mmol) was used instead of 2-(3-chlorophenyl)-4,6-diphenyl-1,3,5-triazine, the same procedure as in [Synthesis Example 1] was performed to obtain a target Compound Inv 287 (4.3 g, yield 62%).

[LCMS]: 708.

[Synthesis Example 21] Synthesis of Compound Inv 293

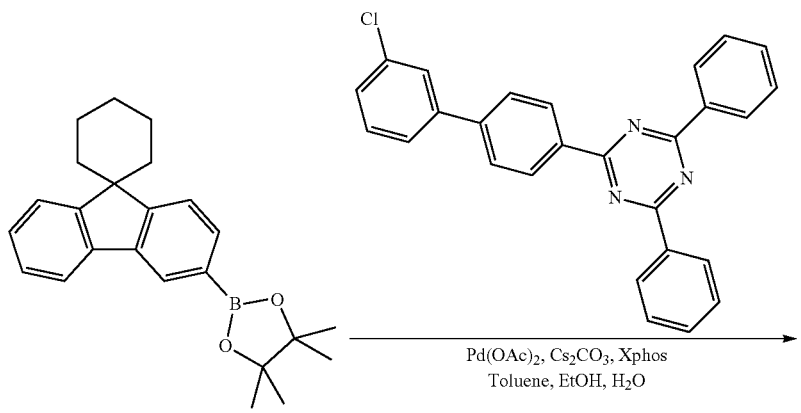

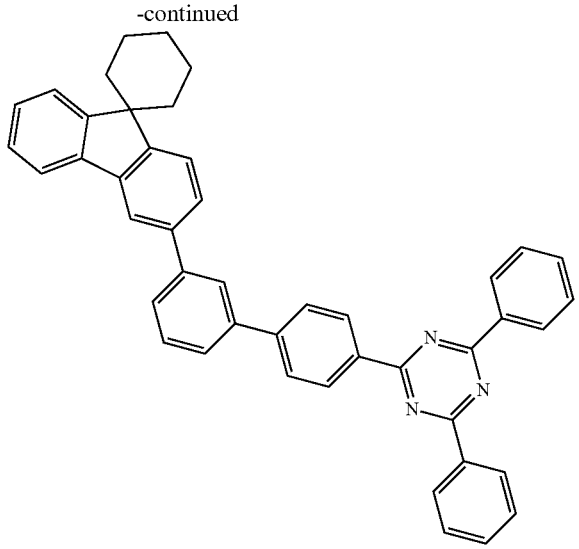
Except that Core 2 (5 g, 9.08 mmol) of [Preparation Example 2] was used instead of Core 1 and that 2-(3'-chloro-[1,1'-biphenyl]-4-yl)-4,6-diphenyl-1,3,5-triazine (4.57 g, 11.90 mmol) was used instead of 2-(3-chlorophenyl)-4,6-diphenyl-1,3,5-triazine, the same procedure as in [Synthesis Example 1] was performed to obtain a target Compound Inv 293 (4.6 g, yield 62%).
[LCMS]: 618.
[Synthesis Example 22] Synthesis of Compound Inv 299
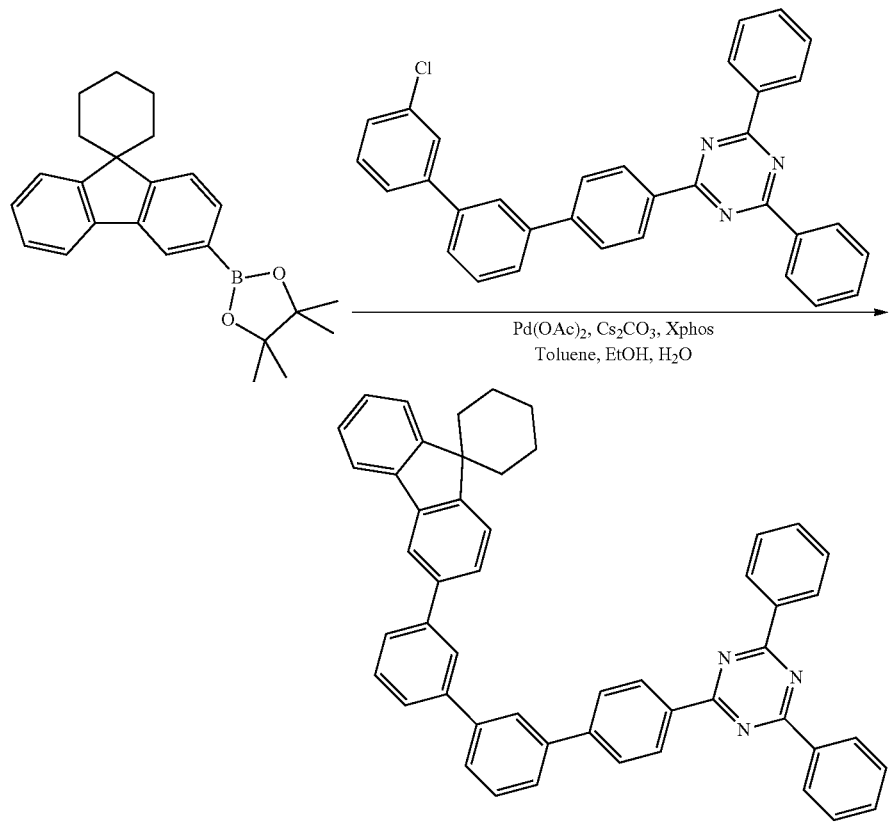

Except that 4-([1,1'-biphenyl]-4-yl)-6-(8-chlorodibenzo[b,d]furan-2-yl)-2-phenylpyrimidine (5.0 g, 10.08 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 299 (4.2 g, yield 60%).
[LCMS]: 694.
[Synthesis Example 23] Synthesis of Compound Inv 310
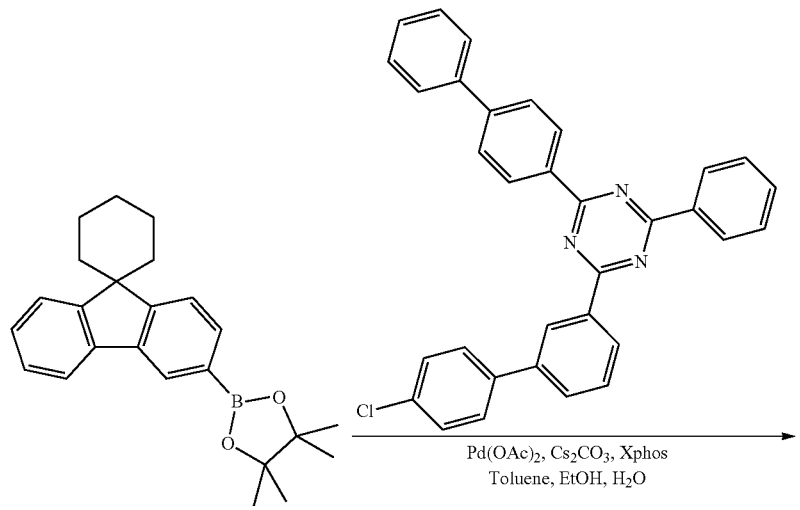
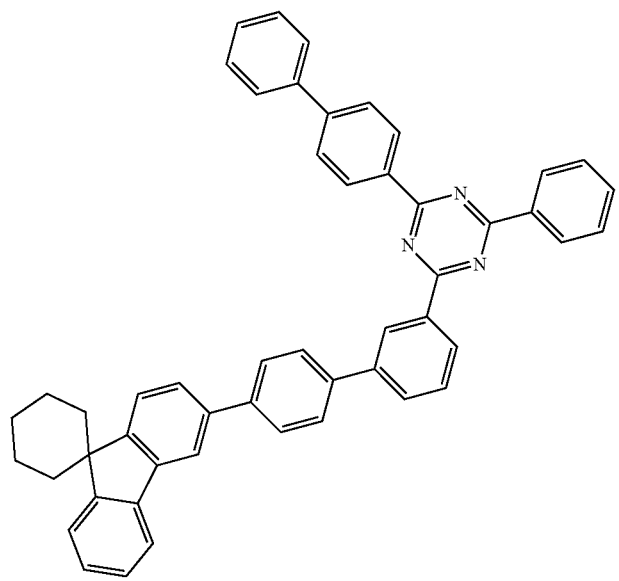

Except that 2-([1,1'-biphenyl]-4-yl)-4-(4'-chloro-[1,1'-biphenyl]-3-yl)-6-phenyl-1,3,5-triazine (5.0 g, 10.08 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 310 (4.3 g, yield 61%).

[LCMS]: 694.

[Synthesis Example 24] Synthesis of Compound Inv 322

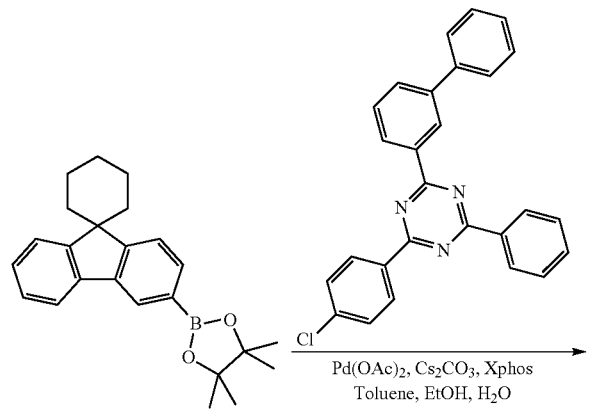

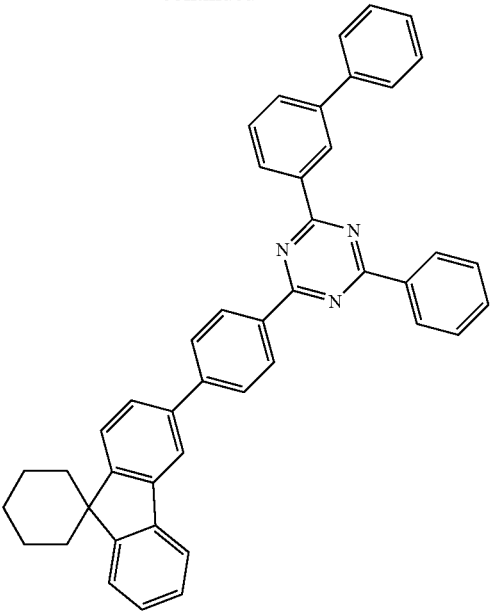

Except that 2-([1,1'-biphenyl]-3-yl)-4-(4-chlorophenyl)-6-phenyl-1,3,5-triazine (5.0 g, 11.95 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 322 (4.6 g, yield 62%).

[LCMS]: 618.

[Synthesis Example 25] Synthesis of Compound Inv 350

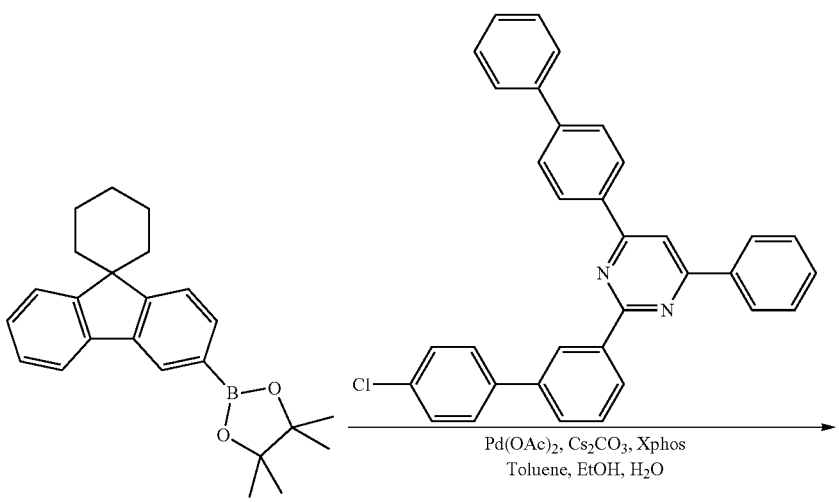

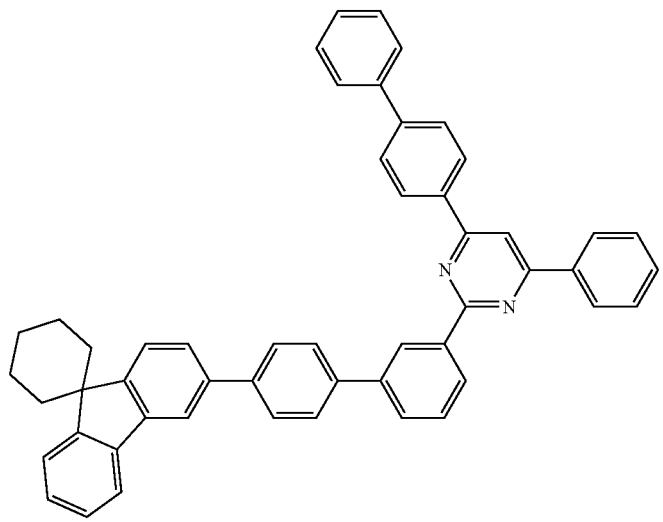
Except that 4-([1,1'-biphenyl]-4-yl)-6-(8-chlorodibenzo[b,d]furan-2-yl)-2-phenylpyrimidine (5.0 g, 10.1 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 350 (4.4 g, yield 62%).
[LCMS]: 694.
[Synthesis Example 26] Synthesis of Compound Inv 356
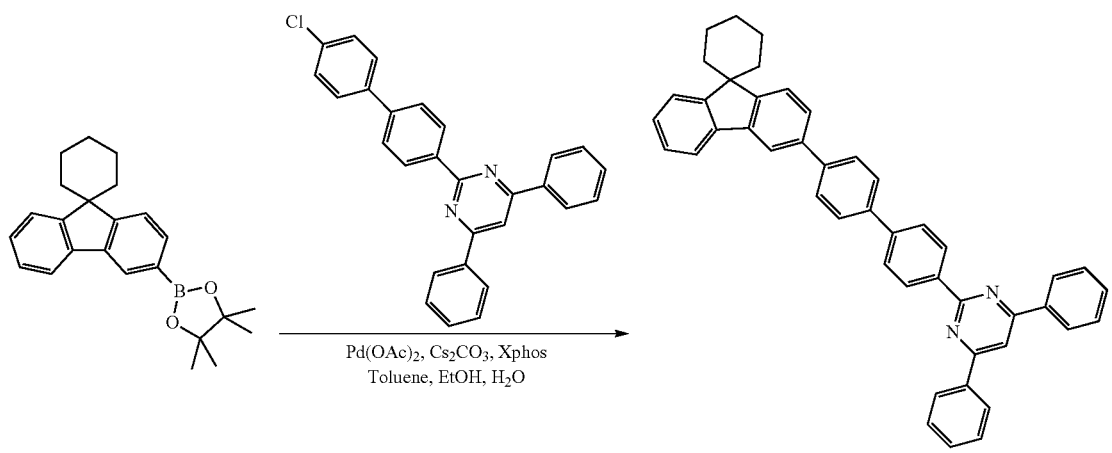 [SMILES: CC1(C)OB(c2ccc3c(c2)-c2ccccc2C32CCCCC2)OC1(C)C ; Clc1ccc(-c2ccc(-c3nc(-c4ccccc4)cc(-c4ccccc4)n3)cc2)cc1 ; c1ccc(-c2cc(-c3ccccc3)nc(-c3ccc(-c4ccc(-c5ccc6c(c5)-c5ccccc5C65CCCCC5)cc4)cc3)n2)cc1]

417

Except that 2-(4'-chloro-[1,1'-biphenyl]-4-yl)-4,6-diphenylpyrimidine (5.0 g, 11.93 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 356 (4.7 g, yield 63%).

[LCMS]: 617.

[Synthesis Example 27] Synthesis of Compound Inv 363

418

[Synthesis Example 28] Synthesis of Compound Inv 374

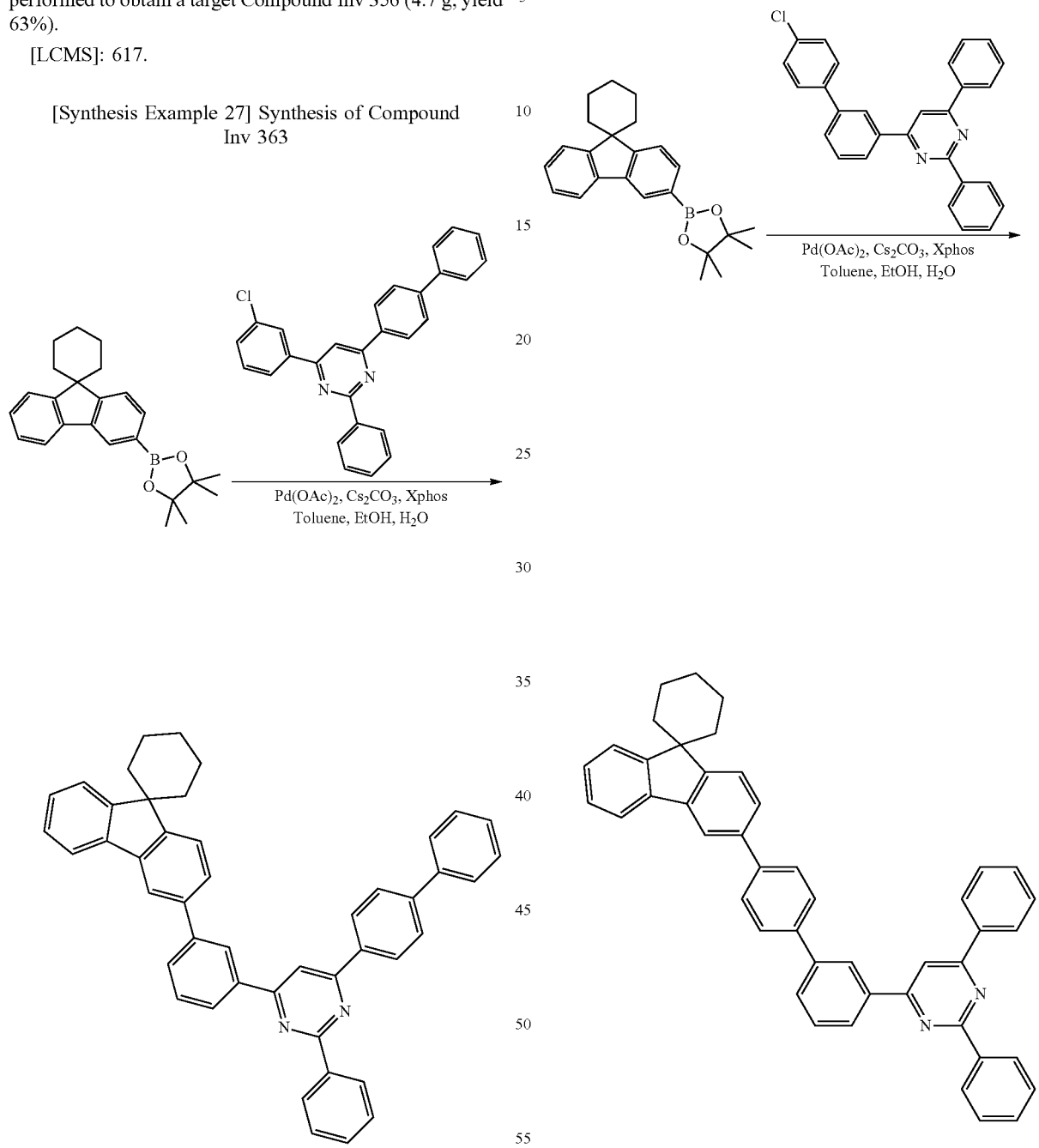

Except that 4-([1,1'-biphenyl]-4-yl)-6-(3-chlorophenyl)-2-phenylpyrimidine (5.0 g, 11.93 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 363 (4.5 g, yield 61%).

[LCMS]: 617.

Except that 4-(4'-chloro-[1,1'-biphenyl]-3-yl)-2,6-diphenylpyrimidine (5.0 g, 11.93 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 374 (4.2 g, yield 57%).

[LCMS]: 617.

[Synthesis Example 29] Synthesis of Compound Inv 383

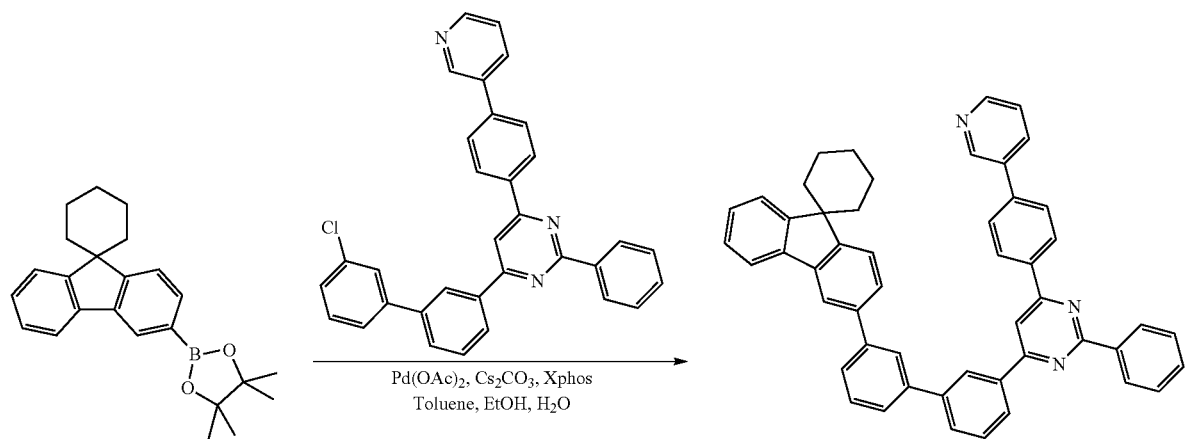 [SMILES: CC1(C)OB(c2ccc3c(c2)-c2ccccc2C32CCCCC2)OC1(C)C ; Clc1cccc(-c2cccc(-c3cc(-c4ccc(-c5cccnc5)cc4)nc(-c4ccccc4)n3)c2)c1 ; c1ccc(-c2nc(-c3ccc(-c4cccnc4)cc3)cc(-c3cccc(-c4cccc(-c5ccc6c(c5)-c5ccccc5C65CCCCC5)c4)c3)n2)cc1]

Except that 4-(3'-chloro-[1,1'-biphenyl]-3-yl)-2-phenyl-6-(4-(pyridin-3-yl)phenyl)pyrimidine (5.0 g, 10.08 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 383 (4.4 g, yield 62%).

[LCMS]: 694.

[Synthesis Example 30] Synthesis of Compound Inv 390

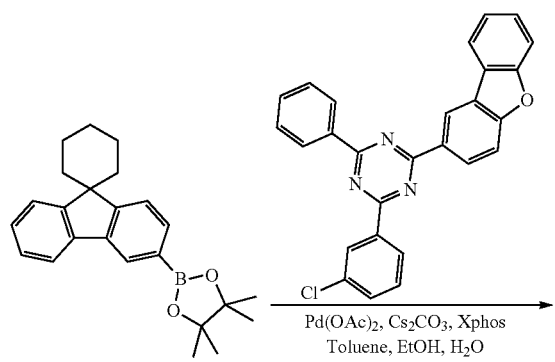

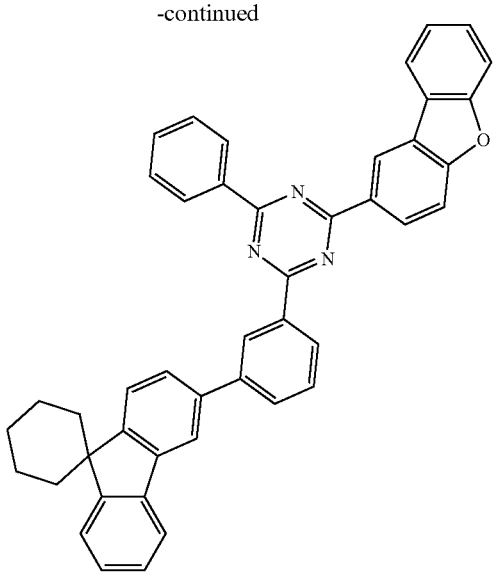

Except that 2-(3'-chloro-[1,1'-biphenyl]-4-yl)-4,6-diphenyl-1,3,5-triazine 2-(3-chlorophenyl)-4-(dibenzo[b,d]furan-2-yl)-6-phenyl-1,3,5-triazine (5.0 g, 11.52 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 390 (4.4 g, yield 60%).

[LCMS]: 632.

[Synthesis Example 31] Synthesis of Compound Inv 400
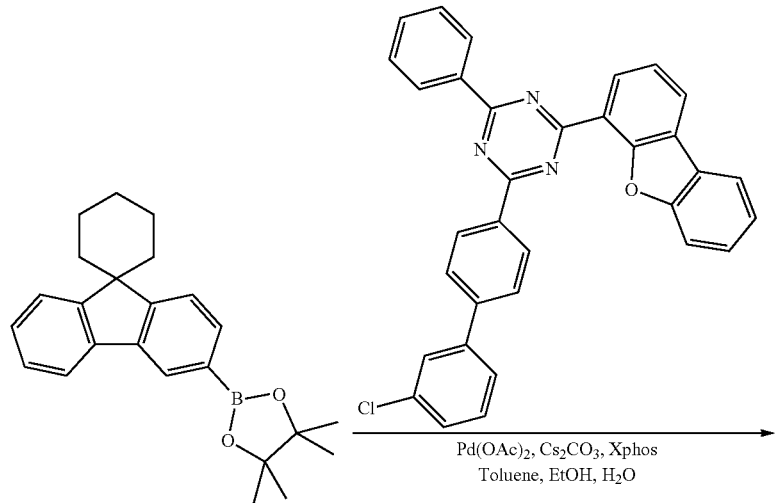
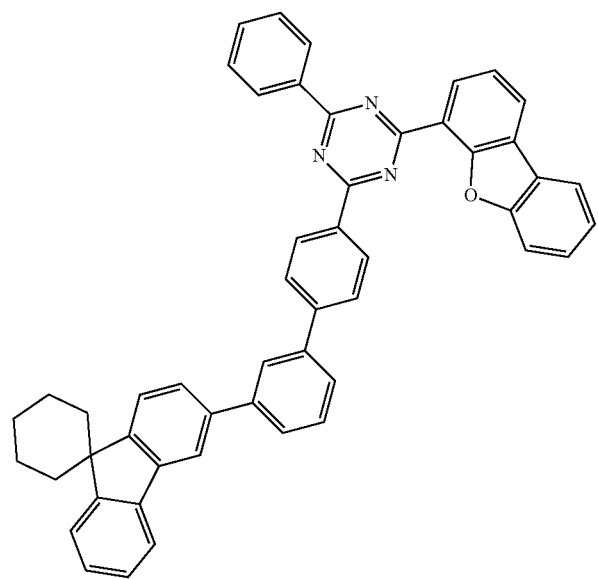

Except that 2-(3'-chloro-[1,1'-biphenyl]-4-yl)-4-(dibenzo[b,d]furan-4-yl)-6-phenyl-1,3,5-triazine (5.0 g, 9.80 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 400 (4.2 g, yield 60%).
[LCMS]: 708.
[Synthesis Example 32] Synthesis of Compound Inv 404
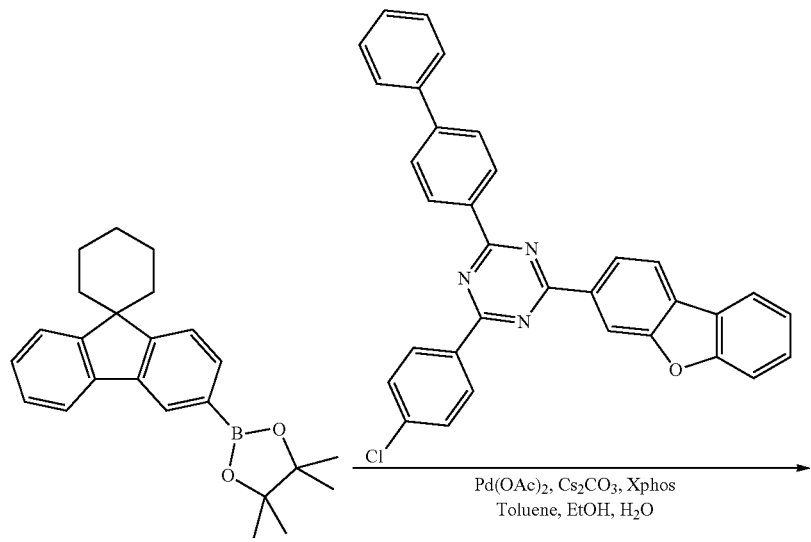
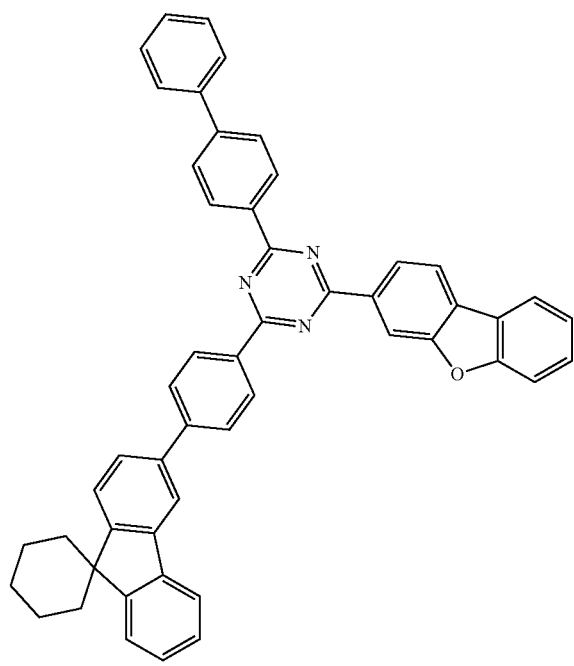

Except that 2-([1,1'-biphenyl]-4-yl)-4-(4-chlorophenyl)-6-(dibenzo[b,d]furan-3-yl)-1,3,5-triazine (5.0 g, 9.80 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 404 (4.5 g, yield 64%).
[LCMS]: 708.
[Synthesis Example 33] Synthesis of Compound Inv 406
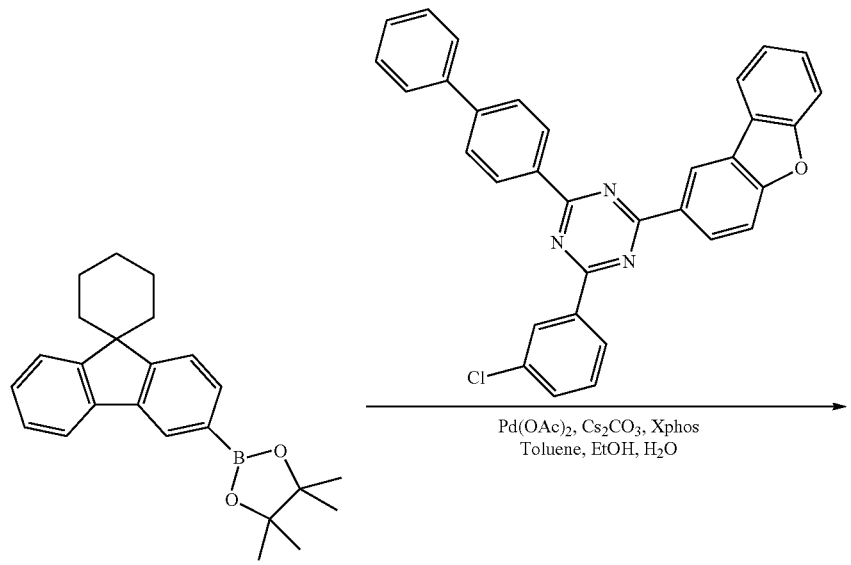
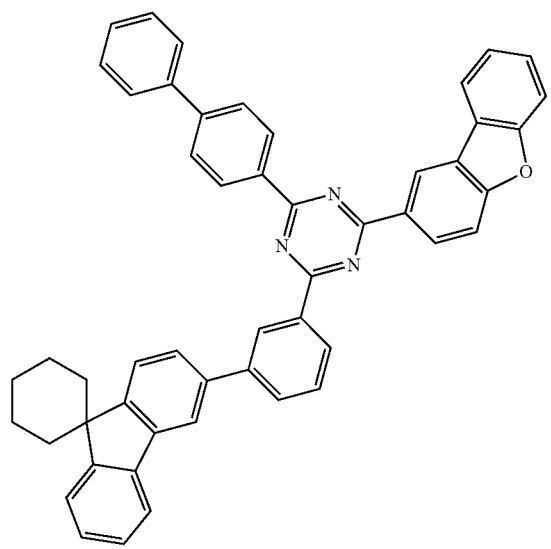

Except that 2-([1,1'-biphenyl]-4-yl)-4-(3-chlorophenyl)-6-(dibenzo[b,d]furan-2-yl)-1,3,5-triazine (5.0 g, 9.80 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 406 (4.4 g, yield 63%).
[LCMS]: 708.
[Synthesis Example 34] Synthesis of Compound Inv 422
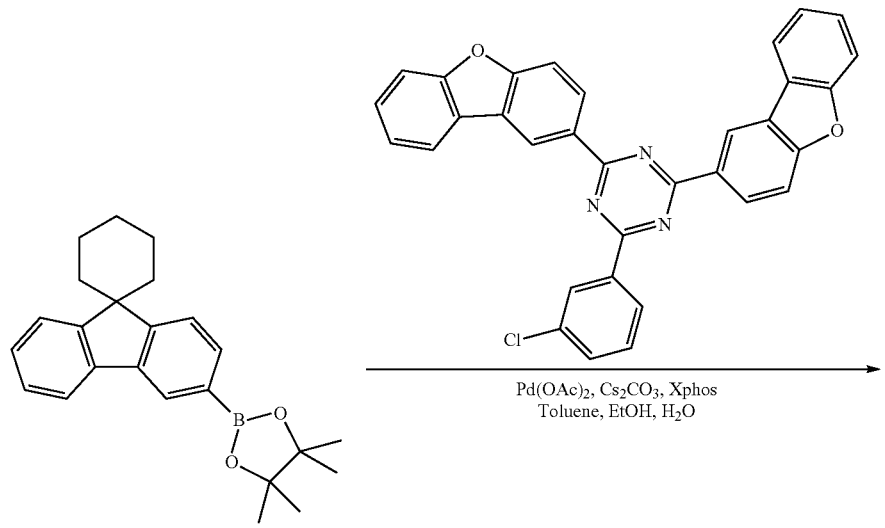
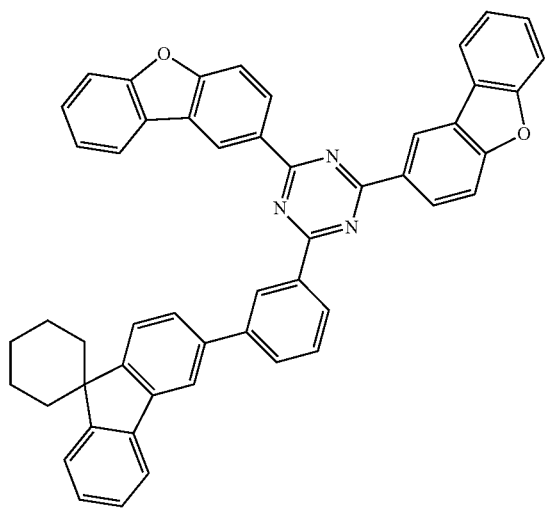

Except that 2-(3-chlorophenyl)-4,6-bis(dibenzo[b,d]furan-2-yl)-1,3,5-triazine (5.0 g, 9.54 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 422 (4.3 g, yield 62%).
[LCMS]: 722.
[Synthesis Example 35] Synthesis of Compound Inv 423
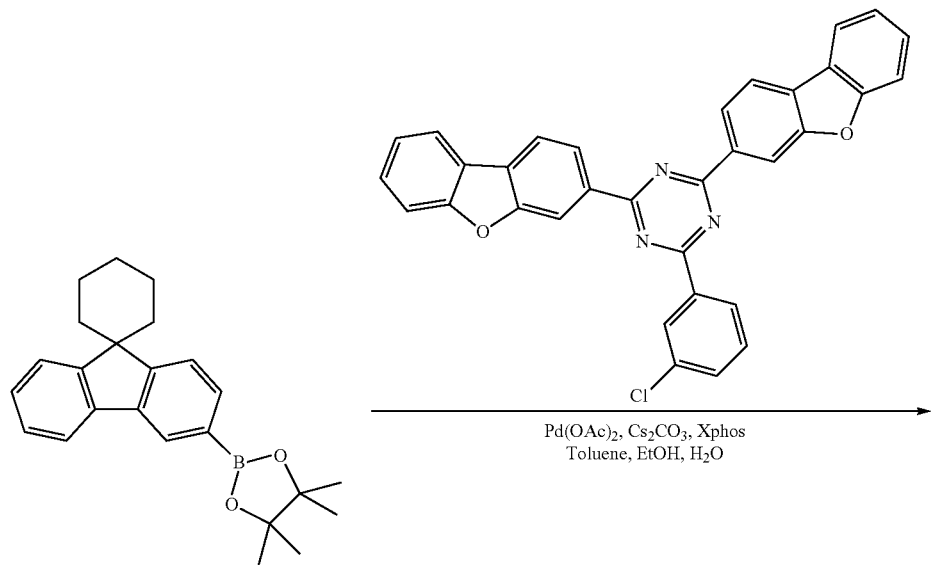
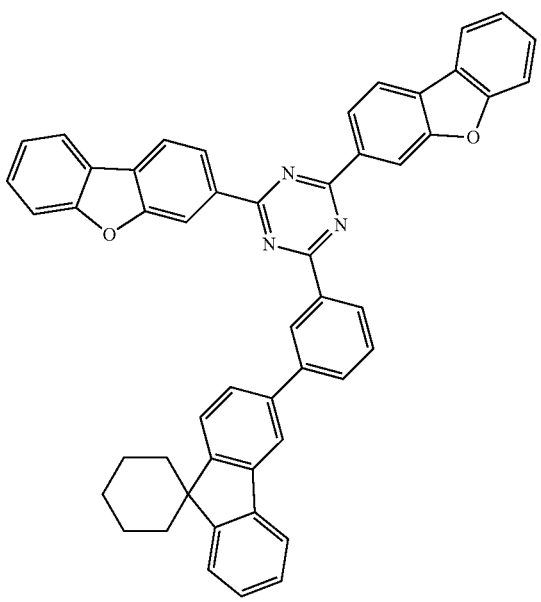

Except that 2-(3-chlorophenyl)-4,6-bis(dibenzo[b,d]furan-3-yl)-1,3,5-triazine (5.0 g, 9.54 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 423 (4.6 g, yield 66%).
[LCMS]: 722.
[Synthesis Example 36] Synthesis of Compound Inv 437
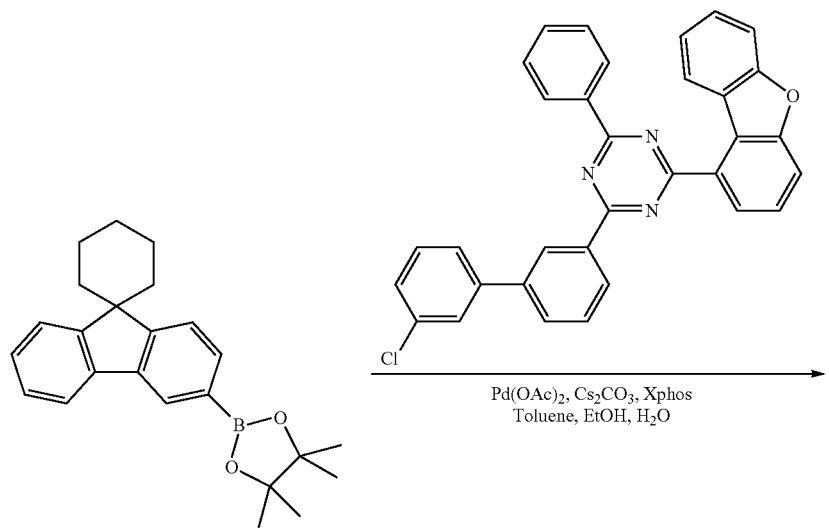
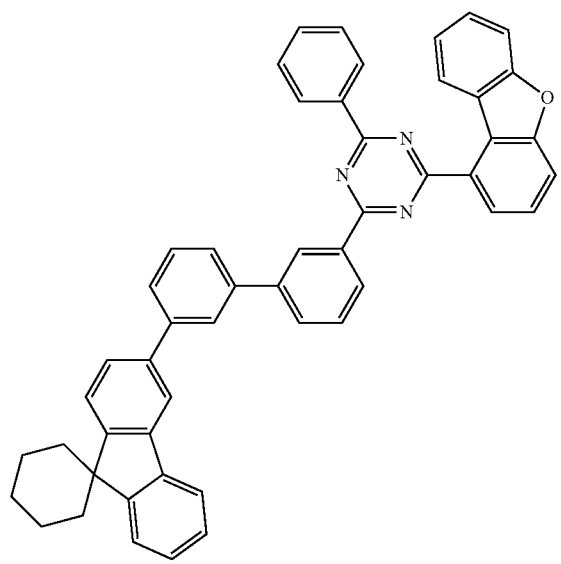

Except that 2-(3'-chloro-[1,1'-biphenyl]-3-yl)-4-(dibenzo[b,d]furan-1-yl)-6-phenyl-1,3,5-triazine (5.0 g, 9.80 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 437 (4.5 g, yield 64%).
[LCMS]: 708.
[Synthesis Example 37] Synthesis of Compound Inv 439
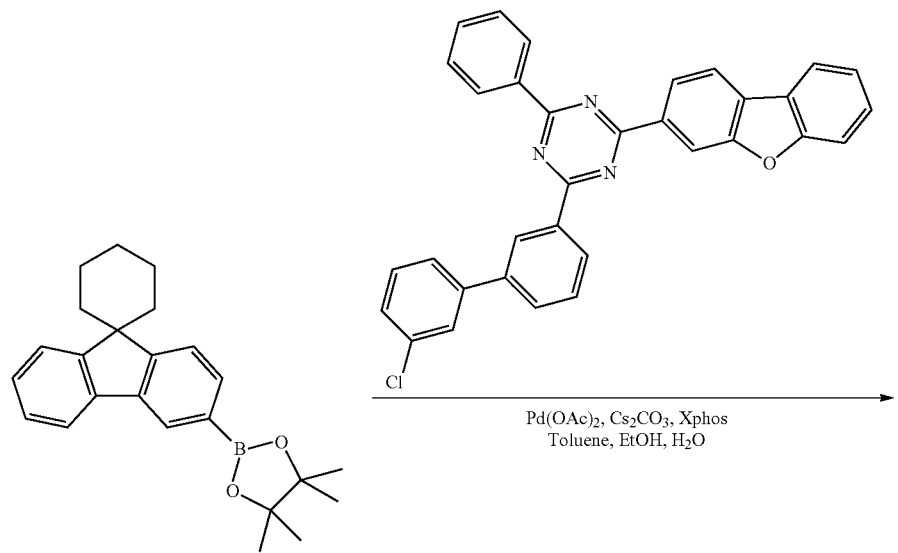
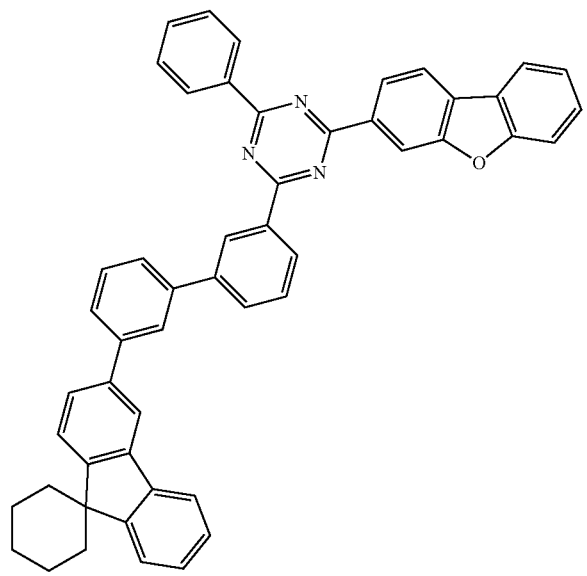

Except that 2-(3'-chloro-[1,1'-biphenyl]-3-yl)-4-(dibenzo[b,d]furan-3-yl)-6-phenyl-1,3,5-triazine (5.0 g, 9.80 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 439 (4.3 g, yield 61%).
[LCMS]: 708.
[Synthesis Example 38] Synthesis of Compound Inv 457
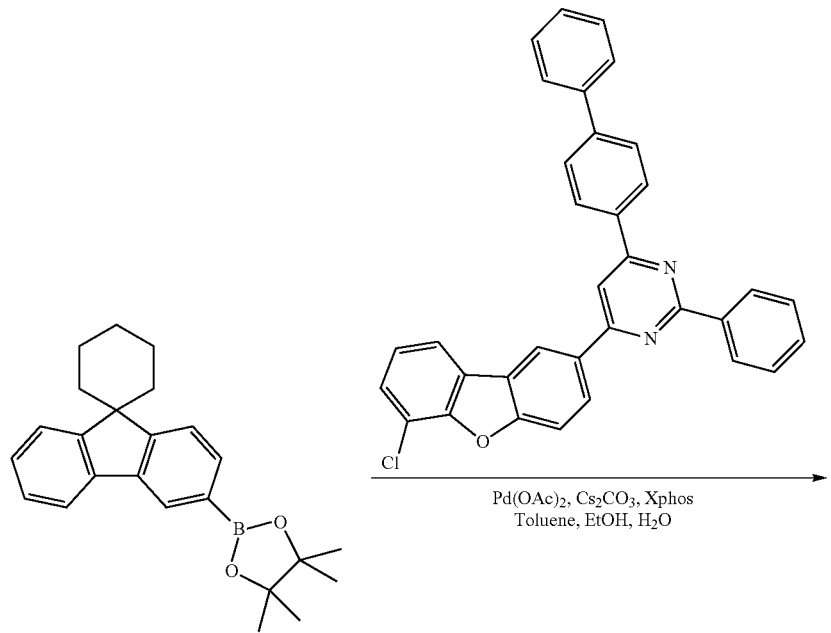
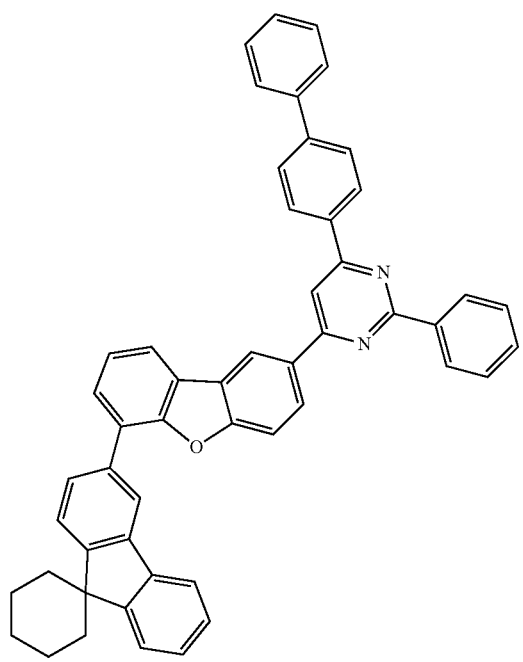

Except that 4-([1,1'-biphenyl]-4-yl)-6-(6-chlorodibenzo[b,d]furan-2-yl)-2-phenylpyrimidine (5.0 g, 9.82 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 457 (4.3 g, yield 61%).

[LCMS]: 707.

[Synthesis Example 39] Synthesis of Compound Inv 475

[Synthesis Example 40] Synthesis of Compound Inv 479

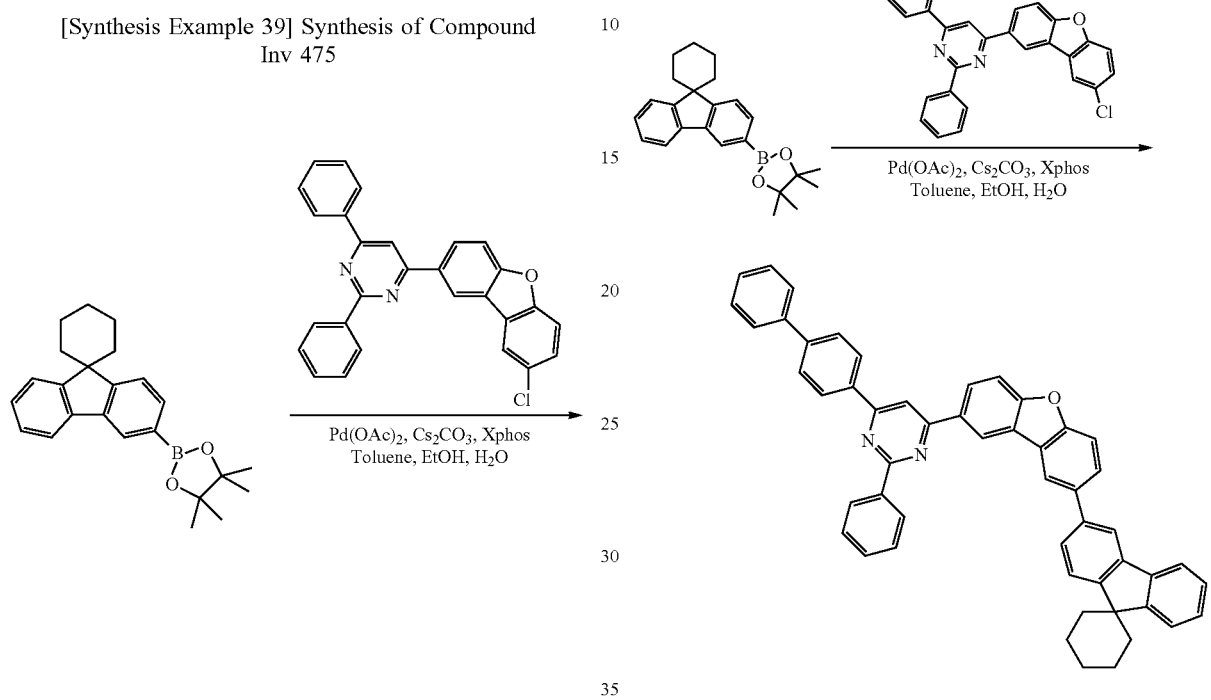

Except that 4-([1,1'-biphenyl]-4-yl)-6-(8-chlorodibenzo[b,d]furan-2-yl)-2-phenylpyrimidine (5.0 g, 9.82 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 479 (4.5 g, yield 64%).

[LCMS]: 707.

[Synthesis Example 41] Synthesis of Compound Inv 483

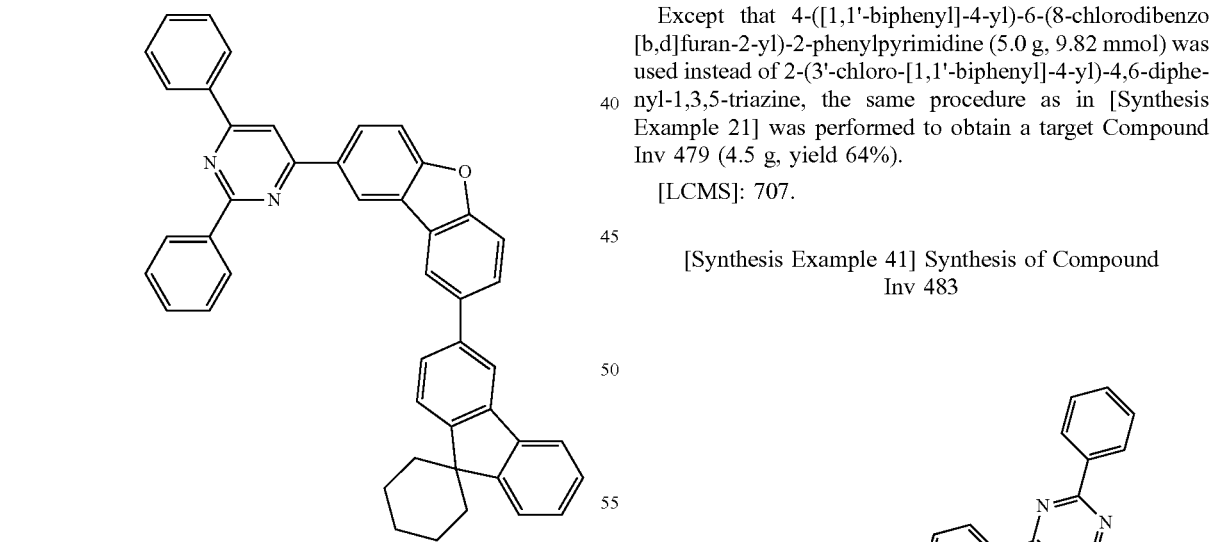

Except that 4-(8-chlorodibenzo[b,d]furan-2-yl)-2,6-diphenylpyrimidine (5.0 g, 11.54 mmol) was used instead of 2-(3'-chloro-[1,1'-biphenyl]-4-yl)-4,6-diphenyl-1,3,5-triazine, the same procedure as in [Synthesis Example 21] was performed to obtain a target Compound Inv 475 (4.6 g, yield 63%).

[LCMS]: 631.

-continued

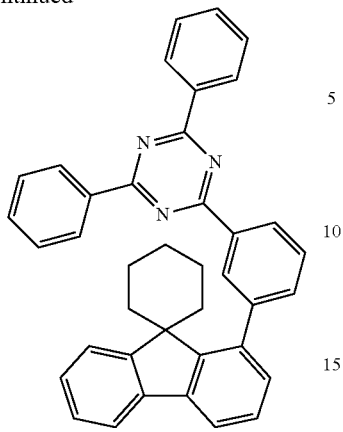

Except that Core 3 (5 g, 14.53 mmol) of [Preparation Example 3] was used instead of Core 1, the same procedure as in [Synthesis Example 1] was performed to obtain a target Compound Inv 483 (4.8 g, yield 60%).

[LCMS]: 542.

[Synthesis Example 42] Synthesis of Compound Inv 486

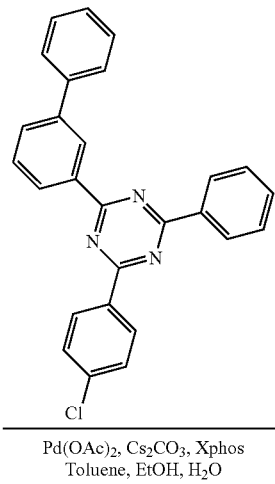

Except that 2-(4'-chloro-[1,1'-biphenyl]-3-yl)-4,6-diphenyl-1,3,5-triazine (5.0 g, 11.9 mmol) was used instead of 2-(3-chlorophenyl)-4,6-diphenyl-1,3,5-triazine, the same procedure as in [Synthesis Example 41] was performed to obtain a target Compound Inv 486 (4.6 g, yield 62%).

[LCMS]: 618.

[Synthesis Example 43] Synthesis of Compound Inv 514

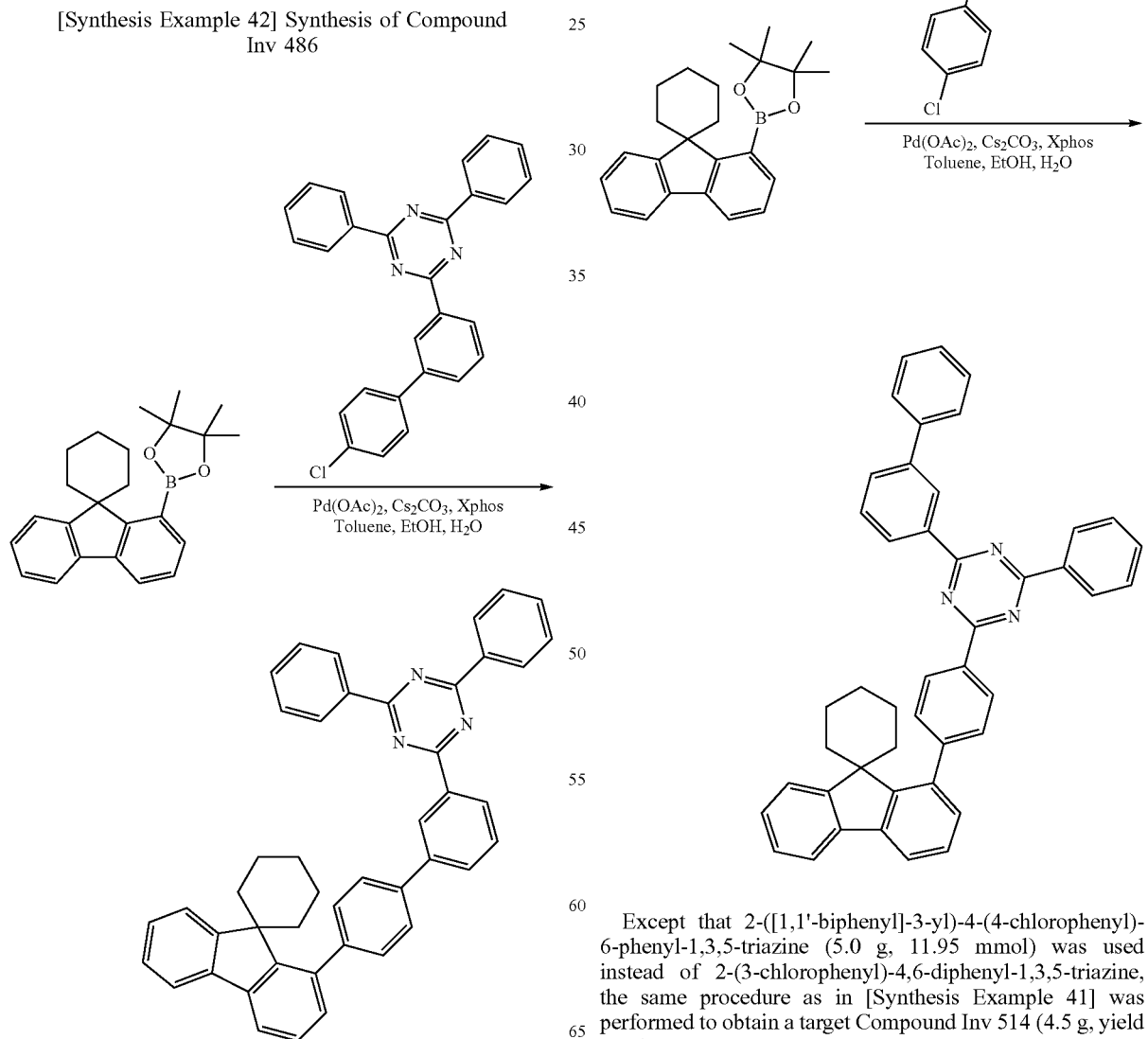

Except that 2-([1,1'-biphenyl]-3-yl)-4-(4-chlorophenyl)-6-phenyl-1,3,5-triazine (5.0 g, 11.95 mmol) was used instead of 2-(3-chlorophenyl)-4,6-diphenyl-1,3,5-triazine, the same procedure as in [Synthesis Example 41] was performed to obtain a target Compound Inv 514 (4.5 g, yield 61%).

[LCMS]: 618.

[Synthesis Example 44] Synthesis of Compound Inv 539

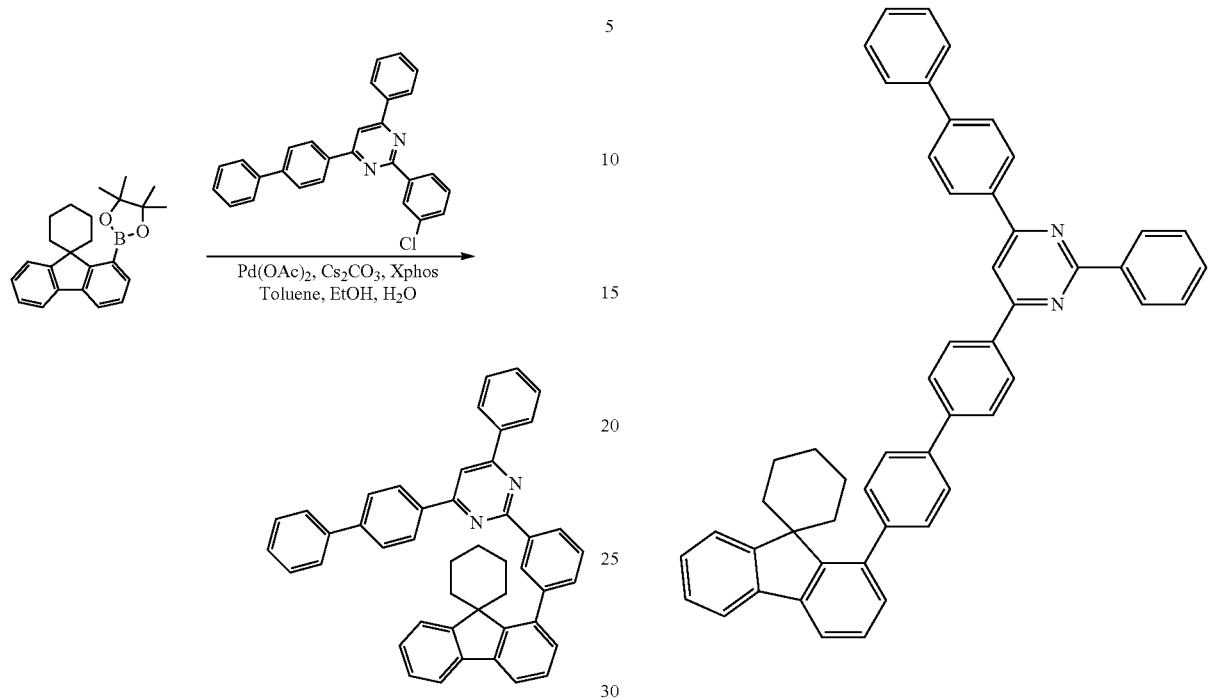

Except that 4-([1,1'-biphenyl]-4-yl)-2-(3-chlorophenyl)-6-phenylpyrimidine (5.0 g, 11.93 mmol) was used instead of 2-(3-chlorophenyl)-4,6-diphenyl-1,3,5-triazine, the same procedure as in [Synthesis Example 41] was performed to obtain a target Compound Inv 539 (4.7 g, yield 63%).

[LCMS]: 617.

[Synthesis Example 45] Synthesis of Compound Inv 556

Except that 4-([1,1'-biphenyl]-4-yl)-6-(4'-chloro-[1,1'-biphenyl]-4-yl)-2-phenylpyrimidine (5.0 g, 10.1 mmol) was used instead of 2-(3-chlorophenyl)-4,6-diphenyl-1,3,5-triazine, the same procedure as in [Synthesis Example 41] was performed to obtain a target Compound Inv 556 (4.4 g, yield 62%).

[LCMS]: 693.

[Synthesis Example 46] Synthesis of Compound Inv 591

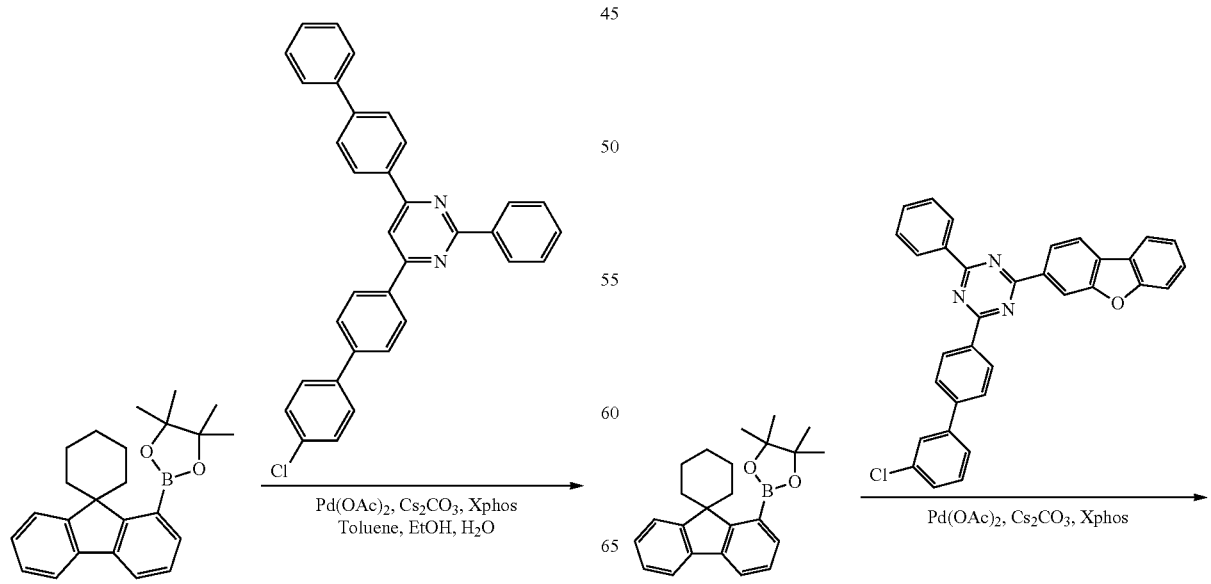

443
-continued

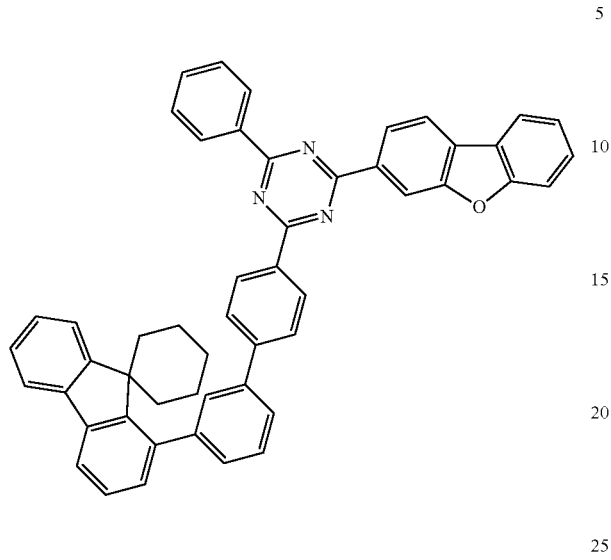

Except that 2-(3'-chloro-[1,1'-biphenyl]-4-yl)-4-(dibenzo[b,d]furan-3-yl)-6-phenyl-1,3,5-triazine (5.0 g, 9.80 mmol) was used instead of 2-(3-chlorophenyl)-4,6-diphenyl-1,3,5-triazine, the same procedure as in [Synthesis Example 41] was performed to obtain a target Compound Inv 591 (4.4 g, yield 63%).

[LCMS]: 708.

[Synthesis Example 47] Synthesis of Compound Inv 613

444
-continued

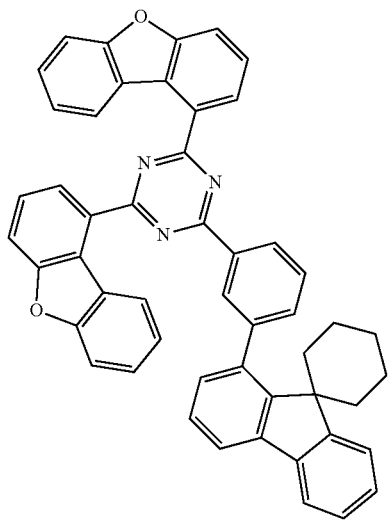

Except that 2-(3-chlorophenyl)-4,6-bis(dibenzo[b,d]furan-1-yl)-1,3,5-triazine (5.0 g, 9.54 mmol) was used instead of 2-(3-chlorophenyl)-4,6-diphenyl-1,3,5-triazine, the same procedure as in [Synthesis Example 41] was performed to obtain a target Compound Inv 613 (4.2 g, yield 60%).

[LCMS]: 722.

[Synthesis Example 48] Synthesis of Compound Inv 631

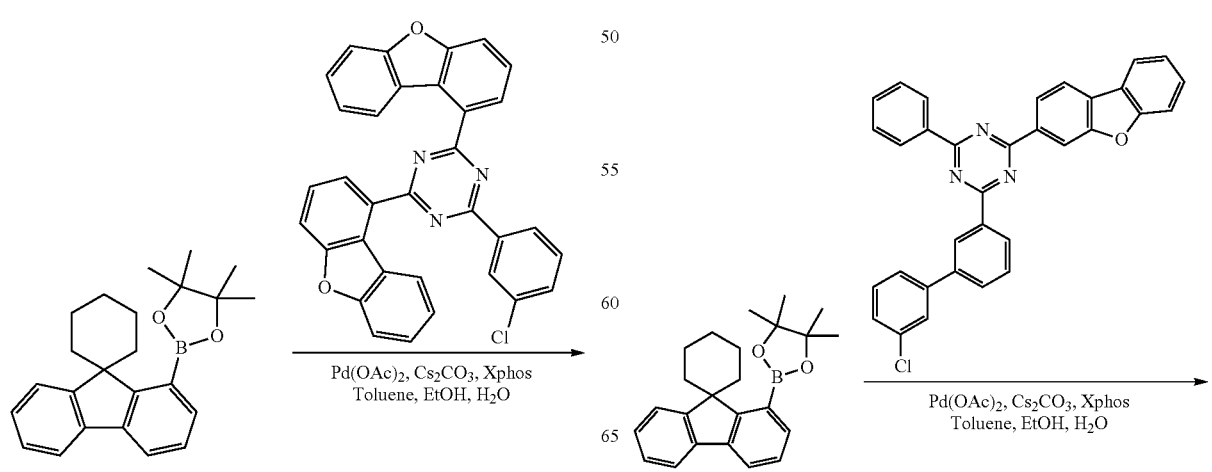

445
-continued

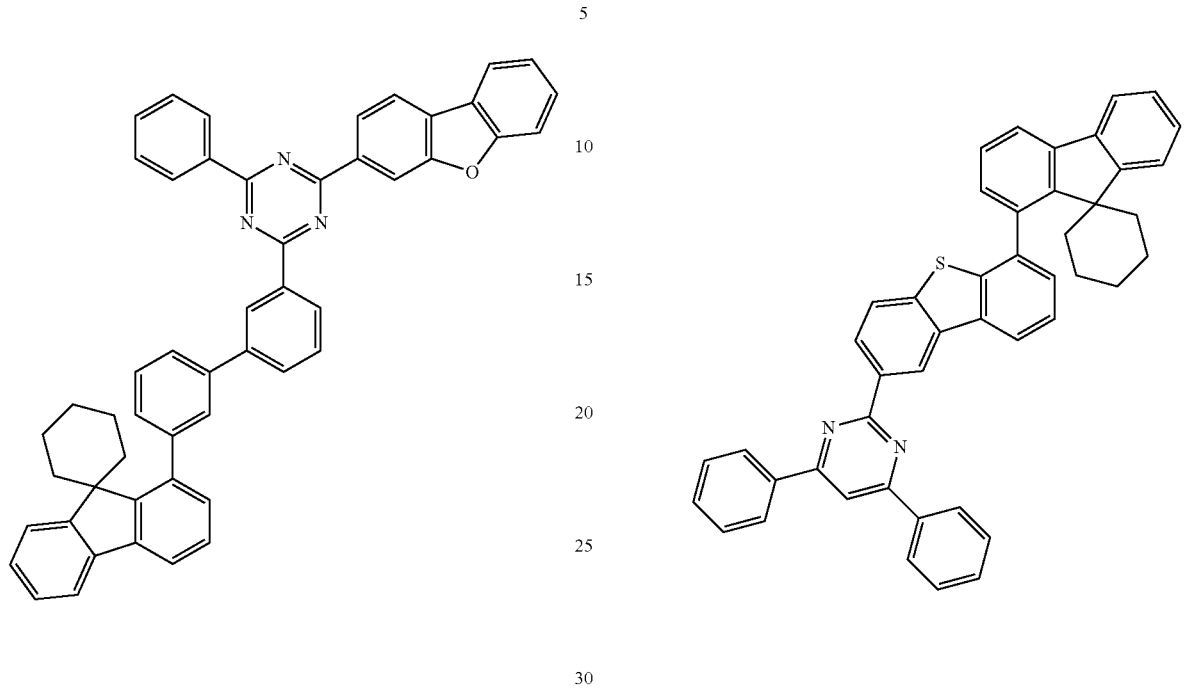

Except that 2-(3'-chloro-[1,1'-biphenyl]-3-yl)-4-(dibenzo[b,d]furan-3-yl)-6-phenyl-1,3,5-triazine (5.0 g, 9.80 mmol) was used instead of 2-(3-chlorophenyl)-4,6-diphenyl-1,3,5-triazine, the same procedure as in [Synthesis Example 41] was performed to obtain a target Compound Inv 631 (4.3 g, yield 61%).

[LCMS]: 708.

[Synthesis Example 49] Synthesis of Compound Inv 642

446
-continued

Except that 2-(6-chlorodibenzo[b,d]thiophen-2-yl)-4,6-diphenylpyrimidine (5.0 g, 11.13 mmol) was used instead of 2-(3-chlorophenyl)-4,6-diphenyl-1,3,5-triazine, the same procedure as in [Synthesis Example 41] was performed to obtain a target Compound Inv 642 (4.3 g, yield 59%).

[LCMS]: 647.

[Synthesis Example 50] Synthesis of Compound Inv 659

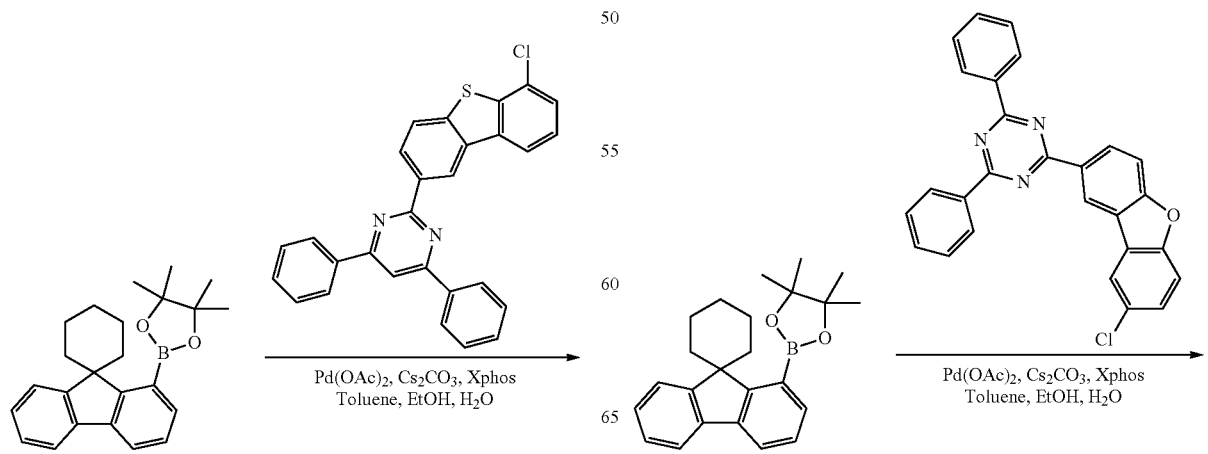

-continued

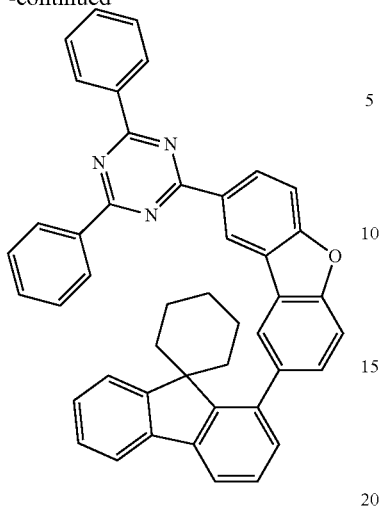

Except that 2-(8-chlorodibenzo[b,d]furan-2-yl)-4,6-diphenyl-1,3,5-triazine (5.0 g, 11.52 mmol) was used instead of 2-(3-chlorophenyl)-4,6-diphenyl-1,3,5-triazine, the same procedure as in [Synthesis Example 41] was performed to obtain a target Compound Inv 659 (4.2 g, yield 57%).

[LCMS]: 632.

[Synthesis Example 51] Synthesis of Compound Inv 677

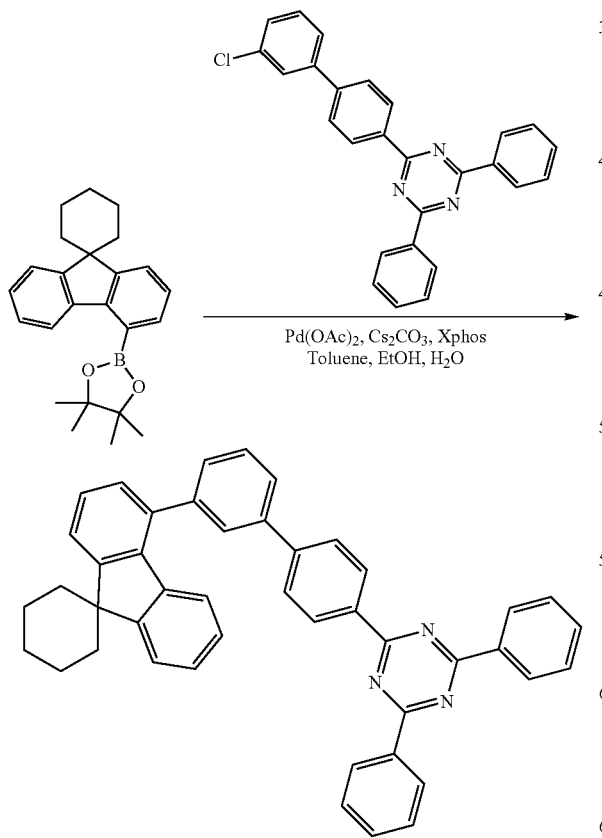

Except that Core 4 (5.14 g, 14.28 mmol) of [Preparation Example 4] was used instead of Core 1 and that 2-(3'-chloro-[1,1'-biphenyl]-4-yl)-4,6-diphenyl-1,3,5-triazine (5.0 g, 11.90 mmol) was used instead of 2-(3-chlorophenyl)-4,6-diphenyl-1,3,5-triazine, the same procedure as in [Synthesis Example 1] was performed to obtain a target Compound Inv 677 (4.6 g, yield 62%).

[LCMS]: 618.

[Synthesis Example 52] Synthesis of Compound Inv 688

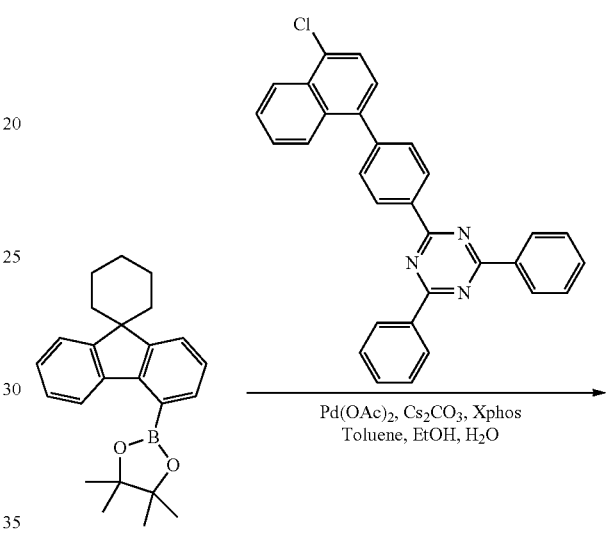

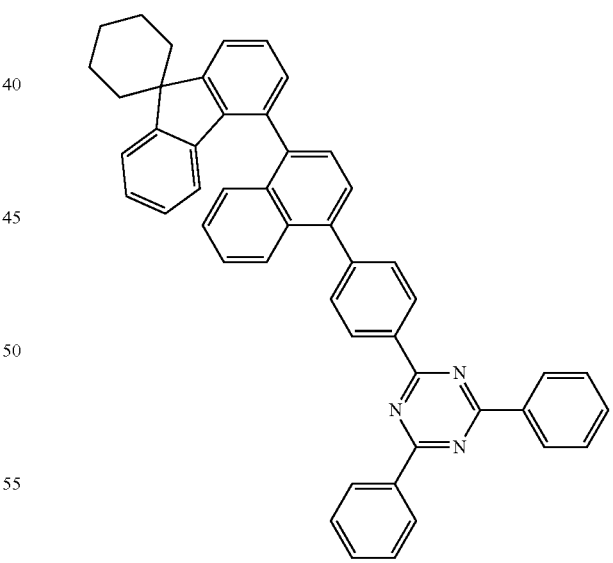

Except that 2-(4-(4-chloronaphthalen-1-yl)phenyl)-4,6-diphenyl-1,3,5-triazine (5.0 g, 10.63 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 688 (4.6 g, yield 64%).

[LCMS]: 668.

[Synthesis Example 53] Synthesis of Compound Inv 690

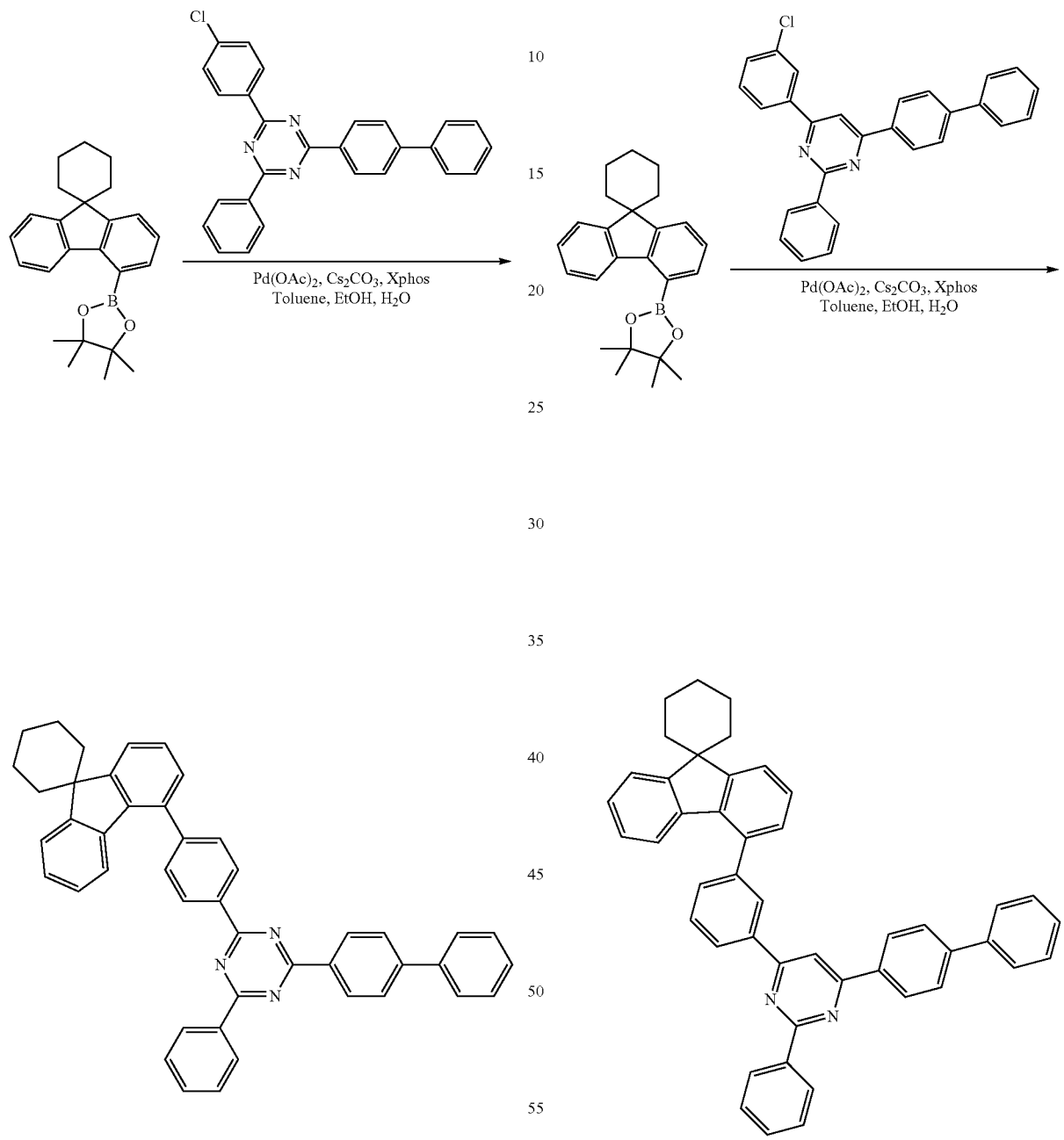

Except that 2-([1,1'-biphenyl]-4-yl)-4-(4-chlorophenyl)-6-phenyl-1,3,5-triazine (5.0 g, 11.90 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 690 (4.6 g, yield 62%).

[LCMS]: 618.

[Synthesis Example 54] Synthesis of Compound Inv 747

Except that 4-([1,1'-biphenyl]-4-yl)-6-(3-chlorophenyl)-2-phenylpyrimidine (5.0 g, 11.93 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 747 (4.7 g, yield 63%).

[LCMS]: 617.

[Synthesis Example 55] Synthesis of Compound Inv 762

[Synthesis Example 56] Synthesis of Compound Inv 771

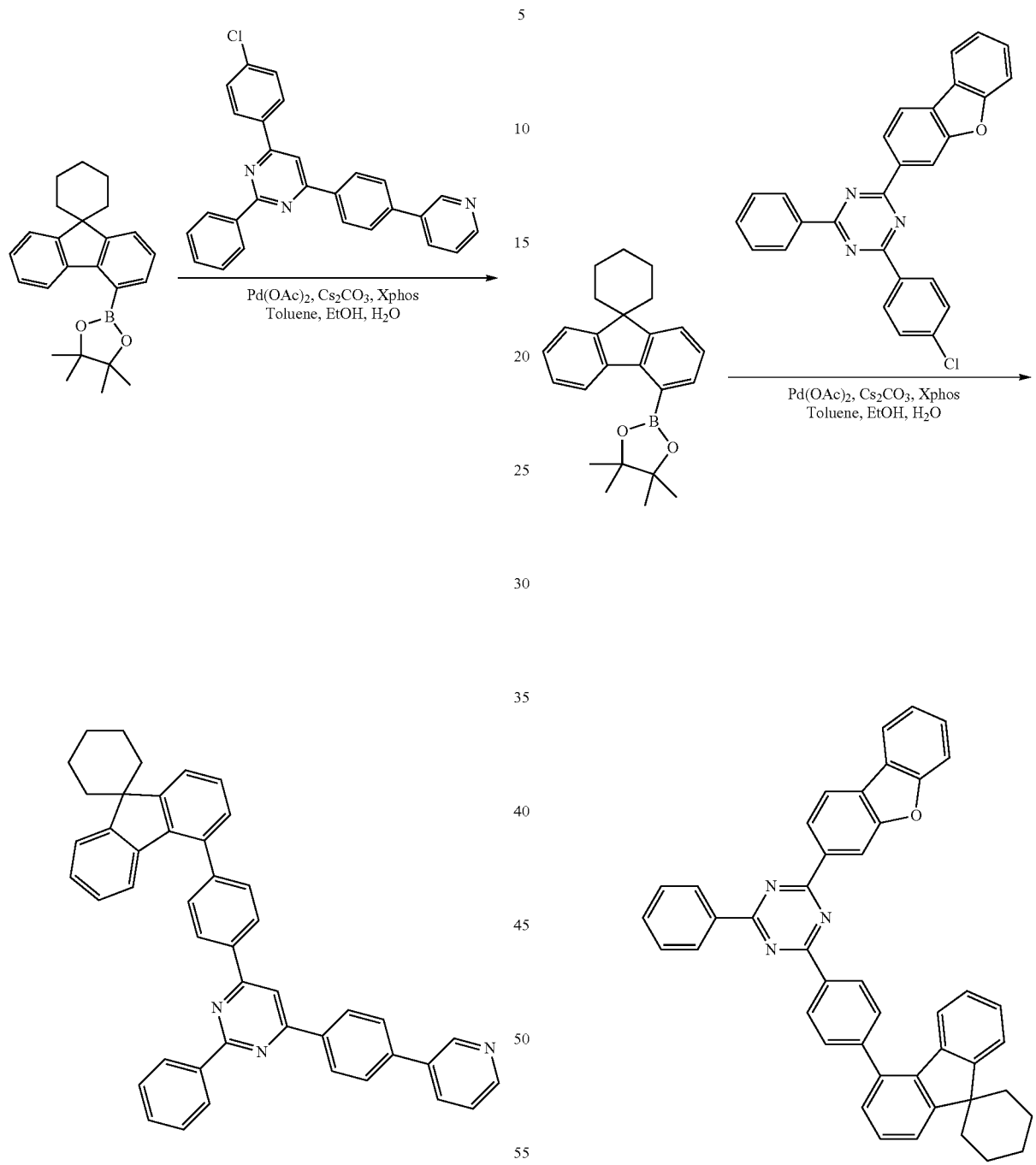

Except that 2-(4-(4-chloronaphthalen-1-yl)phenyl)-4,6-diphenyl-1,3,5-triazine (5.0 g, 11.90 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 762 (4.5 g, yield 61%).

[LCMS]: 618.

Except that 2-(4-chlorophenyl)-4-(dibenzo[b,d]furan-3-yl)-6-phenyl-1,3,5-triazine (5.0 g, 11.52 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 771 (4.6 g, yield 63%).

[LCMS]: 632.

[Synthesis Example 57] Synthesis of Compound Inv 807

[Synthesis Example 58] Synthesis of Compound Inv 819

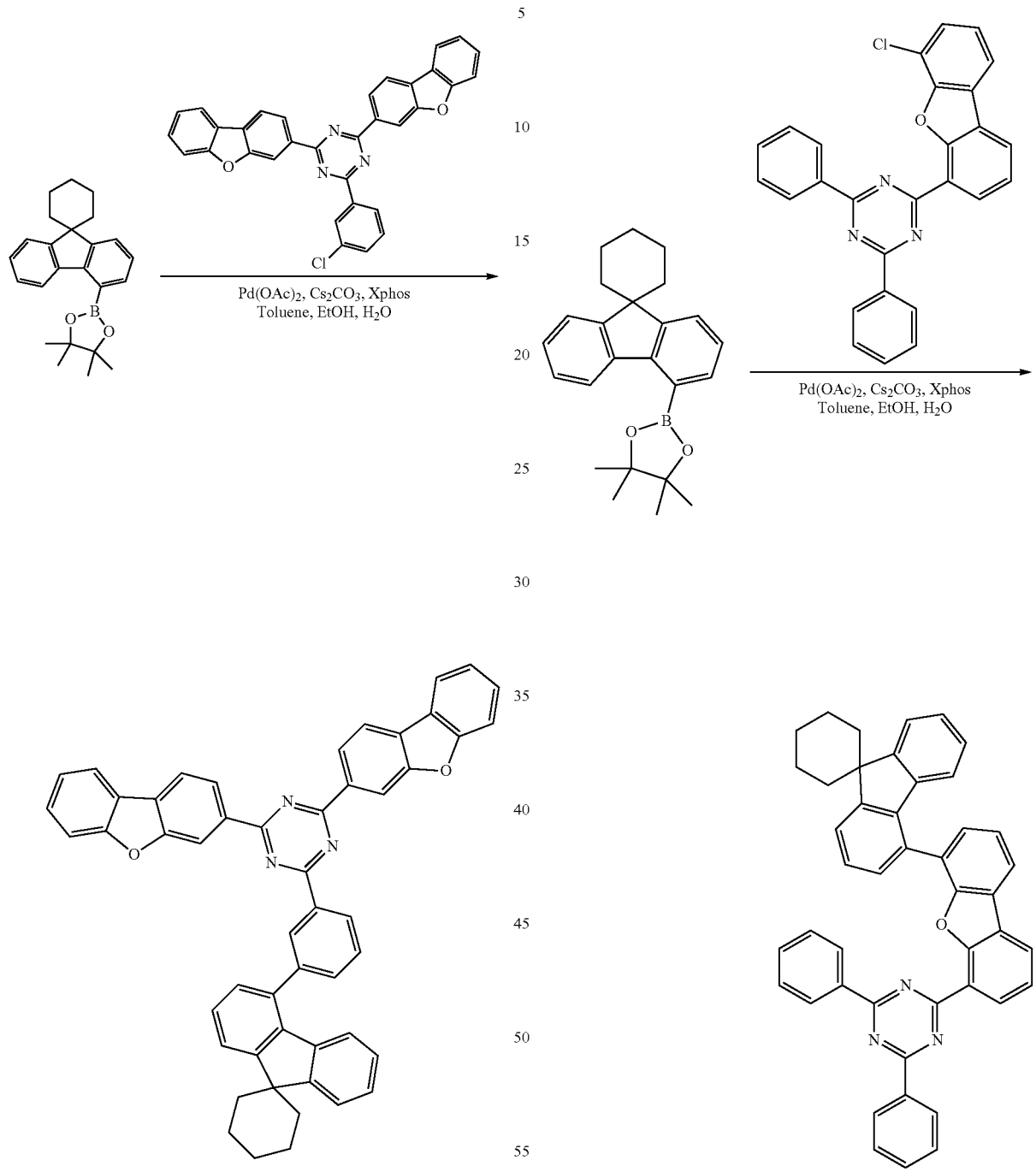

Except that 2-(3-chlorophenyl)-4,6-bis(dibenzo[b,d]furan-3-yl)-1,3,5-triazine (5.0 g, 9.54 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 807 (4.2 g, yield 60%).

[LCMS]: 722.

Except that 2-(6-chlorodibenzo[b,d]furan-4-yl)-4,6-diphenyl-1,3,5-triazine (5.0 g, 11.52 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 819 (4.7 g, yield 64%).

[LCMS]: 632.

[Synthesis Example 59] Synthesis of Compound Inv 824

[Synthesis Example 60] Synthesis of Compound Inv 852

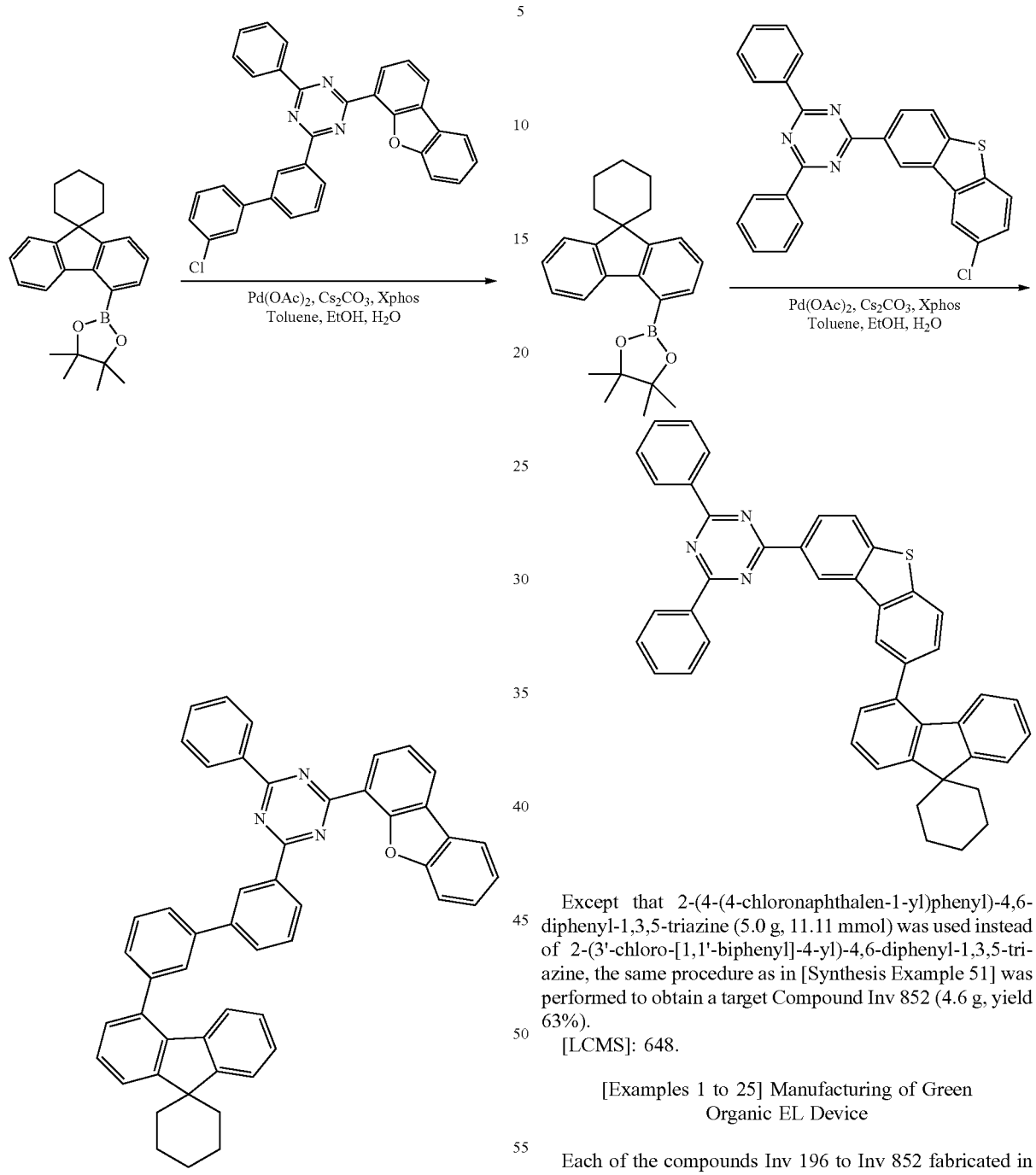

Except that 2-(3'-chloro-[1,1'-biphenyl]-3-yl)-4-(dibenzo[b,d]furan-4-yl)-6-phenyl-1,3,5-triazine (5.0 g, 9.84 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 824 (4.2 g, yield 60%).

[LCMS]: 708.

Except that 2-(4-(4-chloronaphthalen-1-yl)phenyl)-4,6-diphenyl-1,3,5-triazine (5.0 g, 11.11 mmol) was used instead of 2-(3'-chloro-[1,1'-biphenyl]-4-yl)-4,6-diphenyl-1,3,5-triazine, the same procedure as in [Synthesis Example 51] was performed to obtain a target Compound Inv 852 (4.6 g, yield 63%).

[LCMS]: 648.

[Examples 1 to 25] Manufacturing of Green Organic EL Device

Each of the compounds Inv 196 to Inv 852 fabricated in the above Synthesis Examples was subjected to high purity sublimation purification by a commonly known method, and then green organic EL devices were manufactured as follows.

First, a glass substrate coated with indium tin oxide (ITO) into a thin film with a thickness of 1,500 Å was washed with distilled water ultrasonically. After washing with distilled water was completed, the glass substrate was ultrasonically washed with a solvent, such as isopropyl alcohol, acetone and methanol, dried, transferred to a UV OZONE cleaner (POWER SONIC™ 405, Hwasin Tech), and cleaned for 5 minutes using UV, and then the cleaned glass substrate was transferred to a vacuum evaporator.

On the ITO transparent electrode prepared as above, m-MTDATA (60 nm)/TCTA (80 nm)/respective compounds of Inv 196 to Inv 852+10% of Ir(ppy)₃ (30 nm)/BCP (10 nm)/Alq₃ (30 nm)/LiF (1 nm)/Al (200 nm) were stacked sequentially in the order listed, such that organic EL devices were manufactured.

[Comparative Examples 1-5] Manufacturing of Green Organic EL Device

Green organic EL devices of Comparative Examples 1 to 5 were manufactured in the same manner as in Example 1, except that CBP, A, B, C, and D were used, respectively, instead of the Compound Inv 196 as a light emitting host material when forming a light-emitting layer.

The structures of m-MTDATA, TCTA, Ir(ppy)₃, CBP, BCP, and compounds A, B, C and D used in Examples 1 to 25 and Comparative Examples 1 to 5 are as follows, respectively.

-continued

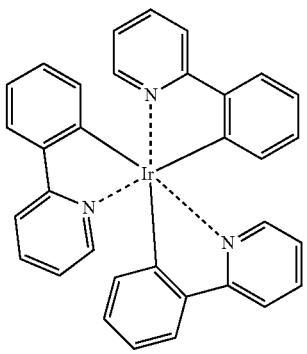

Ir(ppy)₃

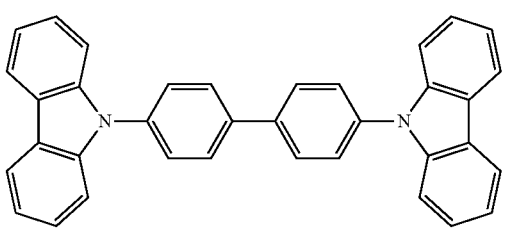

CBP

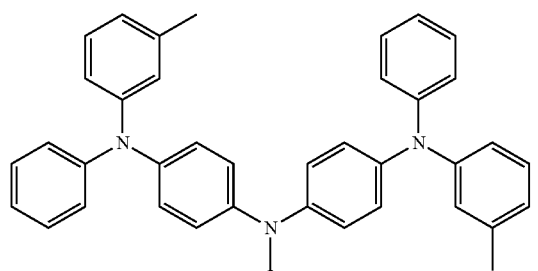

m-MTDATA

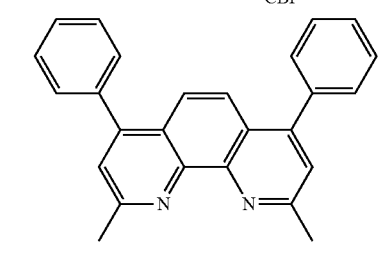

BCP

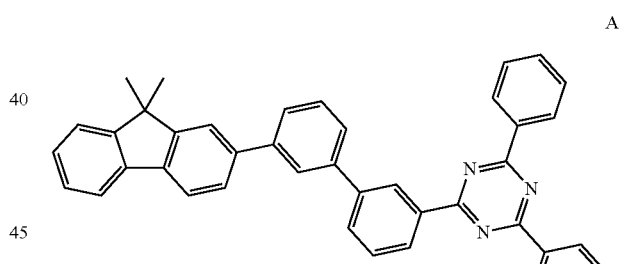

A

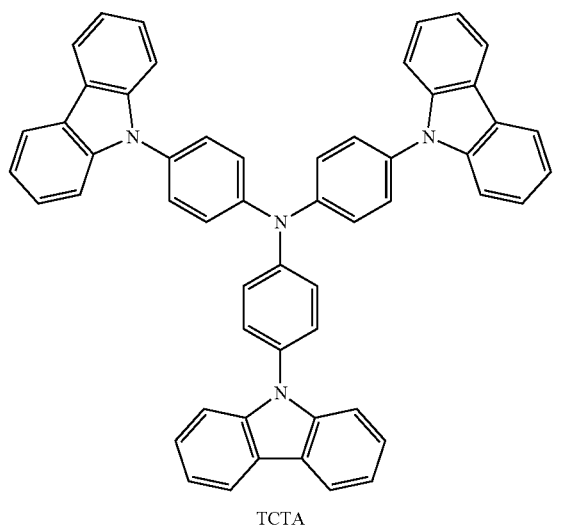

TCTA

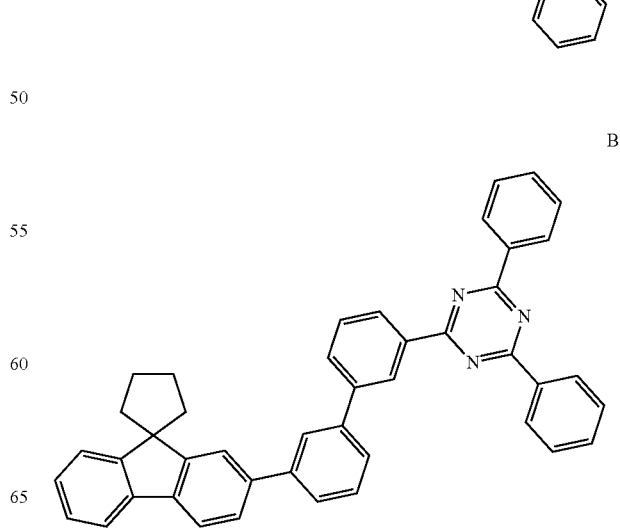

B

C

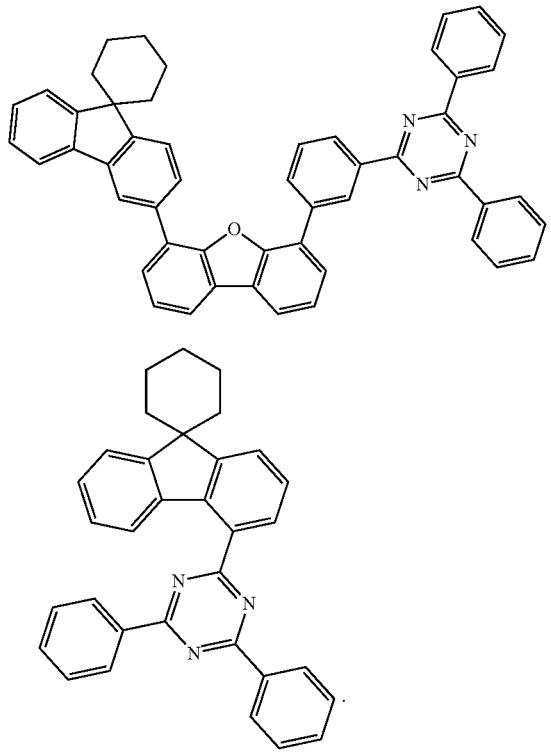

D

Evaluation Example 1

For each of the green organic EL devices manufactured in Examples 1 to 25 and Comparative Examples 1 to 5, driving voltage, current efficiency, and emission peak at a current density of 10 mA/cm² were measured and the results are shown in Table 1 below.

TABLE 1

| Sample | Host | Driving voltage (V) | EL PEAK (nm) | Current efficiency (cd/A) |
|---|---|---|---|---|
| Example 1 | Inv196 | 3.8 | 456 | 64.2 |
| Example 2 | Inv199 | 3.9 | 455 | 65.4 |
| Example 3 | Inv214 | 3.6 | 455 | 66.2 |
| Example 4 | Inv228 | 3.7 | 456 | 64.5 |
| Example 5 | Inv231 | 3.9 | 457 | 66.9 |
| Example 6 | Inv241 | 3.8 | 454 | 64.2 |
| Example 7 | Inv247 | 4.0 | 458 | 68.3 |
| Example 8 | Inv275 | 3.8 | 457 | 66.4 |
| Example 9 | Inv390 | 3.7 | 456 | 61.1 |
| Example 10 | Inv400 | 3.9 | 455 | 62.8 |
| Example 11 | Inv404 | 3.8 | 454 | 62.2 |
| Example 12 | Inv406 | 4.0 | 457 | 63.3 |
| Example 13 | Inv422 | 4.2 | 455 | 61.4 |
| Example 14 | Inv423 | 3.9 | 458 | 61.9 |
| Example 15 | Inv437 | 4.1 | 459 | 62.8 |
| Example 16 | Inv439 | 4.2 | 456 | 60.6 |
| Example 17 | Inv591 | 4.5 | 457 | 59.7 |
| Example 18 | Inv613 | 3.9 | 455 | 58.4 |
| Example 19 | Inv631 | 4.1 | 454 | 59.2 |
| Example 20 | Inv659 | 4.1 | 458 | 58.8 |
| Example 21 | Inv771 | 4.2 | 457 | 60.2 |
| Example 22 | Inv807 | 4.0 | 457 | 59.4 |
| Example 23 | Inv819 | 4.3 | 456 | 58.8 |
| Example 24 | Inv824 | 4.1 | 454 | 58.6 |
| Example 25 | Inv852 | 4.2 | 455 | 57.2 |
| Comparative Example 1 | CBP | 5.6 | 459 | 42.6 |
| Comparative Example 2 | A | 4.9 | 458 | 54.6 |
| Comparative Example 3 | B | 4.9 | 457 | 55.2 |
| Comparative Example 4 | C | 5.2 | 457 | 53.1 |
| Comparative Example 5 | D | 5.0 | 455 | 54.2 |

As shown in Table 1, it was appreciated that the green organic EL devices of Examples 1 to 25 in which the compounds Inv 196 to Inv 852 according to the present invention were applied as light-emitting layers, respectively, exhibit excellent performance in terms of efficiency and driving voltage, as compared to a green organic EL device of Comparative Example 1 using conventional CBP as a light-emitting layer and green organic EL devices of Comparative Examples 2 to 5 using Compounds A to D as light-emitting layers.

Specifically, in embodiments of the present invention, as an aliphatic hexagonal cyclic group is formed in the 9-position of fluorene, the devices may be electrochemically stable and excellent in thermal stability, thus having improved serving life characteristics, as compared to a material A of Comparative Example 2 in which fluorene is substituted in the 9-position with a dimethyl group and a material B of Comparative Example 3 in which an aliphatic pentagonal cyclic group is formed.

In addition, a material C of Comparative Example 4 has a structure including a linker between a dibenzo-based moiety and a hetero ring (e.g., triazine). As the linker is introduced in the above-described position, the device shifts to a long wavelength band, thus making it difficult to obtain high-efficiency characteristics, and derivatives in a high temperature range are designed due to an increase in molecular weight in the case of structure tuning. In contrast, in an Example including the compound represented by Chemical Formula 1 according to the present invention, by not including a linker in the above-described position, high-efficiency characteristics may be obtained in a desired wavelength band.

In addition, a material D of Comparative Example 5 in which fluorene and a hetero ring are directly connected showed a low triplet energy (T1) value, thereby showing relatively low efficiency characteristics. Further, 2-position of fluorene is an active site, and it is appreciated that materials substituted in that position have superior current efficiency and driving voltage, as compared to organic EL devices using, as the light-emitting layer, materials of the core substituted in 1-, 3-, and 4-positions.

[Examples 26 to 35] Manufacturing of Blue Organic EL Device

Each of the compounds Inv 183 to Inv 762 fabricated in the above Synthesis Examples was subjected to high purity sublimation purification by a commonly known method and then blue organic EL devices were manufactured as follows.

First, a glass substrate coated with indium tin oxide (ITO) into a thin film with a thickness of 1,500 Å was washed with distilled water ultrasonically. After washing with distilled water was completed, the glass substrate was ultrasonically washed with a solvent, such as isopropyl alcohol, acetone and methanol, dried, transferred to a UV OZONE cleaner (POWER SONIC™ 405, Hwasin Tech), and cleaned for 5 minutes using UV, and then the cleaned glass substrate was transferred to a vacuum evaporator.

On the ITO transparent electrode prepared as above, DS-205 (Doosan Electronics CO., LTD., 80 nm)/NPB (15 nm)/ADN+5% DS-405 (Doosan Electronics CO., LTD., 30 nm)/respective Compounds of Inv 183 to Inv 762 (30 nm)/LiF (1 nm)/Al (200 nm) were stack sequentially in the order listed, and thus organic EL devices were manufactured.

The structures of NPB, ADN and Alq$_3$ used in such Examples are as follows.

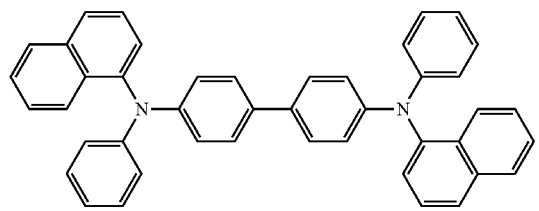

NPB

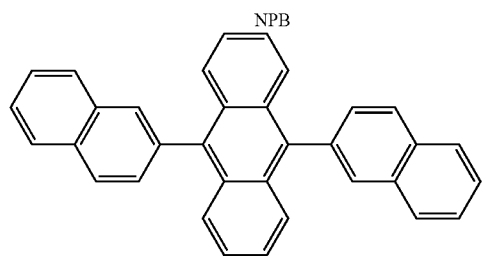

ADN

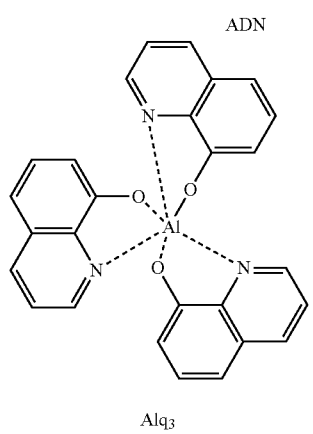

Alq$_3$

[Comparative Example 6] Manufacturing of Blue Organic EL Device

A blue organic EL device was manufactured in the same manner as in Example 26, except that Alq$_3$, instead of the Compound Inv 183, was deposited to 30 nm as an electron transporting layer material.

Evaluation Example 2

For each of the blue organic EL devices prepared in Examples 26 to 35 and Comparative Example 6, driving voltage, current efficiency and emission peak at a current density of 10 mA/cm$^2$ were measured, and the results are shown in Table 2 below.

TABLE 2

| Sample | Electron transporting layer | Driving voltage (V) | EL PEAK (nm) | Current efficiency (cd/A) |
|---|---|---|---|---|
| Example 26 | Inv183 | 4.0 | 458 | 7.0 |
| Example 27 | Inv263 | 4.1 | 459 | 7.0 |
| Example 28 | Inv287 | 3.8 | 459 | 6.9 |
| Example 29 | Inv383 | 3.9 | 459 | 7.0 |
| Example 30 | Inv457 | 3.8 | 459 | 7.1 |
| Example 31 | Inv475 | 3.7 | 458 | 7.1 |
| Example 32 | Inv479 | 4.2 | 459 | 7.1 |
| Example 33 | Inv642 | 3.8 | 459 | 7.2 |
| Example 34 | Inv688 | 3.9 | 458 | 7.0 |
| Example 35 | Inv762 | 4.1 | 459 | 6.9 |
| Comparative Example 6 | Alq$_3$ | 4.8 | 460 | 5.8 |

As shown in Table 2, it was appreciated that the blue organic EL devices of Examples 26 to 35 in which the compounds according to the present invention were applied as electron transporting layers exhibit excellent performance in terms of driving voltage, current efficiency and emission peak, as compared to the blue organic EL device of Comparative Example 6 using conventional Alq$_3$ as the electron transporting layer.

[Examples 36 to 60] Manufacturing of Blue Organic EL Device

Each of the compounds Inv 3 to Inv 747 fabricated in the above Synthesis Examples was subjected to high purity sublimation purification by a commonly known method, and thus blue organic EL devices were manufactured as follows.

First, a glass substrate coated with indium tin oxide (ITO) into a thin film with a thickness of 1,500 Å was washed with distilled water ultrasonically. After washing with distilled water was completed, the glass substrate was ultrasonically washed with a solvent, such as isopropyl alcohol, acetone and methanol, dried, transferred to a UV OZONE cleaner (POWER SONIC™ 405, Hwasin Tech), and cleaned for 5 minutes using UV, and then the cleaned glass substrate was transferred to a vacuum evaporator.

On the ITO transparent electrode prepared as above, DS-205 (80 nm)/NPB (15 nm)/ADN+5% DS-405 (Doosan Electronics CO., LTD., 30 nm)/respective Compounds of Inv 3 to Inv 747 (30 nm)/Alq$_3$ (25 nm)/LiF (1 m)/Al (200 nm) were stack sequentially in the order listed, and thus organic EL devices were manufactured.

The structures of NPB, ADN and Alq$_3$ used in such embodiments are as follows:

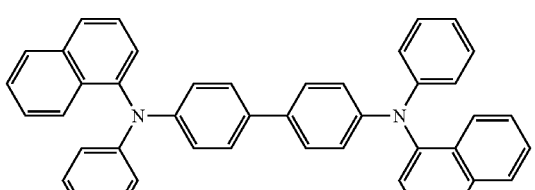

NPB

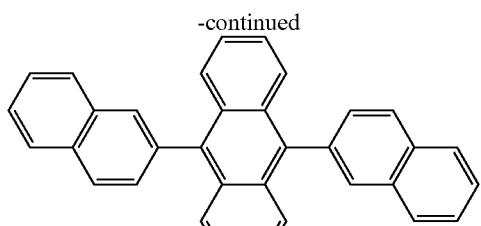

ADN

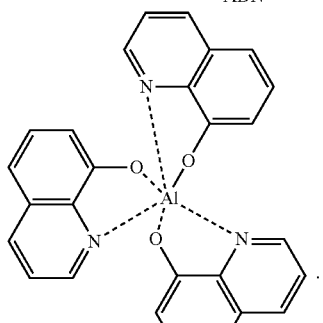

Alq₃

[Comparative Example 7] Manufacturing of Blue Organic EL Device

A blue organic EL device was manufactured in the same manner as in Example 36, except that Inv 3 which was used as a material for the electron transporting auxiliary layer was not used, and Alq₃, which is an electron transporting layer material, was deposited to 30 nm instead of 25 nm.

Evaluation Example 3

For each of the blue organic EL devices prepared in Examples 36 to 60 and Comparative Example 7, driving voltage, current efficiency and emission peak at a current density of 10 mA/cm² were measured, and the results are shown in Table 3 below.

TABLE 3

| Sample | Electron transporting auxiliary layer | Driving voltage (V) | EL PEAK (nm) | Current efficiency (cd/A) |
|---|---|---|---|---|
| Example 36 | Inv3 | 4.3 | 6.8 | 457 |
| Example 37 | Inv7 | 4.0 | 7.2 | 458 |
| Example 38 | Inv14 | 4.1 | 7.3 | 458 |
| Example 39 | Inv18 | 3.9 | 7.4 | 457 |
| Example 40 | Inv51 | 4.0 | 7.2 | 458 |
| Example 41 | Inv119 | 4.4 | 7.1 | 458 |
| Example 42 | Inv149 | 4.3 | 7.2 | 458 |
| Example 43 | Inv162 | 4.1 | 7.3 | 458 |
| Example 44 | In167 | 4.2 | 7.2 | 458 |
| Example 45 | Inv293 | 4.1 | 7.2 | 457 |
| Example 46 | Inv299 | 4.3 | 7.1 | 458 |
| Example 47 | Inv310 | 4.0 | 7.0 | 458 |
| Example 48 | Inv322 | 4.2 | 7.5 | 458 |
| Example 49 | Inv350 | 4.3 | 7.1 | 458 |
| Example 50 | Inv356 | 4.0 | 7.2 | 458 |
| Example 51 | Inv363 | 4.0 | 7.1 | 458 |
| Example 52 | Inv374 | 4.4 | 7.0 | 458 |
| Example 53 | Inv483 | 4.3 | 7.1 | 458 |

TABLE 3-continued

| Sample | Electron transporting auxiliary layer | Driving voltage (V) | EL PEAK (nm) | Current efficiency (cd/A) |
|---|---|---|---|---|
| Example 54 | Inv486 | 4.1 | 7.4 | 457 |
| Example 55 | Inv514 | 4.2 | 7.0 | 458 |
| Example 56 | Inv539 | 4.1 | 7.2 | 458 |
| Example 57 | Inv556 | 3.6 | 7.3 | 458 |
| Example 58 | Inv677 | 3.8 | 7.5 | 458 |
| Example 59 | Inv690 | 3.6 | 7.5 | 458 |
| Example 60 | Inv747 | 3.6 | 7.4 | 458 |
| Comparative Example 7 | — | 4.7 | 5.6 | 457 |

As shown in Table 3, it was appreciated that the blue organic EL devices of Examples 36 to 60 in which the compounds according to the present invention were applied as electron transporting auxiliary layers exhibit excellent performance in terms of driving voltage, current efficiency and emission peak, as compared to the blue organic EL device of Comparative Example 7 including the electron transporting layer formed of Alq₃ and not including an electron transporting auxiliary layer.

The invention claimed is:

1. A compound represented by the following Chemical Formula 1:

Chemical Formula 1

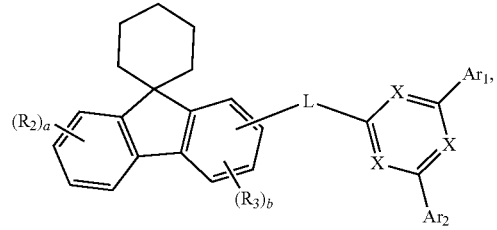

wherein the plurality of X are the same as or different from each other, each independently being C(R₁) or N, provided that at least one of the plurality of X is N, R₁ to R₃ are the same as or different from each other, each independently being selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphonyl group, a $C_6$ to $C_{60}$ arylphosphine group, a $C_6$ to $C_{60}$ arylphosphine oxide group and a $C_6$ to $C_{60}$ arylamine group, a is an integer ranging from 0 to 4, b is an integer ranging from 0 to 3, L is represented by any one of the following:

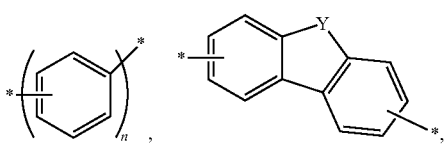

-continued

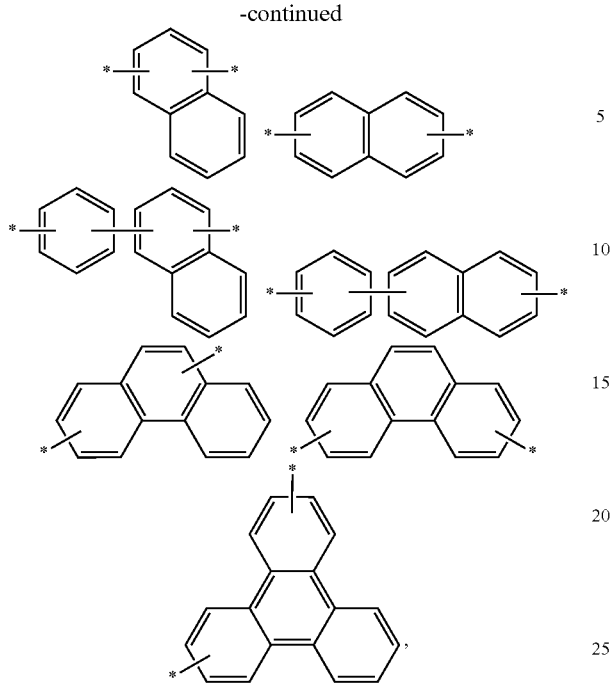

wherein
* is a site in which a bond with the compound represented by Chemical Formula 1 is made,
Y is selected from the group consisting of O, S and Se,
n is an integer ranging from 1 to 5,
Ar$_1$ and Ar$_2$ are the same as or different from each other, each independently being selected from the group consisting of: hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_3$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphonyl group, a C$_6$ to C$_{60}$ arylphosphine group, a C$_6$ to C$_{60}$ arylphosphine oxide group and a C$_6$ to C$_{60}$ arylamine group,
the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphonyl group, the arylphosphine group, the arylphosphine oxide group and the arylamine group of Ar$_1$ and Ar$_2$ and R$_1$, R$_1$ and R$_3$ are each independently substituted or unsubstituted with one or more kinds of substituents selected from the group consisting of hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_1$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphine group, a C$_6$ to C$_{60}$ arylphosphine oxide group and a C$_6$ to C$_{60}$ arylamine group, and when the substituents are plural in number, the substituents are the same as or different from each other.

2. The compound of claim 1, wherein L is represented by any one of the following:

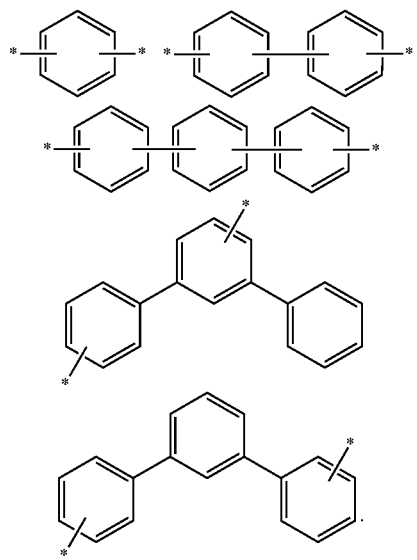

3. The compound of claim 1, wherein Chemical Formula 3 is a linker selected from the following:

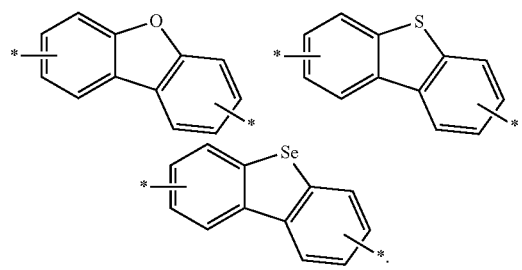

4. The compound of claim 1, wherein

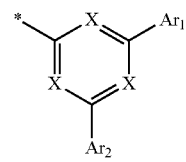

is selected from a group of substituents represented by the following Chemical Formulas A-1 to A-5:

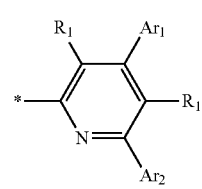

A-1

-continued

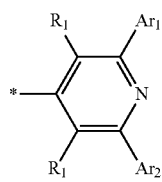
A-2

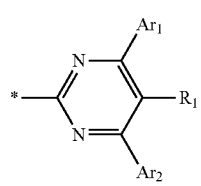
A-3

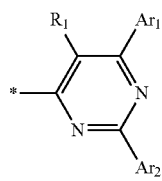
A-4

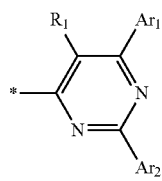
A-5 wherein in Chemical Formulas A-1 to A-5, $R_1$, $Ar_1$ and $Ar_2$ are as defined in claim 1, respectively.

5. The compound of claim 1, wherein $Ar_1$ and $Ar_2$ are the same as or different from each other, each independently being selected from the group consisting of: a $C_6$ to $C_{60}$ aryl group, a heteroaryl group having 5 to 60 nuclear atoms, the aryl group and the heteroaryl group of $Ar_1$ and $Ar_2$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

6. The compound of claim 1, wherein the compound represented by Chemical Formula 1 is a compound represented by any one of the following Chemical Formulas 4 to 7:

Chemical Formula 4

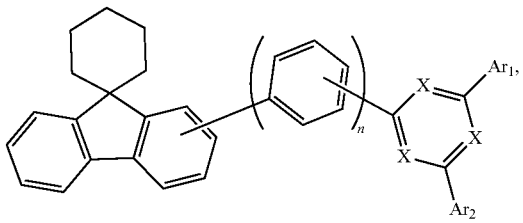

Chemical Formula 5

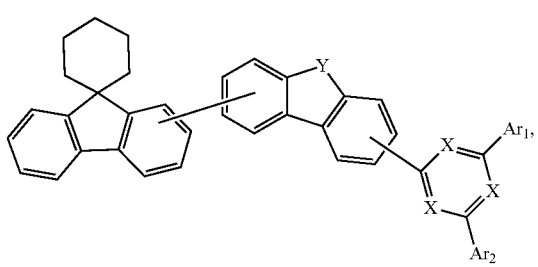

Chemical Formula 6

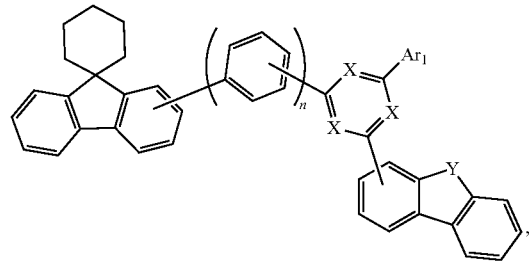

Chemical Formula 7

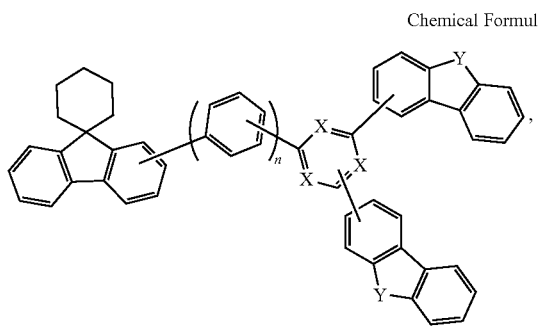

in Chemical Formulas 4 to 7,

X, Y, $Ar_1$, $Ar_2$, and n are as defined in claim 1, respectively.

7. An organic electroluminescent device, comprising an anode, a cathode and one or more organic layers disposed between the anode and the cathode,
wherein at least one of the one or more organic layers includes the compound represented by the following Chemical Formula 1 of claim 1:

Chemical Formula 1

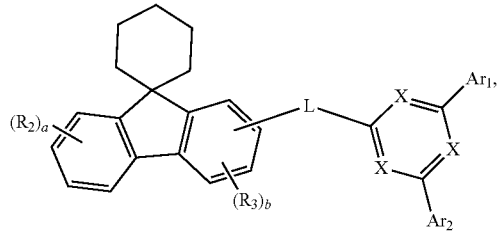

wherein the plurality of X are the same as or different from each other, each independently being C(R$_1$) or N, provided that at least one of the plurality of X is N, R$_1$ to R$_3$ are the same as or different from each other, each independently being selected from the group consisting of: hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_3$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphonyl group, a C$_6$ to C$_{60}$ arylphosphine group, a C$_6$ to C$_{60}$ arylphosphine oxide group and a C$_6$ to C$_{60}$ arylamine group, a is an integer ranging from 0 to 4, b is an integer ranging from 0 to 3, L is represented by any one of the following:

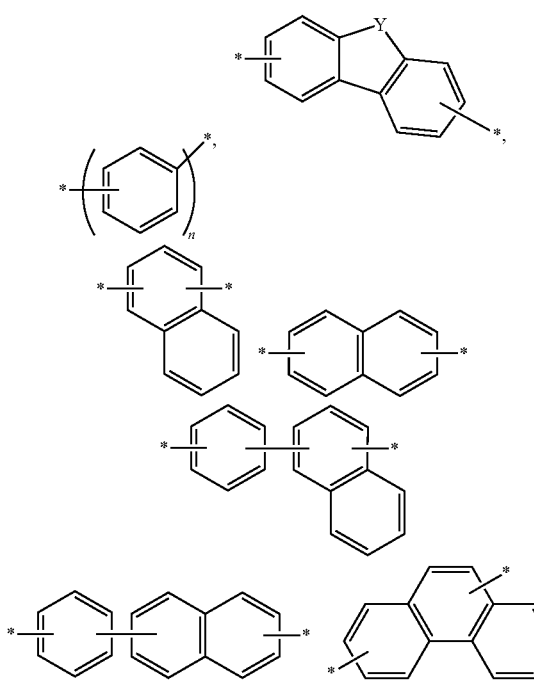

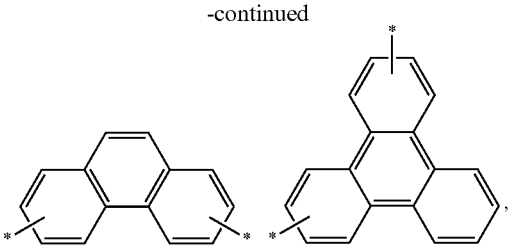

wherein
* is a site in which a bond with the compound represented by Chemical Formula 1 is made,
Y is selected from the group consisting of O, S and Se,
n is an integer ranging from 1 to 5,
Ar$_1$ and Ar$_2$ are the same as or different from each other, each independently being selected from the group consisting of: hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_3$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphonyl group, a C$_6$ to C$_{60}$ arylphosphine group, a C$_6$ to C$_{60}$ arylphosphine oxide group and a C$_6$ to C$_{60}$ arylamine group, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphonyl group, the arylphosphine group, the arylphosphine oxide group and the arylamine group of Ar$_1$ and Ar$_2$ and R$_1$, R$_1$ and R$_3$ are each independently substituted or unsubstituted with one or more kinds of substituents selected from the group consisting of hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_1$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphine group, a C$_6$ to C$_{60}$ arylphosphine oxide group and a C$_6$ to C$_{60}$ arylamine group, and when the substituents are plural in number, the substituents are the same as or different from each other.

8. The organic electroluminescent device of claim 7, wherein L is represented by any one of the following:

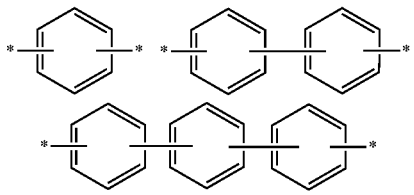

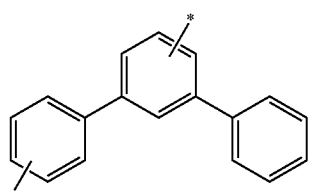

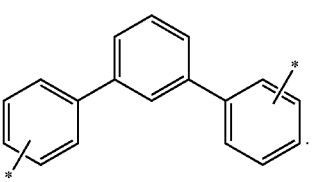

9. The organic electroluminescent device of claim 7, wherein L is represented by any of the following:

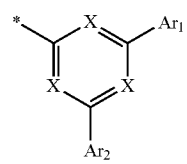

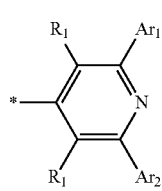

10. The organic electroluminescent device of claim 7, wherein

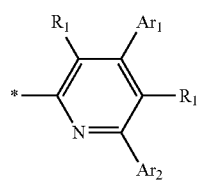

is selected from a group of substituents represented by the following Chemical Formulas A-1 to A-5:

A-1

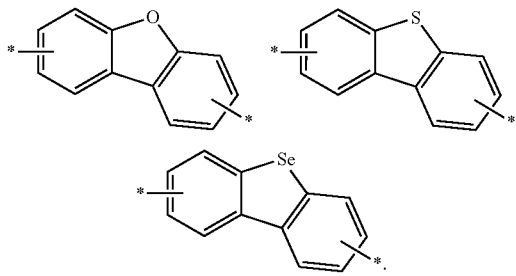

A-2

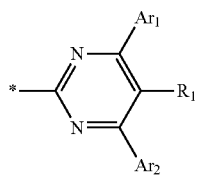

A-3

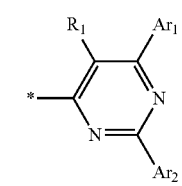

A-4

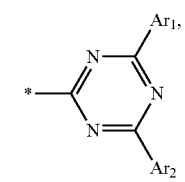

A-5 wherein in Chemical Formulas A-1 to A-5, $R_1$, $Ar_1$ and $Ar_2$ are as defined in claim 7, respectively.

11. The organic electroluminescent device of claim 7, wherein $Ar_1$ and $Ar_2$ are the same as or different from each other, each independently being selected from the group consisting of: a $C_6$ to $C_{60}$ aryl group, a heteroaryl group having 5 to 60 nuclear atoms, the aryl group and the heteroaryl group of $Ar_1$ and $Ar_2$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

12. The organic electroluminescent device of claim 7, wherein the compound represented by Chemical Formula 1 is a compound represented by any one of the following Chemical Formulas 4 to 7:

Chemical Formula 4

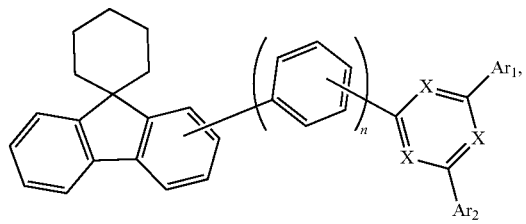

Chemical Formula 5

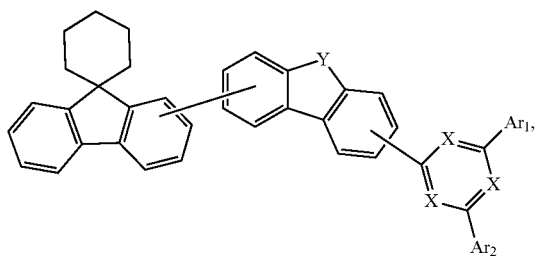

Chemical Formula 6

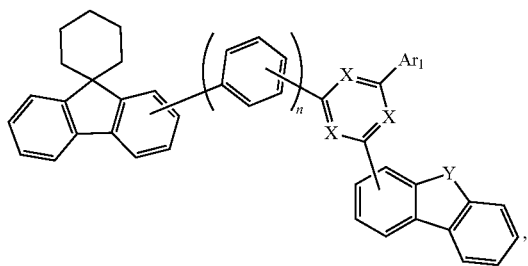

Chemical Formula 7

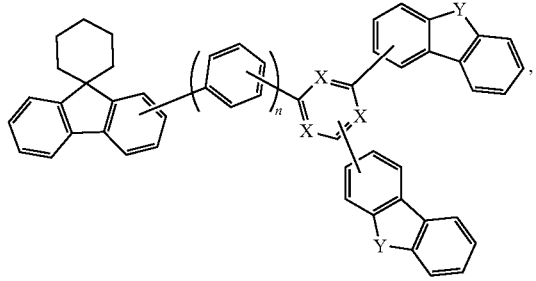

in Chemical Formulas 4 to 7,
X, Y, Ar$_1$, Ar$_2$, and n are as defined in claim 7, respectively.

13. The organic electroluminescent device of claim 7, wherein the one or more organic layers including the compound is selected from the group consisting of: a light-emitting layer, a hole injection layer, a hole transporting layer, an electron injection layer, an electron transporting layer, and an electron transporting auxiliary layer.

14. The organic electroluminescent device of claim 13, wherein the light-emitting layer includes hosts and dopants, and
the hosts include the compound represented by Chemical Formula 1.

* * * * *